US012606848B2

(12) United States Patent
Sadelain et al.

(10) Patent No.: US 12,606,848 B2
(45) Date of Patent: Apr. 21, 2026

(54) GLOBIN GENE THERAPY FOR TREATING HEMOGLOBINOPATHIES

(71) Applicant: MEMORIAL SLOAN-KETTERING CANCER CENTER, New York, NY (US)

(72) Inventors: Michel Sadelain, New York, NY (US); Annalisa Cabriolu, Villacidro (IT)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 46 days.

(21) Appl. No.: 18/355,575

(22) Filed: Jul. 20, 2023

(65) Prior Publication Data

US 2024/0287543 A1 Aug. 29, 2024

Related U.S. Application Data

(60) Division of application No. 16/890,436, filed on Jun. 2, 2020, now Pat. No. 11,753,654, which is a continuation of application No. PCT/US2018/064256, filed on Dec. 6, 2018.

(60) Provisional application No. 62/595,277, filed on Dec. 6, 2017.

(51) Int. Cl.
| | |
|---|---|
| *C12N 15/86* | (2006.01) |
| *A61P 7/00* | (2006.01) |
| *C12N 9/22* | (2006.01) |

(52) U.S. Cl.
CPC .............. *C12N 15/86* (2013.01); *A61P 7/00* (2018.01); *C12N 9/22* (2013.01); *C12N 2310/20* (2017.05); *C12N 2830/008* (2013.01); *C12N 2830/15* (2013.01); *C12N 2830/30* (2013.01)

(58) Field of Classification Search
None
See application file for complete search history.

(56) References Cited

U.S. PATENT DOCUMENTS

| | | | |
|---|---|---|---|
| 4,873,192 | A | 10/1989 | Kunkel |
| 5,399,346 | A | 3/1995 | Anderson et al. |
| 5,399,363 | A | 3/1995 | Liversidge et al. |
| 5,543,158 | A | 8/1996 | Gref et al. |
| 5,641,515 | A | 6/1997 | Ramtoola |
| 5,725,871 | A | 3/1998 | Illum |
| 5,756,353 | A | 5/1998 | Debs |
| 5,780,045 | A | 7/1998 | McQuinn et al. |
| 5,804,212 | A | 9/1998 | Illum |
| 6,797,494 | B1 | 9/2004 | Antoniou et al. |
| 7,541,179 | B2 | 6/2009 | Sadelain et al. |
| 11,717,579 | B2 * | 8/2023 | Sadelain ................ C12N 15/86 |
| | | | 424/93.6 |
| 11,753,654 | B2 * | 9/2023 | Sadelain .............. C07K 14/805 |
| | | | 424/93.2 |
| 2009/0054985 | A1 | 2/2009 | Anderson |
| 2009/0156534 | A1 | 6/2009 | Lisowski et al. |
| 2011/0301073 | A1 | 12/2011 | Gregory et al. |
| 2017/0173185 | A1 | 6/2017 | Sadelain et al. |
| 2020/0109416 | A1 | 4/2020 | Kohn |

FOREIGN PATENT DOCUMENTS

| | | | |
|---|---|---|---|
| WO | WO 2015/138852 A1 | 9/2015 |
| WO | WO 2016/037138 A1 | 3/2016 |

OTHER PUBLICATIONS

Petrus-Reurer et al. Commuication Biology 4:798 pp. 1-16 (Year: 2021).*
Yao et al. Molecular Therapy 32, pp. 103-123, 2024 (Year: 2024).*
Lange et al. Cell Mol Life Sci., 78:4143-4160 (Year: 2021).*
U.S. Appl. No. 16/890,436 (US 2020/0291433), filed Jun. 2, 2020 (Sep. 17, 2020).
U.S. Appl. No. 16/890,436, filed Jul. 20, 2023 Issue Fee Payment.
U.S. Appl. No. 16/890,436, filed Apr. 20, 2023 Notice of Allowance.
U.S. Appl. No. 16/890,436, filed Mar. 9, 2023 Response to Non-Final Rejection.
U.S. Appl. No. 16/890,436, filed Dec. 9, 2022 Non-Final Rejection.
U.S. Appl. No. 16/890,436, filed Oct. 7, 2022 Response to Restriction Requirement.
U.S. Appl. No. 16/890,436, filed Jun. 30, 2022 Restriction Requirement.
Adams et al., "Binding of Disparate Transcriptional Activators to Nucleosomal DNA Is Inherently Cooperative," Molecular and Cellular Biology 15(3):1405-1421 (1995).
Aker et al., "Extended Core Sequences from the cHS4 Insulator Are Necessary for Protecting Retroviral Vectors from Silencing Position Effects," Hum Gene Ther 18:333-343 (2007).
Anderson, "Prospects for Human Gene Therapy," Science 226(4673):401-409 (1984).
Antoniou et al., "The human β-globin gene contains multiple regulatory regions: identification of one promoter and two downstream enhancers," EMBO J., 7(2):377-384 (1988).
Armstrong et al., "NF-E2 Disrupts Chromatin Structure at Human β-Globin Locus Control Region Hypersensitive Site 2 In Vitro," Mol. Cell. Biol. 16(10):5634-5644 (1996).
Arumugam et al., "Genotoxic Potential of Lineage-specific Lentivirus Vectors Carrying the β-Globin Locus Control Region," Mol Ther 17(11):1929-1937 (2009).
Arumugam et al., "Improved Human β-globin Expression from Self-inactivating Lentiviral Vectors Carrying the Chicken Hypersensitive Site-4 (cHS4) Insulator Element," Mol Ther 15(10):1863-1871 (2007).

(Continued)

*Primary Examiner* — Brian Whiteman
(74) *Attorney, Agent, or Firm* — Baker Botts L.L.P.

(57) ABSTRACT

The presently disclosed subject matter provides for expression cassettes that allow for expression of a globin gene or a functional portion thereof, vectors comprising thereof, and cells transduced with such expression cassettes and vectors. The presently disclosed subject matter further provides methods for treating a hemoglobinopathy in a subject comprising administering an effective amount of such transduced cells to the subject.

19 Claims, 21 Drawing Sheets

Specification includes a Sequence Listing.

(56)           References Cited

OTHER PUBLICATIONS

Atweh et al., "Pharmacological Induction of Fetal Hemoglobin in Sickle Cell Disease and β-Thalassemia," Semin Hematol 38:367-373 (2001).

Bank et al., "A Phase I/II Clinical Trial of β-Globin Gene Therapy for β-Thalassemia," Ann N.Y. Acad. Sci. 1054:308-316 (2005).

Barski et al., "High-Resolution Profiling of Histone Methylations in the Human Genome," Cell 129:823-837 (2007).

Baum et al., "Mutagenesis and Oncogenesis by Chromosomal Insertion of Gene Transfer Vectors," Hum Gene Ther 17:253-263 (2006).

Belfort et al., "Homing endonucleases: keeping the house in order," Nucleic Acids Res., 25(17):3379-3388 (1997).

Bell et al., "The Protein CTCF Is Required for the Enhancer Blocking Activity of Vertebrate Insulators," Cell 98:387-396 (1999).

Benton et al., "Screening lambdagt recombinant clones by hybridization to single plaques in situ," Science, 196(4286):180-182 (1977).

Blomer et al., Highly Efficient and Sustained Gene Transfer in Adult Neurons J Virol 6641-9, 1997.

Borgna-Pignatti et al., "Survival and complications in patients with thalassemia major treated with transfusion and deferoxamine," Haematologica 89:1187-1193 (2004).

Boulad et al., "Bone Marrow Transplantation for Homozygous β-Thalassemia. The Memorial Sloan-Kettering Cancer Center Experience," Ann NY Acad Sci 850:498-502 (1998).

Braun et al., "Gene Therapy for Wiskott-Aldrich Syndrome-Long-Term Efficacy and Genotoxicity," Sci Transl Med 6:227ra33 (2014).

Bregni, et al., "Human Peripheral Blood Hematopoietic Progenitors Are Optimal Targets of Retroviral-Mediated Gene Transfer," Blood 80(6):1418-1422 (1992).

Brigham et al., "Rapid Communication: In vivo Transfection of Murine Lungs with a Functioning Prokaryotic Gene Using a Liposome Vehicle," Am. J. Med. Sci. 298(4):278-281 (1989).

Brownell et al., "Special HATs for special occasions: linking histone acetylation to chromatin assembly and gene activation," Curr Opin Genet Dev 6:176-184 (1996).

Bulger et al., "Conservation of sequence and structure flanking the mouse and human β-globin loci: The β-globin genes are embedded within an array of odorant receptor genes," PNAS 1999, 5129-34.

Bungert et al., "Hypersensitive Site 2 Specifies a Unique Function within the Human β-Globin Locus Control Region To Stimulate Globin Gene Transcription," Mol. and Cell Biol. 19(4):3062-3072 (1999).

Burgess-Beusse et al., "The insulation of genes from external enhancers and silencing chromatin," PNAS USA 99(Suppl 4):16433-16437 (2002).

Caterina et al., "Multiple elements in human β-globin locus control region 5' HS 2 are involved in enhancer activity and position-independent, transgene expression," Nucleic Acids Res. 22(6):1006-1011 (1994).

Cavazzana-Calvo et al., "Transfusion independence and HMGA2 activation after gene therapy of human β-thalassaemia," Nature 467:318-322 (2010).

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

Chang et al., "Correction of the sickle cell mutation in embryonic stem cells," Proc Natl Acad Sci 103(4):1036-1040 (2006).

Chang et al., "Epigenetic Modifications and Chromosome Conformations of the Beta Globin Locus throughout Development," Stem Cell Rev and Rep 9:397-407 (2013).

Chang et al., "Lentiviral siRNAs targeting multiple highly conserved RNA sequences of human immunodeficiency virus type 1," Gene Ther 12:1133-1144 (2005).

Chang et al., "The Genetic Engineering of Hematopoietic Stem Cells: the Rise of Lentiviral Vectors, the Conundrum of the LTR, and the Promise of Lineage-Restricted Vectors," Mol Ther 15(3):445-456 (2007).

Charache et al., "Hydroxyurea: Effects on Hemoglobin F Production in Patients With Sickle Cell Anemia," Blood 79(10):2555-2565 (1992).

Chung et al. "A 5' Element of the Chicken β-Globin Domain Serves as an Insulator in Human Erythroid Cells and Protects against Position Effect in *Drosophila*," Cell, 74: 505-514 (1993).

Chung et al., "Characterization of the chicken β-globin insulator," PNAS USA 94:575-580 (1997).

Collis et al., "Definition of the minimal requirements within the human β-globin gene and the dominant control region for high level expression," The EMBO Journal 9(1):233-240 (1990).

Cooley, T.B. & Lee, P., "A Series of Cases of Splenomegaly in Children with Anemia and Peculiar Bone Changes," Trans. Am. Pediatr. Soc. 37:29 (1925).

Cornetta et al., "Gene Transfer into Primates and Prospects for Gene Therapy in Humans," Nucleic Acid Research and Molecular Biology 36:311-322 (1987).

Danos, et al., "Safe and efficient generation of recombinant retroviruses with amphotropic and ecotropic host ranges," Proc. Natl. Acad. Sci. USA 85:6460-6464 (1988).

Dayhoff et al., "A Model of Evolutionary Change in Proteins," Atlas of Protein Sequence and Structure, pp. 345-352 (1978).

Dickson et al., "VEZF1 Elements Mediate Protection from DNA Methylation," PLoS Genet 6:e1000804 (2010).

Dorschner et al., "High-throughput localization of functional elements by quantitative chromatin profiling," Nat Methods 1(3):219-225 (2004).

Dull et al., "A Third-Generation Lentivirus Vector with a Conditional Packaging System," Journal of Virology 72(11):8463-8471 (1998).

Eglitis et al., "Retroviral Vectors for Introduction of Genes into Mammalian Cells," BioTechniques 6(7):608-614 (1988).

Elgin, "DNAase I-Hypersensitive Sites of Chromatin," Cell 27:413-415 (1981).

Elgin, S.C., "Molecular Biology. Anatomy of hypersensitive sites," Nature 309:213-214 (1984).

Ellis et al., "A Dominant chromatin-opening activity in 5' hypersensitive site 3 of the human β-globin locus control region," The EMBO Journal 15(3):562-568 (1996).

Elnitski et al., "Conserved E Boxes Function as Part of the Enhancer in Hypersensitive Site 2 of the β-Globin Locus Control Region," The Journal of Biological Chemistry 272(1):369-378 (1997).

Emery et al., "A chromatin insulator protects retrovirus vectors from chromosomal position effects," PNAS USA 97(16):9150-9155 (2000).

Emery et al., "Development of a Condensed Locus Control Region Cassette and Testing in Retrovirus Vectors for Aγ-Globin," Blood Cells, Molecules, and Diseases 24(16):322-339 (1998).

Emery et al., "Development of virus vectors for gene therapy of β chain hemoglobinopathies: flanking with a chromatin insulator reduces γ-globin gene silencing in vivo," Blood 100:2012-2019 (2002).

Emery, "The Use of Chromatin Insulators to Improve the Expression and Safety of Integrating Gene Transfer Vectors," Hum Gene Ther 22:761-774 (2011).

Evans-Galea et al., "Suppression of Clonal Dominance in Cultured Human Lymphoid Cells by Addition of the cHS4 Insulator to a Lentiviral Vector," Mol Ther 15(4):801-809 (2007).

Felgner et al., "Lipofection: A highly efficient, lipid-mediated DNA-transfection procedure," Proc. Natl. Acad. Sci. USA 84:7413-7417 (1987).

Felsenfeld et al., "Chromatin structure and gene expression," PNAS USA 93:9384-9388 (1996).

Felsenfeld et al., "Controlling the double helix," Nature 421:448-453 (2003).

Felsenfeld, "Chromatin as an essential part of the transcriptional mechanism," Nature 355:219-224 (1992).

Follenzi et al., "Gene transfer by lentiviral vectors is limited by nuclear translocation and rescued by HIV-1 pol sequences," Nature Genetics 25:217-222 (2000).

(56) References Cited

OTHER PUBLICATIONS

Fraser et al., "Each hypersensitive site of the human β-globin locus control region confers a different developmental pattern of expression on the globin genes," Genes & Development 7:106-113 (1993).

Friedmann, "Progress Toward Human Gene Therapy," Science 244(4910):1275-1281 (1989).

Gaszner et al., "Insulators: exploiting transcriptional and epigenetic mechanisms," Nat Rev Genet 7:703-713 (2006).

Giardina et al., "Chelation Therapy in β-Thalassemia: An Optimistic Update," Semin Hematol 38:360-366 (2001).

Giardini et al., "Bone marrow transplantation in the treatment of thalassemia," Current Opinion in Hematology 1:170-176 (1994).

Giles et al., "Chromatin Boundaries, Insulators, and Long-Range Interactions in the Nucleus," Cold Spring Harbor Symposia on Quantitative Biology 75:79-85 (2010).

Gross et al., "Nuclease Hypersensitive Sites in Chromatin," Ann Rev Biochem 57:159-197 (1988).

Grosveld et al., "Position-Independent, High-Level Expression of the Human β-Globin Gene in Transgenic Mice," Cell 51:975-985 (1987).

Grunstein et al., "Colony hybridization: A method for the isolation of cloned DNAs that contain a specific gene," Proc. Natl. Acad. Sci. USA 72(10):3961-3965 (1975).

Hanawa et al., "Optimized Lentiviral Vector Design Improves Titer and Transgene Expression of Vectors Containing the Chicken β-Globin Locus HS4 Insulator Element," Mol Ther 17(4):667-674 (2009).

Hanna et al., Treatment of Sickle Cell Anemia Mouse Model with iPS Cells Generated from Autologous Skin, Science 318:1920-1923 (2007).

Hardison et al., "Locus control regions of mammalian β-globin gene clusters: combining phylogenetic analyses and experimental results to gain functional insights," Gene 205:73-94 (1997).

Hino et al., "Sea urchin insulator protects lentiviral vector from silencing by maintaining active chromatin structure," Gene Ther 11:819-828 (2004).

Horak et al., "GATA-1 binding sites mapped in the β-globin locus by using mammalian chIp-chip analysis," PNAS 99(5):2924-2929 (2002).

Hug et al., "Analysis of Mice Containing a Targeted Deletion of β-Globin Locus Control Region 5' Hypersensitive Site 3," Mol. and Cell Biol. 16(6):2906-2912 (1996).

Hughes et al., "Retroviral Gene Transfer to Primitive Normal and Leukemic Hematopoietic Cells Using Clinically Applicable Procedures," J. Clin. Invest. 89:1817-1824 (1992).

International Search Report dated May 14, 2019 in International Application No. PCT/US18/64256.

Jakobsson et al., "Dynamics of transgene expression in a neural stem cell line transduced with lentiviral vectors incorporating the cHS4 insulator," Experimental Cell Research 298:611-623 (2004).

Jinek et al., A Programmable Dual-RNA—Guided DNA Endonuclease in Adaptive Bacterial Immunity, Science 337:816-821 (2012).

Johnson et al., "Highly Restricted Localization of RNA Polymerase II within a Locus Control Region of a Tissue-Specific Chromatin Domain," Molecular and Cellular Biology 23(18):6484-6493 (2003).

Johnson, "Gene Therapy for Cystic Fibrosis," Chest 107(2):77S-83S (1995).

Kadonaga, "Eukaryotic Transcription: An Interlaced Network of Transcription Factors and Chromatin-Modifying Machines," Cell 92:307-313 (1998).

Kido et al., "Use of retroviral vector with an internal opsin promoter to direct gene expression to retinal photoreceptor cells," Current Eye Research 15:833-844 (1996).

Kim et al., "Analysis of the Vertebrate Insulator Protein CTCF-Binding Sites in the Human Genome," Cell 128:1231-1245 (2007).

Kim et al., "Hybrid restriction enzymes: Zinc finger fusions to Fok I cleavage domain" Proc. Natl. Acad. Sci. USA 93:1156-1160 (1996).

Kimmel, "[54] Identification and Characterization of Specific Clones: Strategy for Confirming the Validity of Presumptive Clones," Methods in Enzymology 152:507-511 (1987).

Kingston et al., "ATP-dependent remodeling and acetylation as regulators of chromatin fluidity," Genes & Development 13:2339-2352 (1999).

Kunkel et al., "Rapid and Efficient Site-Specific Mutagenesis without Phenotypic Selection," Methods in Enzymol, 154:367-382 (1987).

Kunkel, "Rapid and efficient site-specific mutagenesis without phenotypic selection," Proc. Natl. Acad. Sci. USA 82:488-492 (1985).

Ladis et al., "Survival in a large cohort of Greek patients with transfusion-dependent beta thalassaemia and mortality ratios compared to the general population," European Journal of Haematology 86:332-338 (2011).

Le Gal La Salle et al., "An Adenovirus Vector for Gene Transfer into Neurons and Glia in the Brain," Science 259:988-990 (1993).

Leboulch et al., "Mutagenesis of retroviral vectors transducing human β-globin gene and β-globin locus control region derivatives results in stable transmission of an active transcriptional structure," EMBO J 13(13):3065-3076 (1994).

Levasseur et al., Blood, vol. 102, pp. 4312-4319 (2003).

Levings et al., "Recruitment of transcription complexes to the β-globin locus control region and transcription of hypersensitive site 3 prior to erythroid differentiation of murine embryonic stem cells," The FEBS Journal 273:746-755 (2006).

Ley et al., "Reduced β-Globin Gene Expression in Adult Mice Containing Deletions of Locus Control Region 5' HS-2 or 5' HS-3a," Ann. N.Y. Acad. Sci. 850:45-53 (1998).

Li et al., "Evidence that DNase I hypersensitive site 5 of the human β-globin locus control region functions as a chromosomal insulator in transgenic mice," Nucleic Acids Res 30(11):2484-2491 (2002).

Li et al., "Genomic and Functional Assays Demonstrate Reduced Gammaretroviral Vector Genotoxicity Associated With Use of the cHS4 Chromatin Insulator," Mol Ther 17(4):716-724 (2009).

Li et al., "Hypersensitive Site 5 of the Human β Locus Control Region Functions as a Chromatin Insulator," Blood 84(5):1399-1401 (1994).

Li et al., "Nucleotide Sequence of 16-Kilobase Pairs of DNA 5' to the Human ε-Globin Gene," J. Biol. Chem. 260(28):14901-14910 (1985).

Li et al., "Primary Structure of the Goat β-Globin Locus Control Region," Genomics 9:488-499 (1991).

Li et al., "The cHS4 chromatin insulator reduces gammaretroviral vector silencing by epigenetic modifications of integrated provirus," Gene Ther 15:49-53 (2008).

Li et al., "β-Globin locus activation regions: Conservation of organization, structure, and function," Proc. Natl. Acad. Sci. USA 87:8207-8211 (1990).

Lisowski et al., "Locus control region elements HS1 and HS4 enhance the therapeutic efficacy of globin gene transfer in β-thalassemic mice," Blood 110(13):4175-4178 (2007).

Lowrey et al., "Mechanism of DNase I hypersensitive site formation within the human globin locus control region," PNAS USA 89:1143-1147 (1992).

Lucarelli et al., "Bone Marrow Transplantation in Adult Thalassemic Patients," Blood 93(4):1164-1167 (1999).

Luzzatto et al., "Sickle cell anaemia. A simple disease with no cure," Nature 337:17-18 (1989).

Ma et al., "High-Level Sustained Transgene Expression in Human Embryonic Stem Cells Using Lentiviral Vectors," Stem Cells 21:111-117 (2003).

Mancuso et al., "A Prospective Study of Hepatocellular Carcinoma Incidence in Thalassemia," Hemoglobin 30(1):119-124 (2006).

Margot et al., "Complete Nucleotide Sequence of the Rabbit β-like Globin Gene Cluster: Analysis of Intergenic Sequences and Comparison with the Human β-like Globin Gene Cluster," J. Mol. Biol. 205:15-40 (1989).

Maurano et al., "Systematic Localization of Common Disease-Associated Variation in Regulatory DNA," Science 337:1190-1195 (2012).

US 12,606,848 B2

Page 4

(56) References Cited

OTHER PUBLICATIONS

May et al., "Successful treatment of murine β-thalassemia intermedia by transfer of the human β-globin gene," Blood 99:1902-1908 (2002).

May et al., "Therapeutic haemoglobin synthesis in β-thalassaemic mice expressing lentivirus-encoded human β-globin," Nature 406:82-86 (2000).

McArthur et al., "Quantification of DNaseI-sensitivity by Real-time PCR: Quantitative Analysis of DNaseI-hypersensitivity of the Mouse β-Globin LCR," J Mol Biol 313:27-34 (2001).

McGhee et al., "A 200 Base Pair Region at the 5' End of the Chicken Adult β-Globin Gene Is Accessible to Nuclease Digestion," Cell 27:45-55 (1981).

Meissner et al., "Direct reprogramming of genetically unmodified fibroblasts into pluripotent stem cells," Nature Biotechnology 25:1177-1181 (2007).

Miccio et al., "In vivo selection of genetically modified erythroblastic progenitors leads to long-term correction of β-thalassemia," PNAS USA 105(30):10547-10552 (2008).

Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).

Miller et al., "Improved Retroviral Vectors for Gene Transfer and Expression," Biotechniques 7(9):980-990 (1989).

Miller et al., "Redesign of retrovirus packaging cell lines to avoid recombination leading to helper virus production," Mol. Cell. Biol. 6(8):2895-2902 (1986).

Miller, "Retrovirus Packaging Cells," Human Gene Therapy 1:5-14 (1990).

Miyoshi et al., "Development of a Self-Inactivating Lentivirus Vector," J. Virol. 72(10):8150-8157 (1998).

Miyoshi et al., "Stable and efficient gene transfer into the retina using an HIV-based lentiviral vector," Proc. Natl. Acad. Sci. USA 94:10319-10323 (1997).

Moen, "Directions in Gene Therapy," Blood Cells 17:407-416 (1991).

Moi et al., "Synergistic enhancement of globin gene expression by activator protein-1-like proteins," PNAS USA 87:9000-9004 (1990).

Moi et al., "Towards the genetic treatment of β-thalassemia: new disease models, new vectors, new cells," Haematologica 93(3):325-330 (2008).

Nagel et al., "Structural bases of the inhibitory effects of hemoglobin F and hemoglobin A2 on the polymerization of hemoglobin S," PNAS USA 76(2):670-672 (1979).

Nakagawa et al., Generation of induced pluripotent stem cells without Myc from mouse or human fibroblasts Nat Biotechnol 2008, 26, 101-6.

Naldini et al., "In Vivo Gene Delivery and Stable Transduction of Nondividing Cells by a Lentiviral Vector," Science 272:263-267 (1996).

Navas et al., "Developmental specificity of the Interaction between the Locus Control Region and Embryonic or Fetal Globin Genes in Transgenic Mice with an HS3 Core Deletion," Molecular and Cellular Biology 18(7):4188-4196 (1998).

Neph et al., "An expansive human regulatory lexicon encoded in transcription factor footprints," Nature 489:83-90 (2012).

Neph et al., "Circuitry and Dynamics of Human Transcription Factor Regulatory Networks," Cell 150:1274-1286 (2012).

Ney et al., "Tandem AP-1-binding sites within the human β-globin dominant control region function as an inducible enhancer in erythroid cells," Genes & Dev. 4:993-1006 (1990).

Nienhuis et al., "Genotoxicity of Retroviral Integration In Hematopoietic Cells," Mol Ther 13(6):1031-1049 (2006).

Nienhuis, "Development of gene therapy for blood disorders: an update," Blood 122(9):1556-1564 (2013).

Nishino et al. "Partial correction of murine β-thalassemia with a gammaretrovirus vector for human γ-globin," Blood Cells Mol Dis 37:1-7 (2006).

Okita et al., "Generation of germline-competent induced pluripotent stem cells," Nature 448:313-317 (2007).

Ono et al., "Plasmid DNAs directly injected into mouse brain with lipofectin can be incorporated and expressed by brain cells," Neuroscience Letters 117:259-263 (1990).

Papapetrou et al., "Genomic safe harbors permit high β-globin transgene expression in thalassemia induced pluripotent stem cells," Nat Biotechnol. 29(1):73-78 (2011).

Papayannopoulou et al., "Hemopoietic lineage commitment decisions: in vivo evidence from a transgenic mouse model harboring μLCR-βpro-LacZ as a transgene," Blood 95:1274-1282 (2000).

Park et al., "Reprogramming of human somatic cells to pluripotency with defined factors," Nature 451:141-146 (2007).

Pauling et al., "Sickle Cell Anemia, a Molecular Disease," Science 110:543-548 (1949).

Pawliuk et al., "Correction of Sickle Cell Disease in Transgenic Mouse Models by Gene Therapy," Science 294:2368-2371 (2001).

Perrine et al., "Induction of Fetal Globin in β-Thalassemia: Cellular Obstacles and Molecular Progress," Ann. N.Y. Acad. Sci. 1054:257-265 (2005).

Persons et al., "Gene Therapy for the Hemoglobin Disorders," Semin Hematol 41:279-286 (2004).

Persons, "The challenge of obtaining therapeutic levels of genetically modified hematopoietic stem cells in β-thalassemia patients," Ann NY Acad Sci 1202:69-74 (2010).

Perumbeti et al., "Therapy for β-globinopathies: a brief review and determinants for successful and safe correction," Ann NY Acad Sci 1202:36-44 (2010).

Pestina et al., "Correction of Murine Sickle Cell Disease Using γ-Globin Lentiviral Vectors to Mediate High-Level Expression of Fetal Hemoglobin," Molecular Therapy 17(2):245-252 (2009).

Phillips et al., "CTCF: Master Weaver of the Genome," Cell 137:1194-1211 (2009).

Pikaart et al., "Loss of transcriptional activity of a transgene is accompanied by DNA methylation and histone deacetylation and is prevented by insulators," Genes & Development 12:2852-2862 (1998).

Platt et al., "Hydroxyurea Enhances Fetal Hemoglobin Production in Sickle Cell Anemia," J. Clin. Invest. 74:652-656 (1984).

Pluta et al., "Tight control of transgene expression by lentivirus vectors containing second-generation tetracycline-responsive promoters," J Gene Med 7:803-817 (2005).

Prioleau et al., "An insulator element and condensed chromatin region separate the chicken β-globin locus from an independently regulated erythroid-specific folate receptor gene," EMBO J. 18(14):4035-4048 (1999).

Proc. Natl. Acad. Sci. 96:5129-5134 (1999).

Pruzina et al., "Hypersensitive site 4 of the human β globin locus control region," Nucleic Acids Research 19(7):1413-1419 (1991).

Puthenveetil et al., "Successful correction of the human β-thalassemia major phenotype using a lentiviral vector," Blood 104:3445-3453 (2004).

Ramezani et al., "Combinatorial Incorporation of Enhancer-Blocking Components of the Chicken β-Globin 5'HS4 and Human T-cell Receptor α/δ BEAD-1 Insulators in Self-Inactivating Retroviral Vectors Reduces Their Genotoxic Potential," Stem Cells 26:3257-3266 (2008).

Ramezani et al., "Performance-and safety-enhanced lentiviral vectors containing the human interferon-β scaffold attachment region and the chicken β-globin insulator," Blood 101:4717-4724 (2003).

Ramezani et al., "Stable Gammaretroviral Vector Expression during Embryonic Stem Cell-Derived In Vitro Hematopoietic Development," Mol Ther 14(2):245-254 (2006).

Recillas-Targa et al., "Position-effect protection and enhancer blocking by the chicken β-globin insulator are separable activities," PNAS USA 99(10):6883-6888 (2002).

Renda et al., "Critical DNA Binding Interactions Of The Insulator Protein CTCF: A Small Number of Zinc Fingers Mediate Strong Binding, and a Single Finger-DNA Interaction Controls Binding at Imprinted Loci," J Biol Chem 282(46):33336-33345 (2007).

Rivella et al., "A novel murine model of Cooley anemia and its rescue by lentiviral-mediated human β-globin gene transfer," Blood 101:2932-2939 (2003).

(56) References Cited

OTHER PUBLICATIONS

Rivella et al., "The cHS4 Insulator Increases the Probability of Retroviral Expression at Random Chromosomal Integration Sites," J Virol 74(10):4679-4687 (2000).

Rosenberg et al., "Gene Transfer into Humans—Immunotherapy of Patients with Advanced Melanoma, Using Tumor-Infiltrating Lymphocytes Modified by Retroviral Gene Transduction," N. Engl. J. Med 323(9):570-578 (1990).

Ryu et al., "A chromatin insulator blocks interactions between globin regulatory elements and cellular promoters in erythroid cells," Blood Cells Mol Dis 39:221-228 (2007).

Ryu et al., "An experimental system for the evaluation of retroviral vector design to diminish the risk for proto-oncogene activation," Blood 111(4):1866-1875 (2008).

Sabo et al., "Discovery of functional noncoding elements by digital analysis of chromatin structure," PNAS USA 101(48):16837-16842 (2004).

Sabo et al., "Genome-scale mapping of DNase I sensitivity in vivo using tiling DNA microarrays," Nat Methods 3(7):511-518 (2006).

Sabo et al., "Genome-wide identification of DNaseI hypersensitive sites using active chromatin sequence libraries," PNAS USA 101(13):4537-4542 (2004).

Sadelain et al., "Safe Harbours for the integration of new DNA in the human genome," Nature Reviews 12:51-58 (2012).

Sadelain et al., "Generation of a high-titer retroviral vector capable of expressing high levels of the human β-globin gene," PNAS USA 92:6728-6732 (1995).

Sadelain et al., "Stem Cell Engineering for the Treatment of Severe Hemoglobinopathies," Curr Mol Med 8:690-697 (2008).

Sadelain et al., "Therapeutic Options for Patients with Severe β-Thalassemia: The Need for Globin Gene Therapy," Hum Gene Ther 18:1-9 (2007).

Sadelain, "Genetic Treatment of the Haemoglobinopathies: Recombinations and New Combinations," Br J Haematol 98:247-253 (1997).

Sadelain, "Recent advances in globin gene transfer for the treatment of beta-thalassemia and sickle cell anemia," Current Opinion in Hematology 13:142-148 (2006).

Samakoglu et al., "A genetic strategy to treat sickle cell anemia by coregulating globin transgene expression and RNA interference," Nat. Biotechnol 24:89-94 (2006).

Schmidt et al., "Waves of Retrotransposon Expansion Remodel Genome Organization and CTCF Binding in Multiple Mammalian Lineages," Cell 148:335-348 (2012).

Sharp, The Lancet 337:1277-1278 (1991).

Shehee et al., "Nucleotide Sequence of the BALB/c Mouse β-Globin Complex," J. Mol. Biol. 205:41-62 (1989).

Shimotsuma et al., "DNase I Hypersensitivity and e-Globin Transcriptional Enhancement Are Separable in Locus Control Region (LCR) HS1 Mutant Human β-Globin YAC Transgenic Mice," Journal of Biological Chemistry 285(19):14495-14503 (2010).

Shivdasani et al., "Transcription Factor NF-E2 is Required for Platelet Formation Independent of the Actions of Thrombopoietin/MGDF in Megakaryocyte Development," Cell 81:695-704 (1995).

Stamatoyannopoulos, "Prospects for developing a molecular cure for thalassemia," Hematology 10(Suppl 1):255-257 (2005).

Stergachis et al., "Developmental Fate and Cellular Maturity Encoded in Human Regulatory DNA Landscapes," Cell 154:888-903 (2013).

Stergachis et al., "Exonic Transcription Factor Binding Directs Codon Choice and Affects Protein Evolution," Science 342:1367-1372 (2013).

Straubinger et al., "[32] Liposomes as Carriers for Intracellular Delivery of Nucleic Acids," Methods in Enzymology 101:512-527 (1983).

Struhl, "Histone acetylation and transcriptional regulatory mechanisms," Genes & Development 12:599-606 (1998).

Swank et al., "Fetal gene reactivation," Curr Opin Genet Dev 8:366-370 (1998).

Taboit-Dameron et al., "Association of the 5' HS4 sequence of the chicken β-globin locus control region with human EFIα gene promoter induces ubiquitous and high expression of human CD55 and CD59 cDNAs in transgenic rabbits," Transgenic Research, 8:223-235 (1999).

Takahashi et al., "Induction of Pluripotent Stem Cells from Adult Human Fibroblasts by Defined Factors," Cell 131:861-872 (2007).

Takahashi et al., "Induction of pluripotent stem cells from fibroblast cultures," Nature Protocols 2(12):3081-3089 (2007).

Takahashi et al., Induction of Pluripotent Stem Cells from Mouse Embryonic and Adult Fibroblast Cultures by Defined Factors, Cell 126:663-676 (2006).

Talbot et al., "A dominant control region from the human β-globin locus conferring integration site-independent gene expression," Nature 338:352-355 (1989).

Talbot et al., "The 5'HS2 of the globin locus control region enhances transcription through the interaction of a multimeric complex binding at two functionally distinct NF-E2 binding sites," EMBO J 10(6):1391-1398 (1991).

Telfer et al. "Improved survival in thalassemia major patients on switching from desferrioxamine to combined chelation therapy with desferrioxamine and deferiprone," Haematologica 94(12):1777-1778 (2009).

Thurman et al., "The accessible chromatin landscape of the human genome," Nature 489:75-82 (2012).

Tisdale et al., "Toward Gene Therapy for Disorders of Globin Synthesis," Semin Hematol 38(4):382-392 (2001).

Tolstoshev et al., Gene expression using retroviral vectors, Current Opinion in Biotechnology 1:55-61 (1990).

Trudel et al., "A 3' enhancer contributes to the stage-specific expression of the human β-globin gene," Genes & Development 1:954-961 (1987).

Trudel et al., "Upstream Gγ-Globin and Downstream β-Globin Sequences Required for Stage-Specific Expression in Transgenic Mice," Molecular and Cellular Biology 7(11):4024-4029 (1987).

Tsukiyama et al., "Chromatin remodeling and transcription," Curr Opin Genet Dev 7:182-191 (1997).

Vermylen et al., "Haematopoietic stem cell transplantation for sickle cell anaemia: the first 50 patients transplanted in Belgium," Bone Marrow Transplant 22:1-6 (1998).

Vieira et al., "Recruitment of Transcription Complexes to the β-Globin Gene Locus in Vivo and in Vitro," J Biol Chem 279(48):50350-50357 (2004).

Wahl et al., Molecular Hybridization of Immobilized Nucleic Acids: Theoretical Concepts and Practical Considerations, Methods in Enzymology 152:399-407 (1987).

Wallace et al., "We gather together: insulators and genome organization," Curr Opin Genet Dev 17:400-407 (2007).

Wang et al., "Ligand-inducible and liver-specific target gene expression in transgenic mice," Nature Biotechnology 15:239-243 (1997).

Wang et al., "Widespread plasticity in CTCF occupancy linked to DNA methylation," Genome Research 22:1680-1688 (2012).

Weatherall, "Phenotype—Genotype Relationships In Monogenic Disease: Lessons From The Thalassaemias," Nature Reviews Genetics 2:245-255 (2001).

Wernig et al., "In vitro reprogramming of fibroblasts into a pluripotent ES-cell-like state," Nature 448:318-324 (2007).

Wilber et al., "Transcriptional regulation of fetal to adult hemoglobin switching: new therapeutic opportunities," Blood 117(15):3945-3953 (2011).

With a Lentivirus Vector, Journal of Virology 71:6641-6649 (1997).

Wolff et al., "Direct Gene Transfer into Mouse Muscle in Vivo," Science 247(4949):1465-1468 (1990).

Wolffe et al., "Activators and repressors: making use of chromatin to regulate transcription," Genes to Cells 2:291-302 (1997).

Wu et al., "Receptor-mediated Gene Delivery and Expression in Vivo," The Journal of Biological Chemistry 263(29):14621-14624 (1988).

Wu et al., "Targeting Genes: Delivery and Persistent Expression of a Foreign Gene Driven by Mammalian Regulatory Elements in Vivo," The Journal of Biological Chemistry 264(29):16985-16987 (1989).

Wu, "The 5' ends of Drosophila heat shock genes in chromatin are hypersensitive to DNase I," Nature 286:854-860 (1980).

(56)           References Cited

OTHER PUBLICATIONS

Xu et al., Correction of the enzyme deficiency in hematopoietic cells of Gaucher patients using a clinically acceptable retroviral supernatant transduction protocol, Experimental Hematology 22:223-230 (1994).

Yannaki et al., "Gene therapy for β-thalassaemia: the continuing challenge," Expert Reviews in Molecular Medicine 12:e31 (2010).

Yannaki et al., "Topological Constraints Governing the Use of the Chicken HS4 Chromatin Insulator in Oncoretrovirus Vectors," Mol Ther 5(5):589-598 (2002).

Yao et al., "Retrovirus silencer blocking by the cHS4 insulator is CTCF independent," Nucleic Acids Res 31(18):5317-5323 (2003).

Yu et al., "Induced Pluripotent Stem Cell Lines Derived from Human Somatic Cells," Science 318:1917-1920 (2007).

Yusufzai et al., "The 5'-HS4 chicken β-globin insulator is a CTCF-dependent nuclear matrix-associated element," PNAS USA 101(23):8620-8624 (2004).

Zufferey et al., "Self-Inactivating Lentivirus Vector for Safe and Efficient In Vivo Gene Delivery," Journal of Virology 72(12):9873-9880 (1998).

* cited by examiner

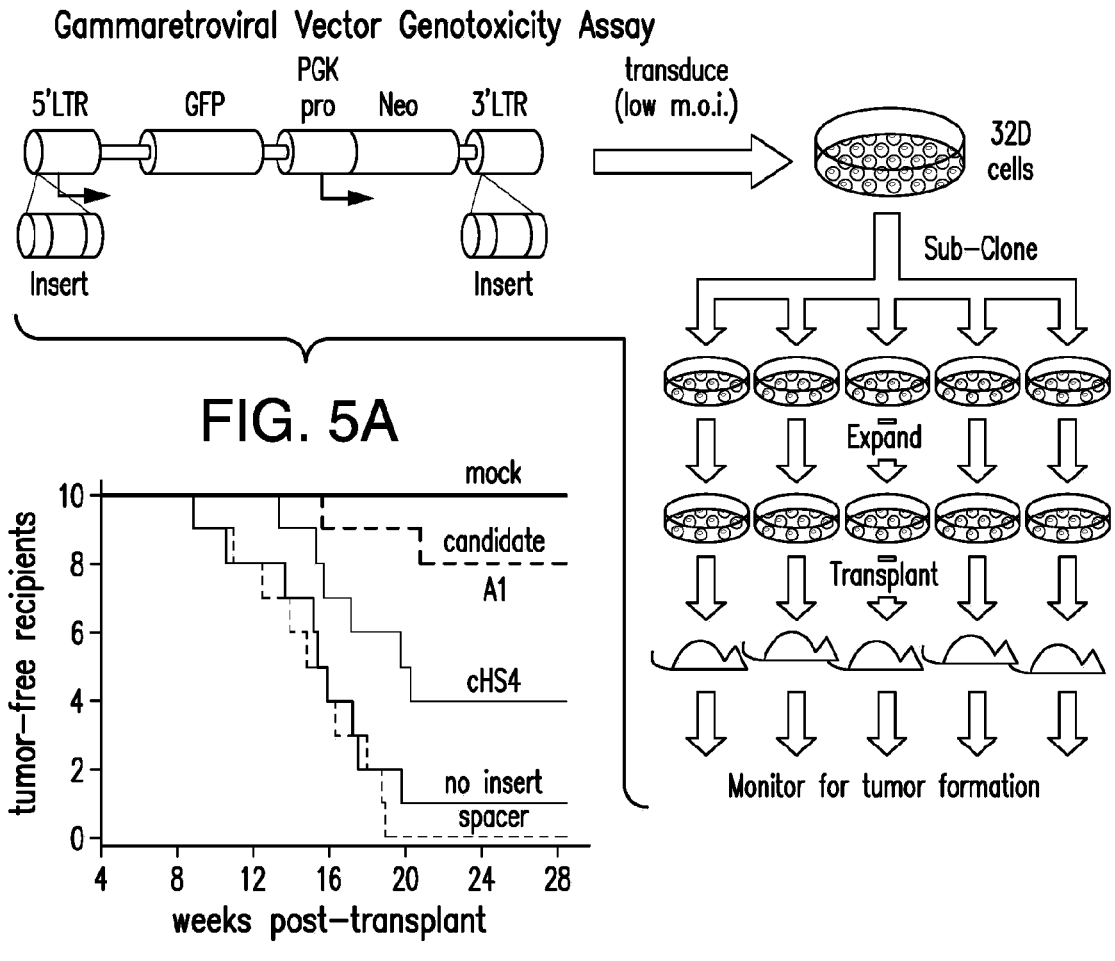

| Vector | (a) Estimated no. Tumors | (b) Estimated no. Provirus | Tumors per $10^5$ Provirs | (c) Probability vs. no insert | (c) Probability vs. cHS4 |
|--------|--------|--------|--------|--------|--------|
| mock | 0 | 0 | 0 | <<0.001 | <<0.001 |
| no insert | 23.0 | $0.49 \times 10^5$ | 46.9 | -- | <0.001 |
| spacer | $\geq 30$ | $0.67 \times 10^5$ | $\geq 44.7$ | n.e. | <0.001 |
| cHS4 | 9.15 | $0.54 \times 10^5$ | 16.9 | <0.001 | -- |
| A1 | 2.23 | $0.64 \times 10^5$ | 3.9 | <0.001 | <0.05 |

(a) Based on the poisson distribution for the fraction of recipients with no tumors; (b) Based on the initial cell numbers and initial transduction rates; (c) Based on the Z-*test* for two proportions.

FIG. 5C

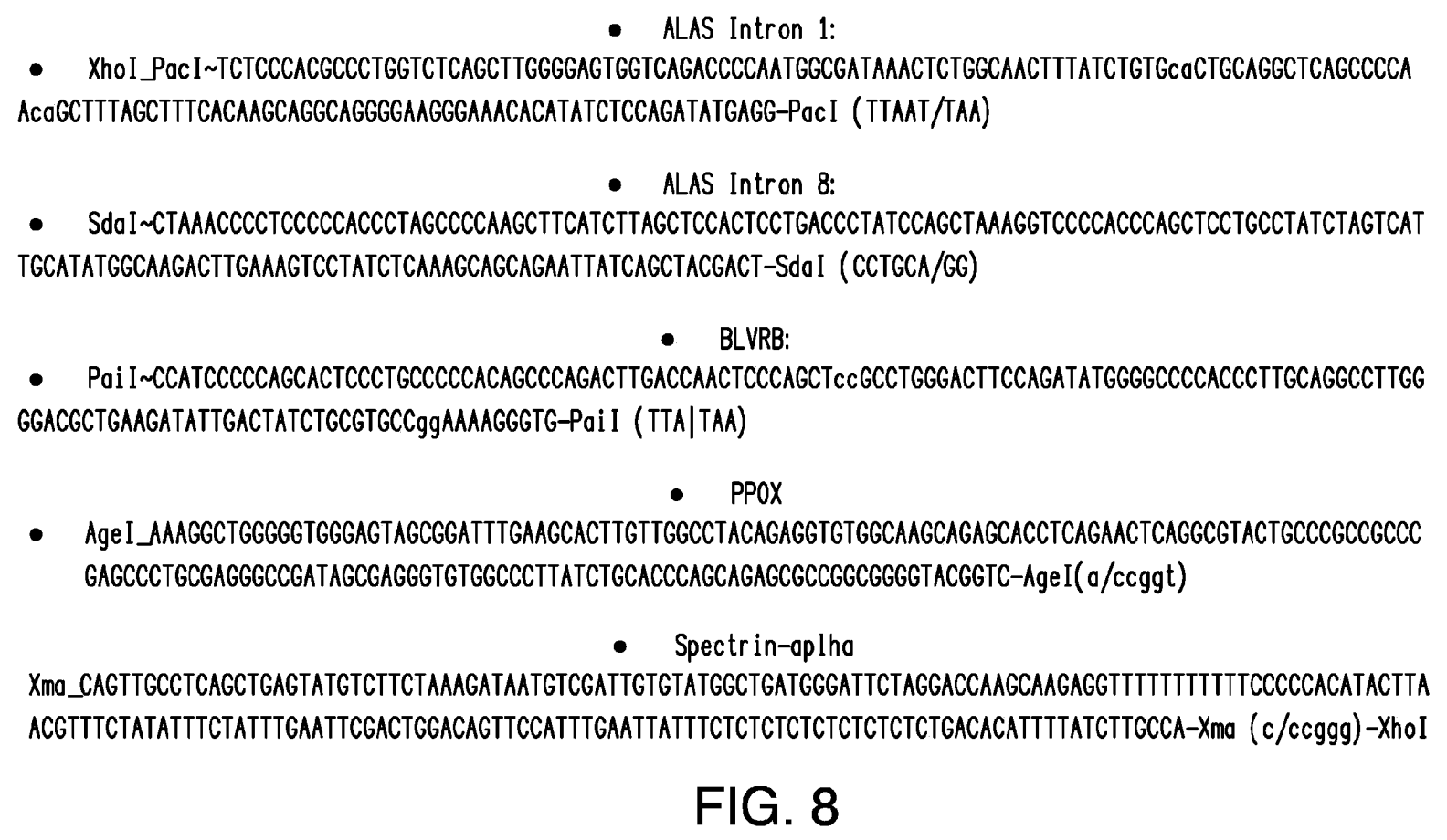

- ALAS Intron 1:
- XhoI_PacI~TCTCCCACGCCCTGGTCTCAGCTTGGGGAGTGGTCAGACCCCAATGGCGATAAAACTCTGGCAACTTTATCTGTGcaCTGCAGGCTCAGCCCCA
AcaGCTTTAGCTTTCACAAGCAGGCAGGGGAAGGGAAACACATATCTCCAGATATGAGG-PacI (TTAAT/TAA)

- ALAS Intron 8:
- SdaI~CTAAACCCCTCCCCCACCCTAGCCCCAAGCTTCATCTTAGCTCCTCCACTCCTGACCCTATCCAGCTAAAGGTCCCCACCCAGCTCCTGCCTATCTAGTCAT
TGCATATGGCAAGACTTGAAAGTCCTATCTCAAAGCAGCAGAATTATCAGCTACGACT-SdaI (CCTGCA/GG)

- BLVRB:
- PaiI~CCATCCCCCAGCACTCCCTGCCCCCACAGCCCAGACTTGACCAACTCCCAGCTccGCCTGGGACTTCCAGATATGGGGCCCCACCCTTGCAGCCCTTGG
GGACGGCTGAAGATATTGACTATCTGCGTGCCggAAAAGGGTG-PaiI (TTA|TAA)

- PPOX
- AgeI_AAAGGCTGGGGGTGGGAGTAGCCGGATTTGAAGCACTTGTTGGCCTACAGAGAGGTGTGGCAAGCAGAGCACCTCAGAACTCAGCGTACTGCCCGCGCGCCC
GAGCCCTGCGAGGGCCGCCGATAGCCGAGGGTGTGGCCCTTATCTGCACCCAGCAGAGCGCGGGGTACGGTC-AgeI(a/ccggt)

- Spectrin-alpha
Xma_CAGTTGCCTCAGCTGAGTATGTCTTCTAAAGATAATGTCGATTGTATGGCTGATGGGATTCTAGGACCAAGCAAGAGGTTTTTTTTTCCCCCACATACTTA
ACGTTTCTATATTTCTATTGAATTCGACTGGACAGTTCCATTGAATTATTTCTCTCTCTCTCTCTCTGACACATTTTATCTTGCCA-Xma (c/ccggg)-XhoI

FIG. 8

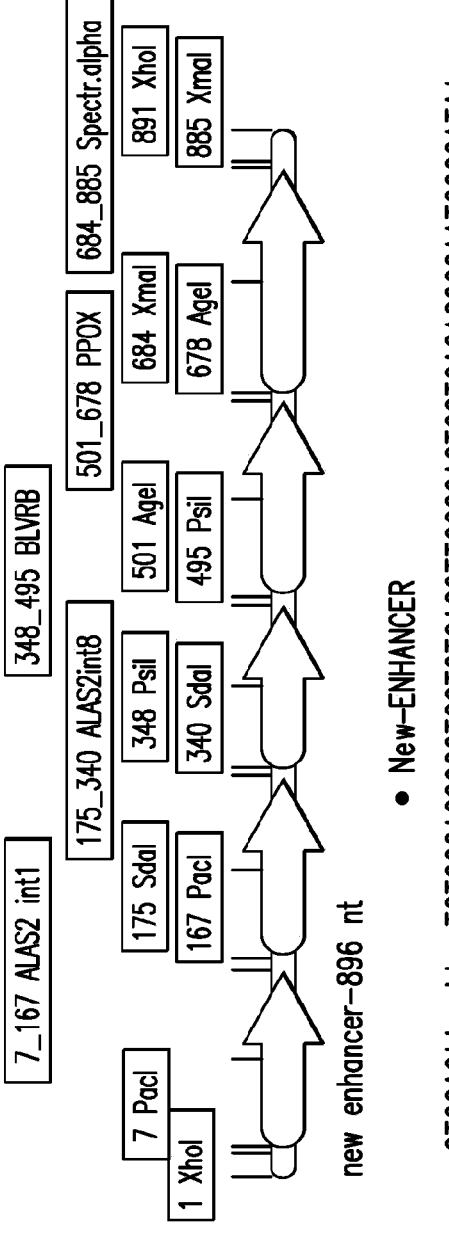

new enhancer-896 nt

● New-ENHANCER

● CTCGAGttaattaaTCTCCCACGCCCTGGTCTCAGCTTGGGGAGTGGTCAGACCCCAATGGCGATAA
ACTCTGGCAACTTTATCTGTGcacTGCAGCGCTCAGCCCCAAcaGCTTTAGCTTTCACAAGCAGGCAGGGG
AAGGGAAACACATATCTCCAGATATGAGGttaattaacctgcaggCTAAACCCCTCCCCCACCCTAGCCC
CAAGCTTCATCTTAGCTCCACTCCTGACCCTATCCAGCTAAAGGTCCCCACCCAGCTCCTGCCTATCTAG
TCATTGCATATGGCAAGACTTGAAAGTCCTATCTCAAAGCAGCAGAATTATCAGCTACGACTcctgcagg
ttataaCCATCCCCCAGCACTCCCTGCCCCCACAGACTTGACCAACTCCCAGCTccGCCTGGGAC
TTCCAGATATGGGGCCCCACCCTTGCCAGGGCCCTTGGGGACGCGGAGTAGCGGATTTGAAGCACTTGTTGGCCTACAGAG
AAGGGGTGttataaaccggtAAAGGCTGGGGGTGGGGGTGGGAGTAGCGGATTTGAAGCACTTGTTGGCCTACAGAG
GTGTGGCAAGCAGAGCACCTCAGAACTCAGCGGTACTGCCCCGCCCGCCCGAGGGCCGATAGC
GAGGGTGTGCGCCCCTTATCTGCACCCAGCAGAGCGCCGCCCGCGGGTACGGTCaccggtcccgggCAGTTGCC
TCAGCTGAGTATGTCTTCTAAAGATAATGTCGATTGTGTATGGCTGATGGGATTCTAGGACCAAGCAAGA
GGTTTTTTTTTTCCCCCACATACTTAACGTTTCTATATTTCTATATTTCTATATTTCTATATTCGACTGGACAGTTCCATT
TGAATTATTTCTCTCTCTCTCTCGACACATTTTATCTTGCCAcccgggCTCGAG

FIG. 9

*Average of total Hb: (TNS9.B87.A1 n=4, SNS23.2.B87.A1 n=5 SNS26.B87.A1=5*
*SNS27.2.B87.A1=5 TH$^3$/$^+$mock n=1)*

*Average of ΔHb normalized per VCN: (TNS9.B87.A1 n=4, SNS23.2.B87.A1 n=5 SNS26.B87.A1=5*
*SNS27.2.B87.A1=5 TH$^3$/$^+$mock n=1)*

SEQUENCE LISTING

```
Sequence total quantity: 78
SEQ ID NO: 1            moltype = DNA  length = 305
FEATURE                 Location/Qualifiers
misc_feature            1..305
                        note = Description of Artificial Sequence: Synthetic
                        polynucleotide
source                  1..305
                        mol_type = other DNA
                        organism = synthetic construct
SEQUENCE: 1
tccttccttt ctaaatgacg agagagacag aagaattctt caaggttagt gtgtccagca   60
tgcaaccttt ccttcctgga tgagcatccc tggagtagga gagccagcct gcctcctgcg  120
ctggcacaga gcccggttcc ctagacaact gcctctccaa atctgatgtc cagcgccacc  180
tggtgtccac atcaagcaga cacaattaat agtcaacctg ttcaggaaaa ctgtgagggg  240
gaaaaaaaag aaagaggatt tatgaaggga aaagaaagtt tagaggatat gccacgattg  300
gctag                                                              305

SEQ ID NO: 2            moltype = DNA  length = 1074
FEATURE                 Location/Qualifiers
misc_feature            1..1074
                        note = Description of Artificial Sequence: Synthetic
                        polynucleotide
```

-continued

```
source                    1..1074
                          mol_type = other DNA
                          organism = synthetic construct
SEQUENCE: 2
aagtaaactt ccacaaccgc aagcttattg aggctaaggc atctgtgaag gaaagaaaca   60
tctcctctaa accactatgc tgctagagcc tcttttctgt actcaagcct cattcagaca  120
ctagtgtcac cagtctcctc atataccttat tgtattttct tcttcttgct ggtttagtca  180
tgttttctgg gagcttaggg gcttatttta ttttgttttg ttttctaatc aacagagatg  240
ggcaaaccca ttattttttt ctttagactt gggatggtga tagctgggca gcgtcagaaa  300
ctgtgtgtgg atatagataa gagctcggac tatgctgagc tgtgatgagg gagggaccta  360
gccaaaggca gtgagagtca gaatgctcct gctattgcct tctcagtccc cacgcttggt  420
ttctacacaa gtagatacat agaaaaggct ataggttagt gtttgagagt cctgcatgag  480
ttagttgctc agaaatgccc gataaatatg ttatgtgtgt ttatgtatat atatgtttta  540
tatatatata tgtgtggtgtg tgtgtgtgtg tgtgttcgt ttacaaatat gtgattatca  600
tcaaaacgtg agggctaaag tgaccagata acttgcaggt cctaggatac caggaaaata  660
aattacattc caaaaattta actgagactt taaaaaaaaa aaaaaaaaaa aaaaaaaaac  720
cagtgatcca tggacacagg gaggggaaca tcacacactg gggcctgttg ggggtggggg  780
gctaggggaa ggatagcatt aggagaaata cctaatgtag atgacgggtt gatgggtgca  840
gcaaaccacc atggcacatg tacccccagaa cttaaagcat attaaaaaaa cagtgatcat  900
aaaagaagct caaatttaac tataagagac ggaatggctc ccacaattct taactataat  960
cttacagaat attctcattg aatagaagta tgcttatcat tagagatttg gacagccagg 1020
aaagcacaga aaaaaaaaaa aggagctctg ttgcctata gcctagaggt gttt         1074

SEQ ID NO: 3            moltype = DNA   length = 602
FEATURE                Location/Qualifiers
misc_feature           1..602
                       note = Description of Artificial Sequence: Synthetic
                        polynucleotide
source                 1..602
                       mol_type = other DNA
                       organism = synthetic construct
SEQUENCE: 3
ggcatctgtg aaggaaagaa acatctcctc taaaccacta tgctgctaga gcctcttttc   60
tgtactcaag cctcattcag acactagtgt caccagtctc ctcatatacc tattgtattt  120
tcttcttctt gctggtttag tcatgttttc tgggagctta ggggcttatt ttattttgtt  180
ttgtttttcta atcaacagag atgggcaaac ccattatttt tttctcttaga cttgggatgg  240
tgatagctgg gcagcgtcag aaactgtgtg tggatatata taagagctcg gactatgctg  300
agctgtgatg agggaggggac ctagccaaag gcagtgagag tcagaatgct cctgctattg  360
ccttctcagt ccccacgctt ggtttctaca caagtagata catagaaaag gctataggtt  420
agtgtttgag agtcctgcat gagttagttg ctcagaaatg cccgataaat atgttatgtg  480
tgtttatgta tatatatgtt ttatatatat atatgtgtgt gtgtgtgtgt gtgtgtgttg  540
tgtttacaaa tatgtgatta tcatcaaaac gtgagggcta aagtgaccag ataacttgca  600
gg                                                                   602

SEQ ID NO: 4            moltype = DNA   length = 489
FEATURE                Location/Qualifiers
misc_feature           1..489
                       note = Description of Artificial Sequence: Synthetic
                        polynucleotide
source                 1..489
                       mol_type = other DNA
                       organism = synthetic construct
SEQUENCE: 4
ggcatctgtg aaggaaagaa acatctcctc taaaccacta tgctgctaga gcctcttttc   60
tgtactcaag cctcattcag acactagtgt caccagtctc ctcatatacc tattgtattt  120
tcttcttctt gctggtttag tcatgttttc tgggagctta ggggcttatt ttattttgtt  180
ttgtttttcta atcaacagag atgggcaaac ccattatttt tttctcttaga cttgggatgg  240
tgatagctgg gcagcgtcag aaactgtgtg tggatatata taagagctcg gactatgctg  300
agctgtgatg agggagggac ctagccaaag gcagtgagag tcagaatgct cctgctattg  360
ccttctcagt ccccacgctt ggtttctaca caagtagata catagaaaag gctataggtt  420
agtgtttgag agtcctgcat gagttagttg ctcagaaatg cccgataaat atgttatgtg  480
tgtttatgt                                                           489

SEQ ID NO: 5            moltype = DNA   length = 1301
FEATURE                Location/Qualifiers
misc_feature           1..1301
                       note = Description of Artificial Sequence: Synthetic
                        polynucleotide
source                 1..1301
                       mol_type = other DNA
                       organism = synthetic construct
SEQUENCE: 5
aagctttcat taaaaaaagt ctaaccagct gcattcgact ttgactgcag cagctggtta   60
gaaggttcta ctggaggagg gtcccagccc attgctaaat taacatcagg ctctgagact  120
ggcagtatat ctctaacagt ggttgatgct atcttctgga acttgcctgc tacattgaga  180
ccactgaccc atacatagga agcccatagc tctgtcctga actgttaggc cactggtcca  240
gagagtgtgc atcctctttg atcctcataa taacccatg agatagacac aattattact  300
cttactttat agatgatgat cctgaaaaca taggagtcaa ggcacttgcc cctagctggg  360
ggtataggggg agcagtccca tgtagtagta gaatgaaaaa tgctgctatg ctgtgcctcc  420
```

```
cccacctttc ccatgtctgc cctctactca tggtctatct ctcctggctc ctgggagtca   480
tggactccac ccagcaccac caacctgacc taaccaccta tctgagcctg ccagcctata   540
acccatctgg gccctgatag ctggtggcca gccctgaccc cacccacc tccctggaac     600
ctctgataga cacatctggc acaccagctc gcaaagtcac cgtgagggtc ttgtgtttgc   660
tgagtcaaaa ttccttgaaa tccaagtcct tagagactcc tgctcccaaa tttacagtca   720
tagacttctt catggctgtc tcctttatcc acagaatgat tcctttgctt cattgcccca   780
tccatctgat cctcctcatc agtgcagcac agggcccatg agcagtagct gcagagtctc   840
acataggtct ggcactgcct ctgacatgtc cgaccttagg caaatgcttg actcttctga   900
gctcagtctt gtcatggcaa aataaagata ataatagtgt ttttttatgg agttagcgtg   960
aggatggaaa acaatagcaa aattgattag actataaaag gtctcaacaa atagtagtag  1020
attttatcat ccattaatcc ttccctctcc tctcttactc atcccatcac gtatgcctct  1080
taattttccc ttacctataa taagagttat tcctcttatt atattcttct tatagtgatt  1140
ctggatatta aagtgggaat gaggggcagg ccactaacga agaagatgtt tctcaaagaa  1200
gccattctcc ccacatagat catctcagca gggttcagga agataaagga ggatcaaggt  1260
cgaaggtagg aactaaggaa gaacactggg caagtggatc c                      1301

SEQ ID NO: 6              moltype = DNA   length = 1065
FEATURE                  Location/Qualifiers
misc_feature             1..1065
                         note = Description of Artificial Sequence: Synthetic
                         polynucleotide
source                   1..1065
                         mol_type = other DNA
                         organism = synthetic construct
SEQUENCE: 6
tgagcccctt ttcctctaac tgaaagaagg aaaaaaaaa tggaacccaa aatattctac     60
atagtttcca tgtcacagcc agggctgggc agtctcctgt tatttctttt aaaataaata   120
tatcatttaa atgcataaat aagcaaaccc tgctcgggaa tgggagggag agtctctgga   180
gtccacccct tctcggccct ggctctgcag atagtgctat caaagccctg acagagccct   240
gccattgct gggccttgga gtgagtcagc ctagtagaga ggggcaa gccatctcat      300
agctgctgag tgggagagag aaaagggctc attgtctata aactcaggtc atggctattc   360
ttattctcac actaagaaaa agaatgagat gtctacatat accctgcgtc ccctcttgtg   420
tactggggcc cccaagagct ctctaaaagt gatggcaaag tcattgcgct agatgccatc   480
ccatctatta taaacctgca tttgtctcca cacaccagtc atggacaata accctcctcc   540
caggtccacg tgcttgtctt tgtataatac tcaagtaatt tcggaaaatg tattctttca   600
atcttgttct gttattcctg tttcaatggc ttagtagaaa aagtacatac ttgtttttccc   660
ataaattgac aatagacaat ttcacatcaa tgtctatatg ggtcgttgtg tttgctgtgt   720
ttgcaaaaac tcacaataac tttatattgt tactactcta agaaagttac aacatggtga   780
atacaagaga aagctattac aagtccagaa aataaaagtt atcatcttga ggcctcagct   840
ttctaggaat aatatcaata ttacaaaatt taatctaaca attatgaaca gcaatgagat   900
aatatgtaca aagtacccag acctatgtgg tagagcatca aggaagcgca ttgcggagca   960
gtttttgtt tgtttgtttt tgtattctgt ttcgtgaggc aaggtttcac tctgctgtcc  1020
aggctggagt gcagtggcaa gatcatgtct cactgcagcc ttgac                  1065

SEQ ID NO: 7              moltype = DNA   length = 1065
FEATURE                  Location/Qualifiers
misc_feature             1..1065
                         note = Description of Artificial Sequence: Synthetic
                         polynucleotide
source                   1..1065
                         mol_type = other DNA
                         organism = synthetic construct
SEQUENCE: 7
tgagcccctt ttcctctaac tgaaagaagg aaaaaaaaa tggaacccaa aatattctac     60
atagtttcca tgtcacagcc agggctgggc agtctcctgt tatttctttt aaaataaata   120
tatcattaaa tgcataaata agcaaaccct gctcgggaat gggagggaga gtctctggag   180
tccacccctt ctcggccctg gctctgcaga tagtgctatc aaagccctga cagagccctg   240
cccattgctg ggccttggag tgagtcagcc tagtagagag gcaggcaag ccatctcata    300
gctgctgagt gggagagaga aaagggctca ttgtctataa actcaggtca tggctattct   360
tattctcaca ctaagaaaaa gaatgagatg tctacatata ccctgcgtcc cctcttgtgt   420
actggggccc ccaagagctc tctaaaagt atggcaaagt cattgcgcta gatgccatcc    480
catctattat aaacctgcat ttgtctccac acaccagtca tggacaataa ccctcctccc   540
aggtccacgt gcttgtcttt gtataatact caagtaattc ggaaaatgt attctttcaa    600
tcttgttctg ttattcctgt ttcaatggct tagtagaaa agtacatact tgtttttcca    660
taaattgaca atagacaatt cacatcaat gtctatatgg gtcgttgtgt ttgctgtgtt    720
tgcaaaaact cacaataact ttatattgtt actactctaa gaaagttaca acatggtgaa   780
tacaagagaa agctattaca agtccagaaa ataaaagtta tcatcttgag gcctcagctt   840
tctaggaata atatcaatat tacaaaatta atctaacaat tatgaacagc aatgagataa   900
tatgtacaaa gtacccagac ctatgtggta gagcatcaag gaagcgcatt gcggagcagt   960
ttttgtttg tttgttttt tattctgttt cgtgaggcaa ggtttcactc tgctgtccag   1020
gctggagtgc agtggcaaga tcatgtctca ctgcagcctt gacac                  1065

SEQ ID NO: 8              moltype = DNA   length = 446
FEATURE                  Location/Qualifiers
misc_feature             1..446
                         note = Description of Artificial Sequence: Synthetic
                         polynucleotide
source                   1..446
                         mol_type = other DNA
```

-continued

```
                         organism = synthetic construct
SEQUENCE: 8
tggaacccaa aatattctac atagtttcca tgtcacagcc agggctgggc agtctcctgt    60
tatttctttt aaaataaata tatcatttaa atgcataaat aagcaaaccc tgctcgggaa   120
tgggaggggag agtctctgga gtccacccct tctcggccct ggctctgcag atagtgctat   180
caaagccctg acagagccct gcccattgct gggccttgga gtgagtcagc ctagtagaga   240
ggcagggcaa gccatctcat agctgctgag tgggagagag aaaagggctc attgtctata   300
aactcaggtc atggctattc ttattctcac actaagaaaa agaatgagat gtctacatat   360
accctgcgtc ccctcttgtg tactggggtc cccaagagct ctctaaaagt gatggcaaag   420
tcattgcgct agatgccatc ccatct                                       446

SEQ ID NO: 9            moltype = DNA  length = 860
FEATURE                 Location/Qualifiers
misc_feature            1..860
                        note = Description of Artificial Sequence: Synthetic
                        polynucleotide
source                  1..860
                        mol_type = other DNA
                        organism = synthetic construct
SEQUENCE: 9
gtatatgtgt atatatatat atatatattc aggaaataat atattctaga atatgtcaca    60
ttctgtctca ggcatccatt ttctttatga tgccgtttga ggtggagttt tagtcaggtg   120
gtcagcttct cctttttttt gccatctgcc ctgtaagcat cctgctgggg acccagatag   180
gagtcatcac tctaggctga gaacatctgg gcacacaccc taagcctcag catgactcat   240
catgactcag cattgctgtg cttgagccag aaggtttgct tagaaggtta cacagaacca   300
gaaggcgggg gtggggcact gacccccgaca ggggcctggc cagaactgct catgcttgga   360
ctatgggagg tcactaatgg agacacacag aaatgtaaca ggaactaagg aaaaactgaa   420
gcttatttaa tcagagatga gatgctggaa gggatagagg gagctgagct tgtaaaaagt   480
atagtaatca ttcagcaaat ggttttgaag cacctgctgg atgctaaaca ctattttcag   540
tgcttgaatc ataaataaga ataaaacatg tatcttattc cccacaagag tccaagtaaa   600
aaataacagt taattataat gtgctctgtc ccccaggctg gagtgcagtg gcacgatctc   660
agctcactgc aacctccgcc tcccgggttc aagcaattct cctgcctcag ccaccctaat   720
agctgggatt acaggtgcac accaccatgc caggctaatt tttgtacttt ttgtagaggc   780
agggtatcac catgttgtcc aagatggtct tgaactcctg agctccaagc agtccaccca   840
cctcagcctc ccaaagtgct                                              860

SEQ ID NO: 10           moltype = DNA  length = 613
FEATURE                 Location/Qualifiers
source                  1..613
                        mol_type = genomic DNA
                        organism = Homo sapiens
SEQUENCE: 10
aagcaataga tggctctgcc ctgactttta tgcccagccc tggctcctgc cctccctgct    60
cctgggagta gattggccaa ccctagggtg tggctccaca gggtgaggtc taagtgatga   120
cagccgtacc tgtccttggc tcttctggca ctggcttagg agttggactt caaaccctca   180
gccctccctc taagatatat ctcttggccc cataccatca gtacaaattg ctactaaaaa   240
catcctcctt tgcaagtgta tttacgtaat atttggaatc acagcttggt aagcatattg   300
aagatcgttt tcccaatttt cttattacac aaataagaaa ttgatgcact aaaagtggaa   360
gagttttgtc taccataatt cagctttggg atatgtagat ggatctcttc ctgcgtctcc   420
agaatatgca aaatacttac aggacagaat ggatgaaaac tctacctcag ttctaagcat   480
atcttctcct tatttggatt aaaaccttct ggtaagaaaa gaaaaaaaat atatatatat   540
atgtgtatat atacacacat acatatacat atatatgcat tcatttgttg ttgtttttct   600
taatttgctc atg                                                     613

SEQ ID NO: 11           moltype = DNA  length = 265
FEATURE                 Location/Qualifiers
source                  1..265
                        mol_type = genomic DNA
                        organism = Homo sapiens
SEQUENCE: 11
aagcaataga tggctctgcc ctgactttta tgcccagccc tggctcctgc cctccctgct    60
cctgggagta gattggccaa ccctagggtg tggctccaca gggtgaggtc taagtgatga   120
cagccgtacc tgtccttggc tcttctggca ctggcttagg agttggactt caaaccctca   180
gccctccctc taagatatat ctcttggccc cataccatca gtacaaattg ctactaaaaa   240
catcctcctt tgcaagtgta tttac                                        265

SEQ ID NO: 12           moltype = DNA  length = 879
FEATURE                 Location/Qualifiers
source                  1..879
                        mol_type = genomic DNA
                        organism = Homo sapiens
SEQUENCE: 12
taggtattga ataagaaaaa tgaagttaag gtggttgatg gtaacactat gctaataact    60
gcagagccag aagcaccata agggacatga taagggagcc agcagacctc tgatctcttc   120
ctgaatgcta atcttaaaca tcctgaggaa gaatgggact tccatttggg gtgggcctat   180
gataggtaa taagacagta gtgaatatca agctacaaaa agcccccttt caaattcttc   240
tcagtcctaa cttttcatac taagcccagt ccttccaaag cagactgtga aagagtgata   300
gttccgggag actagcactg cagattccgg gtcactgtga gtgggggagg cagggaagaa   360
gggctcacag gacagtcaaa ccatgccccc tgttttttcct tcttcaagta gacctctata   420
```

```
agacaacaga gacaactaag gctgagtggc caggcgagga gaaaccatct cgccgtaaaa   480
catggaagga acacttcagg ggaaaggtgg tatctctaag caagagaact gagtggagtc   540
aaggctgaga gatgcaggat aagcaaatgg gtagtgaaaa gacattcatg aggacagcta   600
aaacaataag taatgtaaaa tacagcatag caaaacttta acctccaaat caagcctcta   660
cttgaatcct tttctgaggg atgaataagg cataggcatc aggggctgtt gccaatgtgc   720
attagctgtt tgcagcctca ccttctttca tggagtttaa gatatagtgt attttcccaa   780
ggtttgaact agctcttcat ttcttttatgt tttaaatgca ctgacctccc acattccctt   840
tttagtaaaa tattcagaaa taatttaaat acatcattg                          879

SEQ ID NO: 13              moltype = DNA   length = 152
FEATURE                    Location/Qualifiers
misc_feature               1..152
                           note = Description of Artificial Sequence: Synthetic
                            polynucleotide
source                     1..152
                           mol_type = other DNA
                           organism = synthetic construct
SEQUENCE: 13
tctcccacgc cctggtctca gcttgggggag tggtcagacc ccaatggcga taaactctgg   60
caactttatc tgtgcactgc aggctcagcc ccaacagctt tagctttcac aagcaggcag   120
gggaagggaa acacatatct ccagatatga gg                                 152

SEQ ID NO: 14              moltype = DNA   length = 157
FEATURE                    Location/Qualifiers
misc_feature               1..157
                           note = Description of Artificial Sequence: Synthetic
                            polynucleotide
source                     1..157
                           mol_type = other DNA
                           organism = synthetic construct
SEQUENCE: 14
ctaaacccct ccccccacccct agccccaagc ttcatcttag ctccactcct gaccctatcc   60
agctaaaggt ccccacccag ctcctgccta tctagtcatt gcatatggca agacttgaaa   120
gtcctatctc aaagcagcag aattatcagc tacgact                            157

SEQ ID NO: 15              moltype = DNA   length = 141
FEATURE                    Location/Qualifiers
misc_feature               1..141
                           note = Description of Artificial Sequence: Synthetic
                            polynucleotide
source                     1..141
                           mol_type = other DNA
                           organism = synthetic construct
SEQUENCE: 15
ccatccccca gcactccctg cccccacagc ccagacttga ccaactccca gctccgcctg   60
ggacttccag atatggggcc ccaccctttgc aggccttggg gacgctgaag atattgacta   120
tctgcgtgcc ggaaaagggt g                                             141

SEQ ID NO: 16              moltype = DNA   length = 171
FEATURE                    Location/Qualifiers
misc_feature               1..171
                           note = Description of Artificial Sequence: Synthetic
                            polynucleotide
source                     1..171
                           mol_type = other DNA
                           organism = synthetic construct
SEQUENCE: 16
aaaggctggg ggtgggagta gcggatttga agcacttgtt ggcctacaga ggtgtggcaa   60
gcagagcacc tcagaactca ggcgtactgc ccgccgcccg agccctgcga gggccgatag   120
cgagggtgtg gcccttatct gcacccagca gagcgccggc ggggtacggt c            171

SEQ ID NO: 17              moltype = DNA   length = 195
FEATURE                    Location/Qualifiers
misc_feature               1..195
                           note = Description of Artificial Sequence: Synthetic
                            polynucleotide
source                     1..195
                           mol_type = other DNA
                           organism = synthetic construct
SEQUENCE: 17
cagttgcctc agctgagtat gtcttctaaa gataatgtcg attgtgtatg gctgatggga   60
ttctaggacc aagcaagagg ttttttttttt tccccacat acttaacgtt tctatatttc   120
tatttgaatt cgactggaca gttccatttg aattatttct ctctctctct ctctctgaca   180
cattttatct tgcca                                                    195

SEQ ID NO: 18              moltype = DNA   length = 14
FEATURE                    Location/Qualifiers
misc_feature               1..14
                           note = Description of Artificial Sequence: Synthetic
```

```
                            oligonucleotide
source                      1..14
                            mol_type = other DNA
                            organism = synthetic construct
SEQUENCE: 18
caccaggtgg cgct                                                        14

SEQ ID NO: 19              moltype = DNA   length = 81706
FEATURE                    Location/Qualifiers
source                     1..81706
                           mol_type = genomic DNA
                           organism = Homo sapiens
SEQUENCE: 19
ggatcctcac atgagttcag tatataattg taacagaata aaaaatcaat tatgtgttattca   60
agttgctagt gtcttaagag gttcacattt ttatctaact gattatcaca aaaatacttc   120
gagttacttt tcattataat tcctgactac acatgaagag actgacacgt aggtgcctta   180
cttaggtagg ttaagtaatt tatccaaaac cacacaatgt agaacctaag ctgattcggc   240
catagaaaca caatatgtgg tataaatgag acagagggat ttctctcctt cctatgctgt   300
cagatgaata ctgagataga atatttagtt catctatcac acattaaacg ggactttaca   360
tttctgtctg ttgaagattt gggtgtgggg ataactcaag gtatcatatc caagggatgg   420
atgaaggcag gtgactctaa cagaaaggga aaggatgttg gcaaggctat gttcatgaaa   480
gtatatgtaa aatccacatt aagcttcttt ctgcatgcat tggcaatgtt tatgaataat   540
gtgtatgtaa aagtgtgctg tatattcaaa agtgtttcat gtgcctaggg gtgtcaaata   600
ctttgagttt gtaagtatat acttctctgt aatgtgtctg aatatctcta tttacttgat   660
tctcaataag taggtatcat agtgaacatc tgacaaatgt ttgaggaaca atttagtgtt   720
tacctattca ccaaaattta ttaaatgcct aatctgtcat agatatacaa ttatctggcg   780
aaatctgtaa ttcctaattt aaacagctgt gtagcctaat tagggataaa ggcatgcaaa   840
cccataattt gtgtaggttg aaatgagcta tagaaaaatg cagtatattt atcagaagtc   900
tttagggtca tgaaaaggaa tggtcaactg acactgccag ggactcatat gtaagagata   960
actaatgtga agtgacttta aaggagaaat tagcagaagt tttctttcca tgtctcctca   1020
tcatgttaca ataacggaag agattaaaac aacaaataca tttagacagc aatgtttatc   1080
ctggttagat gttttaatct aaatctatct tggagtgtta aaatgcattt gctcacctac   1140
tttaaaatat aaatgaaggt aggaacctgt agatacaaaa agttggagaa aaaaagacaa   1200
taaagatgac aaaaatctat taatccttga tagaaaatga gagagaataa aacactggtt   1260
tacataaaga aaataagatg gatagatagc agatccttat aaaagtgata atttgagaaa   1320
aaaaatactc catattctga gtttcttcac ataaaataat acaaatctgc tgtggtaagt   1380
tacaaagaga tagatttttt atcattatat aaaagatatt ttaaacagag ttatacaaca   1440
aaggaacaga ctatgtcata tattctcact tatcactata aacatctcag aaaaatctgc   1500
aaaatcattt catagcattt taaatagtta ggaataatgt agaaaactga aacagttcta   1560
agtttcccac aaacttagag tctcaaatgt tgcattacct aacttacctg caaatatttt   1620
atacaaattt gcacatgcta ctctagtcaa aaatatatgt acattatggg tattttctgt   1680
gtgtaacttg gttctagttg cttctttcag aaatagcctc tatttttgat ttacctgata   1740
aaatcacatt cctctccaaa gccttctaaa tacttccaga ctaactactt tttagtacat   1800
ctaagaagaa aagagttttg tctcttatcc acctctgagt caaaaagcag catgtccatc   1860
aattggtaca tagttcccac agccccactt agctctggat tggagttcta cttggcattg   1920
tttgcaacta catggacgta aaatgcatgg attctcttga aaaaatgttt ctgccatgat   1980
gttctctgaa agagactaac cttccctcgc tttgcagaga aagactcgtg taatccttga   2040
caatgtcatc tcatctattt attcccatgt ctacccatat gtgaccttca tgtctttgct   2100
ctaagcccct acatcctcaa tctacacact aggatagtat aaaagtaata gtaataaatag   2160
tagtaatagt aataacaata caatgattat ggcttatact atacacaaga cactgttgat   2220
atattatttc atttagtatt cacagtaact ctgtgcctca agtactattg taataccctt   2280
taagaggagg aaactgaggc acagggccct aaagtaatat tccaagatga agtggctact   2340
aactgacaga gggcataatt caactcatga tatttggctc tagaatacat gctctgaatc   2400
attatacaat aataattcat gaggaaacat ttttaaagc ctaagttatt tgctctgaaa   2460
taagacataa tttgggggtga gaaagcttag attccatgaa gtattacagc atttggtagt   2520
cttttttgcac tccaggtctt attttttactg cttaaacata ataaaacata tggttcagta   2580
tgcctttgat tttacaataa tattcctgtt attttggaa gcacagggtg tgggataatg   2640
ctaattacta gtgattagta ttgagaggtg acagcgtgct ggcagtcctc acagccctcg   2700
ctcgctcttg gcgcctcctc tgcctgggct cccacattgg tggcacttga ggagccttc   2760
agccggccgc tgcactggg gagcccttt ctgggctgac caaggccaga gccggctccc   2820
tcagcttgcc aggaggtgtg gagggacaga cgcgggcagg aaccgggctg tgcgccgtgc   2880
ttgagggagt tccgggtggg catgggctcc gaggaccccg cactcggagc cgccagccgg   2940
ccccaccggc cgcgggcagt gaggggctta gcacctgggc cagcagctgc tgtgctcaat   3000
tcctcgccgg gccttagctg ccttcctgcg gggcagggct aggccctgc agcgcgccat   3060
gcctgagcct ccccaccttc atgggctcct gtgcggcccg agcctcgccg acgagcgccg   3120
ccccctgctc cagggcaccc agtcccatcg accacccaag ggctgaagag tgcgggcgca   3180
cggcagggga ctggcaggca gctccccctg cagcccaggt gcgggatcca ctgggtgaag   3240
ccggctaggc tcctgagttt gctggggatg cgaagaaccc ttatgtctag ataagggatt   3300
gtaaatacac caattggcac tctgtatcta gctcaaggtt tgtaaacaca ccaatcagca   3360
ccctgtgtct agctcagggt ttgtgaatgc accaatcaac actctatcta gctactctgg   3420
tggggccttg gagaacccttt atgtctagct caggggattgt aaatacacca atcggcagtc   3480
tgtatctagc tcaaggtttg taaacacacc aatcagcacc ctgtgtctag ctcagggttt   3540
gtgaatgcac caatcaacac tctgtatcta gctactctgg tggggacgtg gagaaccttt   3600
atgtctagct caggggattgt aaatacacca ctcggcagtc tgtatctagc tcaaggtttg   3660
taaacacacc aatcagcacc ctgtgtctag ctcagggttt gtgaatgcac caatcaacac   3720
tctgtatcta gctactctgg tggggacttg gagaaccttt gtgtggacac tctgtatcta   3780
gctaatctgg tggggacgtg gagaaccttt gtgtctagct catggattgt aaatgcacca   3840
atcagtgccc tgtcaaaaca gaccactggg ctctaccaat cagcaggatg tgggtgggc   3900
cagataagag aataaaagca ggctgcccga gccagcagtg gcaacccgct cgggtcccct   3960
```

-continued

```
tccacactgt ggaagctttg ttctttcgct ctttgcaata aatcttgctc ctgctcactg   4020
tttgggtcta cactgccttt atgagctgta acgctcaccg cgaaggtctg cagcttcact   4080
cttgaagcca gcgagaccac gaacccaccg ggaggaacga acaactccag aggcgccgcc   4140
ttaagagctg gaacgttcac tgtgaaggtc tgcagcttca ctcctgagcc agcgagacca   4200
cgaacccatc agaaggaaga aactccgaac acatccaaat atcagaacga acaaactcca   4260
cacacgcagc ctttaagaac tgtaacactc accacgaggg tccccggctt cattcttgaa   4320
gtcagtgaaa ccaagaaccc accaattccg gacacagtat gtcagaaaca atatgagtca   4380
ctaaatcaat atacttctca acaatttcca acagcccttg caattaactt ggccatgtga   4440
ctggttgtga ctaaaataat gtggagataa taatgtgtta ctccctaagg cagagtgccc   4500
ttctatcatt ctctttccct tcctctatgt ggcagaaagt aaaagattct gaaatgataa   4560
agtcaatcac aggaaggcac ctggactcct ggcccactgc ttggaggaga gcactcagga   4620
ccatgaacat ctgactgtga cgtagcaata aagaaaccca cgtttcatat gaaactgctt   4680
aaaattaatg gcacaagtca tgtttttgat gttgcacatt tgtctcttatt tgtggcttgt   4740
tttgcttcca catcaatcca ctcaaggcct acattctgct ataatgcaat ttcaagttct   4800
ttacaggccg agaaaaatga atctgaattc ctgacctcca aaagtgatca agatattttt   4860
agttcaggct ccaaaatttt ctcattttca taggttttcc tcgattgatc attattcatg   4920
atttgcaagg aatcattcaa tgtttttctaa atctattact gcatcctgac acatatgaca   4980
tttaactat gttccagatt tttgaatgaa gagtgtaaat tttaaatgtt ttcaccacaa   5040
aaaataagta tgtgaagtgg tggatttgtt aattagcctt atttaaccat ttaatattgt   5100
acacgtacac caaagcatca tgttgtaccc catgaataca cacaattatt atttgtcaat   5160
ttaaaatgaa ataataaaaa ataacaaagg cattagcctc tgcattgcct ttaccggtca   5220
tcctcacggt gactaacgca aaaaacgttc tatttcatcc ttacaaacat ccctatcttt   5280
gatgcctctt tgtctagatc tctatccct cctgtttct ctacgttatt tatatgggta   5340
tcatcaccat cctggacaac atcaggacag atatccctca ccaagccaat gttcctctct   5400
atgttggctc aaatgtcctt gaactttcct ttcaccaccc tttccacagt caaaaggata   5460
ttgtagttta atgcctcaga gttcagcttt taagcttcag acaaattatt cttcctcttt   5520
aggttctcct ttatggaatc ttctgtactg atggccatgt cctttaacta ctatgtagat   5580
atctgctact acctgtatta tgcctctacc tttattagca gagttatctg tactgttggc   5640
atgacaatca tttgttaata tgacttgcct ttcctttttc tgctattctt gatcaaatgg   5700
ctcctctttc ttgctcctct catttctcct gccttcactt ggacgtgctt cacgtagtct   5760
gtgcttatga ctggattaaa aattgatatg gacttatcct aatgttgttc gtcataatat   5820
gggtttatg gtccattatt atttcctatg cattgatctg gagaaggctt caatccttt   5880
actctttgtg gaaaatatct gtaaaccttc tggttcactc tgctatagca atttcagttt   5940
aggctagtaa gcatgaggat gcctccttct ctgattttc ccacagtctg ttggtcacag   6000
aataacctga gtgattactg atgaaagagt gagaatgtta ttgatagtca caatgacaaa   6060
aaacaaacaa ctacagtcaa aatgtttctc tttttattag tggattatat ttcctgacct   6120
atatctggca ggactcttta gagaggtagc tgaagctgct gttatgacca ctagagggaa   6180
gaagatacct gtggagctaa tggtccaaga tggtggagcc ccaagcaagg aagttgttaa   6240
ggagcccttt tgattgaagg tgggtgcccc caccttacag ggacaggaca tctggatact   6300
cctcccagtt tctccagttt cccttttttcc taatatatct cctgataaaa tgtctatact   6360
cacttcccca tttctaataa taaagcaaag gctagttagt aagacatcac cttgcatttt   6420
gaaaatgcca tagactttca aaattatttc atacatcggt ctttctttat ttcaagagtc   6480
cagaaatggc aacattacct ttgattcaat gtaatggaaa gagctcttc aagagacaga   6540
gaaaagaata atttaatttc tttccccaca cctccttccc tgtctcttac cctatcttcc   6600
ttccttctac cctccccatt tctctctctc attctctcaga agtatatttt gaaaggattc   6660
atagcagaca gctaaggctg gttttttcta agtgaagaag tgatattgag aaggtagggt   6720
tgcatgagcc ctttcagttt tttagtttat atacatctgt attgttagaa tgtttttataa   6780
tataaataaa attatttctc agttatatac tagctatgta acctgtggat atttccttaa   6840
gtattacaag ctatacttaa ctcacttgga aaactcaaat aaatacctgc ttcatagtta   6900
ttaataagga ttaagtgaga taatgcccat aagattccta ttaataacag ataaatacat   6960
acacacacac acacattgaa aggattctta ctttgtgcta ggaactataa taagttcatt   7020
gatgcattat atcattaagt tctaatttca acactagaag gcaggtatta tctaaatttc   7080
atactggata cctccaaact cataaagata attaaattgc cttttgtcat atatttattc   7140
aaaagggtaa actcaaacta tggcttgtct aattttatat atcaccctac tgaacatgac   7200
cctattgtga tattttataa aattattctc aagttattat gaggatgttg aaagacagag   7260
aggatggggt gctatgcccc aaatcagcct cacaattaag ctaagcagct aagagtcttg   7320
cagggtagtg tagggaccac agggttaagg gggcagtaga attatactcc cactttagtt   7380
tcatttcaaa caatccatac acacacagcc ctgagcactt acaaattata ctacgctcta   7440
tacttttgt ttaaatgtat aaataagtgg atgaaagaat agatagatag atagacagat   7500
agatgataga tagaataaat gcttgccttc atagctgtct ccctaccttg ttcaaaatgt   7560
tcctgtccag accaaagtac cttgccttca cttaagtaat caattcctag gttatattct   7620
gatgtcaaag gaagtcaaaa gatgtgaaaa acaatttctg acccacaact catgctttgt   7680
agatgactag atcaaaaaat ttcagccata tcttaacagt gagtgaacag gaaatctcct   7740
ctttttcccta catctgagat cccagcttct aagaccttca attctcactc ttgatgcaac   7800
agaccttgga agcatacagg agagctgaac ttggtcaaca aaggagaaaa gtttgttggc   7860
ctccaaaggc acagctcaaa cttttcaagc cttctctaat cttaaaggta aacaagggtc   7920
tcatttcttt gagaacttca gggaaaatag acaaggactt gcctggtgct tttggtaggg   7980
gagcttgcac tttcccccctt tctggaggaa atatttatcc ccaggtagtt ccctttttgc   8040
accagtggtt ctttgaagag acttccacct gggaacagtt aaacagcaac tacagggcct   8100
tgaactgcac actttcagtc cggtcctcac agttgaaaag acctaagctt gtgcctgatt   8160
taagcctttt tggtcataaa acattgaatt ctaatctccc tctcaaccct acagtcaccc   8220
atttggtata ttaaagatgt gttgtctact gtctagtatc cctcaagtag tgtcaggaat   8280
tagtcattta aatagtctgc aagccaggag tggtggctca tgtctgtaat tccagcactt   8340
gagaggtaga agtgggagga ctgcttgagc tcaagagttt gatattatcc tggacaacat   8400
agcaagacct cgtctctact taaaaaaaaa aaaaaaatta gccaggcatg tgatgtacac   8460
ctgtagtccc agctactcag gaggccgaaa tgggaggatc ccttgagctc aggaggtcaa   8520
ggctgcagtga agacatgatc ttgccactgc actccagcct ggacagcaga gtgaaacctt   8580
gcctcacgaa acagaataca aaaacaaaca aacaaaaaac tgctccgcaa tgcgcttcct   8640
tgatgctcta ccacataggt ctgggtactt tgtacacatt atctcattgc tgttcataat   8700
```

-continued

```
tgttagatta attttgtaat attgatatta ttcctagaaa gctgaggcct caagatgata  8760
acttttattt tctggacttg taatagcttt ctcttgtatt caccatgttg taactttctt  8820
agagtagtaa caatataaag ttattgtgag tttttgcaaa cacagcaaac acaacgaccc  8880
atatagacat tgatgtgaaa ttgtctattg tcaatttatg ggaaaacaag tatgtacttt  8940
ttctactaag ccattgaaac aggaataaca gaacaagatt gaaagaatac attttccgaa  9000
attacttgag tattatacaa agacaagcac gtggacctgg gaggagggtt attgtccatg  9060
actggtgtgt ggagacaaat gcaggtttat aatagatggg atggcatcta gcgcaatgac  9120
tttgccatca cttttagaga gctcttgggg accccagtac acaagagggg acgcagggta  9180
tatgtagaca tctcattctt tttcttagtg tgagaataag aatagccatg acctgagttt  9240
atagacaatg agccctttc tctctcccac tcagcagcta tgagatggct tgccctgcct  9300
ctctactagg ctgactcact ccaaggccca gcaatgggca gggctctgtc agggctttga  9360
tagcactatc tgcagagcca gggccgagaa ggggtggact ccagagactc tccctcccat  9420
tcccgagcag ggtttgctta tttatgcatt taaatgatat atttatttta aaagaaataa  9480
caggagactg cccagccctg gctgtgacat ggaaactatg tagaatattt tgggttccat  9540
ttttttttcc ttctttcagt tagaggaaaa ggggctcact gcacatacac tagacagaaa  9600
gtcaggagct ttgaatccaa gcctgatcat ttccatgtca tactgagaaa gtccccaccc  9660
ttctctgagc ctcagtttct ctttttataa gtaggagtct ggagtaaatg atttccaatg  9720
gctctcattt caatacaaaa tttccgttta ttaaatgcat gagcttctgt tactccaaga  9780
ctgagaagga aattgaacct gagactcatt gactggcaag atgtccccag aggctctcat  9840
tcagcaataa aattctcacc ttcacccagg cccactgagt gtcagatttg catgcactag  9900
ttcacgtgtg taaaaaggag gatgcttctt tcctttgtat tctcacatac ctttaggaaa  9960
gaacttagca cccttcccac acagccatcc caataactca tttcagtgac tcaacccttg  10020
actttataaa agtcttgggc agtatagagc agagattaag agtacagatg ctggagccag  10080
accacctgag tgattagtga ctcagtttct cttagtagtt gtatgactca gtttcttcat  10140
ctgtaaaatg gagggttttt taattagttt gtttttgaga aagggtctca ctctgtcacc  10200
caaatgggag tgtagtggca aaatctcggc tcactgcaac ttgcacttcc caggctcaag  10260
cggtcctccc acctcaacat cctgagtagc tggaaccaca ggtacacacc accataccta  10320
gctaattttt tgtattttg gtagagatgg ggtttcacat gttacacagg atggtctcag  10380
actccgagc tcaagcaatc tgcccacctc agccttccaa agtgctggga ttataagcat  10440
gattacagga gttttaacag gctcataaga ttgttctgca gcccgagtga gttaatacat  10500
gcaaagagtt taaagcagtg acttataaat gctaactact ctagaaatgt ttgctagtat  10560
tttttgttta actgcaatca ttcttgctgc aggtgaaaac tagtgttctg tactttatgc  10620
ccattcatct ttaactgtaa taataaaaat aactgacatt tattgaaggc tatcagagac  10680
tgtaattagt gctttgcata attaatcata tttaatactc ttggattctt tcaggtagat  10740
actattatta tccccatttt actacagtta aaaaaactac ctctcaactt gctcaagcat  10800
acactctcac acacacaaac ataaactact agcaaatagt agaattgaga tttggtccta  10860
attatgtctt tgctcactat ccaataaata tttattgaca tgtacttctt ggcagtctgt  10920
atgctggatg ctggggatac aaagatgttt aaatttaagc tccagtctct gcttccaaag  10980
gcctcccagg ccaagttatc cattcagaaa gcatttttta ctctttgcat tccactgttt  11040
ttcctaagtg actaaaaaat tacacttat tcgtctgtgt cctgctctgg gatgatagtc  11100
tgactttcct aacctgagcc taacatccct gacatcagga aagactacac catgtggaga  11160
aggggtggtg gtttttgattg ctgctgtctt cagttagatg gttaactttg tgaagttgaa  11220
aactgtggct ctctggttga ctgttagagt tctggcactt gtcactatgc ctattattta  11280
acaaatgcat gaatgcttca gaatatggga atattatctt ctggaatagg gaatcaagtt  11340
atattatgta acccaggatt agaagattct tctgtgtgta agaatttcat aaacattaag  11400
ctgtctagca aaagcaaggg cttggaaaat ctgtgagctc ctcaccatat agaaagcttt  11460
taacccatca ttgaataaat ccctatagg gatttctacc ctgagcaaaa ggctggtctt  11520
gattaattcc caaactcata tagctctgag aaagtctatg ctgttaacgt tttcttgtct  11580
gctaccccat catatgcaca acaatataatg caggcctagg catgactgaa ggctctctca  11640
taattcttgg ttgcatgaat cagattatca acagaaatgt tgagacaaac tatgggggaag  11700
cagggtatga aagagctctg aatgaaatgg aaaccgcaat gcttcctgcc cattcagggc  11760
tccagcatgt agaaatctgg ggctttgtga agactggctt aaaatcagaa gccccattgg  11820
ataagagtag ggaagaacct agagcctacg ctgagcaggt ttccttcatg tgacagggag  11880
cctcctgccc cgaacttcca gggatcctct cttaagtgtt tcctgctgga atctcctcac  11940
ttctatctgg aaatggtttc tccacagtcc agcccctggc tagttgaaag agttacccat  12000
gcagaggccc tcctagcatc cagagactag tgcttagatt cctactttca gcgttggaca  12060
acctggatcc acttgcccag tgttcttcct tagttcctac cttcgacctt gatcctcctt  12120
tatcttcctg aaccctgctg agatgatcta tgtgggggaga atggcttctt tgagaaacat  12180
cttcttcgtt agtggcctgc ccctcattcc cactttaata tccagaatca ctataagaag  12240
aatataataa gaggaataac tcttattata ggtaagggaa aattaagagg catacgtgat  12300
gggatgagta agagaggaga gggaaggatt aatggacgat aaaatctact actatttgtt  12360
gagacctttt atagtctaat caattttgct attgtttttcc atcctcacgc taactccata  12420
aaaaaacact attattatct ttattttgcc atgacaagac tgagctcaga agagtcaagc  12480
atttgcctaa ggtcggacat gtcagaggca gtgccagacc tatgtgagac tctgcagcta  12540
ctgctcatgg gccctgtgct gcactgatga ggaggatcag atggatgggg caatgaagca  12600
aaggaatcat tctgtggata aaggagacag ccatgaagaa gtctatgact gtaaatttgg  12660
gagcaggagt ctctaaggac ttggatttca aggaattttg actcagcaaa cacaagaccc  12720
tcacggtgac tttgcgagct ggtgtgccag atgtgtctat cagaggttcc agggagggtg  12780
gggtgggtc agggctggcc accagctatc agggcccaga tgggttatag gctggcaggc  12840
tcagataggc ggttaggtca ggttggtggt gctgggtgga gtccatgact cccaggagcc  12900
aggagagata gaccatgagt agagggcaga catgggaaag gtgggggagg cacagcatag  12960
cagcattttt cattctacta ctacatggga ctgctcccct ataccccag ctaggggcaa  13020
gtgccttgac tcctatgttt tcaggatcat catctataaa gtaagagtaa taattgtgtc  13080
tatctcatag ggttattatg aggatcaaag gagatgcaca ctctctggac cagtggccta  13140
acagttcagg acagagctat gggcttccta tgtatgggtc agtggtctca atgtagcagg  13200
caagttccag aagatagcat caaccactgt tagagatata ctgccagtct cagagcctga  13260
tgttaattta gcaatgggct gggaccctcc tccagtagaa ccttctaacc agctgctgca  13320
gtcaaagtcg aatgcagctg gttagacttt ttttaatgaa agcttagctt tcattaaaga  13380
ttaagctcct aagcagggca cagatgaaat tgtctaacag caactttgcc atctaaaaaa  13440
```

-continued

```
atctgacttc actggaaaca tggaagccca aggttctgaa catgagaaat tttttaggaat   13500
ctgcacagga gttgagaggg aaacaagatg gtgaagggac tagaaaccac atgagagaca   13560
cgaggaaata gtgtagattt aggctggagg taaatgaaag agaagtggga attaatactt   13620
actgaaatct ttctatatgt caggtgccat tttatgatat ttaataatct cattacatat   13680
ggtaattctg tgagatatgt attattgaac atactataat taatactaat gataagtaac   13740
acctcttgag tacttagtat atgctagaat caaatttaag tttatcatat gaggccgggc   13800
acggtggctc atatatggga ttacatgcct gtaatcccag cactttggga ggccaaggca   13860
attggatcac ctgaggtcag gagttccaga ccagcctggc caacatggtg aaaccccttc   13920
tctactaaaa aatacaaaaa atcagccagg tgtggtggca cgcgtctata atcccagcta   13980
ctcaggaggc tgaggcagga gaatcacttg aacccaggag gtggaggttg cagtgagcta   14040
agattgcacc actgcactcc agcctaggcg acagagtgag actccatctc aaaaaaaaaa   14100
aaagaagttt attatatgaa ttaacttagt tttactcaca ccaatactca gaagtagatt   14160
attacctcat ttattgatga ggagcccaat gtacttgtag tgtagatcaa cttattgaaa   14220
gcacaagcta ataagtagac aattagtaat tagaagtcag atggtctgag ctctcctact   14280
gtctacatta catgagctct tattaactgg ggactcgaaa atcaaagaca tgaaataatt   14340
tgtccaagct tacagaacca ccaagtagta aggctaggat gtagacccag ttctgctacc   14400
tctgaagaca gtgtttttttc cacagcaaaa cacaaactca gatattgtgg atgcgagaaa   14460
ttagaagtag atattcctgc cctgtggccc ttgcttctta cttttacttc ttgtcgattg   14520
gaagttgtgg tccaagccac agttgcagac catacttcct caaccataat tgcatttctt   14580
caggaaagtt tgagggagaa aaaggtaaag aaaaatttag aaacaacttc agaataaaga   14640
gattttctct tgggttacag agattgtcat atgacaaatt ataagcagac acttgagaaa   14700
actgaaggcc catgcctgcc caaattaccc tttgacccct tggtcaagct gcaactttgg   14760
ttaaagggag tgtttatgtg ttatagtgtt catttactct tctggtctaa cccattggct   14820
ccgtcttcat cctgcagtga cctcagtgcc tcagaaacat acatatgttt gtctagttta   14880
agtttgtgtg aaattctaac tagcgtcaag aactgagggc cctaaactat gctaggaata   14940
gtgctgtggt gctgtgatag gtacacaaga aatgagaaga aactgcagat tctctgcatc   15000
tccctttgcc gggtctgaca acaaagtttc cccaaatttt accaatgcaa gccatttctc   15060
catatgctaa ctactttaaa atcatttggg gcttcacatt gtctttctca tctgtaaaaa   15120
gaatggaaga actcattcct acagaactcc ctatgtcttc cctgatgggc tagagttcct   15180
ctttctcaaa aattagccat tattgtattt ccttctaagc caaagctcag aggtcttgta   15240
ttgcccagtg acatgcacac tggtcaaaag taggctaagt agaagggtac tttcacagga   15300
acagagagca aaagaggtgg gtgaatgaga gggtaagtga gaaaagacaa atgagaagtt   15360
acaacatgat ggcttgttgt ctaaatatct cctagggaat tattgtgaga ggtctgaata   15420
gtgttgtaaa ataagctgaa tctgctgcca acattaacag tcaagaaata cctccgaata   15480
actgtacctc caattattct ttaaggtagc atgcaactgt aatagttgca tgtatatatt   15540
tatcataata ctgtaacaga aaacacttac tgaatatata ctgtgtccct agttctttac   15600
acaataaact aatctcatcc tcataattct attagctaat acatattatc atcctatatt   15660
tcagagactt caagaagtta agcaacttgc tcaagatcat ctaagaagta ggtggtattt   15720
ctgggctcat ttggcccctc ctaatctctc atggcaacat ggctgcctaa agtgttgatt   15780
gccttaattc atcagggatg ggctcatact cactgcagac cttaactggc atcctctttt   15840
cttatgtgat ctgcctgacc ctagtagact tatgaaattt ctgatgagaa aggagagagg   15900
agaaaggcag agctgactgt gatgagtgat gaaggtgcct tctcatctgg gtaccagtgg   15960
ggcctctaag actaagtcac tctgtctcac tgtgtcttag ccagttcctt acagcttgcc   16020
ctgatgggag atagagaatg ggtatcctcc aacaaaaaaa taaattttca tttctcaagg   16080
tccaacttat gtttttcttaa tttttaaaaa aatcttgacc attctccact ctctaaaata   16140
atccacagtg agagaaacat tctttttccc catcccataa ataacctctat taaatatgga   16200
aaatctgggc atggtgtctc acacctgtaa tcccagcact ttgggaggcc gaggtgggtg   16260
gactgcttgg agctcaggag ttcaagacca tcttggacaa catggtgata ccctgcctct   16320
acaaaaagta caaaaattag cctggcatgg tggtgtgcac ctgtaatccc agctattagg   16380
gtggctgagg caggagaatt gcttgaaccc gggaggcgga ggttgcagtg agctgagatc   16440
gtgccactgc actccagcct gggggacaga gcacattata attaactgtt attttttact   16500
tggactcttg tggggaataa gatacatgtt ttattcttat ttatgattca agcactgaaa   16560
atagtgttta gcatccagca ggtgcttcaa aaccatttgc tgaatgatta ctatactttt   16620
tacaagctca gctccctcta tcccttccag catcctcatc tctgattaaa taagcttcag   16680
tttttcctta gttcctgtta catttctgtg tgtctccatt agtgacctcc catagtccaa   16740
gcatgagcag ttctggccag gcccctgtcg gggtcagtgc cccacccccg ccttctggtt   16800
ctgtgtaacc ttctaagcaa accttctggc tcaagcacag caatgctgag tcatgatgag   16860
tcatgctgag gcttagggtg tgtgcccaga tgttctcagc ctagagtgat gactcctatc   16920
tgggtcccca gcaggatgct tacagggcag atggcaaaaa aaaggagaag ctgaccacct   16980
gactaaaact ccacctcaaa cggcatcata aagaaaatgg atgcctgaga cagaatgtga   17040
catattctag aatatattat ttcctgaata tatatatata tatacacata tacgtatata   17100
tatatatata tatatatttg ttgttatcaa ttgccataga atgattagtt attgtgaatc   17160
aaatatttat cttgcaggtg gcctctatac ctagaagcgg cagaatcagg ctttattaat   17220
acatgtgtat agatttttag gatctataca catgtattaa tatgaaacaa ggatatgaac   17280
gaggaaggca tgaaaacagg aaaagaaaac aaaccttgtt tgccatttta aggcacccct   17340
ggacagctag gtggcaaaag gcctgtgctt ttagaggaca catgctcaca tacggggtca   17400
gatctgactt ggggtgctac tgggaagctc tcatcttaag gatacatctc aggccagtct   17460
tggtgcatta ggaagatgta ggcaactctg atcctgagag gaaagaaaca ttcctccagg   17520
agagctaaaa gggttcacct gtgtgggtaa ctgtgaagga ctacaagagg atgaaaaaca   17580
atgacagaca gacataatgc ttgtgggaga aaaaacagga ggtcaagggg atagagaagg   17640
cttccagaag aatggctttg aagctggctt ctgtaggagt tcacagtggc aaagatgttt   17700
cagaaatgtg acatgactta aggaactata caaaaaggaa caaatttaag gagaggcaga   17760
taaattagtt caacagacat gcaaggaatt ttcagatgaa tgttatgtct ccactgagct   17820
tcttgaggtt agcagctgtg agggttttgc aggcccaaga cccattacag gacctcacgt   17880
atacttgaca ctgttttttg tattcatttg tgaatgaatg acctcttgtc agtctactcg   17940
gtttcgctgt gaatgaatga tgtcttgtca gcctacttgg tttcgctaag agcacagaga   18000
gaagatttag tgatgctatg taaaaacttc cttttttggtt caagtgtatg tttgtgatag   18060
aaatgaagac aggctacatg atgcatatct aacataaaca caaacattaa gaaaggaaat   18120
caacctgaag agtatttata cagataacaa aatacagaga gtgagttaaa tgtgtaataa   18180
```

-continued

```
ctgtggcaca ggctggaata tgagccattt aaatcacaaa ttaattagaa aaaaaacagt  18240
ggggaaaaaa ttccatggat gggtctagaa agactagcat tgtttttaggt tgagtggcag  18300
tgtttaaagg gtgatatcag actaaacttg aaatatgtgg ctaaataact agaatactct  18360
ttattttttc gtatcatgaa tagcagatat agcttgatgg ccccatgctt ggtttaacat  18420
ccttgctgtt cctgacatga aatccttaat ttttgacaaa ggggctattc attttcattt  18480
tatattgggc ctagaaatta tgtagatggt cctgaggaaa agtttatagc ttgtctattt  18540
ctctctctaa catagttgtc agcacaatgc ctaggctata ggaagtactc aaagcttgtt  18600
aaattgaatt ctatccttct tattcaattc tacacatgga ggaaaaactc atcagggatg  18660
gaggcacgcc tctaaggaag gcaggtgtgg ctctgcagtg tgattgggta cttgcaggac  18720
gaagggtggg gtgggagtgg ctaaccttcc attcctagtg cagaggtcac agcctaaaca  18780
tcaaattcct tgaggtgcgg tggctccactc ctgtaatcac agcagtttgg gacgccaagg  18840
tgggcagatc acttgaggtc aggagttgga caccagccca gccaacatag tgaaacctgg  18900
tctctgctta aaaatataaa aattagctgg acgtggtgac gggagcctgt aatccaacta  18960
cttgggaggc tgaggcagga gaatcgcttg aaccggggag gtggagtttg cactgagcag  19020
agatcatgcc attgcactcc agcctccaga gcgagactct gtctaaagaa aaacgaaaac  19080
aaacaaacaa acaaacaaac aaaacccatc aaattccctg accgaacaga attctgtctg  19140
attgttctct gacttatcta ccattttccc tccttaaaga aactgtgaac ttccttcagc  19200
tagaggggcc tggctcagaa gcctctggtc agcatccaag aaatacttga tgtcactttg  19260
gctaaaggta tgatgtgtag acaagctcca gagatggttt ctcatttcca tatccaccca  19320
cccagctttc caattttaaa gccaattctg aggtagagac tgtgatgaac aaacaccttg  19380
acaaaattca acccaaagac tcactttgcc tagcttcaaa atccttactc tgacatatac  19440
tcacagccag aaattagcat gcactagagt gtgcatgagt gcaacacaca cacacaccaa  19500
ttccatattc tctgtcagaa aatcctgttg gttttttcgtg aaaggatgtt ttcagaggct  19560
gacccettgc cttcacctcc aatgctacca ctctggtcta agtcactgtc accaccacct  19620
aaattatagc tgttgactca taacaatctt cctgcttcta ccactgcccc actacaattt  19680
cttcccaata tactatccaa attagtcttt tcaaaatgta agtcatatat ggtcacctct  19740
ttgttcaaag tcttctgata gtttcctata tcatttataa taaaaccaaa tccttacaat  19800
tctctacaat agttgttcat gcatatatta tgtttattac agatacatat atatagctct  19860
catataaata aatatatata tttatgtgta tgtgtgtaga gtgttttttc ttacaactct  19920
atgatgtagg tattattagt gtcccaaatt ttataattta ggacttctat gatctcatct  19980
tttattctcc ccttcaccga atctcatcct acattggcct tattgatatt ccttgaaaat  20040
tctaagcatc ttacatcttt agggtattta catttgccat tccctatgcc ctaaatattt  20100
aatcatagtt tcatataaat gggttcctca tcatctatgg gtactctctc aggtgttaac  20160
tttatagtga ggactttcct gccatactac ttaaagtagc gatacccttt caccctgtcc  20220
taatcacact ctggccttca tttcagtttt tttttttttct ccatagcacc taatctcatt  20280
ggtatataac atgtttcatt tgcttattta atgtcaagct cttttccacta tcaagtccat  20340
gaaaacagga actttattcc tctattctgt ttttgtgctg tattcttagc aattttacaa  20400
ttttgaatga atgaatgagc agtcaaacac atatacaact ataattaaaa ggatgtatgc  20460
tgacacatcc actgctatgc acacacaaag aaatcagtgg agtagagctg gaagtgctaa  20520
gcctgcatag agctagttag ccctccgcag gcagagcctt gatgggatta ctgagttcta  20580
gaattggact catttgtttt gtaggctgag atttgctctt gaaaacttgt tctgaccaaa  20640
ataaaaggct caaaagatga atatcgaaac cagggtgttt tttacactgg aatttataac  20700
tagagcactc atgtttcatg aagcaattaa ttgtttcatc agtcaggtaa aagtaaagaa  20760
aaactgtgcc aaggcaggta gcctaatgca atatgccact aaagtaaaca ttatttcata  20820
ggtgtcagat atggcttatt catccatctt catgggaagg atggccttgg cctggacatc  20880
agtgttatgt gaggttcaaa acacctctag gctataaggc aacagagctc cttttttttt  20940
tttctgtgct ttcctggctg tccaaatctc taatgataag catacttcta ttcaatgaga  21000
atattctgta agattatagt taagaattgt gggagccatt ccgtctctta tagttaaatt  21060
tgagcttctt ttatgatcac tgtttttttta atatgcttta agttctgggg tacatgtgcc  21120
atggtggttt gctgcaccca tcaacccgtc atctacatta ggtatttctc ctaatgctat  21180
ccttccccta gccccccacc cccaacaggc cccagtgtgt gatgttcccc tccctgtgtc  21240
catggatcac tggtttttt ttgtttttttt tttttttta aagtctcagt taaattttttg  21300
gaatgtaatt tattttcctg gtatcctagg acttgcaagt tatctggtca ctttagccct  21360
cacgtttga tgataatcac atatttgtaa acacaacaca cacacacaca cacacacaca  21420
tatatatata tataaaacat atatatacat aaacacacat aacatattta tcgggcattt  21480
ctgagcaact aatcatgcag gactctcaaa cactaaccta tagccttttc tatgtatcta  21540
cttgtgtaga aaccaagcgt ggggactgag aaggcaatag caggagcatt ctgactctca  21600
ctgcctttag ctaggcccct ccctcatcac agctcagcat agtcctgagc tcttatctat  21660
atccacacac agtttctgac gctgcccagc tatcaccatc ccaagtctaa agaaaaaaat  21720
aatgggtttg cccatctctg ttgattagaa aacaaaacaa aataaaataa gccectaagc  21780
tcccagaaaa catgactaaa ccagcaagaa gaagaaaata caataggtat atgaggagac  21840
tggtgacact agtgtctgaa tgaggcttga gtacagaaaa gaggctctag cagcatagtg  21900
gtttagagga gatgtttctt tccttcacag atgccttagc ctcaataagc ttgcggttgt  21960
ggaagtttac tttcagaaca aactcctgtg gggctagaat tattgatggc taaaagaagc  22020
ccgggggagg gaaaaatcat tcagcatcct cacccttagt gacacaaaac agaggggggcc  22080
tggtttttcca tatttcctca tgatggatga tctcgttaat gaaggtggtc tgacgagatc  22140
attgcttctt ccatttaagc cttgctcact tgccaatcct cagttttaac cttctccaga  22200
gaaatacaca tttttttattc aggaaacata ctatgttata gtttcaatac taaataatca  22260
aagtactgaa gatagcatgc ataggcaaga aaaagtcctt agctttatgt tgctgttgtt  22320
tcagaattta aaaaagatca ccaagtcaag gacttctcag ttctagcact agaggtggaa  22380
tcttagcata taatcagagg ttttttcaaaa tttctagaca taagattcaa agccctgcac  22440
ttaaaatagt ctcatttgaa ttaactcttt atataaattg aaagcacatt ctgaactact  22500
tcagagtatt gttttatttc tatgttctta gttcataaat acattaggca atgcaattta  22560
attaaaaaaa cccaagaatt tcttagaatt ttaatcatga aaataaatga aggcatcttt  22620
acttactcaa ggtcccaaaa ggtcaaagaa accaggaaag taaagctata tttcagcgga  22680
aaatgggata tttatgagtt ttctaagttg acagactcaa gttttaacct tcagtgccca  22740
tcatgtagga aagtgtggca taactggctg attctggctt tctactcctt tttcccatta  22800
aagatcctc ctgcttaatt aacattcaca agtaactctg gttgtacttt aggcacagtg  22860
gctcccgagg tcagtcacac aataggatgt ctgtgctcca agttgccaga gagagagatt  22920
```

```
actcttgaga atgagcctca gccctggctc aaactcacct gcaaacttcg tgagagatga 22980
ggcagaggta cactacgaaa gcaacagtta gaagctaaat gatgagaaca catggactca 23040
tagagggaaa caacgcatac tggggcctat cagagggtgg agggtgagag aaggagagga 23100
tcaggaaaaa tcactaatgg atgctaagcg taatacctga gtgatgagat catctataca 23160
acaaacccc ttgacattca tttatctatg taacaaacct gcacatcctg tacatgtacc 23220
cctgaactta aaataaaagt tgaaaacaag aaagcaacag tttgaacact tgttatggtc 23280
tattctctca ttctttacaa ttacactaga aaatagccac aggcttcctg caaggcagcc 23340
acagaattta tgacttgtga tatccaagtc attcctggat aatgcaaaat ctaacacaaa 23400
atctagtaga atcatttgct tacatctatt tttgttctga gaatatagat ttagatacat 23460
aatggaagca gaataattta aaatctggct aatttagaat cctaagcagc tcttttccta 23520
tcagtggttt acaagccttg tttatatttt tcctattta aaaataaaaa taaagtaagt 23580
tatttgtggt aaagaatatt cattaaagta tttatttctt agataatacc atgaaaaaca 23640
ttcagtgaag tgaagggcct actttactta acaagaatct aatttatata atttttcata 23700
ctaatagcat ctaagaacag tacaatattt gactcttcag gttaaacata tgtcataaat 23760
tagccagaaa gatttaagaa aatattggat gtttccttgt ttaaattagg catcttacag 23820
tttttagaat cctgcataga acttaagaaa ttacaaatgc taaagcaaac ccaaacaggc 23880
aggaattaat cttcatcgaa tttgggtgtt tctttctaaa agtcctttat acttaaatgt 23940
cttaagacat acatagattt tattttacta attttaatta tatagacaat aaatgaatat 24000
tcttactgat tactttttct gactgtctaa tcttttctgat ctatcctgga tggccataac 24060
acttatctct ctgaactttg ggcttttaat ataggaaaga aaagcaataa tccattttc 24120
atggtatctc atatgataaa caaataaaat gcttaaaaat gagcaggtga agcaatttat 24180
cttgaaccaa caagcatcga agcaataatg agactgcccg cagcctacct gacttctgag 24240
tcaggattta taagccttgt tactgagaca caaacctggg cctttcaatg ctataaactt 24300
tcttgaagct cctccctacc accttagcc ataaggaaac atggaatggg tcagatccct 24360
ggatgcaagc caggtctgga accataggca gtaaggagag aagaaaatgt gggctctgca 24420
actggctccg agggagcagg agaggatcaa ccccatactc tgaatctaag agaagactga 24480
tgtccatact ctgaatggga agaatgatgg gattacccat agggcttgtt ttagggagaa 24540
acctgttctc caaactcttg gccttgagat acctggtcct tattccttgg actttggcaa 24600
tgtctgaccc tcacattcaa gttctgagga agggccactg ccttcatact gtggatctgt 24660
agcaaattcc ccctgaaaac ccagagctgt atcttaattg gttaaaaaaa attatattat 24720
ctcaacgact gttcttctct gagtagccaa gctcagcttg gttcaagcta caagcagctg 24780
agctgctttt tgtctagtca ttgttctttt atttcagtgg atcaaatacg ttctttccaa 24840
acctaggatc ttgtcttcct aggctatata ttttgtccca ggaagtctta atctggggtc 24900
cacagaacac taggggctg gtgaagttta tagaaaaaaa atctgtattt ttacttacat 24960
gtaactgaaa tttagcattt tcttctactt tgaatgcaaa ggacaaacta gaatgacatc 25020
atcagtacct attgcatagt tataaagaga aaccacagat attttcatac tacaccatag 25080
gtattgcaga tctttttgtt tttgtttttg tttgagatgg agtttcgctc ttattgccca 25140
ggctggagtg cagtggcatg atttcggctc actgcaacct ccccttcctg cattcaagca 25200
attctcctgc cttggcctcc tgagtagctg gggattacag gcacctgcca ccatgccagt 25260
ctaatttttg tattttagt agagatgggg tttcgccatg ttggccaggc tggtcttgaa 25320
ctcctgacct cagatgatct gcccgccttg gcctcctgaa gtgctgggat tataggtgtg 25380
agccaccacg cctggcccat tgcagatatt tttaattcac atttatctgc atcactactt 25440
ggatcttaag gtagctgtag acccaatcct agatctaatg ctttcataaa gaagcaaata 25500
taataaatac tataccacaa atgtaatgtt tgatgtctga taatgatatt tcagtgtaat 25560
taaacttagc actcctatgt atattatttg atgcaataaa aacatatttt tttagcactt 25620
acagtctgcc aaactggcct gtgacacaaa aaaagtttag gaattcctgg ttttgtctgt 25680
gttagccaat ggttagaata tatgctcaga aagataccat tggttaatag ctaaaagaaa 25740
atggagtaga aattcagtgg cctgaataa taacaatttg ggcagtcatt aagtcaggtg 25800
aagacttctg gaatcatggg agaaaagcaa gggagacatt cttacttgcc acaagtgttt 25860
tttttttttt tttttttat cacaaacata agaaaatata ataaataaca aagtcaggtt 25920
atagaagaga gaaacgctct tagtaaactt ggaatatgga atcccaaag gcacttgact 25980
tgggagacag gagccatact gctaagtgaa aaagacgaag aacctctagg gcctgaacat 26040
acaggaaatt gtaggaacag aaattcctag atctggtggg gcaaggggag ccataggaga 26100
aagaaatggt agaaatggat ggagacggag gcagaggtgg gcagatcatg aggtcaagag 26160
atcgagacca tcctggcaaa catggtgaaa tcccgtctct actaaaaata aaaaaattag 26220
ctgggcatgg tggcatgcgc ctgtagtccc agctgctcgg gaggctgagg caggagaatc 26280
gtttgaaccc aggaggcgaa ggttgcagtg agctgagata gtgccattgc actccagtct 26340
ggcaacagag tgagactccg tctcaaaaaa aaaaaaaaaa gaaagaaaga aaagaaaaag 26400
aaaaaagaaa aaataaatgg atgtagaaca agccagaagg aggaactggg ctggggcaat 26460
gagattatgg tgatgtaagg gacttttata gaattaacaa tgctggaatt tgtggaactc 26520
tgcttctatt attcccccaa tcattacttc tgtcacattg atagttaaat aatttctgtg 26580
aatttattcc ttgattctaa aatatgagga taatgacaat ggtattataa gggcagatta 26640
agtgatatag catgagcaat attcttcagg cacatggatc gaattgaata cactgtaaat 26700
cccaacttcc agtttcagct ctaccaagta aagagctagc aagtcatcaa aatggggaca 26760
tacagaaaaa aaaaaggaca ctagaggaat aatataccct gactcctagc ctgattaata 26820
tatcgattca cttttttctc tgtttgatga caaattctgg cttaaataa ttttaggatt 26880
ttaggcttct cagctccctt cccagtgaga agtataagca ggacagacag gcaagcaaga 26940
agagagcccc aggcaatact cacaaagtag ccaatgtccc ctgtggtcat agagaaatga 27000
aaagagagag gattctctgg aagcactgga tgtaatcttt tctgtctgtc ctctctaggg 27060
aatcacccca aggtactgta ctttgggatt aaggctttag tcccactgtg gactacttgc 27120
tattctgttc agtttctaga aggaactatg tacggttttt gtctccctag agaaactaag 27180
gtacagaagt tttgtttaca atgcactcct taagagagct agaactgggt gagattctgt 27240
tttaacagct ttatttttctt ttccttggcc ctgtttttgt cactgtcacc accttttaagg 27300
caaatgttaa atgcgctttg gctgaaactt tttttcctat tttgagattt gctccttat 27360
atgaggcttt cttggaaaag gagaatggga gagatggata tcattttgga agatgatgaa 27420
gagggtaaaa aaggggacaa atggaaattt gtgttgcaga tagatgagga gccaacaaaa 27480
aagagcctca ggatccagca cacattatca caaacttagt gtccatccat cactgctgac 27540
cctctccgga cctgactcca cccctgaggg acacaggtca gccttgacca atgactttta 27600
agtaccatgg agaacagggg gccagaactt cggcagtaaa gaataaaagg ccagacagag 27660
```

-continued

```
aggcagcagc acatatctgc ttccgacaca gctgcaatca ctagcaagct ctcaggcctg   27720
gcatcatggt gcattttact gctgaggaga aggctgccgt cactagcctg tggagcaaga   27780
tgaatgtgga agaggctgga ggtgaagcct tgggcaggta agcattggtt ctcaatgcat   27840
gggaatgaag ggtgaatatt accctagcaa gttgattggg aaagtcctca agattttttg   27900
catctctaat tttgtatctg atatggtgtc atttcataga ctcctcgttg tttacccctg   27960
gacccagaga tttttgaca gctttggaaa cctgtcgtct ccctctgcca tcctgggcaa   28020
ccccaaggtc aaggcccatg gcaagaaggt gctgacttcc tttggagatg ctattaaaaa   28080
catggacaac ctcaagcccg cctttgctaa gctgagtgag ctgcactgtg acaagctgca   28140
tgtggatcct gagaacttca aggtgagttc aggtgctggt gatgtgattt tttggcttta   28200
tattttgaca ttaattgaag ctcataatct tattggaaag accaacaaag atctcagaaa   28260
tcatgggtcg agcttgatgt tagaacagca gacttctagt gagcataacc aaaacttaca   28320
tgattcagaa ctagtgacag taaaggacta ctaacagcct gaattggctt aacttttcag   28380
gaaatcttgc cagaacttga tgtgtttatc ccagagaatt gtattataga attgtagact   28440
tgtgaaagaa gaatgaaatt tggctttttgg tagatgaaag tccatttcaa ggaaatagaa   28500
atgccttatt ttatgtgggt catgataatt gaggtttaga aagagatttt tgcaaaaaaa   28560
ataaaagatt tgctcaaaga aaaataagac acattttcta aaatatgtta aatttcccat   28620
cagtattgtg accaagtgaa ggcttgtttc cgaatttgtt ggggattta aactcccgct   28680
gagaactctt gcagcactca cattctacat ttacaaaaat tagacaattg cttaaagaaa   28740
aacaggggaga gagggaaccc aataatactg gtaaaatggg gaaggggggtg agggtgtagg   28800
taggtagaat gttgaatgta gggctcatag aataaaattg aacctaagct catctgaatt   28860
ttttgggtgg gcacaaacct tggaacagtt tgaggtcagg gttgtctagg aatgtaggta   28920
taaagccgtt tttgtttgtt tgtttcggga ttcatcaagt tgttttcgga aacttctact   28980
caacatgcct gtgtgttatt ttgtctttttg cctaacagct cctgggtaac gtgatggtaa   29040
ttattctggc tactcacttt ggcaaggagt tcacccctga agtgcaggct gcctggcaga   29100
agctggtgtc tgctgtcgcc attgccctgg cccataagta ccactgagtt ctcttccagt   29160
ttgcaggtgt tcctgtgacc ctgacaccct ccttctgcac atggggactg ggcttggcct   29220
tgagagaaag ccttctgttt aataaagtac attttcttca gtaatcaaaa attgcaattt   29280
tatcttctcc atctttttact cttgtgttaa aaggaaaaag tgttcatggg ctgagggatg   29340
gagagaaaca taggaagaac caagagcttc cttaagaaat gtatggggggc ttgtaaaatt   29400
aatgtggatg ttatgggaga attccaggat tccaaggagg atgatatgat ggagaaaaat   29460
ctttatcggg gtgggaaaat ggttaattaa gtggacagag actcctaggc agttttttact   29520
gcaccgggga aagaaggagc tgttagtggt acctgagaaa gcagatttgt ggtacatgtc   29580
acttttcatt aaaaacaaaa acaaaacaaa acaaaacttc atagatatcc aagatatagg   29640
ctagaattac tattttaatt tactcttatt tacattttga agtagctagc ttgtcacatg   29700
ttttatgaaa ttgatttgga gataagatga gtgtgtatca acaatagcct gctctttcca   29760
tgaaggattc cattatttca tggggttagct gaagctaaga cacatgatat cattgtgcat   29820
tatcttctga tagaatgtaa catgcactaa aataaagtta gagttaggac ctgagtggga   29880
aagttttttgg agagtgtgat gaagactttc cgtgggagat agaatactaa taaaggctta   29940
aattctaaaa ccagcaagct agggcttcgt gacttgcatg aaactggctc tctggaagta   30000
gaagggagag taagacatac gtagaggact aggaaagacc agatagtaca gggcctggct   30060
acaaaaatac aagcttttac tatgctattg caatactaaa cgataagcat taggatgtta   30120
agtgactcag gaaataagat tttgggaaaa agtaatctgc ttatgtgcac aaaatggatt   30180
caagtttgca gataaaataa aatatggatg atgattcaag ggacagata caatggttca   30240
aacccaagag gagcagtgag tctgtggaat ttgaaggatg gacaaaggtg gggtgagaaa   30300
gacatagtat tcgactgact gtgggagatg agaaggaaga aggaggtgat aaatgactga   30360
aagctcccag actggtgaag ataacaggag gaaaccatgc actgacctgg tgactctcat   30420
gtgtgaaggg tagagggata ttaacagatt tactttttag gaagtgctag attggtcagg   30480
gagtttttgac cttcaggtct tgtgtctttc atatcaagga accttttgcat tttccaagtt   30540
agagtgccat attttggcaa atataacttt attagtaatt ttatagtgct ctcacattga   30600
tcagactttt tcctgtgaat tacttttgaa tttggctgta tatatccaga atatgggaga   30660
gagacaaata attattgtag ttgcaggcta tcaacaatac tggtctctct gagccttata   30720
acctttcaat atgcccataa acagagtaaa cagggattat tcatggcact aaatatttttc   30780
acctagtcag tcaacaaatg gggagcaatgt gcatttttttg atacatattt ttatatattt   30840
atggggtaca tgtgatactt acatgcctag aacatgtgat gattaagtct agatatttag   30900
gatatccatt gctttgagca tttatcattt ctatgtattg agaaaatttc aaatcctcat   30960
ttctagccat tttgaaatat ataataaata gtaattaact atagtcaccc tactcaaata   31020
tcaaacatta tggcttaatc cttctatcca actgtgtttg tacctattaa ccaacatctc   31080
ttaaatcccc tcccatacac actcacactt tttccagcct ctgataacta tcattctact   31140
ctctaccacc atgagaccca ctttttttagc tcccacagat gaataaaaac atgtgatatt   31200
tgacttttctg tatctggctt attttattat ctatctcttt ggcataccaa gagtttgttt   31260
ttgttctgct tcagggctttt caattaacat aatgacctct ggttccatcc atgttgctac   31320
aaaatgacaag atttcattct tttcatggc aaaaatagtac tgtgcaaaaa tacaatttttt   31380
taatccgttc atctgttgat agacacttag gttgatccca aaccttaact attgtgaata   31440
gtgcttcaat aaacatgagt gtaatgtgtc cattggatat actgattttcc tttcttttgg   31500
ataaataacc actagtgaga ttgctggatt gtatgatagt tctgttttta gtttactgag   31560
aaatcttcat actgtttttcc ataatggttg tactatttta cattcccacc aacagtgtgt   31620
aagaaagagt tcccttttct ccatatcctc acaaggatct gttatttttt gtctttttttg   31680
ttaatagccg ttttaactag agtaagtaga tatctcattg tagtgtttgat ttgcatttcc   31740
ctgatcatta gtgatgttga gaatttttctc atatgtattg ttggtcatttg tatatctttt   31800
tctgagaatt gtctgttcat gtccttagcc tacttttttat tgggattgtt tgttattttc   31860
ttgataatct attttgtgttc attttagagc ctggatatta ttcttttttgtc agatgtatag   31920
attgtgaaga tttttctccca ctctgtgggt tgtctgttta ttctgcagac tcttcctttt   31980
gccatgcaaa agctctttag tttaatttag tcccagatat tttctttgtt tttatgtatt   32040
tgcattttgtg ttcttggtca tgaaatcctt tcctaagcca atgtgtaaga gggtttttcc   32100
gatgttattt tctagaattg ttacagtttc agggcttaga tttaagtcct tgatccatct   32160
tgagttgatt tttgtataag gtgagagatg aagatccagt ttcattctcc tacatgtagc   32220
ttgccagcta tccccgcacc atttgttgaa tagggtgccc tttcccccact ttatgttttt   32280
gtttgctttg tcaaagatca gttggatgta agtatttgag tttatttctg ggttctctat   32340
tctgttccat tggtcgatgt gcctatttgt acaccagcat catgctgttt tggtgactat   32400
```

-continued

```
ggccttattg tatagttttga aatgaggtaa tgtaatgcct tcagatttgt tctttttttt  32460
agacttgctt gtttattggg ctcttttttg gttccataag aatttaggaa ttgtttttttc  32520
tagttctgtg aagactaatg gtggtatttt gatgggaatt gcaatgaatt tgtaggttgc  32580
ttctggcatt atggccattt tcacaatatt gattctaccc atctatgaga atggcatgtg  32640
tttccatttg tttgtgtctt atatgattac tttcagccgt gttttgtagt tttccttgta  32700
gatgtctttc acctccttgg ttaggtatat attcctaagt ttttgttttg ttttgttttg  32760
tttttttgcag ctattgtaaa aggggttgag ttcttgattt tattctcagc ttggtcattg  32820
ctggtatgta agaaagcaac tcattggtgt acgttaattt tgtatccaga aactttgctg  32880
aattatttta tcagttctag ggggtttttgg aggagtcttt agagtttttct acatacacaa  32940
tcatatcatc agcaaacagt gacagtttga ctttctcttt aacaatttgg atgtgctta  33000
cttgtttctc ttgtctgatt gctcttgcta ggacttccag taatatgtta aagagaagtg  33060
gtgagagtgg gtatccttgt ctcattccag ttttcagaca gaatgctttt aacttttttcc  33120
cattcaatat aatgttggct gtgtgtttac catagctggc ttttattaca ttgaggtatg  33180
tcctttgtaa accgattttg ctgagtttta gtcataaagt gatgttgaat tttgttgaat  33240
gcagtttctg tggctattga gataatcaca tgattttttgt ttccaattct ctttatgttg  33300
tgtatcacac ttattgactt gcgtatgtta aaccatccgt gcatccctcg catgaaaccc  33360
acttgatcat gggttttgat atgctgtcgg atgctattag ctagtatttt gtcaaggatg  33420
ttggcatcta tgttcatcag ggatattgat ctgtagtgtt tttttttttt ggttatgttc  33480
tttcccagtt ttggtattaa ggtgatactg gcttcataga atgatttagg gaggattctc  33540
tctttctcta tcttgtagaa tactgtcaat aggattggta tcaattcttc tttgaatgtc  33600
tggtagaatt cagctgtgaa tctatctggt cctggacttt tttgttgttg gtaaatttt  33660
attatcattt cagtcttgct gctcttattact ggtctgttca gggtatctaa ttcttcctga  33720
cttaagctag agccctgtat ctttccagga attcgaacgt ctcctttagg tttttctagtt  33780
tatgcatgta aaggtgttca tagtagccttt gaataatctt ttgtatttct gtggtatcag  33840
taatagtatc tcctgttttg tttctaattg agtttatttg cacttctctc ctcttttcttt  33900
ggttaatctt gctaatggtc tacagtttt atttatcttt tcaaagaacc agcttttat  33960
ttcatttagc ttttgtattt ttttgcagtt gttttaattt catttagttc tcctcttatc  34020
ttagttattc cctttcttttt gctgggtttt ggttctgttt gttttttgttt ctctagtttc  34080
ttgtggtgtg accttatatt gtctgtctgt cctcttttcag actctttgac atcgacattt  34140
agggctgtga acttttccttt tagcaccatc tttgctgtat cctagaggtt ttgataggtt  34200
gtgtcactat tgtcggtcag ttcaagtaat tttgttgttc ttattatact ttaagttctg  34260
ggatacatgt gcagaatgtg caggtttgtt acataggtat agatgtgcca tggtggtttg  34320
ctgcacccat caacctgtca tctacattag gtatttcttt taatgttatc cctctcctaa  34380
ccccctcacc ccccgacagg ccctggtgtg tgatgttccc ctccctgtgt ccatgtgttc  34440
tcattgttca actcccactt atgagtgaga acgtgtggtg tttggtttct ctgttcctgt  34500
gttagtttgc tcagaatgat ggtttccacc ttcatccatg tccctgcaaa gacatgaact  34560
catcatttttt atggctgcat agtattccat ggtgtatatg tgccacattt tctttatcca  34620
ttatatcgct gatggccatt tgggttggtt ccaagtcttt gctattgtga atagtgccac  34680
aataaacata cgtgtgcacg tgtctttata gtagaatgat ttctaattct ttgggtatat  34740
acccagtaat gggattgctg ggtcaaacag tatttctggt tctagatcct tgaggaatcg  34800
ccacactgtc ttccacaatg gttgaactaa tttacacacc catcaacagt gtaaaatttt  34860
tcctattctt ccacatcctc tccagcacct tttgtttcct gactttttaa taattgccat  34920
tctaactggc atgagatggt atctcattgt ggttttgatt tgcatttctc taatgaccag  34980
tgatgatgag cttcttttca tgtgtttctt ggccacataa atgacttctt tagagaagca  35040
tctgttcata tcctttgtcc actttttgat ggggtcgtta ggtttttttct tgtaaatttg  35100
ttgaagttct ttgtagattt tggatgttag cccttttgtca gatggataga ttgcaaaaat  35160
tttctcccat tctgtaggtt gcctgttcac tctgatgata gtcttttgct gtgcagaagc  35220
tctttagttt aattagatcc catatgtcaa tttttggcctt tgttgtcatt gcttttgatg  35280
ttttagtcgt gaattttttgc ccatgcctat gtcctgaatg gtattgccta ggttatcttc  35340
taggatttt atggttttag gttgcacatt taagtcttta atccaccttg agttaatttt  35400
tgtataaggt gtaaggaagg ggtacagttt cagttttagg catattgcta gccagttttt  35460
ccagcaccat ttattaaaata gggaattctt tctccattgc ttttgtgatg tttgtcaaag  35520
atcagatggt cgtagatgtg tggcattatt tctgaggctt ctgttctgtt ccactggtct  35580
atatatctgt tttggtacca gtaccatgct gtttttgtta ctgtagcctt gtagtatagt  35640
ttgaagtcag gtagcatcat gcctccagct ttgttcttt tgtttaggat tgtcttggct  35700
atatgggctc tttttttgatt ccatatgaca tttaaagtag tttttttctaa ttctttgaaa  35760
aaagtcagtg gtagcttgat ggggatagca ttgaatctat aaaattacttt gggcagtatg  35820
gccattttaa agatattgat tctttctatc tatgagcatg gaatgttttt ccatttgttt  35880
gtgtcctctc ttatttccttt gagcagtgag tggtttgtag ctctccttga agaggttctt  35940
cacatcccttt agaagttgta tttctaggta ttttattttta ttctctttgc agcaattgtg  36000
aatgggagtt cacccatgat ttggctctct gcttgtctat tattggtgta taggaacgct  36060
tgtgatttct gcacactgat tttgtatctt gagactttgc tgaagctgtt tatcagctta  36120
agattttggg ctgagatgac agggtcttct aaatatacaa tcatgtcatc tgcaaacaga  36180
gacaatttga cttcctctct tcctatttga atatgcttta tttctttctc ttgcctgatt  36240
gtcctggcga gaacttccaa tactatgttg agtaagagtg gcgagagggc atccttgtct  36300
tgtgccggtt ttcaaagcaa atgattttta aattccatc ttgatttcat tgttgaccca  36360
atgatcattc aggagcaggt tatttaattt ccctgtattt gcatggtttt gaaggttcct  36420
tttgtagttg atttccaatt ttattctact gtggtctgag agagtgcttg atataatttc  36480
aatttttaaa aatttattga ggcttgtttt gtggcatatc atatggccta tcttggagaa  36540
agttccatgt gctgatgaat agaatgtgta ttctgcagtt gttgggtaga atgtcctgta  36600
aatatctgtt aagtccattt gttctttaaa tccattgttt ctttgtagac tgtcttgatg  36660
acctgcctag tgcagtcagt ggagtattga agtcccccac tattattatg ttgctgtcta  36720
gtctagtagt aattgtttta taaatttggg atctccagta ttagatgcat atatattaag  36780
aattgtaata ttctcccatt ggacaagggc ttttatcatt atatgatgtc cctctttgtc  36840
tttttttaact gctgtttctt taaagtttgt tttgtctgac ataagaatag ctgctttggc  36900
tcgcttttgg tgtccatttg tgtggaatgt cattttccac ccctttacct taagtttatg  36960
tgagtccttat tgtgttaggt gagtctcctg aaggcggcag ataactggtt ggtgaattct  37020
tattcattct gcaattctgt atctttttaag tggagcattt agtccattta cattcaacat  37080
cagtattgag gtgtgaggta ctattccatt cttcgtggta tttgttgcct gtgtatctttt  37140
```

-continued

```
ttatctgtat ttttgttgta tatgtcctat gggatttatg cttttaaagag gttctgtttt   37200
gatgtgcttc cagggtttat ttcaagattt agagctcctt ttatcagttc ttgtagtgtt   37260
ggcttggtag tgccgaattc tctcagcatt tgttttt ctg aaaaacactg tgtattttct   37320
tcatttgtga agcttagttt cactggatat aaaattcttg gctgataatt gttttgttta   37380
agaaggctga agatagggcc atattcactt ctagctttta cggtttctgc tgagaaatct   37440
gctgttaatc tgataggttt tctttcatag gttacctggt agtttcacct cacagctctt   37500
aagattctct ttgtctttag ataactttgg atactctgat gacaatgtac ctaggcaatg   37560
atatttttgc aatgaatttc ccaggtgttt attgagcttc ttgtatttgg atatctaggt   37620
ctctagcaag gtgggggaag ttttccttga ttatttccct ggataagttt tccaaacttt   37680
tagatttctc ttctttctca ggaatgctga ttattcttag gtttgattgt ttaacataat   37740
cccagatttc ttggaggctt tgttcatatt ttcttattct tttttctttg tctttgttgg   37800
attgggttaa ttcaaaaact ttgtcttcaa gctctgaatt tcttctgctt ggattctatt   37860
gctgagactt tctagagcat tttgcatttc tataagtgca tccattcatc cattgtttcc   37920
tgaagttttg aatgtttttt atttatgcta tctctttaac tgaagatttc tcccctcatt   37980
tcttgtatca tattttttggt tttttttaaaa ttggacttca ccttcctcgg atgcctcctt   38040
gattagctta ataactgacc ttctgaatta tttttcaggt aaatcaggga tttcttcttg   38100
gtttggatgc attgctggtg agctagtatg atttttttggg gggtgttaaa gaaccttgtt   38160
tttcatatta ccagagttag ttttctggtt ccttctcact tgggtaggct ctgtcagagg   38220
gaaagtctag gcctcaaggc tgagactttt gtcccatgag gtgttccctt gatgtagcac   38280
agtcccccctt ttcctaggcg tggggcttcc tgagagccga actgtagtga ttgttatctc   38340
tcttctggat ctagccaccc atcaggtcta ccagactcca ggctggtact ggggtttgtc   38400
tgcacagagt cttgtgacgt gaaccatctg tgggtctctc agccatagat acaaccacct   38460
gctccaatgg aggtggcaga ggatgaaatg gactctgtga gggtccttac tttttggttgt   38520
tcaatgcact atttttgtgc tggttggcct cctgccagga ggtggcactt tctagaaagc   38580
atcagcagag gcagtcaggt ggtggtggct gggggggctg gggcaccta gaactcccaa   38640
gaatatatgc cctttgtctt cagctaccag ggtgagtaag gaaggaccat caggtggggg   38700
caggactagt cgtgtctgag ctcagagtct ccttgggcag gtctttctgt ggctactgtg   38760
ggaggatggg ggtgtagttt ccaggtcaat ggatttatgt tcctaggaca attatgtgctg   38820
cctctgctgt gtcatgcagg tcatcaggaa agtgggggaa agcaagcagt cacgtgactt   38880
gcccagctcc catgcaactc aaaaggttgg tctcacttcc agcgtgcacc ctcccccgca   38940
acagcaccga atctgtttcc atgcagtcag tgagcaaggc tgagaacttg ccccaggcta   39000
ccagctgcga aaccaagtag ggctgtccta cttccctgcc agtggagtct gcacaccaaa   39060
ttcatgtccc cccaccaacc cccccactgc ccagcccta gatctggcca ggtggagatt   39120
ttctttttcc tgtcatcttt tcccagttcc tctggcagcc ctcccaaatg accctgtga   39180
ggcaaggcag aaatggcttc ctaggggacc cagagagccc acagggcttt tcccgctgct   39240
tcctctaccc ctgtattttg cttggccctc taaattgact cagctccagg taaggtcaga   39300
atcttctcct gtggtctaga tcttcaggtt ccccagtgag gatgtgtgtt tggggggtaga   39360
cggtccccct tttccacttc cacagtttgg gcactcacaa tatttgggggt gtttcccggg   39420
tcctgcagga gcaatctgct tctttcagag ggtgtgtgtg ttctctcagc tttcttgatt   39480
tatttctgca ggtggttctg caaaaaaaat tcctgatggg agacttcaca tgctgctctg   39540
tgcatccgag tgggagctgc aatgtacttc tgctgcctcc catctgccat caccctctaa   39600
tttgtcggta atatgcattt ttaatcaatc ttttttttctc tctctctctt tttcttctcc   39660
cccaaaacta tactgccctt tgatatcaag gaatcaagga cgtgatgttg aggggtgggc   39720
agtggataca ctctttaccc cttagggagc tatatctaga tttagatatt gccaattcaa   39780
gataacttaa ttgaaagcaa attcataatg aatacacaca cacacacaca catctgcatg   39840
acaagatttt taatagttga aagaataact aataattgtc cacaggcaat aagggctttt   39900
taagcaaaac agttgtgata aacaggtcat tcttagaata gtaatccagc caatagtaca   39960
ggttgcttag agattatgtc attaccagag ttaaaattct ataatggctt ctcactccct   40020
accactgagg acaagtttat gtccttaggt ttatgcttcc ctgaaacaat accacctgct   40080
attctccact ttacatatca acggcactgg ttctttatct aactctctgg cacagcagga   40140
gtttgttttc ttctgcttca gagctttgaa tttatatttt cagcttctaa actttatttg   40200
gcaatgcctt cccatggcag attccttctg tcattttgcc tctgttcgaa tactttctcc   40260
ttaatttcat tcttagttaa taatatctga aattattttg ttgtttaact taattattaa   40320
ttttatgtat gttctaccta gattataatc ttcagaggaa agttttattc tctgacttat   40380
ttaacttaaa tgcccactac tttaaaaatt atgacattta tttaacagat atttgctgaa   40440
caaatgtttg aaaatacatg ggaaagaatg cttgaaaaca cttgaaattg cttgtgtaaa   40500
gaaacagttt tatcagttag gatttaatca atgtcagaag caatgatata ggaaaaatcg   40560
aggaataaga cagttatgga taaggagaaa tcaacaaact cttaaaagat attgcctcaa   40620
aagcataaga ggaaataagg gtttatacat gactttttaga acactgcctt ggttttttgga   40680
taaatgggga agttgtttga aaacaggagg gatcctagat attccttagt ctgaggagga   40740
gcaattaaga ttcacttgtt tagaggctgg gagtggtggc tcacgcctgt aatcccagaa   40800
ttttgggagg ccaaggcagg cagatcacct gaggtcaaga gttcaagacc aacctggcca   40860
acatggtgaa atcccatctc tacaaaaata caaaaattag acaggcatga tggcaagtgc   40920
ctgtaatccc agctacttgg gaggctgagg caggagaatt gcttgaacct ggaaggcagg   40980
agttgcagtg agccgagatc ataccactgc actccagcct gggtgacaga acaagactct   41040
gtctcaaaaa aaaaaaagag agattcaaaa gattcacttg tttaggcctt agcgggctta   41100
gacaccagtc tctgacacat tcttaaaggt caggctctac aaatgaaacc caaccagact   41160
ctcagatatg gccaaagatc tatacacacc catctcacag atcccctatc ttaaagagac   41220
cctaatttgg gttcacctca gtctctataa tctgtaccag cataccaata aaaatctttc   41280
tcacccatcc ttagattgag agaagtcact tattattatg tgagtaactg gaagatactc   41340
ataagttgac aaatctttt cttttccttttc ttattcaact tttatttaa cttccaaaga   41400
acaagtgcaa tatgtgcagc tttgttgcgc aggtcaacat gtatctttct ggtcttttag   41460
ccgcctaaca ctttgagcag atataagcct tacacaggat tatgaagtct gaaaggattc   41520
caccaatatt attataattc ctatcaacct gataggttag gtgaaggtag agctctcctc   41580
caataagcca gatttccaga gtttctgacg tcataatcta ccaagtgcat ggatcgagtt   41640
cagagaaaaa acaaaagcaa aaccaaacct accaaaaaat aaaaatccca aagaaaaaat   41700
aaagaaaaaa acagcatgaa tacttcctgc catgttaagt ggccaatatg tcagaaacag   41760
cactgagtta cagataaaga tgtctaaact acagtgacat cccagctgtc acagtgtgtg   41820
gactattagt caataaaaca gtccctgcct cttaagagtt gttttccatg caaatacatg   41880
```

-continued

```
tcttatgtct tagaataaga ttccctaaga agtgaaccta gcattttatac aagataatta   41940
attctaatcc atagtatctg gtaaagagca ttctaccatc atctttaccg agcatagaag   42000
agctacacca aaaccctggg tcatcagcca gcacatacac ttatccagtg ataaatacac   42060
atcatcgggt gcctacatac atacctgaat ataaaaaaaa tacttttgct gagatgaaac   42120
aggcgtgatt tatttcaaat aggtacggat aagtagatat tgaagtaagg attcagtctt   42180
atattatatt acataacatt aatctattcc tgcactgaaa ctgttgcttt ataggatttt   42240
tcactacact aatgagaact taagagataa tggcctaaaa ccacagagag tatattcaaa   42300
gataagtata gcacttctta tttggaaacc aatgcttact aaatgagact aagacgtgtc   42360
ccatcaaaaa tcctggacct atgcctaaaa cacatttcac aatccctgaa cttttcaaaa   42420
attggtacat gctttaactt taaactacag gcctcactgg agctacagac aagaaggtga   42480
aaaacggctg acaaaagaag tcctggtatc ttctatggtg ggagaagaaa actagctaaa   42540
gggaagaata aattagagaa aaattggaat gactgaatcg gaacaaggca aaggctataa   42600
aaaaaattaa gcagcagtat cctcttgggg gccccttccc cacactatct caatgcaaat   42660
atctgtctga aacggtccct ggctaaactc cacccatggg ttggccagcc ttgccttgac   42720
caatagcctt gacaaggcaa acttgaccaa tagtcttaga gtatccagtg aggccagggg   42780
ccggcggctg gctagggatg aagaataaaa ggaagcaccc ttcagcagtt ccacacactc   42840
gcttctggaa cgtctgaggt tatcaataag ctcctagtcc agacgccatg ggtcatttca   42900
cagaggagga caaggctact atcacaagcc tgtggggcaa ggtgaatgtg gaagatgctg   42960
gaggagaaac cctgggaagg taggctctgg tgaccaggac aagggaggga aggaaggacc   43020
ctgtgcctgg caaaagtcca ggtcgcttct caggatttgt ggcaccttct gactgtcaaa   43080
ctgttcttgt caatctcaca ggctcctggt tgtctaccca tggacccaga ggttctttga   43140
cagctttggc aacctgtcct ctgcctctgc catcatgggc aaccccaaag tcaaggcaca   43200
tggcaagaag gtgctgactt ccttgggaga tgccataaag cacctggatg atctcaaggg   43260
caccttttgcc cagctgagtg aactgcactg tgacaagctg catgtggatc ctgagaactt   43320
caaggtgagt ccaggagatg tttcagcact gttgccttta gtctcgaggc aacttagaca   43380
actgagtatt gatctgagca cagcagggtg tgagctgttt gaagatactg gggttgagtg   43440
tgaagaaact gcagaggact aactgggctg agacccagtg gcaatgtttt agggcctaag   43500
gagtgcctct gaaaatctag atggacaact ttgactttga gaaaagagag gtggaaatga   43560
ggaaaatgac ttttctttat tagatttcgg tagaaagaac tttcaccttt ccctattttt   43620
tgttattcgt tttaaaacat ctatctggag gcaggacaag tatggtcatt aaaaagatgc   43680
aggcagaagg catatattgg ctcagtcaaa gtggggaact ttggtggcca aacatacatt   43740
gctaaggcta ttcctatatc agctggacac atataaaatg ctgctaatgc ttcattacaa   43800
acttatatcc tttaattcca gatgggggca aagtatgtcc aggggtgagg aacaattgaa   43860
acatttgggc tggagtagat tttgaaagtc agctctgtgt gtgtgtgtgt gtgtgtgcgc   43920
gcgtgtgttt gtgtgtgtgt gagagcgtgt gtttctttta acgttttcag cctacagcat   43980
acagggttca tggtggcaag aagataacaa gatttcaaatt atggccagtg actagtgctg   44040
caagaagaac aactacctgc atttaatggg aaagcaaaat ctcaggcttt gagggaagtt   44100
aacataggct tgattctggg tggaagcttg gtgtgtagtt atctggaggc caggctggag   44160
ctctcagctc actatgggtt catctttatt gtctcctttc atctcaacag ctcctgggaa   44220
atgtgctggt gaccgttttg gcaatccatt tcggcaaaga attcacccct gaggtgcagg   44280
cttcctggca gaagatggtg actggagtgg ccagtgccct gtcctccaga taccactgag   44340
ctcactgccc atgatgcaga gctttcaagg ataggcttta ttctgcaagc aatcaaataa   44400
taaatctatt ctgctaagag atcacacatg gttgtcttca gttctttttt tatgtctttt   44460
taaatatatg agccacaaag ggtttttatgt tgagggatgt gtttatgtgt atttatacat   44520
ggctatgtgt gtttgtgtca tgtgcacact ccacactttt ttgtttacgt tagatgtggg   44580
ttttgatgag caaataaaag aactaggcaa taaagaaact tgtacatggg agttctgcaa   44640
gtgggagtaa aaggtgcagg agaaatctgg ttggaagaaa gacctctata ggacaggact   44700
cctcagaaac agatgttttg gaagagatgg ggaaaggttc agtgaaggggg gctgaacccc   44760
cttccctgga ttgcagcaca gcagcgagga aggggctcaa cgaagaaaaa gtgttccaag   44820
ctttaggaag tcaaggttta ggcagggata gccattctat tttattaggg gcaatactat   44880
ttccaacggc atctggcttt tctcagccct tgtgaggctc tacaggggag ttgaggtgtt   44940
agagatcaga gcaggaaaca ggttttttctt tccacggtaa ctacaatgaa gtgatcctta   45000
ctttactaag gaactttttca ttttaagtgt tgacgcatgc ctaaagaggt gaaattaatc   45060
ccatacccctt aagtctacag actggtcaca gcatttcaag gaggagacct cattgtaagc   45120
ttctagggag gtggggactt aggtgaagga aatgagccag cagaagctca caagtcagca   45180
tcagcgtgtc atgtctcagc agcagaacag cacggtcaga tgaaaatata gtgtgaagaa   45240
tttgtataac attaattgag aaggcagatt cactggagtt cttatataat tgaaagttaa   45300
tgcacgttaa taagcaagag tttagtttaa tgtgatggtg ttatgaactt aacgcttgtg   45360
tctccagaaa attcacatgc tgaatcccca actcccaatt ggctccattt gtggggggagg   45420
ctttggaaaa gtaatcaggt ttagaggagc tcatgagagc agatccccat catagaatta   45480
ttttcctcat cagaagcaga gagattagcc atttctcttc cttctggtga ggacacagtg   45540
ggaagtcagc cacctgcaac ccaggaagag agccctgacc aggaaccagc agaaaagtga   45600
gaaaaaatcc tgttgttgaa gtcacccagt ctatgctatt ttgttatagc accttgcact   45660
aagtaaggca gatgaagaaa gagaaaaaaa taagcttcgg tgttcagtgg attagaaacc   45720
atgtttatct caggtttaca aatctccact tgtcctctgt gtttcagaat aaaataccaa   45780
ctctactact ctcatctgta agatgcaaat agtaagcctg agcccttctg tctaactttg   45840
aattctattt tttcttcaac gtactttagg cttgtaatgt gtttatatac agtgaaatgt   45900
caagttcttt ctttatattt cttttctttct tttttttcct cagcctcaga gttttccaca   45960
tgcccttcct actttcagga acttctttct ccaaacgtct tctgcctggc tccatcaaat   46020
cataaaggac ccacttcaaa tgccatcact cactaccatt tcacaattcg cactttcttt   46080
ctttgtcctt tttttttta gtaaaacaag tttataaaaa attgaaggaa taaatgaatg   46140
gctacttcat aggcagagta gacgcaaggg ctactggttg ccgattttta ttgttatttt   46200
tcaatagtat gctaaacaag gggtagatta tttatgctgc ccattttttag accataaaag   46260
ataacttcct gatgttgcca tggcattttt ttccttttaa ttttatttca tttcattttta   46320
atttcgaagg tacatgtgca ggatgtgcag gcttgttaca tgggtaaatg tgtgtctttc   46380
tggccttttta gccatctgta tcaatgagca gatataagct ttacacagga tcatgaagga   46440
tgaaagaatt tcaccaatat tataataatt tcaatcaacc tgatagctta ggggataaac   46500
taatttgaag atacagcttg cctccgataa gccagaattc cagagcttct ggcattataa   46560
tctagcaagg ttagagatca tggatcactt tcagagaaaa acaaaaacaa actaaccaaa   46620
```

```
agcaaaacag aaccaaaaaa ccaccataaa tacttcctac cctgttaatg gtccaatatg 46680
tcagaaacag cactgtgtta gaaataaagc tgtctaaagt acactaatat tcgagttata 46740
atagtgtgtg gactattagt caataaaaac aacccttgcc tctttagagt tgttttccat 46800
gtacacgcac atcttatgtc ttagagtaag attccctgag aagtgaacct agcatttata 46860
caagataatt aattctaatc cacagtacct gccaaagaac attctaccat catctttact 46920
gagcatagaa gagctacgcc aaaaccctgg gtcatcagcc agcacacaca cttatccagt 46980
ggtaaatac a catcatctgg tgtatacata cataacctgaa tatggaatca aatattttc 47040
taagatgaaa cagtcatgat ttatttcaaa taggtacgga taagtagata ttgaggtaag 47100
cattaggtct tatattatgt aacactaatc tattactgcg ctgaaactgt ggctttatag 47160
aaattgtttt cactgcacta ttgagaaatt aagagataat ggcaaaagtc acaaagagta 47220
tattcaaaaa gaagtatagc acttttttcct tagaaaccac tgctaactga aagagactaa 47280
gatttgtccc gtcaaaaatc ctggacctat gcctaaaaca catttcacaa tccctgaact 47340
tttcaaaaat tggtacatgc tttagcttta aactacaggc ctcactggag ctagagacaa 47400
gaaggtaaaa aacggctgac aaaagaagtc ctggtatcct ctatgatggg agaaggaaac 47460
tagctaaagg gaagaataaa ttagagaaaa actggaatga ctgaatcgga acaaggcaaa 47520
ggctataaaa aaaattagca gtatcctctt gggggcccct tccccacact atctcaatgc 47580
aaatatctgt ctgaaacggt ccctggctaa actccaccca tgggttggcc agccttgcct 47640
tgaccaatag ccttgacaag gcaaacttga ccaatagtct tagagtatcc agtgaggcca 47700
ggggccggcg gctggctagg gatgaagaat aaaaggaagc accettcagc agttccacac 47760
actcgcttct ggaacgtctg aggttatcaa taagctccta gtccagacgc catgggtcat 47820
ttcacagagg aggacaaggc tactatcaca agcctgtggg gcaaggtgaa tgtggaagat 47880
gctggaggag aaaccctggg aaggtaggct ctggtgacca ggacaaggga gggaaggaag 47940
gaccctgtgc ctggcaaaag tccaggtcgc ttctcaggat ttgtggcacc ttctgactgt 48000
caaactgttc ttgtcaatct cacaggctcc tggttgtcta cccatggacc cagaggttct 48060
ttgacagctt tggcaacctg tcctctgcct ctgccatcat gggcaacccc aaagtcaagg 48120
cacatggcaa gaaggtgctg acttccttgg gagatgccac aaagcacctg gatgatctca 48180
agggcacctt tgcccagctg agtgaactgc actgtgacaa gctgcatgtg gatcctgaga 48240
acttcaaggt gagtccagga gatgtttcag ccctgttgcc tttagtctcg aggcaactta 48300
gacaacggag tattgatctg agcacagcag ggtgtgagct gtttgaagat actggggttg 48360
ggggtgaaga aactgcagag gactaactgg gctgagaccc agtggtaatg ttttagggcc 48420
taaggagtgc ctctaaaaat ctagatggac aattttgact ttgagaaaag agaggtggaa 48480
atgaggaaaa tgacttttct ttattagatt ccagtagaaa gaactttcat ctttccctca 48540
tttttgttgt tttaaaacat ctatctggag gcaggacaag tatggtcgtt aaaaagatgc 48600
aggcagaagg catatattgg ctcagtcaaa gtggggaact ttggtggcca aacatacatt 48660
gctaaggcta ttcctatatc agctggacac atataaaatg ctgctaatgc ttcattacaa 48720
acttatatcc tttaattcca gatgggggca aagtatgtcc aggggtgagg aacaattgaa 48780
acatttgggc tggagtagat tttgaaagtc agctctgtgt gtgtgtgtgt gtgtgcgcgc 48840
gcgcgtgtgt gtgtgtgtgt cagcgtgtgt ttcttttaac gtcttcagcc tacaacatac 48900
agggttcatg gtggcaagaa gatagcaaga tttaaattat ggccagtgac tagtgcttga 48960
aggggaacaa ctacctgcat ttaatgggaa ggcaaaatct caggctttga gggaagttaa 49020
cataggcttg attctgggtg gaagcttggt gtgtagttat ctggaggcca ggctggagct 49080
ctcagctcac tatgggttca tctttattgt ctcctttcat ctcaacagct cctgggaaat 49140
gtgctggtga ccgttttggc aatccatttc ggcaaagaat tcaccccctga ggtgcaggct 49200
tcctggcaga agatggtgac tgcagtggcc agtgccctgt cctccagata ccactgagct 49260
cactgcccat gattcagagc tttcaaggat aggctttatt ctgcaagcaa tacaaataat 49320
aaatctattc tgctgagaga tcacacatga tttttcttcag ctcttttttt tacatctttt 49380
taaatatatg agccacaaag ggtttatatt gagggaagtg tgtatgtgta tttctgcatg 49440
cctgtttgtg tttgtggtgt gtgcatgctc ctcatttatt tttatatgag atgtgcattt 49500
tgatgagcaa ataaaagcag taaagacact tgtacacggg agttctgcaa gtgggagtaa 49560
atggtgtagg agaaatccgg tgggaagaaa gacctctata ggacaggact tctcagaaac 49620
agatgttttg gaagagatgg gaaaaggttc agtgaagacc tgggggctgg attgattgca 49680
gctgagtagc aaggatggtt cttaaggaag ggaaagtgtt ccaagcttta ggaattcaag 49740
gtttagtcag gtgtagcaat tctatttat taggaggaat actatttcta atggcactta 49800
gcttttcaca gcccttgtgg atgcctaaga aagtgaaatt aatcccatgc cctcaagtgt 49860
gcagattggt cacagcattt caagggagag acctcattgt aagactctgg gggaggtggg 49920
gacttaggtg taagaaatga atcagcagag gctcacaagt cagcatgagc atgttatgtc 49980
tgagaaacag accagcactg tgagatcaaa atgtagtggg aagaatttgt acaacattaa 50040
ttggaaggct tacttaatgg aatttttgta tagttggatg ttagtgcatc tctataagta 50100
agagtttaat atgatggtgt tacggaccta atgtttgtgt ctcctcaaaa ttcacatgct 50160
gaatccccaa ctcccaactg accttatctg tgggggaggc ttttgaaaag taattaggtt 50220
tagatgagct cataagagca gatccccatc ataaaattat tttccttatc agaagcagag 50280
agacaagcca tttctctttc ctcccggtga ggacacagtg agaagtccgc catctgcaat 50340
ccaggaagag aaccctgacc acgagtcagc cttcagaaat gtgagaaaaa actctgttgt 50400
tgaagccacc cagtcctttg tattttgtta tagcacctgg cactgagtaa ggcagatgaa 50460
gaaggagaaa aaaataagct tgggtttttga gtggactaca gaccatgttt atctcaggtt 50520
tgcaaagctc ccctcgtccc ctatgtttca gtataaaata cctactctac tactctcatc 50580
tataagaccc aaataataag cctgcgccct tctctctaac tttgatttct cctatttta 50640
cttcaacatg ctttactcta gccttgtaat gtctttacat acagtgaaat gtaaagttct 50700
ttattctttt tttctttctt tcttttttct cctcagcctc agaatttggc acatgccctt 50760
ccttctttca ggaacttctc caacatctct gcctggctcc atcatatcat aaaggtccca 50820
cttcaaatgc agtcactacc gtttcagaat atgcactttc tttcttttttt gtttttttgtt 50880
tttttaagt caaagcaaat ttcttgagag agtaaagaaa taaacgaatg actactgcat 50940
aggcagagca gccccgaggg ccgctggttg ttcctttat ggttatttct tgatgatatg 51000
ttaaacaagt tttggattat ttatgccttc tcttttttagg ccatataggg taactttcag 51060
acattgccat ggcattttttc tttttaattta atttactgtt accttaaatt caggggtaca 51120
cgtacaggat atgcaggttt gtttttatagg taaaagtgtg ccatggtttt aatgggtttt 51180
tttttttcttg taaagttgtt taagtttctt gtttactctg gatattaggc ctttgtcaga 51240
agaatagatt ggaaaatctt tttcccattc tgtagattgt ctttcgctct gatggtagtt 51300
tcttttttgctg agcaggagct ctttagttta attagattcc attggtcaat ttttgctttt 51360
```

```
gctgcaattg cttttcacgc tttcatcatg aaatctgtgc ccgtgtttat atcatgaata   51420
gtattgcctt gattttttc taggcttttt atagtttggg gttttttcatt taagtctcta   51480
atccatctgg agttaatttt ggataaggta taaggaagga gtccagtttc atttttcagc   51540
atatggctag ccagttctcc cccatcattt attaaattga aaatcctttc cccattgctt   51600
gcttttgtca ggtttctaaa agaccagatg gttgtaggta caatatgcag tttcttcaag   51660
tcatataata ccatctgaaa tctcttatta attcatttct tttagtatgt atgctggtct   51720
cctctgctca ctatagtgag ggcaccatta gccagagaat ctgtctgtct agttcatgta   51780
agattctcag aattaagaaa aatggatggc atatgaatga aacttcatgg atgacatatg   51840
gaatctaata tgtatttgtt gaattaatgc ataagatgca acagagagaa gttgacaact   51900
gcaatgataa cctggtattg atgatataag agtctataga tcacagtaga agcaataatc   51960
atggaaaaca attggaaatg gggaacagcc acaaacaaga aagaatcaat acttccagga   52020
aagtgactgc aggtcacttt tcctggagcg ggtgagagaa aagtggaagt tagcagtaac   52080
tgctgaattc ctggttggct gatggaaaga tggggcagct gttcactggt acgcagggtt   52140
ttagatgtat gtacctaagg atatgaggta tggcaatgaa cagaaattct tttgggaatg   52200
agttttaggg ccattaaagg acatgacctg aagtttcctc tgaggccagt ccccacaact   52260
caatataaat gtgtttcctg catatagtca aagttgccac ttcttttttct tcatatcatc   52320
gatctctgct cttaaagata atcttggttt tgcctcaaac tgtttgtcac tacaaacttt   52380
ccccatgttc ctaagtaaaa caggtaactg cctctcaact atatcaagta gactaaaata   52440
ttgtgtctct aatatcagaa attcagcttt aatatattgg gtttaactct ttgaaattta   52500
gagtctcctt gaaatacaca tggggggtgat ttcctaaact ttatttcttg taaggattta   52560
tctcagggggt aacacacaaa ccagcatcct gaacctctaa gtatgaggac agtaagcctt   52620
aagaatataa aataaactgt tcttctctct gccggtgaaa gtgtgccctg tctattcctg   52680
aaattgcttg tttgagacgc atgagacgtg cagcacatga gacacgtgca gcagcctgtg   52740
gaatattgtc agtgaagaat gtctttgcct gattagatat aaagacaagt taaacacagc   52800
attagactat agatcaagcc tgtgccgac acaaatgacc taatgcccag cacgggccac   52860
ggaatctcct atcctcttgc ttgaacagag cagcacactt ctcccccaac actattagat   52920
gttctggcat aattttgtag atatgtagga tttgacatgg actattgttc aatgattcag   52980
aggaaatctc ctttgttcag ataagtacac tgactactaa atggattaaa aaacacagta   53040
ataaaaccca gtttttcccct tacttcccta gtttgtttct tattctgctt tcttccaagt   53100
tgatgctgga tagaggtgtt tatttctatt ctaaaaagtg atgaaattgg ccgggcgcgg   53160
tggctcacac ctgtaatccc agcactttgg gaggctgagg tgggcggatc acgaggtcag   53220
gagatcaaga ccatcctggc taacatggtg aaacccatc tctactaaaa atacaaaaaa   53280
ttagccagac acagtggcgg gtgcctgtag tcccagctac tcgggaggct gaggcaggag   53340
aatggcgtga acctgggagg cagagcttgc ggtgagccaga gatcgcgcca ctgcacactc   53400
cagcctgggt gacaaagcga gactccatct caaaaaaaaa aaaaaaaaaa agaaaaagaa   53460
agaaagaaag aaaaaaaaac tgatgaaatt gtgtattcaa tgtagtctca agagaattga   53520
aaaccaagaa aggctgtggc ttcttccaca taaagcctgg atgaataaca ggataacacg   53580
ttgttacatt gtcacaactc ctgatccagg aattgatggc taagatattc gtaattctta   53640
tccttttcag ttgtaactta ttcctatttg tcagcattca ggttattagc ggctgctggc   53700
gaagtccttg agaaataaac tgcacacttg atggtggggg tagtgtagga aaatggaggg   53760
gaaggaagta aagtttcaaa ttaagcctga acagcaaagt tccccctgaga aggccacctg   53820
gattctatca gaaactcgaa tgtccatctt gcaaaacttc cttgcccaaa ccccacccct   53880
ggagtcacaa cccacccttg accaatagat tcattttact gagggaggca aaggctggt   53940
caatagattc atttcactgg gagaggcaaa gggctggggg ccagagagga gaagtaaaaa   54000
gccacacatg aagcagcaat gcaggcatgc ttctggctca tctgtgatca ccaggaaact   54060
cccagatctg acactgtagt gcatttcact gctgacaaga aggctgctgc caccagcctg   54120
tgaagcaagg ttaaggtgag aaggctggag gtgagattct gggcaggtga gtactggaag   54180
ccggacaag gtgcagaaag gcagaaagtg tttctgaaag agggattagc ccgttgtctt   54240
acatagtctg actttgcacc tgctctgtga ttatgactat cccacagtct cctggttgtc   54300
tacccatgga cctagaggta ctttgaaagt tttggatatc tgggctctga ctgtgcaata   54360
atgggcaacc ccaaagtcaa ggcacatggc aagaaggtgc tgatctcctt cggaaaagct   54420
gttatgctca cggatgacct caaaggcacc tttgctacac tgagtgacct gcactgtaac   54480
aagctgcacg tggaccctga gaacttcctg gtgagtagta agtacactca cgctttcttc   54540
tttacccta gatatttgca ctatgggtac tttttgaaagc agaggtggct ttctcttgtg   54600
ttatgagtca gctatgggat atgatatttc agcagtggga ttttgagagt tatgttgctg   54660
taaataacat aactaaaatt tggtagagca aggactatga ataatggaag gccacttacc   54720
atttgatagc tctgaaaaac acatcttata aaaaattctg gccaaaatca aactgagtgt   54780
ttttggatga gggaacagaa gttgagatag agaaaataac atctttcctt tggtcagcga   54840
aattttctat aaaaattaat agtcactttt ctgcatagtc ctggaggtta gaaaaagatc   54900
aactgaacaa agtagtggga agctgttaaa aagaggattg tttccctccg aatgatgatg   54960
gtatactttt gtacgcatgg tacaggattc tttgttatga gtgtttggga aaattgtatg   55020
tatgtatgta tgtatgtatg tgatgactgg ggacttatcc tatccattac tgttccttga   55080
agtactatta tcctacttttt taaaaggacg aagtctctaa aaaaaaaatg aaacaatcac   55140
aatatgttgg ggtagtgagt tggcatagca agtaagagaa ggataggaca caatgggagg   55200
tgcaggggctg ccagtcatat tgaagctgat atctagccca taatggtgag agttgctcaa   55260
actctggtga aaaaggatgt aagtgttata tctatttact gcaagtccag cttgaggcct   55320
tctattcact atgtaccatt ttcttttttta tcttcactcc ctcccagct cttaggcaac   55380
gtgatattga ttgtttttggc aacccacttc agcgaggatt ttaccctaca gatacaggct   55440
tcttggcagt aactaacaaa tgctgtggtt aatgctgtag cccacaagac cactgagttc   55500
cctgtccact atgtttgtac ctatggtcca ctatgtttgt acctatgtcc caaaatctca   55560
tctcctttag atgggggagg ttggggagaa gagcagtatc ctgcctgctg attcagttcc   55620
tgcatgataa aaatagaata aagaaatatg ctctctaaga aatatcattg tactcttttt   55680
ctgtcttttat attttacccct gattcagcca aaaggacgca ctatttctga tggaaatgag   55740
aatgttggag aatgggagtt taaggacaga gaagatactt tcttgcaatc ctgcaagaaa   55800
agagagaact cgtgggtgga tttagtgggg tagttactcc taggaagggg aaatcgtctc   55860
tagaataaga caatgttttt acagaaaggg aggtcaatgg aggtactctt tggaggtgta   55920
agaggattgt tggtagtgtg tagaggtatg ttaggactca aattagaagt tctgtatagg   55980
ctattatttg tatgaaactc aggatatagc tcatttggtg actgcagttc acttctactt   56040
attttaaaca acatattttt tattatttat aatgaagtgg ggatgggggct tcctagagac   56100
```

-continued

```
caatcaaggg ccaaaccttg aactttctct taacgtcttc aatggtatta atagagaatt   56160
atctctaagg catgtgaact ggctgtcttg gttttcatct gtacttcatc tgctacctct   56220
gtgacctgaa acatatttat aattccatta agctgtgcat atgatagatt tatcatatgt   56280
attttcctta aaggattttt gtaagaacta attgaattga tacctgtaaa gtctttcatca   56340
cactacccaa taaataataa atctctttgt tcagctctct gtttctataa atatgtacaa   56400
gttttattgt ttttagtggt agtgatttta ttctctttct atatatatac acacacatgt   56460
gtgcattcat aaatatatac aatttttatg aataaaaaat tattagcaat caatattgaa   56520
aaccactgat ttttgtttat gtgagcaaac agcagattaa aaggctgaga tttaggaaac   56580
agcacgttaa gtcaagttga tagaggagaa tatggacatt taaaagaggc aggatgatat   56640
aaaattaggg aaactggatg cagagaccag atgaagtaag aaaaatagct atcgttttga   56700
gcaaaaatca ctgaagtttc ttgcatatga gagtgacata ataaatagggg aaacgtagaa   56760
aattgattca catgtatata tatatataga actgattaga caaagtctaa cttgggtata   56820
gtcagaggag cttgctgtaa ttatattgag gtgatggata aagaactgaa gttgatggaa   56880
acaatgaagt taagaaaaaa aatcgagtaa gagaccattg tggcagtgat tgcacagaac   56940
tggaaaacat tgtgaaacag agagtcagag atgacagcta aaatccctgt ctgtgaatga   57000
aaagaaggaa atttattgac agaacagcaa atgcctacaa gcccctgtt tggatctggc    57060
aatgaacgta gccattctgt ggcaatcact tcaaactcct gtacccaaga cccttaggaa   57120
gtatgtagca ccctcaaacc taaaacctca aagaaagagg ttttagaaga tataataccc   57180
tttcttctcc agtttcatta atcccaaaac ctctttctca aagtatttcc tctatgtgtc    57240
cacccccaaag agctcacctc accatatctc ttgagtggga gcacatagat aggcggtgct   57300
accatctaac agcttctgaa attcctttgt catattttg agtccccact aataacccac   57360
aaagcagaat aaatacccagt tgctcatgta caataatcac tcaactgctg tcttgtagca   57420
tacattaatt aagcacattc tttgaataat tactgtgtcc aaacaatcac actttaaaat   57480
ctcacacttg tgctatccct tgcccttctg aatgtcactc tgtattttaa atgaagagat   57540
gagggttgaa tttcctgtgt tacttattgt tcatttctcg atgaggagtt ttcacattca   57600
cctttagtgg aaaacacata agtacacatc ttacaggaaa aatataccaa actgacatgt   57660
agcatgaatg cttgtgcatg tagtcatata aaatcttgta gcaatgtaaa cattctctga   57720
tatacacata cagatgtgtc tatatgtcta cacaatttct tatgctccat gaacaaacat   57780
tccatgcaca cataagaaca cacactgtta cagatgcata cttgagtgca ttgacaaaat   57840
taccccagtc aatctagaga atttggattt ctgcatttga ctctgttagc tttgtacatg   57900
ctgttcattt actctgggtg atgtctttcc ctcattttgc cttgtctatc ttgtactcat   57960
actttaagtc ctaacttata tgttatctca actaagaagc tatttttttt taatttaac    58020
tgggcttaaa gccctgtcta taaactctgc tacaattatg ggctctttct tataatattt   58080
agtgtttttc ctactaatgt acttaatctg ctcattgtat attcctacca ctaaatttta   58140
acctctttta tggtagagac attgtcttgt aaactcttat ttccctagta tttggagatg   58200
aaaaaaaaga ttaaattatc caaaattaga tctctctttt ctacattatg agtattacac   58260
tatccataga gaagtttgtt tgagacctaa actgaggaac ctttggttct aaaatgacta   58320
tgtgatatct tagtatttat aggtcatgag gttccttcct ctgcctctgc tatagtttga   58380
ttagtcaaca agcatgtgtc atgcatttat tcacatcaga atttcataca ctaataaagac   58440
atagtatcag aagtcagttt attagttata tcagttaggg tccatcaagg aaaggacaaa   58500
ccattatcag ttactcaacc tagaattaaa tacagctctt aatagttaat tatccttgta   58560
ttggaagagc taaaatatca aataaaggac agtgcagaaa tctagatgtt agtaacatca   58620
gaaaacctct tccgccatta ggcctagaag ggcagaagga gaaatgttt ataccaccag   58680
agtccagaac cagagcccat aaccagaggt ccactggatt cagtgagcta gtgggtgctc   58740
cttggagaga gccagaactg tctaatgggg gcatcaaagt atcagccata aaaaaccata   58800
aaaaagactg tctgctgtag gagatccgtt cagagagaga gagagaccag aaataatctt   58860
gcttatgctt tccctcagcc agtgtttacc attgcagaat gtacatgcga ctgaaagggt   58920
gaggaaacct gggaaatgtc agttcctcaa atacagagaa cactgagggg aaggatgagaa   58980
ataaatgtga aagcagacat gaatggtaat tgacagaagg aaactaggat gtgtccagta   59040
aatgaataat tacagtgtgc agtgattatt gcaatgatta atgtattgat aagataatat   59100
gaaaacacag aattcaaaca gcagtgaact gagattgaaa ttgtggagag cactggcatt   59160
taagaatgtc acacttagaa tgtgtctcta ggcattgttc tgtgcatata tcatctcaat   59220
attcattatc tgaaaattat gaattaggta caaagctcaa ataatttatt ttttcaggtt   59280
agcaagaact tttttttttt ttttctgaga tagagcattg ctatggttgc ccaggctgga   59340
gtgcaatggc atgatccagg ctcactgcaa catctgcctc ccaggttcaa gcgattctcc   59400
tgcctcagcc tcccaagtag ctggcactac aggcatgtgc caccaccatg cctggctaat   59460
tttctatttt tagtagatag ggggtttcac catgttggtc aggctgatct cgaactccta   59520
acatcaggta atccaccctc ctcggcctct gaaagtgctg ggatcacagg cgtgagccac   59580
cacacccagc caagaatgtg aattttgtag aaggatataa cccatatttc tctgaccct   59640
gagtccttag tatacctccc ataccatgtg gctcatcctc cttacataca tttcccatct   59700
ttcaccctac ctttttccttt ttgtttcagc ttttcactgt gtcaaaatct agaaccttat   59760
ctcctacctg ctctgaaacc aacagcaagt tgacttccat tctaacccac attggcatta   59820
cactaattaa aatcgatact gagttctaaa atcatcgggg attttgggga ctatgtctta   59880
cttcatactt ccttgagatt tcacattaaa tgttggtgtt cattaaaggt ccttcattta   59940
actttgtatt catcacactc ttggattcac agttatatct aaactcttaa atacagcctg   60000
tataatccca attcccaact ctgatttcta acctctgacc tccaacctca gtgccaaacc   60060
catatatcaa acaatgtact gggcttattt atatagatgt cctataggca cctcagactc   60120
agcatgggta tttcacttgt tatactaaaa ctgtttctct tccagtgttt tccattttag   60180
tcattagata gctacttgcc cattcaccaa ggtcacagat taaaatcatt tccctacctc   60240
taatcaacag ttcgattctg cttcaatttg tccctatcta ttaatcacca ctcttactgc   60300
ccagtcaggt cctcattgtt tcctgaacaa gagtagatgc tattctttcc acttttagac   60360
cttatcctgg ctggatgcgg tggctcaggc ttgtaaaccc agcactttgg gaggccaagg   60420
caggcagatc acttgaggtc aggagttcaa gaccagcctg accaacatgg tgaaacccca   60480
tctctactaa aaatacaaaa tcagccgggc gtgtggtgca tgcctgtaat cccagctatt   60540
caggtggctg aggcaggaga attgcttgaa cccaggaggc agaggttgcg gtgagcctag   60600
attgcaccat tgcactctag cttgggcaat agggatgaaa ctccatctca gaagagaaaa   60660
gaaaaaaaga cctattctg ttatacaaat cctctcaatg caatccatat agaataaaca   60720
tgtaaccaga tctcccaatg tgtaaaatca tttcaggtag aacagaatta aagtgaaaag   60780
ccaagtcttt ggaattaaca gacaaagatc aaataacagt cctcatggcc ttaagaattt   60840
```

```
acctaacatt ttttttagaa tcaattttct tatatatgaa ttggaaacat aattcctccc   60900
tcacaaacac attctaagat tttaaggaga tattgatgaa gtacatcatc tgtcattttt   60960
aacaggtagt ggtagtgatt cacacagcac attatgatct gttcttgtat gttctgttcc   61020
attctgtatt cttgacctgg ttgtattctt tctgagctcc agatccacat atctaagtac   61080
atctttttgc attttacaag agtgcataca atacaatgta tccaagactg tatttctgat   61140
tttatcgtac cactaaactc acaaatgtgg ccctattctt gtgttcacga ctgacatcac   61200
cgtcatggtc caagtctgat aatagaaatg gcattgtcac tttcttccct actgcaacag   61260
aagcccagct atttgtctcc cattttctct acttctaaaa tacatttctt cactaagtga   61320
gaataatctt ttaaagacac aaatcaaacc atgccaccac ctttcttgaa ttattcaata   61380
tctttcgttg gcttccaggt tacagaaaaa taacttgtaa caaagtttaa aggtcattca   61440
tggctcctct ctaccctatt ttataacatt tccccttgtg atcagaatct caggcacatc   61500
atccatcttt ctatatacaa ataaagtcat atagtttgaa ctcacctctg gttacttta   61560
atcaaccaaa tgctgtaaaa tgcatttgta tcgctacgtg ttaagcagta gttgattctt   61620
ttcatttctg tgtaatattc tattctttga ctataccgta atttatcaat tctactgttg   61680
gtaagcattt aagtggctac cggtttgagg tttttatgat tattgctgtc ataagcattt   61740
ctatacatgt ctttggatac acacatgcat gtgtttctga atatctaaaa atgtaattgc   61800
taggtaatag acttatcaag catccagcat ttgtggatac tattaaaggt tttccaaagg   61860
ggttatacta ttgtacagtg tcaccaacag agtttgagtt tctattgatc catatcacca   61920
ccaaaatttg aactgtcagt cttatctctt ctcttgtctc ttttttcctc tttttttcc   61980
ttcccttccc ctctcttcgt ttcttttctc tcctcttctc ttctttcctc tcttcccttc   62040
cctttctctt tctcttccct atcccttctc ctctcctctc ccctccttt ttctcctctc   62100
ctctccatta tttatttttc cttcttctcc tccatccctt ccatcctctc tcttccccctc   62160
ttccttcctt cctttctcca tttcttcctc ctctttcctt caatccttcc ttttggatat   62220
gctcatgggt gtgtatttgt ctgccattgt ggcattattt gaattcagaa aagagtgaaa   62280
aactactggg atcttcattc ctgggtctaa ttccacattt tttttttaaga acacatctgt   62340
aaaaatgttc tgtactagca tattcccagg aacttcgtta aatttaatct ggctgaatat   62400
ggtaaatcta ctttttcactt tgcattcttt ctttagtcat accataattt taaacattca   62460
aaatatttgt atataatatt tgattttatc tgtcattaaa atgttaacct taaaattcat   62520
gtttccagaa cctatttcaa taactggtaa ataaacacta ttcattttt aaatattctt   62580
ttaatggata tttatttcaa tataataaaa aattagagtt ttattatagg aagaatttac   62640
caaaagaagg aggaagcaag caagtttaaa ctgcagcaat agatttgtcc attccaacct   62700
ctcaaaattc ccttggagac aaaaatctct agaggcaaag aagaacttta tattgagtca   62760
acttgttaaa acatctgctt ttagataagt tttcttagta taaagtgaca gaaacaaata   62820
agttaaactc taagatacat tccactatat tagcctaaaa cacttctgca aaaatgaaac   62880
taggaggata ttttttagaaa caactgctga aagagatgcg gtggggagat atgtagagga   62940
gaacagggtt tctgagtcaa gacacacatg acagaacagc caatctcagg gcaagttaag   63000
ggaatagtgg aatgaaggtt cattttttcat tctcacaaac taatgaaacc ctgcttatct   63060
taaaccaacc tgctcactgg agcagggagg acaggaccag cataaaaggc agggcagagt   63120
cgactgttgc ttacactttc ttctgacata acagtgttca ctagcaacct caaacagaca   63180
ccatggtgca tctgactcct gaggagaaga ctgctgtcaa tgccctgtgg ggcaaagtga   63240
acgtggatgc agttggtggt gaggccctgg gcaggttggt atcaaggtta taagagaggc   63300
tcaaggaggc aaatggaaac tgggcatgtg tagacagaga agactcttgg gtttctgata   63360
ggcactgact ctctgtccct tgggctgtttt cctcaccctc agattactgg tggtctaccc   63420
ttggacccag aggttctttg agtccttgg ggatctgtcc tctcctgatg ctgttatggg   63480
caaccctaag gtgaaggctc atggcaagaa ggtgctaggt gcctttagtg atggcctggc   63540
tcacctggac aacctcaagg gcactttttc tcagctgagt gagctgcact gtgacaagct   63600
gcacgtggat cctgagaact tcagggtgag tccaggagat gcttcacttt tctctttta   63660
ctttctaatc ttacattttg gttctttac ctacctgctc ttctcccaca tttttgtcat   63720
tttactatat tttatcattt aatgcttcta aaattttgtt aattttttat ttaaatattc   63780
tgcatttttt ccttcctcac aatcttgcta tttttaaatta tttaatatcc tgtctttctc   63840
tcccaacccc ctcccttcat ttttccttct ctaacaacaa ctcaaattat gcataccagt   63900
tctcacctgc taattctgca cttagaataa tcctttgtc tctccacatg ggtatgggag   63960
aggctccaac tcaaagatga gaggcataga atactgtttt agaggctata aatcatttta   64020
caataaggaa taattggaat tttataaatt ctgtagtaaa tggaatggaa aggaaagtga   64080
atatttgatt atgaaagact aggcagttac actggaggtg gggcagaagt cgttgctagg   64140
agacagccca tcatcacact gattaatcaa ttaatttgta tctattaatc tgtttatagt   64200
aattaatttg tatatgctat atacacatac aaaattaaaa ctaatttgga attaatttgt   64260
atatagtatt atacagcata tatagcatat atgtacatat atagactaca tgctagttaa   64320
gtacatagag gatgtgtgtg tatagatata tgttatatgt atgcattcat atatgtactt   64380
atttatgctg atgggaataa cctgggatc agtttgtct aagatttggg cagaaaaaaa   64440
tgggtgttgg ctcagtttct cagaagccag tctttatttc tctgttaacc atatgcatgt   64500
atctgcctac ctcttctccg cagctcttgg gcaatgtgct ggtgtgtgtg ctggcccgca   64560
actttggcaa ggaattcacc ccacaaatgc aggctgccta tcagaaggtg gtggctggtg   64620
tggctaatgc cctggctcac aagtaccatt gagatcctgg actgtttcct gataaccata   64680
agaagaccct atttccctag attctatttt ctgaacttgg gaacacaatg cctacttcaa   64740
gggtatggct tctgcctaat aaagaatgtt cagctcaact tcctgattaa tttcacttat   64800
ttcattttttt tgtccaggtg tgtaagaagg ttcctgaggc tctacagata gggagcactt   64860
gtttatttta caaagagtac atgggaaaag agaaaagcaa gggaaccgta caaggcatta   64920
atgggtgaca cttctacctc caaagagcag aaattatcaa gaactcttga tacaaagata   64980
atactggcac tgcagaggtt ctagggaaga cctcaaccct aagacatagc ctcaagggta   65040
atgctacgat taaactccaa caattactga gaaaataatg tgctcaatta aaggcataat   65100
gattactcaa gacaatgtta tgttgtcttt cttcctcctt cctttgcctg cacattgtag   65160
cccataatac tatacccat caagtgttcc tgctccaaga aatagcttcc tcctcttact   65220
tgcccagaa catctctgta aagaatttcc tcttatcttc ccatatttca gtcaagattc   65280
attgctcacg tattacttgt gacctctctt gaccccagcc acaataaact tctctatact   65340
acccaaaaaa tcttttccaaa ccctcccca caccattttt tatattttta tatttttctt   65400
atttatttca tgcacacaca cacactccgt gctttataag caattctgcc tattctctac   65460
cttcttacat gcctactgtg cctcatatta aattcatcaa tgggcagaaa gaaaatattt   65520
attcaagaaa acagtgaatg aatgaacgaa tgagtaaatg agtaaatgaa ggaatgatta   65580
```

-continued

```
ttccttgctt tagaacttct ggaattagag gacaatatta ataataccat cgcacagtgt   65640
ttctttgttg ttaatgctac aacatacaaa gaggaagcat gcagtaaaca accgaacagt   65700
tatttccttt ctgatcatag gagtaatatt tttttccttg agcaccattt ttgccatagg   65760
taaaattaga aggattttta gaactttctc agttgtatac atttttaaaa atctgtatta   65820
tatgcatgtt gattaatttt aaacttactt gaatacctaa acagaatctg ttgtttcctt   65880
gtgtttgaaa gtgctttcac agtaactctg tctgtactgc cagaatatac tgacaatgtg   65940
ttatagttaa ctgtttgat cacaacattt tgaattgact ggcagcagaa gctctttat    66000
atccatgtgt tttccttaag tcattataca tagtaggcac tgagaactct ttatatctga   66060
ataagatatt taggaaccac tggtttacat atcagaagca gagctactca gggcattttg   66120
gggaagatca ctttcacatt cctgagcata gggaagttct cataagagta agatattaaa   66180
aggagatact tgtgtggtat tcgaaagaca gtaagagaga ttgtagacct tatgatcttg   66240
atagggaaaa caaactacat tcctttctcc aaaagtcaaa aaaaaagagc aaatatagct   66300
tactatacct tctattccta caccattaga agtagtcagt gagtctaggc aagatgttgg   66360
ccctaaaaat ccaaatacca gagaattcat gagaacatca cctggatggg acatgtgccg   66420
agcacacaca attactatat gctaggcatt gctatcttca tattgaagat gaggaggtca   66480
agagatgaaa aaagacttgg caccttgttg ttatattaaa attatttgtt agagtagagc   66540
ttttgtaaga gtctaggagt gtgggagcta aatgatgata cacatggaca caaaaaatag   66600
atcaacagac acccaggcct acttgagggt tgagggtggg aagagggaga cgatgaaaaa   66660
gaacctattg ggtattaagt tcatcactga gtgatgaaat aatctgtaca tcaagaccca   66720
gtgatatgca atttacctat ataacttgta catgtacccc caaatttaaa atgaaagtta   66780
aaacaaagta taggaatgga attaattcct caagatttgg cttttaatttt atttgataat   66840
ttatcaaatg gttgtttttc tttttctcact atggcgttgc tttataaact atgttcagta   66900
tgtctgaatg aaagggtgtg tgtgtgtgtg aaagagaggg agagaggaag ggaagagagg   66960
acgtaataat gtgaatttga gttcatgaaa attttttcaat aaaataattt aatgtcagga   67020
gaattaagcc taatagtctc ctaaatcatc catctcttga gcttcagagc agtcctctga   67080
attaatgcct acatgtttgt aaagggtgtt cagactgaag ccaagattct acctctaaag   67140
agatgcaatc tcaaatttat ctgaagactg tacctctgct ctccataaat tgacaccatg   67200
gcccacttaa tgaggttaaa aaaaagctaa ttctgaatga aaatctgagc ccagtggagg   67260
aaatattaat gaacaaggtg cagactgaaa tataaatttt tctgtaataa ttatgcatat   67320
actttagcaa agttctgtct atgttgactt tattgctttt ggtaagaaa tacaactttt    67380
taaagtgaac taaactatcc tatttccaaa ctattttgtg tgtgtgcggt ttgtttctat   67440
gggttctggt tttcttggag cattttatt tcattttaat taattaattc tgagagctgc     67500
tgagttgtgt ttactgagag attgtgtatc tgcgagagaa gtctgtagca agtagctaga   67560
ctgtgcttga cctaggaaca tatacagtag attgctaaaa tgtctcactt ggggaatttt   67620
agactaaaca gtagagcatg tataaaaata ctctagtcaa gtgctgcttt tgaaacaaat   67680
gataaaacca cactcccata gatgagtgtc atgattttca tggaggaagt taatattcat   67740
cctctaagta tacccagact agggccattc tgatataaaa cattaggact taagaaagat   67800
taatagactg gagtaaagga aatggacctc tgtctctctc gctgtctctt ttttgaggac   67860
ttgtgtgtgt gtgtgtgtgt gtgtgtgtgt gtgtgttgtg gtcagtgggg ctggaataaa   67920
agtagaaatag acctgcacct gctgtggcat ccattcacag agtagaagca agctcacaat   67980
agtgaagatg tcagtaagct tgaatagtt ttcaggaact ttgaatgctg atttagattt     68040
gaaactgagg ctctgaccat aaccaaattt gcactattta ttgcttcttg aaacttattt   68100
gcctggtatg cctgggctt tgatggtctt agtatagctt gcagccttgt ccctgcaggg    68160
tattatgggt aatagaaaga aaagtctgcg ttacactcta gtcacactaa gtaactacca   68220
ttggaaaagc aacccctgcc ttgaagccag gatgatggta tctgcagcag ttgccaacac   68280
aagagaagga tccatagttc atcatttaaa aaagaaaaca aaatagaaaa aggaaaacta   68340
tttctgagca taagaagttg tagggtaagt ctttaagaag gtgacaattt ctgccaatca   68400
ggatttcaaa gctcttgctt tgacaatttt ggtctttcag aatactataa atataaccta   68460
tattataatt tcataaagtc tgtgcatttt ctttgaccca ggatatttgc aaaagacata   68520
ttcaaacttc cgcagaacac tttatttcac atatacatgc ctcttatatc agggatgtga   68580
aacagggtct tgaaaactgt ctaaatctaa aacaatgcta atgcaggttt aaatttaata   68640
aaataaaatc caaaatctaa cagccaagtc aaatctgcat gttttaacat ttaaaatatt   68700
ttaaagacgt ctttttcccag gattcaacat gtgaaatctt ttctcaggga tacacgtgtg   68760
cctagatcct cattgcttta gttttttaca gaggaatgaa tataaaaaga aaatacttaa   68820
attttatccc tcttacctct ataatcatac ataggcataa tttttttaacc taggctccag   68880
atagccatag aagaaccaaa cactttctgc gtgtgtgaga ataatcagag tgagatttt     68940
tcacaagtac ctgatgaggg ttgagacagg tagaaaaagt gagagatctc tatttatta    69000
gcaataatag agaaagcatt taagagaata aagcaatgga aataagaaat ttgtaaattt   69060
cctctgata actagaaata gaggatccag tttcttttgg ttaacctaaa ttttatttca   69120
ttttattgtt ttatttatt ttattttatt ttattttgtg taatcgtagt ttcagagtgt    69180
tagagctgaa aggaagaagt aggagaaaca tgcaaagtaa aagtataaca ctttccttac   69240
taaaccgaca tgggtttcca ggtaggggca ggattcagga tgactgacag ggcccttagg   69300
gaacactgag accctacgct gacctcataa atgcttgcta cctttgctgt tttaattaca   69360
tcttttaata gcaggaagca gaactctgca cttcaaaagt tttttcctcac ctgaggagtt   69420
aatttagtac aagggggaaa agtacagggg gatgggagaa aggcgatcac gttgggaagc   69480
tatagagaaa gaagagtaaa tttttagtaaa ggaggtttaa acaaacaaaa tataaagaga   69540
aataggaact tgaatcaagg aaatgatttt aaaacgcagt attcttagtg gactagagga   69600
aaaaaataat ctgagccaag tagaagacct tttccctcc tacccctact ttctaagtca    69660
cagaggcttt ttgttcccc agacactctt gcagattagt ccaggcagaa acagttagat    69720
gtccccagtt aacctcctat ttgacaccac tgattacccc attgatagtc acactttggg   69780
ttgtaagtga ctttttattt atttgtattt ttgactgcat taagaggtct ctagtttttt   69840
atctcttgtt tcccaaaacc taataagtaa ctaatgcaca gagcacattg atttgtattt   69900
attctatttt tagacataat ttattagcat gcatgagcaa attaagaaaa acaacaacaa   69960
atgaatgcat atatatgtat atgtatgtgt gtatatatac acacatatat atatatattt   70020
tttcttttct taccagaagg ttttaatcca aataaggaga agatatgctt agaaccgagg   70080
tagagttttc atccattctg tcctgtaagt attttgcata ttctggagac gcaggaagag   70140
atccatctac atatcccaaa gctgaattat ggtagacaaa actcttccac ttttagtgca   70200
tcaacttctt atttgtgtaa taagaaaatt gggaaaacga tcttcaatat gcttaccaag   70260
ctgtgattcc aaatattacg taaatacact tgcaaaggag gatgtttta gtagcaattt     70320
```

-continued

```
gtactgatgg tatggggcca agagatatat cttagaggga gggctgaggg tttgaagtcc   70380
aactcctaag ccagtgccag aagagccaag gacaggtacg gctgtcatca cttagacctc   70440
accctgtgga gccacaccct agggttggcc aatctactcc caggagcagg gagggcagga   70500
gccagggctg ggcataaaag tcagggcaga gccatctatt gcttacattt gcttctgaca   70560
caactgtgtt cactagcaac ctcaaacaga caccatggtg catctgactc ctgaggagaa   70620
gtctgccgtt actgccctgt ggggcaaggt gaacgtggat gaagttggtg gtgaggccct   70680
gggcaggttg gtatcaaggt tacaagacag gtttaaggag accaatagaa actgggcatg   70740
tggagacaga gaagactctt gggtttctga taggcactga ctctctctgc ctattggtct   70800
attttcccac ccttaggctg ctggtggtct acccttggac ccagaggttc tttgagtcct   70860
ttggggatct gtccactcct gatgctgtta tgggcaaccc taaggtgaag gctcatggca   70920
agaaagtgct cggtgccttt agtgatggcc tggctcacct ggacaacctc aagggcacct   70980
ttgccacact gagtgagctg cactgtgaca agctgcacgt ggatcctgag aacttcaggc   71040
tgagtctatg ggacgcttga tgttttcttt cccttcttt tctatggtta agttcatgtc   71100
ataggaaggg gataagtaac agggtacagt ttagaatggg aaacagacga atgattgcat   71160
cagtgtggaa gtctcaggat cgtttagtt tctttattt gctgttcata acaattgttt   71220
tcttttgttt aattcttgct ttctttttt ttcttctccg caattttttac tattatactt   71280
aatgccttaa cattgtgtat aacaaaagga aatatctctg agatacatta agtaacttaa   71340
aaaaaaactt tacacagtct gcctagtaca ttactatttg gaatatatgt gtgcttattt   71400
gcatattcat aatctcccta ctttattttc ttttatttt aattgataca taatcattat   71460
acatatttat gggttaaagt gtaatgtttt aatatgtgta cacatattga ccaaatcagg   71520
gtaattttgc atttgtaatt ttaaaaaatg ctttcttctt ttaatatact tttttgttta   71580
tcttatttct aatactttcc ctaatctctt tctttcaggg caataatgat acaatgtatc   71640
atgcctcttt gcaccattct aaagaataac agtgataatt tctgggttaa ggcaatagca   71700
atatctctgc atataaatat ttctgcatat aaattgtaac tgatgtaaga ggtttcatat   71760
tgctaatagc agctacaatc cagctaccat tctgctttta ttttatggtt gggataaggc   71820
tggattattc tgagtccaag ctaggccctt ttgctaatca tgttcatacc tcttatcttc   71880
ctcccacagc tcctgggcaa cgtgctggtc tgtgtgctgg cccatcactt ggcaaagaa   71940
ttcaccccac cagtgcaggc tgcctatcag aaagtggtgg ctggtgtggc taatgccctg   72000
gcccacaagt atcactaagc tcgctttctt gctgtccaat ttctattaaa ggttcctttg   72060
ttccctaagt ccaactacta aactggggga tattatgaag ggccttgagc atctggattc   72120
tgcctaataa aaaacattta ttttcattgc aatgatgtat ttaaattatt tctgaatatt   72180
ttactaaaaa gggaatgtgg gaggtcagtg catttaaaac ataaagaaat gaagagctag   72240
ttcaaacctt gggaaaatac actatatctt aaactccatg aaagaaggtg aggctgcaaa   72300
cagctaatgc acattggcaa cagcccctga tgcatatgcc ttattcatcc ctcagaaaag   72360
gattcaagta gaggcttgat ttggaggtta aagttttgct atgctgtatt ttacattact   72420
tattgttta gctgtcctca tgaatgtctt ttcactaccc atttgcttat cctgcatctc   72480
tcagccttga ctccactcag ttctcttgct tagagatacc accttcccc tgaagtgttc   72540
cttccatgtt ttacggcgag atggtttctc ctcgcctggc cactcagcct tagttgtctc   72600
tgttgtctta tagaggtcta cttgaagaag gaaaaacagg ggtcatggtt tgactgtcct   72660
gtgagccctt cttccctgcc tcccccactc acagtgaccc ggaatctgca gtgctagtct   72720
cccggaacta tcactctttc acagtctgct ttggaaggac tgggcttagt atgaaaagtt   72780
aggactgaga agaatttgaa aggcggcttt ttgtagcttg atattcacta ctgtcttatt   72840
accctgtcat aggcccaccc caaatggaag tcccattctt cctcaggatg tttaagatta   72900
gcattcagga agagatcaga ggtctgctgg ctcccttatc atgtcccta tggtgcttct   72960
ggctctgcag ttattagcat agtgttacca tcaaccacct taacttcatt tttcttattc   73020
aatacctagg taggtagatg ctagattctg gaaataaaat atgagtctca agtggtcctt   73080
gtcctctctc ccagtcaaat tctgaatcta gttggcaaga ttctgaaatc aaggcatata   73140
atcagtaata agtgatgata gaagggtata tagaagaatt ttattatatg agagggtgaa   73200
accctcaaaa tgaaatgaaa tcagaccctt gtcttacacc ataaacaaaa ataaatttga   73260
atgggttaaa gaattaaact aagacctaaa accataaaaa tttttaaaga aatcaaaaga   73320
agaaaattct aatattcacg ttgcagccgt tttttgaatt tgatatgaga agcaaaggca   73380
acaaaaggaa aaataaagaa gtgaggctac atcaaactaa aaaatttcca cacaaaaaac   73440
aaaacaatga acaaatgaaa ggtgaaccat gaaatggcat atttgcaaac caaatatttc   73500
ttaaatattt tggttaatat ccaaaatata taagaaacac agatgattca ataacaaaca   73560
aaaaattaaa aataggaaaa taaaaaaatt aaaaagaaga aaatcctgcc atttatggca   73620
gaattgatga acctggagga tgtaaaacta agaaaaataa gcctgacaca aaaagacaaa   73680
tactacacaa ccttgctcat atgtgaaaca taaaaaagtc actctcatgg aaacagacag   73740
tagaggtatg gtttccaggg gttgggggtg ggagaatcag gaaactatta ctcaaagggt   73800
ataaaatttc agttatgtgg gatgaataaa ttctagatat ctaatgtaca gcatcgtgac   73860
tgtagttaat tgtactgtaa gtatatttaa aatttgcaaa gagagtagat ttttttttt   73920
ttttagatgg agttttgctc ttgttgtcca ggctggagtg caatggcaag atcttggctc   73980
actgcaacct ccgcctcctg ggttcaagca aatctcctgc ctcagcctcc cgagtagctg   74040
ggattacagg catgcgacac catgcccagc taattttgta ttttttagtag agacggggtt   74100
tctccatgtt ggtcaggctg atccgcctgc ctcggcccac caaggggctg ggattacagg   74160
cgtgagccac cgggcctggc cgagagtaga tcttaaaagc atttaccaca agaaaaaggt   74220
aactatgtga gataatgggt atgttaatta gcttgattgt ggtaatcatt tcacaaggta   74280
tacatatatt aaaacatcat gttgtacacc ttaaatatat acaatttta tttgtgaatg   74340
atacctcaat aaagttgaag aataataaaa aagaatagac atcacatgaa ttaaaaaact   74400
aaaaaataaa aaaatgcatc ttgatgatta gaattgcatt cttgattttt cagatacaaa   74460
tatccatttg actgtttact cttttccaaa acaatacaat aaattttagc actttatctt   74520
cattttcccc ttcccaatct ataattatat atatatatat tttagatatt ttgtatagtt   74580
ttactcccta gattttctag tgttattatt aaatagtgaa gaaatgttta cacttatgta   74640
caaaatgttt tgcatgcttt tcttcatttc taacattctc tctaagttta ttctattttt   74700
ttctgattat ccttaatatt atctctttct gctggaaata cattgttact tttggtttat   74760
ctaaaaatgg cttcattttc ttcattctaa aatcatgtta aattaatacc actcatgtgt   74820
aagtaagata gtggaataaa tagaaatcca aaaactaaat ctcactaaaa tataataatg   74880
tgatatataa aaatatagct tttaaatttta gcttggaaat aaaaaacaaa cagtaattga   74940
acaactatac ttttttgaaaa gagtaaagtg aaatgcttaa ctgcatatac cacaatcgat   75000
tacacaatta ggtgtgaagg taaaattcag tcacgaaaaa actagaataa aaatatggga   75060
```

-continued

```
agacatgtat ataatcttag agataacact gttatttaat tatcaaccca aagtagaaac   75120
tatcaaggga gaaataaatt cagtcaacaa taaaagcatt taagaagtta ttctaggctg   75180
ggagcggtgg ctcacacctg caattgcagc actttgggag gcctagacag gcggatcacg   75240
acgtcaggag ttcaagatca gcctggccaa catagtgaaa cctcatcgct actaaaaata   75300
taaaaactta gcctggcgtg gtggcaggca tgtgtaatcc cagcaatttg ggaggctgag   75360
gcaggagaat cgcttgatcc tgggaggcag aggttgcagt gagccaagat tgtgccactg   75420
cattccagcc caggtgacag catgagactc cgtcacaaaa aaaaaagaaa aaaaaagggg   75480
ggggggagc ggtggagcca agatgaccga ataggaacag ctccagtcta tagctcccat   75540
cgtgagtgac gcagaagacg ggtgatttct gcatttccaa ctgaggtacc aggttcatct   75600
cacagggaag tgccaggcag tgggtgcagg acagtaggtg cagtgcactg tgcatgagcc   75660
aaagcagggc gaggcatcac ctcacccggg aagcacaagg ggtcagggaa ttcccttcc    75720
tagtcaaaga aaagggtgac agatggcacc tggaaaatcg ggtcactccc gccctaatac   75780
tgcgctcttc caacaagctt aacaaatggc acaccaggag attatatccc atgcctggct   75840
cagagggtcc tacgcccatg gagcctcgct cattgctagc acagcagtct gaggtcaaac   75900
tgcaaggtgg cagtgaggct ggggggaggg tgcccaccat tgtccaggct tgagcaggta   75960
aacaaagccg cctggaagct cgaactgggt ggagcccacc acagctcaag gaggcctgcc   76020
tgcctctgta ggctccacct ctaggggcag ggcacagaca aacaaaagac aacaagaacc   76080
tctgcagact taaatgtccc tgtctgacag ctttgaagag agtagtggtt ctcccagcac   76140
atagcttcag atctgagaac aggcagactg cctcctcaag tgggtccctg accccgagt    76200
agcctaactg ggaggcatcc cccagtaggg gcagactgac acctcacatg gctggtactc   76260
ctctaagaca aaacttccag aggaatgatc aggcagcagc atttgcggtt caccaatatc   76320
cactgttctg cagccaccgc tgttgatacc caggaaaaca gcttctggag tggacctcca   76380
gtaaactcca acagacctgc agctgagggt cctgactgtt agaaggaaaa ctaacaaaca   76440
gaaaggacat ccacaccaaa aacccatctg tacatcgcca tcatcaaaga ccaaaggtag   76500
ataaaaccat aaagatgggg aaaaagcaga gcagaaaaac tggacactct aaaaatgaga   76560
gtgcctctcc tcctccaaag taacgcagct cctcaccagc aatggaacaa agctgggcag   76620
agaatgactt tgacgagttg agagaggaag gcttcagaag atcaaactac tccaagctaa   76680
aggaggaagt tcgaacaaac ggcaaagaag taaaaaactt tgaaaaaaaa ttagatgaat   76740
ggataactag aataaccaat gcacagaagt ccttaaagga cctgatggag ctgaaaacca   76800
aggcaggaaa actacgtgac aaatacacaa gcctcagtaa ccgatgagat caactggaag   76860
aaagggtatc aatgacgaaa gatgaaatga atgaaatgaa gcatgaagag aagtttagag   76920
aaaaagaat aaaaagaaac gaacaaagcc tccaagaaat atgggactat gtgaaaagac   76980
caaatctaca tctaattggt gtagctgaaa gtgatgggga gaatggaacc aagttggaaa   77040
acactctgca ggatattatc caggagaact tccccaatct agcaaggcaa gcccaaattc   77100
acattcagga aatacagaga acgccacaaa gatactccta gagaaaagca actccaagac   77160
acataactgt cagattcacc aaagttgaaa tgaaggaaaa aatgttaagg gcagccagag   77220
agaaaggtcg ggttacccac aaagggaagc ccatcagact aacagctgat ctatcggcag   77280
aaactctaca agccagaaga aagtggggc caatattcaa cattgttaaa gaaaagaatt   77340
ttcaacccag aatttcatat ccagccaaac taagcttcat aagtgaagga gaaataaaat   77400
cctttacaga caagcaaatg ctgagagatt ttgtcaccac caggcctgcc ctacaagagc   77460
tcctgaagga agcactaaac atggaaagga acaactagta tcagccactg caaaaacatg   77520
ccaaattgta aagaccatca aggctaggaa gaaactgcat caacgagcaa aataaccagc   77580
taacatcata atgacaggat caaattcata cataacaata ctcaccttaa atgtaaatag   77640
gctaaatgct ccaattaaaa gacacagact ggcaaattgg ataaggagtc aagacccatc   77700
tgtgttctgt attcaggaaa cccatctcac gtgcagagac acacataggc tcgaaataaa   77760
aggatggagg aatatctacc aagcaaatgg aaaacaaaaa aaggcagggg ttgcaatcct   77820
agtctctgat aaaacagatt ttaaaccaac aaagatcaaa agagacaaag aaggccatta   77880
cataatggca aagggatcta ttcaagaaga agaactaact atactaaata tatatgcacc   77940
caatacagga gcacccagat tcataaaaca agtcctgagt gacctacaaa gagacttaga   78000
tgcccacaca ataataatgg gagactttaa cacccccactg tcaacattag acagatcaac   78060
gagacagaaa gttaacaagg atatccagga attggactca gctctgcacc aagcagacat   78120
aatagacatc tacagaactc tccaccccaa atcaacagaa tatacattct tttcagcacc   78180
acaccacacc tattccaaaa ctgaccacat agttggaagt aaagctctcc tcagcaaatg   78240
taaaagaaca gaaactataa caaactgtct ctcagaccac agtgcaatca aactagaact   78300
caggattaag aaactcactc aaaaccactc agctacatgg aactgaaca gcctgctcct   78360
gaatgactac tgggtacata acaaaatgaa ggcagaaata aagatgttct ttgaaaccaa   78420
cgagaacaaa gacacaacac accagaatct ctgagacaca ttcaaagcag tgtgtagagg   78480
gaaatttata gcactaaatg cccacaaggg aaagcaggaa agatctaaaa ttgacaccct   78540
aacatcacaa ttaaaaaact agagaaacag gagcaaacac attcaaaagc taacagaaga   78600
caagaaataa ctaagatcag gagcagaagtg aaggacatag agacacaaaa aaaccccttca   78660
aaaaaatcaa tgaatccaga agctgttttt ttgaaaagat caacaaaatt gatagactgc   78720
tagcaagact aataaagaag aaaagagaga agaatcaaat agacgcaata aaaaatgaca   78780
cggggtatca ccactgatcc cacagaaata caaactaccg tcagagaata ctataaacac   78840
ctctacgcaa ataaactaga aaatctagaa gaaatggata aattcctcga cacatacact   78900
ctgccaagac taaaccagga agaagttgta tctctgaata gaccaataac aggctctgaa   78960
attgaggcaa taattaatag cttatcaacc aaaaaaagtc cgggaccagt aggattcata   79020
gccgaattct accagaggta caaggaggag ctggtaccat tccttctgaa actattccaa   79080
tcaatagaaa aagagggaat cctccctaac tcattttatg aggccagcat catcctgata   79140
ccaaagcctg acagagacac aacaaaaaaa gagaatgtta caccaatatc cttgatgaac   79200
attgatgcaa aaatcctcaa taaaatactg gcaaactgat ccaccatgat caagtgggct   79260
tcatccctgc catgcaaggc tggttcaaca tacgaaaatc aataaacata atccagcata   79320
taaacagaac caaagacaca aaccatatga ttatctcaat agatgcagaa aaggcctttg   79380
acaaaattca acaacgcttc atgctaaaaa ctctcaataa attaggtatt gatgggacat   79440
atctcaaaat aataagagct atctatgaca aacccacagc cagtaggaca catgattgtg   79500
aaaaactgga agcattccct ttgaaaactg gcacaaggca gggatgccct ctctcaccac   79560
tcctattcaa catagtgttg taagttctgg ccagggcaat caggcaggag aaggaaataa   79620
agggcattca attaggaaaa gaggaagtga aattgtccct gtttgcagat gacatgattg   79680
tatatctaga aaaccccatt gtctcagccc aaaatctcct taagctgata agcaacttca   79740
gcaaagtctc aggatataaa atcagtgtgc aaaaatcaca agtattccta tgcaccaata   79800
```

```
acagacaaac agagagccaa atcatgagtg aactcccatt cacaattgct tcaaagagaa   79860
taaaatacct aggaatccaa cttacaaggg atgtgaagga cctcttcaag gagaactaca   79920
aaccactgct caatgaaata aaagaggata caaacaaatg gaagaacatt ccatgctcat   79980
gggtaggaag aatcaatatc gtgaaaatgg tcatactgcc caaggtaatt tatagattca   80040
atgccatccc catcaagcta ccaatgactt tcttcacaga actggaaaaa actactttaa   80100
agttcatatg gaaccaaaaa agagcccaca tcaccaaggc aatcctaagc caaaagaaca   80160
aagctggagg catcacgcta cctgacttca aactatacta caatgctacg gtaaccaaaa   80220
cagcatggta ctggtaccaa aacagagatc tagaccaatg gaacagaaca gagccctcag   80280
aaataatgcc gcatatctac aactatctga tctttgacaa acctgagaga aacaagcaat   80340
ggggaaagga ttccctattt aataaatggt gctgggaaaa ctggctagcc atatgtagaa   80400
agctgaaact ggatcccttc cttacacctt atacaaaaat taattcaaga tggattaaag   80460
acttacatgt tagacctaaa accataaaaa ccctagaaaa aaacctaggc aataccattc   80520
aggacatagg catgggcaag gacttcatgt ctaaaacacc aaaagcaatg gcaacaaaag   80580
acaaaatgga caaacgggat ctaattaaac taaagagctt ctgcacagct aaagaaacta   80640
ccatcagagt gaacaggcaa cctacaaaat gggagaaaat ttttgcaatc tactcatctg   80700
acaaagggct aatatccaga atctacaatg aactcaaaca aatttacaag aaaaaacaaa   80760
caaccccatc aaaaagtggg caaaggatat gaacagacac ttcgcaaaag aagacattta   80820
tgtaatcaaa aaacacatga aaaaatgctc atcatcacta gccatcagag aaatgcaaat   80880
caaaaccaca atgagatacc atctcacacc agttagaatg gcgatcatta aaaagtcagg   80940
aaacaacagg tgctggagag gatgtggaga aacaggaaca acttttacac tgttggtggg   81000
actgtaaact agttcaacca ttgcggaagt cagtgtggca attcctcagg aatctagaac   81060
tagaaatacc atttgaccca gccatcccat tactgggtac ataccaaag gattataaat   81120
catgctgcta taaagacaca tgcacacgta tgtttattgc agcactattc acaatagcaa   81180
agacttggaa ccaacccaaa tgtccaacaa cgatagactg gattaagaaa atgtggcaca   81240
tatacaccat ggaatactat gcagccataa aaaatgatga gttcatgtcc tttgtaggga   81300
catggatgaa gctggaaact atcattctca gcaaactaca acaaggagaa taaaccaaac   81360
accgcatgtt ctcactcata ggtgggaatt gaacaatgag aacacatgga cacatgaaga   81420
ggaacatcac actctgggga ctgttatggg gtgggggca ggggcaggga tagcactagg   81480
agatatacct aatgctaaat gacgagttaa tgggtgcagc acaccaacat ggcacatgta   81540
tacatatata acaaacctgc atgttgtgca catgtaccct aaaacttgaa gtataataat   81600
aaaaaaaagt tatcctatta aaactgatct cacacatccg tagagccatt atcaagtctt   81660
tctctttgaa atagacagaa atttagtgtt ttctcagtca gttaac          81706
```

```
SEQ ID NO: 20              moltype = DNA  length = 388
FEATURE                    Location/Qualifiers
source                     1..388
                           mol_type = genomic DNA
                           organism = Homo sapiens
SEQUENCE: 20
taagcttcag tttttcctta gttcctgtta catttctgtg tgtctccatt agtgacctcc   60
catagtccaa gcatgagcag ttctggccag gcccctgtcg gggtcagtgc cccacccccg  120
ccttctggtt ctgtgtaacc ttctaagcaa accttctggc tcaagcacag caatgctgag  180
tcatgatgag tcatgctgag gcttagggtg tgtgcccaga tgttctcagc ctagagtgat  240
gactcctatc tgggtcccca gcaggatgct tacagggcag atggcaaaaa aaaggagaag  300
ctgaccacct gactaaaact ccacctcaaa cggcatcata agaaaatgg atgcctgaga  360
cagaatgtga catattctag aatatatt                                      388
```

```
SEQ ID NO: 21              moltype = DNA  length = 387
FEATURE                    Location/Qualifiers
source                     1..387
                           mol_type = genomic DNA
                           organism = Homo sapiens
SEQUENCE: 21
taagcttcag tttttcctta gttcctgtta catttctgtg tgtctccatt agtgacctcc   60
catagtccaa gcatgagcag ttctggccag gcccctgtcg gggtcagtgc cccacccccg  120
ccttctggtt ctgtgtaacc ttctaagcaa accttctggc tcaagcacag caatgctgag  180
tcatgatgag tcatgctgag gctagggtgt gtgcccagat gttctcagcc tagagtgatg  240
actcctatct gggtccccag caggatgctt acagggcaga tggcaaaaaa aaggagaagc  300
tgaccacctg actaaaactc cacctcaaac ggcatcataa agaaatgga tgcctgagac  360
agaatgtgac atattctaga atatatt                                       387
```

```
SEQ ID NO: 22              moltype = DNA  length = 286
FEATURE                    Location/Qualifiers
source                     1..286
                           mol_type = genomic DNA
                           organism = Homo sapiens
SEQUENCE: 22
ctgagcaact aactcatgca ggactctcaa acactaacct atagcctttt ctatgtatct   60
acttgtgtag aaaccaagcg tggggactga gaaggcaata gcaggagcat tctgactctc  120
actgcctttg gctaggtccc tccctcatca cagctcagca tagtccgagc tcttatctat  180
atccacacac agtttctgac gctgcccagc tatcaccatc ccaagtctaa agaaaaaaat  240
aatgggtttg cccatctctg ttgattagaa aacaaaacaa aataaa                  286
```

```
SEQ ID NO: 23              moltype = DNA  length = 286
FEATURE                    Location/Qualifiers
source                     1..286
                           mol_type = genomic DNA
                           organism = Homo sapiens
SEQUENCE: 23
```

-continued

```
ctgagcaact aatcatgcag gactctcaaa cactaaccta tagcctttc tatgtatcta   60
cttgtgtaga aaccaagcgt gggggactgag aaggcaatag caggagcatt ctgactctca  120
ctgcctttag ctaggcccct ccctcatcac agctcagcat agtcctgagc tcttatctat  180
atccacacac agtttctgac gctgcccagc tatcaccatc ccaagtctaa agaaaaaaat  240
aatgggtttg cccatctctg ttgattagaa aacaaaacaa aataaa                  286
```

```
SEQ ID NO: 24              moltype = DNA   length = 301
FEATURE                    Location/Qualifiers
misc_feature               1..301
                           note = Description of Artificial Sequence: Synthetic
                            polynucleotide
source                     1..301
                           mol_type = other DNA
                           organism = synthetic construct
SEQUENCE: 24
ccaatcgtgg catatcctct aaactttctt ttcccttcat aaatcctctt tctttttttt   60
cccctcaca gttttcctga acaggttgac tattaattgt gtctgcttga tgtggacacc   120
aggtggcgct ggacatcaga tttggagagg cagttgtcta gggaaccggg ctctgtgcca  180
gcgcaggagg caggctggct ctcctattcc agggatgctc atccaggaag gaaaggttgc  240
atgctggaca cactaacctt gaagaattct tctgtctctc tcgtcattta gaaaggaagg  300
a                                                                   301
```

```
SEQ ID NO: 25              moltype = DNA   length = 305
FEATURE                    Location/Qualifiers
misc_feature               1..305
                           note = Description of Artificial Sequence: Synthetic
                            polynucleotide
source                     1..305
                           mol_type = other DNA
                           organism = synthetic construct
SEQUENCE: 25
ctagccaatc gtggcatatc ctctaaactt tcttttccct tcataaatcc tcttctttt   60
ttttcccct cacagttttc ctgaacaggt tgactattaa ttgtgtctgc ttgatgtgga   120
caccaggtgg cgctggacat cagatttgga gaggcagttg tctagggaac cgggctctgt  180
gccagcgcag gaggcaggct ggctctccta ctccagggat gctcatccag gaaggaaagg  240
ttgcatgctg gacacactaa ccttgaagaa ttcttctgtc tctctcgtca tttagaaagg  300
aagga                                                               305
```

```
SEQ ID NO: 26              moltype = DNA   length = 896
FEATURE                    Location/Qualifiers
misc_feature               1..896
                           note = Description of Artificial Sequence: Synthetic
                            polynucleotide
source                     1..896
                           mol_type = other DNA
                           organism = synthetic construct
SEQUENCE: 26
ctcgagttaa ttaatctccc acgccctggt ctcagcttgg ggagtggtca gaccccaatg   60
gcgataaact ctggcaactt tatctgtgca ctgcaggctc agccccaaca gctttagctt  120
tcacaagcag gcagggggaag ggaaacacat atctccagat atgaggttaa ttaacctgca  180
ggctaaaccc ctccccccacc ctagcccaa gcttcatctt agctccactc ctgaccctat  240
ccagctaaag gtcccaccc agctcctgcc tatctagtca ttgcatatgg caagacttga  300
aagtcctatc tcaaagcagc agaattatca gctacgactc ctgcaggtta taaccatccc  360
ccagcactcc ctgcccccac agcccagact tgaccaactc ccagctccgc ctgggacttc  420
cagatatggg gccccaccct tgcaggcctt ggggacgctg aagatattga ctatctgcgt  480
gccggaaaag ggtgttataa accggtaaag gctggggggtg ggagtagcgg atttgaagca  540
cttgttggcc tacagaggtg tggcaagcag agcacctcag aactcaggcg tactgcccgc  600
cgcccgagcc ctgcgagggc cgatagcgag ggtgtggccc ttatctgcac ccagcagagc  660
gccggcgggg tacggtcacc ggtcccgggc agttgcctca gctgagtatg tcttctaaag  720
ataatgtcga ttgtgtatgg ctgatgggat tctaggacca agcaagaggt tttttttttt  780
cccccacata cttaacgttt ctatatttct atttgaattc gactggacag ttccatttga  840
attatttctc tctctctctc tctctgacac attttatctt gccacccggg ctcgag       896
```

```
SEQ ID NO: 27              moltype = DNA   length = 320
FEATURE                    Location/Qualifiers
misc_feature               1..320
                           note = Description of Artificial Sequence: Synthetic
                            polynucleotide
source                     1..320
                           mol_type = other DNA
                           organism = synthetic construct
SEQUENCE: 27
ctggttctac tcattacatt ccaatcgtgg catatcctct aaactttctt ttcccttcat   60
aaatcctctt tctttttttt cccctcaca gttttcctga acaggttgac tattaattgt  120
gtctgcttga tgtggacacc aggtggcgct ggacatcaga tttggagagg cagttgtcta  180
gggaaccggg ctctgtgcca gcgcaggagg caggctggct ctcctattcc agggatgctc  240
atccaggaag gaaaggttgc atgctggaca cactaacctt gaagaattct tctgtctctc  300
tcgtcattta gaaaggaagg                                               320
```

```
SEQ ID NO: 28              moltype = DNA   length = 300
FEATURE                    Location/Qualifiers
misc_feature               1..300
                           note = Description of Artificial Sequence: Synthetic
                           polynucleotide
source                     1..300
                           mol_type = other DNA
                           organism = synthetic construct
SEQUENCE: 28
ccaatcgtgg catatcctct aaactttctt ttcccttcat aaatcctctt tctttttttt   60
cccctcaca gttttcctga acaggttgac tattaattgt gtctgcttga tgtggacacc   120
aggtggcgct ggacatcaga tttggagagg cagttgtcta gggaaccggg ctctgtgcca   180
gcgcaggagg caggctggct ctcctattcc agggatgctc atccaggaag gaaaggttgc   240
atgctggaca cactaacctt gaagaattct tctgtctctc tcgtcattta gaaaggaagg   300

SEQ ID NO: 29              moltype = DNA   length = 120
FEATURE                    Location/Qualifiers
misc_feature               1..120
                           note = Description of Artificial Sequence: Synthetic
                           polynucleotide
source                     1..120
                           mol_type = other DNA
                           organism = synthetic construct
SEQUENCE: 29
tcataaatcc tctttctttt ttttcccccct cacagttttc ctgaacaggt tgactattaa   60
ttgtgtctgc ttgatgtgga caccaggtgg cgctggacat cagatttgga gaggcagttg   120

SEQ ID NO: 30              moltype = DNA   length = 170
FEATURE                    Location/Qualifiers
misc_feature               1..170
                           note = Description of Artificial Sequence: Synthetic
                           polynucleotide
source                     1..170
                           mol_type = other DNA
                           organism = synthetic construct
SEQUENCE: 30
tcataaatcc tctttctttt ttttcccccct cacagttttc ctgaacaggt tgactattaa   60
ttgtgtctgc ttgatgtgga caccaggtgg cgctggacat cagatttgga gaggcagttg   120
tctagggaac cgggctctgt gccagcgcag gaggcaggct ggctctccta             170

SEQ ID NO: 31              moltype = DNA   length = 240
FEATURE                    Location/Qualifiers
misc_feature               1..240
                           note = Description of Artificial Sequence: Synthetic
                           polynucleotide
source                     1..240
                           mol_type = other DNA
                           organism = synthetic construct
SEQUENCE: 31
tcataaatcc tctttctttt ttttcccccct cacagttttc ctgaacaggt tgactattaa   60
ttgtgtctgc ttgatgtgga caccaggtgg cgctggacat cagatttgga gaggcagttg   120
tctagggaac cgggctctgt gccagcgcag gaggcaggct ggctctccta ttccagggat   180
gctcatccag gaaggaaagg ttgcatgctg gacacactaa ccttgaagaa ttcttctgtc   240

SEQ ID NO: 32              moltype = DNA   length = 320
FEATURE                    Location/Qualifiers
misc_feature               1..320
                           note = Description of Artificial Sequence: Synthetic
                           polynucleotide
source                     1..320
                           mol_type = other DNA
                           organism = synthetic construct
SEQUENCE: 32
ctggttctac tcattacatt ccaatcgtgg catatcctct aaactttctt ttcccttcat   60
aaatcctctt tctttttttt cccctcaca gttttcctga acaggttgac tattaattgt   120
gtctgcttga tgtggacacc aggtggcgct ggacatcaga tttggagagg cagttgtcta   180
gggaaccggg ctctgtgcca gcgcaggagg caggctggct ctcctattcc agggatgctc   240
atccaggaag gaaaggttgc atgctggaca cactaacctt gaagaattct tctgtctctc   300
tcgtcattta gaaaggaagg                                              320

SEQ ID NO: 33              moltype = DNA   length = 816
FEATURE                    Location/Qualifiers
misc_feature               1..816
                           note = Description of Artificial Sequence: Synthetic
                           polynucleotide
source                     1..816
                           mol_type = other DNA
                           organism = synthetic construct
SEQUENCE: 33
```

-continued

```
tctagaatat gtcacattct gtctcaggca tccattttct ttatgatgcc gtttgaggtg   60
gagtttttagt caggtggtca gcttctcctt tttttttgcca tctgccctgt aagcatcctg   120
ctggggaccc agataggagt catcactcta ggctgagaac atctgggcac acaccctaag   180
cctcagcatg actcatcatg actcagcatt gctgtgcttg agccagaagg tttgcttaga   240
aggttacaca gaaccagaag gcgggggtgg ggcactgacc ccgacagggg cctggccaga   300
actgctcatg cttggactat gggaggtcac taatggagac acacagaaat gtaacaggaa   360
ctaaggaaaa actgaagctt atttaatcag agatgagatg ctggaaggga tagagggagc   420
tgagcttgta aaaagtatag taatcattca gcaaatggtt ttgaagcacc tgctggatgc   480
taaacactat tttcagtgct tgaatcataa ataagaacaa aacatgtatc ttattcccca   540
caagagtcca agtaaaaaat aacagttaat tataatgtgc tctgtccccc aggctggagt   600
gcagtggcac gatctcagct cactgcaacc tccgcctccc gggttcaagc aattctcctg   660
cctcagccac cctaatagct gggattacag gtgcacacca ccatgccagg ctaatttttg   720
tactttttgt agaggcaggg tatcaccatg ttgtccaaga tggtcttgaa ctcctgagct   780
ccaagcagtc cacccacctc agcctcccaa agtgct   816

SEQ ID NO: 34              moltype = DNA   length = 1301
FEATURE                    Location/Qualifiers
misc_feature               1..1301
                           note = Description of Artificial Sequence: Synthetic
                           polynucleotide
source                     1..1301
                           mol_type = other DNA
                           organism = synthetic construct SEQUENCE: 34
aagctttcat caaaaaaagt ctaaccagct gcattcgact ttgactgcag cagctggtta   60
gaaggttcta ctggaggagg gtcccagccc attgctaaat taacatcagg ctctgagact   120
ggcagtatat ctctaacagt ggttgatgct atcttctgga acttgcctgc tacattgaga   180
ccactgaccc atacatagga agcccatagc tctgtcctga actgttaggc cactggtcca   240
gagagtgtgc atctcctttg atcctcataa taacccatg agatagacac aattattact   300
cttactttat agatgatgat cctgaaaaca taggagtcaa ggcacttgcc cctagctggg   360
ggtataggg agcagtccca tgtagtagta gaatgaaaaa tgctgctatg ctgtgcctcc   420
cccacctttc ccatgtctgc cctctactca tggtctatct ctcctggctc ctgggagtca   480
tggactccac ccagcaccac caacctgacc taaccaccta tctgagcctg ccagcctata   540
acccatctgg gccctgatag ctggtggcca gccctgaccc caccccaccc tccctggaac   600
ctctgataga cacatctggc acaccagctc gcaaagtcac cgtgagggtc ttgtgtttgc   660
tgagtcaaaa ttccttgaaa tccaagtcct tagagactcc tgctcccaaa tttacagtca   720
tagacttctt catggctgtc tcctttatcc acagaatgat tcctttgctt cattgcccca   780
tccatctgat cctcctcatc agtgcagcac agggcccatg agcagtagct gcagagtctc   840
acataggtct ggcactgcct ctgacatgtc cgaccttagg caaatgcttg actcttctga   900
gctcagtctt gtcatggcaa aacaaagata ataatagtgt tttttttatgg agttagcgtg   960
aggatggaaa acaatagcaa aattgattag actataaaag gtctcaacaa atagtagtag   1020
attttatcat ccattaatcc ttccctctcc tctcttactc atcccatcac gtatgcctct   1080
taattttccc ttacctataa taagagttat tcctcttatt atattcttct tatagtgatt   1140
ctggatatca aagtgggaat gaggggcagg ccactaacga agaagatgtt tctcaaagaa   1200
gccattctcc ccacatagat catctcagca gggttcagga agataaagga ggatcaaggt   1260
cgaaggtagg aactaaggaa gaacactggg caagtggatc c   1301

SEQ ID NO: 35              moltype = DNA   length = 754
FEATURE                    Location/Qualifiers
misc_feature               1..754
                           note = Description of Artificial Sequence: Synthetic
                           polynucleotide
source                     1..754
                           mol_type = other DNA
                           organism = synthetic construct SEQUENCE: 35
taaatatatc atttaaatgc ataaataagc aaaccctgct cgggaatggg agggagagtc   60
tctggagtcc accccttctc ggccctggct ctgcagatag tgctatcaaa gccctgacag   120
agccctgccc attgctgggc cttggagtga gtcagcctag tagagaggca gggcaagcca   180
tctcatagct gctgagtggg agagagaaaa gggctcattg tctataaact caggtcatgg   240
ctattcttat tctcacacta agaaaaagaa tgagatgtct acatatacc tgcgtcccct   300
cttgtgtact ggggcccca agagctctct aaaagtgatg gcaaagtcat tgcgctagat   360
gccatcccat ctattataaa cctgcatttg tctccacaca ccagtcatgg acaataaccc   420
tcctcccagg tccacgtgct tgtctttgta taatactcaa gaatttggg aaaatgtatt   480
ctttcaatct tgttctgtta ttcctgtttc aatggcttag tagaaaaagt acatacttgt   540
tttcccataa attgacaata gacaatttca catcaatgtc tatatgggtc gttgtgtttg   600
ctgtgtttgc aaaaactcac aataactttta tattgttact actctaagaa agttacaaca   660
tggtgaatac aagagaaagc tattacaagt ccagaaaaca aaagttatca tcttgaggcc   720
tcagctttct aggaataata tcaatattac aaaa   754

SEQ ID NO: 36              moltype = DNA   length = 1232
FEATURE                    Location/Qualifiers
misc_feature               1..1232
                           note = Description of Artificial Sequence: Synthetic
                           polynucleotide
source                     1..1232
                           mol_type = other DNA
                           organism = synthetic construct

SEQUENCE: 36
```

-continued

```
gcaatgaaaa taaatgtttt ttattaggca gaatccagat gctcaaggcc cttcataata   60
tcccccagtt tagtagttgg acttaggbaa caaaggaacc tttaataga attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagatauga ggtatgaaca tgattagcaa   300
aagggcctag cttggactca gaataatcca gccttatccc aaccatauaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagct gggcaaaggt gcccttgagg ttgtccaggt gagccaggcc atcactaagt   840
gcaccgagca cttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacttcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232
```

```
SEQ ID NO: 37            moltype = DNA  length = 12142
FEATURE                  Location/Qualifiers
misc_feature             1..12142
                         note = Description of Artificial Sequence: Synthetic
                          polynucleotide
source                   1..12142
                         mol_type = other DNA
                         organism = synthetic construct
SEQUENCE: 37
attggccatt gcatacgttg tatccatatc ataatatgta catttatatt ggctcatgtc   60
caacattacc gccatgttga cattgattat tgactagtta ttaatagtaa tcaattacgg   120
ggtcattagt tcatagccca tatatggagt tccgcgttac gtaacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg gaggtctat ataagcagag   660
ctcgtttagt gaaccggggt ctctctggtt agaccagatc tgagcctggg agctctctgg   720
ctaactaggg aacccactgc ttaagcctca ataaagcttg ccttgagtgc ttcaagtagt   780
gtgtgcccgt ctgttgtgtg actctggtaa ctagagatcc ctcagaccct tttagtcagt   840
gtggaaaatc tctagcagtg gcgcccgaac agggacttga aagcgaaagg gaaaccagag   900
gagctctctc gacgcaggac tcggcttgct gaagcgcgca cggcaagagg cgaggggcgg   960
cgactggtga gtacgccaaa aattttgact agcggaggct agaaggagag agacgggtgc   1020
gagagcgtca gtattaagcg ggggtgaata agatcgcgat gggaaaaaat tcggttaagg   1080
ccaggggga agaaaaaata taattaaaa catatagtat gggcaagcag ggagctagaa   1140
cgattcgcag ttaatcctgg cctgttagaa acatcagaag gctgtagaca aatactggta   1200
cagctacaac catcccttca gacaggatca gaagaactta gatcattata taatacagta   1260
gcaaccctct attgtgtgca tcaaaggata gagataaaag acaccaagga agctttagac   1320
aagatagag aagagcaaaa caaaagtaag accaccgcac agcaagcggc cgctgatctt   1380
cagacctgga ggaggagata tgagggacaa ttggagaagt gaattatata aatataaagt   1440
agtaaaaatt gaaccattag gagtagcacc caccaaggca aagagaagag tggtgcagag   1500
agaaaaaaga gcagtgggaa taggagcttt gttccttggg ttcttgggag cagcaggaag   1560
cactatgggc gcagcgtcaa tgacgctgac ggtacaggcc agacaattat tgtctggtat   1620
agtgcagcag cagaacaatt tgctgagggc tattgagggc gcagcatc tgttgcaact   1680
cacagtctgtg ggcatcaagc agctccaggc aagaatcctg gctgtggaaa gatacctaaa   1740
ggatcaacag ctcctgggga tttgggttg ctctggaaaa ctcatttgca ccactgctgt   1800
gccttggaat gctagttgga gtaataaatc tctggaacag atttggaatc acacgacctg   1860
gatggagtgg gacagagaaa ttaacaatta cacaagctta atacactcct taattgaaga   1920
atcgcaaaac cagcaagaaa agaatgaaca agaattattg gaattagata aatgggcaag   1980
tttgtggaat tggtttaaca taacaaattg gctgtggtat ataaaattat tcataatgat   2040
agtaggaggc ttggtaggtt taagaatagt ttttgctgta ctttctatag tgaatagagt   2100
taggcaggga tattcaccat tatcgtttca gacccacctc ccaaccccga ggggacccga   2160
caggcccgaa ggaatagaag aagaaggtgg agagagagac agagacagat ccattcgatt   2220
agtgaacgga tctcgacggt atcgttttaa aagaaaaggg gggattgggg ggtacagtgc   2280
aggggaaaga atagtagaca taatagcaac agacatacaa actaaagaat tacaaaaaca   2340
aattacaaaa attcaaaatt ttatcggcgt gttggggtg gaccatcctc taggtattga   2400
ataagaaaaa tgaagttaag gtggttgatg gtaacactat gctaataact gcagagccag   2460
aagcaccata agggacatga taaggagcc agcagacctc tgatctcttc ctgaatgcta   2520
atcttaaaca tcctgaggaa gaatgggact tccatttggg gtgggcctat gatagggtaa   2580
taagacagta gtgaatatca agctacaaaa agccccottt caaattcttc tcagtcctaa   2640
cttttcatac taagcccagt ccttccaaag cagactgtga aagagtgata gttccgggag   2700
actagcactg cagattccgg gtcactgtga gtgggggagg cagggaagaa gggctcacag   2760
gacagtcaaa ccatgccccc tgttttccct tcttccagta gacctctata agacaacaga   2820
gacaactaag gctgagtggc caggcgagga gaaaccatct cgccgtaaaa catggaagga   2880
```

-continued

```
acacttcagg ggaaaggtgg tatctctaag caagagaact gagtggagtc aaggctgaga  2940
gatgcaggat aagcaaatgg gtagtgaaaa gacattcatg aggacagcta aaacaataag  3000
taatgtaaaa tacagcatag caaaacttta acctccaaat caagcctcta cttgaatcct  3060
tttctgaggg atgaataagg cataggcatc aggggctgtt gccaatgtgc attagctgtt  3120
tgcagcctca ccttctttca tggagtttaa gatatagtgt attttcccaa ggtttgaact  3180
agctcttcat ttctttatgt tttaaatgca ctgacctccc acattccctt tttagtaaaa  3240
tattcagaaa taatttaaat acatcattgc aatgaaaata aatgtttttt attaggcaga  3300
atccagatgc tcaaggccct tcataatatc ccccagttta gtagttggac ttagggaaca  3360
aaggaacctt taatagaaat tggacagcaa gaaagcgagc ttagtgatac ttgtgggcca  3420
gggcattagc cacaccagcc accactttct gataggcagc ctgcactggt ggggtgaatt  3480
ctttgccaaa gtgatgggcc agcacacaga ccagcacgtt gcccaggagc tgtgggagga  3540
agataagagg tatgaacatg attagcaaaa gggcctagct tggactcaga ataatccagc  3600
cttatcccaa ccataaaata aaagcagaat ggtagctgga ttgtagctgc tattagcaat  3660
atgaaacctc ttacatcagt tacaatttat atgcagaaat atttatatgc agaaatattg  3720
ctattgcctt aacccagaaa ttatcactgt tattctttag aatggtgcaa agaggcatga  3780
tacattgtat cattattgcc ctgaaagaaa gagattaggg aaagtattag aaataagata  3840
aacaaaaaag tatattaaaa gaagaaagca tttttttaaaa ttacaaatgc aaaattaccc  3900
tgatttggtc aatatgtgta ccctgttact tctcccccttc ctatgacatg aacttaacca  3960
tagaaaagaa ggggaaagaa aacatcaagg gtccccataga ctcaccctga agttctcagg  4020
atccacgtgc agcttgtcac agtgcagctc actcagctgg gcaaaggtgc ccttgaggtt  4080
gtccaggtga gccaggccat cactaaaggc accgagcact ttcttgccat gagccttcac  4140
cttagggttg cccataacag catcaggagt ggacagatcc ccaaaggact caaagaacct  4200
ctgggtccaa gggtagacca ccagcagcct aaggtgggga aaatagacca ataggcagag  4260
agagtcagtg cctatcagaa acccaagagt cttctctgtc tccacatgcc cagtttctat  4320
tggtctcctt aaacctgtct tgtaaccttg ataccaacct gcccagggcc tcaccaccaa  4380
cttcatccac gttcaccttg ccccacaggg cagtaacggc agacttctcc tcaggagtca  4440
ggtgcaccat ggtgtctgtt tgaggttgct agtgaacaca gttgtgtcag aagcaaatgt  4500
aagcaataga tggctctgcc ctgacttta tgcccagccc tggctcctgc cctccctgct  4560
cctgggagta gattggccaa ccctaggggtg tggctccaca gggtgaggtc taagtgatga  4620
cagccgtacc tgtccttggc tcttctggca ctggcttagg agttggactt caaaccctca  4680
gccctccctc taagatatat ctcttggccc cataccatca gtacaaattg ctactaaaaa  4740
catcctcctt tgcaagtgta tttacgtaat atttggaatc acagcttggt aagcatattg  4800
aagatcgttt tcccaatttt cttattacac aaataagaaa ttgatgcact aaaagtggaa  4860
gagtttttgtc taccataatt cagctttggg atatgtagat ggatctcttc ctgcgtctac  4920
agaatatgca aaatacttac aggacagaat ggatgaaaac tctacctcag ttctaagcat  4980
atcttctcct tatttggatt aaaaccttct ggtaagaaaa gaaaaaaaat atatatatat  5040
atgtgtatat atacacacat acatatacat atatatgcat tcatttgttg ttgtttttct  5100
taatttgctc atggtatatg tgtatatata tatatatata ttcaggaaat aatatattct  5160
agaatatgtc acattctgtc tcaggcatcc attttcttta tgatgccgtt tgaggtggag  5220
ttttagtcag gtggtcagct tctccttttt tttgccatct gccctgtaag catcctgctg  5280
gggacccaga taggagtcat cactctaggc tgagaacatc tgggcacaca ccctaagcct  5340
cagcatgact catcatgact cagcattgct gtgcttgagc cagaaggttt gcttagaagg  5400
ttacacagaa ccagaaggcg ggggtggggc actgaccccg acagggggcct ggccagaact  5460
gctcatgctt ggactatggg aggtcactaa tggagacaca cagaaatgta acaggaacta  5520
aggaaaaact gaagcttatt taatcagaga tgagatgctg gaagggatag agggagctga  5580
gcttgtaaaa agtatagtaa tcattcagca aatggttttg aagcacctgc tggatgctaa  5640
acactatttt cagtgcttga atcataaata agaataaaac atgtatctta ttccccacaa  5700
gagtccaagt aaaaaataac agttaattat aatgtgctct gtcccccagg ctggagtgca  5760
gtggcacgat ctcagctcac tgcaacctcc gcctcccggg ttcaagcaat tctcctgcct  5820
cagccaccct aatagctggg attacaggtg cacaccacca tgccaggcta attttttgtac  5880
tttttgtaga ggcagggtat caccatgttg tccaagatgg tcttgaactc ctgagctcca  5940
agcagtccac ccacctcagc ctcccaaagt gctatctgcg gccgcctatc tgtaccacta  6000
gtctcgagaa gctttcatta aaaaaagtct aaccagctgc attcgacttt gactgcagca  6060
gctggttaga aggttctact ggaggaggggt cccagcccat tgctaaatta acatcaggct  6120
ctgagactgg cagtatatct ctaacagtgg ttgatgctat cttctggaac ttgcctgcta  6180
cattgagacc actgacccat acataggaag cccatagctc tgtcctgaac tgttaggcca  6240
ctggtccaga gagtgtgcat ctcctttgat cctcataata accctatgag atagacacaa  6300
ttattactct tactttatag atgatgatcc tgaaaacata ggagtcaagg cacttgcccc  6360
tagctggggg tataggggag cagtcccatg tagtagtaga atgaaaaatg ctgctatgct  6420
gtgcctcccc cacctttccc atgtctgccc tctactcatg gtctatctct cctggctcct  6480
gggagtcatg gactccaccc agcaccacca acctgaccta accacctatc tgagcctgcc  6540
agcctataac ccatctgggc cctgatagct ggtggccagc cctgacccca ccccaccctc  6600
cctggaacct ctgatagaca catctggcac accagctcgc aaagtcaccg tgagggtctt  6660
gtgtttgctg agtcaaaatt ccttgaaatc caagtcctta gagactcctg ctcccaaatt  6720
tacagtcata gacttcttca tggctgtctc ctttatccac agaatgattc ctttgcttca  6780
ttgccccatc catctgatcc tcctcatcag tgcacacag ggcccatgag cagtagctgc  6840
agagtctcac ataggtctgg cactgcctct gacatgtccg accttaggca aatgcttgac  6900
tcttctgagc tcagtcttgt catggcaaaa taaagataat aatagtgttt ttttatggag  6960
ttagcgtgag gatggaaaac aatagcaaaa ttgattagac tataaaaggt ctcaacaaat  7020
agtagtagat tttatcatcc attaatcctt ccctctcctc tcttactcat cccatcacgt  7080
atgcctctta attttccctt acctataata agagttattc ctcttattat attcttctta  7140
tagtgattct ggatattaaa gtgggaatga ggggcaggcc actaacgaag aagatgtttc  7200
tcaaagaagc cattctcccc acatagatca tctcagcagg gttcaggaag ataaaggagg  7260
atcaaggtcg aaggtaggaa ctaaggaaga acactgggca agtggatcct gagcccctttt  7320
tcctctaact gaaagaagga aaaaaaaaat ggaacccaaa atattctaca tagtttccat  7380
gtcacagcca gggctgggca gtctcctgtt atttctttta aaataaaatat atcatttaaa  7440
tgcataaata agcaaaccct gctcgggaat gggaggggga gtctctggag tccacccctt  7500
ctcggccctg gctctgcaga tagtgctatc aaagccctga cagagccctg cccattgctg  7560
ggccttggag tgagtcagcc tagtagagag gcagggcaag ccatctcata gctgctgagt  7620
```

-continued

```
gggagagaga aaagggctca ttgtctataa actcaggtca tggctattct tattctcaca   7680
ctaagaaaaa gaatgagatg tctacatata ccctgcgtcc cctcttgtgt actgggcgcc    7740
ccaagagctc tctaaaagtg atggcaaagt cattgcgcta gatgccatcc catctattat    7800
aaacctgcat ttgtctccac acaccagtca tggacaataa ccctcctccc aggtccacgt    7860
gcttgtcttt gtataatact caagtaattt cggaaaatgt attctttcaa tcttgttctg    7920
ttattcctgt ttcaatggct tagtagaaaa agtacatact tgtttttccca taaaattgaca   7980
atagacaatt tcacatcaat gtctatatgg gtcgttgtgt ttgctgtgtt tgcaaaaact    8040
cacaataact ttatattgtt actactctaa gaaagttaca acatggtgaa tacaagagaa    8100
agctattaca agtccagaaa ataaaagtta tcatcttgag gcctcagctt tctaggaata    8160
atatcaatat tacaaaattt aatctaacaa ttatgaacag caatgagata atatgtacaa    8220
agtacccaga cctatgtggt agagcatcaa ggaagcgcat tgcggagcag ttttttgttt    8280
gtttgttttt gtattctgtt tcgtgaggca aggtttcact ctgctgtcca ggctggagtg    8340
cagtggcaag atcatgtctc actgcagcct tgacacgcgt cgacggtacc gttaacgatc    8400
ttagccactt tttaaaagaa aagggggggac tggaaggact aattcactcc caacgaagac    8460
aagatatcct gctagtcctt cctttctaaa tgacgagaga gacagaagaa ttcttcaagg    8520
ttagtgtgtc cagcatgcaa cctttccttc ctggatgagc atccctggag taggagagcc    8580
agcctgcctc ctgcgctggc acagagcccg gttccctaga caactgcctc tccaaatctg    8640
atgtccagcg ccacctggtg tccacatcaa gcagacacaa ttaatagtca acctgttcag    8700
gaaaactgtg aggggggaaa aaaagaaaga ggatttatga agggaaaaga aagtttagag    8760
gatatgccac gattggctag cagctgcttt ttgcctgtac tgggtctctc tggttagacc    8820
agatctgagc ctgggagctc tctggctaac tagggaaccc actgcttaag cctcaataaa    8880
gcttgccttg agtgcttcat ccggaatcaa cctctggatt acaaaatttg tgaaagattg    8940
actggtattc ttaactatgt tgctcctttt acgctatgtg gatacgctgc tttaatgcct    9000
ttgtatcatg ctattgcttc ccgtatggct ttcattttct cctccttgta taaatcctgg    9060
ttgctgtctc tttatgagga gttgtggccc gttgtcaggc aacgtggcgt ggtgtgcact    9120
gtgtttgctg acgcaacccc cactggttgg ggcattgcca ccacctgtca gctcctttcc    9180
gggactttcg ctttccccct ccctattgcc acggcggaac tcatcgccgc ctgccttgcc    9240
cgctgctgga caggggctcg gctgttgggc actgacaatt ccgtggtgtt gtcggggaag    9300
ctgacgtcct ttccatggct gctcgcctgt gttgccacct ggattctgcg cgggacgtcc    9360
ttctgctacg tcccttcggc cctcaatcca gcggaccttc cttcccgcgg cctgctgccg    9420
gctctgcggc ctcttccgcg tcttcgcctt cgccctcaga cgagtcggat ctccctttgg    9480
gccgcctccc cgcctgtccg gtagcttgcc agcctcgact gtgccttcta gttgccagcc    9540
gtctgttgtt tgcccctccc ccgtgccttc cttgaccctg gaaggtgcca ctcccactgt    9600
cctttcctaa taaaatgagg aaattgcatc gcattgtctg agtaggtgtc attctattct    9660
ggggggtggg gtggggcagg acagcaaggg ggaggattgg gaagacaata gcaggcatgc    9720
aagcttggcg taatcatggt catagctgtt tcctgtgtga aattgttatc cgctcacaat    9780
tccacacaac atacgagccg gaagcataaa gtgtaaagcc tggggtgcct aatgagtgag    9840
ctaactcaca ttaattgcgt tgcgctcact gcccgctttc cagtcgggaa acctgtcgtg    9900
ccagctgcat taatgaatcg gccaacgcgc ggggagaggc ggtttgcgta ttgggcgctc    9960
ttccgcttcc tcgctcactg actcgctgcg ctcggtcgtt cggctgcggc gagcggtatc    10020
agctcactca aaggcggtaa tacggttatc cacagaatca ggggataacg caggaaagaa    10080
catgtgagca aaaggccagc aaaaggccag gaaccgtaaa aaggccgcgt tgctggcgtt    10140
tttccatagg ctccgccccc ctgacgagca tcacaaaaat cgacgctcaa gtcagaggtg    10200
gcgaaacccg acaggactat aaagatacca ggcgtttccc cctggaagct ccctcgtgcg    10260
ctctcctgtt ccgaccctgc cgcttaccgg atacctgtcc gcctttctcc cttcgggaag    10320
cgtggcgctt tctcatagct cacgctgtag gtatctcagt tcggtgtagg tcgttcgctc    10380
caagctgggc tgtgtgcacg aaccccccgt tcagcccgac cgctgcgcct tatccggtaa    10440
ctatcgtctt gagtccaacc cggtaagaca cgacttatcg ccactggcag cagccactgg    10500
taacaggatt agcagagcga ggtatgtagg cggtgctaca gagttcttga agtggtggcc    10560
taactacggc tacactagaa gaacagtatt tggtatctgc gctctgctga gccagttac     10620
cttcggaaaa agagttggta gctcttgatc cggcaaacaa accaccgctg gtagcggtgg    10680
tttttttgtt tgcaagcagc agattacgcg cagaaaaaaa ggatctcaag aagatccttt    10740
gatctttct acggggtctg acgctcagtg gaacgaaaac tcacgttaag ggattttggt     10800
catgagatta tcaaaaagga tcttcaccta gatcctttta aattaaaaat gaagttttaa    10860
atcaatctaa agtatatatg agtaaacttg gtctgacagt taccaatgct taatcagtga    10920
ggcacctatc tcagcgatct gtctatttcg ttcatccata gttgcctgac tccccgtcgt    10980
gtagataact acgatacggg agggcttacc atctggcccc agtgctgcaa tgataccgcg    11040
agacccacgc tcaccggctc cagatttatc agcaataaac cagccagccg gaagggccga    11100
gcgcagaagt ggtcctgcaa ctttatccgc ctccatccag tctattaatt gttgccggga    11160
agctagagta agtagttcgc cagttaatag tttgcgcaac gttgttgcca ttgctacagg    11220
catcgtggtg tcacgctcgt cgtttggtat ggcttcattc agctccggtt cccaacgatc    11280
aaggcgagtt acatgatccc ccatgttgtg caaaaaagcg gttagctcct tcggtcctcc    11340
gatcgttgtc agaagtaagt tggccgcagt gttatcactc atggttatgg cagcactgca    11400
taattctctt actgtcatgc catccgtaag atgcttttct gtgactggtg agtactcaac    11460
caagtcattc tgagaatagt gtatgcggcg accgagttgc tcttgcccgg cgtcaatacg    11520
ggataatacc gcgccacata gcagaacttt aaaagtgctc atcattggaa aacgttcttc    11580
ggggcaaaac tctcaaggat cttaccgctg ttgagatcca gttcgatgta acccactcgt    11640
gcacccaact gatcttcagc atcttttact ttcaccagcg tttctgggtg agcaaaaaca    11700
ggaaggcaaa atgccgcaaa aaagggaata agggcgacac ggaaatgttg aatactcata    11760
ctcttccttt ttcaatatta ttgaagcatt tatcagggtt attgtctcat gagcggatac    11820
atatttgaat gtatttagaa aaataaacaa ataggggttc cgcgcacatt tccccgaaaa    11880
gtgccacctg acgtctaaga aaccattatt atcatgacat taacctataa aaataggcgt    11940
atcacgaggc cctttcgtct cgcgcgtttc ggtgatgacg gtgaaaacct ctgacacatg    12000
cagctcccgg agacggtcac agcttgtctg taagcggatg ccgggagcag acaagcccgt    12060
cagggcgcgt cagcgggtgt tggcgggtgt cggggctggc ttaactatgc ggcatcagag    12120
cagattgtac tgagagtgca cc                                             12142
```

SEQ ID NO: 38    moltype = DNA  length = 12040
FEATURE           Location/Qualifiers -continued

```
misc_feature        1..12040
                    note = Description of Artificial Sequence: Synthetic
                     polynucleotide
source              1..12040
                    mol_type = other DNA
                    organism = synthetic construct SEQUENCE: 38
attggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt ggcagtacaa   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg gagtgctctat ataagcagag   660
ctcgtttagt gaaccggggt ctctctggtt agaccagatc tgagcctggg agctctctgg   720
ctaactaggg aacccactgc ttaagcctca ataaagcttg ccttgagtgc ttcaagtagt   780
gtgtgcccgt ctgttgtgtg actctggtaa ctagagatcc ctcagaccct tttagtcagt   840
gtggaaaatc tctagcagtg gcgcccgaac agggacttga aagcgaaagg gaaaccagag   900
gagctctctc gacgcaggac tcggcttgct gaagcgcgca cggcaagagg cgaggggcgg   960
cgactggtga gtacgccaaa aattttgact agcggaggct agaaggagag agacgggtgc  1020
gagagcgtca gtattaagcg ggggtgaata agatcgcgat gggaaaaaat tcggttaagg  1080
ccaggggaa agaaaaaata taaattaaaa catatagtat gggcaagcag ggagctagaa  1140
cgattcgcag ttaatcctgg cctgttagaa acatcagaag gctgtagaca aatactggga  1200
cagctacaac catcccttca gacaggatca gaagaactta gatcattata taatacagta  1260
gcaaccctct attgtgtgca tcaaaggata gagataaaag acaccaagga agctttagac  1320
aagatagagg aagagcaaaa caaaagtaag accaccgcac agcaagcggc cgctgatctt  1380
cagacctgga ggaggagata tgagggacaa ttggagaagt gaattatata aatataaagt  1440
agtaaaaatt gaaccattag gagtagcacc caccaaggca aagagaagag tggtgcagag  1500
agaaaaaaga gcagtgggaa taggagcttt gttccttggg ttcttgggag cagcaggaag  1560
cactatgggc gcagcgtcaa tgacgctgac ggtacaggcc agacaattat tgtctggtat  1620
agtgcagcag cagaacaatt tgctgagggc tattgaggcg caacagcatc tgttgcaact  1680
cacagtctgg ggcatcaagc agctccaggc aagaatcctg gctgtggaaa gatacctaaa  1740
ggatcaacag ctcctgggga tttggggttg ctctggaaaa ctcatttgca ccactgctgt  1800
gccttggaat gctagttgga gtaataaatc tctggaacag atttggaatc acacgacctg  1860
gatggagtgg gacagagaaa ttaacaatta cacaagctta atacactcct taattgaaga  1920
atcgcaaaac cagcaagaaa agaatgaaca agaattattg gaattagata aatgggcaag  1980
tttgtggaat tggtttaaca taacaaattg gctgtggtat ataaaattat tcataatgat  2040
agtaggaggc ttggtaggtt taagaatagt ttttgctgta ctttctatag tgaatagagt  2100
taggcaggga tattcaccat tatcgtttca gacccacctc ccaacccga ggggaccega  2160
caggcccgaa ggaatagaag aagaaggtgg agagagagac agagacagat ccattcgatt  2220
agtgaacgga tctcgacggt atcgttttaa aagaaaaggg gggattgggg ggtacagtgc  2280
aggggaaaga atagtagaca taatagcaac agacatacaa actaaagaat acaaaaaaca  2340
aattacaaaa attcaaaatt ttatcggcgt gttggggggac gaccatcctc taggtattga  2400
ataagaaaaa tgaagttaag gtggttgatg gtaacactat gctaataact gcagagccag  2460
aagcaccata agggacatga taagggagcc agcagacctc tgatctcttc ctgaatgcta  2520
atcttaaaca tcctgaggaa gaatgggact tccatttggg gtgggcctat gatagggtaa  2580
taagcagta gtgaatatca agctacaaaa agccccttt caaattcttc tcagtcctaa  2640
cttttcatac taagcccagt ccttccaaag cagactgtga aagagtgata gttccgggag  2700
actagcactg cagattccgg gtcactgtga gtggggagg cagggaagaa gggctcacag  2760
gacagtcaaa ccatgccccc tgtttttcct tcttcaagta gacctctata agacaacaga  2820
gacaactaag gctgagtggc caggcgagga gaaaccatct cgccgtaaaa catggaagga  2880
acacttcagg ggaaaggtgg tatctctaag caagagaact gagtggagtc aaggctgaga  2940
gatgcaggat aagcaaatgg gtagtgaaaa gacattcatg aggacagcta aaacaataag  3000
taatgtaaaa tacagcatag caaaacttta acctccaaat caagcctcta cttgaatcct  3060
tttctgaggg atgaataagg cataggcatc aggggctgtt gccaatgtgc attagctgtt  3120
tgcagcctca ccttctttca tggagtttaa gatatagtgt attttcccaa ggtttgaact  3180
agctcttcat ttctttatgt tttaaatgca ctgacctccc acattccctt tttagtaaaa  3240
tattcagaaa taatttaaat acatcattgc aatgaaaata aatgttttt attaggcaga  3300
atccagatgc tcaaggccct tcataatatc ccccagttta gtagttggac ttagggaaca  3360
aaggaacctt taatagaaat tggacagcaa gaaagcgagc ttagtgatac ttgtgggcca  3420
gggcattagc cacaccagcc accacttct gataggcagc ctgcactggt ggggtgaatt  3480
ctttgccaaa gtgatgggcc agcacacaga ccagcacgtt gcccaggagc tgtgggagga  3540
agataagagg tatgaacatg attagcaaaa gggcctagct tggactcaga ataatccagc  3600
cttatcccaa ccataaaata aaagcagaat ggtagctgga ttgtagctgc tattagcaat  3660
atgaaacctc ttacatcagt tacaatttat atgcagaaat atttatatgc agaaatattg  3720
ctattgcctt aacccagaaa ttatcactgt tattctttag aatggtgcaa agaggcatga  3780
tacattgtat cattattgcc ctgaaagaaa gagattaggg aaagtattag aaataagata  3840
aacaaaaaag tatattaaaa gaagaaagca ttttttaaaa ttacaaatgc aaaattaccc  3900
tgatttggtc aatatgtgta ccctgttact tctccccttc ctatgacatg aacttaacca  3960
tagaaaagaa gggggaaagaa aacatcaagg gtcccataga agttctcagg  4020
atccacgtgc agcttgtcac agtgcagctc actcagctgg gcaaaggtgc ccttgaggtt  4080
gtccaggtga gccaggccat cactaaaggc accgagcact ttcttgccat gagccttcac  4140
cttagggttg cccataacag catcaggagt ggacagatcc ccaaaggact caaagaacct  4200
ctgggtccaa gggtagacca ccagcagcct aagggtggga aaatagacca ataggcagag  4260
agagtcagtg cctatcagaa acccaagagt cttctctgtc tccacatgcc cagtttctat  4320
```

-continued

```
tggtctcctt aaacctgtct tgtaaccttg ataccaacct gcccaggtgcc tcaccaccaa  4380
cttcatccac gttcaccttg ccccacaggg cagtaacggc agacttctcc tcaggagtca  4440
ggtgcaccat ggtgtctgtt tgaggttgct agtgaacaca gttgtgtcag aagcaaatgt  4500
aagcaataga tggctctgcc ctgactttta tgcccagccc tggctcctgc cctccctgct  4560
cctgggagta gattggccaa ccctagggtg tggctccaca gggtgaggtc taagtgatga  4620
cagccgtacc tgtccttggc tcttctggca ctggcttagg agttggactt caaaccctca  4680
gccctccctc taagatatat ctcttggccc cataccatca gtacaaattg ctactaaaaa  4740
catcctcctt tgcaagtgta tttacggcat ctgtgaagga aagaaacatc tcctctaaac  4800
cactatgctg ctagagcctc ttttctgtac tcaagcctca ttcagacact agtgtcacca  4860
gtctcctcat ataccttattg tatttttcttc ttcttgctgg tttagtcatg ttttctggga  4920
gcttaggggc ttattttatt ttgtttgtt ttctaatcaa cagagatggg caaacccatt  4980
attttttct ttagacttgg gatggtgata gctgggcagc gtcagaaact gtgtgtggat  5040
atagataaga gctcggacta tgctgagctg tgatgaggga gggacctagc caaaggcagt  5100
gagagtcaga atgctcctgc tattgccttc tcagtcccca cgcttggttt ctacacaagt  5160
agatacatag aaaaggctat aggttagtgt ttgagagtcc tgcatgagtt agttgctcag  5220
aaatgcccga taaatatgtt atgtgtgttt atgtatatat atgtttttata tatatatatg  5280
tgtgtgtgtg tgtgtgtgtg tgttgtgttt acaaatatgt gattatcatc aaaacgtgag  5340
ggctaaagtg accagataac ttgcaggtct agaatatgtc acattctgtc tcaggcatcc  5400
atttctttta tgatgccgtt tgaggtggag ttttagtcag gtggtcagct tctccttttt  5460
tttgccatct gccctgtaag catcctgctg gggacccaga taggagtcat cactctaggc  5520
tgagaacatc tgggcacaca ccctaagcct cagcatgact catcatgact cagcattgct  5580
gtgcttgagc cagaaggttt gcttagaagg ttacacagaa ccagaaggcg ggggtggggc  5640
actgacccecg acaggggcct ggccagaact gctcatgctt ggactatggg aggtcactaa  5700
tggagacaca cagaaatgta acaggaacta aggaaaaact gaagcttatt taatcagaga  5760
tgagatgctg gaagggatag agggagctga gcttgtaaaa agtatagtaa tcattcagca  5820
aatggttttg aagcacctgc tggatgctaa acactatttt cagtgcttga atcataaata  5880
agaacaaaac atgtatctta ttccccacaa gagtccaagt aaaaaataac agttaattat  5940
aatgtgctct gtcccccagg ctggagtgca gtggcacgat ctcagctcac tgcaacctcc  6000
gcctcccggg ttcaagcaat tctcctgcct cagccaccct aatagctggg attacaggtg  6060
cacaccacca tgccaggcta attttgtac tttttgtgta ggcagggtat caccatgttg  6120
tccaagatgg tcttgaactc ctgagctcca agcagtccac ccacctcagc ctcccaaagt  6180
gctatctgcg gccgcctatc tgtaccacta gtctcgagaa gctttcatca aaaaaagtct  6240
aaccagctgc attcgacttt gactgcagca gctggttaga aggttctact ggaggagggt  6300
cccagcccat tgctaaatta acatcaggct ctgagactgg cagtatatct ctaacagtgg  6360
ttgatgctat cttctggaac ttgcctgcta cattgagacc actgacccat acataggaag  6420
cccatagctc tgtcctgaac tgttaggcca ctggtccaga gagtgtgcat ctcctttgat  6480
cctcataata accctatgag atagacacaa ttattactct tactttatag atgatgatcc  6540
tgaaaacata ggagtcaagg cacttgcccc tagctggggg tataggggag cagtcccatg  6600
tagtagtaga atgaaaaatg ctgctatgct gtgcctcccc cacctttccc atgtctgccc  6660
tctactcatg gtctatctct cctggctcct gggagtcatg gactccaccc agcaccacca  6720
acctgaccta accacctatc tgagcctgcc agcctataac ccatctgggc cctgatagct  6780
ggtggccagc cctgacccca ccccaccctc cctggaacct ctgatagaca catctggcac  6840
accagctgc aaagtcaccg tgagggtctt gtgtttgctg agtcaaaatt ccttgaaatc  6900
caagtcctta gagactcctg ctcccaaatt tacagtcata gacttcttca tggctgtctc  6960
ctttatccac agaatgattc ctttgcttca ttgcccatc catctgatcc tcctcatcag  7020
tgcagcacag ggcccatgag cagtagctgc agagtctcac ataggtctgg cactgcctct  7080
gacatgtccg accttaggca aatgcttgac tcttctgagc tcagtcttgt catggcaaaa  7140
caaagataat aatagtgttt ttttatggag ttagcgtgag gatggaaaac aatagcaaaa  7200
ttgattagac tataaaaggt ctcaacaaat agtagtagat tttatcatcc attaatcctt  7260
ccctctcctc tcttactcat cccatcacgt atgcctctta attttccctt acctataata  7320
agagttattc ctcttattat attcttctta tagtgattct ggatatcaaa gtgggaattga  7380
ggggcaggcc actaacgaag aagatgtttc tcaaagaagc cattctcccc acatagatca  7440
tctcagcagg gttcaggaag ataaaggagg atcaaggtcg aaggtaggaa ctaaggaaga  7500
acactgggca agtggatcct aaatatatca tttaaatgca taaataagca aaccctgctc  7560
gggaatggga gggagagtct ctggagtcca ccccttctcg gccctggctc tgcagatagt  7620
gctatcaaag ccctgacaga gccctgccca ttgctgggcc ttggagtgag tcagcctagt  7680
agagaggcag ggcaagccat ctcatagctg ctgagtggga gagagaaaag ggctcattgt  7740
ctataaactc aggtcatggc tattcttatt ctcacactaa gaaaaagaat gagatgtcta  7800
catataccct gcgtcccctc ttgtgtactg gggcccccaa gagctctcta aaagtgatgg  7860
caaagtcatt gcgctagatg ccatcccatc tattataaac ctgcatttgt ctccacacac  7920
cagtcatgga caataaccct cctcccaggt ccacgtgctt gtctttgtat aatactcaag  7980
taatttcgga aaatgtattc tttcaatctt gttctgttat tcctgtttca atggcttagt  8040
agaaaaagta catacttgtt ttcccataaa ttgacaatag acaatttcac atcaatgtct  8100
atatgggtcg ttgtgtttgc tgtgtttgca aaaactcaca ataactttat attgttacta  8160
ctctaagaaa gttacaacat ggtgaataca agagaaagct attacaagtc cagaaaacaa  8220
aagttatcat cttgaggcct cagctttcta ggaataatat caatattaca aaacgcgtcg  8280
acggtaccgt taacgatctt agccacttt taaaagaaaa gggggggactg gaagggctaa  8340
ttcactccca acgaagacaa gatatccttg cagtccttcc tttctaaatg acgagagaga  8400
cagaagaatt cttcaaggtt agtgtgtcca gcatgcaacc tttccttcct ggatgagcat  8460
ccctggagta ggagagccag cctgcctcct gcgctggcac agagcccggt tccctagaca  8520
actgcctctc caaatctgat gtccagcgcc acctggtgtc cacatcaagc agacacaatt  8580
aatagtcaac ctgttcagga aaactgtgag ggggaaaaaa aagaaagagg atttatgaag  8640
ggaaagaaa gtttagagga tatgccacga ttggctagca gctgcttttt gcctgtactg  8700
ggtctctctg gttagaccag atctgagcct gggagctctc tggctaacta gggaacccac  8760
tgcttaagcc tcaataaagc ttgccttgag tgcttcatcc ggaatcaacc tctggattac  8820
aaaatttgtg aaagattgac tggtattctt aactatgttg ctcctttttac gctatgtgga  8880
tacgctgctt taatgccttt gtatcatgct attgcttccc gtatggcttt catttctcc  8940
tccttgtata aatcctggtt gctgtctctt tatgaggagt tgtggcccgt tgtcaggcaa  9000
cgtggcgtgg tgtgcactgt gtttgctgac gcaacccca ctggttgggg cattgccacc  9060
```

```
acctgtcagc tcctttccgg gactttcgct ttcccccctcc ctattgccac ggcggaactc   9120
atcgccgcct gccttgcccg ctgctggaca ggggctcggc tgttgggcac tgacaattcc   9180
gtggtgttgt cggggaagct gacgtccttt ccatggctgc tcgcctgtgt tgccacctgg   9240
attctgcgcg ggacgtcctt ctgctacgtc ccttcggccc tcaatccagc ggaccttcct   9300
tcccgcggcc tgctgccggc tctgcggcct cttccgcgtc ttcgccttcg ccctcagacg   9360
agtcggatct ccctttgggc cgcctccccg cctgtccggt agcttgccag cctcgactgt   9420
gccttctagt tgccagccgt ctgttgtttg cccctccccc gtgccttcct tgaccctgga   9480
aggtgccact cccactgtcc tttcctaata aaatgaggaa attgcatcgc attgtctgag   9540
taggtgtcat tctattctgg ggggtggggt ggggcaggac agcaagggg aggattggga    9600
agacaatagc aggcatgcaa gcttggcgta atcatggtca tagctgtttc ctgtgtgaaa   9660
ttgttatccg ctcacaattc cacacaacat acgagccgga agcataaagt gtaaagcctg   9720
gggtgcctaa tgagtgagct aactcacatt aattgcgttg cgctcactgc ccgctttcca   9780
gtcgggaaac ctgtcgtgcc agctgcatta atgaatcggc caacgcgcgg ggagaggcgg   9840
tttgcgtatt gggcgctctt ccgcttcctc gctcactgac tcgctgcgct cggtcgttcg   9900
gctgcggcga gcggtatcag ctcactcaaa ggcggtaata cggttatcca cagaatcagg   9960
ggataacgca ggaaagaaca tgtgagcaaa aggccagcaa aaggccagga accgtaaaaa  10020
ggccgcgttg ctggcgtttt tccataggct ccgcccccct gacgagcatc acaaaaatcg  10080
acgctcaagt cagaggtggc gaaacccgac aggactataa agataccagg cgtttccccc  10140
tggaagctcc ctcgtgcgct ctcctgttcc gaccctgccg cttaccggat acctgtccgc  10200
ctttctccct tcgggaagcg tggcgctttc tcatagctca cgctgtaggt atctcagttc  10260
ggtgtaggtc gttcgctcca agctgggctg tgtgcacgaa ccccccgttc agcccgaccg  10320
ctgcgcctta tccggtaact atcgtcttga gtccaacccg gtaagacacg acttatcgcc  10380
actggcagca gccactggta acaggattag cagagcgagg tatgtaggcg gtgctacaga  10440
gttcttgaag tggtggccta actacggcta cactagaaga acagtatttg gtatctgcgc  10500
tctgctgaag ccagttacct tcggaaaaag agttggtagc tcttgatccg gcaaacaaac  10560
caccgctggt agcggtggtt tttttgtttg caagcagcag attacgcgca gaaaaaaagg  10620
atctcaagaa gatcctttga tcttttctac ggggtctgac gctcagtgga acgaaaactc  10680
acgttaaggg attttggtca tgagattatc aaaaaggatc ttcacctaga tccttttaaa  10740
ttaaaaatga agttttaaat caatctaaag tatatatgag taaacttggt ctgacagtta  10800
ccaatgctta atcagtgagg cacctatctc agcgatctgt ctatttcgtt catccatagt  10860
tgcctgactc cccgtcgtgt agataactac gatacgggag ggcttaccat ctggccccag  10920
tgctgcaatg ataccgcgag acccacgctc accggctcca gatttatcag caataaacca  10980
gccagccgga agggccgagc gcagaagtgg tcctgcaact ttatccgcct ccatccagtc  11040
tattaattgt tgccgggaag ctagagtaag tagttcgcca gttaatagtt tgcgcaacgt  11100
tgttgccatt gctacaggca tcgtggtgtc acgctcgtcg tttggtatgg cttcattcag  11160
ctccggttcc caacgatcaa ggcgagttac atgatccccc atgttgtgca aaaaagcggt  11220
tagctccttc ggtcctccga tcgttgtcag aagtaagttg gccgcagtgt tatcactcat  11280
ggttatggca gcactgcata attctcttac tgtcatgcca tccgtaagat gcttttctgt  11340
gactggtgag tactcaacca agtcattctg agaatagtgt atgcggcgac cgagttgctc  11400
ttgcccggcg tcaatacggg ataataccgc gccacatagc agaactttaa aagtgctcat  11460
cattggaaaa cgttcttcgg ggcaaaactc tcaaggatct taccgctgtt gagatccagt  11520
tcgatgtaac ccactcgtgc acccaactga tcttcagcat cttttacttt caccagcgtt  11580
tctgggtgag caaaaacagg aaggcaaaat gccgcaaaaa agggaataag ggcgacacgg  11640
aaatgttgaa tactcatact cttccttttt caatattatt gaagcattta tcagggttat  11700
tgtctcatga gcggatacat atttgaatgt atttagaaaa ataaacaaat aggggttccg  11760
cgcacatttc cccgaaaagt gccacctgac gtctaagaaa ccattattat catgacatta  11820
acctataaaa ataggcgtat cacgaggccc tttcgtctcg cgcgtttcgg tgatgacggt  11880
gaaaacctct gacacatgca gctcccggag acggtcacag cttgtctgta agcggatgcc  11940
gggagcagac aagcccgtca gggcgcgtca gcgggtgttg gcgggtgtcg gggctggctt  12000
aactatgcgg catcagagca gattgtactg agagtgcacc                         12040
```

```
SEQ ID NO: 39           moltype = DNA  length = 11438
FEATURE                 Location/Qualifiers
misc_feature            1..11438
                        note = Description of Artificial Sequence: Synthetic
                        polynucleotide
source                  1..11438
                        mol_type = other DNA
                        organism = synthetic construct
SEQUENCE: 39
attggccatt gcatacgttg tatccatatc ataatatgta catttatatt ggctcatgtc   60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg gaggtctat ataagcagag    660
ctcgtttagt gaaccggggt ctctctggtt agaccagatc tgagcctggg agctctctgg   720
ctaactaggg aacccactgc ttaagcctca ataaagcttg ccttgagtgc ttcaagtagt   780
gtgtgcccgt ctgttgtgtg actctggtaa ctagagatcc ctcagaccct tttagtcagt   840
gtggaaaatc tctagcagtg gcgcccgaac agggacttga aagcgaaagg gaaaccagag   900
gagctctctc gacgcaggac tcggcttgct gaagcgcgca cggcaagagg cgaggggcgg   960
cgactggtgt gtacgccaaa aattttgact agcggaggct agaaggagag agacgggtgc  1020
gagagcgtca gtattaagcg ggggtgaata agatcgcgat gggaaaaaat tcggttaagg  1080
ccagggggaa agaaaaaata taaattaaaa catatagtat gggcaagcag ggagctagaa  1140
```

-continued

```
cgattcgcag ttaatcctgg cctgttagaa acatcagaag gctgtagaca aatactggga   1200
cagctacaac catcccttca gacaggatca gaagaactta gatcattata taatacagta   1260
gcaaccctct attgtgtgca tcaaaggata gagataaaag acaccaagga agctttagac   1320
aagatagagg aagagcaaaa caaaagtaag accaccgcac agcaagcggc cgctgatctt   1380
cagacctgga ggaggagata tgagggacaa ttggagaagt gaattatata aatataaagt   1440
agtaaaaatt gaaccattag gagtagcacc caccaaggca aagagaagag tggtgcagag   1500
agaaaaaaga gcagtgggaa taggagcttt gttccttggg ttcttgggag cagcaggaag   1560
cactatgggc gcagcgtcaa tgacgctgac ggtacaggcc agacaattat tgtctggtat   1620
agtgcagcag cagaacaatt tgctgagggc tattgaggcg caacagcatc tgttgcaact   1680
cacagtctgg ggcatcaagc agctccaggc aagaatcctg gctgtggaaa gatacctaaa   1740
ggatcaacag ctcctgggga tttgggggttg ctctggaaaa ctcatttgca ccactgctgt   1800
gccttggaat gctagttgga gtaataaatc tctggaacag atttggaatc acacgacctg   1860
gatggagtgg gacagagaaa ttaacaatta cacaagctta atacactcct taattgaaga   1920
atcgcaaaac cagcaagaaa agaatgaaca agaattattg gaattagata aatgggcaag   1980
tttgtggaat tggtttaaca taacaaattg gctgtggtat ataaaattat tcataatgat   2040
agtaggaggc ttggtaggtt taagaatagt ttttgctgta ctttctatag tgaatagagt   2100
taggcaggga tattcaccat tatcgtttca gacccacctc ccaaccccga ggggacccga   2160
caggcccgaa ggaatagaag aagaaggtgg agagagagac ccattcgatt ccattcgatt   2220
agtgaacgga tctcgacggt atcgttttaa aagaaaaggg gggattgggg ggtacagtgc   2280
aggggaaaga atagtagaca taatagcaac agacatacaa actaaagaat tacaaaaaca   2340
aattacaaaa attcaaaatt ttatcggcgt gttgggggtg gaccatcctc taggtattga   2400
ataagaaaaa tgaagttaag gtggttgatg gtaacactat gctaataact gcagagccag   2460
aagcaccata agggacatga taagggagcc agcagacctc tgatctcttc ctgaatgcta   2520
atcttaaaca tcctgaggaa gaatgggact tccatttggg gtgggcctat gatagggtaa   2580
taagacagta gtgaatatca agctacaaaa agccccttt caaattcttc tcagtcctaa   2640
ctttcatac taagcccagt ccttccaaag cagactgtga aagagtgata gttccgggag   2700
actagcactg cagattccgg gtcactgtga gtggggggagg cagggaagaa gggctcacag   2760
gacagtcaaa ccatgcccc tgttttcct tcttcaagta gacctctata agacaacaga   2820
gacaactaag gctgagtggc caggcgagga gaaaccatct cgccgtaaaa catggaagga   2880
acacttcagg ggaaaggtgg tatctctaag caagagaact gagtggagtc aaggctgaga   2940
gatgcaggat aagcaaatgg gtagtgaaaa gacattcatg aggacagcta aaacaataag   3000
taatgtaaaa tacagcatag caaaacttta acctccaaat caagcctcta cttgaatcct   3060
tttctgaggg atgaataagg cataggcatc aggggctgtt gccaatgtgc attagctgtt   3120
tgcagcctca ccttctttca tggagtttaa gatatagtat attttcccaa ggtttgaact   3180
agctcttcat ttctttatgt tttaaatgca ctgacctccc acattccctt tttagtaaaa   3240
tattcagaaa taatttaaat acatcattgc aatgaaaata aatgtttttt attaggcaga   3300
atccagatgc tcaaggccct tcataatatc ccccagttta gtagttggac ttagggaaca   3360
aaggaacctt taatagaaat tggacagcaa gaaagcgagc ttagtgatac ttgtgggcca   3420
gggcattagc cacaccagcc accactttct gataggcagc ctgcactggt ggggtgaatt   3480
ctttgccaaa gtgatgggcc agcacacaga ccagcacgtt gcccaggagc tgtgggagga   3540
agataagagg tatgaacatg attagcaaaa gggcctagct tggactcaga ataatccagc   3600
cttatcccaa ccataaaata aaagcagaat ggtagctgga ttgtagctgc tattagcaat   3660
atgaaacctc ttacatcagt tacaatttat atgcagaaat atttatatgc agaaatattg   3720
ctattgcctt aacccagaaa ttatcactgt tattctttag aatggtgcaa agaggcatga   3780
tacattgtat cattattgcc ctgaaagaaa gagattaggg aaagtattag aaataagata   3840
aacaaaaaag tatattaaaa gaagaaagca ttttttaaaa ttacaaatgc aaaattaccc   3900
tgatttggtc aatatgtgta ccctgttact tctcccctte ctatgacatg aacttaacca   3960
tagaaaagaa ggggaaagaa aacatcaagg gtcccataga ctcaccctga agttctcagg   4020
atccacgtgc agcttgtcac agtgcagctc actcagctgg gcaaaggtgc ccttgaggtt   4080
gtccaggtga gccaggccat cactaaaggc accgagcact ttcttgccat gagccttcac   4140
cttaggggttg cccataacag catcaggagt ggacagatcc ccaaaggact caaagaacct   4200
ctgggtccaa gggtagacca ccagcagcct aagggtggga aaatagacca ataggcagag   4260
agagtcagtg cctatcagaa acccaagagt cttctctgtc tccacatgcc cagtttctat   4320
tggtctcctt aaacctgtct tgtaaccttg ataccaacct gcccagggcc tcaccaccaa   4380
cttcatccac gttcaccttg ccccacaggg cagtaacggc agacttctcc tcaggagtca   4440
ggtgcaccat ggtgtctgtt tgaggttgac agtgaacaca gttgtgtcag aagcaaatgt   4500
aagcaataga tggctctgcc ctgactttta tgcccagccc tggctcctgc cctccctgct   4560
cctgggagta gattggccaa ccctaggggtg tggctccaca gggtgaggtc taagtgatga   4620
cagccgtacc tgtccttggc tcttctggca ctggcttagg agttggactt caaaccctca   4680
gccctccctc taagatatat ctcttggccc cataccatca gtacaaattg ctactaaaaa   4740
catcctcctt tgcaagtgta tttactctag aatatgtcac attctgtctc aggcatccat   4800
tttctttatg atgccgtttg aggtggagtt ttagtcaggt ggtcagcttc tccttttttt   4860
tgccatctgc cctgtaagca tcctgctggg gacccagata ggagtcatca ctctaggctg   4920
agaacatctg ggcacacacc ctaagcctca gcatgactca tcatgactca gcattgctgt   4980
gcttgagcca gaaggtttgc ttagaaggtt acacagaacc agaaggcggg ggtggggcac   5040
tgaccccgac aggggcctgg ccagaactgc tcatgcttgg actatgggag gtcactaatg   5100
gagacacaca gaaatgtaac aggaactaag gaaaaactga agcttattta atcagagatg   5160
agatgctgga agggatagag ggagctgagc ttgtaaaaag tatagtaatc attcagcaaa   5220
tggttttgaa gcacctgctg gatgctaaac actattttca gtgcttgaat cataaataag   5280
aacaaaacat gtatcttatt ccccacaaga gtccaagtaa aaaataacag ttaattataa   5340
tgtgctctgt cccccaggct ggagtgcagt ggcacgatct cagctcactg caacctccgc   5400
ctcccgggtt caagcaattc tcctgcctca gccaccctaa tagctgggat tacaggtgca   5460
caccaccatg ccaggctaat ttttgtactt tttgtagagg cagggtatca ccatgttgtc   5520
caagatggtc ttgaactcct gagctccaag cagtccaccc acctcagcct cccaaagtgc   5580
tatctgcggc cgcctatctt taccactagt ctcgagaagc tttcatcaaa aaaagtctaa   5640
ccagctgcat tcgactttga ctgcagcagc tggttagaag gttctactgg aggagggtcc   5700
cagcccattg ctaaattaac atcaggctct gagactggca gtatatctct aacagtggtt   5760
gatgctatct tctggaactt gcctgctaca ttgagaccac tgacccatac ataggaagcc   5820
catagctctg tcctgaactg ttaggccact ggtccagaga gtgtgcatct cctttgatcc   5880
```

-continued

```
tcataataac cctatgagat agacacaatt attactctta cttttatagat gatgatcctg    5940
aaaacatagg agtcaaggca cttgcccta gctgggggta tagggggagca gtcccatgta    6000
gtagtagaat gaaaaatgct gctatgctgt gcctccccca cctttcccat gtctgccctc    6060
tactcatggt ctatctctcc tggctcctgg gagtcatgga ctccacccag caccaccaac    6120
ctgacctaac cacctatctg agcctgccag cctataaccc atctgggccc tgatagctgg    6180
tggccagccc tgaccccacc ccaccctccc tggaacctct gatagacaca tctggcacac    6240
cagctcgcaa agtcaccgtg agggtcttgt gtttgctgag tcaaaattcc ttgaaatcca    6300
agtccttaga gactcctgct cccaaattta cagtcataga cttcttcatg gctgtctcct    6360
ttatccacag aatgattcct ttgcttcatt gccccatcca tctgatcctc ctcatcagtg    6420
cagcacaggg cccatgagca gtagctgcag agtctcacat aggtctggca ctgcctctga    6480
catgtccgac cttaggcaaa tgcttgactc ttctgagctc agtcttgtca tggcaaaaca    6540
aagataataa tagtgttttt ttatggagtt agcgtgagga tggaaaacaa tagcaaaatt    6600
gattagacta taaaaggtct caacaaatag tagtagattt tatcatccat taatccttcc    6660
ctctcctctc ttactcatcc catcacgtat gcctcttaat tttcccttac ctataataag    6720
agttattcct cttattatat tcttcttata gtgattctgg atatcaaagt gggaatgagg    6780
ggcaggccac taacgaagaa gatgtttctc aaagaagcca ttctcccac atagatcatc    6840
tcagcagggt tcaggaagat aaaggaggat caaggtcgaa ggtaggaact aaggaagaac    6900
actgggcaag tggatcctaa atatatcatt taaatgcata aataagcaaa ccctgctcgg    6960
gaatgggagg gagagtctct ggagtccacc ccttctcggc cctggctctg cagatagtgc    7020
tatcaaagcc ctgacagagc cctgcccatt gctgggcctt ggagtgagtc agcctagtag    7080
agaggcaggg caagccatct catagctgct gagtgggaga gagaaaaggg ctcattgtct    7140
ataaactcag gtcatggcta ttcttattct cacactaaga aaaagaatga gatgtctaca    7200
tatacctgc gtcccctctt gtgtactggg gcccccaaga gctctctaaa agtgatggca    7260
aagtcattgc gctagatgcc atcccatcta ttataaacct gcatttgtct ccacacacca    7320
gtcatggaca ataaccctcc tcccaggtcc acgtgcttgt ctttgtataa tactcaagta    7380
atttcggaaa atgtattctt tcaatcttgt tctgttcatt ctgtttcaat ggcttagtag    7440
aaaaagtaca tacttgtttt cccataaatt gacaatagac aatttcacat caatgtctat    7500
atgggtcgtt gtgtttgctg tgtttgcaaa aactcacaat aactttatat tgttactact    7560
ctaagaaagt tacaacatgg tgaatacaag agaaagctat tacaagtcca gaaaacaaaa    7620
gttatcatct tgaggcctca gctttctagg aataatatca atattacaaa acgcgtcgac    7680
ggtaccgtta acgatcttag ccactttta aaagaaaagg ggggactgga agggctaatt    7740
cactcccaac gaagacaaga tatcctgcta gtccttcctt tctaaatgac gagagagaca    7800
gaagaattct tcaaggttag tgtgtccagc atgcaacctt tccttcctgg atgagcatcc    7860
ctggagtagg agagccagcc tgcctcctgc gctggcacag agcccggttc cctagacaac    7920
tgcctctcca aatctgatgt ccagcgccac ctggtgtcca catcaagcag acacaattaa    7980
tagtcaacct gttcaggaaa actgtgaggg ggaaaaaaaa gaaagaggat ttatgaaggg    8040
aaaagaaagt ttagaggata tgccacgatt ggctagcagc tgcttttttgc ctgtactggg    8100
tctctctggt tagaccagat ctgagcctgg gagctctctg gctaactagg gaacccactg    8160
cttaagcctc aataaagctt gccttgagtg cttcatccgg aatcaacctc tggattacaa    8220
aatttgtgaa agattgactg gtattcttaa ctatgttgct ccttttacgc tatgtggata    8280
cgctgcttta atgcctttgt atcatgctat tgcttcccgt atggctttca ttttctcctc    8340
cttgtataaa tcctggttgc tgtctcttta tgaggagttg tggcccgttg tcaggcaacg    8400
tggcgtggtg tgcactgtgt ttgctgacgc aacccccact ggttggggca ttgccaccac    8460
ctgtcagctc cttttcggga ctttcgcttt ccccctccct attgccacgg cggaactcat    8520
cgccgcctgc cttgcccgct gctggacagg ggctcggctg ttgggcactg acaattccgt    8580
ggtgttgtcg gggaagctga cgtcctttcc atggctgctc gcctgtgttg ccacctggat    8640
tctgcgcggg acgtccttct gctacgtccc ttcggccctc aatccagcgg accttccttc    8700
ccgcggcctg ctgccggctc tgcggcctct tccgcgtctt cgccttcgcc ctcagacgag    8760
tcggatctcc ctttgggccg cctccccgcc tgtccggtag cttgccagcc tcgactgtgc    8820
cttctagttg ccagccgtct gttgtttgcc cctcccccgt gccttccttg accctggaag    8880
gtgccactcc cactgtcctt tcctaataaa atgaggaaat tgcatcgcat tgtctgagta    8940
ggtgtcattc tattctgggg ggtgggggtg ggcaggacag caaggggagg attgggaag    9000
acaatagcag gcatgcaagc ttggcgtaat catggtcata gctgtttcct gtgtgaaatt    9060
gttatccgct cacaattcca cacaacatac gagccggaag cataaagtgt aaagcctggg    9120
gtgcctaatg agtgagctaa ctcacattaa ttgcgttgcg ctcactgccc gctttccagt    9180
cgggaaacct gtcgtgccag ctgcattaat gaatcggcca acgcgcgggg agaggcggtt    9240
tgcgtattgg cgctcttccg cttcctcgc tcactgactc gctgcgctcg gtcgttcggc    9300
tgcggcgagc ggtatcagct cactcaaagg cggtaatacg gttatccaca gaatcagggg    9360
ataacgcagg aaagaacatg tgagcaaaag gccagcaaaa ggccaggaac cgtaaaaagg    9420
ccgcgttgct ggcgtttttc cataggctcc gcccccctga cgagcatcac aaaaatcgac    9480
gctcaagtca gaggtggcga aacccgacag gactataaag ataccaggcg tttccccctg    9540
gaagctccct cgtgcgctct cctgttccga cctgccgct taccggatac ctgtccgcct    9600
ttctcccttc gggaagcgtg gcgctttctc atagctcacg ctgtaggtat ctcagttcgg    9660
tgtaggtcgt tcgctccaag ctgggctgtg tgcacgaacc cccgttcag cgccgaccgct    9720
gcgccttatc cggtaactat cgtcttgagt ccaacccggt aagacacgac ttatcgccac    9780
tggcagcagc cactggtaac aggattagca gagcgaggta tgtaggcggt gctacagagt    9840
tcttgaagtg gtggcctaac tacggctaca ctagaagaac agtatttggt atctgcgctc    9900
tgctgaagcc agttaccttc ggaaaaagag ttggtagctc ttgatccggc aaacaaacca    9960
ccgctggtag cggtggtttt tttgtttgca agcagcagat tacgcgcaga aaaaaaggat   10020
ctcaagaaga tcctttgatc ttttctacgg ggtctgacgc tcagtggaac gaaaactcac   10080
gttaagggat tttggtcatg agattatcaa aaaggatctt cacctagatc cttttaaatt   10140
aaaaatgaag ttttaaatca atctaaagta tatatgagta aacttggtct gacagttacc   10200
aatgcttaat cagtgaggca cctatctcag cgatctgtct atttcgttca tccatagttg   10260
cctgactccc cgtcgtgtag ataactacga tacgggaggg cttaccatct ggccccagtg   10320
ctgcaatgat accgcgagac ccacgctcac cggctccaga tttatcagca ataaaccagc   10380
cagccggaag ggccgagcgc agaagtggtc ctgcaacttt atccgcctcc atccagtcta   10440
ttaattgttg ccgggaagct agagtaagta gttcgccagt taatagtttg cgcaacgttg   10500
ttgccattgc tacaggcatc gtggtgtcac gctcgtcgtt tggtatggct tcattcagct   10560
ccggttccca acgatcaagg cgagttacat gatccccat gttgtgcaaa aaagcggtta   10620
```

-continued

```
gctccttcgg tcctccgatc gttgtcagaa gtaagttggc cgcagtgtta tcactcatgg    10680
ttatggcagc actgcataat tctcttactg tcatgccatc cgtaagatgc ttttctgtga    10740
ctggtgagta ctcaaccaag tcattctgag aatagtgtat gcggcgaccg agttgctctt    10800
gcccggcgtc aatacgggat aataccgcgc cacatagcag aactttaaaa gtgctcatca    10860
ttggaaaacg ttcttcgggg caaaactctc aaggatctta ccgctgttga gatccagttc    10920
gatgtaaccc actcgtgcac ccaactgatc ttcagcatct tttactttca ccagcgtttc    10980
tgggtgagca aaaacaggaa ggcaaaatgc cgcaaaaaag ggaataaggg cgacacggaa    11040
atgttgaata ctcatactct tcctttttca atattattga agcatttatc agggttattg    11100
tctcatgagc ggatacatat ttgaatgtat ttagaaaaat aaacaaatag gggttccgcg    11160
cacatttccc cgaaaagtgc cacctgacgt ctaagaaacc attattatca tgacattaac    11220
ctataaaaat aggcgtatca cgaggccctt tcgtctcgcg cgtttcggtg atgacggtga    11280
aaacctctga cacatgcagc tcccggagac ggtcacagct tgtctgtaag cggatgccgg    11340
gagcagacaa gcccgtcagg gcgcgtcagc gggtgttggc gggtgtcggg gctggcttaa    11400
ctatgcggca tcagagcaga ttgtactgag agtgcacc                           11438
```

SEQ ID NO: 40              moltype = DNA   length = 11342
FEATURE                    Location/Qualifiers
misc_feature               1..11342
                           note = Description of Artificial Sequence: Synthetic
                            polynucleotide
source                     1..11342
                           mol_type = other DNA
                           organism = synthetic construct
SEQUENCE: 40

```
attggccatt gcatacgttg tatccatatc ataaatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt ggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg ggaggtctat ataagcagag   660
ctcgtttagt gaaccggggt ctctctggtt agaccagatc tgagcctggg agctctctgg   720
ctaactaggg aacccactgc ttaagcctca ataaagcttg ccttgagtgc ttcaagtagt   780
gtgtgcccgt ctgttgtgtg actctggtaa ctagagatcc ctcagaccct tttagtcagt   840
gtggaaaatc tctagcagtg gcgcccgaac agggacttga aagcgaaagg gaaaccagag   900
gagctctctc gacgcaggac tcggcttgct gaagcgcgca cggcaagagg cgaggggcgg   960
cgactggtga gtacgccaaa aattttgact agcggaggct agaaggagag agacgggtgc  1020
gagagcgtca gtattaagcg ggggtgaata agatcgcgat gggaaaaaat tcggttaagg  1080
ccaggggaa agaaaaaata taaattaaaa catatagtat gggcaagcag gagctagaa   1140
cgattcgcag ttaatcctgg cctgttagaa acatcagaag gctgtagaca aatactggga  1200
cagctacaac catcccttca gacaggatca gaagaactta gatcattata taatacagta  1260
gcaaccctct attgtgtgca tcaaaggata gagataaaag acaccaagga agctttagac  1320
aagatagagg aagagcaaaa caaaagtaag accaccgcac agcaagcggc cgctgatctt  1380
cagacctgga ggaggagata tgagggacaa ttggagaagt gaattatata aatataaagt  1440
agtaaaaatt gaaccattag gagtagcacc caccaaggca aagagaagag tggtgcagag  1500
agaaaaaaga gcagtgggaa taggagcttt gttccttggg ttcttgggag cagcaggaag  1560
cactatgggc gcagcgtcaa tgacgctgac ggtacaggcc agacaattat tgtctggtat  1620
agtgcagcag cagaacaatt tgctgagggc tattgaggcg caacagcatc tgttgcaact  1680
cacagtctgg ggcatcaagc agctccaggc aagaatcctg gctgtggaaa gatacctaaa  1740
ggatcaacag ctcctgggga tttggggttg ctctggaaaa ctcatttgca ccactgctgt  1800
gccttggaat gctagttgga gtaataaatc tctggaacag atttggaatc acacgacctg  1860
gatggagtgg gacagagaaa ttaacaatta cacaagctta atacactcct taattgaaga  1920
atcgcaaaac cagcaagaaa agaatgaaca agaattattg gaattagata atgggcaag  1980
tttgtggaat tggtttaaca taacaaattg gctgtggtat ataaaattat tcataatgat  2040
agtaggaggc ttggtaggtt taagaatagt ttttgctgta ctttctatag tgaatagagt  2100
taggcaggga tattcaccat tatcgtttca gacccacctc ccaacCccga ggggacccga  2160
caggcccgaa ggaatagaag aagaaggtgg agagagagac agagacagat ccattcgatt  2220
agtgaacgga tctcgacggt atcgttttaa aagaaaaggg gggattgggg ggtacagtgc  2280
aggggaaaga atagtagaca taatagcaac agacatacaa actaaagaat tacaaaaaca  2340
aattacaaaa attcaaaatt ttatcggcgt gttgggggtac gaccatcctc taggtattga  2400
ataagaaaaa tgaagttaag gtggttgatg gtaacactaa gctaataact gcagagccag  2460
aagcaccata agggacatga taagggagcc agcagacctc tgatctcttc ctgaatgcta  2520
atcttaaaca tcctgaggaa gaatgggact tccatttggg gtgggcctat gatagggtaa  2580
taagcagta gtgaatatca agctacaaaa agcccccttt caaattcttc tcagtcctaa  2640
cttttcatac taagcccagt ccttccaaag cagactgtga aagagtgata gttccgggac  2700
actagcactg cagattccgg gtcactgtga gtgggggagg cagggaagaa gggctcacag  2760
gacagtcaaa ccatgcgccc tgttttttcct tcttcaagta gacctctata agacaacaga  2820
gacaactaag gctgagtggc caggcgagga gaaaccatct cgccgtaaaa catggaagga  2880
acacttcagg ggaaaggtgg tatctctaag caagagaact gagtggagtc aaggctgaga  2940
gatgcaggat aagcaaatgg gtagtgaaaa gacattcatg aggacagcta aaacaataag  3000
taatgtaaaa tacagcatag caaaactttta acctccaaat caagcctcta cttgaatcct  3060
tttctgaggg atgaataagg cataggcatc aggggctgtt gccaatgtgc attagctgtt  3120
tgcagcctca ccttctttca tggagtttaa gatatagtgt attttcccaa ggtttgaact  3180
agctcttcat ttctttatgt tttaaatgca ctgacctccc acattccctt tttagtaaaa  3240
tattcagaaa taatttaaat acatcattgc aatgaaaata aatgtttttt attaggcaga  3300
```

-continued

```
atccagatgc tcaaggccct tcataatatc ccccagttta gtagttggac ttagggaaca   3360
aaggaacctt taatagaaat tggacagcaa gaaagcgagc ttagtgatac ttgtgggcca   3420
gggcattagc cacaccagcc accactttct gataggcagc ctgcactggt ggggtgaatt   3480
ctttgccaaa gtgatgggcc agcacacaga ccagcacgtt gcccaggagc tgtgggagga   3540
agataagagg tatgaacatg attagcaaaa gggcctagct tggactcaga ataatccagc   3600
cttatcccaa ccataaaata aaagcagaat ggtagctgga ttgtagctgc tattagcaat   3660
atgaaacctc ttacatcagt tacaatttat atgcagaaat atttatatgc agaaatattg   3720
ctattgcctt aacccagaaa ttatcactgt tattctttag aatggtgcaa agaggcatga   3780
tacattgtat cattattgcc ctgaaagaaa gagattaggg aaagtattag aaataaagata   3840
aacaaaaaag tatattaaaa gaagaaagca tttttttaaaa ttacaaatgc aaaattaccc   3900
tgatttggtc aatatgtgta ccctgttact tctcccccttc ctatgacatg aacttaacca   3960
tagaaaagaa ggggaaagaa aacatcaagg gtcccccataga ctcaccctga agttctcagg   4020
atccacgtgc agcttgtcac agtgcagctc actcagctgg gcaaaggtgc ccttgaggtt   4080
gtccaggtga gccaggccat cactaaaggc accgagcact ttcttgccat gagccttcac   4140
cttaggggttg cccataacag catcaggagt ggacagatcc ccaaaggact caaagaacct   4200
ctgggtccaa gggtagacca ccagcagcct aagggtggga aaatagacca ataggcagag   4260
agagtcagtg cctatcagaa acccaagagt cttctctgtc tccacatgcc cagtttctat   4320
tggtctcctt aaacctgtct tgtaaccttg ataccaacct gcccagggcc tcaccaccaa   4380
cttcatccac gttcaccttg ccccacaggg cagtaacggc agacttctcc tcaggagtca   4440
ggtgcaccat ggtgtctgtt tgaggttgct agtgaacaca gttgtgtcag aagcaaatgt   4500
aagcaataga tggctctgcc ctgactttta tgcccagccc tggctcctgc cctcctgct   4560
cctggagta gattggccaa ccctagggtg tggctccaca gggtgaggtc taagtgatga   4620
cagccgtacc tgtccttggc tcttctggca ctggcttagg agttggactt caaaccctca   4680
gccctccctc taagatatat ctcttggccc cataccatca gtacaaattg ctactaaaaa   4740
catcctcctt tgcaagtgta tttacggcat ctgtgaagga aagaaacatc tcctctaaac   4800
cactatgctg ctagagcctc tttttctgtac tcaagcctca ttcagacact agtgtcacca   4860
gtctcctcat atacctattg tattttcttc ttcttgctgg tttagtcatg ttttctggga   4920
gcttaggggc ttatttttatt ttgtttttgtt ttctaatcaa cagagatggg caaacccatt   4980
attttttttct ttagacttgg gatggtgata gctgggcagc gtcagaaact gtgtgtggat   5040
atagataaga gctcggacta tgctgagctg tgatgaggga gggacctagc caaaggcagt   5100
gagagtcaga atgctcctgc tattgccttc tcagtcccca cgcttggttt ctacacaagt   5160
agatacatag aaaaggctat aggttagtgt ttgagagtcc tgcatgagtt agttgctcag   5220
aaatgcccga taaatatgtt atgtgtgtttt atgtatatat atgtttttata tatatatatg   5280
tgtgtgtgtg tgtgtgtgtg tgttgtgttt acaaatatgt gattatcatc aaaacgtgag   5340
ggctaaagtg accagataac ttgcaggtct agacacccctt ttccggcacg cagatagtca   5400
atatcttcag cgtccccaag gcctgcaagg gtggggcccc atatctggaa gtcccaggcg   5460
gagctgggag ttggtcaagt ctgggctgtg ggggcaggga gtgctgggggg atggctcgag   5520
aagctttcat caaaaaaagt ctaaccagct gcattcgact ttgactgcag cagctggtta   5580
gaaggttcta ctggaggagg gtcccagccc attgctaaat taacatcagg ctctgagact   5640
ggcagtatat ctctaacagt ggttgatgct atcttctgga acttgcctgc tacattgaga   5700
ccactgaccc atacatagga agcccatagc tctgtcctga actgttaggc cactggtcca   5760
gagagtgtgc atctcctttg atcctcataa taacccctatg agatagacac aattattact   5820
cttactttat agatgatgat cctgaaaaca taggagtcaa ggcacttgcc cctagctaggg   5880
ggtataggg agcagtccca tgtagtagta gaatgaaaaa tgctgctatg ctgtgcctcc   5940
cccaccttttc ccatgtctgc cctctactca tggtctatct ctcctggctc ctgggagtca   6000
tggactccac ccagcaccac caacctgacc taaccaccta tctgagcctg ccagcctata   6060
acccatctgg gccctgatag ctggtggcca gccctgaccc caccccaccc tccctggaac   6120
ctctgataga cacatctggc acaccagctc gcaaagtcac cgtcgagggtc ttgtgtttgc   6180
tgagtcaaaa ttccttgaaa tccaagtcct tagagactcc tgctcccaaa tttacagtca   6240
tagacttctt catggctgtc tcctttatcc acagaatgat tcctttgctt cattgcccca   6300
tccatctgat cctcctcatc agtgcagcac agggcccatg agcagtagct gcagagtctc   6360
acataggtct ggcactgcct ctgacatgtc cgaccttagg caaatgcttg actcttctga   6420
gctcagtctt gtcatggcaa aacaaagata ataatagtgt tttttttatgg agttagcgtg   6480
aggatggaaa acaatagcaa aattgattag actataaaag gtctcaacaa atagtagtag   6540
attttatcat ccattaatcc ttccctctcc tctcttactc atcccatcac gtatgcctct   6600
taattttccc ttacctataa taagagttat tcctccttatt atattcttct tatagtgatt   6660
ctggatatca aagtgggaat gaggggcagg ccactaacga agaagatgtt tctcaaagaa   6720
gccattctcc ccacatagat catctcagca gggttcagga agataaagga ggatcaaggt   6780
cgaaggtagg aactaaggaa gaacactggg caagtggatc ctaaatatat catttaaatg   6840
cataaataag caaaccctgc tcgggaatgg gaggggagt ctctggagtc caccccttct   6900
cggccctggc tctgcagata gtgctatcaa agccctgaca gagccctgcc cattgctggg   6960
ccttggagtg agtcagccta gtagagaggc agggcaagcc atctcatagc tgctgagtgg   7020
gagagagaaa agggctcatt gtctataaac tcaggtcatg gctattctta ttctcacact   7080
aagaaaaaga atgagatgtc tacatatacc ctgcgtcccg tcttgtgtac tggggcccccc   7140
aagagctctc taaaagtgat ggcaaagtca ttgcgctaga tgccatccca tctattataa   7200
acctgcattt gtctccacac accagtcatg gacaataacc ctcctcccag gtccacgtgc   7260
ttgtctttgt ataatactca agtaatttcg gaaaatgtat tctttcaatc ttgttctgtt   7320
attcctgttt caatggctta gtagaaaaag tacatacttg ttttcccata aattgacaat   7380
agacaatttc acatcaatgt ctatatgggt cgttgtgttt gctgtgtttg caaaaactca   7440
caataacttt atattgttac tactctaaga aagttacaac atggtgaata caagagaaag   7500
ctattacaag tccagaaaac aaaagttatc atcttgaggc ctcagctttc taggaataat   7560
atcaatatta caaaacgcgt cgacggtacc gttaacgatc ttagccactt tttaaaagaa   7620
aagggggac tggaagggct aattcactcc caacgaagac aagatatcct gctagtcctt   7680
cctttctaaa tgacgagaga gacagaagaa ttcttcaagg ttagttgtc cagcatgcaa   7740
cctttccttc ctggatgagc atccctggag taggagagca agctgcctc ctgcgctggc   7800
acagagcccg gttccctaga caactgcctc tccaaatctg atgtccagcg ccacctggtg   7860
tccacatcaa gcagacacaa ttaatagtca acctgttcag gaaaactgtg aggggaaaaa   7920
aaaagaaaga ggatttatga agggaaaaga agttttagag gatatgccac gattggctag   7980
cagctgcttt ttgcctgtac tgggtctctc tggttagacc agatctgagc ctgggagctc   8040
```

-continued

```
tctggctaac tagggaaccc actgcttaag cctcaataaa gcttgccttg agtgcttcat   8100
ccggaatcaa cctctggatt acaaaatttg tgaaagattg actggtattc ttaactatgt   8160
tgctcctttt acgctatgtg gatacgctgc tttaatgcct ttgtatcatg ctattgcttc   8220
ccgtatggct ttcattttct cctccttgta taaatcctgg ttgctgtctc tttatgagga   8280
gttgtggccc gttgtcaggc aacgtggcgt ggtgtgcact gtgtttgctg acgcaaccc   8340
cactggttgg ggcattgcca ccacctgtca gctcctttcc gggactttcg ctttccccct   8400
ccctattgcc acggcggaac tcatcgccgc ctgccttgcc cgctgctgga caggggctcg   8460
gctgttgggc actgacaatt ccgtggtgtt gtcggggaag ctgacgtcct ttccatggct   8520
gctcgcctgt gttgccacct ggattctgcg cgggacgtcc ttctgctacg tcccttcggc   8580
cctcaatcca gcggaccttc cttcccgcgg cctgctgccg gctctgcggc ctcttccgcg   8640
tcttcgcctt cgccctcaga cgagtcggat ctcccttgg gccgcctccc cgcctgtccg   8700
gtagcttgcc agcctcgact gtgccttcta gttgccagcc gtctgttgtt tgcccctccc   8760
ccgtgccttc cttgacctg gaaggtgcca ctcccactgt cctttcctaa taaaatgagg   8820
aaattgcatc gcattgtctg agtaggtgtc attctattct gggggtggg gtggggcagg   8880
acagcaaggg ggaggattgg gaagacaata gcaggcatgc aagcttggcg taatcatggt   8940
catagctgtt tcctgtgtga aattgttatc cgctcacaat tccacacaac atacgagccg   9000
gaagcataaa gtgtaaagcc tggggtgcct aatgagtgag ctaactcaca ttaattgcgt   9060
tgcgctcact gcccgctttc cagtcgggaa acctgtcgtg ccagctgcat taatgaatcg   9120
gccaacgcgc ggggagaggc ggtttgcgta ttgggcgctc ttccgcttcc tcgctcactg   9180
actcgctgcg ctcggtcgtt cggctgcggc gagcggtatc agctcactca aaggcggtaa   9240
tacggttatc cacagaatca ggggataacg caggaaagaa catgtgagca aaaggccagc   9300
aaaaggccag gaaccgtaaa aaggccgcgt tgctggcgtt tttccatagg ctccgcccccc   9360
ctgacgagca tcacaaaaat cgacgctcaa gtcagaggtg gcgaaacccg acaggactat   9420
aaagatacca ggcgtttccc cctggaagct ccctcgtgcg ctctcctgtt ccgaccctgc   9480
cgcttaccgg atacctgtcc gcctttctcc cttcgggaag cgtggcgctt tctcatagct   9540
cacgctgtag gtatctcagt tcggtgtagg tcgttcgctc caagctgggc tgtgtgcacg   9600
aaccccccgt tcagcccgac cgctgcgcct tatccggtaa ctatcgtctt gagtccaacc   9660
cggtaagaca cgacttatcg ccactggcag cagccactgg taacaggatt agcagagcga   9720
ggtatgtagg cggtgctaca gagttcttga agtggtggcc taactacggc tacactagaa   9780
gaacagtatt tggtatctgc gctctgctga agccagttac cttcggaaaa agagttggta   9840
gctcttgatc cggcaaacaa accaccgctg gtagcggtgg tttttttgtt tgcaagcagc   9900
agattacgcg cagaaaaaaa ggatctcaag aagatccttt gatcttttct acggggtctg   9960
acgctcagtg gaacgaaaac tcacgttaag ggattttggt catgagatta tcaaaaagga  10020
tcttcaccta gatcctttta aattaaaaat gaagttttaa atcaatctaa agtatatatg  10080
agtaaacttg gtctgacagt taccaatgct taatcagtga ggcacctatc tcagcgatct  10140
gtctatttcg ttcatccata gttgcctgac tccccgtcgt gtagataact acgatacggg  10200
agggcttacc atctggcccc agtgctgcaa tgataccgcg agacccacgc tcaccggctc  10260
cagatttatc agcaataaac cagccagccg gaagggccga gcgcagaagt ggtcctgcaa  10320
ctttatccgc ctccatccag tctattaatt gttgccggga agctagagta agtagttcgc  10380
cagttaatag tttgcgcaac gttgttgcca ttgctacagg catcgtggtg tcacgctcgt  10440
cgtttggtat ggcttcattc agctccggtt cccaacgatc aaggcgagtt acatgatccc  10500
ccatgttgtg caaaaaagcg gttagctcct tcggtcctcc gatcgttgtc agaagtaagt  10560
tggccagcagt gttatcactc atggttatgg cagcactgca taattctctt actgtcatgc  10620
catccgtaag atgcttttct gtgactggtg agtactcaac caagtcattc tgagaatagt  10680
gtatgcggcg accgagttgc tcttgcccgg cgtcaatacg ggataatacc gcgccacata  10740
gcagaacttt aaaagtgctc atcattggaa aacgttcttc gggggcaaaac tctcaaggat  10800
cttaccgctg ttgagatcca gttcgatgta acccactcgt gcacccaact gatcttcagc  10860
atcttttact ttcaccagcg tttctgggtg agcaaaaaca ggaaggcaaa atgccgcaaa  10920
aaagggaata agggcgacac ggaaatgttg aatactcata ctcttccttt ttcaatatta  10980
ttgaagcatt tatcagggtt attgtctcat gagcggatac atatttgaat gtatttagaa  11040
aaataaacaa ataggggttc cgcgcacatt tccccgaaaa gtgccacctg acgtctaaga  11100
aaccattatt atcatgacat taacctataa aaataggcgt atcacgaggc cctttcgtct  11160
cgcgcgtttc ggtgatgacg gtgaaaacct ctgacacatg cagctcccgg agacggtcac  11220
agcttgtctg taagcggatg ccgggagcag acaagcccgt cagggcgcgt cagcgggtgt  11280
tggcgggtgt cggggctggc ttaactatgc ggcatcagag cagattgtac tgagagtgca  11340
cc                                                                 11342
```

```
SEQ ID NO: 41               moltype = DNA  length = 30
FEATURE                     Location/Qualifiers
misc_feature               1..30
                            note = Description of Artificial Sequence: Synthetic probe
source                     1..30
                            mol_type = other DNA
                            organism = synthetic construct
SEQUENCE: 41
acagccttct gatgtttcta acaggccagg                                    30

SEQ ID NO: 42               moltype = DNA  length = 22
FEATURE                     Location/Qualifiers
misc_feature               1..22
                            note = Description of Artificial Sequence: Synthetic primer
source                     1..22
                            mol_type = other DNA
                            organism = synthetic construct
SEQUENCE: 42
ggagctagaa cgattcgcag tt                                            22

SEQ ID NO: 43               moltype = DNA  length = 24
FEATURE                     Location/Qualifiers
```

-continued

```
misc_feature            1..24
                        note = Description of Artificial Sequence: Synthetic primer
source                  1..24
                        mol_type = other DNA
                        organism = synthetic construct
SEQUENCE: 43
gttgtagctg tcccagtatt tgtc                                         24

SEQ ID NO: 44           moltype = DNA   length = 27
FEATURE                 Location/Qualifiers
misc_feature            1..27
                        note = Description of Artificial Sequence: Synthetic probe
source                  1..27
                        mol_type = other DNA
                        organism = synthetic construct
SEQUENCE: 44
tgctgaaaca ttcaccttcc atgcagt                                      27

SEQ ID NO: 45           moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 45
tgaaacatac gttcccaaag agttt                                        25

SEQ ID NO: 46           moltype = DNA   length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 46
ctctccttct cagaaagtgt gcatat                                       26

SEQ ID NO: 47           moltype = DNA   length = 26
FEATURE                 Location/Qualifiers
misc_feature            1..26
                        note = Description of Artificial Sequence: Synthetic probe
source                  1..26
                        mol_type = other DNA
                        organism = synthetic construct
SEQUENCE: 47
tacgagggct atgctctccc tcacgc                                       26

SEQ ID NO: 48           moltype = DNA   length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 48
tcacccacac tgtgcccat                                               19

SEQ ID NO: 49           moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 49
agccaggtcc agacgcag                                                18

SEQ ID NO: 50           moltype = DNA   length = 114
FEATURE                 Location/Qualifiers
misc_feature            1..114
                        note = Description of Artificial Sequence: Synthetic
                         polynucleotide
source                  1..114
                        mol_type = other DNA
                        organism = synthetic construct
SEQUENCE: 50
tgagcccctt ttcctctaac tgaaagaagg aaaaaaaaaa tggaacccaa aatattctac  60
atagtttcca tgtcacagcc agggctgggc agtctcctgt tatttctttt aaaa        114
```

```
SEQ ID NO: 51          moltype = DNA   length = 197
FEATURE                Location/Qualifiers
misc_feature           1..197
                       note = Description of Artificial Sequence: Synthetic
                        polynucleotide
source                 1..197
                       mol_type = other DNA
                       organism = synthetic construct
SEQUENCE: 51
tttaatctaa caattatgaa cagcaatgag ataatatgta caaagtaccc agacctatgt   60
ggtagagcat caaggaagcg cattgcggag cagtttttg tttgtttgtt tttgtattct   120
gtttcgtgag gcaaggtttc actctgctgt ccaggctgga gtgcagtggc aagatcatgt   180
ctcactgcag ccttgac                                                  197

SEQ ID NO: 52          moltype = DNA   length = 44
FEATURE                Location/Qualifiers
misc_feature           1..44
                       note = Description of Artificial Sequence: Synthetic
                        oligonucleotide
source                 1..44
                       mol_type = other DNA
                       organism = synthetic construct
SEQUENCE: 52
gtatatgtgt atatatat atatatattc aggaaataat atat                      44

SEQ ID NO: 53          moltype = DNA   length = 1232
FEATURE                Location/Qualifiers
misc_feature           1..1232
                       note = Description of Artificial Sequence: Synthetic
                        polynucleotide
source                 1..1232
                       mol_type = other DNA
                       organism = synthetic construct
SEQUENCE: 53
gcaatgaaaa taaatgtttt ttattaggca gaatccagat gctcaaggcc cttcataata   60
tcccccagtt tagtagttgg acttagggaa caaaggaacc tttaatagaa attggacagc   120
aagaaagcga gcttagtgat acttgtgggc caggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
catttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtt gggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacttcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232

SEQ ID NO: 54          moltype = DNA   length = 1232
FEATURE                Location/Qualifiers
misc_feature           1..1232
                       note = Description of Artificial Sequence: Synthetic
                        polynucleotide
source                 1..1232
                       mol_type = other DNA
                       organism = synthetic construct
SEQUENCE: 54
gcaatgaaaa taaatgtttt ttattaggca gaatccagat gctcaaggcc cttcataata   60
tcccccagtt tagtagttgg acttagggaa caaaggaacc tttaatagaa attggacagc   120
aagaaagcga gcttagtgat acttgtgggc caggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
catttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
```

```
tcactcagtg tggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aacggcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232
```

SEQ ID NO: 55                  moltype = DNA   length = 1232
FEATURE                        Location/Qualifiers
misc_feature                   1..1232
                               note = Description of Artificial Sequence: Synthetic
                                polynucleotide
source                         1..1232
                               mol_type = other DNA
                               organism = synthetic construct
SEQUENCE: 55

```
gcaatgaaaa taaatgtttt ttattaggca gaatccagat gctcaaggcc cttcataata    60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtg tggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aactgcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232
```

SEQ ID NO: 56                  moltype = DNA   length = 1232
FEATURE                        Location/Qualifiers
misc_feature                   1..1232
                               note = Description of Artificial Sequence: Synthetic
                                polynucleotide
source                         1..1232
                               mol_type = other DNA
                               organism = synthetic construct
SEQUENCE: 56

```
gcaatgaaaa taaatgtttt ttattaggca gaatccagat gctcaaggcc cttcataata    60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtg tggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aacagcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232
```

SEQ ID NO: 57                  moltype = DNA   length = 1232
FEATURE                        Location/Qualifiers
misc_feature                   1..1232
                               note = Description of Artificial Sequence: Synthetic
                                polynucleotide
source                         1..1232
                               mol_type = other DNA
                               organism = synthetic construct

```
SEQUENCE: 57
gcaatgaaaa taaatgtttt ttattaggca gaatccagat gctcaaggcc cttcataata    60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtgggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtg tggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aaccgcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232

SEQ ID NO: 58         moltype = DNA   length = 1232
FEATURE               Location/Qualifiers
misc_feature         1..1232
                     note = Description of Artificial Sequence: Synthetic
                     polynucleotide
source               1..1232
                     mol_type = other DNA
                     organism = synthetic construct
SEQUENCE: 58
gcaatgaaaa taaatgtttt ttattaggca gaatccagat gctcaaggcc cttcataata    60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtgggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtg tggcaaaggt gcccttgagc ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aacttcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232

SEQ ID NO: 59         moltype = DNA   length = 1232
FEATURE               Location/Qualifiers
misc_feature         1..1232
                     note = Description of Artificial Sequence: Synthetic
                     polynucleotide
source               1..1232
                     mol_type = other DNA
                     organism = synthetic construct
SEQUENCE: 59
gcaatgaaaa taaatgtttt ttattaggca gaatccagat gctcaaggcc cttcataata    60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtgggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtg tggcaaaggt gcccttgagt ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
```

```
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacttcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232
```

SEQ ID NO: 60                moltype = DNA   length = 1232
FEATURE                      Location/Qualifiers
misc_feature                 1..1232
                             note = Description of Artificial Sequence: Synthetic
                              polynucleotide
source                       1..1232
                             mol_type = other DNA
                             organism = synthetic construct
SEQUENCE: 60

```
gcaatgaaaa taaatgtttt ttattaggca gaatccagat gctcaaggcc cttcataata   60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtg tggcaaaggt gcccttgagc ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacggcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232
```

SEQ ID NO: 61                moltype = DNA   length = 1232
FEATURE                      Location/Qualifiers
misc_feature                 1..1232
                             note = Description of Artificial Sequence: Synthetic
                              polynucleotide
source                       1..1232
                             mol_type = other DNA
                             organism = synthetic construct
SEQUENCE: 61

```
gcaatgaaaa taaatgtttt ttattaggca gaatccagat gctcaaggcc cttcataata   60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtg tggcaaaggt gcccttgagt ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacggcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232
```

SEQ ID NO: 62                moltype = DNA   length = 1232
FEATURE                      Location/Qualifiers
misc_feature                 1..1232
                             note = Description of Artificial Sequence: Synthetic
                              polynucleotide
source                       1..1232
                             mol_type = other DNA
                             organism = synthetic construct
SEQUENCE: 62

```
gcaatgaaaa taaatgtttt ttattaggca gaatccagat gctcaaggcc cttcataata   60
tcccccagtt tagtagttgg acttagggaa caaaggaacc tttaatagaa attggacagc   120
```

-continued

```
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa aagaagaaag  600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagtg tggcaaaggt gcccttgagc ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aactgcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                 1232
```

```
SEQ ID NO: 63          moltype = DNA  length = 1232
FEATURE                Location/Qualifiers
misc_feature           1..1232
                       note = Description of Artificial Sequence: Synthetic
                       polynucleotide
source                 1..1232
                       mol_type = other DNA
                       organism = synthetic construct
SEQUENCE: 63
gcaatgaaaa taaatgtttt ttattaggca gaatccagat gctcaaggcc cttcataata  60
tcccccagtt tagtagttgg acttaggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa aagaagaaag  600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagtg tggcaaaggt gcccttgagc ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aacagcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                 1232
```

```
SEQ ID NO: 64          moltype = DNA  length = 1232
FEATURE                Location/Qualifiers
misc_feature           1..1232
                       note = Description of Artificial Sequence: Synthetic
                       polynucleotide
source                 1..1232
                       mol_type = other DNA
                       organism = synthetic construct
SEQUENCE: 64
gcaatgaaaa taaatgtttt ttattaggca gaatccagat gctcaaggcc cttcataata  60
tcccccagtt tagtagttgg acttaggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa aagaagaaag  600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagtg tggcaaaggt gcccttgagc ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aaccgcatcc acgttcacct tgccccacag  1140
```

-continued

```
ggcagtaacg gcagacttct cctcaggagt caggtgcacc atggtgtctg tttgaggttg  1200
ctagtgaaca cagttgtgtc agaagcaaat gt                                 1232

SEQ ID NO: 65           moltype = DNA  length = 1232
FEATURE                 Location/Qualifiers
misc_feature            1..1232
                        note = Description of Artificial Sequence: Synthetic
                         polynucleotide
source                  1..1232
                        mol_type = other DNA
                        organism = synthetic construct
SEQUENCE: 65
gcaatgaaaa taaatgtttt ttattaggca gaatccagat gctcaaggcc cttcataata  60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa agaagaaag   600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagtg tggcaaaggt gcccttgagt ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aactgcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                 1232

SEQ ID NO: 66           moltype = DNA  length = 1232
FEATURE                 Location/Qualifiers
misc_feature            1..1232
                        note = Description of Artificial Sequence: Synthetic
                         polynucleotide
source                  1..1232
                        mol_type = other DNA
                        organism = synthetic construct
SEQUENCE: 66
gcaatgaaaa taaatgtttt ttattaggca gaatccagat gctcaaggcc cttcataata  60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa agaagaaag   600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagtg tggcaaaggt gcccttgagt ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aacagcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                 1232

SEQ ID NO: 67           moltype = DNA  length = 1232
FEATURE                 Location/Qualifiers
misc_feature            1..1232
                        note = Description of Artificial Sequence: Synthetic
                         polynucleotide
source                  1..1232
                        mol_type = other DNA
                        organism = synthetic construct
SEQUENCE: 67
gcaatgaaaa taaatgtttt ttattaggca gaatccagat gctcaaggcc cttcataata  60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
```

```
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa agaagaaag   600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagtg tggcaaaggt gcccttgagt ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aaccgcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232
```

SEQ ID NO: 68          moltype = DNA  length = 1232
FEATURE                Location/Qualifiers
misc_feature          1..1232
                       note = Description of Artificial Sequence: Synthetic
                       polynucleotide
source                 1..1232
                       mol_type = other DNA
                       organism = synthetic construct
SEQUENCE: 68

```
gcaatgaaaa taaatgtttt ttattaggca gaatccagat gctcaaggcc cttcataata  60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa agaagaaag   600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagct gggcaaaggt gcccttgagg ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aaccggcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232
```

SEQ ID NO: 69          moltype = DNA  length = 1232
FEATURE                Location/Qualifiers
misc_feature          1..1232
                       note = Description of Artificial Sequence: Synthetic
                       polynucleotide
source                 1..1232
                       mol_type = other DNA
                       organism = synthetic construct
SEQUENCE: 69

```
gcaatgaaaa taaatgtttt ttattaggca gaatccagat gctcaaggcc cttcataata  60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa agaagaaag   600
cattttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagtt gggcaaaggt gcccttgagg ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aaccggcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232
```

-continued

```
SEQ ID NO: 70          moltype = DNA  length = 1232
FEATURE                Location/Qualifiers
misc_feature           1..1232
                       note = Description of Artificial Sequence: Synthetic
                       polynucleotide
source                 1..1232
                       mol_type = other DNA
                       organism = synthetic construct
SEQUENCE: 70
gcaatgaaaa taaatgtttt ttattaggca gaatccagat gctcaaggcc cttcataata   60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa aagaagaaag  600
catttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagct gggcaaaggt gcccttgagg ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga 1020
gtcttctctg tctccacatg cccagtttct attggtctcc ttaaacctgt cttgtaacct 1080
tgataccaac ctgcccaggg cctcaccacc aactgcatcc acgttcacct tgccccacag 1140
ggcagtaacg gcagacttct cctcaggagt caggtgcacc atggtgtctg tttgaggttg 1200
ctagtgaaca cagttgtgtc agaagcaaat gt                                1232

SEQ ID NO: 71          moltype = DNA  length = 1232
FEATURE                Location/Qualifiers
misc_feature           1..1232
                       note = Description of Artificial Sequence: Synthetic
                       polynucleotide
source                 1..1232
                       mol_type = other DNA
                       organism = synthetic construct
SEQUENCE: 71
gcaatgaaaa taaatgtttt ttattaggca gaatccagat gctcaaggcc cttcataata   60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa aagaagaaag  600
catttttaa aattacaaat gcaaaattac cctgatttgg tcaatatgtg taccctgtta  660
cttctcccct tcctatgaca tgaacttaac catagaaaag aaggggaaag aaaacatcaa  720
gggtcccata gactcaccct gaagttctca ggatccacgt gcagcttgtc acagtgcagc  780
tcactcagct gggcaaaggt gcccttgagg ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga 1020
gtcttctctg tctccacatg cccagtttct attggtctcc ttaaacctgt cttgtaacct 1080
tgataccaac ctgcccaggg cctcaccacc aacagcatcc acgttcacct tgccccacag 1140
ggcagtaacg gcagacttct cctcaggagt caggtgcacc atggtgtctg tttgaggttg 1200
ctagtgaaca cagttgtgtc agaagcaaat gt                                1232

SEQ ID NO: 72          moltype = DNA  length = 1232
FEATURE                Location/Qualifiers
misc_feature           1..1232
                       note = Description of Artificial Sequence: Synthetic
                       polynucleotide
source                 1..1232
                       mol_type = other DNA
                       organism = synthetic construct
SEQUENCE: 72
gcaatgaaaa taaatgtttt ttattaggca gaatccagat gctcaaggcc cttcataata   60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
```

-continued

```
gttattctttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcacccct gaagttctca ggatccacgt gcagcttgtc acagtgcagc   780
tcactcagct gggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aaccgcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                 1232
```

SEQ ID NO: 73          moltype = DNA  length = 1232
FEATURE                Location/Qualifiers
misc_feature           1..1232
                       note = Description of Artificial Sequence: Synthetic
                       polynucleotide
source                 1..1232
                       mol_type = other DNA
                       organism = synthetic construct
SEQUENCE: 73

```
gcaatgaaaa taaatgtttt ttattaggca gaatccagat gctcaaggcc cttcataata    60
tcccccagtt tagtagttgg acttaggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcacccct gaagttctca ggatccacgt gcagcttgtc acagtgcagc   780
tcactcagtt gggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aactgcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                 1232
```

SEQ ID NO: 74          moltype = DNA  length = 1232
FEATURE                Location/Qualifiers
misc_feature           1..1232
                       note = Description of Artificial Sequence: Synthetic
                       polynucleotide
source                 1..1232
                       mol_type = other DNA
                       organism = synthetic construct
SEQUENCE: 74

```
gcaatgaaaa taaatgtttt ttattaggca gaatccagat gctcaaggcc cttcataata    60
tcccccagtt tagtagttgg acttaggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcacccct gaagttctca ggatccacgt gcagcttgtc acagtgcagc   780
tcactcagtt gggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aacagcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                 1232
```

SEQ ID NO: 75          moltype = DNA  length = 1232
FEATURE                Location/Qualifiers
misc_feature           1..1232

-continued

```
                                  note = Description of Artificial Sequence: Synthetic
                                   polynucleotide
source                            1..1232
                                  mol_type = other DNA
                                  organism = synthetic construct
SEQUENCE: 75
gcaatgaaaa taaatgtttt ttattaggca gaatccagat gctcaaggcc cttcataata   60
tcccccagtt tagtagttgg acttagggaa caaaggaacc tttaatagaa attggacagc  120
aagaaagcga gcttagtgat acttgtgggc cagggcatta gccacaccag ccaccacttt  180
ctgataggca gcctgcactg gtggggtgaa ttctttgcca aagtgatggg ccagcacaca  240
gaccagcacg ttgcccagga gctgtgggag gaagataaga ggtatgaaca tgattagcaa  300
aagggcctag cttggactca gaataatcca gccttatccc aaccataaaa taaaagcaga  360
atggtagctg gattgtagct gctattagca atatgaaacc tcttacatca gttacaattt  420
atatgcagaa atatttatat gcagaaatat tgctattgcc ttaacccaga aattatcact  480
gttattcttt agaatggtgc aaagaggcat gatacattgt atcattattg ccctgaaaga  540
aagagattag ggaaagtatt agaaataaga taaacaaaaa agtatattaa aagaagaaag  600
catttttttaa aattacaaat gcaaaattac cctgatttgg tcaatatgtg taccctgtta  660
cttctccccct tcctatgaca tgaacttaac catagaaaag aagggaaag aaaacatcaa  720
gggtcccata gactcaccct gaagttctca ggatccacgt gcagcttgtc acagtgcagc  780
tcactcagtt gggcaaaggt gcccttgagg ttgtccaggt gagccaggcc atcactaaag  840
gcaccgagca ctttcttgcc atgagccttc accttagggt tgcccataac agcatcagga  900
gtggacagat ccccaaagga ctcaaagaac ctctgggtcc aagggtagac caccagcagc  960
ctaagggtgg gaaaatagac caataggcag agagagtcag tgcctatcag aaacccaaga 1020
gtcttctctg tctccacatg cccagtttct attggtctcc ttaaacctgt cttgtaacct 1080
tgataccaac ctgcccaggg cctcaccacc aaccgcatcc acgttcacct tgccccacag 1140
ggcagtaacg gcagacttct cctcaggagt caggtgcacc atggtgtctg tttgaggttg 1200
ctagtgaaca cagttgtgtc agaagcaaat gt                                1232

SEQ ID NO: 76              moltype = DNA  length = 8674
FEATURE                   Location/Qualifiers
misc_feature              1..8674
                          note = Description of Artificial Sequence: Synthetic
                           polynucleotide
source                    1..8674
                          mol_type = other DNA
                          organism = synthetic construct
SEQUENCE: 76
attggccatt gcatacgttg tatccatatc ataatatgta catttatatt ggctcatgtc   60
caacattacc gccatgttga cattgattat tgactagtta ttaatagtaa tcaattacgg  120
ggtcattagt tcatagccca tatatggagt tccgcgttac ataacttacg gtaaatggcc  180
cgcctggctg accgcccaac gacccccgcc cattgacgtc aataatgacg tatgttccca  240
tagtaacgcc aatagggact ttccattgac gtcaatgggt ggagtattta cggtaaactg  300
cccacttggc agtacatcaa gtgtatcata tgccaagtac gccccctatt gacgtcaatg  360
acggtaaatg gcccgcctgg cattatgccc agtacatgac cttatgggac tttcctactt  420
ggcagtacat ctacgtatta gtcatcgcta ttaccatggt gatgcggttt ggcagtacaa  480
tcaatgggcg tggatagcgg tttgactcac ggggatttcc aagtctccac cccattgacg  540
tcaatgggag tttgttttgg caccaaaatc aacgggactt tccaaaatgt cgtaacaact  600
ccgccccatt gacgcaaatg ggcggtaggc gtgtacggtg gaggtctat ataagcagag  660
ctcgtttagt gaaccggggt ctctctggtt agaccagatc tgagcctggg agctctctgg  720
ctaactaggg aacccactgc ttaagcctca ataaagcttg ccttgagtgc ttcaagtagt  780
gtgtgcccgt ctgttgtgtg actctggtaa ctagagatcc ctcagaccct tttagtcagt  840
gtggaaaatc tctagcagtg gcgcccgaac agggacttga aagcgaaagg gaaaccagag  900
gagctctctc gacgcaggac tcggcttgct gaagcgcgca cggcaagagg cgaggggcgg  960
cgactggtga gtacgccaaa aattttgact agcggaggct agaaggagag agacgggtgc 1020
gagagcgtca gtattaagcg ggggtgaata agatcgcgat gggaaaaaat tcggttaagg 1080
ccagggggaa agaaaaaata taaattaaaa catatagtat gggcaagcag ggagctagaa 1140
cgattcgcag ttaatcctgg cctgttagaa acatcagaag gctgtagaca aatactggga 1200
cagctacaac catcccttca gacaggatca gaagaactta gatcattata taatacagta 1260
gcaaccctct attgtgtgca tcaaaggata gagataaaag acaccaagga agctttagac 1320
aagatagagg aagagcaaaa caaaagtaag accaccgcac agcaagcggc cgctgatctt 1380
cagacctgga ggaggagata tgagggacaa ttggagaagt gaattatata aatataaagt 1440
agtaaaaatt gaaccattag gagtagcacc caccaaggca aagagaagag tggtgcagag 1500
agaaaaaaga gcagtgggaa taggagcttt gttccttggg ttcttgggag cagcaggaag 1560
cactatgggc gcagcgtcaa tgacgctgac ggtacaggcc agacaattat tgtctggtat 1620
agtgcagcag cagaacaatt tgctgagggc tattgaggcg caacagcatc tgttgcaact 1680
cacagtctgg ggcatcaagc agctccaggc aagaatcctg gctgtggaaa gatacctaaa 1740
ggatcaacag ctcctgggga tttggggttg ctctggaaaa ctcatttgca ccactgctgt 1800
gccttggaat gctagttgga gtaataaatc tctggaacag atttggaatc acacgacctg 1860
gatggagtgg gacagagaaa ttaacaatta cacaagctta atacactcct taattgaaga 1920
atcgcaaaac cagcaagaaa agaatgaaca agaattattg gaattagata atgggcaag 1980
tttgtggaat tggtttaaca taacaaattg gctgtggtat ataaaattat tcataatgat 2040
agtaggaggc ttggtaggtt taagaatagt ttttgctgta ctttctatag tgaatagagt 2100
taggcaggga tattcaccat tatcgtttca gacccacctc ccaaccccga ggggacccga 2160
caggcccgaa ggaatagaag aagaaggtgg agagagagac ccattcgatt 2220
agtgaacgga tctcgacggt atcgtttaa aagaaaaggg gggattgggg ggtacagtgc 2280
aggggaaaga atagtagaca taatagcaac agacatacaa actaaagaat acaaaaaaca 2340
aattacaaaa attcaaaatt ttatcggcgt gttggggtg gaccatcctc taggtattga 2400
ataagaaaaa tgaagttaag gtggttgatg gtaacactat gctaataact gcagagccag 2460
aagcaccata agggacatga taagggagcc agcagacctc tgatctcttc ctgaatgcta 2520
```

-continued

```
atcttaaaca tcctgaggaa gaatgggact tccatttggg gtgggcctat gataggtaa  2580
taagacagta gtgaatatca agctacaaaa agcccccttt caaattcttc tcagtcctaa  2640
cttttcatac taagcccagt ccttccaaag cagactgtga aagagtgata gttccgggag  2700
actagcactg cagattccgg gtcactgtga gtgggggagg cagggaagaa gggctcacag  2760
gacagtcaaa ccatgccccc tgttttttcct tcttcaagta gacctctata agacaacaga  2820
gacaactaag gctgagtggc caggcgagga gaaaccatct cgccgtaaaa catggaagga  2880
acacttcagg ggaaaggtgg tatctctaag caagagaact gagtggagtc aaggctgaga  2940
gatgcaggat aagcaaatgg gtagtgaaaa gacattcatg aggacagcta aaacaataag  3000
taatgtaaaa tacagcatag caaaacttta acctccaaat caagcctcta cttgaatcct  3060
tttctgaggg atgaataagg cataggcatc aggggctgtt gccaatgtgc attagctgtt  3120
tgcagcctca ccttctttca tggagtttaa gatatagtgt attttcccaa ggtttgaact  3180
agctcttcat ttctttatgt tttaaatgca ctgacctccc acattccctt tttagtaaaa  3240
tattcagaaa taatttaaat acatcattgc aatgaaaata aatgtttttt attaggcaga  3300
atccagatgc tcaaggccct tcataatatc ccccagttta gtagttggac ttagggaaca  3360
aaggaacctt taatagaaat tggacagcaa gaaagcgagc ttagtgatac ttgtgggcca  3420
gggcattagc cacaccagcc accactttct gataggcagc ctgcactggt ggggtgaatt  3480
ctttgccaaa gtgatgggcc agcacacaga ccagcacgtt gcccaggagc tgtgggagga  3540
agataagagg tatgaacatg attagcaaaa gggcctagct tggactcaga ataatccagc  3600
cttatcccaa ccataaaata aaagcagaat ggtagctgga ttgtagctgc tattagcaat  3660
atgaaacctc ttacatcagt tacaatttat atgcagaaat atttatatgc agaaatattg  3720
ctattgcctt aacccagaaa ttatcactgt tattctttag aatggtgcaa agaggcatga  3780
tacattgtat cattattgcc ctgaaagaaa gagattaggg aaagtattag aaataagata  3840
aacaaaaaag tatattaaaa gaagaaagca ttttttaaaa ttacaaatgc aaaattaccc  3900
tgatttggtc aatatgtgta ccctgttact tctcccttc ctatgacatg aacttaacca  3960
tagaaaagaa ggggaaagaa aacatcaagg gtcccataga ctcaccctga agttctcagg  4020
atccacgtgc agcttgtcac agtgcagctc actcagctga gcaaaggtgc ccttgaggtt  4080
gtccaggtga gccaggccat cactaaaggc accgagcact ttcttgccat gagccttcac  4140
cttagggttg cccataacag catcaggagt ggacagatcc ccaaaggact caaagaacct  4200
ctgggtccaa gggtagacca ccagcagcct aagggtggga aaatagacca ataggcagag  4260
agagtcagtg cctatcagaa acccaagagt cttctctgtc tccacatgcc cagtttctat  4320
tggtctcctt aaacctgtct tgtaaccttg ataccaacct gcccagggcc tcaccaccaa  4380
cttcatccac gttcaccttg ccccacaggg cagtaacggc agacttctcc tcaggagtca  4440
ggtgcaccat ggtgtctgtt tgaggttgct agtgaacaca gttgtgtcag aagcaaatgt  4500
aagcaataga tggctctgcc ctgacttta tgcccagccc tggctcctgc cctccctgct  4560
cctgggagta gattggccaa ccctagggtg tggctccaca gggtgaggtc taagtgatga  4620
cagccgtacc tgtccctggc tcttctggca ctggcttagg agttggactt caaaccctca  4680
gccctccctc taagatatat ctcttggccc cataccatca gtacaaattg ctactaaaaa  4740
catcctcctt tgcaagtgta tttaccaccc ttttccggca cgcagatagt caatatcttc  4800
agcgtcccca aggcctgcaa gggtggggcc ccatatctgg aagtcccagg cggagctgga  4860
agttggtcaa gtctgggctg tgggggcagg gagtgctggg ggatggacgc gtcgacggta  4920
ccgttaacga tcttagccac ttttttaaaag aaaaggggg actggaaggg ctaattcact  4980
cccaacgaag acaagatatc ctgctagtcc ttcctttcta aatgacgaga gagacagaag  5040
aattcttcaa ggttagtgtg tccagcatgc aacctttcct tcctggatga gcatccctgg  5100
agtaggagag ccagcctgcc tcctgcgctg gcacagagcc cggttcccta gacaactgcc  5160
tctccaaatc tgatgtccag cgccacctgg tgtccacatc aagcagacac aattaatagt  5220
caacctgttc aggaaaactg tgaggggaa aaaaagaaa gaggatttat gaagggaaa   5280
gaaagtttag aggatatgcc acgattggct agcagctgtt ttttgcctgt actgggtctc  5340
tctggttaga ccagatctga gcctgggagc tctctggcta actagggaac ccactgctta  5400
agcctcaata aagcttgcct tgagtgcttc atccggaatc aacctctgga ttacaaaatt  5460
tgtgaaagat tgactggtat tcttaactat gttgctcctt ttacgctatg tggatacgct  5520
gctttaatgc ctttgtatca tgctattgct tcccgtatgg ctttcatttt ctctccttg   5580
tataaatcct ggttgctgtc tctttatgag gagttgtggc ccgttgtcag gcaacgtggc  5640
gtggtgtgca ctgtgtttgc tgacgcaacc cccactggtt ggggcattgc caccacctgt  5700
cagctccttt ccgggacttt cgctttcccc ctccctattg ccacggcgga actcatcgcc  5760
gcctgccttg cccgctgctg gacaggggct cggctgttgg gcactgacaa ttccgtggtg  5820
ttgtcgggga agctgacgtc ctttccatgg ctgctcgcct gtgttgccac ctggattctg  5880
cgcgggacgt ccttctgcta cgtcccttcg gccctcaatc cagcggacct tccttcccgc  5940
ggcctgctgc cggctctgcg gcctcttccg cgtcttcgcc ttcgccctca gacgagtcgg  6000
atctcccttt gggccgcctc cccgcctgtc cggtagcttg ccagcctcga ctgtgccttc  6060
tagttgccag ccgtctgttg tttgcccctc cccgtgcct tccttgaccc tggaaggtgc  6120
cactccact gtcctttcct aataaaatga ggaaattgca tcgcattgtc tgagtaggtg  6180
tcattctatt ctggggggtg gggtggggca ggacagcaag gggggaggatt gggaagacaa  6240
tagcaggcat gcaagcttgg cgtaatcatg gtcatagctg tttcctgtgt gaaattgtta  6300
tccgctcaca attccacaca acatacgagc cggaagcata aagtgtaaag cctggggtgc  6360
ctaatgagtg agctaactca cattaattgc gttgcgctca ctgcccgctt tccagtcggg  6420
aaacctgtcg tgccagctgc attaatgaat cggccaacgc gcggggagag gcggtttgcg  6480
tattgggcgc tcttccgctt cctcgctcac tgactcgctg cgctcggtcg ttcggctgcg  6540
gcgagcggta tcagctcact caaaggcggt aatacggtta tccacagaat caggggataa  6600
cgcaggaaag aacatgtgag caaaaggcca gcaaaaggcc aggaaccgta aaaaggccgc  6660
gttgctggcg tttttccata ggctccgccc cctgacgag catcacaaaa atcgacgctc   6720
aagtcagagg tggcgaaacc cgacaggact ataaagatac caggcgtttc ccctggaag   6780
ctccctcgtg cgctctcctg ttccgaccct gccgcttacc ggatacctgt ccgcctttct  6840
cccttcggga agcgtggcgc tttctcatag ctcacgctgt aggtatctca gttcggtgta  6900
ggtcgttcgc tccaagctgg gctgtgtgca cgaacccccc gttcagcccg accgctgcgc  6960
cttatccggt aactatcgtc ttgagtccaa cccggtaaga cacgacttat cgccactggc  7020
agcagccact ggtaacagga ttagcagagc gaggtatgta ggcggtgcta cagagttctt  7080
gaagtggtgg cctaactacg gctacactag aagaacagta tttggtatct gcgctctgct  7140
gaagccagtt accttcggaa aaagagttgg tagctcttga tccggcaaac aaaccaccgc  7200
tggtagcggt ggtttttttg tttgcaagca gcagattacg cgcagaaaaa aaggatctca  7260
```

-continued

```
agaagatcct ttgatctttt ctacgggtc tgacgctcag tggaacgaaa actcacgtta  7320
agggattttg gtcatgagat tatcaaaaag gatcttcacc tagatccttt taaattaaaa  7380
atgaagtttt aaatcaatct aaagtatata tgagtaaact tggtctgaca gttaccaatg  7440
cttaatcagt gaggcaccta tctcagcgat ctgtctattt cgttcatcca tagttgcctg  7500
actccccgtc gtgtagataa ctacgatacg ggagggctta ccatctggcc ccagtgctgc  7560
aatgataccg cgagacccac gctcaccggc tccagattta tcagcaataa accagccagc  7620
cggaagggcc gagcgcagaa gtggtcctgc aactttatcc gcctccatcc agtctattaa  7680
ttgttgccgg gaagctagag taagtagttc gccagttaat agtttgcgca acgttgttgc  7740
cattgctaca ggcatcgtgg tgtcacgctc gtcgtttggt atggcttcat tcagctccgg  7800
ttcccaacga tcaaggcgag ttacatgatc ccccatgttg tgcaaaaaag cggttagctc  7860
cttcggtcct ccgatcgttg tcagaagtaa gttggccgca gtgttatcac tcatggttat  7920
ggcagcactg cataattctc ttactgtcat gccatccgta agatgctttt ctgtgactgg  7980
tgagtactca accaagtcat tctgagaata gtgtatgcgg cgaccgagtt gctcttgccc  8040
ggcgtcaata cgggataata ccgcgccaca tagcagaact ttaaaagtgc tcatcattgg  8100
aaaacgttct cgggggcaaa actctcaagg atcttaccgc tgttgagatc cagttcgatg  8160
taacccactc gtgcacccaa ctgatcttca gcatctttta ctttcaccag cgtttctggg  8220
tgagcaaaaa caggaaggca aaatgccgca aaaaagggaa taagggcgac acggaaatgt  8280
tgaatactca tactcttcct ttttcaatat tattgaagca tttatcaggg ttattgtctc  8340
atgagcggat acatatttga atgtatttag aaaaataaac aaataggggt tccgcgcaca  8400
tttccccgaa aagtgccacc tgacgtctaa gaaaccatta ttatcatgac attaacctat  8460
aaaaatagg c gtatcacgag gccctttcgt ctcgcgcgtt tcggtgatga cggtgaaaac  8520
ctctgacaca tgcagctccc ggagacggtc acagcttgtc tgtaagcgga tgccgggagc  8580
agacaagccc gtcagggcgc gtcagcgggt gttggcgggt gtcggggctg gcttaactat  8640
gcggcatcag agcagattgt actgagagtg cacc  8674
```

```
SEQ ID NO: 77           moltype = DNA   length = 10011
FEATURE                 Location/Qualifiers
misc_feature            1..10011
                        note = Description of Artificial Sequence: Synthetic
                        polynucleotide
source                  1..10011
                        mol_type = other DNA
                        organism = synthetic construct
SEQUENCE: 77
attggccatt gcatacgttg tatccatatc ataatatgta catttatatt ggctcatgtc  60
caacattacc gccatgttga cattgattat tgactagtta ttaatagtaa tcaattacgg  120
ggtcattagt tcatagccca tatatggagt tccgcgttac ataacttacg gtaaatggcc  180
cgcctggctg accgcccaac gacccccgcc cattgacgtc aataatgacg tatgttccca  240
tagtaacgcc aatagggact ttccattgac gtcaatgggt ggagtattta cggtaaactg  300
cccacttggc agtacatcaa gtgtatcata tgccaagtac gccccctatt gacgtcaatg  360
acggtaaatg gcccgcctgg cattatgccc agtacatgac cttatgggac tttcctactt  420
ggcagtacat ctacgtatta gtcatcgcta ttaccatggt gatgcggttt tggcagtaca  480
tcaatgggcg tggatagcgg tttgactcac ggggatttcc aagtctccac cccattgacg  540
tcaatgggag tttgttttgg caccaaaatc aacgggactt tccaaaatgt cgtaacaact  600
ccgccccatt gacgcaaatg ggcggtaggc gtgtacggtg ggaggtctat ataagcagag  660
ctcgtttagt gaaccggggt ctctctggtt agaccagatc tgagcctggg agctctctgg  720
ctaactaggg aacccactgc ttaagcctca ataaagcttg ccttgagtgc ttcaagtagt  780
gtgtgcccgt ctgttgtgtg actctggtaa ctagagatcc ctcagaccct tttagtcagt  840
gtggaaaatc tctagcagtg gcgcccgaac agggacttga agcgaaagg gaaaccagag  900
gagctctctc gacgcaggac tcggcttgct gaagcgcgca cggcaagagg cgaggggcgg  960
cgactggtga gtacgccaaa aatttttgact agcggaggct agaaggagag agacgggtgc  1020
gagagcgtca gtattaagcg ggggtgaata agatcgcgat gggaaaaaat tcggttaagg  1080
ccagggggaa agaaaaaata taaattaaaa catatagtat gggcaagcag ggagctagaa  1140
cgattcgcag ttaatcctgg cctgttagaa acatcagaag gctgtagaca aatactggga  1200
cagctacaac catcccttca gacaggatca gaagaactta gatcattata taatacagta  1260
gcaaccctct attgtgtgca tcaaaggata gagataaaag acaccaagga agctttagac  1320
aagatagagg aagagcaaaa caaaagtaag accaccgcac agcaagcggc cgctgatctt  1380
cagacctgga ggaggagata tgagggacaa ttggagaagt gaattatata aatataaagt  1440
agtaaaaatt gaaccattag gagtagcacc caccaaggca agaagaagag tggtgcagag  1500
agaaaaaaga gcagtgggaa taggagcttt gttccttggg ttcttgggag cagcaggaag  1560
cactatgggc gcagcgtcaa tgacgctgac ggtacaggcc agacaattat tgtctggtat  1620
agtgcagcag cagaacaatt tgctgagggc tattgaggcg caacagcatc tgttgcaact  1680
cacagtctgg ggcatcaagc agctccaggc aagaatcctg gctgtggaaa gatacctaaa  1740
ggatcaacag ctcctgggga tttggggttg ctctggaaaa ctcatttgca ccactgctgt  1800
gccttggaat gctagttgga gtaataaatc tctggaacag atttggaatc acacgacctg  1860
gatggagtgg gacagagaaa ttaacaatta cacaagctta atacactcct taattgaaga  1920
atcgcaaaac cagcaagaaa agaatgaaca agaattattg gaattagata aatgggcaag  1980
tttgtggaat tggtttaaca taacaaattg gctgtggtat ataaaattat tcataatgat  2040
agtaggaggc ttggtaggtt taagaatagt ttttgctgtg ctttctatag tgaatagagt  2100
taggcaggga tattcaccat tatcgtttca gacccacctc ccaacccccga ggggacccga  2160
caggcccgaa ggaatagaag aagaaggtgg agagagagac agagacagat ccattcgatt  2220
agtgaacgga tctcgacggt atcgtttaa aagaaaaggg gggattgggg ggtacagtgc  2280
aggggaaaga atagtagaca aatagcaac agacatacaa actaaagaat tacaaaaaca  2340
aattacaaaa attcaaaatt ttatcggcgt gttggggtg gaccatctcc taggattaga  2400
ataagaaaaa tgaagttaag gtggttgatg gtaacactat gctaataact gcagagccag  2460
aagcaccata agggacatga taagggagcc agcagacctc tgatctcttc ctgaatgcta  2520
atcttaaaca tcctgaggaa gaatgggact tccatttggg gtgggcctat gatagggtaa  2580
taagacagta gtgaatatca agctacaaaa agccccctttt caaattcttc tcagtcctaa  2640
cttttcatac taagcccagt ccttccaaag cagactgtga aagagtgata gttccgggag  2700
```

-continued

```
actagcactg cagattccgg gtcactgtga gtgggggagg cagggaagaa gggctcacag  2760
gacagtcaaa ccatgccccc tgttttttcct tcttcaagta gacctctata agacaacaga  2820
gacaactaag gctgagtggc caggcgagga gaaaccatct cgccgtaaaa catggaagga  2880
acacttcagg ggaaaggtgg tatctctaag caagagaact gagtggagtc aaggctgaga  2940
gatgcaggat aagcaaatgg gtagtgaaaa gacattcatg aggacagcta aaacaataag  3000
taatgtaaaa tacagcatag caaaacttta acctccaaat caagcctcta cttgaatcct  3060
tttctgaggg atgaataagg cataggcatc aggggctgtt gccaatgtgc attagctgtt  3120
tgcagcctca ccttctttca tggagtttaa gatatagtgt attttcccaa ggtttgaact  3180
agctcttcat ttctttatgt tttaaatgca ctgacctccc acattccctt tttagtaaaa  3240
tattcagaaa taatttaaat acatcattgc aatgaaaata aatgttttt attaggcaga  3300
atccagatgc tcaaggccct tcataatatc ccccagttta gtagttggac ttagggaaca  3360
aaggaacctt taatagaaat tggacagcaa gaaagcgagc ttagtgatac ttgtgggcca  3420
gggcattagc cacaccagcc accactttct gataggcagc ctgcactggt ggggtgaatt  3480
ctttgccaaa gtgatgggcc agcacacaga ccagcacgtt gcccaggagc tgtgggagga  3540
agataagagg tatgaacatg attagcaaaa gggcctagct tggactcaga ataatccagc  3600
cttatcccaa ccataaaata aaagcagaat ggtagctgga ttgtagctgc tattagcaat  3660
atgaaacctc ttacatcagt tacaatttat atgcagaaat atttatatgc agaaatattg  3720
ctattgcctt aacccagaaa ttatcactgt tattctttag aatggtgcaa agaggcatga  3780
tacattgtat cattattgcc ctgaaagaaa gagattaggg aaagtattag aaataagata  3840
aacaaaaaag tatattaaaa gaagaaagca ttttttaaaa ttacaaatgc aaaattaccc  3900
tgatttggtc aatatgtgta ccctgttact tctcccccttc ctatgacatg aacttaacca  3960
tagaaaagaa ggggaaagaa aacatcaagg gtcccataga ctcaccctga agttctcagg  4020
atccacgtgc agcttgtcac agtgcagctc actcagctgg gcaaaggtgc ccttgaggtt  4080
gtccaggtga gccaggccat cactaaaggc accgagcact ttcttgccat gagccttcac  4140
cttagggttg cccataacag catcaggagt ggacagatcc ccaaaggact caaagaacct  4200
ctgggtccaa gggtagacca ccagcagcct aagggtggga aaatagacca ataggcagag  4260
agagtcagtg cctatcagaa acccaagagt cttctctgtc tccacatgcc cagtttctat  4320
tggtctcctt aaacctgtct tgtaaccttg ataccaacct gcccagggcc tcaccaccaa  4380
cttcatccac gttcaccttg ccccacaggg cagtaacggc agacttctcc tcaggagtca  4440
ggtgcaccat ggtgtctgtt tgaggttgct agtgaacaca gttgtgtcag aagcaaatgt  4500
aagcaataga tggctctgcc ctgactttta tgcccagccc tggctcctgc cctccctgct  4560
cctgggagta gattggccaa ccctcagggtg tggctccaca gggtgaggtc taagtgatga  4620
cagccgtacc tgtccttggc tcttctggca ctggcttagg agttggactt caaaccctca  4680
gccctccctc taagatatat ctcttggccc cataccatca atacaaattg ctactaaaaa  4740
catcctcctt tgcaagtgta tttaccaccc ttttccggca cgcagatagt caatatcttc  4800
agcgtcccca aggcctgcaa gggtgggggcc ccatatctgg aagtcccagg cggagctggg  4860
agttggtcaa gtctgggctg tgggggcagg gagtgctggg ggatggacgc gtatctgcgg  4920
ccgcctatct gtaccactag tctcgagaag ctttcatcaa aaaaagtcta accagctgca  4980
ttcgactttg actgcagcag ctggttagaa ggttctactg gaggagggtc ccagcccatt  5040
gctaaattaa catcaggctc tgagactggc agtatatctc taacagtggt tgatgctatc  5100
ttctggaact tgcctgctac attgagacca ctgacccata cataggaagc ccatagctct  5160
gtcctgaact gttaggccac tggtccagag agtgtgcatc tcctttgatc ctcataataa  5220
ccctatgaga tagacacaat tattactctt actttataga tgatgatcct gaaaacatag  5280
gagtcaaggc acttgcccct agctgggggt ataggggagc agtcccatgt agtagtagaa  5340
tgaaaaatgc tgctatgctg tgcctccccc acctttccca tgtctgccct ctactcatgg  5400
tctatctctc ctggctcctg ggagtcatgg actccaccca gcaccaccaa cctgacctaa  5460
ccacctatct gagcctgcca gcctataacc catctgggcc ctgatagctg gtggccagcc  5520
ctgaccccac cccaccctcc ctggaacctc tgatagacac atctggcaca ccagctcgca  5580
aagtcaccgt gagggtcttg tgtttgctga gtcaaaattc cttgaaatcc aagtccttag  5640
agactcctgc tcccaaattt acagtcatag acttcttcat ggctgtctcc tttatccaca  5700
gaatgattcc tttgcttcat tgccccatcc atctgatcct cctcatcagt gcagcacagg  5760
gcccatgagc agtagctgca gagtctcaca taggtctggc actgcctctg acatgtccga  5820
ccttaggcaa atgcttgact cttctgagct cagtcttgtc atggcaaaac aaagataata  5880
atagtgtttt tttatggagt tagcgtgagg atggaaaaca atagcaaaat tgattagact  5940
ataaaggtc tcaacaaata gtagtagatt ttatcatcca ttaatccttc cctctcctct  6000
cttactcatc ccatcacgta tgcctcttaa ttttcccctta cctataataa gagttattcc  6060
tcttattata ttcttcttat agtgattctg gatatcaaag tgggaatgag gggcaggcca  6120
ctaacgaaga agatgtttct caaagaagcc attctcccca catagatcat ctcagcaggg  6180
ttcaggaaga taaaggagga tcaaggtcga aggtaggaac taaggaagaa cactgggcaa  6240
gtgacgcgtc gacggtaccg ttaacgatct tagccacttt ttaaaagaaa aggggggact  6300
ggaagggcta attcactccc aacgaagaca agatatcctg ctagtccttc ctttctaaat  6360
gacgagagag acagaagaat tcttcaaggt tagtgtgtcc agcatgcaac ctttccttcc  6420
tggatgagca tccctggagt aggagagcca gcctgcctcc tgcgctggca cagagcccgg  6480
ttccctagac aactgcctct ccaaatctga tgtccaagcc cacctggtgt ccacatcaag  6540
cagacacaat taatagtcaa cctgttcagg aaaactgtga gggggaaaaa aagaaaagag  6600
gatttatgaa gggaaaagaa agtttagagg atatgccacg attggctagc agctgctttt  6660
tgcctgtact gggtctctct ggttagacca gatctgagcc tgggagctct ctggctaact  6720
agggaaccca ctgcttaagc ctcaataaag cttgccttga gtgcttcatc cggaatcaac  6780
ctctggatta caaaatttgt gaaagattga ctggtattct taactatgtt gctccttttt  6840
cgctatgtgg atacgctgct ttaatgcctt tgtatcatgc tattgcttcc cgtatggctt  6900
tcattttctc ctccttgtat aaatcctggt tgctgtctct ttatgaggag ttgtggcccg  6960
ttgtcaggca acgtggcgtg gtgtgcactg tgtttgctga cgcaacccccc actggttggg  7020
gcattgccac cacctgtcag ctcctttccg ggactttcgc tttccccctc cctattgcca  7080
cggcggaact catcgccgcc tgccttgccc gctgctggac aggggctcgg ctgttgggca  7140
ctgacaattc cgtggtgttg tcggggaagc tgacgtcctt tccatggctg ctcgcctgtg  7200
ttgccacctg gattctgcgc gggacgtcct tctgctacgt cccttcggcc ctcaatccag  7260
cggaccttcc ttcccgcggc ctgctgccgg ctctgcggcc tcttccgcgt cttcgccttc  7320
gccctcagac gagtcggatc tccctttggg ccgcctcccc gcctgtccgg tagcttgcca  7380
gcctcgactg tgccttctag ttgccagccg tctgttgttt gccctccccc gtgccttcc  7440
```

-continued

```
ttgaccctgg aaggtgccac tcccactgtc ctttcctaat aaaatgagga aattgcatcg   7500
cattgtctga gtaggtgtca ttctattctg gggggtgggg tggggcagga cagcaagggg   7560
gaggattggg aagacaatag caggcatgca agcttggcgt aatcatggtc atagctgttt   7620
cctgtgtgaa attgttatcc gctcacaatt ccacacaaca tacgagccgg aagcataaag   7680
tgtaaagcct ggggtgccta atgagtgagc taactcacat taattgcgtt gcgctcactg   7740
cccgctttcc agtcgggaaa cctgtcgtgc cagctgcatt aatgaatcgg ccaacgcgcg   7800
gggagaggcg gtttgcgtat tgggcgctct tccgcttcct cgctcactga ctcgctgcgc   7860
tcggtcgttc ggctgcggcg agcggtatca gctcactcaa aggcggtaat acggttatcc   7920
acagaatcag gggataaacgc aggaaagaac atgtgagcaa aaggccagca aaaggccagg   7980
aaccgtaaaa aggccgcgtt gctggcgttt ttccataggc tccgcccccc tgacgagcat   8040
cacaaaaatc gacgctcaag tcagaggtgg cgaaacccga caggactata aagataccag   8100
gcgtttcccc ctggaagctc cctcgtgcgc tctcctgttc cgaccctgcc gcttaccgga   8160
tacctgtccg cctttctccc ttcgggaagc gtggcgcttt ctcatagctc acgctgtagg   8220
tatctcagtt cggtgtaggt cgttcgctcc aagctgggct gtgtgcacga acccccgtt    8280
cagcccgacc gctgcgcctt atccggtaac tatcgtcttg agtccaaccc ggtaagacac   8340
gacttatcgc cactggcagc agccactggt aacaggatta gcagagcgag gtatgtaggc   8400
ggtgctacag agttcttgaa gtggtggcct aactacggct acactagaag aacagtattt   8460
ggtatctgcg ctctgctgaa gccagttacc ttcggaaaaa gagttggtag ctcttgatcc   8520
ggcaaacaaa ccaccgctgg tagcggtggt tttttgttt gcaagcagca gattacgcgc   8580
agaaaaaaag gatctcaaga agatcctttg atctttcta cggggtctga cgctcagtgg   8640
aacgaaaact cacgttaagg gattttggtc atgagattat caaaaaggat cttcacctag   8700
atccttttaa attaaaaatg aagttttaaa tcaatctaaa gtatatatga gtaaacttgg   8760
tctgacagtt accaatgctt aatcagtgag gcacctatct cagcgatctg tctatttcgt   8820
tcatccatag ttgcctgact ccccgtcgtg tagataacta cgatacggga gggcttacca   8880
tctggcccca gtgctgcaat gataccgcga gacccacgct caccggctcc agatttatca   8940
gcaataaacc agccagccgg aagggccgag cgcagaagtg gtcctgcaac tttatccgcc   9000
tccatccagt ctattaattg ttgccgggaa gctagagtaa gtagttcgcc agttaatagt   9060
ttgcgcaacg ttgttgccat tgctacaggc atcgtggtgt cacgctcgtc gtttggtatg   9120
gcttcattca gctccggttc ccaacgatca aggcgagtta catgatcccc catgttgtgc   9180
aaaaaagcgg ttagctcctt cggtcctccg atcgttgtca gaagtaagtt ggccgcagtg   9240
ttatcactca tggttatggc agcactgcat aattctctta ctgtcatgcc atccgtaaga   9300
tgcttttctg tgactggtga gtactcaacc aagtcattct gagaatagtg tatgcggcga   9360
ccgagttgct cttgcccggc gtcaatacgg gataataccg cgccacatag cagaacttta   9420
aaagtgctca tcattggaaa acgttcttcg gggcaaaact ctcaaggatc ttaccgctgt   9480
tgagatccag ttcgatgtaa cccactcgtg cacccaactg atcttcagca tcttttactt   9540
tcaccagcgt ttctgggtga gcaaaaacag gaaggcaaaa tgccgcaaaa aagggaataa   9600
gggcgacacg gaaatgttga atactcatac tcttccttt tcaatattat tgaagcattt    9660
atcagggtta ttgtctcatg agcggataca tatttgaatg tatttagaaa aataaacaaa   9720
taggggttcc gcgcacattt ccccgaaaag tgccacctga cgtctaagaa accattatta   9780
tcatgacatt aacctataaa aataggcgta tcacgaggcc ctttcgtctc gcgcgtttcg   9840
gtgatgacgg tgaaaacctc tgacacatgc agctcccgga cacggtcaca gcttgtctgt   9900
aagcggatgc cgggagcaga caagcccgtc agggcgcgtc agcgggtgtt ggcgggtgtc   9960
ggggctggct taactatgcg gcatcagagc agattgtact gagagtgcac c           10011
```

```
SEQ ID NO: 78          moltype = DNA   length = 879
FEATURE                Location/Qualifiers
source                 1..879
                       mol_type = genomic DNA
                       organism = Homo sapiens
SEQUENCE: 78
ctaggtattg aataagaaaa atgaagttaa ggtggttgat ggtaacacta tgctaataac   60
tgcagagcca gaagcaccat aagggacatg ataagggagc cagcagacct ctgatctctt   120
cctgaatgct aatcttaaac atcctgagga agaatgggac ttccatttgg ggtgggccta   180
tgatagggta ataagacagt agtgaatatc aagctacaaa aagccccctt tcaaattctt   240
ctcagtccta acttttcata ctaagcccag tccttccaaa gcagactgtg aaagagtgat   300
agttccggga gactagcact gcagattccg ggtcactgtg agtgggggag gcagggaaga   360
agggctcaca ggacagtcaa accatgcccc ctgtttttcc ttcttcaagt agacctctat   420
aagacaacag agacaactaa ggctgagtgg ccaggcgagg agaaaccatc tcgccgtaaa   480
acatggaagg aacacttcag gggaaaggtg gtatctctaa gcaagagaac tgagtggagt   540
caaggctgag agatgcagga taagcaaatg ggtagtgaaa agacattcat gaggacagct   600
aaaacaataa gtaatgtaaa atacagcata gcaaaacttt aacctccaaa tcaagcctct   660
acttgaatcc ttttctgagg gatgaataag gcataggcat caggggctgt tgccaatgtg   720
cattagctgt ttgcagcctc accttcttt atggagttta agatatagtg tatttttccca  780
aggtttgaac tagctcttca tttctttatg ttttaaatgc actgacctcc cacattccct   840
ttttagtaaa atattcagaa ataatttaaa tacatcatt                          879
```

GLOBIN GENE THERAPY FOR TREATING HEMOGLOBINOPATHIES

CROSS-REFERENCE TO RELATED APPLICATIONS

This application is a divisional of U.S. patent application Ser. No. 16/890,436, filed Jun. 2, 2020, which is a continuation of International Patent Application No. PCT/US18/064256 filed on Dec. 6, 2018, which claims priority to U.S. Provisional Application No. 62/595,277 filed on Dec. 6, 2017, the content of each of which is incorporated by reference in its entirety, and to each of which priority is claimed.

SEQUENCE LISTING

The specification further incorporates by reference the Sequence Listing submitted on Jul. 20, 2023. The Sequence Listing file, identified as 0727341469.xml, is 293,034 bytes in size and was created on Jul. 20, 2023. The Sequence Listing, electronically filed on Jul. 20, 2023, does not extend beyond the scope of the specification and thus does not contain new matter.

INTRODUCTION

The presently disclosed subject matter provides expression cassettes and vectors comprising such expression cassettes that express a globin protein, e.g., a human β-globin protein. The presently disclosed. subject matter further provides expression cassettes that comprise a globin gene or a functional portion thereof operably linked to a β-globin locus control region (LCR) comprising a plurality of Dnase I hypersensitive sites. The expression cassettes of the presently disclosed subject matter comprise one or more insulators that counteract the effect of enhancer elements. The insulators disclosed herein do not substantially adversely impact the titer of a vector that comprises the presently disclosed expression cassettes. The expression cassettes and vectors can be used for treating a hemoglobinopathy, e.g., β-thalassemia, and sickle cell anemia.

BACKGROUND

β-thalassemia and sickle cell anemia are severe congenital anemias that are caused by defective production of the β chain of hemoglobin. In β-thalassemia, the β chain deficit leads to the intracellular precipitation of excess α-globin chains, causing ineffective erythropoiesis and hemolytic anemia (Weatherall and Clegg (1981), Stamatoyannopoulos et al., (1994), Weatherall (2001), Steinberg (2001)). In the most severe forms found in homozygotes or compound heterozygotes, anemia is lethal within the first years of life in the absence of any treatment (Cooley and Lee (1925)). Lifelong transfusion therapy is needed to correct anemia, suppress ineffective erythropoiesis and inhibit gastrointestinal iron absorption (Weatherall and Clegg (1981), Stamatoyannopoulos et al. (1994), Weatherall (2001), Steinberg (2001)). However, transfusion therapy itself leads to iron overload, which is lethal if untreated. The prevention and treatment of iron overload are the major goals of current patient management (Giardina (2001)). The only current curative treatment to cure β-thalassemia is to provide erythroid precursors harboring normal globin genes through allogeneic bone marrow transplantation (BMT) (Giardini and Lucarelli (1994), Boulad et al. (1998), Lucarelli et al. (1999), Tisdale and Sadelain (2001)).

In sickle cell anemia, the hemoglobin β chain is mutated at amino acid position 6 (Glu→Val), leading to the synthesis of $\beta^S$ instead of the normal $\beta^A$ chain (Steinberg (2001), Pauling et al. (1949)). The resulting hemoglobin, HbS, causes accelerated red cell destruction, erythroid hyperplasia and painful vaso-occlusive 'crises' (Steinberg (2001)). Vaso-occlusion can damage organs, eventually causing long-term disabilities (e.g. following stroke or bone necrosis), and sometimes sudden death. While a very serious disorder, the course of sickle cell disease is typically unpredictable (Steinberg (2001)). By increasing production of fetal hemoglobin (Swank and Stamatoyannopoulos (1998)) and suppressing hematopoiesis, hydroxyurea can produce a measurable clinical benefit (Platt et al. (1984)), Charache et al. (1992), Atweh and Loukopoulos (2001)). Since hydroxyurea is a cytotoxic agent, there is a great need for alternative, less toxic drugs to induce y-globin gene expression (Perrine et al. (2005), Stamatoyannopoulos (2005)). As for β-thalassemia, allogeneic bone marrow transplantation (BMT) is at present the only curative therapy for sickle cell disease (Tisdale and Sadelain (2001), Vermylen et al. (1998), Luzzatto and Goodfellow (1989)).

BMT, however, is not available as a therapeutic option to most patients suffering from β-thalassemia or sickle cell disease, due to the lack of an HLA-matched bone marrow donor for most individuals. Furthermore, although potentially curative, allogeneic BMT is not devoid of complications. Safe transplantation requires the identification of a histo-compatible donor to minimize the risks of graft rejection and graft-versus-host disease (Tisdale and Sadelain (2001), Vermylen et al. (1998), Luzzatto and Goodfellow (1989)). Because of the greater risks associated with matched-unrelated or mismatched transplants, most patients have to settle for life-long transfusion therapy, which does not correct ineffective erythropoiesis and exacerbates systemic iron accumulation. Moreover, despite the considerable improvement in life expectancy in the last decades (Borgna-Pignatti et al. (2004), Telfer et al. (2009), Ladis et al. (2011)), the risk of some serious complications arising over the long term from viral infections, iron toxicity and liver cirrhosis, remain (Mancuso et al. (2006)). These medical risks, together with the socio-economic cost of chronic β-thalassemia, underscore the need for safe, effective and curative therapies.

The only means to cure rather than treat severe β-thalassemia is to provide the patient with healthy hematopoietic stem cells (HSCs). HSCs normally give rise to all blood cell types, including 20 billion RBCs per day in adults. HSCs can be harvested from a donor with wild-type β-globin genes to yield long-lived red blood cells (RBCs) with a normal content in hemoglobin. Alternatively, one may genetically correct the patient's own HSCs, which at once resolves the search for a donor and eliminates the risks of graft-versus-host disease and graft rejection associated with allogeneic BMT (Sadelain (1997), Sadelain et al. (2007)). Globin gene transfer aims to restore the capacity of the β-thalassemic subject's own blood-forming stem cells to generate RBCs with a sufficient hemoglobin content Sadelain et al. (2007), Persons and Tisdale (2004), Sadelain (2006)). The goal in patients with sickle cell anemia is to prevent sickling, which can be achieved by diluting the endogenous HbS with a non-sickling Hb that incorporates the vector-encoded globin chain. The patient's own HSCs are the cells that have to be genetically modified to ensure long-lasting therapeutic benefits and achieve a curative stem cell-based therapy.

The implementation of globin gene transfer for the treatment of severe β-thalassemia and sickle cell anemia requires the efficient introduction of a regulated human β- or β-like globin gene in HSCs. The β-globin gene (or β-like variant) must be expressed in erythroid-specific fashion and at high level, especially for the treatment of transfusion-dependent beta-zero thalassemias.

The globin vectors developed to date present shortcomings that may limit or even preclude their safe use in thalassemia and sickle cell patients. Some of the β-globin locus control region (LCR) components contained in the vectors, in particular Dnase I hypersensitive site-2 (HS2), may have non-erythroid activity, exposing patients to the risk of insertional oncogenesis as seen with non-specific expression vectors. Further, the use of large LCR segments can be detrimental to the production of high titer vectors and the efficient transduction of patients HSCs. Accordingly, there is a need for novel globin expression cassettes that allow for therapeutic expression of a globin gene (e.g., human β-globin gene) in erythroid-specific and differentiation stage-specific fashion with minimal risk of insertional oncogenesis, and that enable high level transduction, thus improving their safety when used in treating thalassemia and sickle cell patients.

SUMMARY OF THE INVENTION

The presently disclosed subject matter generally provides enhancer blocking insulators, and certain insulators additionally possess barrier insulator activity. The presently disclosed subject matter also provides expression cassettes comprising one or more insulators and allows for expression of a globin gene (e.g., a human β globin gene). Also provided are vectors comprising such expression cassettes, cells transduced with such expression cassettes or such vectors, and uses of such expression cassettes for treating hemoglobinopathies (e.g., β-thalassemia and sickle cell anemia).

In certain non-limiting embodiments, the presently disclosed subject matter provides an expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, which is provided below.

```
                                    [SEQ ID NO: 50]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAA
```

In certain embodiments, the HS2 region does not comprise the nucleotide sequence set forth in SEQ ID NO: 52, which is provided below.

```
                                    [SEQ ID NO: 52]
GTATATGTGTATATATATATATATATATTCAGGAAATAATATAT
```

In certain embodiments, the HS2 region has nucleotides 45-860 of SEQ ID NO: 9. In certain embodiments, the HS2 region has the nucleotide sequence set forth in SEQ ID NO: 33.

In certain embodiments, the expression cassette further comprises a Dnase I hypersensitive 1-site-1 (HS1) region.

The presently disclosed subject matter also provides an expression cassette comprising a globin gene or a functional portion thereof operably linked to a β-globin locus control region (LCR) that comprises a HS1 region, a HS3 region, and a HS4 region and does not comprise a core sequence of HS2 region, wherein the HS4 region has a length of less than about 800 bp and does not comprise the nucleotide sequence set forth in SEQ ID NO: 50. In certain embodiments, the core sequence of HS2 has the nucleotide sequence set forth in SEQ ID NO:20 or SEQ ID NO:21. In certain embodiments, the β-globin LCR does not comprise a HS2 region that sustains the enhancer activity of HS2.

In various of these embodiments, the HS4 region has a length of between about 700 bp and about 800 bp. In certain embodiments, the HS4 region has a length of about 750 bp. In certain embodiments, the HS4 region does not comprise the nucleotide sequence set forth in SEQ ID NO: 51, which is provided below.

```
                                    [SEQ ID NO: 51]
TTTAATCTAACAATTATGAACAGCAATGAGATAATATGTACAAAGTACCC

AGACCTATGTGGTAGAGCATCAAGGAAGCGCATTGCGGAGCAGTTTTTTG

TTTGTTTGTTTTTGTATTCTGTTTCGTGAGGCAAGGTTTCACTCTGCTGT

CCAGGCTGGAGTGCAGTGGCAAGATCATGTCTCACTGCAGCCTTGAC
```

In various of these embodiments, the HS3 region has a length of about 1300 bp. In certain embodiments, the HS3 region has the nucleotide sequence set forth in SEQ ID NO: 5. In certain embodiments, the HS3 region has the nucleotide sequence set forth in SEQ ID NO: 34.

In various of these embodiments, the HS1 region has a length of about 600 bp. In certain embodiments, the HS1 region has the nucleotide sequence set forth in SEQ ID NO: 3.

In certain embodiments, the β-globin LCR comprises or consists essentially of a HS2 region having nucleotides 45-860 of SEQ ID NO: 9, a HS3 region having the nucleotide sequence set forth in SEQ ID NO: 5, and a HS4 region having nucleotides 115-868 of SEQ ID NO: 6.

In certain embodiments, the β-globin LCR comprises or consists essentially of a HS2 region having the nucleotide sequence set forth in SEQ ID NO: 33, a HS3 region having the nucleotide sequence set forth in SEQ ID NO: 34, and a HS4 region having the nucleotide sequence set forth in SEQ ID NO: 35.

In certain embodiments, the β-globin LCR comprises or consists essentially of a HS1 region having the nucleotide sequence set forth in SEQ ID NO: 3, a HS3 region having the nucleotide sequence set forth in SEQ ID NO: 5, and a HS4 region having nucleotides 115-868 of SEQ ID NO: 6.

In certain embodiments, the β-globin LCR comprises or consists essentially of a HS1 region having the nucleotide sequence set forth in SEQ ID NO: 3, a HS3 region having the nucleotide sequence set forth in SEQ ID NO: 34, and a HS4 region having the nucleotide sequence set forth in SEQ ID NO: 35.

In certain embodiments, the β-globin LCR comprises or consists essentially of a HS1 region having the nucleotide sequence set forth in SEQ ID NO: 3, a HS2 region having nucleotides 45-860 of SEQ ID NO: 9, a HS3 region having the nucleotide sequence set forth in SEQ ID NO: 5, and a HS4 region having nucleotides 115-868 of SEQ ID NO: 6.

In certain embodiments, the β-globin LCR comprises or consists essentially of a HS1 region having the nucleotide sequence set forth in SEQ ID NO: 3, a HS2 region having the nucleotide sequence set forth in SEQ ID NO: 33, a HS3 region having the nucleotide sequence set forth in SEQ ID NO: 34, and a HS4 region having the nucleotide sequence set forth in SEQ ID NO: 35.

In various of these embodiments, the expression cassette further comprises at least one an insulator comprising the CTCF binding site sequence set forth in SEQ ID NO:18. In certain embodiments, the at least one insulator has the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, or SEQ ID NO: 31. In certain embodiments, the expression cassette comprises two insulators, each comprising the CTCF binding site sequence set forth in SEQ ID NO:18, for example, but not limited to, where one or both insulators comprise the nucleotide sequence set forth in SEQ ID NO: 1, SEQ ID NO: 24, SEQ ID NO:25, SEQ ID NO: 27, SEQ ID NO: 28, SEQ ID NO: 29, SEQ ID NO: 30, or SEQ ID NO: 31.

In certain embodiments, the expression cassette further comprises at least one erythroid-specific enhancer. In certain embodiments, the at least one erythroid-specific enhancer is positioned within the β-globin LCR. In certain embodiments, the at least one erythroid-specific enhancer is positioned between the HS1 region and the HS3 region of the β-globin LCR. In certain embodiments, the at least one erythroid-specific enhancer has the nucleotide sequence set forth in SEQ ID NO: 13, SEQ ID NO: 14, SEQ ID NO: 15, SEQ ID NO: 16, or SEQ ID NO: 17. In certain embodiments, the at least one erythroid-specific enhancer has the nucleotide sequence set forth in SEQ ID NO: 15. In certain embodiments, the at least one erythroid-specific enhancer is between about 100 and about 200 bp in length. In certain embodiments, the expression cassette comprises one, two or three erythroid-specific enhancers.

The presently disclosed subject matter also provides an expression cassette comprising at least one erythroid-specific enhancer disclosed herein and a globin gene or a functional portion thereof, wherein the expression cassette does not comprise a β-globin locus control region (LCR).

The presently disclosed subject matter further provides an expression cassette comprising at least one erythroid-specific enhancer disclosed herein and a globin gene or a functional portion thereof that is operatively linked to a β-globin locus control region (LCR) that comprises a HS3 region, and does not comprise a core sequence of a HS1 region, a core sequence of a HS2 region, or a core sequence of a HS4 region.

In certain embodiments, the globin gene is selected from the group consisting of β-globin gene, γ-globin gene, and δ-globin gene. In certain non-limiting embodiments, the globin gene is human β-globin gene. In certain non-limiting embodiments, the human β-globin gene is a wild-type human β-globin gene. In certain non-limiting embodiments, the human β-globin gene is a non-wild-type human β-globin gene, including, but not limited to, a human β-globin gene comprising one or more deletions of intron sequences, a human β-globin gene encoding at least one (e.g., one or two) anti-sickling amino acid residue (e.g., a human β-globin gene encoding anti-sickling hemoglobin 1 (HB AS1), and a human β-globin gene encoding anti-sickling hemoglobin 2 (HB AS2)), and a human β-globin gene comprising one or more deletions of intron sequences and encoding at least one anti-sickling amino acid residue. In certain non-limiting embodiments, the human β-globin gene is a human BAglobin gene encoding a threonine to glutamine mutation at codon 87 ($B^{A-T87Q}$). In certain non-limiting embodiments, the human β-globin gene is a human $β^A$-globin gene encoding a threonine to glutamine mutation at codon 87 ($B^{A-T87Q}$) and comprising a deletion in intron 2. In certain non-limiting embodiments, the human β-globin gene is a human $β^A$-globin gene encoding a glutamic acid to alanine mutation at codon 22 ($B^{A-E22A}$). In certain non-limiting embodiments, the human β-globin gene is a human $β^A$-globin gene encoding a glutamic acid to alanine mutation at codon 22 ($B^{A-E22A}$) and comprising a deletion in intron 2. In certain non-limiting embodiments, the human β-globin gene is a human $β^A$-globin gene encoding an asparagine to lysine mutation at codon 80 ($β^{-N80K}$). In certain non-limiting embodiments, the human β-globin gene is a human $β^A$-globin gene encoding an asparagine to lysine mutation at codon 80 ($β^{-N80K}$) and comprising a deletion in intron 2. In certain non-limiting embodiments, the human β-globin gene is a human $β^A$-globin gene encoding a glutamic acid to alanine mutation at codon 22 and an asparagine to lysine mutation at codon 80. In certain non-limiting embodiments, the human β-globin gene is a human $β^A$-globin gene encoding a glutamic acid to alanine mutation at codon 22 and an asparagine to lysine mutation at codon 80 and comprising a deletion in intron 2. In certain non-limiting embodiments, the human β-globin gene is a human $β^A$-globin gene encoding a glutamic acid to alanine mutation at codon 22 and a threonine to glutamine mutation at codon 87. In certain non-limiting embodiments, the human β-globin gene is a human $β^A$-globin gene encoding a glutamic acid to alanine mutation at codon 22 and a threonine to glutamine mutation at codon 87 and comprising a deletion in intron 2. In certain embodiments, the deletion in intro 2 is a deletion of about 370 bp.

In certain embodiments, the expression cassette further comprises a β-globin promoter. In certain embodiments, the β-globin promoter is positioned between the globin gene or functional portion thereof and β-globin LCR. In certain non-limiting embodiments, the β-globin promoter is a human β-globin promoter that is about 265 bp in length. In certain non-limiting embodiments, the β human β-globin promoter has the nucleotide sequence set forth in SEQ ID NO:11.

In certain embodiments, the expression cassette further comprises a human β-globin 3' enhancer. In certain embodiments, the human β-globin 3' enhancer is positioned in the upstream of the globin gene or functional portion thereof. In certain embodiments, the β-globin 3' enhancer is between about 700 and about 900 bp in length, e.g., between about 800 and 900 bp in length. In certain embodiments, the human β-globin 3' enhancer is about 880 bp in length. In certain embodiments, the human β-globin 3' enhancer has the nucleotide sequence set forth in SEQ ID NO:12.

In certain embodiments, the expression cassette allows for expression of the globin gene or functional portion thereof in a mammal. In certain embodiments, the expression cassette allows for expression of a human β-globin gene. In certain embodiments, the expression of the globin gene or functional portion thereof is restricted to erythroid tissue.

The presently disclosed subject matter also provides recombinant vectors comprising the above-described expression cassettes. In certain embodiments, the recombinant vector is a retroviral vector. In certain embodiments, the retroviral vector is a lentivirus vector. In certain embodiments, the expression cassette comprised in the recombinant vector comprises one insulator. In certain embodiments, the expression cassette comprised in the recombinant vector comprises two insulators, e.g., two of the insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32. In certain embodiments, the recombinant vector further comprises a Woodchuck hepatitis post-regulatory element (WPRE) in 3' long terminal repeat (LTR) of the vector. In certain embodiments, the recombinant vector further comprises a bovine growth hormone polyadenylation signal in 3' long terminal repeat (LTR) of the vector.

In addition, the presently disclosed subject matter provides non-naturally occurring or engineered nucleases comprising the above-described expression cassettes. In certain embodiments, the nuclease is selected from the group consisting of a non-naturally occurring or engineered zinc-finger nuclease (ZFN), a non-naturally occurring or engineered meganuclease, and a non-naturally occurring or engineered transcription activator-like effector nuclease (TALEN). In certain embodiments, the nuclease comprises a DNA binding domain and a nuclease cleavage domain. In certain embodiments, the nuclease binds to a genomic safe harbor site. In certain embodiments, the nuclease generates a double strand break (DSB) at the genomic safe harbor site. In certain embodiments, the expression cassette comprised in the nuclease comprises two insulators, e.g., two of the insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32. In certain embodiments, the nuclease allows for targeted delivery of the expression cassette. The presently disclosed subject matter also provides polynucleotides encoding the above-described nucleases, and vectors comprising the polynucleotides. In certain embodiments, the vector is a lentiviral vector.

Furthermore, the presently disclosed subject matter provides non-naturally occurring or engineered CRISPR-Cas systems comprising the above-described expression cassettes. In certain embodiments, the CRISPR-Cas system comprises a CRISPR-Cas nuclease and single-guide RNA. In certain embodiments, the CRISPR-Cas system binds to a genomic safe harbor site. In certain embodiments, the CRISPR-Cas system generates a double strand break (DSB) at the genomic safe harbor site. In certain embodiments, the expression cassette comprised in the CRISPR-Cas system comprises two insulators, e.g., two of the insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32. In certain embodiments, the CRISPR-Cas allows for targeted delivery of the expression cassette. The presently disclosed subject matter also provides polynucleotides encoding the above-described CRISPR-Cas systems, and vectors comprising the polynucleotides. In certain non-limiting embodiments, the vector is a lentiviral vector.

In certain embodiments, the genomic safe harbor site is an extragenic genomic safe harbor site. In certain embodiments, the genomic safe harbor site is located on chromosome 1. In certain embodiments, the genomic safe harbor meets all of the following five criteria: (1) distance of at least 50 kb from the 5' end of any gene (e.g., from the 5' end of the gene), (ii) distance of at least 300 kb from any cancer-related gene, (iii) within an open/accessible chromatin structure (measured by DNA cleavage with natural or engineered nucleases), (iv) location outside a gene transcription unit and (v) location outside ultraconserved regions (UCRs), microRNA or long non-coding RNA of the human genome.

Additionally, the presently disclosed subject matter provides cells transduced with the above-described expression cassettes, cells transduced with the above-described recombinant vectors, cells transduced with the above-described nucleases, cells transduced with the above-described CRISPR-Cas systems. In addition, the presently disclosed subject matter provides cells transduced with the above-described vectors. In certain embodiments, the cell is selected from the group consisting of a hematopoietic stem cell, an embryonic stem cell, an induced pluripotent stem cell, and a hemogenic endothelium cell. In certain non-limiting embodiments, the hematopoietic stem cell is a CD34$^+$ hematopoietic stem cell. In certain embodiments, the cell is transduced ex vivo.

Also provided are pharmaceutical compositions comprising an effective amount of the above-described cells and a pharmaceutically acceptable carrier. The presently disclosed subject matter also provides pharmaceutical compositions for treating a hemoglobinopathy comprising an effective amount of the above-described cells and a pharmaceutically acceptable carrier.

Furthermore, the presently disclosed subject matter provides kits for treating a hemoglobinopathy comprising the above-described cells. In certain embodiments, the kits further comprise written instructions for using the cell for treating a subject having a hemoglobinopathy.

In addition, the presently disclosed subject matter provides methods of treating a hemoglobinopathy in a subject, comprising administering an effective amount of the above-described cells to the subject, thereby restoring the subject's ability to produce red blood cells containing normal hemoglobin. In certain embodiments, a therapeutically relevant level of hemoglobin is produced in the subject following administering the cell to the subject. In certain amendments, the method comprises administering an effective amount of the cell transduced with the above-described recombinant vector. In certain embodiments, the vector copy number of the recombinant vector in the cell that provides for the therapeutically relevant level of hemoglobin in the subject is about 0.5-2 vector copy number per cell. In certain embodiments, the method corrects ineffective erythropoiesis in the subject. In certain embodiments, the method does not incur the risk of graft-versus-host disease in the subject. In certain embodiments, the method does not comprise administering an immunosuppressive agent. In certain embodiments, the cell is selected from the group consisting of a hematopoietic stem cell, an embryonic stem cell, an induced pluripotent stem cell, and a hemogenic endothelium cell. In certain non-limiting embodiments, the subject is a human. In certain embodiments, the cell is from the subject. In certain non-limiting embodiments, the cell is from bone marrow of the subject.

In accordance with the presently disclosed subject matter, the hemoglobinopathy can be selected from the group consisting of hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. In certain non-limiting embodiments, the hemoglobinopathy is β-thalassemia. In certain non-limiting embodiments, the hemoglobinopathy is sickle cell anemia.

BRIEF DESCRIPTION OF THE FIGURES

The following Detailed Description, given by way of example, but not intended to limit the invention to specific embodiments described, may be understood in conjunction
with the accompanying drawings.

FIGS. 5A-5C represent the genotoxicity of insulator A1.
FIG. 5A demonstrates the gammaretroviral vector genotox-
icity assay used. FIG. 5B notices the increased survival of
mice receiving 32D cells transduced with insulated gam-
maretroviral vector. Also notice the results obtained with
cHS4 and with the uninsulated control. FIG. 5C shows that
insulator A1 decreased the risk of genotoxicity.

FIG. 8 represents the erythroid-specific enhancers in
accordance with certain embodiments of the presently dis-
closed subject matter (SEQ ID NOS 13-17, respectively, in
order of appearance).

FIG. 9 represents the erythroid-specific enhancers in
accordance with certain embodiments of the presently dis-
closed subject matter (SEQ ID NO: 26).

FIG.
10A depicts recombinant vector #18, and #49-#55.
FIG. 10B
shows recombinant vector #18, #40, #49, #52-#55, and
57-#62.

DETAILED DESCRIPTION OF THE INVENTION

Figure 1:
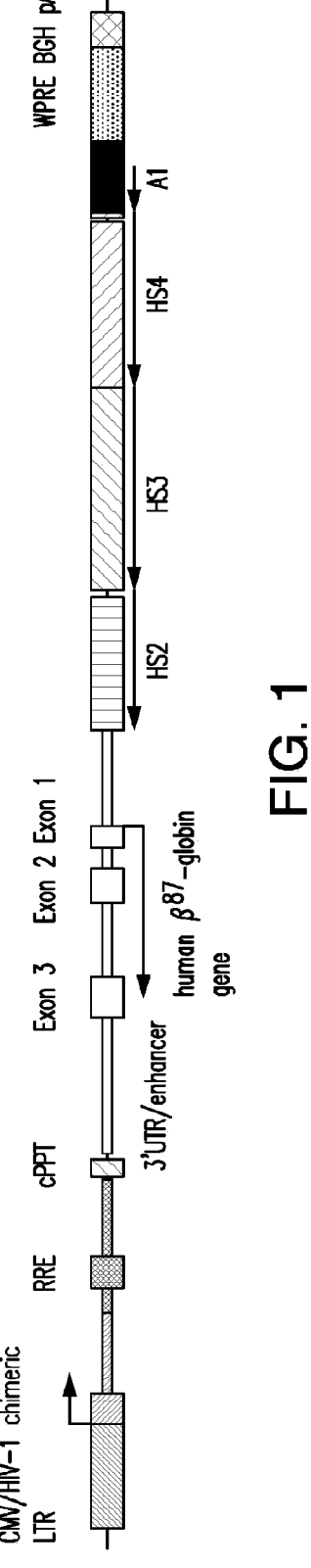
FIG. 1 depicts a recombinant vector comprising an
expression cassette in accordance with one non-limiting
embodiment of the presently disclosed subject matter.
"RRE" represents for "Rev Response Element". cPPT rep-
resents for "Central Polypurine tract".

The presently disclosed subject matter generally provides
expression cassettes that allow for expression of a globin
gene (e.g., human β-globin gene). In certain non-limiting
embodiments, the expression cassette comprises at least one
insulator comprising the CTCF binding site sequence set
forth in SEQ ID NO:18, for example, but not limited to, an
insulator comprising the nucleotide sequence set forth in
SEQ ID NO: 1, SEQ ID NO: 24, SEQ ID NO: 25, or SEQ
ID NO: 27 and a globin gene or a functional portion thereof
operably linked to a β-globin locus control region (LCR).
The expression of the globin gene induced by the presently
disclosed expression cassettes is erythroid-specific, differ-
entiation stage-specific, high-level, and sustained. The pres-
ently disclosed subject matter also provides recombinant
vectors, non-naturally occurring or engineered nucleases,
and non-naturally occurring or engineered CRISPR-Cas
systems comprising such expression cassettes, and cells
transduced with such expression cassettes, recombinant vec-
tors, nucleases and CRISPR-Cas systems. The presently
disclosed expression cassettes and vectors comprising
thereof provide for a safe gene transfer therapy as therapeu-
tic transgene expression is achieved (e.g., a therapeutically
relevant level of hemoglobin is produced) with a low vector
copy number per cell (e.g., 0.5-2, 1-2, or even 0.5-1). In
addition, the presently disclosed subject matter provides
methods of using such transduced cells for treating a hemo-
globinopathy (e.g., β-thalassemia and sickle cell anemia).

I. Definitions

Unless defined otherwise, all technical and scientific
terms used herein have the meaning commonly understood
by a person skilled in the art to which this invention belongs.
The following references provide one of skill with a general
definition of many of the terms used in this invention:
Singleton et al., Dictionary of Microbiology and Molecular
Biology (2nd ed. 1994); The Cambridge Dictionary of
Science and Technology (Walker ed., 1988); The Glossary
of Genetics, 5th Ed., R. Rieger et al. (eds.), Springer Verlag
(1991); and Hale & Marham, The Harper Collins Dictionary
of Biology (1991). As used herein, the following terms have
the meanings ascribed to them below, unless specified
otherwise.

As used herein, the term "expression cassette" refers to a
nucleic acid construct, generated recombinantly or syntheti-
cally, with a series of specified nucleic acid elements, which
permit transcription of a particular nucleic acid in a target
cell. The expression cassette can be incorporated into a
plasmid, chromosome, mitochondrial DNA, plastid DNA,
virus or nucleic acid region. The expression cassette portion
can include a gene to be transcribed and elements that
control the expression of the gene (e.g., a promoter).

As used herein, the term "β-globin locus control region
(LCR)" refers to a polynucleotide composed of one or more
Dnase I hypersensitive site (HS) regions, including a HS1
region, a HS2 region, a HS3 region, and a HS4 region. The
structure of many LCRs of the β-globin genes have been
published, e.g., human (Li et al., *J. Biol. Chem.* (1985);
260:14,901; Li et al., *Proc. Natl. Acad. Sci.* (1990) 87:8207);
mouse (Shehee et al., J. Mol. Biol. (1989); 205:41); rabbit
(Margot et al., J. Mol. Biol. (1989); 205:15); and goat (Li,
Q., et al., *Genomics* (1991); 9:488), each of which are
incorporated by reference herein. In certain embodiments,
the β-globin LCR comprises a HS2 region (e.g., a β-globin LCR comprising a HS2 region, a HS3 region and a HS4 region; and a β-globin LCR comprising a HS1 region, a HS2 region, a HS3 region and a HS4 region). In certain embodiments, the β-globin LCR does not comprise a HS2 region (e.g., a β-globin LCR comprising or consisting essentially of a HS1 region, a HS3 region, a HS4 region). In certain embodiments, the β-globin LCR does not comprise a HS2 region or a HS1 region (e.g., a β-globin LCR comprising or consisting essentially of a HS3 region and a HS4 region). In certain embodiments, the β-globin LCR does not comprise a HS1 region, a HS2 region or a HS4 region (e.g., a β-globin LCR comprising or consisting essentially of a HS3 region).

As used herein, the term "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene.

As used herein, the term "globin" refers to a family of heme-containing proteins that are involved in the binding and transport of oxygen. Subunits of vertebrate and invertebrate hemoglobins, vertebrate and invertebrate myoglobins or mutants thereof are included by the term globin.

As used herein, the term "wild-type" refers to the normal gene, virus, or organism found in nature without any mutation or modification.

The terms "polynucleotide", "nucleotide", "nucleotide sequence", "nucleic acid" and "oligonucleotide" are used interchangeably. They refer to a polymeric form of nucleotides of any length, cither deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene region, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide can comprise one or more modified nucleotides, such as methylated nucleotides and nucleotide analogs. In particular embodiments, the presently disclosed subject matter provides polynucleotides encoding one or more globin genes or functional portions thereof. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. Such polynucleotides need not be about 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration can ordinarily be less than about 750 mM NaCl and 75 mM trisodium citrate, e.g., less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, e.g., at least about 50% formamide. Stringent temperature conditions can ordinarily include temperatures of at least about 30° C., e.g., of at least about 37° C. or of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In certain embodiments, hybridization occurs at 37° C. in 500 mM NaCl, 50 mM trisodium citrate, 1% SDS, 35% formamide, and 100 μg/ml denatured salmon sperm DNA (ssDNA). In certain embodiments, hybridization occurs at 42° C. in 250 mM NaCl, 25 mM trisodium citrate, 1% SDS, 50% formamide, and 200 μg/ml ssDNA. Useful variations on these conditions can be readily apparent to those skilled in the art.

For most applications, washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, e.g., less than about 15 mM NaCl and 1.5 mM trisodium citrate. Stringent temperature conditions for the wash steps can ordinarily include a temperature of at least about 25° C., e.g., of at least about 42° C., or of at least about 68° C. In certain embodiments, wash steps occur at 25° C. in 30 mM NaCl, 3 mM trisodium citrate, and 0.1% SDS. In certain embodiments, wash steps occur at 42° C. in 15 mM NaCl, 1.5 mM trisodium citrate, and 0.1% SDS. In certain embodiments, wash steps occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook, et al., Molecular Cloning: A Laboratory Manual, Cold Spring Harbor Laboratory Press, New York.

As used herein, the terms "polypeptide" and "protein" are used interchangeably to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Particular embodiments of the presently disclosed subject matter also include polypeptide "variants." Polypeptide "variant" refers to polypeptides that are distinguished from a reference polypeptide by the addition, deletion, truncations, and/or substitution of at least one amino acid residue, and that retain a biological activity. In certain embodiments, a polypeptide variant is distinguished from a reference polypeptide by one or more substitutions, which may be conservative or non-conservative, as known in the art. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, the amino acid additions or deletions occur at the C-terminal end and/or the N-terminal end of the reference polypeptide. In certain embodiments, the amino acid deletions include C-terminal truncations of about 1, about 2, about 3, about 4, about 5, about 6, about 7, about 8, about 9, about 10, about 15, about 20, about 25, about 30, about 35, about 40, about 45, 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, or about 175 or more amino acids, including all intervening numbers of amino acids, e.g., 25, 26, 27, 29, 30 . . . 100, 101, 102, 103, 104, 105 . . . 170, 171, 172, 173, 174, etc.

As noted above, polypeptides of the presently disclosed subject matter may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, Proc. Natl. Acad. Sci. USA. 82:488-492), Kunkel et al., (1987, Methods in Enzymol, 154:367-382), U.S. Pat. No. 4,873,192, Watson, J. D. et al., Molecular Biology of the Gene, Fourth Edition, Benjamin/Cummings, Menlo Park, Calif, 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

As used herein, the term "substantially identical" refers to a polypeptide or a polynucleotide exhibiting at least 50% identity to a reference amino acid sequence (for example, any one of the amino acid sequences described herein) or a nucleic acid sequence (for example, any one of the nucleic acid sequences described herein). Preferably, such a sequence is at least about 60%, e.g., about 80%, about 85%, about 90%, about 95%, or about 99% identical at the amino acid level or nucleic acid to the sequence used for comparison.

Sequence identity or homology is typically measured using sequence analysis software (for example, Sequence Analysis Software Package of the Genetics Computer Group, University of Wisconsin Biotechnology Center, 1710 University Avenue, Madison, Wis. 53705, BLAST, BEST-FIT, GAP, or PILEUP/PRETTYBOX programs). Such software matches identical or similar sequences by assigning degrees of homology to various substitutions, deletions, and/or other modifications. In an exemplary approach to determining the degree of identity or homology, a BLAST program may be used, with a probability score between e-3 and e-100 indicating a closely related sequence. The percentage of identity between two sequences can also be determined with programs such as DNAMAN (Lynnon Biosoft, version 3.2). Using this program two sequences can be. aligned using the optimal alignment algorithm (Smith and Waterman, 1981). After alignment of the two sequences the percentage identity can be calculated by dividing the number of identical nucleotides between the two sequences by the length of the aligned sequences minus the length of all gaps.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in 5' to 3' orientation or the 3' to 5' orientation.

As used herein, a "single guide RNA" or a "synthetic guide RNA" refers to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

As used herein, the term "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" or "individual" refers to a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys. The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

As used herein, the term "isolated cell" refers to a cell that is separated from the molecular and/or cellular components that naturally accompany the cell. As used herein, the term "isolated" refers to material that is free, substantially free, or essentially free to varying degrees from components which normally accompany it as found in its native state. "Isolate" denotes a degree of separation from original source or surroundings.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 103 cells, at least about 104 cells, at least about $10^5$ cells, at least about $10^6$ cells, at least about $10^7$ cells, or at least about $10^8$ cells expressing similar or different phenotypes.

As used herein, the term "cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

As used herein, the term "cleavage half-domain" refers to a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

As used herein, the term "chromosome" refers to a chromatin complex comprising all or a portion of the genome of a cell. The genome of a cell is often characterized by its karyotype, which is the collection of all the chromosomes that comprise the genome of the cell. The genome of a cell can comprise one or more chromosomes.

As used herein, the term "gene" includes a DNA region encoding a gene product, as well as all DNA regions which regulate the production of the gene product, whether or not such regulatory sequences are adjacent to coding and/or transcribed sequences. Accordingly, a gene includes, but is not limited to, promoter sequences, terminators, translational regulatory sequences such as ribosome binding sites and internal ribosome entry sites, enhancers, silencers, insulators, boundary elements, replication origins, matrix attachment sites and locus control regions The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional region" or "functional portion" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional region can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical.

As used herein, the term "promoter" refers to a recognition site of a polynucleotide (DNA or RNA) to which an RNA polymerase binds. The term "enhancer" refers to a segment of DNA which contains sequences capable of providing enhanced transcription and in some instances can function independent of their orientation relative to another control sequence. An enhancer can function cooperatively or additively with promoters and/or other enhancer elements.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "modulate" refers to altering positively or negatively. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value.

II. Insulators

Several cases of vector-related malignant transformation have been reported in clinical settings, associated with the activation of cellular oncogenes by vector-encoded enhancers (Baum et al. (2006), Nienhuis et al. (2006), Ramezani et al. (2006)) and various vector modifications have been performed or proposed to reduce vector genotoxicity (Baum et al. (2006), Nienhuis et al. (2006), Ramezani et al. (2006)). A class of DNA elements known as chromatin insulators has been recognized as one approach to improve vector safety and performance (Emery (2011)).

Insulators are naturally occurring DNA elements that help from the functional boundaries between adjacent chromatin domains. Insulators bind proteins that modify chromatin and alter regional gene expression. The placement of insulators in the vectors described herein offer various potential benefits including, but not limited to, 1) shielding of the vector from positional effect variegation of expression by flanking chromosomes (i.e., barrier activity, which may decrease position effects and vector silencing); and 2) shielding flanking chromosomes from insertional trans-activation of endogenous gene expression by the vector (enhancer blocking). There are two basic classes of chromatin insulators: (a) barrier insulators that block the encroachment of silencing heterochromatin into adjoining regions of open chromatin that are transcriptionally permissive, and (b) enhancer blocking insulators that prevent enhancer-mediated transcriptional activation of adjoining regions. The sequences that mediate these activities are physically separable and mechanistically distinct (Recillas-Targa et al. (2002)). Chromatin insulators do not exhibit inherent transcriptional enhancing or repressing activities on their own. As such, they make ideal elements for reducing the interaction between gene transfer vectors and the target cell genome. Insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Nat'l Acad. Sci. USA,* 99:16433; and Zhan et al. (2001) *Hum. Genet.,* 109:471).

The problems created by insertional mutagenesis of viral vectors are widely known (Nienhuis (2013), Baum et al. (2006), Nienhuis et al. (2006)) as is the evidence that the risks of genotoxicity can be reduced by the use of chromatin insulators (Arumugam et al. (2007), Emery (2011), Evans-Galea et al. (2007), Rivella et al. (2000), Emery et al. (2000), Emery et al. (2002), Yannaki et al. (2002), Hino et al. (2004), Ramezani et al. (2003), Ramezani et al. (2008)). The presently disclosed subject matter provides novel insulators that are powerful enhancer blocking insulators, and certain insulators additionally possess barrier insulator activity. In vertebrates, the function of enhancer blocking insulators is mediated through the zinc-finger DNA-binding factor CTCF (Gaszner and Felsenfeld (2006), Wallace and Felsenfeld (2007)). In general, these elements are thought to function through physical loop structures, which are established by CTCF-mediated interactions between adjacent insulator elements or through CTCF-mediated tethering of the chromatin fiber to structural elements within the nucleus. The first characterized vertebrate chromatin insulator is located within the chicken β-globin locus control region. This element, which contains a DNase-I hypersensitive site-4

(cHS4), appears to constitute 5' boundary of the chicken β-globin locus (Prioleau et al. (1999) EMBO J. 18:4035-4048). A 1.2-kb region containing the cHS4 element displays classic insulator activities, including the ability to block the interaction of globin gene promoters and enhancers in cell lines (Chung et al. (1993) *Cell,* 74:505-514), and the ability to protect expression cassettes in *Drosophila* (Id.), transformed cell lines (Pikaart et al. (1998) *Genes Dev.* 12:2852-2862), and transgenic mammals (Wang et al. (1997) *Nat. Biotechnol.,* 15:239-243; Taboit-Dameron et al. (1999) Transgenic Res., 8:223-235) from position effects. Much of this activity is contained in a 250-bp region. Within this stretch is a 49-bp cHS4 element (Chung et al. (1997) *Proc. Natl. Acad. Sci., USA,* 94:575-580) that interacts with the zinc finger DNA binding protein CTCF implicated in enhancer-blocking assays (Bell et al. (1999) *Cell,* 98:387-396).

Insulators, such as cHS4, can block the interaction between enhancers and promoters when placed between these elements (Evans-Galea et al. (2007), Chung et al. (1997), Bell et al. (1999), Ryu et al. (2007), Ryu et al. (2008)). Several studies have demonstrated the ability of the cHS4 insulator to reduce position-effect silencing of gammaretroviral vectors (Evans-Galea et al. (2007), Rivella et al. (2000), Emery et al. (2000), Emery et al. (2002), Yannaki et al. (2002), Hino et al. (2004), Ramezani et al. (2006), Yao et al. (2003), Nishino et al. (2006), Aker et al. (2007), Li and Emery (2008)), and lentiviral vectors (Bank et al. (2005), Arumugam et al. (2007), Puthenveetil et al. (2004), Evans-Galea et al. (2007), Ramezani et al. (2003), Aker et al. (2007), Ma et al. (2003), Chang et al. (2005), Pluta et al. (2005)). Those appropriately designed studies demonstrated that inclusion of the 1.2 kb version of the cHS4 insulator increased the likelihood and/or consistency of vector transgene expression in at least some settings (Arumugam et al. (2007), Emery (2011), Evans-Galea et al. (2007), Emery et al. (2002), Yannaki et al. (2002), Hino et al. (2004), Ramezani et al. (2006), Aker et al. (2007), Li and Emery (2008), Pluta et al. (2005). Jakobsson et al. (2004)). Nevertheless, the degree of protection afforded by the cHS4 insulator is far from complete. In addition, the inclusion of the 1.2 Kb cHS4 can adversely affect vector titers while the smallest cHS4 core has been proven ineffective (Aker et al. (2007), Jakobsson et al. (2004)). By contrast, the insulators of the presently disclosed subject matter do not affect adversely the titers of viral vectors, and are more powerful and effective than the cHS4 insulator.

The presently disclosed insulators are identified through genomic approaches, e.g., using genomic approaches to identify insulators that are powerful enhancer blockers as well as barrier insulators of the human genome. The presently disclosed insulators enhance the safety of gene therapy (e.g., stem cell gene therapy, globin gene therapy). For gene therapy of the hemoglobinopathies, powerful enhancers are required to achieve therapeutic levels of globin gene expression. Powerful insulators therefore represent one means to protect the genomic environment from the powerful enhancers of the integrating vectors.

The presently disclosed insulators possess powerful enhancer blocking activity. For example, and not by way of limitation, an insulator of the present disclosure can reduce the activity of an enhancer element by at least about 10%, at least about 20%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98% or at least about 99%. In certain embodiments, the insulators possess barrier activity in addition to enhancer blocking activity. The presently disclosed insulators substantially decrease the risks of insertional mutagenesis and genotoxicity associated with viral vectors. Furthermore, when at least one presently disclosed insulator is incorporated into a vector, the insulator(s) does not adversely effect vector titers of the vector. In certain embodiments, the presently disclosed insulators (e.g., insulator A1) increase the in vivo expression of the globin gene or functional portion thereof.

In certain embodiments, the insulator comprises a Transcriptional repressor CTCF binding site, which has the nucleotide sequence set forth in SEQ ID NO: 18, which is provided below:

```
                                       [SEQ ID NO: 18]
               CACCAGGTGGCGCT.
```

In certain embodiments, the insulator has the nucleotide sequence set forth in SEQ ID NO:1, which is provided below, or a sequence which is at least about 80%, about 85%, about 90%, about 95%, about 98, about 99% or about 100% % identical (homologous), to SEQ ID NO:1. SEQ ID NO: 1 is provided below.

```
                                        [SEQ ID NO: 1]
TCCTTCCTTTCTAAATGACGAGAGAGACAGAAGAATTCTTCAAGGTTAGT

GTGTCCAGCATGCAACCTTTCCTTCCTGGATGAGCATCCCTGGAGTAGGA

GAGCCAGCCTGCCTCCTGCGCTGGCACAGAGCCCGGTTCCCTAGACAACT

GCCTCTCCAAATCTGATGTCCAGCGCCACCTGGTGTCCACATCAAGCAGA

CACAATTAATAGTCAACCTGTTCAGGAAAACTGTGAGGGGGAAAAAAAAG

AAAGAGGATTTATGAAGGGAAAAGAAAGTTTAGAGGATATGCCACGATTG

GCTAG
```

In certain embodiments, the insulator comprises or has the nucleotide sequence as set forth in SEQ ID NO:24, or a sequence which is at least about 80%, about 85%, about 90%, about 95%, about 98, about 99% or about 100% identical (homologous), to SEQ ID NO: 24. SEQ ID NO: 24 is provided below.

```
                                       [SEQ ID NO: 24]
   CCAATC GTGGCATATC CTCTAAACTT TCTTTTCCCT

TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG

TCTAGGGAAC CGGGCTCTGT GCCAGCGCAG GAGGCAGGCT

GGCTCTCCTA TTCCAGGGAT GCTCATCCAG GAAGGAAAGG

TTGCATGCTG GACACACTAA CCTTGAAGAA TTCTTCTGTC

TCTCTCGTCA TTTAGAAAGG AAGGA.
```

In certain embodiments, the insulator comprises or has the nucleotide sequence as set forth in SEQ ID NO:25 (which is the reverse complement of SEQ ID NO: 1), or a sequence which is at least about 80%, about 85%, about 90%, about 95%, about 98, about 99% or about 100% identical (homologous), to SEQ ID NO: 25. SEQ ID NO: 25 is provided below.

```
                                       [SEQ ID NO: 25]
CTAGCCAATCGTGGCATATCCTCTAAACTTTCTTTTCCCTTCATAAATCC

TCTTTCTTTTTTTTCCCCCTCACAGTTTTCCTGAACAGGTTGACTATTAA

TTGTGTCTGCTTGATGTGGACACCAGGTGGCGCTGGACATCAGATTTGGA

GAGGCAGTTGTCTAGGGAACCGGGCTCTGTGCCAGCGCAGGAGGCAGGCT

GGCTCTCCTACTCCAGGGATGCTCATCCAGGAAGGAAAGGTTGCATGCTG

GACACACTAACCTTGAAGAATTCTTCTGTCTCTCTCGTCATTTAGAAAGG

AAGGA
```

In certain embodiments, the insulator comprises or has the nucleotide sequence as set forth in SEQ ID NO: 27, or a sequence which is at least about 80%, about 85%, about 90%, about 95%, about 98, about 99% or about 100% identical (homologous), to SEQ ID NO: 27. SEQ ID NO: 27 is provided below.

```
                                        [SEQ ID NO: 27]
   ctggttctac tcattacatt ccaatcgtgg catatcctct aaactttctt ttcccttcat aaatcctctt tcttttttt cccctcaca gttttcctga acaggttgac tattaattgt gtctgcttga tgtggacacc aggtggcgct ggacatcaga tttggagagg cagttgtcta gggaaccggg ctctgtgcca gcgcaggagg caggctggct ctcctattcc agggatgctc atccaggaag gaaaggttgc atgctggaca cactaacctt gaagaattct tctgtctctc tcgtcattta gaaaggaagg
```

In certain embodiments, the insulator comprises or has the nucleotide sequence as set forth in SEQ ID NO: 28, or a sequence which is at least about 80%, about 85%, about 90%, about 95%, about 98, about 99% or about 100% identical (homologous), to SEQ ID NO: 28. SEQ ID NO: 28 is provided below.

```
                                       [SEQ ID NO: 28]
   CCAATC GTGGCATATC CTCTAAACTT TCTTTTCCCT

TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG

TCTAGGGAAC CGGGCTCTGT GCCAGCGCAG GAGGCAGGCT

GGCTCTCCTA TTCCAGGGAT GCTCATCCAG GAAGGAAAGG

TTGCATGCTG GACACACTAA CCTTGAAGAA TTCTTCTGTC

TCTCTCGTCA TTTAGAAAGG AAGG
```

In certain embodiments, the insulator comprises or has the nucleotide sequence as set forth in hg18 coordinates 76229933 to 76230115 of chromosome 1.

In certain embodiments, the insulator comprises or has the nucleotide sequence between residues 68041 and 68160 (or SEQ ID NO: 29 provided below), or between residues and 68041 and 68210 (or SEQ ID NO: 30 provided below), or between residues 68041 and 68280 (or SEQ ID NO: 31 provided below), or between residues 68005 and 68305 (or SEQ ID NO: 24), of *Homo sapiens* chromosome 1 clone RP11-550H2, GenBank Accession No. AC092813.2, or a sequence at least about 80%, about 85%, about 90%, about 95%, about 98, about 99% or about 100% identical (homologous) thereto.

```
                                      (SEQ ID NO: 29)
TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG (SEQ ID NO: 30)
TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG

TCTAGGGAAC CGGGCTCTGT GCCAGCGCAG GAGGCAGGCT

GGCTCTCCTA (SEQ ID NO: 31)
TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG
```

```
                -continued
TCTAGGGAAC CGGGCTCTGT GCCAGCGCAG GAGGCAGGCT

GGCTCTCCTA TTCCAGGGAT GCTCATCCAG GAAGGAAAGG

TTGCATGCTG GACACACTAA CCTTGAAGAA TTCTTCTGTC
```

III. Expression Cassettes

The presently disclosed subject matter provides expression cassettes comprising one or more insulators. In certain embodiments, an expression cassette comprises at least one insulator disclosed in Section II, and a globin gene or a functional portion thereof. In certain embodiments, an expression cassette comprises at least one insulator comprising or having the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, or SEQ ID NO: 31, and a globin gene or a functional portion thereof.

In certain embodiments, an expression cassette comprises a globin gene or a functional portion thereof, and at least one insulator disclosed in International Patent Publication No. WO2015/138852. WO2015/138852 is herein incorporated by reference in its entirety. In certain embodiments, an expression cassette comprises a globin gene or a functional portion thereof operably and at least one insulator comprising or having the nucleotide sequence set forth in SEQ ID NO: 32, or a fragment thereof (e.g., nucleotides 1 to 320, 10 to 320, 20 to 320, 21 to 320, 55 to 320, 55 to 300, 57 to 300, 57 to 296, 57 to 226, 57 to 200, or 57 to 176 of SEQ ID NO: 32). SEQ ID NO:32 is provided below.

```
                                                   (SEQ ID NO: 32)
CTGGTTCTAC TCATTACATT CCAATCGTGG CATATCCTCT AAACTTTCTT TTCCCTTCAT  60

AAATCCTCTT TCTTTTTTTT CCCCCTCACA GTTTTCCTGA ACAGGTTGAC TATTAATTGT  120

GTCTGCTTGA TGTGGACACC AGGTGGCGCT GGACATCAGA TTTGGAGAGG CAGTTGTCTA  180

GGGAACCGGG CTCTGTGCCA GCGCAGGAGG CAGGCTGGCT CTCCTATTCC AGGGATGCTC  240

ATCCAGGAAG GAAAGGTTGC ATGCTGGACA CACTAACCTT GAAGAATTCT TCTGTCTCTC  300

TCGTCATTTA GAAAGGAAGG                                              320
```

In certain embodiments, the globin gene or functional portion thereof is operably linked to a β-globin LCR, e.g., a β-globin LCR disclosed in section 3.1.

In certain embodiments, the expression cassette does not comprise a β-globin LCR. In certain embodiments, the expression cassette comprises at least one insulator (e.g., one disclosed in Section II and 3.6), and does not comprise a β-globin LCR. In certain embodiments, the expression cassette comprises at least one insulator comprising or having the nucleotide sequence set forth in SEQ ID NO: 1, and does not comprise a β-globin LCR. In certain embodiments, the expression cassette comprises an erythroid-specific enhancer (e.g., an erythroid-specific enhancer disclosed in section 3.5) and does not comprise a β-globin LCR. In certain embodiments, the expression cassette comprises an erythroid-specific enhancer having the nucleotide sequence set forth in SEQ ID NO:15, and does not comprise a β-globin LCR. In certain embodiments, the expression cassette comprises at least one insulator comprising or having the nucleotide sequence set forth in SEQ ID NO: 1, and an erythroid-specific enhancer having the nucleotide sequence set forth in SEQ ID NO:15, and does not comprise a β-globin LCR.

3.1. β-Globin LCR

The human β-globin gene cluster consists of five genes embedded within one of many olfactory receptor gene arrays (Bulger et al., *PNAS* (1999); 96:5129-5134). The cluster spans over 80 kb on chromosome 11p15.4, and includes the five expressed β-like genes and cis-acting regulatory elements that direct their stage-specific expression during ontogeny (Forget (2001), Molecular Mechanism of Beta Thalassemia. Steinberg M H et al., Eds. Disorders of Hemoglobin. Genetics, Pathophysiology and Clinical Management, Cambridge University Press, Cambridge). The genes are arranged in the order of their developmental expression (Stamatoyannopoulos et al., (2001) Hemoglobin Switching. In: Stamatoyannopoulos G, et al., Eds. Molecular Basis of Blood Disorders, W.B. Saunders, Philadelphia, PA), 5'-ε-$^{G}$γ-$^{A}$γ-ψη-δ-β-3'. The a-like globin gene cluster (5'-ξ2-ψξ 1-ψα2-ψα1-α2-α1-θ-3') is located very close to the telomere of the short arm of chromosome 16 and spans about 40 kb. The expression of genes encoded within these two independent clusters is limited to erythroid cells and balanced so that the output of the β-globin-like chains matches that of the α-chains. This fine-tuned balance is regulated at the transcriptional, posttranscriptional and posttranslational levels.

Developmental stage-specific expression is controlled by a number of proximal or distal cis-acting elements and the transcriptional factors that bind to them. In the case of the β-globin gene (HBB), the proximal regulatory elements comprise the β-globin promoter and two downstream enhancers, one located in the second intron of β-globin and the other approximately 800 bp downstream of the gene (Antoniou et al., *EMBO J.* (1988); 7:377-384; Trudel et al., *Genes Dev.* (1987); 1:954-961; Trudel et al., *Mol. Cell. Biol.* (1987); 7:4024-4029). The most prominent distal regulatory element is the β-globin LCR, located 50-60 kb upstream of the HBB and composed of several sub-regions with heightened sensitivity to DNaseI in erythroid cells (Forget (2001); Grosveld et al., Cell (1987); 51:975-985; Talbot et al., *Nature* (1989); 338:352). The most prominent property of the LCR is its strong, transcription-enhancing activity. An exemplary nucleotide sequence of the human β-globin region on chromosome 11 is set forth in SEQ ID NO:19 (GenBank Access No.: NG_000007.3), which is provided below:

[SEQ ID NO: 19]

```
ggatcctcacatgagttcagtatataattgtaacagaataaaaaatcaattatgtattcaagttgctagtgtcttaagaggttcacatt tttatctaactgattatcacaaaaatacttcgagttacttttcattataattcctgactacacatgaagagactgacacgtaggtgcct tacttaggtaggttaagtaatttatccaaaaccacacaatgtagaacctaagctgattcggccatagaaacacaatatgtggtataaat gagacagagggatttctctccttcctatgctgtcagatgaatactgagatagaatatttagttcatctatcacacattaaacgggactt tacatttctgtctgttgaagatttgggtgtggggataactcaaggtatcatatccaagggatggatgaaggcaggtgactctaacagaa agggaaaggatgttggcaaggctatgttcatgaaagtatatgtaaaatccacattaagcttctttctgcatgcattggcaatgtttatg aataatgtgtatgtaaaagtgtgctgtatattcaaaagtgtttcatgtgcctaggggtgtcaaatactttgagtttgtaagtatatact tctctgtaatgtgtctgaatatctctatttacttgattctcaataagtaggtatcatagtgaacatctgacaaatgtttgaggaacaat ttagtgtttacctattcaccaaaatttattaaatgcctaatctgtatcagatatacaattatctggcgaaatctgtaattcctaattta aacagctgtgtagcctaattaggggataaaggcatgcaaacccataatttgtgtaggttgaaatgagctatagaaaaatgcagtatattt atcagaagtctttagggtcatgaaaaggaatggtcaactgacactgccagggactcatatgtaagagataactaatgtgaagtgacttt aaaggagaaattagcagaagttttctttccatgtctcctcatcatgttacaataacggaagagattaaaacaacaaatacatttagaca gcaatgtttatcctggttagatgtgtttaatctaaatctatcttggagtgttaaaatgcatttgctcacctactttaaaatataaatgaa ggtaggaacctgtagatacaaaaagttggagaaaaaaagacaataaagatgacaaaaatctattaatccttgatagaaaatgagaagag ataaaacactggtttacataaagaaaataagatggatagatagcagatccttataaaagtgataatttgagaaaaaaaatactccatat tctgagtttcttcacataaaataatacaaatctgctgtggtaagttacaaagagatagattttttatcattatataaaagatattttaa acagagttatacaacaaaggaacagactatgtcatatattctcacttatcactataaacatctcagaaaaatctgcaaaatcatttcat agcattttaaatagttaggaataatgtagaaaactgaaacagttctaagtttcccacaaacttagagtctcaaatgttgcattacctaa cttacctgcaaatattttatacaaatttgcacatgctactctagtcaaaaatatatgtacattatgggtattttctgtgtgtaacttgg
``` ttctagttgcttctttcagaaatagcctctattttttgatttacctgataaaatcacattcctctccaaagccttctaaatacttccaga ctaactacttttttagtacatctaagaagaaaagagttttgtctcttatccacctctgagtcaaaaagcagcatgtccatcaattggtac atagttcccacagccccacttagctctggattggagttctacttggcattgtttgcaactacatggacgtaaaatgcatggattctctt gaaaaaatgtttctgccatgatgttctctgaaagagactaaccttccctcgctttgcagagaaagactcgtgtaatccttgacaatgtc atctcatctatttattcccatgtctacccatatgtgaccttcatgtctttgctctaagcccctacatcctcaatctacacactaggata gtataaaagtaatagtaataatagtagtaatagtaataacaatacaatgattatggcttatactatacacaagacactgttgatatatt atttcatttagtattcacagtaactctgtgcctcaagtactattgtaatacccctttaagaggaggaaactgaggcacagggccctaaag taatattccaagatgaagtggctactaactgacagagggcataattcaactcatgatatttggctctagaatacatgctctgaatcatt atacaataataattcatgaggaaacattttttaaagcctaagttatttgctctgaaataagacataatttggggtgagaaagcttagat tccatgaagtattacagcatttggtagtcttttgcactccaggtcttattttttactgcttaaacataataaaacatatggttcagtat gcctttgattttacaataatattcctgttattttttggaagcacagggtgtgggataatgctaattactagtgattagtattgagaggtg acagcgtgctggcagtcctcacagccctcgctcgctcttggcgcctcctctgcctgggctcccacattggtggcacttgaggagcccctt cagccggccgctgcactgtgggagcccttttctgggctggccaaggccagagccggctccctcagcttgccaggaggtgtggagggaca gacgcgggcaggaaccgggctgtgcgccgtgcttgagggagttccgggtgggcatggctccgaggacccccgcactcggagccgccagc cggccccaccggccgcgggcagtgaggggcttagcacctgggccagcagctgctgtgctcaattcctcgccgggccttagctgccttcc tgcggggcagggctcgggacctgcagcgcgccatgcctgagcctccccaccttcatgggctcctgtgcggcccgagcctcgccgacgag cgccgcccctgctccagggcacccagtcccatcgaccacccaagggctgaagagtgcgggcgcacggcaggggactggcaggcagctc cccctgcagcccaggtgcgggatccactgggtgaagccggctaggctcctgagtttgctggggatgcgaagaaccccttatgtctagata agggattgtaaatacaccaattggcactctgtatctagctcaaggtttgtaaacacaccaatcagcaccctgtgtctagctcagggttt gtgaatgcaccaatcaacactctatctagctactctggtggggccttggagaacctttatgtctagctcagggattgtaaatacaccaa tcggcagtctgtatctagctcaaggtttgtaaacacaccaatcagcaccctgtgtctagctcagggtttgtgaatgcaccaatcaacac tctgtatctagctactctggtggggacgtggagaacctttatgtctagctcaggattgtaaatacaccactcggcagtctgtatctag ctcaaggtttgtaaacacaccaatcagcaccctgtgtctagctcagggtttgtgaatgcaccaatcaacactctgtatctagctactct ggtggggacttggagaacctttgtgtggacactctgtatctagctaatctggtggggacgtggagaacctttgtgtctagctcatggat tgtaaatgcaccaatcagtgccctgtcaaaacagaccactgggctctaccaatcagcaggatgtgggtggggccagataagagaataaa agcaggctgcccgagccagcagtggcaacccgctcgggtcccttccacactgtggaagctttgttctttcgctctttgcaataaatct tgctgctgctcactgtttgggtctacactgcctttatgagctgtaacgctcaccgcgaaggtctgcagcttcactcttgaagccagcga gaccacgaacccaccgggaggaacgaacaactccagaggcgccgccttaagagctggaacgttcactgtgaaggtctgcagcttcactc ctgagccagcgagaccacgaacccatcagaaggaagaaactccgaacacatccaaacatcagaacgaacaaactccacacacgcagcct ttaagaactgtaacactcaccacgagggtccccggcttcattcttgaagtcagtgaaaccaagaacccaccaattccggacacagtatg tcagaaacaatatgagtcactaaatcaatatacttctcaacaatttccaacagcccttgcaattaacttggccatgtgactggttgtga ctaaaataatgtggagataataatgtgttactccctaaggcagagtgcccttctatcattctctttcccttcctctatgtggcagaaag taaaagattctgaaatgataaagtcaatcacaggaaggcacctggactcctggcccactgcttggaggagagcactcaggaccatgaac atctgactgtgacgtagcaataaagaaacccacgtttcatatgaaactgcttaaaattaatggcacaagtcatgttttttgatgttgcac atttgtctttatttgtggcttgttttgcttccacatcaatccactcaaggcctacattctgctataatgcaatttcaagttctttacag gccgagaaaaatgaatctgaattcctgacctccaaaagtgatcaagatattttttagttcaggctccaaaattttctcattttcataggt tttcctcgattgatcattattcatgatttgcaaggaatcattcaatgttttctaaatctattactgcatcctgacacatatgacatttt aactatgttccagattttttgaatgaagagtgtaaattttaaatgttttcaccacaaaaaataagtatgtgaagtggtggatttgttaat tagccttatttaaccatttaatattgtacacgtacaccaaagcatcatgttgtaccccatgaatacacacaattattatttgtcaattt aaaatgaaataataaaaaataacaaaggcattagcctctgcattgcctttaccggtcatcctcacggtgactaacgcaaaaaacgttct -continued

```
atttcatccttacaaacatccctatctttgatgcctctttgtctagatctctatcccctcctgttttctctacgttatttatatgggta tcatcaccatcctggacaacatcaggacagatatccctcaccaagccaatgttcctctctatgttggctcaaatgtccttgaactttcc tttcaccaccctttccacagtcaaaaggatattgtagtttaatgcctcagagttcagcttttaagcttctgacaaattattcttcctct ttaggttctcctttatggaatcttctgtactgatggccatgtcctttaactactatgtagatatctgctactacctgtattatgcctct acctttattagcagagttatctgtactgttggcatgacaatcatttgttaatatgacttgcctttccttttctgctattcttgatcaa atggctcctctttcttgctcctctcatttctcctgccttcacttggacgtgcttcacgtagtctgtgcttatgactggattaaaaattg atatggacttatcctaatgttgttcgtcataatatgggttttatggtccattattatttcctatgcattgatctggagaaggcttcaat ccttttactctttgtggaaaatatctgtaaaccttctggttcactctgctatagcaatttcagtttaggctagtaagcatgaggatgcc tccttctctgattttttcccacagtctgttggtcacagaataacctgagtgattactgatgaaagagtgagaatgttattgatagtcaca atgacaaaaaacaaacaactacagtcaaaatgtttctcttttttattagtggattatatttcctgacctatatctggcaggactctttag agaggtagctgaagctgctgttatgaccactagagggaagaagatacctgtggagctaatggtccaagatggtggagccccaagcaagg aagttgttaaggagcccttttgattgaaggtgggtgcccccaccttacagggacaggacatctggatactcctcccagtttctccagtt tccctttttcctaatatatctcctgataaaatgtctatactcacttccccatttctaataataaagcaaaggctagttagtaagacatc accttgcattttgaaaatgccatagactttcaaaattatttcatacatcggtctttctttatttcaagagtccagaaatggcaacatta cctttgattcaatgtaatgtggaaagagctctttcaagagacagagaaaagaataatttaatttctttccccacacctccttccctgtctc ttaccctatcttccttccttctaccctccccatttctctctctcatttctcagaagtatattttgaaaggattcatagcagacagctaa ggctggtttttttctaagtgaagaagtgatattgagaaggtagggttgcatgagcccctttcagttttttagtttatatacatctgtattg ttagaatgtttatataataaaataaaattatttctcagttatatactagctatgtaacctgtggatatttccttaagtattacaagcta tacttaactcacttggaaaactcaaatgaaatacctgcttcatagttattaataaggattaagtgagataatgcccataagattcctatt aataacagataaatacatacacacacacacacattgaaaggattcttactttgtgctaggaactataataagttcattgatgcattata tcattaagttctaatttcaacactagaaggcaggtattatctaaatttcatactggatacctccaaactcataaagataattaaattgc cttttgtcatatatttattcaaaagggtaaactcaaactatggcttgtctaattttatatatcaccctactgaacatgaccctattgtg atattttataaaattattctcaagttattatgaggatgttgaaagacagagaggatggggtgctatgcgccccaaatcagcctcacaatta agctaagcagctaagagtcttgcagggtagtgtagggaccacagggttaaggggcagtagaattatactcccactttagtttcatttc aaacaatccatacacacacagccctgagcacttacaaattatactacgctctatactttttgtttaaatgtataaataagtggatgaaa gaatagatagatagatagacagatagatgatagatagaataaatgcttgccttcatagctgtctccctaccttgttcaaaatgttcctg tccagaccaaagtaccttgccttcacttaagtaatcaattcctaggttatattctgatgtcaaaggaagtcaaaagatgtgaaaaacaa tttctgacccacaactcatgctttgtagatgactagatcaaaaaatttcagccatatcttaacagtgagtgaacaggaaatctcctctt ttccctacatctgagatcccagcttctaagaccttcaattctcactcttgatgcaacagaccttggaagcatacaggagagctgaactt ggtcaacaaaggagaaaagtttgttggcctccaaaggcacagctcaaacttttcaagccttctctaatcttaaaggtaaacaagggtct catttctcttgagaacttcagggaaaatagacaaggacttgcctggtgcttttggtaggggagcttgcactttccccctttctggaggaa atatttatccccaggtagttcccttttttgcaccagtggttctttgaagagacttccacctgggaacagttaaacagcaactacagggcc ttgaactgcacactttcagtccggtcctcacagttgaaaagacctaagcttgtgcctgatttaagccttttttggtcataaaacattgaa ttctaatctccctctcaaccctacagtcacccatttggtatattaaagatgtgttgtctactgtctagtatccctcaagtagtgtcagg aattagtcatttaaatagtctgcaagccaggagtggtggctcatgtctgtaattccagcacttgagaggtagaagtgggaggactgctt gagctcaagagtttgatattatcctggacaacatagcaagacctcgtctctacttaaaaaaaaaaaaaaaattagccaggcatgtgatg tacacctgtagtcccagctactcaggaggccgaaatgggaggatcccttgagctcaggaggtcaaggctgcagtgagacatgatcttgc cactgcactccagcctggacagcagagtgaaaccttgcctcacgaaacagaatacaaaaacaaacaaacaaaaaactgctccgcaatgc gcttccttgatgctctaccacataggtctgggtactttgtacacattatctcattgctgttcataattgttagattaattttgtaatat tgatattattcctagaaagctgaggcctcaagatgataacttttattttctggacttgtaatagcttttctcttgtattcaccatgttgt aactttcttagagtagtaacaatataaagttattgtgagtttttgcaaacacagcaaacacaacgacccatatagacattgatgtgaaa
```

-continued

```
ttgtctattgtcaatttatgggaaaacaagtatgtactttttctactaagccattgaaacaggaataacagaacaagattgaaagaata cattttccgaaattacttgagtattatacaaagacaagcacgtggacctgggaggagggttattgtccatgactggtgtgtggagacaa atgcaggtttataatagatgggatggcatctagcgcaatgactttgccatcacttttagagagctcttggggaccccagtacacaagag gggacgcagggtatatgtagacatctcattctttttcttagtgtgagaataagaatagccatgacctgagtttatagacaatgagccct tttctctctcccactcagcagctatgagatggcttgccctgcctctctactaggctgactcactccaaggcccagcaatgggcagggct ctgtcagggctttgatagcactatctgcagagccagggccgagaaggggtggactccagagactctccctcccattcccgagcagggtt tgcttatttatgcatttaaatgatatatttattttaaaagaaataacaggagactgcccagccctggctgtgacatggaaactatgtag aatattttgggttccatttttttttccttctttcagttagaggaaaaggggctcactgcacatacactagacagaaagtcaggagcttt gaatccaagcctgatcatttccatgtcatactgagaaagtccccacccttctctgagcctcagtttctcttttttataagtaggagtctg gagtaaatgatttccaatggctctcatttcaatacaaaatttccgtttattaaatgcatgagcttctgttactccaagactgagaagga aattgaacctgagactcattgactggcaagatgtccccagaggctctcattcagcaataaaattctcaccttcacccaggcccactgag tgtcagatttgcatgcactagttcacgtgtgtaaaaaggaggatgcttctttcctttgtattctcacataccttaggaaagaacttag cacccttcccacacagccatcccaataactcatttcagtgactcaacccttgactttataaaagtcttgggcagtatagagcagagatt aagagtacagatgctggagccagaccacctgagtgattagtgactcagtttctcttagtagttgtatgactcagtttcttcatctgtaa aatggagggtttttaattagtttgtttttgagaaagggtctcactctgtcacccaaatgggagtgtagtggcaaaatctcggctcact gcaacttgcacttccaggctcaagcggtcctcccacctcaacatcctgagtagctggaaccacaggtacacaccaccatacctcgcta atttttgtatttttggtagagatggggtttcacatgttacacaggatggtctcagactccggagctcaagcaatctgcccacctcagc cttccaaagtgctgggattataagcatgattacaggagttttaacaggctcataagattgttctgcagcccgagtgagttaatacatgc aaagagtttaaagcagtgacttatataaatgctaactactctagaaatgtttgctagtattttttgtttaactgcaatcattcttgctgca ggtgaaaactagtgttctgtacttatgcccattcatcttttaactgtaataataaaaataactgacatttattgaaggctatcagagac tgtaattagtgctttgcataattaatcatatttaatactcttggattctttcaggtagatactattattatccccattttactacagtt aaaaaaactacctctcaacttgctcaagcatacactctcacacacacaaacataaactactagcaaatagtagaattgagatttggtcc taattatgtctttgctcactatccaataaatatttattgacatgtacttcttggcagtctgtatgctggatgctggggatacaaagatg tttaaatttaagctccagtctctgcttccaaaggcctcccaggccaagttatccattcagaaagcatttttttactctttgcattccact gtttttcctaagtgactaaaaaattacactttattcgtctgtgtcctgctctgggatgatagtctgactttcctaacctgagcctaaca tccctgacatcaggaaagactacaccatgtggagaaggggtggtggttttgattgctgctgtcttcagttagatggttaactttgtgaa gttgaaaactgtggctctctggttgactgttagagttctggcacttgtcactatgcctattatttaacaaatgcatgaatgcttcagaa tatgggaatattatcttctggaataggaatcaagttatattatgtaacccaggattagaagattcttctgtgtgtaagaatttcataa acattaagctgtctagcaaaagcaagggcttggaaaatctgtgagctcctcaccatatagaaagcttttaacccatcattgaatataatc cctataggggatttctaccctgagcaaaaggctggtcttgattaattcccaaactcatatagctctgagaaagtctatgctgttaacgt tttcttgtctgctaccccatcatatgcacaacaatataaatgcaggcctaggcatgactgaaggctctctcataattcttggttgcatgaa tcagattatcaacagaaatgttgagacaaactatggggaagcagggtatgaaagagctctgaatgaaatggaaaccgcaatgcttcctg cccattcagggctccagcatgtagaaatctggggctttgtgaagactggcttaaaatcagaagccccattggataagagtagggaagaa cctagagcctacgctgagcaggtttccttcatgtgacagggagcctcctgccccgaacttccagggatcctctcttaagtgtttcctgc tggaatctcctcacttctatctggaaatggttctccacagtccagccctggctagttgaaagagttacccatgcagaggccctccta gcatccagagactagtgcttagattcctactttcagcgttggacaacctggatccacttgcccagtgttcttccttagttcctaccttc gaccttgatcctccttttatcttcctgaacctgctgagatgatctatgtggggagaatggcttctttgagaaacatcttcttcgttagt ggcctgcccctcattcccactttaatatccagaatcactataagaagaatataataagaggaataactcttattataggtaagggaaaa ttaagaggcatacgtgatgggatgagtaagagaggagagggaaggattaatggacgataaaatctactactatttgttgagacctttta tagtctaatcaattttgctattgttttccatcctcacgctaactccataaaaaaacactattattatctttattttgccatgacaagac
```

-continued

```
tgagctcagaagagtcaagcatttgcctaaggtcggacatgtcagaggcagtgccagacctatgtgagactctgcagctactgctcatg ggccctgtgctgcactgatgaggaggatcagatggatggggcaatgaagcaaaggaatcattctgtggataaaggagacagccatgaag aagtctatgactgtaaatttgggagcaggagtctctaaggacttggatttcaaggaattttgactcagcaaacacaagaccctcacggt gactttgcgagctggtgtgccagatgtgtctatcagaggttccagggagggtggggtggggtcagggctggccaccagctatcagggcc cagatgggttataggctggcaggctcagataggtggttaggtcaggttggtggtgctgggtggagtccatgactcccaggagccaggag agatagaccatgagtagagggcagacatgggaaaggtgggggaggcacagcatagcagcatttttcattctactactacatgggactgc tcccctataccccagctaggggcaagtgccttgactcctatgttttcaggatcatcatctataaagtaagagtaataattgtgtctat ctcatagggttattatgaggatcaaaggagatgcacactctctggaccagtggcctaacagttcaggacagagctatgggcttcctatg tatgggtcagtggtctcaatgtagcaggcaagttccagaagatagcatcaaccactgttagagatatactgccagtctcagagcctgat gttaatttagcaatgggctgggaccctcctccagtagaaccttctaaccagctgctgcagtcaaagtcgaatgcagctggttagacttt ttttaatgaaagcttagcttcattaaagattaagctcctaagcagggcacagatgaaattgtctaacagcaactttgccatctaaaaa aatctgacttcactggaaacatggaagcccaaggttctgaacatgagaaattttaggaatctgcacaggagttgagagggaaacaaga tggtgaagggactagaaaccacatgagagacacgaggaaatagtgtagatttaggctggaggtaaatgaaagagaagtgggaattaata cttactgaaatctttctatatgtcaggtgccattttatgatatttaataatctcattacatatggtaattctgtgagatatgtattatt gaacatactataattaatactaatgataagtaacacctcttgagtacttagtatatgctagaatcaaatttaagtttatcatatgaggc cgggcacggtggctcatatatgggattacatgcctgtaatcccagcactttgggaggccaaggcaattggatcacctgaggtcaggagt tccagaccagcctggccaacatggtgaaacccccttctctactaaaaaatacaaaaatcagccaggtgtggtggcacgcgtctataatc ccagctactcaggaggctgaggcaggagaatcacttgaacccaggaggtggaggttgcagtgagctaagattgcaccactgcactccag cctaggcgacagagtgagactccatctcaaaaaaaaaaaaagaagtttattatatgaattaacttagttttactcacaccaatactcag aagtagattattacctcatttattgatgaggagcccaatgtacttgtagtgtagatcaacttattgaaagcacaagctaataagtagac aattagtaattagaagtcagatggtctgagctctcctactgtctacattacatgagctcttattaactggggactcgaaaatcaaagac atgaaataatttgtccaagcttacagaaccaccaagtagtaaggctaggatgtagacccagttctgctacctctgaagacagtgtttt tccacagcaaaacacaaactcagatattgtggatgcgagaaattagaagtagatattcctgccctgtggcccttgcttcttacttttac ttcttgtcgattggaagttgtggtccaagccacagttgcagaccatacttcctcaaccataattgcatttcttcaggaaagtttgaggg agaaaaaggtaaagaaaaatttagaaacaacttcagaataaagagatttctcttgggttacagagattgtcatatgacaaattataag cagacacttgagaaaactgaaggcccatgcctgcccaaattacccctttgaccccttggtcaagctgcaactttggttaaagggagtgtt tatgtgttatagtgttcatttactcttctggtctaacccattggctccgtcttcatcctgcagtgacctcagtgcctcagaaacataca tatgtttgtctagtttaagtttgtgtgaaattctaactagcgtcaagaactgagggccctaaactatgctaggaatagtgctgtggtgc tgtgataggtacacaagaaatgagaagaaactgcagattctctgcatctccctttgccgggtctgacaacaaagtttccccaaatttta ccaatgcaagccatttctccatatgctaactactttaaaatcatttggggcttcacattgtctttctcatctgtaaaaagaatggaaga actcattcctacagaactccctatgtcttccctgatgggctagagttcctctcttttctcaaaaattagccattattgtatttccttctaag ccaaagctcagaggtcttgtattgcccagtgacatgcacactggtcaaaagtaggctaagtagaagggtactttcacaggaacagagag caaaagaggtgggtgaatgagagggtaagtgagaaaagacaaatgagaagttacaacatgatggcttgttgtctaaatatctcctaggg aattattgtgagaggtctgaatagtgttgtaaaataagctgaatctgctgccaacattaacagtcaagaaataacctccgaataactgta cctccaattattctttaaggtagcatgcaactgtaatagttgcatgtatatatttatcataatactgtaacagaaaacacttactgaat atatactgtgtccctagttctttacacaataaactaatctcatcctcataattctattagctaatacatattatcatcctatatttcag agacttcaagaagttaagcaacttgctcaagatcatctaagaagtaggtggtatttctgggctcatttggcccctcctaatctctcatg gcaacatggctgcctaaagtgttgattgccttaattcatcagggatgggctcatactcactgcagaccttaactggcatcctcttttct tatgtgatctgcctgacccctagtagacttatgaaatttctgatgagaaaggagagaggagaaaggcagagctgactgtgatgagtgatg aaggtgccttctcatctgggtaccagtggggcctctaagactaagtcactctgtctcactgtgtcttagccagttccttacagcttgcc ctgatgggagatagagaatgggtatcctccaacaaaaaaataaatttcatttctcaaggtccaacttatgttttcttaatttttaaaa
```

-continued

```
aaatcttgaccattctccactctctaaaataatccacagtgagagaaacattcttttcccccatcccataaatacctctattaaatatg gaaaatctgggcatggtgtctcacacctgtaatcccagcactttgggaggctgaggtgggtggactgcttggagctcaggagttcaaga ccatcttggacaacatggtgataccctgcctctacaaaaagtacaaaaattagcctggcatggtggtgtgcacctgtaatcccagctat tagggtggctgaggcaggagaattgcttgaacccgggaggcggaggttgcagtgagctgagatcgtgccactgcactccagcctggggg acagagcacattataattaactgttatttttttacttggactcttgtggggaataagatacatgttttattcttatttatgattcaagca ctgaaaatagtgtttagcatccagcaggtgcttcaaaaccatttgctgaatgattactatacttttttacaagctcagctccctctatcc cttccagcatcctcatctctgattaaataagcttcagttttttccttagttcctgttacatttctgtgtgtctccattagtgacctccca tagtccaagcatgagcagttctggccaggcccctgtcggggtcagtgccccaccccgccttctggttctgtgtaaccttctaagcaaa ccttctggctcaagcacagcaatgctgagtcatgatgagtcatgctgaggcttagggtgtgtgcccagatgttctcagcctagagtgat gactcctatctgggtccccagcaggatgcttacagggcagatggcaaaaaaaaggagaagctgaccacctgactaaaactccacctcaa acggcatcataaagaaatggatgcctgagacagaatgtgacatattctagaatatattatttcctgaatatatatatatatatacaca tatacgtatatatatatatatatatatatttgttgttatcaattgccatagaatgattagttattgtgaatcaaatatttatcttgcag gtggcctctataacctagaagcggcagaatcaggctttattaatacatgtgtatagattttttaggatctatacacatgtattaatatgaa acaaggatatggaagaggaaggcatgaaaacaggaaaagaaaacaaaccttgtttgccattttaaggcacccctggacagctaggtggc aaaaggcctgtgctgttagaggacacatgctcacatacggggtcagatctgacttggggtgctactgggaagctctcatcttaaggata catctcaggccagtcttggtgcattaggaagatgtaggcaactctgatcctgagaggaaagaaacattcctccaggagagctaaaaggg ttcacctgtgtgggtaactgtgaaggactacaagaggatgaaaaacaatgacagacagacataatgcttgtgggagaaaaaacaggagg tcaaggggatagagaaggcttccagaagaatggctttgaagctggcttctgtaggagttcacagtggcaaagatgtttcagaaatgtga catgacttaaggaactatacaaaaaggaacaaatttaaggagaggcagataaattagttcaacagacatgcaaggaattttcagatgaa tgttatgtctccactgagcttcttgaggttagcagctgtgagggttttgcaggcccaggacccattacaggacctcacgtatacttgac actgtttttgtattcatttgtgaatgaatgacctcttgtcagtctactcggtttcgctgtgaatgaatgatgtcttgtcagcctactt ggtttcgctaagagcacagagagaagatttagtgatgctatgtaaaaacttcctttttggttcaagtgtatgtttgtgatagaaatgaa gacaggctacatgatgcatatctaacataaacacaaacattaagaaaggaaatcaacctgaagagtatttatacagataacaaaataca gagagtgagttaaatgtgtaataactgtggcacaggctggaatatgagccatttaaatcacaaattaattagaaaaaaaaacagtgggga aaaaattccatggatgggtctagaaagactagcattgtttaggttgagtggcagtgtttaaagggtgatatcagactaaacttgaaat atgtggctaaataactagaatactctttattttttcgtatcatgaatagcagatatagcttgatggccccatgcttggtttaacatcct tgctgttcctgacatgaaatccttaattttttgacaaaggggctattcattttcattttatattgggcctagaaattatgtagatggtcc tgaggaaaagtttatagcttgtctatttctctctctaacatagttgtcagcacaatgcctaggctataggaagtactcaaagcttgtta aattgaattctatccttcttattcaattctacacatggaggaaaaactcatcagggatggaggcacgcctctaaggaaggcaggtgtgg ctctgcagtgtgattgggtacttgcaggacgaagggtggggtgggagtggctaaccttccattcctagtgcagaggtcacagcctaaac atcaaattccttgaggtgcggtggctcactcctgtaatcacagcagtttgggacgccaaggtgggcagatcacttgaggtcaggagttg gacaccagcccagccaacatagtgaaacctggtctctgcttaaaaatataaaaattagctggacgtggtgacgggagcctgtaatccaa ctacttgggaggctgaggcaggagaatcgcttgaacccggggaggtggagtttgcactgagcagagatcatgccattgcactccagcctc cagagcgagactctgtctaaagaaaaacgaaaacaaacaaacaaacaaacaaacaaaacccatcaaattccctgaccgaacagaattct gtctgattgttctctgacttatctaccattttccctccttaaagaaactgtgaacttccttcagctagaggggcctggctcagaagcct ctggtcagcatccaagaaatacttgatgtcactttggctaaaggtatgatgtgtagacaagctccagagatggtttctcatttccatat ccacccacccagctttccaattttaaagccaattctgaggtagagactgtgatgaacaaacaccttgacaaaattcaacccaaagactc actttgcctagcttcaaaatccttactctgacatatactcacagccagaaattagcatgcactagagtgtgcatgagtgcaacacacac acacaccaattccatattctctgtcagaaaatcctgttggttttttcgtgaaaggatgttttcagaggctgaccccttgccttcacctcc aatgctaccactctggtctaagtcactgtcaccaccacctaaattatagctgttgactcataacaatcttcctgcttctaccactgccc
```

-continued

```
cactacaatttcttcccaatatactatccaaattagtcttttcaaaatgtaagtcatatatggtcacctctttgttcaaagtcttctga tagtttcctatatcatttataataaaaccaaatccttacaattctctacaatagttgttcatgcatatattatgtttattacagataca tatatatagctctcatataaataaatatatatatttatgtgtatgtgtgtagagtgttttttcttacaactctatgatgtaggtattat tagtgtcccaaattttataatttaggacttctatgatctcatcttttattctcccttcaccgaatctcatcctacattggccttattg atattccttgaaaattctaagcatcttacatctttagggtatttacatttgccattccctatgccctaaatatttaatcatagtttcat ataaatgggttcctcatcatctatgggtactctctcaggtgttaactttatagtgaggactttcctgccatactacttaaagtagcgat accctttcaccctgtcctaatcacactctggccttcatttcagttttttttttttttctccatagcacctaatctcattggtatataacat gtttcatttgcttatttaatgtcaagctctttccactatcaagtccatgaaaacaggaactttattcctctattctgttttttgtgctgt attcttagcaattttacaattttgaatgaatgaatgagcagtcaaacacatatacaactataattaaaaggatgtatgctgacacatcc actgctatgcacacacaaagaaatcagtggagtagagctggaagtgctaagcctgcatagagctagttagccctccgcaggcagagcct tgatgggattactgagttctagaattggactcatttgttttgtaggctgagatttgctcttgaaaacttgttctgaccaaaataaaagg ctcaaaagatgaatatcgaaaccagggtgttttttacactggaatttataactagagcactcatgtttatgtaagcaattaattgtttc atcagtcaggtaaaagtaaagaaaaactgtgccaaggcaggtagcctaatgcaatatgccactaaagtaaacattatttcataggtgtc agatatggcttattcatccatcttcatgggaaggatggccttggcctggacatcagtgttatgtgaggttcaaaacacctctaggctat aaggcaacagagctcctttttttttttttctgtgctttcctggctgtccaaatctctaatgataagcatacttctattcaatgagaatat tctgtaagattatagttaagaattgtgggagccattccgtctcttatagttaaatttgagcttcttttatgatcactgttttttttaata tgctttaagttctggggtacatgtgccatggtggtttgctgcacccatcaacccgtcatctacattaggtatttctcctaatgctatcc ttcccctagccccccaccccccaacaggccccagtgtgtgatgttcccctccctgtgtccatggatcactggttttttttttgttttttttt ttttttttaaagtctcagttaaattttggaatgtaatttattttcctggtatcctaggacttgcaagttatctggtcactttagccct cacgttttgatgataatcacatatttgtaaacacaacacacacacacacacacacacatatatatatatataaaacatatatataca taaacacacataacatatttatcgggcatttctgagcaactaatcatgcaggactctcaaacactaacctatagccttttctatgtatc tacttgtgtagaaaccaagcgtgggactgagaaggcaatagcaggagcattctgactctcactgcctttagctaggcccctccctcat cacagctcagcatagtcctgagctcttatctatatccacacacagtttctgacgctgcccagctatcaccatcccaagtctaaagaaaa aaataatgggtttgcccatctctgttgattagaaaacaaaacaaaataaaataagcccctaagctcccagaaaacatgactaaaccagc aagaagaagaaaatacaataggtatatgaggagactggtgacactagtgtctgaatgaggcttgagtacagaaaagaggctctagcagc atagtggtttagaggagatgtttctttccttcacagatgccttagcctcaataagcttgcggttgtggaagtttactttcagaacaaac tcctgtggggctagaattattgatggctaaaagaagcccggggggagggaaaaatcattcagcatcctcacccttagtgacacaaaacag aggggggcctggttttccatatttcctcatgatggatgatctcgttaatgaaggtggtctgacgagatcattgcttcttccatttaagcc ttgctcacttgccaatcctcagttttaaccttctccagagaaatacacattttttattcaggaaacatactatgttatagtttcaatac taaataatcaaagtactgaagatagcatgcataggcaagaaaaagtccttagctttatgttgctgttgtttcagaatttaaaaaagatc accaagtcaaggacttctcagttctagcactagaggtggaatcttagcatataatcagaggttttcaaaatttctagacataagattc aaagccctgcacttaaaatagtctcatttgaattaactctttatataaattgaaagcacattctgaactacttcagagtattgttttat ttctatgttcttagttcataaatacattaggcaatgcaatttaattaaaaaaacccaagaatttcttagaattttaatcatgaaaataa atgaaggcatctttacttactcaaggtcccaaaaggtcaaagaaaccaggaaagtaaagctatatttcagcggaaatgggatatttat gagttttctaagttgacagactcaagttttaaccttcagtgcccatcatgtaggaaagtgtggcataactggctgattctggctttcta ctcctttttcccattaaagatccctcctgcttaattaacattcacaagtaactctggttgtactttaggcacagtggctcccgaggtca gtcacacaataggatgtctgtgctccaagttgccagagagagagattactcttgagaatgagcctcagccctggctcaaactcacctgc aaacttcgtgagagatgaggcagaggtacactacgaaagcaacagttagaagctaaatgatgagaacacatggactcatagagggaaac aacgcatactggggcctatcagagggtggagggtgagagaaggagaggatcaggaaaaatcactaatggatgctaagcgtaatacctga gtgatgagatcatctatacaacaaaccccccttgacattcatttatctcatgtaacaaacctgcacatcctgtacatgtaccccctgaactt aaaataaaagttgaaaacaagaaagcaacagtttgaacacttgttatggtctattctctcattctttacaattacactagaaaatagcc
```

-continued

```
acaggcttcctgcaaggcagccacagaatttatgacttgtgatatccaagtcattcctggataatgcaaaatctaacacaaaatctagt agaatcatttgcttacatctatttttgttctgagaatatagatttagatacataatggaagcagaataatttaaaatctggctaattta gaatcctaagcagctctttcctatcagtggtttacaagccttgtttatattttttcctattttaaaaataaaaataaagtaagttattt gtggtaaagaatattcattaaagtatttatttcttagataataccatgaaaaacattcagtgaagtgaagggcctactttacttaacaa gaatctaatttatataattttttcatactaatagcatctaagaacagtacaatatttgactcttcaggttaaacatatgtcataaattag ccagaaagatttaagaaaatattggatgtttccttgtttaaattaggcatcttacagttttttagaatcctgcatagaacttaagaaatt acaaatgctaaagcaaacccaaacaggcaggaattaatcttcatcgaatttgggtgtttctttctaaaagtcctttatacttaaatgtc ttaagacatacatagatttfattttactaattttaattatatagacaatsaatgaatattcttactgattactttttctgactgtctaa tctttctgatctatcctggatggccataacacttatctctctgaactttgggcttttaatataggaaagaaaagcaataatccattttt catggtatctcatatgataaacaaataaaatgcttaaaaatgagcaggtgaagcaatttatcttgaaccaacaagcatcgaagcaataa tgagactgcccgcagcctacctgacttctgagtcaggatttataagccttgttactgagacacaaacctgggcctttcaatgctataac ctttcttgaagctcctccctaccacctttagccataaggaaacatggaatgggtcagatccctggatgcaagccaggtctggaaccata ggcagtaaggagagaagaaaatgtgggctctgcaactggctccgagggagcaggagaggatcaaccccatactctgaatctaagagaag actggtgtccatactctgaatgggaagaatgatgggattacccatagggcttgtttagggagaaacctgttctccaaactcttggcct tgagatacctggtccttattccttggactttggcaatgtctgaccctcacattcaagttctgaggaagggccactgccttcatactgtg gatctgtagcaaattcccctgaaaacccagagctgtatcttaattggttaaaaaaaattatattatctcaacgactgttcttctctga gtagccaagctcagcttggttcaagctacaagcagctgagctgcttttgtctagtcattgttcttttattcagtggatcaaatacgt tctttccaaacctaggatcttgtcttcctaggctatatattttgtcccaggaagtcttaatctggggtccacagaacactaggggctg gtgaagtttatagaaaaaaatctgtattttttacttacatgtaactgaaatttagcatttcttctactttgaatgcaaaggacaaact agaatgacatcatcagtacctattgcatagttataaagagaaaccacagatattttcatactacaccataggtattgcgatcttttg ttttgttttttgtttgagatggagtttcgctcttattgcccaggctggagtgcagtggcatgatttcggctcactgcaacctcccttc ctgcattcaagcaattctcctgccttggcctcctgagtagctggggattacaggcacctgccaccatgccagtctaattttttgtatttt tagtagagatggggtttcgccatgttggccaggctggtcttgaactcctgacctcagatgatctgcccgccttggcctcctgaagtgct gggattataggtgtgagccaccacgcctggcccattgcagatattttaattcacatttatctgcatcactacttggatcttaaggtag ctgtagacccaatcctagatctaatgctttcataaagaagcaaatataataaatactataccacaaatgtaatgtttgatgtctgataa tgatatttcagtgtaattaaacttagcactcctatgtatattatttgatgcaataaaaacatatttttttagcacttacagtctgccaa actggcctgtgacacaaaaaaagtttaggaattcctggttttgtctgtgttagccaatggttagaatatatgctcagaaagataccatt ggttaatagctaaaagaaaatggagtagaaattcagtggcctggaataataacaatttgggcagtcattaagtcaggtgaagacttctg gaatcatgggagaaaagcaagggagacattcttacttgccacaagtgttttttttttttttttttttttatcacaaacataagaaaatat aataaataacaaagtcaggttatagaagagagaaacgctcttagtaaacttggaatatggaatccccaaaggcacttgacttgggagac aggagccatactgctaagtgaaaaagacgaagaacctctagggcctgaacatacaggaaattgtaggaacagaaattcctagatctggt ggggcaaggggagccataggagaaagaaatggtagaaatggatggagacggaggcagaggtgggcagatcatgaggtcaagagatcgag accatcctggcaaacatggtgaaatcccgtctctactaaaaataaaaaaaattagctgggcatggtggcatgcgcctgtagtcccagctg ctcgggaggctgaggcaggagaatcgtttgaacccaggaggcgaaggttgcagtgagctgagatagtgccattgcactccagtctggca acagagtgagactccgtctcaaaaaaaaaaaaaaagaaagaaagaaaagaaaaagaaaaaataaatggatgtagaacaagc cagaaggaggaactgggctggggcaatgagattatggtgatgtaagggacttttatagaattaacaatgctggaatttgtggaactctg cttctattattcccccaatcattacttctgtcacattgatagttaaataatttctgtgaatttattccttgattctaaaatatgaggat aatgacaatggtattataagggcagattaagtgatatagcatgagcaatattcttcaggcacatggatcgaattgaatacactgtaaat cccaacttccagtttcagctctaccaagtaaagagctagcaagtcatcaaaatggggacatacagaaaaaaaaaaggacactagaggaa taatatacccctgactcctagcctgattaatatatcgattcacttttttctctgtttgatgacaaattctggctttaaataattttagga
```

-continued ttttaggcttctcagctccctttcccagtgagaagtataagcaggacagacaggcaagcaagaagagagcccaggcaatactcacaaag tagccaatgtcccctgtggtcatagagaaatgaaaagagagaggattctctggaagcactggatgtaatcttttctgtctgtcctctct agggaatcaccccaaggtactgtactttgggattaaggctttagtcccactgtggactacttgctattctgttcagtttctagaaggaa ctatgtacggttttgtctccctagagaaactaaggtacagaagtttgtttacaatgcactccttaagagagctagaactgggtgaga ttctgtttttaacagctttattttcttttccttggccctgtttttgtcactgtcaccacctttaaggcaaatgttaaatgcgctttggct gaaactttttttcctattttgagatttgctcctttatatgaggctttcttggaaaaggagaatgggagagatggatatcatttttggaag atgatgaagagggtaaaaaggggacaaatggaaatttgtgttgcagatagatgaggagccaacaaaaaagagcctcaggatccagcac acattatcacaaacttagtgtccatccatcactgctgaccctctccggacctgactccaccctgagggacacaggtcagccttgacca atgacttttaagtaccatggagaacaggggggccagaacttcggcagtaaagaataaaaggccagacagagaggcagcagcacatatctg cttccgacacagctgcaatcactagcaagctctcaggcctggcatcatggtgcattttactgctgaggagaaggctgccgtcactagcc tgtggagcaagatgaatgtggaagaggctggaggtgaagccttgggcaggtaagcattggttctcaatgcatgggaatgaagggtgaat attaccctagcaagttgattgggaaagtcctcaagatttttttgcatctctaattttgtatctgatatggtgtcatttcatagactcctc gttgtttaccccctggacccagagatttttttgacagctttggaaacctgtcgtctccctctgccatcctgggcaaccccaaggtcaaggc ccatggcaagaaggtgctgacttccttttggagatgctattaaaaacatggacaacctcaagcccgcctttgctaagctgagtgagctgc actgtgacaagctgcatgtggatcctgagaacttcaaggtgagttcaggtgctggtgatgtgattttttggctttatattttgacatta attgaagctcataatcttattggaaagaccaacaaagatctcagaaatcatgggtcgagcttgatgttagaacagcagacttctagtga gcataaccaaaacttacatgattcagaactagtgacagtaaaggactactaacagcctgaattggcttaacttttcaggaaatcttgcc agaacttgatgtgtttatcccagagaattgtattatagaattgtagacttgtgaaagaagaatgaaatttggcttttggtagatgaaag tccatttcaaggaaatagaaatgccttattttatgtgggtcatgataattgaggtttagaaagagatttttgcaaaaaaaataaaagat ttgctcaaagaaaaataagacacattttctaaaatatgttaaatttcccatcagtattgtgaccaagtgaaggcttgtttccgaatttg ttggggattttaaactcccgctgagaactcttgcagcactcacattctacatttacaaaaattagacaattgcttaaagaaaaacaggg agagagggaacccaataatactggtaaaatggggaagggggtgagggtgtaggtaggtagaatgttgaatgtagggctcatagaataaa attgaacctaagctcatctgaatttttttgggtgggcacaaaccttggaacagtttgaggtcagggttgtctaggaatgtaggtataaag ccgttttttgtttgtttgtttgtttttttcatcaagttgttttcggaaacttctactcaacatgcctgtgtgttattttgtcttttgccta acagctcctgggtaacgtgatggtgattattctggctactcactttggcaaggagttcacccctgaagtgcaggctgcctggcagaagc tggtgtctgctgtcgccattgccctggcccataagtaccactgagttctcttccagtttgcaggtgttcctgtgaccctgacaccctcc ttctgcacatggggactgggcttggccttgagagaaagccttctgtttaataaagtacattttcttcagtaatcaaaaattgcaatttt atcttctccatcttttactcttgtgttaaaaggaaaaagtgttcatgggctgagggatggagagaaacataggaagaaccaagagcttc cttaagaaatgtatgggggcttgtaaaattaatgtggatgttatgggagaattccaggattccaaggaggatgatatgatggagaaaaa tctttatcggggtgggaaaatggttaattaagtggacagagactcctaggcagttttt actgcaccggggaaagaaggagctgttagtg gtacctgagaaagcagatttgtggtacatgtcacttttcattaaaaacaaaaacaaaacaaaacaaaacttcatagatatccaagatat aggctagaattactattttaatttactcttatttacattttgaagtagctagcttgtcacatgtttt atgaaattgatttggagataag atgagtgtgtatcaacaatagcctgctctttccatgaaggattccattatttcatgggttagctgaagctaagacacatgatatcattg tgcattatcttctgatagaatgtaacatgcactaaaataaagttagagttaggacctgagtgggaaagttttt ggagagtgtgatgaag actttccgtgggagatagaatactaataaaggcttaaattctaaaaccagcaagctagggcttcgtgacttgcatgaaactggctctct ggaagtagaagggagagtaagacatacgtagaggactaggaaagaccagatagtacagggcctggctacaaaaatacaagctttacta tgctattgcaatactaaacgataagcattaggatgttaagtgactcaggaaataagattttgggaaaaagtaatctgcttatgtgcaca aaatggattcaagtttgcagataaaatgaaatatggatgatgattcaaggggacagatacaatggttcaaacccaagaggagcagtgag tctgtggaattttgaaggatggacaaaggtggggtgagaaagacatagtattcgactgactgtgggagatgagaaggaagaaggaggtga taaatgactgaaagctcccagactggtgaagataacaggaggaaaccatgcactgacctggtgactctcatgtgtgaagggtagaggga tattaacagatttactttttaggaagtgctagattggtcagggagttttt gaccttcaggtcttgtgtgtctttcatatcaaggaacctttg -continued

```
cattttccaagttagagtgccatattttggcaaatataactttattagtaattttatagtgctctcacattgatcagacttttttcctgt gaattacttttgaatttggctgtatatatccagaatatgggagagagacaaataattattgtagttgcaggctatcaacaatactggtc tctctgagccttataacctttcaatatgcccataaacagagtaaacagggattattcatggcactaaatattttcacctagtcagtcaa caaatgggagcaatgtgcattttttgatacatattttttatatatttatggggtacatgtgatacttacatgcctagaacatgtgatgat taagtctagatatttaggatatccattgctttgagcatttatcatttctatgtattgagaaaatttcaaatcctcatttctagccattt tgaaatatataataaaatagtaattaactatagtcaccctactcaaatatcaaacattatggcttaatccttctatccaactgtgtttgt acctattaaccaacatctcttaaatcccctcccatacacactcacacttttttccagcctctgataactatcattctactctctaccacc atgagacccacttttttagctcccacagatgaataaaaacatgtgatatttgactttctgtatctggcttattttattatctatctctt tggcataccaagagtttgttttttgttctgcttcagggctttcaattaacataatgacctctggttccatccatgttgctacaaatgaca agatttcattcttttttcatggcaaaatagtactgtgcaaaaatacaattttttaatccgttcatctgttgatagacacttaggttgatc ccaaaccttaactattgtgaatagtgcttcaataaacatgagtgtaatgtgtccattggatatactgatttcctttcttttggataaat aaccactagtgagattgctggattgtatgatagtctgtttttagtttactgagaaatcttcatactgttttccataatggttgtacta ttttacattcccaccaacagtgtgtaagaaagagttcccttttctccatatcctcacaaggatctgttattttttgtctttttttgttaa tagccgttttaactagagtaagtagatatctcattgtagttttgatttgcatttccctgatcattagtgatgttgagaatttttttcata tgtttgttggtcatttgtatatctttttctgagaattgtctgttcatgtccttagcctactttttattgggattgtttgttattttctt gataatctatttgtgttcattttagagcctggatattattcttttgtcagatgtatagattgtgaagattttctcccactctgtgggtt gtctgtttattctgcagactcttccttttgccatgcaaaagctctttagtttaatttagtcccagatattttctttgtttttatgtatt tgcatttgtgttcttggtcatgaaatcctttcctaagccaatgtgtagaagggtttttccgatgttattttctagaattgttacagttt cagggcttagatttaagtccttgatccatcttgagttgattttttgtataaggtgagagatgaagatccagtttcattctcctacatgta gcttgccagctatccccgcaccatttgttgaataggtgcccttccccactttatgttttttgtttgctttgtcaaagatcagttggat gtaagtatttgagtttatttctgggttctctattctgttccattggtcgatgtgcctattgtacaccagcatcatgctgtttttggtga ctatggccttattgtatagtttgaaatgaggtaatgtaatgccttcagatttgttctttttttttagacttgcttgtttattgggctctt ttttggttccataagaattttaggattgttttttctagttctgtgaagactaatggtggtattttgatgggaattgcaatgaatttgta ggttgcttctggcattatggccattttcacaatattgattctacccatctatgagaatggcatgtgtttccatttgtttgtgtcttata tgattactttcagccgtgtttttgtagttttccttgtagatgtctttcacctccttggttaggtatatattcctaagtttttgtttttgtt ttgtttttgtttttttgcagctattgtaaaaggggttgagttcttgattttattctcagcttggtcattgctggtatgtaagaaagcaact cattggtgtacgttaattttgtatccagaaactttgctgaattattttatcagttctaggggggtttggaggagtctttagagttttct acatacacaatcatatcatcagcaaacagtgacagtttgactttctctttaacaatttggatgtgctttacttgtttctcttgtctgat tgctcttgctaggacttccagtaatatgttaaagagaagtggtgagagtgggtatccttgtctcattccagttttcagcacagaatgctt ttaactttttcccattcaatataatgttggctgtgtgtgtttaccatagctggcttttattacattgaggtatgtcctttgtaaaccgatt ttgctgagtttttagtcataaagtgatgttgaattttgttgaatgcagtttctgtggctattgagataatcacatgattttttgtttccaa ttctctttatgttgtgtatcacacttattgacttgcgtatgttaaaccatccgtgcatccctcgcatgaaacccacttgatcatgggtt ttgatatgctgtcggatgctattagctagtattttgtcaaggatgttggcatctatgttcatcagggatattgatctgtagtgttttttt tttttttggttatgttctttcccagtttttggtattaaggtgatactggcttcatagaatgatttagggaggattctctctttctctatct tgtagaatactgtcaataggattggtatcaattcttctttgaatgtctggtagaattcagctgtgaatcatctggtcctggactttttt tgttgttggtaaattttttattatcatttcagtcttgctgcttattactggtctgttcagggtatctaattcttcctgacttaagctaga gccctgtatctttccaggaattcgaacgtctcctttaggttttctagtttatgcatgtaaaggtgttcatagtagccttgaataatctt ttgtatttctgtggtatcagtaatagtatctcctgttttgtttctaattgagtttatttgcacttctctcctcttttcttggttaatct tgctaatggtctatcagttttatttatcttttcaaagaaccagcttttttatttcatttagcttttgtattttttttgcagttgtttttaat ttcatttagttctcctcttatcttagttattcccttttcttttgctgggtttggttctgtttgttttttgtttctctagtttcttgtggt
```

-continued

```
gtgaccttatattgtctgtctgtcctctttcagactctttgacatcgacatttagggctgtgaactttccttttagcaccatctttgct gtatcctagaggttttgataggttgtgtcactattgtcggtcagttcaagtaattttgttgttcttattatactttaagttctgggata catgtgcagaatgtgcaggtttgttacataggtatagatgtgccatggtggtttgctgcacccatcaacctgtcatctacattaggtat ttcttttaatgttatccctctcctaacccccctcacccccgacaggccctggtgtgtgatgttccctccctgtgtccatgtgttctca ttgttcaactcccacttatgagtgagaacgtgtggtgtttggtttctctgttcctgtgttagtttgctcagaatgatggtttccaccttt catccatgtccctgcaaagacatgaactcatcattttt atggctgcatagtattccatggtgtatatgtgccacatttttctttatccat tatatcgctgatggccatttgggttggttccaagtctttgctattgtgaatagtgccacaataaacatacgtgtgcacgtgtctttata gtagaatgatttctaattctttgggtatatacccagtaatgggattgctgggtcaaacagtatttctggttctagatccttgaggaatc gccacactgtcttccacaatggttgaactaatttacacacccatcaacagtgtaaaattttcctattcttccacatcctctccagcac cttttgtttcctgactttttaataattgccattctaactggcatgagatggtatctcattgtggttttgatttgcatttctctaatgac cagtgatgatgagcttcttttcatgtgtttcttggccacataaatgacttctttagagaagcatctgttcatatcctttgtccactttt tgatggggtcgttaggtttttt cttgtaaatttgttgaagttctttgtagattttggatgttagcccctttgtcagatggatagattgca aaaattttctcccattctgtaggttgcctgttcactctgatgatagtcttttgctgtgcagaagctcttt agtttaattagatcccata tgtcaatttt ggcctttgttgtcattgcttttgatgtttt agtcgtgaatttttgcccatgcctatgtcctgaatggtattgcctaggt tatcttctaggattttt atggtttt aggttgcacatttaagtctttaatccaccttgagttaatttttgtataaggtgtaaggaaggg tacagtttcagtttt atgcatattgctagccagtttttccagcaccatttattaaatagggaattctttctccattgcttttgtgatgt ttgtcaaagatcagatggtcgtagatgtgtggcattatttctgaggcttctgttctgttccactggtctatatatctgtttt ggtacca gtaccatgctgttttt gttactgtagccttgtagtatagtttgaagtcaggtagcatcatgcctccagctttgttcttttttgtttagga ttgtcttggctatatgggctctttttttgattccatatgacatttaaagtagtttttt ctaattctttgaaaaaagtcagtggtagcttg atggggatagcattgaatctataaattactttgggcagtatggccattttaaagatattgattctttctatctatgagcatggaatgtt tttccatttgttgtgtcctctctttattt ccttgagcagtgagtggtttgtagctctccttgaagaggttcttcacatcccttagaagt tgtatttctaggtatttt attttattctctttgcagcaattgtgaatgggagttcacccatgatttggctctctgcttgtctattattg gtgtataggaacgcttgtgatttctgcacactgattttgtatcttgagactttgctgaagctgtttatcagcttaagattttgggctga gatgacagggtcttctaaatatacaatcatgtcatctgcaaacagagacaatttgacttcctctcttcctatttgaatatgctttatt t ctttctcttgcctgattgtcctggcgagaacttccaatactatgttgagtaagagtggcgagagggcatccttgtcttgtgccggtttt caaagcaaatgatttttaaatttccatcttgatttcattgttgacccaatgatcattcaggagcaggttatttaatttccctgtatttg catggttttgaaggttccttttgtagttgatttccaatttt attctactgtggtctgagagagtgcttgatataatttcaatttttaaa aatttattgaggcttgtttt gtggcatatcatatggcctatcttggagaaagttccatgtgctgatgaatagaatgtgtattctgcagt tgttgggtagaatgtcctgtaaatatctgttaagtccatttgttctttaaatccattgtttctttgtagactgtcttgatgacctgcct agtgcagtcagtggagtattgaagtcccccactatt attatgttgctgtctagtctagtagtaattgttttataaatttgggatctcca gtattagatgcatatatattaagaattgtaatattctcccattggacaagggcttttatcattatatgatgtccctctttgtctttttt aactgctgtttcttt aaagtttgtttt gtctgacataagaatagctgctttggctcgcttttggtgtccatttgtgtggaatgtcattt tccacccctttaccttaagtttatgtgagtccttatgtgttaggtgagtctcctgaaggcggcagataactggttggtgaattcttatt cattctgcaattctgtatcttttt aagtggagcatttagtccatttacattcaacatcagtattgaggtgtgaggtactattccattctt cgtggtatttgttgcctgtgtatcttttt atctgtattttt gttgtatatgtcctatgggatttatgctttaaagaggttctgtttt ga tgtgcttccaggatttatttcaagatttagagctcctttt atcagttcttgtagtgttggcttggtagtgccgaattctctcagcattt gtttttctgaaaaacactgtgtattttt cttcatttgtgaagcttagtttcactggatataaaattcttggctgataattgtttt gttta agaaggctgaagatagggccatattcacttctagcttttacggtttctgctgagaaatctgctgttaatctgataggtttt cttt cata ggttacctggtagtttcacctcacagctcttaagattctctttt gtctttagataactttggatactctgatgacaatgtacctaggcaa tgatattttt gcaatgaatttcccaggtgtttattgagcttcttgtatttggatatctaggtctctagcaaggtgggggaagttttcct tgattattt ccctggataagtttt ccaaacttttagatttctcttctttctcaggaatgctgattattcttaggtttgattgtttaaca
```

-continued

```
taatcccagatttcttggaggctttgttcatattttcttattcttttttctttgtctttgttggattgggttaattcaaaaactttgtc ttcaagctctgaatttcttctgcttggattctattgctgagactttctagagcattttgcatttctataagtgcatccattcatccatt gtttcctgaagttttgaatgttttttatttatgctatctctttaactgaagatttctcccctcatttcttgtatcatattttttggtttt tttaaaattggacttcaccttcctcggatgcctccttgattagcttaataactgaccttctgaattattttttcaggtaaatcagggatt tcttcttggtttggatgcattgctggtgagctagtatgattttttgggggtgttaaagaaccttgttttttcatattaccagagttagt tttctggttccttctcacttgggtaggctctgtcagagggaaagtctaggcctcaaggctgagacttttgtcccatgaggtgttccctt gatgtagcacagtccccctttttcctaggcgtgggcttcctgagagccgaactgtagtgattgttatctctcttctggatctagccacc catcaggtctaccagactccaggctggtactgggggtttgtctgcacagagtcttgtgacgtgaaccatctgtgggtctctcagccatag atacaaccacctgctccaatggaggtggcagaggatgaaatggactctgtgagggtccttacttttggttgttcaatgcactattttttg tgctggttggcctcctgccaggaggtggcactttctagaaagcatcagcagaggcagtcaggtggtggtggctgggggggctggggcac cctagaactcccaagaatatatgccctttgtcttcagctaccagggtgagtaaggaaggaccatcaggtgggggcaggactagtcgtgt ctgagctcagagtctccttgggcaggtctttctgtggctactgtgggaggatgggggtgtagtttccaggtcaatggatttatgttcct aggacaattatggctgcctctgctgtgtcatgcaggtcatcaggaaagtgggggaaagcaagcagtcacgtgacttgcccagctcccat gcaactcaaaaggttggtctcacttccagcgtgcaccctcccccgcaacagcaccgaatctgtttccatgcagtcagtgagcaaggctg agaacttgccccaggctaccagctgcgaaaccaagtagggctgtcctacttccctgccagtggagtctgcacaccaaattcatgtcccc ccaccaacccccccactgcccagcccctagatctggccaggtggagattttcttttctgtcatctttccagttcctctggcagcc ctcccaaatgaccctgtgaggcaaggcagaaatggcttcctaggggacccagagagcccacagggcttttcccgctgcttcctctacc cctgtattttgcttggccctctaaattgactcagctccaggtaaggtcagaatcttctcctgtggtctagatcttcaggttcccagtg aggatgtgtgtttgggggtagacggtccccctttccacttccacagtttgggcactcacaatatttggggtgtttcccgggtcctgca ggagcaatctgcttctttcagagggtgtgtgcgttctctcagctttcttgatttatttctgcaggtggttctgcaaaaaaaattcctga tgggagacttcacatgctgctctgtgcatccgagtgggagctgcaatgtacttctgctgcctcccatctgccatcaccctctaatttgt cggtaatatgcatttttaatcaatcttttttttctctctctctctctttttcttctcccccaaaactatactgcccctttgatatcaaggaat caaggacgtgatgttgaggggtgggcagtggatacactctttaccccttagggagctatatctagatttagatattgccaattcaagat aacttaattgaaagcaaattcataatgaataCaCaCaCaCaCacacatctgcatgacaagattttttaatagttgaaagaataaactaa taattgtccacaggcaataagggctttttaagcaaaacagttgtgataaacaggtcattcttagaatagtaatccagccaatagtacag gttgcttagagattatgtcattaccagagttaaaattctataatggcttctcactccctaccactgaggacaagtttatgtccttaggt ttatgcttccctgaaacaataccacctgctattctccactttacatatcaacggcactggttctttatctaactctctggcacagcagg agtttgttttcttctgcttcagagctttgaatttactatttcagcttctaaactttatttggcaatgccttcccatggcagattccttc tgtcattttgcctctgttcgaatactttctcctttaatttcattcttagttaataatatctgaaattattttgttgtttaacttaattat taattttatgtatgttctacctagattataatcttcagaggaaagttttattctctgacttatttaacttaaatgcccactactttaaa aattatgacatttatttaacagatatttgctgaacaaatgtttgaaaatacatgggaaagaatgcttgaaaacacttgaaattgcttgt gtaaagaaacagttttatcagttaggatttaatcaatgtcagaagcaatgatataggaaaaatcgaggaataagacagttatggataag gagaaatcaacaaactcttaaaagatattgcctcaaaagcataagaggaaataagggtttatacatgacttttagaacactgccttggt ttttggataaatggggaagttgtttgaaaacaggagggatcctagatattccttagtctgaggaggagcaattaagattcacttgttta gaggctgggagtggtggctcacgcctgtaatcccagaattttgggaggccaaggcaggcagatcacctgaggtcaagagttcaagacca acctggccaacatggtgaaatcccatctctacaaaaatacaaaaattagacaggcatgatggcaagtgcctgtaatcccagctacttgg gaggctgaggaaggagaattgcttgaacctggaaggcaggagttgcagtgagccgagatcataccactgcactccagcctgggtgacag aacaagactctgtctcaaaaaaaaaaaagagagattcaaaagattcacttgtttaggccttagcgggcttagacaccagtctctgacac attcttaaaggtcaggctctacaaatggaacccaaccagactctcagatatggccaaagatctatacacacccatctcacagatcccct atcttaaagagaccctaatttgggttcacctcagtctctataatctgtaccagcataccaataaaaatctttctcacccatccttagat
```

-continued

```
tgagagaagtcacttattattatgtgagtaactggaagatactgataagttgacaaatcttttttctttcctttcttattcaacttttat tttaacttccaaagaacaagtgcaatatgtgcagctttgttgcgcaggtcaacatgtatctttctggtcttttagccgcctaacacttt gagcagatataagccttacacaggattatgaagtctgaaaggattccaccaatattattataattcctatcaacctgataggttagggg aaggtagagctctcctccaataagccagatttccagagtttctgacgtcataatctaccaaggtcatggatcgagttcagagaaaaaac aaaagcaaaaccaaacctaccaaaaaataaaaatcccaaagaaaaaataaagaaaaaaacagcatgaatacttcctgccatgttaagtg gccaatatgtcagaaacagcactgagttacagataaagatgtctaaactacagtgacatcccagctgtcacagtgtgtggactattagt caataaaacagtccctgcctcttaagagttgttttccatgcaaatacatgtcttatgtcttagaataagattccctaagaagtgaacct agcatttatacaagataattaattctaatccatagtatctggtaaagagcattctaccatcatctttaccgagcatagaagagctacac caaaaccctgggtcatcagccagcacatacacttatccagtgataaatacacatcatcgggtgcctacatacatacctgaatataaaaa aaatacttttgctgagatgaaacaggcgtgatttatttcaaataggtacggataagtagatattgaagtaaggattcagtcttatatta tattacataacattaatctattcctgcactgaaactgttgctttataggattttttcactacactaatgagaacttaagagataatggcc taaaaccacagagagtatattcaaagataagtatagcacttcttatttggaaaccaatgcttactaaatgagactaagacgtgtcccat caaaaatcctggacctatgcctaaaacacatttcacaatccctgaacttttcaaaaattggtacatgctttaactttaaactacaggcc tcactggagctacagacaagaaggtgaaaaacggctgacaaaagaagtcctggtatcttctatggtgggagaagaaaactagctaaagg gaagaataaattagagaaaaattggaatgactgaatcggaacaaggcaaaggctataaaaaaaattaagcagcagtatcctcttggggg cccottccccacactatctcaatgcaaatatctgtctgaaacggtccctggctaaactccacccatgggttggccagccttgccttgac caatagccttgacaaggcaaacttgaccaatagtcttagagtatccagtgaggccaggggccggcggctggctagggatgaagaataaa aggaagcacccttcagcagttccacacactcgcttctggaacgtctgaggttatcaataagctcctagtccagacgccatgggtcattt cacagaggaggacaaggctactatcacaagcctgtgtgggcaaggtgaatgtggaagatgctggaggagaaaccctgggaaggtaggctc tggtgaccaggacaagggagggaaggaaggaccctgtgcctggcaaaagtccaggtcgcttctcaggatttgtggcaccttctgactgt caaactgttcttgtcaatctcacaggctcctggttgtctacccatggacccagaggttctttgacagctttggcaacctgtcctctgcc tctgccatcatgggcaaccccaaagtcaaggcacatggcaagaaggtgctgacttccttgggagatgccataaagcacctggatgatct caagggcacctttgcccagctgagtgaactgcactgtgacaagctgcatgtggatcctgagaacttcaaggtgagtccaggagatgtttt cagcactgttgcctttagtctcgaggcaacttagacaactgagtattgatctgagcacagcagggtgtgagctgtttgaagatactggg gttgggagtgaagaaactgcagaggactaactgggctgagacccagtggcaatgtttttagggcctaaggagtgcctctgaaaatctaga tggacaacttttgactttgagaaaagagaggtggaaatgaggaaaatgacttttctttattagatttcggtagaaagaactttcacctt ccoctatttttgttattcgttttaaaacatctatctggaggcaggacaagtatggtcattaaaaagatgcaggcagaaggcatatattg gctcagtcaaagtggggaactttggtggccaaacatacattgctaaggctattcctatatcagctggacacatataaaatgctgctaat gcttcattacaaacttatatcctttaattccagatggggggcaaagtatgtccaggggtgaggaacaattgaaacatttgggctggagta gattttgaaagtcagctctgtgtgtgtgtgtgtgtgtgcgcgcgtgtgtttgtgtgtgtgtgagagcgtgtgtttcttttaacgttt tcagcctacagcatacagggttcatggtggcaagaagataacaagatttaaattatggccagtgactagtgctgcaagaagaacaacta cctgcatttaatgggaaagcaaaatctcaggctttgagggaagttaacataggcttgattctgggtggaagcttggtgtgtagttatct ggaggccaggctggagctctcagctcactatgggttcatctttattgtctcctttcatctcaacagctcctgggaaatgtgctggtgac cgttttggcaatccatttcggcaaagaattcacccctgaggtgcaggcttcctggcagaagatggtgactggagtggccagtgccctgt cctccagataccactgagctcactgcccatgatgcagagctttcaaggataggctttattctgcaagcaatcaaataataaatctattc tgctaagagatcacacatggttgtcttcagttctttttttatgtcttttttaaatatatgagccacaaagggtttttatgttgagggatgt gtttatgtgtatttatacatggctatgtgtgtttgtgtcatgtgcacactccacactttttttgtttacgttagatgtgggttttgatga gcaaataaaagaactaggcaataaagaaacttgtacatgggagttctgcaagtgggagtaaaaggtgcaggagaaatctggttggaaga aagacctctataggacaggactcctcagaaacagatgtttttggaagagatggggaaaggttcagtgaaggggggctgaaccccccttccct ggattgcagcacagcagcgaggaaggggctcaacgaagaaaaagtgttccaagctttaggaagtcaaggtttaggcagggatagccatt ctatttttattaggggcaatactatttccaacggcatctggctttttctcagcccttgtgaggctctacaggggaggttgaggtgttagaga
```

-continued

```
tcagagcaggaaacaggtttttctttccacggtaactacaatgaagtgatccttactttactaaggaacttttcattttaagtgttgac gcatgcctaaagaggtgaaattaatcccatacccttaagtctacagactggtcacagcatttcaaggaggagacctcattgtaagcttc tagggaggtggggacttaggtgaaggaaatgagccagcagaagctcacaagtcagcatcagcgtgtcatgtctcagcagcagaacagca cggtcagatgaaaatatagtgtgaagaatttgtataacattaattgagaaggcagattcactggagttcttatataattgaaagttaat gcacgttaataagcaagagtttagtttaatgtgatggtgttatgaacttaacgcttgtgtctccagaaaattcacatgctgaatcccca actcccaattggctccattgtgggggaggctttggaaaagtaatcaggtttagaggagctcatgagagcagatccccatcatagaatt attttcctcatcagaagcagagagattagccatttctcttccttctggtgaggacacagtgggaagtcagccacctgcaacccaggaag agagccctgaccaggaaccagcagaaaagtgagaaaaaatcctgttgttgaagtcacccagtctatgctattttgttatagcaccttgc actaagtaaggcagatgaagaaagagaaaaaaataagcttcggtgttcagtggattagaaaccatgtttatctcaggtttacaaatctc cacttgtcctctgtgtttcagaataaaataccaactctactactctcatctgtaagatgcaaatagtaagcctgagcccttctgtctaa ctttgaattctattttttcttcaacgtactttaggcttgtaatgtgtttatatacagtgaaatgtcaagttctttctttatatttcttt ctttcttttttttcctcagcctcagagttttccacatgcccttcctactttcaggaacttctttctccaaacgtcttctgcctggctcc atcaaatcataaaggacccacttcaaatgccatcactcactaccatttcacaattcgcactttctttctttgtcctttttttttttagt aaaacaagtttataaaaaattgaaggaataaatgaatggctacttcataggcagagtagacgcaagggctactggttgccgattttat tgttattttcaatagtatgctaaacaaggggtagattatttatgctgcccattttttagaccataaaagataacttcctgatgttgcca tggcattttttttccttttaattttatttcatttcattttaatttcgaaggtacatgtgcaggatgtgcaggcttgttacatgggtaaat gtgtgtctttctggcctttttagccatctgtatcaatgagcagatataagctttacacaggatcatgaaggatgaaagaatttcaccaat attataataatttcaatcaacctgatagcttaggggataaaactaatttgaagatacagcttgcctccgataagccagaattccagagct tctggcattataatctagcaaggttagagatcatggatcactttcagagaaaaacaaaaacaaactaaccaaaagcaaaacagaaccaa aaaaccaccataaatacttcctaccctgttaatggtccaatatgtcagaaacagcactgtgttagaaataaagctgtctaaagtacact aatattcgagttataatagtgtgtggactattagtcaataaaaacaacccttgcctctttagagttgttttccatgtacacgcacatct tatgtcttagagtaagattccctgagaagtgaacctagcatttatacaagataattaattctaatccacagtacctgccaaagaacatt ctaccatcatctttactgagcatagaagagctacgccaaaaccctgggtcatcagccagcacacacacttatccagtggtaaatacaca tcatctggtgtatacatacatacctgaatatggaatcaaatattttttctaagatgaaacagtcatgatttatttcaaataggtacggat aagtagatattgaggtaagcattaggtcttatattatgtaacactaatctattactgcgctgaaactgtggctttatagaaattgtttt cactgcactattgagaaattaagagataatggcaaaagtcacaaagagtatattcaaaaagaagtatagcactttttccttagaaacca ctgctaactgaaagagactaagatttgtcccgtcaaaaatcctggacctatgcctaaaacacatttcacaatccctgaacttttcaaaa attggtacatgctttagctttaaactacaggcctcactggagctagagacaagaaggtaaaaaacggctgacaaaagaagtcctggtat cctctatgatgggagaaggaaactagctaaagggaagaataaaattagagaaaaactggaatgactgaatcggaacaaggcaaaggctat aaaaaaaattagcagtatcctcttgggggcccccttccccacactatctcaatgcaaatatctgtctgaaacggtccctggctaaactcc acccatgggttggccagccttgccttgaccaatagccttgacaaggcaaacttgaccaatagtcttagagtatccagtgaggccagggg ccggcggctggctagggatgaagaataaaaggaagcacccttcagcagttccacacactcgcttctggaacgtctgaggttatcaataa gctcctagtccagacgccatgggtcatttcacagaggaggacaaggctactatcacaagcctgtggggcaaggtgaatgtggaagatgc tggaggagaaaccctgggaaggtaggctctggtgaccaggacaagggagggaaggaaggaccctgtgcctggcaaaagtccaggtcgct tctcaggatttgtggcaccttctgactgtcaaactgttcttgtcaatctcacaggctcctggttgtctacccatggacccagaggttct ttgacagctttggcaacctgtcctctgcctctgccatcatgggcaaccccaaagtcaaggcacatggcaagaaggtgctgacttccttg ggagatgccacaaagcacctggatgatctcaagggcacctttgcccagctgagtgaactgcactgtgacaagctgcatgtggatcctga gaacttcaaggtgagtccaggagatgtttcagccctgttgcctttagtctcgaggcaacttagacaacggagtattgatctgagcacag cagggtgtgagctgtttgaagatactggggttgggggtgaagaaactgcagaggactaactgggctgagacccagtggtaatgtttag ggcctaaggagtgcctctaaaaatctagatggacaattttgactttgagaaaagagaggtggaaatgaggaaaatgacttttctttatt
```

-continued

```
agattccagtagaaagaactttcatctttccctcattttttgttgttttaaaacatctatctggaggcaggacaagtatggtcgttaaaa agatgcaggcagaaggcatatattggctcagtcaaagtggggaactttggtggccaaacatacattgctaaggctattcctatatcagc tggacacatataaaatgctgctaatgcttcattacaaacttatatcctttaattccagatgggggcaaagtatgtccaggggtgaggaa caattgaaacatttgggctggagtagattttgaaagtcagctctgtgtgtgtgtgtgtgtgtgcgcgcgcgcgtgtgtgtgtgtgtgtc agcgtgtgtttcttttaacgtcttcagcctacaacatacagggttcatggtggcaagaagatagcaagatttaaattatggccagtgac tagtgcttgaaggggaacaactacctgcatttaatgggaaggcaaaatctcaggctttgagggaagttaacataggcttgattctgggt ggaagcttggtgtgtagttatctggaggccaggctggagctctcagctcactatgggttcatctttattgtctcctttcatctcaacag ctcctgggaaatgtgctggtgaccgttttggcaatccatttcggcaaagaattcacccctgaggtgcaggcttcctggcagaagatggt gactgcagtggccagtgccctgtcctccagataccactgagctcactgcccatgattcagagctttcaaggataggctttattctgcaa gcaatacaaataataaatctattctgctgagagatcacacatgattttcttcagctctttttttttacatctttttaaatatatgagcca caaagggtttatattgagggaagtgtgtatgtgtatttctgcatgcctgtttgtgtttgtggtgtgtgcatgctcctcatttattttta tatgagatgtgcattttgatgagcaaataaaagcagtaaagacacttgtacacgggagttctgcaagtgggagtaaatggtgtaggaga aatccggtgggaagaaagacctctataggacaggacttctcagaaacagatgtttttggaagagatgggaaaaggttcagtgaagacctg ggggctggattgattgcagctgagtagcaaggatggttcttaaggaagggaaagtgttccaagctttaggaattcaaggtttagtcagg tgtagcaattctattttattaggaggaatactatttctaatggcacttagcttttcacagccccttgtggatgcctaagaaagtgaaatt aatcccatgccctcaagtgtgcagattggtcacagcatttcaagggagagacctcattgtaagactctgggggaggtggggacttaggt gtaagaaatgaatcagcagaggctcacaagtcagcatgagcatgttatgtctgagaaacagaccagcactgtgagatcaaaatgtagtg ggaagaatttgtacaacattaattggaaggcttacttaatggaattttttgtatagttggatgttagtgcatctctataagtaagagttt aatatgatggtgttacggacctaatgtttgtgtctcctcaaaattcacatgctgaatccccaactcccaactgaccttatctgtgggg aggcttttgaaaagtaattaggtttagatgagctcataagagcagatccccatcataaaattattttccttatcagaagcagagagaca agccatttctctttcctcccggtgaggacacagtgagaagtccgccatctgcaatccaggaagagaaccctgaccacgagtcagccttc agaaatgtgagaaaaaactctgttgttgaagccacccagtcttttgtattttgttatagcaccttgcactgagtaaggcagatgaagaa ggagaaaaaataagcttgggttttgagtggactacagaccatgtttatctcaggtttgcaaagctcccctcgtcccctatgtttcagt ataaaatacctactctactactctcatctataagacccaaataataagcctgcgcccttctctctaactttgatttctcctattttttac ttcaacatgctttactctagccttgtaatgtgtctttacatacagtgaaatgtaaagtttctttattctttttttcttttcttttcttttttct cctcagcctcagaatttggcacatgcccttccttctttcaggaacttctccaacatctctgcctggctccatcatatcataaaggtccc acttcaaatgcagtcactaccgtttcagaatatgcactttctttcttttttgtttttgttttttttaagtcaaagcaaatttcttgag agagtaaagaaatAaacgaatgactactgcataggcagagcagccccgagggccgctggttgttcctttatggttatttcttgatgat atgttaaacaagttttggattatttatgccttctcttttaggccatataggtaactttctgacattgccatggcattttttctttaa tttaatttactgttaccttaaattcaggggtacacgtacaggatatgcaggtttgttttataggtaaaagtgtgccatggtttaatgg gttttttttttcttgtaaagttgtttaagtttcttgtttactctggatattaggcctttgtcagaagaatagattggaaaatcttttc ccattctgtagattgtctttcgctctgatggtagtttcttttgctgagcaggagctctttagtttaattagattccattggtcaatttt tgcttttgctgcaattgcttttcacgctttcatcatgaaatctgtgcccgtgtttatatcatgaatagtattgccttgatttttttcta ggcttttatagtttgggggttttcatttaagtctctaatccatctggagttaattttggataaggtataaggaaggagtccagtttca tttttcagcatatggctagccagttctcccccatcatttattaaattgaaaatcctttccccattgcttgcttttgtcaggtttctaaa agaccagatggttgtaggtacaatatgcagtttcttcaagtcatataataccatctgaaatctcttattaattcatttcttttagtatg tatgctggtctcctctgctcactatagtgagggcaccattagccagagaatctgtctgtctagttcatgtaagattctcagaattaaga aaaatggatggcatatgaatgaaacttcatggatgacatatggaatctaatatgtatttgttgaattaatgcataagatgcaacagaga gaagttgacaactgcaatgataacctggtattgatgatataagagtctatagatcacagtagaagcaataatcatggaaaacaattgga aatggggaacagccacaaacaagaaagaatcaatacttccaggaaagtgactgcaggtcacttttcctggagcgggtgagagaaaagtg gaagttagcagtaactgctgaattcctggttggctgatggaaagatggggcagctgttcactggtacgcagggttttagatgtatgtac
```

-continued

```
ctaaggatatgaggtatggcaatgaacagaaattcttttgggaatgagttttagggccattaaaggacatgacctgaagtttcctctga ggccagtccccacaactcaatatAAAtgtgtttcctgcatatagtcaaagttgccacttctttttcttcatatcatcgatctctgctct taaagataatcttggttttgcctcaaactgtttgtcactacaaactttccccatgttcctaagtaaaacaggtaactgcctctcaacta tatcaagtagactaaaatattgtgtctctaatatcagaaattcagctttaatatattgggtttaactctttgaaatttagagtctcctt gaaatacacatgggggtgatttcctaaactttatttcttgtaaggatttatctcaggggtaacacacaaaccagcatcctgaacctcta agtatgaggacagtaagccttaagaatataaaataaactgttcttctctctgccggtggaagtgtgccctgtctattcctgaaattgct tgtttgagacgcatgagacgtgcagcacatgagacacgtgcagcagcctgtggaatattgtcagtgaagaatgtctttgcctgattaga tataaagacaagttaaacacagcattagactatagatcaagcctgtgccagacacaaatgacctaatgcccagcacgggccacggaatc tcctatcctcttgcttgaacagagcagcacacttctcccccaacactattagatgttctggcataattttgtagatatgtaggatttga catggactattgttcaatgattcagaggaaatctcctttgttcagataagtacactgactactaaatggattaaaaaacacagtaataa aacccagttttcccccttacttccctagtttgtttcttattctgctttcttccaagttgatgctggatagaggtgtttatttctattcta aaaagtgatgaaattggccgggcgcggtggctcacacctgtaatcccagcactttgggaggctgaggtgggcggatcacgaggtcagga gatcaagaccatcctggctaacatggtgaaaccccatctctactaaaaatacaaaaaattagccagagacagtggcgggtgcctgtagt cccagctactcgggaggctgaggcaggagaatggcgtgaacctgggaggcagagcttgcggtgagcagagatcgcgccactgcacactc cagcctgggtgacaaagcgagactccatctcaaaaaaaaaaaaaaaaaaagaaaagaaagaaagaaagaaaaaaaaactgatgaaat tgtgtattcaatgtagtctcaagagaattgaaaaccaagaaaggctgtggcttcttccacataaagcctggatgaataacaggataaca cgttgttacattgtcacaactcctgatccaggaattgatggctaagatattcgtaattcttatccttttcagttgtaacttattcctat ttgtcagcattcaggttattagcggctgctggcgaagtccttgagaaataaactgcacactggatggtgggggtagtgtaggaaaatgg aggggaaggaagtaaagtttcaaattaagcctgaacagcaaagttcccctgagaaggccacctggattctatcagaaactcgaatgtcc atcttgcaaaacttccttgcccaaaccccacccctggagtcacaacccacccttgaccaatagattcattttactgagggaggcaaagg gctggtcaatagattcatttcactgggagaggcaaagggctggggccagagaggagaagtaaaaagccacacatgaagcagcaatgca ggcatgcttctggctcatctgtgatcaccaggaaactcccagatctgacactgtagtgcatttcactgctgacaagaaggctgctgcca ccagcctgtgaagcaaggttaaggtgagaaggctggaggtgagattctgggcaggtaggtactggaagccgggacaaggtgcagaaagg cagaaagtgtttctgaaagagggattagcccgttgtcttacatagtctgactttgcacctgctctgtgattatgactatcccacagtct cctggttgtctacccatggacctagaggtactttgaaagttttggatatctgggctctgactgtgcaataatgggcaaccccaaagtca aggcacatggcaagaaggtgctgatctccttcggaaaagctgttatgctcacggatgacctcaaaggcacctttgctacactgagtgac ctgcactgtaacaagctgcacgtggaccctgagaacttcctggtgagtagtaagtacactcacgctttcttctttacccttagatattt gcactatgggtacttttgaaagcagaggtggctttctcttgtgttatgagtcagctatgggatatgatatttcagcagtgggattttga gagttatgttgctgtaaataacataactaaaatttggtagagcaaggactatgaataatggaaggccacttaccatttgatagctctga aaaacacatcttataaaaaattctggccaaaatcaaactgagtgttttttggatgagggaacagaagttgagatagagaaaataacatct ttcctttggtcagcgaaattttctataaaaattaatagtcacttttctgcatagtcctggaggttagaaaaagatcaactgaacaaagt agtgggaagctgttaaaaagaggattgtttccctccgaatgatgatggtatacttttgtacgcatggtacaggattctttgttatgagt gtttgggaaaattgtatgtatgtatgtatgtatgtgatgactgggggacttatcctatccattactgttccttgaagtactattat cctactttttaaaaggacgaagtctctaaaaaaaaaaatgaaacaatcacaatatgttggggtagtgagttggcatagcaagtaagagaa ggataggacacaatgggaggtgcagggctgccagtcatattgaagctgatatctagcccataatggtgagagttgctcaaactctggtg aaaaaggatgtaagtgttatatctatttactgcaagtccagcttgaggccttctattcactatgtaccattttcttttttatcttcact ccctccccagctcttaggcaacgtgatattgattgtttttggcaacccacttcagcgaggattttaccctacagatacaggcttcttggc agtaactaacaaatgctgtggttaatgctgtagcccacaagaccactgagttccctgtccactatgtttgtacctatggtccactatgt ttgtacctatgtcccaaaatctcatctcctttagatgggggaggttggggagaagagcagtatcctgcctgctgattcagttcctgcat gataaaaatagaataaagaaatatgctctctaagaaatatcattgtactcttttttctgtctttatattttaccctgattcagccaaaag
```

-continued gacgcactatttctgatggaaatgagaatgttggagaatgggagtttaaggacagagaagatactttcttgcaatcctgcaagaaaga gagaactcgtgggtggatttagtggggtagttactcctaggaaggggaaatcgtctctagaataagacaatgtttttacagaaagggag gtcaatggaggtactctttggaggtgtaagaggattgttggtagtgtgtagaggtatgttaggactcaaattagaagttctgtataggc tattatttgtatgaaactcaggatatagctcatttggtgactgcagttcacttctacttattttaaacaacatatttttttattatttat aatgaagtggggatggggcttcctagagaccaatcaagggccaaaccttgaactttctcttaacgtcttcaatggtattaatagagaat tatctctaaggcatgtgaactggctgtcttggttttcatctgtacttcatctgctacctctgtgacctgaaacatatttataattccat taagctgtgcatatgatagatttatcatatgtattttccttaaaggattttttgtaagaactaattgaattgatacctgtaaagtcttta tcacactacccaataaataataaatctctttgttcagctctctgtttctataaatatgtacaagtttattgttttttagtggtagtgat tttattctctttctatatatatacacacatgtgtgcattcataaatatatacaatttttatgaataaaaaattattagcaatcaata ttgaaaaccactgattttgtttatgtgagcaaacagcagattaaaaggctgagatttaggaaacagcacgttaagtcaagttgataga ggagaatatggacatttaaaagaggcaggatgatataaaattagggaaactggatgcagagaccagatgaagtaagaaaaatagctatc gttttgagcaaaaatcactgaagtttcttgcatatgagagtgacataataaaatagggaaacgtagaaaattgattcacatgtatatata tatatagaactgattagacaaagtctaacttgggtatagtcagaggagcttgctgtaattatattgaggtgatggataaagaactgaag ttgatggaaacaatgaagttaagaaaaaaaatcgagtaagagaccattgtggcagtgattgcacagaactggaaaacattgtgaaacag agagtcagagatgacagctaaaatccctgtctgtgaatgaaaagaaggaaatttattgacagaacagcaaatgcctacaagcccccctgt ttggatctggcaatgaacgtagccattctgtggcaatcacttcaaactcctgtacccaagacccttaggaagtatgtagcaccctcaaa cctaaaacctcaaagaaagaggtttttagaagatataataccctttcttctccagtttcattaatcccaaaacctctttctcaaagtatt tcctctatgtgtccaccccaaagagctcacctcaccatatctcttgagtgggagcacatagataggcggtgctaccatctaacagcttc tgaaattcctttgtcatattttttgagtcccccactaataacccacaaagcagaataaataccagttgctcatgtacaataatcactcaac tgctgtcttgtagcatacattaattaagcacattctttgaataattactgtgtccaaacaatcacactttaaaatctcacacttgtgct atcccttgcccttctgaatgtcactctgtattttaaatgaagagatgagggttgaatttcctgtgttacttattgttcatttctcgatg aggagttttcacattcacctttagtggaaaacacataagtacacatcttacaggaaaaatataccaaactgacatgtagcatgaatgct tgtgcatgtagtcatataaaaatcttgtagcaatgtaaacattctctgatatacacatacagatgtgtctatatgtctacacaatttctt atgctccatgaacaaacattccatgcacacataagaacacacactgttacagatgcatacttgagtgcattgacaaaattaccccagtc aatctagagaatttggatttctgcatttgactctgttagctttgtacatgctgttcatttactctgggtgatgtctttccctcattttg ccttgtctatcttgtactcatactttaagtcctaacttatatgttatctcaactaagaagctattttttttttaattttaactgggctta aagccctgtctataaactctgctacaattatgggctcttcttataatatttagtgttttttcctactaatgtacttaatctgctcattg tatattcctaccactaaattttaacctctttttatggtagagacattgtcttgtaaactcttatttccctagtatttggagatgaaaaaa aagattaaattatccaaaattagatctctcttttctacattatgagtattacactatccatagagaagtttgtttgagacctaaactga ggaacctttggttctaaaatgactatgtgatatcttagtatttataggtcatgaggttccttcctctgcctctgctatagtttgattag tcaacaagcatgtgtcatgcatttattcacatcagaatttcatacactaataagacatagtatcagaagtcagtttattagttatatca gttagggtccatcaaggaaaggacaaaccattatcagttactcaacctagaattaaatacagctcttaatagttaattatccttgtatt ggaagagctaaaatatcaaataaaggacagtgcagaaatctagatgttagtaacatcagaaaacctcttccgccattaggcctagaagg gcagaaggagaaaatgtttataccaccagagtccagaaccagagcccataaccagaggtccactggattcagtgagctagtgggtgctc cttggagagagccagaactgtctaatgggggcatcaaagtatcagccataaaaaaccataaaaaagactgtctgctgtaggagatccgt tcagagagagagagagaccagaaataatcttgcttatgctttccctcagccagtgtttaccattgcagaatgtacatgcgactgaaagg gtgaggaaacctgggaaatgtcagttcctcaaatacagagaacactgagggaaggatgagaaataaatgtgaaagcagacatgaatggt aattgacagaaggaaactaggatgtgtccagtaaatgaataattacagtgtgcagtgattattgcaatgattaatgtattgataagata atatgaaaacacagaattcaaacagcagtgaactgagattagaattgtggagagcactggcatttaagaatgtcacacttagaatgtgt ctctaggcattgttctgtgcatatatcatctcaatattcattatctgaaaattatgaattaggtacaaagctcaaataaatttattttttt caggttagcaagaactttttttttttttttttctgagatagagcattgctatggttgcccaggctggagtgcaatggcatgatccaggctc -continued

```
actgcaacatctgcctcccaggttcaagcgattctcctgcctcagcctcccaagtagctggcactacaggcatgtgccaccaccatgcc tggctaattttctattttagtagatagggggtttcaccatgttggtcaggctgatctcgaactcctaacatcaggtgatccaccctcc tcggcctctgaaagtgctgggatcacaggcgtgagccaccacacccagccaagaatgtgaattttgtagaaggatataacccatatttc tctgaccctagagtcctagtatacctcccataccatgtggctcatcctccttacatacatttcccatctttcaccctacctttttcctt tttgtttcagcttttcactgtgtcaaaatctagaaccttatctcctacctgctctgaaaccaacagcaagttgacttccattctaaccc acattggcattacactaattaaaatcgatactgagttctaaaatcatcggggattttggggactatgtcttacttcatacttccttgag atttcacattaaatgttggtgttcattaaaggtccttcatttaactttgtattcatcacactcttggattcacagttatatctaaactc ttaaatacagcctgtataatcccaattcccaactctgatttctaacctctgacctccaacctcagtgccaaacccatatatcaaacaat gtactgggcttatttatatagatgtcctataggcacctcagactcagcatgggtatttcacttgttatactaaaactgtttctcttcca gtgttttccattttagtcattagatagctacttgcccattcaccaaggtcacagattaaaatcatttccctacctctaatcaacagttc gattctgcttcaatttgtccctatctattaatcaccactcttactgcccagtcaggtcctcattgtttcctgaacaagagtagatgcta ttctttccacttttagaccttatcctggctggatgcggtggctcaggcttgtaaacccagcactttgggaggccaaggcaggcagatca cttgaggtcaggagttcaagaccagcctgaccaacatggtgaaacccatctctactaaaaatacaaaatcagccgggcgtgtggtgca tgcctgcagtcccagctattcaggtggctgaggcaggagaattgcttgaacccaggaggcagaggttgcggtgagcctagattgcacca ttgcactctagcttgggcaatagggatgaaactccatctcagaagagaaaagaaaaaaagaccttattctgttatacaaatcctctcaa tgcaatccatatagaataaacatgtaaccagatctcccaatgtgtaaaatcatttcaggtagaacagaattaaagtgaaaagccaagtc tttggaattaacagacaaagatcaaataacagtcctcatggccttaagaatttacctaacatttttttttagaatcaattttcttatata tgaattggaaacataattcctccctcacaaacacattctaagattttaaggagatattgatgaagtacatcatctgtcatttttaacag gtagtggtagtgattcacacagcacattatgatctgttcttgtatgttctgttccattctgtattcttgacctggttgtattctttctg agctccagatccacatatctaagtacatcttttgcattttacaagagtgcatacaatacaatgtatccaagactgtatttctgatttt atcgtaccactaaactcacaaatgtggccctattcttgtgttcacgactgacatcaccgtcatggtccaagtctgataatagaaatggc attgtcactttcttccctactgcaacagaagcccagctatttgtctcccattttctctacttctaaaatacatttcttcactaagtgag aataatcttttaaagacacaaatcaaaccatgccaccacctttcttgaattattcaatatctttcgttggcttccaggttacagaaaaa taacttgtaacaaagtttaaaggtcattcatggctcctctctaccctattttataacatttcccttgtgatcagaatctcaggcacat catccatctttctatatacaaataaagtcatatagtttgaactcacctctggttacttttaatcaaccaaatgctgtaaaatgcatttg tatcgctacgtgttaagcagtagttgattcttttcatttctgtgtaatattctattctttgactataccgtaatttatcaattctactg ttggtaagcatttaagtggctaccggtttgaggttttatgattattgctgtcataagcatttctatacatgtctttggatacacacat gcatgtgtttctgaatatctaaaaatgtaattgctaggtaatagacttatcaagcatccagcatttgtggatactattaaaggttttcc aaaggggttatactattgtacagtgtcaccaacagagtttgagtttctattgatccatatcaccaccaaaatttgaactgtcagtctta tctcttctcttgtctcttttttcctctttttttttccttcccttcccctctcttcgtttctttttctctcctcttctcttctttcctctct tcccttccctttctctttctcttccctatcccttctcctctcctctccccctcctttttctcctctcctctccattatttattttttcct tcttctcctccatcccttccatcctctctcttccctcttccttccttcctttctccatttcttcctcctctttccttcaatccttcct tttggatatgctcatgggtgtgtatttgtctgccattgtggcattatttgaattcagaaaagagtgaaaaactactgggatcttcattc ctgggtctaattccacatttttttttaagaacacatctgtaaaaatgttctgtactagcatattcccaggaacttcgttaaatttaatc tggctgaatatggtaaatctacttttcactttgcattctttctttagtcataccataattttaaacattcaaatatttgtatataata tttgattttatctgtcattaaaatgttaaccttaaaattcatgtttccagaacctatttcaataactggtaaataaacactattcattt tttaaatattctttttaatggatatttatttcaatataataaaaaattagagtttttattataggaagaatttaccaaaagaaggaggaag caagcaagtttaaactgcagcaatagatttgtccattccaacctctcaaaattcccttggagacaaaaatctctagaggcaaagaagaa ctttatattgagtcaacttgttaaaacatctgcttttagataagttttcttagtataaagtgacagaaacaaataagttaaactctaag atacattccactatattagcctaaaacacttctgcaaaaatgaaactaggaggatattttttagaaacaactgctgaaagagatgcggtg
```

-continued

```
gggagatatgtagaggagaacagggtttctgagtcaagacacacatgacagaacagccaatctcagggcaagttaagggaatagtggaa tgaaggttcattttttcattctcacaaactaatgaaaccctgcttatcttaaaccaacctgctcactggagcagggaggacaggaccagc ataaaaggcagggcagagtcgactgttgcttacactttcttctgacataacagtgttcactagcaacctcaaacagacaccatggtgca tctgactcctgaggagaagactgctgtcaatgccctgtggggcaaagtgaacgtggatgcagttggtggtgaggccctgggcaggttgg tatcaaggttataagagaggctcaaggaggcaaatggaaactgggcatgtgtagacagagaagactcttgggtttctgataggcactga ctctctgtcccttgggctgttttcctaccctcagattactggtggtctaccttggacccagaggttctttgagtcctttggggatctg tcctctcctgatgctgttatgggcaaccctaaggtgaaggctcatggcaagaaggtgctaggtgcctttagtgatggcctggctcacct ggacaacctcaagggcacttttctcagctgagtgagctgcactgtgacaagctgcacgtggatcctgagaacttcagggtgagtccag gagatgcttcacttttctcttttt tactttctaatcttacattttggttctttt acctacctgctcttctcccacattttttgtcatttta ctatattttatcatttaatgcttctaaaattttgttaattttttattt aaatattctgcattttttccttcctcacaatcttgctattt taaattatttaatatcctgtctttctctcccaacccctcccttcattttt ccttctctaacaacaactcaaattatgcataccagctc tcacctgctaattctgcacttagaataatcctttt gtctctccacatgggt atgggagaggctccaactcaaagatgagaggcatagaa tactgttttagaggctataaatcattttacaataaggaataattggaatttt atcaaattctgtagt aaatggaatggaaaggaaagtga atatttgattatgaaagactaggcagttacactggaggtggggcagaagtcgttgctaggagacagcccatcatcacactgattaatca attaatttgtatctattaatctgtttatagtaattaatttgtatatgctatatacacatacaaaattaaaactaatttggaattaattt gtatatagtattatacagcatatatagcatatatgtacatatatagactacatgctagttaagtacatagaggatgtgtgtgtatagat atatgttatatgtatgcattcatatatgtacttatttatgctgatgggaataacctggggatcagttttgtctaagatttgggcagaaa aaaatgggtgttggctcagtttctcagaagccagtctttatttctctgttaaccatatgcatgtatctgcctacctcttctccgcagct cttgggcaatgtgctggtgtgtgtgctggcccgcaactttggcaaggaattcaccccacaaatgcaggctgcctatcagaaggtggtgg ctggtgtggctaatgccctggctcacaagtaccattgagatcctggactgtttcctgataaccataagaagaccctatttccctagatt ctattttctgaacttgggaacacaatgcctacttcaagggt atggcttctgcctaataaagaatgttcagctcaacttcctgattaatt tcacttatttcattttttt gtccaggtgtgtaagaaggttcctgaggctctacagatagggagcacttgtttattttt acaaagagt aca tgggaaaagagaaaagcaagggaaccgtacaaggcattaatgggtgacacttctacctccaaagagcagaaattatcaagaactcttga tacaaagataaatactggcactgcagaggttctagggaagacctcaaccctaagacatagcctcaagggt aatgctacgattaaactcca acaattactgagaaaataatgtgctcaattaaaggcataatgattactcaagacaatgttatgttgtctttcttcctccttcctttgcc tgcacattgtagcccataatactataccccatcaagtgttcctgctccaagaaatagcttcctcctcttacttgccccagaacatctct gtaaagaatttcctcttatcttcccatatttcagtcaagattcattgctcacgtattacttgtgacctctcttgaccccagccacaata aacttctctatactacccaaaaaatctttccaaaccctcccccacaccattttttatatttttatattttttcttatttatttcatgcac acacacacactccgtgcttt ataagcaattctgcctattctctaccttcttacatgcctactgtgcctcatattaaattcatcaatggg cagaaagaaaatatttattcaagaaacagtgaatgaatgaacgaatgagtaaatgagtaaatgaaggaatgattattccttgctttag aacttctggaattagaggacaatattaataataccatcgcacagtgtttctttgttgttaatgctacaacatacaaagaggaagcatgc agtaaacaaccgaacagttatttcctttctgatcataggagtaatattttttttccttgagcaccattttt gccataggtaaaattagaa ggattttt agaactttctcagttgtatacattttt aaaaatctgtattatatgcatgttgattaattttt aaacttacttgaatacctaa acagaatctgttgtttccttgtgtttgaaagtgctttcacagtaactctgtctgtactgccagaatatactgacaatgtgttatagtta actgttttgatcacaacattttgaattgactggcagcagaagctcttttatatccatgtgttttccttaagtcattatacatagtaggc actgagaactctttatatctgaataagatatttaggaaccactggtttacatatcagaagcagagctactcagggcattttt ggggaaga tcactttcacattcctgagcatagggaagttctcataagagtaagatattaaaaggagatacttgtgtggtattcgaaagacagtaaga gagattgtagacctt atgatcttgataggg aaaacaaactacattcctttctccaaaagtcaaaaaaaaagagcaaatatagcttacta taccttctattcctacaccattagaagtagtcagtgagtctaggcaagatgttggccctaaaaatccaaat accagagaattcatgaga acatcacctggatgggacatgtgccgagcacacacaattactatatgctaggcattgctatcttcatattgaagatgaggaggtcaaga gatgaaaaaagacttggcaccttgttgttatattaaaattatttgttagagtagagctttt gtaagagtctaggagtgtgggagctaaa
```

-continued tgatgatacacatggacacaaaaaatagatcaacagacacccaggcctacttgagggttgagggtgggaagagggagacgatgaaaaag aacctattgggtattaagttcatcactgagtgatgaaataatctgtacatcaagacccagtgatatgcaatttacctatataacttgta catgtacccccaaatttaaaatgaaagttaaaacaaagtataggaatggaattaattcctcaagatttggctttaattttatttgataa tttatcaaatggttgtttttctttctcactatggcgttgctttataaactatgttcagtatgtctgaatgaaagggtgtgtgtgtgtg tgaaagagagggagagaggaagggaagagaggacgtaataatgtgaatttgagttcatgaaaattttttcaataaaataatttaatgtca ggagaattaagcctaatagtctcctaaatcatccatctcttgagcttcagagcagtcctctgaattaatgcctacatgtttgtaaagggg tgttcagactgaagccaagattctacctctaaagagatgcaatctcaaatttatctgaagactgtacctctgctctccataaattgaca ccatggcccacttaatgaggttaaaaaaaagctaattctgaatgaaaatctgagcccagtggaggaaatattaatgaacaaggtgcaga ctgaaatataaatttttctgtaataattatgcatatactttagcaaagttctgtctatgttgactttattgcttttttggtaagaaatac aacttttaaagtgaactaaactatcctatttccaaactattttgtgtgtgtgcggtttgtttctatgggttctggttttcttggagca ttttatttcattttaattaattaattctgagagctgctgagttgtgtttactgagagattgtgtatctgcgagagaagtctgtagcaa gtagctagactgtgcttgacctaggaacatatacagtagattgctaaaatgtctcacttgggaattttagactaaacagtagagcatg tataaaaatactctagtcaagtgctgcttttgaaacaaatgataaaaccacactcccatagatgagtgtcatgattttcatggaggaag ttaatattcatcctctaagtatacccagactagggccattctgatataaaacattaggacttaagaaagattaatagactggagtaaag gaaatggacctctgtctctctcgctgtctcttttttgaggacttgtgtgtgtgtgtgtgtgtgtgtgtgtgtgttgtggtcagtg gggctggaataaaagtagaatagacctgcacctgctgtggcatccattcacagagtagaagcaagctcacaatagtgaagatgtcagta agcttgaatagttttttcaggaactttgaatgctgatttagatttgaaactgaggctctgaccataaccaaatttgcactatttattgct tcttgaaacttatttgcctggtatgcctgggcttttgatggtcttagtatagcttgcagccttgtccctgcagggtattatgggtaata gaaagaaagtctgcgttacactctagtcacactaagtaactaccattggaaaagcaacccctgccttgaagccaggatgatggtatct gcagcagttgccaacacaagagaaggatccatagttcatcatttaaaaaagaaaacaaaatagaaaaaggaaaactatttctgagcata agaagttgtagggtaagtctcttaagaaggtgacaatttctgccaatcaggatttcaaagctcttgctttgacaattttggtctttcaga atactataaatataacctatattataaatttcataaagtctgtgcattttctttgacccaggatatttgcaaaagacatattcaaacttc cgcagaacactttatttcacatatacatgcctcttatatcagggatgtgaaacagggtcttgaaaactgtctaaatctaaaacaatgct aatgcaggtttaaatttaataaaataaaatccaaaatctaacagccaagtcaaatctgcatgtttttaacatttaaaatattttaaagac gtcttttcccaggattcaacatgtgaaatcttttctcagggatacacgtgtgcctagatcctcattgctttagtttttttacagaggaat gaatataaaaagaaaatacttaaattttatccctcttacctctataatcatacataggcataatttttttaacctaggctccagatagcc atagaagaaccaaacactttctgcgtgtgtgagaataatcagagtgagattttttcacaagtacctgatgagggttgagacaggtagaa aaagtgagagatctctatttatttagcaataatagagaaagcatttaagagaataaagcaatggaaataagaaatttgtaaatttcctt ctgataactagaaatagaggatccagtttcttttggttaacctaaattttatttcattttattgttttatttttattttatttttatttta ttttgtgtaatcgtagtttcagagtgttagagctgaaaggaagaagtaggagaaacatgcaaagtaaaagtataacactttccttacta aaccgacatgggtttccaggtaggggcaggattcaggatgactgacagggcccttagggaacactgagaccctacgctgacctcataaa tgcttgctacctttgctgtttttaattacatctttttaatagcaggaagcagaactctgcacttcaaaagttttttcctcacctgaggagtt aatttagtacaaggggaaaaagtacaggggggatgggagaaaggcgatcacgttgggaagctatagagaagaagagtaaattttagtaa aggaggtttaaacaaacaaaatataaagagaaataggaacttgaatcaaggaaatgattttaaaacgcagtattcttagtggactagag gaaaaaaataatctgagccaagtagaagacctttccctcctacccctactttctaagtcacagaggctttttgttcccccagacact cttgcagattagtccaggcagaaacagttagatgtccccagttaacctcctatttgacaccactgattacccattgatagtcacactt tgggttgtaagtgactttttatttatttgtattttttgactgcattaagaggtctctagttttttatctcttgtttcccaaaacctaata agtaactaatgcacagagcacattgatttgtatttattctattttttagacataatttattagcatgcatgagcaaattaagaaaaacaa caacaaatgaatgcatatatatgtatatgtatgtgtgtatatatacacacatatatatatattttttcttttcttaccagaaggttt taatccaaataaggagaagatatgcttagaaccgaggtagagtttttcatccattctgtcctgtaagtattttgcatattctggagacgc -continued

```
aggaagagatccatctacatatcccaaagctgaattatggtagacaaaactcttccacttttagtgcatcaacttcttatttgtgtaat aagaaaattgggaaaacgatcttcaatatgcttaccaagctgtgattccaaatattacgtaaatacacttgcaaaggaggatgttttta gtagcaatttgtactgatggtatggggccaagagatatatcttagagggagggctgagggtttgaagtccaactcctaagccagtgcca gaagagccaaggacaggtacggctgtcatcacttagacctcaccctgtggagccacaccctaggggttggccaatctactcccaggagca gggagggcaggagccagggctgggcataaaagtcagggcagagccatctattgcttacatttgcttctgacacaactgtgttcactagc aacctcaaacagacaccatggtgcatctgactcctgaggagaagtctgccgttactgccctgtggggcaaggtgaacgtggatgaagtt ggtggtgaggccctgggcaggttggtatcaaggttacaagacaggtttaaggagaccaatagaaactgggcatgtggagacagagaaga ctcttgggtttctgataggcactgactctctctgcctattggtctattttcccacccttaggctgctggtggtctaccttggacccag aggttctttgagtcctttggggatctgtccactcctgatgctgttatgggcaaccctaaggtgaaggctcatggcaagaaagtgctcgg tgcctttagtgatggcctggctcacctggacaacctcaagggcacctttgccacactgagtgagctgcactgtgacaagctgcacgtgg atcctgagaacttcagggtgagtctatgggacgcttgatgttttctttcccccttcttttctatggttaagttcatgtcataggaagggg ataagtaacagggtacagtttagaatgggaaacagacgaatgattgcatcagtgtggaagtctcaggatcgtttttagtttctttttattt gctgttcataacaattgttttctttttgtttaattcttgctttctttttttttcttctccgcaatttttactattatacttaatgcctta acattgtgtataacaaaaggaaatatctctgagatacattaagtaacttaaaaaaaaactttacacagtctgcctagtacattactatt tggaatatatgtgtgcttatttgcatattcataatctccctactttattttctttttatttttaattgatacataatcattatacatatt tatgggttaaagtgtaatgttttaatatgtgtacacatattgaccaaatcagggtaattttgcatttgtaattttaaaaaatgctttct tcttttaatatacttttttgtttatcttatttctaatactttccctaatctctttctttcagggcaataatgatacaatgtatcatgcc tctttgcaccattctaaagaataacagtgataatttctgggttaaggcaatagcaatatctctgcatataaatatttctgcatataaat tgtaactgatgtaagaggtttcatattgctaatagcagctacaatccagctaccattctgcttttattttatggttgggataaggctgg attattctgagtccaagctaggcccttttgctaatcatgttcatacctcttatcttcctcccacagctcctgggcaacgtgctggtctg tgtgctggcccatcactttggcaaagaattcaccccaccagtgcaggctgcctatcagaaagtggtggctggtgtggctaatgccctgg cccacaagtatcactaagctcgctttcttgctgtccaatttctattaaaggttcctttgttccctaagtccaactactaaactgggggga tattatgaagggccttgagcatctggattctgcctaataaaaaacatttattttcattgcaatgatgtatttaaattatttctgaatat tttactaaaaagggaatgtgggaggtcagtgcatttaaaacataaagaaatgaagagctagttcaaaccttgggaaaatacactatatc ttaaactccatgaaagaaggtgaggctgcaaacagctaatgcacattggcaacagcccctgatgcatatgcccttattcatccctcagaa aaggattcaagtagaggcttgatttggaggttaaagttttgctatgctgtatttttacattacttattgttttagctgtcctcatgaatg tcttttcactacccatttgcttatcctgcatctctcagccttgactccactcagttctcttgcttagagataccacctttcccctgaag tgttccttccatgtttttacggcgagatggtttctcctcgcctggccactcagccttagttgtctctgttgtcttatagaggtctacttg aagaaggaaaaacaggggtcatggtttgactgtcctgtgagcccttcttccctgcctcccccactcacagtgacccggaatctgcagtg ctagtctcccggaactatcactctttcacagtctgctttggaaggactgggcttagtatgaaaagttaggactgagaagaatttgaaag gcggcttttgtagcttgatattcactactgtctcttattaccctgtcataggcccacccccaaatggaagtcccattcttcctcaggatgt ttaagattagcattcaggaagagatcagaggtctgctggctcccttatcatgtcccttatggtgcttctggctctgcagttattagcat agtgttaccatcaaccaccttaacttcattttttcttattcaatacctaggtaggtagatgctagattctggaaataaaatatgagtctc aagtggtccttgtcctctctcccagtcaaattctgaatctagttggcaagattctgaaatcaaggcatataatcagtaataagtgatga tagaagggtatatagaagaattttattatatgagagggtgaaaccctcaaaatgaaatgaaatcagaccccttgtcttacaccataaaca aaaataaatttgaatgggtaaagaattaaactaagacctaaaaccataaaaattttttaaagaaatcaaaagaagaaaattctaatatt cacgttgcagccgtttttttgaatttgatatgagaagcaaaggcaacaaaaggaaaaataaagaagtgaggctacatcaaactaaaaaat ttccacacaaaaaacaaaacaatgaacaaatgaaaggtgaaccatgaaatggcatatttgcaaaccaaatatttcttaaatattttggt taatatccaaaatatataagaaacacagatgattcaataacaaacaaaaaattaaaaataggaaaataaaaaaattaaaaagaagaaaa tcctgccatttatggcagaattgatgaacctggaggatgtaaaactaagaaaaataagcctgacacaaaaagacaaatactacacaacc ttgctcatatgtgaaacataaaaaaagtcactctcatggaaacagacagtagaggtatggtttccaggggttgggggtgggagaatcagg
```

-continued

```
aaactattactcaaagggtataaaatttcagttatgtgggatgaataaaattctagatatctaatgtacagcatcgtgactgtagttaat tgtactgtaagtatatttaaaatttgcaaagagagtagattttttttttttttttagatggagttttgctcttgttgtccaggctggagt gcaatggcaagatcttggctcactgcaacctccgcctcctgggttcaagcaaatctcctgcctcagcctcccgagtagctgggattaca ggcatgcgacaccatgcccagctaattttgtattttttagtagagacggggtttctccatgttggtcaggctgatccgcctgcctcggcc acccaaagggctgggattacaggcgtgagccaccgggcctggccgagagtagatcttaaaagcatttaccacaagaaaaaggtaactat gtgagataatgggtatgttaattagcttgattgtggtaatcatttcacaaggtatacatatattaaaacatcatgttgtacaccttaaa tatatacaattttttatttgtgaatgatacctcaataaagttgaagaataataaaaaagaatagacatcacatgaattaaaaaactaaaa aataaaaaaatgcatcttgatgattagaattgcattcttgattttttcagatacaaatatccatttgactgtttactcttttccaaaaca atacaataaattttagcactttatcttcattttcccttcccaatctataattatatatatatatattttagatattttgtatagtttt actccctagattttctagtgttattattaaatagtgaagaaatgtttacacttatgtacaaaatgttttgcatgctttttcttcatttct aacattctctctaagtttattctattttttttctgattatccttaatattatctctttctgctggaaatacattgttacttttggtttat ctaaaaatggcttcattttcttcattctaaaatcatgttaaattaataccactcatgtgtaagtaagatagtggaataaatagaaatcc aaaaactaaatctcactaaaatataataatgtgatatataaaaatatagcttttaaatttagcttggaaataaaaaaacaaacagtaatt gaacaactatacttttttgaaaagagtaaagtgaaatgcttaactgcatataccacaatcgattacacaattaggtgtgaaggtaaaatt cagtcacgaaaaaactagaataaaaatatgggaagacatgtatataatcttagagataacactgttatttaattatcaacccaaagtag aaactatcaagggagaaataaattcagtcaacaataaaagcatttaagaagttattctaggctgggagcggtggctcacacctgcaatt gcagcactttgggaggcctagacaggcggatcacgacgtcaggagttcaagatcagcctggccaacatagtgaaacctcatcgctacta aaaatataaaaaacttagcctggcgtggtggcaggcatgtgtaatcccagcaatttgggaggctgaggcaggagaatcgcttgatcctgg gaggcagaggttgcagtgagccaagattgtgccactgcattccagcccaggtgacagcatgagactccgtcacaaaaaaaaaagaaaaa aaaagggggggggggagcggtggagccaagatgaccgaataggaacagctccagtctatagctcccatcgtgagtgacgcagaagacgg gtgatttctgcatttccaactgaggtaccaggttcatctcacagggaagtgccaggcagtgggtgcaggacagtaggtgcagtgcactg tgcatgagccaaagcagggcgaggcatcacctcacccgggaagcacaaggggtcagggaattccctttcctagtcaaagaaaagggtga cagatggcacctggaaaatcgggtcactcccgccctaatactgcgctcttccaacaagcttaacaaatggcacaccaggagattatatc ccatgcctggctcagagggtcctacgcccatggagcctcgctcattgctagcacagcagtctgaggtcaaactgcaaggtggcagtgag gctggggagggggtgcccaccattgtccaggcttgagcaggtaaacaaagccgcctggaagctcgaactgggtggagcccaccacagct caaggaggcctgcctgcctctgtaggctccacctctaggggcagggcacagacaaacaaaagacaacaagaacctctgcagacttaaat gtccctgtctgacagctttgaagagagtagtggttctcccagcacatagcttcagatctgagaacaggcagactgcctcctcaagtggg tccctgacccccgagtagcctaactgggaggcatcccccagtaggggcagactgacacctcacatggctggtactcctctaagacaaaa cttcagaggaatgatcaggcagcagcatttgcggttcaccaatatccactgttctgcagccaccgctgttgatacccaggaaaacagc ttctggagtggacctccagtaaactccaacagacctgcagctgagggtcctgactgttagaaggaaaactaacaaacagaaaggacatc cacaccaaaaacccatctgtacatcgccatcatcaaagaccaaaggtagataaaaccataaagatgggaaaaagcagagcagaaaaac tggacactctaaaaatgagagtgcctctcctcctccaaagtaacgcagctcctcaccagcaatggaacaaagctgggcagagaatgact ttgacgagttgagagaggaaggcttcagaagatcaaactactccaagctaaaggaggaagttcgaacaaacggcaaagaagtaaaaaac tttgaaaaaaaattagatgaatggataactagaataaccaatgcacagaagtccttaaaggacctgatggagctgaaaaccaaggcagg agaactacgtgacaaatacacaagcctcagtaaccgatgagatcaactggaagaaagggtatcaatgacgaaagatgaaatgaatgaaa tgaagcatgaagagaagtttagagaaaaaagaataaaaagaaacgaacaaagcctccaagaaatatgggactatgtgaaaagaccaaat ctacatctaattggtgtagctgaaagtgatgggagaatggaaccaagttggaaaacactctgcaggatattatccaggagaacttccc caatctagcaaggcaagcccaaattcacattcaggaaatacagagaacgccacaaagatactcctagagaaaagcaactccaagacaca taactgtcagattcaccaaagttgaaatgaaggaaaaaatgttaagggcagccagagagaaaaggtcgggttacccacaaagggaagccc atcagactaacagctgatctatcggcagaaactctacaagccagaagaaagtggggggccaatattcaacattgttaaagaaaagaattt
```

-continued tcaacccagaatttcatatccagccaaactaagcttcataagtgaaggagaaataaaatcctttacagacaagcaaatgctgagagatt ttgtcaccaccaggcctgccctacaagagctcctgaaggaagcactaaacatggaaaggaacaactagtatcagccactgcaaaaacat gccaaattgtaaagaccatcaaggctaggaagaaactgcatcaacgagcaaaataaccagctaacatcataatgacaggatcaaattca tacataacaatactcaccttaaatgtaaataggctaaatgctccaattaaaagacacagactggcaaattggataaggagtcaagaccc atctgtgttctgtattcaggaaacccatctcacgtgcagagacacacataggctcgaaataaaaggatggaggaatatctaccaagcaa atggaaaacaaaaaaggcaggggttgcaatcctagtctctgataaaacagattttaaaccaacaaagatcaaaagagacaaagaaggc cattacataatggcaaagggatctattcaagaagaagaactaactatactaaatatatatgcacccaatacaggagcacccagattcat aaaacaagtcctgagtgacctacaaagagacttagatgcccacacaataataatgggagactttaacaccccactgtcaacattagaca gatcaacgagacagaaagttaacaaggatatccaggaattggactcagctctgcaccaagcagacctaatagacatctacagaactctc caccccaaatcaacagaatatacattcttttcagcaccacaccacacctattccaaaactgaccacatagttggaagtaaagctctcct cagcaaatgtaaaagaacagaaactataacaaactgtctctcagaccacagtgcaatcaaactagaactcaggattaagaaactcactc aaaaccactcagctacatggaaactgaacagcctgctcctgaatgactactgggtacataacaaaatgaaggcagaaataaagatgttc tttgaaaccaacgagaacaaagacacaacacaccagaatctctgagacacattcaaagcagtgtgtagagggaaatttatagcactaaa tgcccacaagggaaagcaggaaagatctaaaattgacaccctaacatcacaattaaaaaactagagaagcaggagcaaacacattcaaa agctaacagaagacaagaaataaactaagatcagagcagaagtgaaggacatagagacacaaaaaaacccttcaaaaaaatcaatgaatc cagaagctgtttttttgaaaagatcaacaaaattgatagactgctagcaagactaataaagaagaaaagagagaagaatcaaatagacg caataaaaaatgacacggggtatcaccactgatcccacagaaatacaaactaccgtcagagaatactataaacacctctacgcaaataa actagaaaatctagaagaaatggataaattcctcgacacatacactctgccaagactaaaccaggaagaagttgtatctctgaatagac caataacaggctctgaaattgaggcaataattaatagcttatcaaccaaaaaaagtccgggaccagtaggattcatagccgaattctac cagaggtacaaggaggagctggtaccattccttctgaaactattccaatcaatagaaaaagagggaatcctccctaactcattttatga ggccagcatcatcctgataccaaagcctgacagagacacaacaaaaaaagagaatgttacaccaatatccttgatgaacattgatgcaa aaatcctcaataaaatactggcaaactgatccaccatgatcaagtgggcttcatccctgccatgcaaggctggttcaacatacgaaaat caataaacataatccagcatataaacagaaccaaagacacaaaccatatgattatctcaatagatgcagaaaaggcctttgacaaaatt caacaacgcttcatgctaaaaactctcaatataattaggtattgatgggacatatctcaaaataataagagctatctatgacaaacccac agccaatatcatactgagtggacaaaaactggaagcattccctttgaaaactggcacaaggcagggatgccctctctcaccactcctat tcaacatagtgttgtaagttctggccagggcaatcaggcaggagaaggaaataaagggcattcaattaggaaaagaggaagtgaaattg tccctgtttgcagatgacatgattgtatatctagaaaaccccattgtctcagcccaaaatctccttaagctgataagcaacttcagcaa agtctcaggatataaaatcagtgtgcaaaaatcacaagtattcctatgcaccaataacagacaaacagagagccaaatcatgagtgaac tcccattcacaattgcttcaaagagaataaaatacctaggaatccaacttacaagggatgtgaaggacctcttcaaggagaactacaaa ccactgctcaatgaaataaaagaggatacaaacaaatggaagaacattccatgctcatgggtaggaagaatcaatatcgtgaaaatggt catactgcccaaggtaatttatagattcaatgccatccccatcaagctaccaatgactttcttcacagaactggaaaaaactactttaa agttcatatggaaccaaaaaagagcccacatcaccaaggcaatcctaagccaaaagaacaaagctggaggcatcacgctacctgacttc aaactatactacaatgctacggtaaccaaaacagcatggtactggtaccaaaacagagatctagaccaatggaacagaacagagccctc agaaataatgccgcatatctacaactatctgatctttgacaaacctgagagaaacaagcaatggggaaaggattccctatttaataaat ggtgctgggaaaactggctagccatatgtagaaagctgaaactggatcccttccttacaccttatacaaaaattaattcaagatggatt aaagacttacatgttagacctaaaaccataaaaaccctagaaaaaaacctaggcaataccattcaggacataggcatgggcaaggactt catgtctaaaacaccaaaagcaatggcaacaaaagacaaaatggacaaacgggatctaattaaactaaagagcttctgcacagctaaag aaactaccatcagagtgaacaggcaacctacaaaatgggagaaaatttttgcaatctactcatctgacaaagggctaatatccagaatc tacaatgaactcaaacaaatttacaagaaaaaacaaacaaccccatcaaaaagtgggcaaaggatatgaacagacacttcgcaaaagaa gacatttatgtaatcaaaaacacatgaaaaaatgctcatcatcactagccatcagagaaatgcaaatcaaaaccacaatgagatacca tctcacaccagttagaatggcgatcattaaaaagtcaggaaacaacaggtgctggagaggatgtggagaaacaggaacaacttttacac -continued

```
tgttggtgggactgtaaactagttcaaccattgcggaagtcagtgtggcaattcctcaggaatctagaactagaaataccatttgaccc agccatcccattactgggtacatacccaaaggattatataaatcatgctgctataaagacacatgcacacgtatgtttattgcagcactat tcacaatagcaaagacttggaaccaacccaaatgtccaacaacgatagactggattaagaaaatgtggcacatatacaccatggaatac tatgcagccataaaaaatgatgagttcatgtcctttgtagggacatggatgaagctggaaactatcattctcagcaaactatcacaagg agaataaaccaaacaccgcatgttctcactcataggtgggaattgaacaatgagaacacatggacacatgaagaggaacatcacactct ggggactgttatggggtgggggccaggggcagggatagcactaggagatatacctaatgctaaatgacgagttaatgggtgcagcacac caacatggcacatgtatacatatataacaaacctgcatgttgtgcacatgtaccctaaaacttgaagtataataataaaaaaaagttat cctattaaaactgatctcacacatccgtagagccattatcaagtctttctctttgaaatagacagaaatttagtgttttctcagtcagt taac
```

Five 5' hypersensitive site (HS) sites (HS1-HS5) and one 3' HS site have been identified in the human β-globin LCR (Stamatoyannopoulos et al., (2001)). The 5' HSs 1-4 are Dnase I hypersensitive sites. The HS2 and HS3 elements are the most powerful single elements within the LCR (Ellis et al., *EMBO J.* (1996), 15:562-568; Collis et al., *EMBO J.* (1990) 9:233-240), as corroborated by many groups. Deleting HS2 in the context of βYAC in transgenic mice severely affects HS site formation as well as expression of all of the human β-globin genes at every developmental stage (Bungert et al., *Mol. Cell Biol.* (1999); 19:3062-3072). It was reported that deletion of HS2 minimally reduced the expression of the embryonic εy and Bhi globin genes in yolk sac-derived erythrocytes (Ley et al., Ann. N.Y. Acad. Sci. (1998); 850:45-53; Hug et al., *Mol. Cell Biol.* (1996); 26:2906-2912). HS2 functions primarily as an enhancer.

In certain embodiments, the β-globin LCR comprises a HS2 region. In non-limiting example, the β-globin LCR comprises a HS2 region, a HS3 region, and a HS4 region. In certain embodiments, the HS2 region, HS3 region and HS4 region within the β-globin LCR are contiguous. In certain embodiments, the β-globin LCR consists essentially of a HS2 region, a HS3 region and a HS4 region. In another embodiment, the β-globin LCR comprises two introduced GATA-1 binding sites at the junction between the HS3 region and the HS4 region. The HS3 region can lie between the HS2 region and the HS4 region. The length and the sequence of the HS2 region can vary. The HS2 region can have a length of from about 400 bp to about 1000 bp, e.g., from about 400 bp to about 500 bp, from about 500 bp to about 600 bp, from about 600 bp to about 700 bp, from about 700 bp to about 800 bp, from about 800 bp to about 850 bp, from about 800 bp to about 820 bp, from about 820 bp to about 830 bp, from about 830 bp to about 840 bp, from about 840 bp to about 850 bp, from about 850 bp to about 900 bp, from about 800 bp to about 900 bp, or from about 900 bp to about 1000 bp.

In certain embodiments, the HS2 region has a length of from about 850 bp to about 900 bp. In certain non-limiting embodiments, the HS2 region has a length of about 860 bp. In certain non-limiting embodiments, the HS2 region comprises or has the nucleotide sequence set forth in SEQ ID NO: 9, which is provided below:

```
                                      [SEQ ID NO: 9]
GTATATGTGTATATATATATATATATATTCAGGAAATAATATATTCTAGA

ATATGTCACATTCTGTCTCAGGCATCCATTTTCTTTATGATGCCGTTTGA
```

-continued
```
GGTGGAGTTTTAGTCAGGTGGTCAGCTTCTCCtttttttttGCCATCTGCC

CTGTAAGCATCCTGCTGGGGACCCAGATAGGAGTCATCACTCTAGGCTGA

GAACATCTGGGCACACACCCTAAGCCTCAGCATGACTCATCATGACTCAG

CATTGCTGTGCTTGAGCCAGAAGGTTTGCTTAGAAGGTTACACAGAACCA

GAAGGCGGGGGTGGGGCACTGACCCCGACAGGGGCCTGGCCAGAACTGCT

CATGCTTGGACTATGGGAGGTCACTAATGGAGACACACAGAAATGTAACA

GGAACTAAGGAAAAACTGAAGCTTATTTAATCAGAGATGAGATGCTGGAA

GGGATAGAGGGAGCTGAGCTTGTAAAAAGTATAGTAATCATTCAGCAAAT

GGTTTTGAAGCACCTGCTGGATGCTAAACACTATTTTCAGTGCTTGAATC

ATAAATAAGAATAAAACATGTATCTTATTCCCCACAAGAGTCCAAGTAAA

AAATAACAGTTAATTATAATGTGCTCTGTCCCCCAGGCTGGAGTGCAGTG

GCACGATCTCAGCTCACTGCAACCTCCGCCTCCCGGGTTCAAGCAATTCT

CCTGCCTCAGCCACCCTAATAGCTGGGATTACAGGTGCACACCACCATGC

CAGGCTAATTTTTGTACTTTTTGTAGAGGCAGGGTATCACCATGTTGTCC

AAGATGGTCTTGAACTCCTGAGCTCCAAGCAGTCCACCCACCTCAGCCTC

CCAAAGTGCT
```

In certain embodiments, the HS2 region has a length of from about 800 bp to about 850 bp. In certain embodiments, the HS2 region has a length of about 840 bp. In certain embodiments, the HS2 region has a length of about 820 bp. In certain embodiments, the HS2 region has a length of about 816 bp.

In certain non-limiting embodiments, the HS2 region comprises or has the nucleotide sequence that is a consecutive portion of SEQ ID NO:9. In certain embodiments, the consecutive portion of SEQ ID NO: 9 is at least about 600 bp, or at least about 700 bp, or at least about 800 bp, or at least about 820 bp, and up to about 860 bp in length. Alternatively or additionally, in non-limiting various embodiments, the HS2 region comprises or has nucleotides 1 to 860, 20 to 860, 30 to 860, 40 to 860, 45 to 860, 50 to 860, 100 to 860, or 200 to 860 of SEQ ID NO: 9. In certain embodiments, the HS2 region comprises or has nucleotides 45 to 860 of SEQ ID NO: 9.

In certain embodiments, the HS2 region comprises or has a nucleotide sequence that is at least about 80%, at least about 85%, at least about 90%, at least about 99%, or at least about 100% homologous to the nucleotide sequence set forth in SEQ ID NO:9 or a consecutive portion thereof. In certain embodiments, the HS2 region comprises or has a nucleotide sequence that is at least about 99% homologous to the nucleotide sequence set forth in SEQ ID NO:9. In certain embodiments, the HS2 region comprises or has a nucleotide sequence that is about 100% homologous to nucleotides 45 to 860 of SEQ ID NO: 9, e.g., the HS2 region has a nucleotide sequence that includes up to 5, up to 4, up to 3, up to 2, or up to 1 mutations of nucleotides 45 to 860 of SEQ ID NO: 9. In certain embodiments, the HS2 region comprises or has the nucleotide sequence set forth in SEQ ID NO: 33, which is provided below.

```
                                        (SEQ ID NO: 33)
TCTAGAATATGTCACATTCTGTCTCAGGCATCCATTTTCTTTATGATGCC

GTTTGAGGTGGAGTTTTAGTCAGGTGGTCAGCTTCTCCttttttttGCCA

TCTGCCCTGTAAGCATCCTGCTGGGGACCCAGATAGGAGTCATCACTCTA

GGCTGAGAACATCTGGGCACACACCCTAAGCCTCAGCATGACTCATCATG

ACTCAGCATTGCTGTGCTTGAGCCAGAAGGTTTGCTTAGAAGGTTACACA

GAACCAGAAGGCGGGGGTGGGGCACTGACCCCGACAGGGGCCTGGCCAGA

ACTGCTCATGCTTGGACTATGGGAGGTCACTAATGGAGACACACAGAAAT

GTAACAGGAACTAAGGAAAAACTGAAGCTTATTTAATCAGAGATGAGATG

CTGGAAGGGATAGAGGGAGCTGAGCTTGTAAAAAGTATAGTAATCATTCA

GCAAATGGTTTTGAAGCACCTGCTGGATGCTAAACACTATTTTCAGTGCT

TGAATCATAAATAAGAACAAAACATGTATCTTATTCCCCACAAGAGTCCA

AGTAAAAAATAACAGTTAATTATAATGTGCTCTGTCCCCCAGGCTGGAGT

GCAGTGGCACGATCTCAGCTCACTGCAACCTCCGCCTCCCGGGTTCAAGC

AATTCTCCTGCCTCAGCCACCCTAATAGCTGGGATTACAGGTGCACACCA

CCATGCCAGGCTAATTTTTGTACTTTTTGTAGAGGCAGGGTATCACCATG

TTGTCCAAGATGGTCTTGAACTCCTGAGCTCCAAGCAGTCCACCCACCTC

AGCCTCCCAAAGTGCT.
```

In certain embodiments, the HS2 region comprises or has a nucleotide sequence that is a modification of the nucleotide sequence set forth in SEQ ID NO: 9 or a consecutive portion thereof. Non-limiting modifications include deletion, mutations, additions, or combinations thereof. In certain embodiments, the modification comprises one or more mutation, e.g., up to 5, up to 4, up to 3, up to 2, or up to 1 mutations. In certain embodiments, the modification comprises one mutation. In certain embodiments, the one or more mutation is located within a polyadenylation site (or polyadenylation signal motif), e.g., a polyadenylation site on SEQ ID NO: 9. In certain embodiments, the polyadenylation site has the nucleotide sequence AATAAA. In certain embodiments, the one or more mutation comprises a mismatch mutation T>C at a polyadenylation site having the nucleotide sequence AATAAA, e.g., the mutated sequence is AACAAA. In certain embodiments, the polyadenylation site has the nucleotide sequence ATTAAA. In certain embodiments, the one or more mutation comprises a mismatch mutation T>C at a polyadenylation site having the nucleotide sequence ATTAAA, e.g., the mutated sequence is ATCAAA or ACTAAA. In certain embodiments, the one or more mutation comprises two mismatch mutations T>C at a polyadenylation site having the nucleotide sequence ATTAAA, e.g., the mutated sequence is ACCAAA. The inventors discovered that a modification (e.g., one or more mismatch mutation) at a polyadenylation site can preempt premature termination of RNA transcription, thereby increasing the titer of the expression cassette (e.g., expression vector) without compromising the expression of the globin gene.

In certain embodiments, the HS2 region has a length of about 650 bp (e.g., 646-bp). In certain embodiments, the HS2 region has a length of about 420 bp (e.g., 423 bp).

The length and the sequence of the HS3 region can vary. The HS3 region can have a length of from about 200 bp to about 1400 bp, e.g., from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, from about 1100 bp to about 1200 bp, from about 1200 bp to about 1300 bp, or from about 1300 bp to about 1400 bp. In certain embodiments, the HS3 region has a length of about 1300 bp. In certain non-limiting embodiments, the HS3 region has a length of 1308 bp. In certain non-limiting embodiments, the HS3 region has a length of 1301 bp. In certain non-limiting embodiments, the HS3 region comprises or has the nucleotide sequence set forth in SEQ ID NO:5, which is provided below:

```
                                        [SEQ ID NO: 5]
AAGCTTTCATTAAAAAAAGTCTAACCAGCTGCATTCGACTTTGACTGCAG

CAGCTGGTTAGAAGGTTCTACTGGAGGAGGGTCCCAGCCCATTGCTAAAT

TAACATCAGGCTCTGAGACTGGCAGTATATCTCTAACAGTGGTTGATGCT

ATCTTCTGGAACTTGCCTGCTACATTGAGACCACTGACCCATACATAGGA

AGCCCATAGCTCTGTCCTGAACTGTTAGGCCACTGGTCCAGAGAGTGTGC

ATCTCCTTTGATCCTCATAATAACCCTATGAGATAGACACAATTATTACT

CTTACTTTATAGATGATGATCCTGAAAACATAGGAGTCAAGGCACTTGCC

CCTAGCTGGGGGTATAGGGGAGCAGTCCCATGTAGTAGTAGAATGAAAAA

TGCTGCTATGCTGTGCCTCCCCCACCTTTCCCATGTCTGCCCTCTACTCA

TGGTCTATCTCTCCTGGCTCCTGGGAGTCATGGACTCCACCCAGCACCAC

CAACCTGACCTAACCACCTATCTGAGCCTGCCAGCCTATAACCCATCTGG

GCCCTGATAGCTGGTGGCCAGCCCTGACCCCACCCCACCCTCCCTGGAAC

CTCTGATAGACACATCTGGCACACCAGCTCGCAAAGTCACCGTGAGGGTC

TTGTGTTTGCTGAGTCAAAATTCCTTGAAATCCAAGTCCTTAGAGACTCC

TGCTCCCAAATTTACAGTCATAGACTTCTTCATGGCTGTCTCCTTTATCC

ACAGAATGATTCCTTTGCTTCATTGCCCCATCCATCTGATCCTCCTCATC

AGTGCAGCACAGGGCCCATGAGCAGTAGCTGCAGAGTCTCACATAGGTCT

GGCACTGCCTCTGACATGTCCGACCTTAGGCAAATGCTTGACTCTTCTGA

GCTCAGTCTTGTCATGGCAAAATAAAGATAATAATAGTGTTTTTTTATGG

AGTTAGCGTGAGGATGGAAAACAATAGCAAAATTGATTAGACTATAAAG

GTCTCAACAAATAGTAGTAGATTTTATCATCCATTAATCCTTCCCTCTCC

TCTCTTACTCATCCCATCACGTATGCCTCTTAATTTTCCCTTACCTATAA

TAAGAGTTATTCCTCTTATTATATTCTTCTTATAGTGATTCTGGATATTA

AAGTGGGAATGAGGGGCAGGCCACTAACGAAGAAGATGTTTCTCAAAGAA
```

-continued

GCCATTCTCCCCACATAGATCATCTCAGCAGGGTTCAGGAAGATAAAGGA

GGATCAAGGTCGAAGGTAGGAACTAAGGAAGAACACTGGGCAAGTGGATC

C

In certain embodiments, the HS2 region comprises or has the nucleotide sequence that is a consecutive portion of SEQ ID NO: 5. In certain embodiments, the consecutive portion of SEQ ID NO: 5 is at least about 600 bp, or at least about 700 bp, or at least about 800 bp, at least about 900 bp, at least about 1000 bp, at least about 1100 bp, or at least about 1200 bp, and up to about 1300 bp in length.

In certain embodiments, the HS3 region comprises or has a nucleotide sequence that is at least about 80%, at least about 85%, at least about 90%, at least about 99%, or at least about 100% homologous to the nucleotide sequence set forth in SEQ ID NO: 5 or a consecutive portion thereof. In certain embodiments, the HS3 region comprises or has a nucleotide sequence that is at least about 99% homologous to the nucleotide sequence set forth in SEQ ID NO: 5. In certain embodiments, the HS3 region comprises or has a nucleotide sequence that is about 100% homologous to the nucleotide sequence set forth in SEQ ID NO: 5, e.g., the HS3 region has a nucleotide sequence that includes up to 5, up to 4, up to 3, up to 2, or up to 1 mutations of SEQ ID NO: 5. In certain embodiments, the HS3 region comprises or has the nucleotide sequence set forth in SEQ ID NO: 34, which is provided below.

(SEQ ID NO: 34)
AAGCTTTCATCaaaaaaaGTCTAACCAGCTGCATTCGACTTTGACTGCAG

CAGCTGGTTAGAAGGTTCTACTGGAGGAGGGTCCCAGCCCATTGCTAAAT

TAACATCAGGCTCTGAGACTGGCAGTATATCTCTAACAGTGGTTGATGCT

ATCTTCTGGAACTTGCCTGCTACATTGAGACCACTGACCCATACATAGGA

AGCCCATAGCTCTGTCCTGAACTGTTAGGCCACTGGTCCAGAGAGTGTGC

ATCTCCTTTGATCCTCATAATAACCCTATGAGATAGACACAATTATTACT

CTTACTTTATAGATGATGATCCTGAAAACATAGGAGTCAAGGCACTTGCC

CCTAGCTGGGGGTATAGGGGAGCAGTCCCATGTAGTAGTAGAATGAAAAA

TGCTGCTATGCTGTGCCTCCCCCACCTTTCCCATGTCTGCCCTCTACTCA

TGGTCTATCTCTCCTGGCTCCTGGGAGTCATGGACTCCACCCAGCACCAC

CAACCTGACCTAACCACCTATCTGAGCCTGCCAGCCTATAACCCATCTGG

GCCCTGATAGCTGGTGGCCAGCCCTGACCCCCACCCCACCCTCCCTGGAAC

CTCTGATAGACACATCTGGCACACCAGCTCGCAAAGTCACCGTGAGGGTC

TTGTGTTTGCTGAGTCAAAATTCCTTGAAATCCAAGTCCTTAGAGACTCC

TGCTCCCAAATTTACAGTCATAGACTTCTTCATGGCTGTCTCCTTTATCC

ACAGAATGATTCCTTTGCTTCATTGCCCCATCCATCTGATCCTCCTCATC

AGTGCAGCACAGGGCCCATGAGCAGTAGCTGCAGAGTCTCACATAGGTCT

GGCACTGCCTCTGACATGTCCGACCTTAGGCAAATGCTTGACTCTTCTGA

GCTCAGTCTTGTCATGGCAAAACAAAGATAATAATAGTGttttttttATGG

AGTTAGCGTGAGGATGGAAAACAATAGCAAAATTGATTAGACTATAAAAG

GTCTCAACAAATAGTAGTAGATTTTATCATCCATTAATCCTTCCCTCTCC

-continued
TCTCTTACTCATCCCATCACGTATGCCTCTTAATTTTCCCTTACCTATAA

TAAGAGTTATTCCTCTTATTATATTCTTCTTATAGTGATTCTGGATATCA

AAGTGGGAATGAGGGGCAGGCCACTAACGAAGAAGATGTTTCTCAAAGAA

GCCATTCTCCCCACATAGATCATCTCAGCAGGGTTCAGGAAGATAAAGGA

GGATCAAGGTCGAAGGTAGGAACTAAGGAAGAACACTGGGCAAGTGGATC

C.

In certain embodiments, the HS3 region comprises or has a nucleotide sequence that is a modification of the nucleotide sequence set forth in SEQ ID NO: 5 or a consecutive portion thereof. Non-limiting modifications include deletion, mutations, additions, or combinations thereof. In certain embodiments, the modification comprises one or more mutation, e.g., up to 5, up to 4, up to 3, up to 2, or up to 1 mutations. In certain embodiments, the modification comprises three mutations. In certain embodiments, the one or more mutation is located within a polyadenylation site (or polyadenylation signal motif), e.g., a polyadenylation site on SEQ ID NO: 5. In certain embodiments, the polyadenylation site has the nucleotide sequence AATAAA. In certain embodiments, the one or more mutation comprises a mismatch mutation T>C at a polyadenylation site having the nucleotide sequence AATAAA, e.g., the mutated sequence is AACAAA. In certain embodiments; the polyadenylation site has the nucleotide sequence ATTAAA. In certain embodiments, the one or more mutation comprises a mismatch mutation T>C at a polyadenylation site having the nucleotide sequence ATTAAA, e.g., the mutated sequence is ATCAAA or ACTAAA. In certain embodiments, the one or more mutation comprises two mismatch mutations T>C at a polyadenylation site having the nucleotide sequence ATTAAA, e.g., the mutated sequence is ACCAAA.

A modification (e.g., one or more mismatch mutation) at a polyadenylation site can preempt premature termination of RNA transcription, thereby increasing the titer of the expression cassette (e.g., expression vector) without compromising the expression of the globin gene.

In certain embodiments, the HS3 region has a length of about 850 bp (e.g., 845 bp). In certain embodiments, the HS3 region has a length of from about 280 bp to about 290 bp (e.g., 280 bp and 287 bp).

Similarly, the length and the sequence of the HS4 region can vary. The HS4 region can have a length of from about 200 bp to about 1200 bp, e.g., from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, or from about 1100 bp to about 1200 bp.

In certain embodiments, the HS4 region has a length of about 1.0 kb or more. In certain embodiments, the HS4 region has a length of about 1.1 kb. In certain embodiments, the HS4 region has a length of about 1150 bp (e.g., 1153 bp). In certain non-limiting embodiments, the HS4 region has a length of 1100 bp. In certain non-limiting embodiments, the HS4 region has a length of 1065 bp. In certain non-limiting embodiments, the HS4 region has the nucleotide sequence set forth in SEQ ID NO: 6, which is provided below:

[SEQ ID NO: 6]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAATAAATATATCATTTAAATGCATAAATAAGCAAACCC

TGCTCGGGAATGGGAGGGAGAGTCTCTGGAGTCCACCCCTTCTCGGCCCT

GGCTCTGCAGATAGTGCTATCAAAGCCCTGACAGAGCCCTGCCCATTGCT

GGGCCTTGGAGTGAGTCAGCCTAGTAGAGAGGCAGGGCAAGCCATCTCAT

AGCTGCTGAGTGGGAGAGAGAAAAGGGCTCATTGTCTATAAACTCAGGTC

ATGGCTATTCTTATTCTCACACTAAGAAAAAGAATGAGATGTCTACATAT

ACCCTGCGTCCCCTCTTGTGTACTGGGGCCCCCAAGAGCTCTCTAAAAGT

GATGGCAAAGTCATTGCGCTAGATGCCATCCCATCTATTATAAACCTGCA

TTTGTCTCCACACACCAGTCATGGACAATAACCCTCCTCCCAGGTCCACG

TGCTTGTCTTTGTATAATACTCAAGTAATTTCGGAAAATGTATTCTTTCA

ATCTTGTTCTGTTATTCCTGTTTCAATGGCTTAGTAGAAAAAGTACATAC

TTGTTTTCCCATAAATTGACAATAGACAATTTCACATCAATGTCTATATG

GGTCGTTGTGTTTGCTGTGTTTGCAAAAACTCACAATAACTTTATATTGT

TACTACTCTAAGAAAGTTACAACATGGTGAATACAAGAGAAAGCTATTAC

AAGTCCAGAAAATAAAAGTTATCATCTTGAGGCCTCAGCTTTCTAGGAAT

AATATCAATATTACAAAATTTAATCTAACAATTATGAACAGCAATGAGAT

AATATGTACAAAGTACCCAGACCTATGTGGTAGAGCATCAAGGAAGCGCA

TTGCGGAGCAGTTTTTTGTTTGTTTGTTTTTGTATTCTGTTTCGTGAGGC

AAGGTTTCACTCTGCTGTCCAGGCTGGAGTGCAGTGGCAAGATCATGTCT

CACTGCAGCCTTGAC

In certain non-limiting embodiments, the HS4 region has the nucleotide sequence set forth in SEQ ID NO:7, which is provided below:

[SEQ ID NO: 7]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAATAAATATATCATTAAATGCATAAATAAGCAAACCCT

GCTCGGGAATGGGAGGGAGAGTCTCTGGAGTCCACCCCTTCTCGGCCCTG

GCTCTGCAGATAGTGCTATCAAAGCCCTGACAGAGCCCTGCCCATTGCTG

GGCCTTGGAGTGAGTCAGCCTAGTAGAGAGGCAGGGCAAGCCATCTCATA

GCTGCTGAGTGGGAGAGAGAAAAGGGCTCATTGTCTATAAACTCAGGTCA

TGGCTATTCTTATTCTCACACTAAGAAAAAGAATGAGATGTCTACATATA

CCCTGCGTCCCCTCTTGTGTACTGGGGCCCCCAAGAGCTCTCTAAAAGTG

ATGGCAAAGTCATTGCGCTAGATGCCATCCCATCTATTATAAACCTGCAT

TTGTCTCCACACACCAGTCATGGACAATAACCCTCCTCCCAGGTCCACGT

GCTTGTCTTTGTATAATACTCAAGTAATTTCGGAAAATGTATTCTTTCAA

TCTTGTTCTGTTATTCCTGTTTCAATGGCTTAGTAGAAAAAGTACATACT

TGTTTTCCCATAAATTGACAATAGACAATTTCACATCAATGTCTATATGG

GTCGTTGTGTTTGCTGTGTTTGCAAAAACTCACAATAACTTTATATTGTT

-continued

ACTACTCTAAGAAAGTTACAACATGGTGAATACAAGAGAAAGCTATTACA

AGTCCAGAAAATAAAAGTTATCATCTTGAGGCCTCAGCTTTCTAGGaATA

ATATCAATATTACAAAATTAATCTAACAATTATGAACAGCAATGAGATAA

TATGTACAAAGTACCCAGACCTATGTGGTAGAGCATCAAGGAAGCGCATT

GCGGAGCAGTTTTTTGTTTGTTTGTTTTTGTATTCTGTTTCGTGAGGCAA

GGTTTCACTCTGCTGTCCAGGCTGGAGTGCAGTGGCAAGATCATGTCTCA

CTGCAGCCTTGACAC

In certain embodiments, the HS4 region has a length of less than about 1.0 kb, less than about 900 bp, or less than about 800 bp. In certain embodiments, the HS4 region has a length of from about 700 bp to about 800 bp, e.g., from about 700 bp to about 750 bp, or from about 750 bp to about 800 bp. In certain embodiments, the HS4 region has a length of about 750 bp. In certain embodiments, the HS4 region has a length of about 754 bp.

In certain embodiments, the HS4 region comprises or has the nucleotide sequence that is a consecutive portion of SEQ ID NO: 6 or 7. In certain embodiments, the consecutive portion of SEQ ID NO: 6 or 7 is at least about 600 bp or at least about 700 bp and up to about 800 bp or up to about 900 bp, or up to about 1.0 kb in length. Alternatively or additionally, in non-limiting various embodiments, the HS4 region comprises or has nucleotides 1 to 900, 100 to 900, 100 to 1000, 110 to 900, 115 to 900, 115 to 890, 115 to 880, 115 to 870, 115 to 868, 115 to 860, 115 to 1000 of SEQ ID NO: 6 or 7. In certain embodiments, the HS4 region comprises or has nucleotides 115 to 868 of SEQ ID NO: 6.

In certain embodiments, the HS4 region comprises or consists essentially of a core sequence of the HS4 region. In certain embodiments, the HS4 region or consists essentially of the full length of a 280 bp core sequence of a human HS4 region (e.g., the 280 bp core sequence of human HS4 disclosed in Pruzina et al., *Nucleic Acdis Research* (1991); 19:7:1413-1419, which is incorporated by reference in its entirety).

In certain embodiments, the HS4 region does not comprise the nucleotide sequence set forth in SEQ ID NO: 50, which is provided below.

[SEQ ID NO: 50]
TGAGCCCCTTTTCCTCTAACTGAAAGAAGGAAAAAAAAAATGGAACC

CAAAATATTCTACATAGTTTCCATGTCACAGCCAGGGCTGGGCAGTC

TCCTGTTATTTCTTTTAAAA

In certain embodiments, the HS4 region does not comprise the nucleotide sequence set forth in SEQ ID NO: 51, which is provided below.

[SEQ ID NO: 51]
TTTAATCTAACAATTATGAACAGCAATGAGATAATATGTACAAAGTA

CCCAGACCTATGTGGTAGAGCATCAAGGAAGCGCATTGCGGAGCAGT

TTTTTGTTTGTTTGTTTTTGTATTCTGTTTCGTGAGGCAAGGTTTCA

CTCTGCTGTCCAGGCTGGAGTGCAGTGGCAAGATCATGTCTCACTGC

AGCCTTGAC

In certain embodiments, the HS4 region does not comprise the nucleotide sequence set forth in SEQ ID NO: 50 or the nucleotide sequence set forth in SEQ ID NO: 51.

In certain embodiments, the HS4 region comprises or has a nucleotide sequence that is at least about 80%, at least about 85%, at least about 90%, at least about 99%, or at least about 100% homologous to the nucleotide sequence set forth in SEQ ID NO: 6 or a consecutive portion thereof. In certain embodiments, the HS4 region comprises or has a nucleotide sequence that is at least about 80%, at least about 85%, at least about 90%, at least about 99%, or at least about 100% homologous to the nucleotide sequence set forth in SEQ ID NO: 7 or a consecutive portion thereof. In certain embodiments, the HS4 region comprises or has a nucleotide sequence that is at least about 99% homologous to the nucleotide sequence set forth in SEQ ID NO: 6 or 7. In certain embodiments, the HS4 region comprises or has a nucleotide sequence that is at least about 99% (e.g., about 100%) homologous to nucleotides 115 to 868 of SEQ ID NO: 6, e.g., the HS4 region has a nucleotide sequence that includes up to 5, up to 4, up to 3, up to 2, or up to 1 mutations of nucleotides 115 to 868 of SEQ ID NO: 6. In certain embodiments, the HS4 region comprises or has the nucleotide sequence set forth in SEQ ID NO: 35, which is provided below.

[SEQ ID NO: 35]

```
TAAATATATCATTTAAATGCATAAATAAGCAAACCCTGCTCGGGAAT

GGGAGGGAGAGTCTCTGGAGTCCACCCCTTCTCGGCCCTGGCTCTGC

AGATAGTGCTATCAAAGCCCTGACAGAGCCCTGCCCATTGCTGGGCC

TTGGAGTGAGTCAGCCTAGTAGAGAGGCAGGGCAAGCCATCTCATAG

CTGCTGAGTGGGAGAGAGAAAAGGGCTCATTGTCTATAAACTCAGGT

CATGGCTATTCTTATTCTCACACTAAGAAAAAGAATGAGATGTCTAC

ATATACCCTGCGTCCCCTCTTGTGTACTGGGGCCCCCAAGAGCTCTC

TAAAAGTGATGGCAAAGTCATTGCGCTAGATGCCATCCCATCTATTA

TAAACCTGCATTTGTCTCCACACACCAGTCATGGACAATAACCCTCC

TCCCAGGTCCACGTGCTTGTCTTTGTATAATACTCAAGTAATTTCGG

AAAATGTATTCTTTCAATCTTGTTCTGTTATTCCTGTTTCAATGGCT

TAGTAGAAAAAGTACATACTTGTTTTCCCATAAATTGACAATAGACA

ATTTCACATCAATGTCTATATGGGTCGTTGTGTTTGCTGTGTTTGCA

AAAACTCACAATAACTTTATATTGTTACTACTCTAAGAAAGTTACAA

CATGGTGAATACAAGAGAAAGCTATTACAAGTCCAGAAAACAAAAGT

TATCATCTTGAGGCCTCAGCTTTCTAGGAATAATATCAATATTACAA

AA.
```

In certain embodiments, the HS4 region comprises or has a nucleotide sequence that is a modification of the nucleotide sequence set forth in SEQ ID NO: 6 or a consecutive portion thereof. In certain embodiments, the HS4 region comprises or has a nucleotide sequence that is a modification of the nucleotide sequence set forth in SEQ ID NO: 7 or a consecutive portion thereof. Non-limiting modifications include deletion, mutations, additions, or combinations thereof. In certain embodiments, the modification comprises one or more mutation, e.g., up to 5, up to 4, up to 3, up to 2, or up to 1 mutations. In certain embodiments, the modification comprises one mutation. In certain embodiments, the one or more mutation is located within a polyadenylation site (or polyadenylation signal motif), e.g., a polyadenylation site on SEQ ID NO: 6 or a polyadenylation site on SEQ ID NO: 7. In certain embodiments, the polyadenylation site has the nucleotide sequence AATAAA. In certain embodiments, the one or more mutation comprises a mismatch mutation T>C at a polyadenylation site having the nucleotide sequence AATAAA, e.g., the mutated sequence is AACAAA. In certain embodiments, the polyadenylation site has the nucleotide sequence ATTAAA. In certain embodiments, the one or more mutation comprises a mismatch mutation T>C at a polyadenylation site having the nucleotide sequence ATTAAA, e.g., the mutated sequence is ATCAAA or ACTAAA. In certain embodiments, the one or more mutation comprises two mismatch mutations T>C at a polyadenylation site having the nucleotide sequence ATTAAA, e.g., the mutated sequence is ACCAAA. A modification (e.g., one or more mismatch mutation) at a polyadenylation site can preempt premature termination of RNA transcription, thereby increasing the titer of the expression cassette (e.g., expression vector) without compromising the expression of the globin gene.

In certain embodiments, the HS4 region has a length of less than about 500 bp. In certain embodiments, the HS4 region has a length of about 450 bp. In certain non-limiting embodiments, the HS4 region has a length of about 446 bp. In certain non-limiting embodiments, the HS4 region comprises or has the nucleotide sequence set forth in SEQ ID NO:8, which is provided below:

[SEQ ID NO: 8]

```
TGGAACCCAAAATATTCTACATAGTTTCCATGTCACAGCCAGGGCTG

GGCAGTCTCCTGTTATTTCTTTTAAAATAAATATATCATTTAAATGC

ATAAATAAGCAAACCCTGCTCGGGAATGGGAGGGAGAGTCTCTGGAG

TCCACCCCTTCTCGGCCCTGGCTCTGCAGATAGTGCTATCAAAGCCC

TGACAGAGCCCTGCCCATTGCTGGGCCTTGGAGTGAGTCAGCCTAGT

AGAGAGGCAGGGCAAGCCATCTCATAGCTGCTGAGTGGGAGAGAGAA

AAGGGCTCATTGTCTATAAACTCAGGTCATGGCTATTCTTATTCTCA

CACTAAGAAAAAGAATGAGATGTCTACATATACCCTGCGTCCCCTCT

TGTGTACTGGGGTCCCCAAGAGCTCTCTAAAAGTGATGGCAAAGTCA

TTGCGCTAGATGCCATCCCATCT
```

In certain embodiments, the HS4 region has a length of about 280 bp (e.g., 283 bp). In certain embodiments, the HS4 region has a length of about 240 bp (e.g., 243 bp).

In certain non-limiting embodiments, the β-globin LCR comprises or consists essentially of a HS2 region having the nucleotide sequence set forth in SEQ ID NO:9 or a consecutive portion thereof, a modification of SEQ ID NO: 9, a modification of a consecutive portion of SEQ ID NO: 9 (e.g., SEQ ID NO: 33), SEQ ID NO:20, SEQ ID NO:21; a HS3 region having the nucleotide sequence set forth in SEQ ID NO:5 or a modification of SEQ ID NO: 5 (e.g., SEQ ID NO: 34); and a HS4 region having the nucleotide sequence set forth in SEQ ID NO:6 or a consecutive portion thereof, SEQ ID NO:7 or a consecutive portion thereof, a modification of SEQ ID NO: 6, a modification of a consecutive portion of SEQ ID NO: 6 (e.g., SEQ ID NO: 35), a modification of SEQ ID NO: 7, a modification of a consecutive portion of SEQ ID NO: 7, or SEQ ID NO:8, and the β-globin LCR does not comprise a HS1 region.

In certain non-limiting embodiments, the β-globin LCR comprises or consists essentially of a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7, as shown in FIG. 1.

Figure 15:
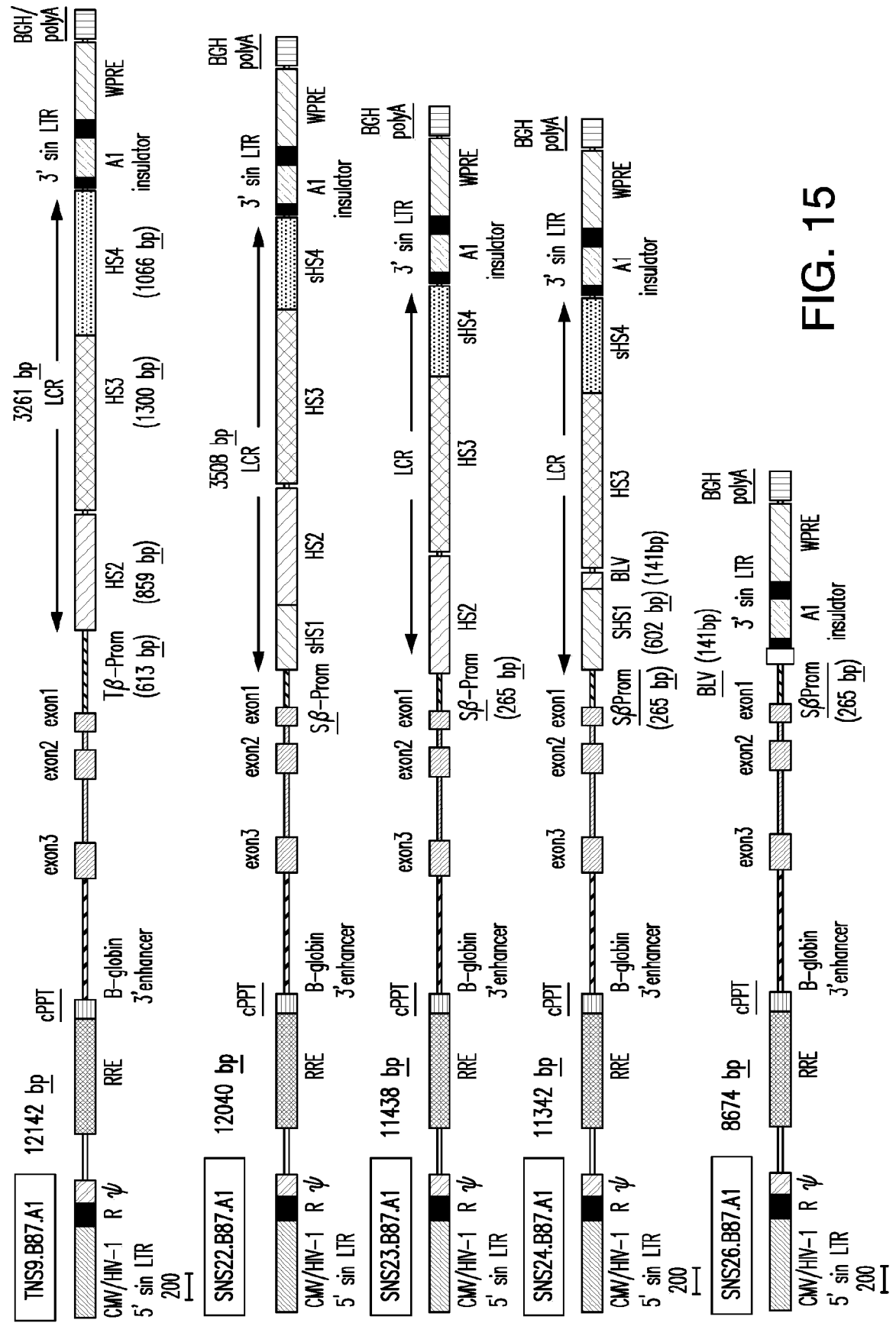
FIG. 15 depicts recombinant vectors comprising expres-
sion cassettes in accordance with certain non-limiting
embodiments of the presently disclosed subject matter.

In certain non-limiting embodiments, the β-globin LCR comprises or consists essentially of a HS2 region having nucleotides 45 to 860 of SEQ ID NO: 9; a HS3 region having the nucleotide sequence set forth in SEQ ID NO: 5; and a HS4 region having nucleotides 115 to 868 of SEQ ID NO: 6, and the β-globin LCR does not comprise a HS1 region, e.g., the β-globin LCR of SNS23.B87.A1 shown in FIG. 15.

Figure 13:
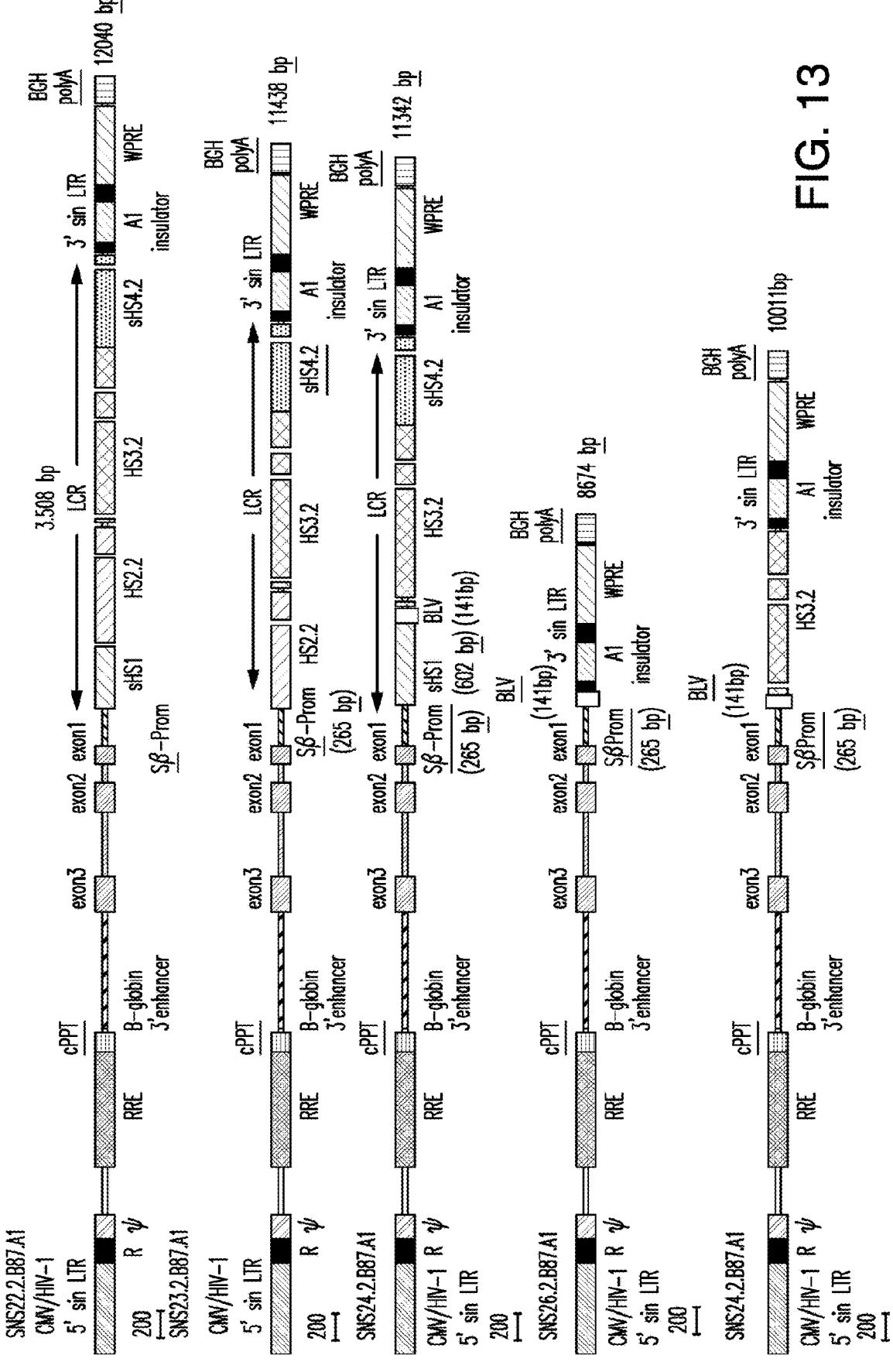
FIG. 13 depicts recombinant vectors comprising expres-
sion cassettes in accordance with certain non-limiting
embodiments of the presently disclosed subject matter.
Figure 14:
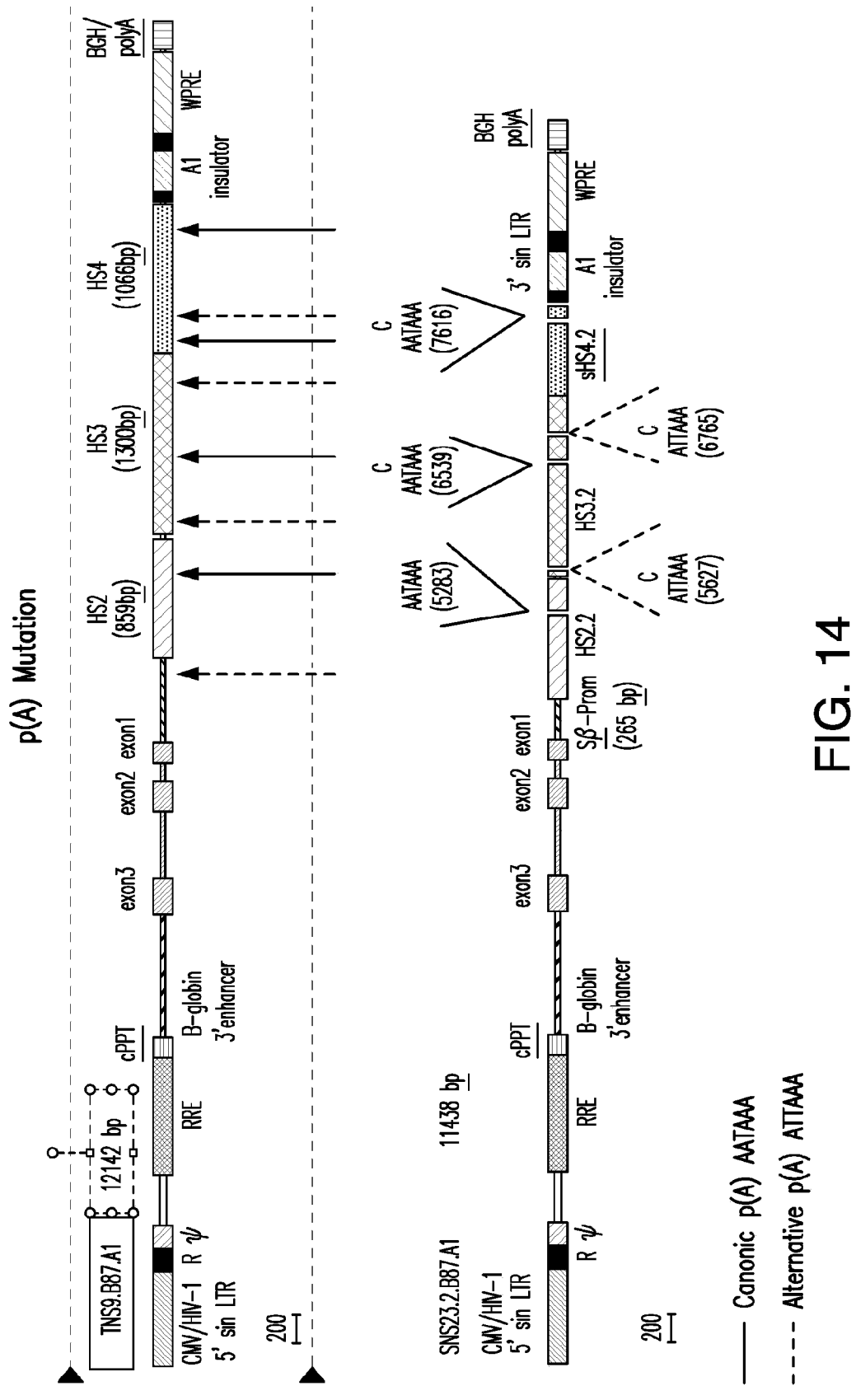
FIG. 14 depicts recombinant vectors comprising expres-
sion cassettes in accordance with certain non-limiting
embodiments of the presently disclosed subject matter.

In certain non-limiting embodiments, the β-globin LCR comprises or consists essentially of a HS2 region having the nucleotide sequence set forth in SEQ ID NO: 33; a HS3 region having the nucleotide sequence set forth in SEQ ID NO: 34; and a HS4 region having the nucleotide sequence set forth in SEQ ID NO: 35, and the β-globin LCR does not comprise a HS1 region, e.g., the β-globin LCR of SNS23.2.B87.A1 shown in FIGS. 13 and 14.

In certain non-limiting embodiments, the β-globin LCR further comprises a HS1 region, i.e., a β-globin LCR comprising a HS1 region, a HS2 region, a HS3 region, and a HS4 region. In certain embodiments, the HS1 region, HS2 region, HS3 region and HS4 region within the β-globin LCR are contiguous. In certain non-limiting embodiments, the β-globin LCR consisting essentially of a HS1 region, a HS2 region, a HS3 region and a HS4 region. In certain embodiments, the β-globin LCR comprises two introduced GATA-1 binding sites at the junction between the HS3 region and the HS4 region.

The length and the sequence of the HS1 region can vary. In certain embodiments, the HS1 region is from about 300 bp to about 1500 bp in length, e.g., from about 300 bp to about 1100 bp in length. In certain embodiments, the HS1 region has a length of about 1.0 kb or more, e.g., about 1.1 kb, about 1.2 kb, about 1.3 kb, about 1.4 kb, or about 1.5 kb. In certain embodiments, the HS1 region has a length of about 1.1 kb. In certain non-limiting embodiments, the HS1 region has a length of 1074 bp. In certain non-limiting embodiments, the HS1 region comprises or has the nucleotide sequence set forth in SEQ ID NO:2, which is provided below:

```
                                      [SEQ ID NO: 2]
AAGTAAACTTCCACAACCGCAAGCTTATTGAGGCTAAGGCATCTGTG

AAGGAAAGAAACATCTCCTCTAAACCACTATGCTGCTAGAGCCTCTT

TTCTGTACTCAAGCCTCATTCAGACACTAGTGTCACCAGTCTCCTCA

TATACCTATTGTATTTTCTTCTTCTTGCTGGTTTAGTCATGTTTTCT

GGGAGCTTAGGGGCTTATTTTATTTTGTTTTGTTTTCTAATCAACAG

AGATGGGCAAACCCATTATTTTTTTCTTTAGACTTGGGATGGTGATA

GCTGGGCAGCGTCAGAAACTGTGTGTGGATATAGATAAGAGCTCGGA

CTATGCTGAGCTGTGATGAGGGAGGGACCTAGCCAAAGGCAGTGAGA

GTCAGAATGCTCCTGCTATTGCCTTCTCAGTCCCCACGCTTGGTTTC

TACACAAGTAGATACATAGAAAAGGCTATAGGTTAGTGTTTGAGAGT

CCTGCATGAGTTAGTTGCTCAGAAATGCCCGATAAATATGTTATGTG

TGTTTATGTATATATATGTTTTATATATATATATGTGTGTGTGTGTG
```

```
-continued
TGTGTGTGTGTTGTGTTTACAAATATGTGATTATCATCAAAACGTGA

GGGCTAAAGTGACCAGATAACTTGCAGGTCCTAGGATACCAGGAAAA

TAAATTACATTCCAAAAATTTAACTGAGACTTTAAAAAAAAAAAAAA

AAAAAAAAAAAAAACCAGTGATCCATGGACACAGGGAGGGGAACATC

ACACACTGGGGCCTGTTGGGGGTGGGGGGCTAGGGGAAGGATAGCAT

TAGGAGAAATACCTAATGTAGATGACGGGTTGATGGGTGCAGCAAAC

CACCATGGCACATGTACCCCAGAACTTAAAGCATATTAAAAAAACAG

TGATCATAAAAGAAGCTCAAATTTAACTATAAGAGACGGAATGGCTC

CCACAATTCTTAACTATAATCTTACAGAATATTCTCATTGAATAGAA

GTATGCTTATCATTAGAGATTTGGACAGCCAGGAAAGCACAGAAAAA

AAAAAAAGGAGCTCTGTTGCCTTATAGCCTAGAGGTGTTT
```

In certain embodiments, the HS1 region has a length of less than about 1.0 kb, e.g., from about 400 bp to about 700 bp, from about 400 bp to about 500 bp, from about 500 bp to about 600 bp, from about 600 bp to about 700 bp, from about 700 bp to about 800 bp, from about 800 bp to about 900 bp, or from about 900 bp to about 1.0 kb. In certain embodiments, the HS1 region has a length of less than about 700 bp. In certain embodiments, the HS1 region has a length of about 600 bp. In certain non-limiting embodiments, the HS1 region has a length of 602 bp. In certain non-limiting embodiments, the HS1 region comprises or has the nucleotide sequence set forth in SEQ ID NO:3, which is provided below:

```
                                      [SEQ ID NO: 3]
GGCATCTGTGAAGGAAAGAAACATCTCCTCTAAACCACTATGCTGCT

AGAGCCTCTTTTCTGTACTCAAGCCTCATTCAGACACTAGTGTCACC

AGTCTCCTCATATACCTATTGTATTTTCTTCTTCTTGCTGGTTTAGT

CATGTTTTCTGGGAGCTTAGGGGCTTATTTTATTTTGTTTTGTTTTC

TAATCAACAGAGATGGGCAAACCCATTATTTTTTTCTTTAGACTTGG

GATGGTGATAGCTGGGCAGCGTCAGAAACTGTGTGTGGATATAGATA

AGAGCTCGGACTATGCTGAGCTGTGATGAGGGAGGGACCTAGCCAAA

GGCAGTGAGAGTCAGAATGCTCCTGCTATTGCCTTCTCAGTCCCCAC

GCTTGGTTTCTACACAAGTAGATACATAGAAAAGGCTATAGGTTAGT

GTTTGAGAGTCCTGCATGAGTTAGTTGCTCAGAAATGCCCGATAAAT

ATGTTATGTGTGTTTATGTATATATATGTTTTATATATATATATGTG

TGTGTGTGTGTGTGTGTGTGTTGTGTTTACAAATATGTGATTATCAT

CAAAACGTGAGGGCTAAAGTGACCAGATAACTTGCAGG
```

In certain embodiments, the HS1 region has a length of less than about 500 bp. In certain embodiments, the HS1 region has a length of about 490 bp. In certain non-limiting embodiments, the HS1 region has a length of 489 bp. In certain non-limiting embodiments, the HS1 region comprises or has the nucleotide sequence set forth in SEQ ID NO:4, which is provided below:

[SEQ ID NO: 4]
GGCATCTGTGAAGGAAAGAAACATCTCCTCTAAACCACTATGCTGCT

AGAGCCTCTTTTCTGTACTCAAGCCTCATTCAGACACTAGTGTCACC

AGTCTCCTCATATACCTATTGTATTTTCTTCTTCTTGCTGGTTTAGT

CATGTTTTCTGGGAGCTTAGGGGCTTATTTTATTTTGTTTTGTTTTC

TAATCAACAGAGATGGGCAAACCCATTATTTTTTCTTTAGACTTGG

GATGGTGATAGCTGGGCAGCGTCAGAAACTGTGTGTGGATATAGATA

AGAGCTCGGACTATGCTGAGCTGTGATGAGGGAGGGACCTAGCCAAA

GGCAGTGAGAGTCAGAATGCTCCTGCTATTGCCTTCTCAGTCCCCAC

GCTTGGTTTCTACACAAGTAGATACATAGAAAAGGCTATAGGTTAGT

GTTTGAGAGTCCTGCATGAGTTAGTTGCTCAGAAATGCCCGATAAAT

ATGTTATGTGTGTTTATGT

In certain non-limiting embodiments, the β-globin LCR comprises or consists essentially of a HS1 region disclosed herein, a HS2 region disclosed herein, a HS3 region disclosed herein, and a HS4 region disclosed herein.

In certain non-limiting embodiments, the β-globin LCR comprises or consists essentially of a HS1 region having the nucleotide sequence set forth in SEQ ID NO: 3, SEQ ID NO: 4, SEQ ID NO: 22 or SEQ ID NO: 23; a HS2 region having the nucleotide sequence set forth in SEQ ID NO: 9 or a consecutive portion thereof, a modification of SEQ ID NO: 9, a modification of a consecutive portion of SEQ ID NO: 9 (e.g., SEQ ID NO: 33), SEQ ID NO:20, SEQ ID NO:21; a HS3 region having the nucleotide sequence set forth in SEQ ID NO: 5 or a modification thereof (e.g., SEQ ID NO: 34); and a HS4 region having the nucleotide sequence set forth in SEQ ID NO: 6 or a consecutive portion thereof, SEQ ID NO: 7 or a consecutive portion thereof, a modification of SEQ ID NO: 6, a modification of a consecutive portion of SEQ ID NO: 6 (e.g., SEQ ID NO: 35), a modification of SEQ ID NO: 7, or a modification of a consecutive portion of SEQ ID NO: 7, or SEQ ID NO:8.

In certain non-limiting embodiments, the β-globin LCR comprises or consists essentially of a HS1 region having the nucleotide sequence set forth in SEQ ID NO: 3; a HS2 region having nucleotides 45 to 860 of SEQ ID NO: 9; a HS3 region having the nucleotide sequence set forth in SEQ ID NO: 5; and a HS4 region having nucleotides 115 to 868 of SEQ ID NO: 6 e.g., the β-globin LCR of SNS22.B87.A1 shown in FIG. 15.

In certain non-limiting embodiments, the β-globin LCR comprises or consists essentially of a HS1 region having the nucleotide sequence set forth in SEQ ID NO: 3; a HS2 region having nucleotide sequence set forth in SEQ ID NO: 33; a HS3 region having the nucleotide sequence set forth in SEQ ID NO: 34; and a HS4 region having the nucleotide sequence set forth in SEQ ID NO: 35, e.g., as the β-globin LCR of SNS22.2.B87.A1 shown in FIG. 13.

Recent studies have shown that HS2 is not erythroid-specific, but is expressed in other cell lines and lineages (See Example 3 and FIG. 7) and is also present in undifferentiated human embryonic stem cells (Chang et al., *Stem cell reviews* (2013); 9:397-407). Due to the non-erythroid activity of HS2, HS2-containing globin vectors may pose a risk for their safe use in clinical treatment, e.g., for treating thalassemia and sickle cell patients. In certain embodiments, the β-globin LCR does not comprise a HS2 region. In certain embodiments, the β-globin LCR does not comprise a core sequence of HS2. A core sequence of HS2 provides position independent, high level expression. In addition, a core sequence of HS2 sustains the enhancer activity of HS2. For example, the core sequence of HS2 enhances the transcription of a globin gene (e.g., human β-globin gene). Additionally, a core sequence of HS2 comprises one or more binding sites or binding motifs for ubiquitous as well as tissue-specific (e.g., erythroid-specific) proteins (e.g., transcription factors), including, but not limited to, members of AP1 family of proteins (e.g., NF-E2), GATA-1 (also known as "NF-E1" or "NFE1"), Krüppel-like Zn finger proteins (e.g., ubiquitous proteins Sp1 and YY1, and erythroid-restricted factor erythroid Krüppel-like factor (EKLF)), and basic helix-loop-helix (bHLH) proteins (E boxes) (e.g., USF and TALI). AP1 binding sites are required for enhancement and induction (Moi and Kan (1990); Ney et al., (1990); Talbot and Grosveld (1991)). Furthermore, binding of NF-E2 can cause disruption of in vitro reconstituted chromatin at HS2 (Armstrong and Emerson (1996)). Mutations in the GATA-1 binding sites can cause a reduction in enhancer activity of HS2 in transgenic mice (Caterina et al., (1994)). Although both AP1 (e.g., AP1/NF-E2) and GATA1 binding sites are important for core function, mice lacking these factors do not show impaired globin gene expression (Weiss et al., 1994).

In certain embodiments, the β-globin LCR does not comprise the full length of a core sequence of HS2. In certain embodiments, the core sequence of a HS2 region is a core sequence of human HS2. In certain non-limiting embodiments, the core sequence of human HS2 comprises a tandem pair of binding sites for members of AP1 family of proteins (e.g., NF-E2) (referred to as "AP1/NF-E2" binding sites) (e.g., GCTGAGTCA, and GATGAGTCA), one binding site for Kruppel-like Zn finger proteins (e.g., AGGGTGTGT), one GATA-1 binding site (e.g., CTATCT), and three E boxes (CANNTG, e.g., CAGATG, and CACCTG). In certain non-limiting embodiments, the β-globin LCR does not comprise the full length of a 388 bp core sequence of human HS2, which has the nucleotide sequence set forth in SEQ ID NO:20 provided below:

[SEQ ID NO: 20]
TAAGCTTCAGTTTTTCCTTAGTTCCTGTTACATTTCTGTGTGTCTCC

ATTAGTGACCTCCCATAGTCCAAGCATGAGCAGTTCTGGCCAGGCCC

CTGTCGGGGTCAGTGCCCCACCCCCGCCTTCTGGTTCTGTGTAACCT

TCTAAGCAAACCTTCTGGCTCAAGCACAGCAATGCTGAGTCATGATG

AGTCATGCTGAGGCTTAGGGTGTGTGCCCAGATGTTCTCAGCCTAGA

GTGATGACTCCTATCTGGGTCCCCAGCAGGATGCTTACAGGGCAGAT

GGCAAAAAAAGGAGAAGCTGACCACCTGACTAAAACTCCACCTCAA

ACGGCATCATAAAGAAAATGGATGCCTGAGACAGAATGTGACATATT

CTAGAATATATT

The nucleotide sequence set forth in SEQ ID NO:20 corresponds to nucleotides position 16671 to position 17058 of SEQ ID NO:19 (GenBank Access No.: NG_000007.3). In SEQ ID NO:20, one AP1/NF-E2 binding site having the nucleotide sequence of GCTGAGTCA is located at position 175 to position 183, one AP1/NF-E2 binding site having the nucleotide sequence of GATGAGTCA is located at position 185 to position 193, one binding site for Krüppel-like Zn finger proteins having the nucleotide sequence of AGGGTGTGT is located as position 205 to position 213, two E boxes, each of which have the nucleotide sequence of CAGATG, is located at position 217 to position 222, and position 278 to position 283, one GATA-1 binding site having the nucleotide sequence of CTATCT is located at position 246 to position 251, one E box having the nucleotide sequence of CACCTG is located at position 306 to position 311.

In certain non-limiting embodiments, the β-globin LCR does not comprise the full length of a 387 bp core sequence of human HS2, which has the nucleotide sequence set forth in SEQ ID NO:21 provided below:

[SEQ ID NO: 21]
```
TAAGCTTCAGTTTTTCCTTAGTTCCTGTTACATTTCTGTGTGTCTCC

ATTAGTGACCTCCCATAGTCCAAGCATGAGCAGTTCTGGCCAGGCCC

CTGTCGGGGTCAGTGCCCCACCCCCGCCTTCTGGTTCTGTGTAACCT

TCTAAGCAAACCTTCTGGCTCAAGCACAGCAATGCTGAGTCATGATG

AGTCATGCTGAGGCTAGGGTGTGTGCCCAGATGTTCTCAGCCTAGAG

TGATGACTCCTATCTGGGTCCCCAGCAGGATGCTTACAGGGCAGATG

GCAAAAAAAGGAGAAGCTGACCACCTGACTAAAACTCCACCTCAAA

CGGCATCATAAAGAAAATGGATGCCTGAGACAGAATGTGACATATTC

TAGAATATATT
```

In SEQ ID NO:21, one AP1/NF-E2 binding site having the nucleotide sequence of GCTGAGTCA is located at position 175 to position 183, one AP1/NF-E2 binding site having the nucleotide sequence of GATGAGTCA is located at position 185 to position 193, one binding site for Krüppel-like Zn finger proteins having the nucleotide sequence of AGGGTGTGT is located as position 204 to position 212, two E boxes, each of which have the nucleotide sequence of CAGATG, is located at position 216 to position 221, and position 277 to position 282, one GATA-1 binding site having the nucleotide sequence of CTATCT is located at position 245 to position 250, one E box having the nucleotide sequence of CACCTG is located at position 305 to position 310.

In certain embodiments, the β-globin LCR does not comprise a HS2 region that comprises a core sequence of HS2. A HS2 region that comprises a core sequence of HS2 can vary in length and sequence. In non-limiting examples, a HS2 region that comprises a core sequence of HS2 is from about 400 bp to about 1000 bp, e.g., from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp, in length. In certain non-limiting embodiments, the β-globin LCR does not comprise a 840 bp HS2 region (e.g., the HS2 region comprised in the globin vector TNS9 disclosed in U.S. Pat. No. 7,541,179). In certain non-limiting embodiments, the β-globin LCR does not comprise a 860 bp HS2 region. In certain non-limiting embodiments, the β-globin LCR does not comprise an about 650 bp HS2 region. In certain non-limiting embodiments, the β-globin LCR does not comprise a 646 bp HS2 region (e.g., the HS2 region comprised in the globin vector Lenti-Globin™, also known as "β87"). In certain non-limiting embodiments, the β-globin LCR does not comprise an about 420 bp HS2 region. In certain non-limiting embodiments, the β-globin LCR does not comprise a 423 bp HS2 region (e.g., the HS2 region comprised in the globin vector disclosed in Sadelain et al., *Proc. Nat'l Acad. Sci.* (USA) (1995); 92:6728-6732).

In certain embodiments, the β-globin LCR does not comprise a HS2 region that sustains the enhancer activity of HS2. In certain embodiments, the β-globin LCR does not comprise a HS2 region that is capable of enhancing the transcription of a globin gene (e.g., human β-globin gene). In non-limiting examples, the β-globin LCR does not comprise a HS2 region whose ability to enhance the transcription of a globin gene (e.g., human β-globin gene) is no less than about 60%, no less than about 70%, no less than about 80%, no less than about 90%, or no less than about 95% in comparison to a native HS2 region.

In certain embodiments, the β-globin LCR does not comprise a HS2 region that comprises one, two, three, four, five, six or seven of the following binding sites: two (a tandem pair of) AP1/NF-E2 binding sites (e.g., GCT-GAGTCA, and GATGAGTCA), one binding site for Krup-pel-like Zn finger proteins (e.g., AGGGTGTGT), one GATA-1 binding site (e.g., CTATCT), and three E boxes (CANNTG, e.g., CAGATG, and CACCTG). In certain embodiments, the β-globin LCR does not comprise a HS2 region that comprises six of the above-described binding sites. For example, in certain embodiments, the β-globin LCR does not comprise a HS2 region that comprises two AP1/NF-E2 binding sites, one binding site for Kruppel-like Zn finger proteins, one GATA-1 binding site, and two not three E boxes. In certain embodiments, the β-globin LCR does not comprise a HS2 region that comprises one not two AP1/NF-E2 binding site, one binding site for Kruppel-like Zn finger proteins, one GATA-1 binding site, and three E boxes. In certain embodiments, the β-globin LCR does not comprise a HS2 region that comprises two AP1/NF-E2 binding sites, one GATA-1 binding site, and three E boxes and does not comprise one binding site for Kruppel-like Zn finger proteins. In certain embodiments, the β-globin LCR does not comprise a HS2 region that comprises two AP1/NF-E2 binding sites, one binding site for Kruppel-like Zn finger proteins, and three E boxes, and does not comprise one GATA-1 binding site.

In certain embodiments, the β-globin LCR comprises a HS1 region, a HS3 region, and a HS4 region, and does not comprise a HS2 region. In certain embodiments, the HS1 region, HS3 region and HS4 region within the β-globin LCR are contiguous. In certain non-limiting embodiments, the β-globin LCR consists essentially of a HS1 region, a HS3 region and a HS4 region. In certain embodiments, the β-globin LCR comprises two introduced GATA-1 binding sites at the junction between the HS3 region and the HS4 region. The HS3 region can lie between the HS1 region and the HS4 region. The HS1, HS3, and HS4 regions can be any HS1, HS3, and HS4 regions disclosed herein. The HS2 region can also be any HS2 region disclosed herein.

In certain non-limiting embodiments, the β-globin LCR comprises or consists essentially of a HS1 region disclosed herein, a HS3 region disclosed herein, and a HS4 region disclosed herein, and does not comprise a HS2 region.

In certain non-limiting embodiments, the β-globin LCR comprises or consists essentially of a HS1 region having the nucleotide sequence set forth in SEQ ID NO:2, SEQ ID NO:3, SEQ ID NO:4, SEQ ID NO:22 or SEQ ID NO:23; a HS3 region having the nucleotide sequence set forth in SEQ ID NO: 5 or a modification thereof (e.g., SEQ ID NO: 34); and a HS4 region having the nucleotide sequence set forth in SEQ ID NO:6 or a consecutive portion thereof, SEQ ID NO:7 or a consecutive portion thereof, a modification of SEQ ID NO: 6, a modification of a consecutive portion of SEQ ID NO: 6 (e.g., SEQ ID NO: 35), a modification of SEQ ID NO: 7, or a modification of a consecutive portion of SEQ ID NO: 7, or SEQ ID NO:8, and the β-globin LCR does not comprise a HS2 region.

Figure 2:
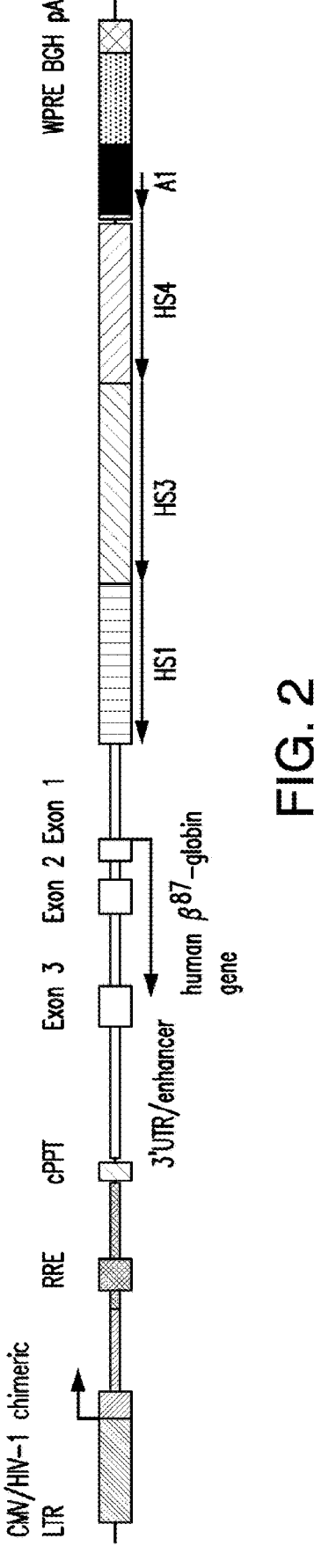
FIG. 2 depicts a recombinant vector an expression cas-
sette in accordance with one non-limiting embodiment of the
presently disclosed subject matter.

In certain non-limiting embodiments, the β-globin LCR comprises or consists essentially of a HS1 region having the nucleotide sequence set forth in SEQ ID NO:2, a HS3 region having the nucleotide sequence set forth in SEQ ID NO:5, and a HS4 region having the nucleotide sequence set forth in SEQ ID NO:6, and the β-globin LCR does not comprise a HS2 region, as shown in FIG. 2.

Figure 3:
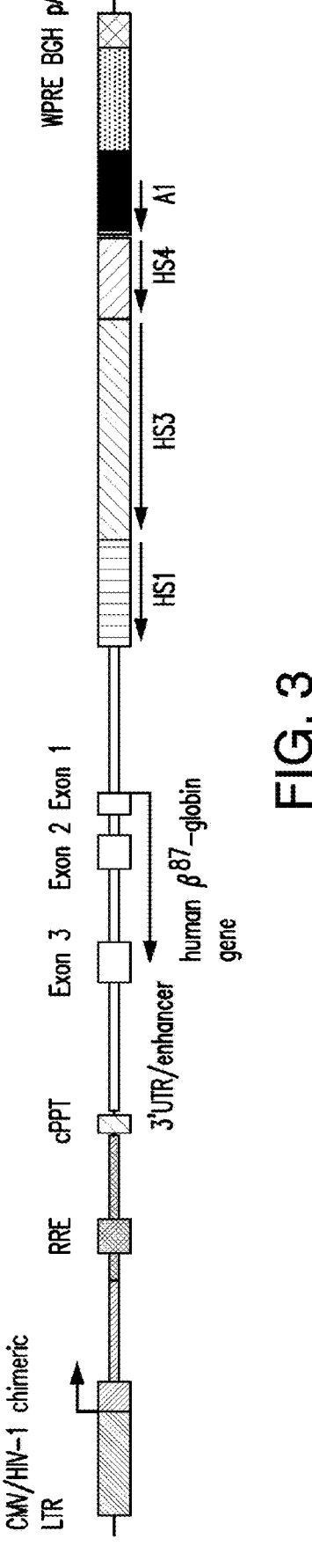
FIG. 3 depicts a recombinant vector an expression cas-
sette in accordance with one non-limiting embodiment of the
presently disclosed subject matter.

In certain non-limiting embodiments, the β-globin LCR comprises or consists essentially of a HS1 region having the nucleotide sequence set forth in SEQ ID NO:3, a HS3 region having the nucleotide sequence set forth in SEQ ID NO:5, and a HS4 region having the nucleotide sequence set forth in SEQ ID NO:8, and the β-globin LCR does not comprise a HS2 region, as shown in FIG. 3.

In certain non-limiting embodiments, the β-globin LCR comprises or consists essentially of a HS1 region having the nucleotide sequence set forth in SEQ ID NO:4, a HS3 region having the nucleotide sequence set forth in SEQ ID NO:5, and a HS4 region having the nucleotide sequence set forth in SEQ ID NO:8, and the β-globin LCR does not comprise a HS2 region.

In certain non-limiting embodiments, the β-globin LCR comprises or consists essentially of a HS1 region having the nucleotide sequence set forth in SEQ ID NO: 3; a HS3 region having the nucleotide sequence set forth in SEQ ID NO: 5; and a HS4 region having nucleotides 115 to 868 of SEQ ID NO: 6 e.g., the β-globin LCR of SNS24.B87.A1 shown in FIG. 15.

In certain non-limiting embodiments, the β-globin LCR comprises or consists essentially of a HS1 region having the nucleotide sequence set forth in SEQ ID NO: 3; a HS3 region having the nucleotide sequence set forth in SEQ ID NO: 34; and a HS4 region having the nucleotide sequence set forth in SEQ ID NO: 35, e.g., as the β-globin LCR of SNS24.2.B87.A1 shown in FIG. 13.

In certain embodiments, the β-globin LCR does not comprise a HS1 region or a HS2 region. In certain embodiments, the β-globin LCR does not comprise a core sequence of HS1. A core sequence of HS1 sustains the activity of HS1, e.g., enhancer activity, or functioning as a facilitator or regulatory element to tether the enhancer activity of other HS regions, e.g., HS2-4. In addition, a core sequence of HS1 comprises one or more binding sites or binding motifs for ubiquitous as well as tissue-specific (e.g., erythroid-specific) proteins (e.g., transcription factors), including, but not limited to, GATA-1, and Krüppel-like Zn finger proteins (e.g., erythroid-restricted factor EKLF).

In certain embodiments, the β-globin LCR does not comprise the full length of a core sequence of HS1. In certain embodiments, the core sequence of a HS1 region is a core sequence of human HS1. In certain non-limiting embodiments, the core sequence of human HS1 comprises two GATA-1 binding sites (e.g., TTATCT, and CTATCA), and one binding site for EKLF (e.g., CCACACACA). In certain embodiments, the β-globin LCR does not comprise the full length of a 286 bp core sequence of human HS1. In certain non-limiting embodiments, the 286 bp core sequence of human HS1 has the nucleotide sequence set forth in SEQ ID NO:22 provided below:

```
                                          [SEQ ID NO: 22]
CTGAGCAACTAACTCATGCAGGACTCTCAAACACTAACCTATAGCCT

TTTCTATGTATCTACTTGTGTAGAAACCAAGCGTGGGGACTGAGAAG

GCAATAGCAGGAGCATTCTGACTCTCACTGCCTTTGGCTAGGTCCCT

CCCTCATCACAGCTCAGCATAGTCCGAGCTCTTATCTATATCCACAC

ACAGTTTCTGACGCTGCCCAGCTATCACCATCCCAAGTCTAAAGAAA

AAAATAATGGGTTTGCCCATCTCTGTTGATTAGAAAACAAAACAAAA

TAAA
```

In SEQ ID NO:22, one GATA-1 binding site having the nucleotide sequence of TTATCT is located at position 173 to position 178, one GATA-1 binding site having the nucleotide sequence of CTATCA located at position 210 to position 215, and one binding site for EKLF having the nucleotide sequence of CCACACACA is located at position 183 to position 191.

In certain non-limiting embodiments, the 286 bp core sequence of human HS1 has the nucleotide sequence set forth in SEQ ID NO:23 provided below:

```
                                          [SEQ ID NO: 23]
CTGAGCAACTAATCATGCAGGACTCTCAAACACTAACCTATAGCCTT

TTCTATGTATCTACTTGTGTAGAAACCAAGCGTGGGGACTGAGAAGG

CAATAGCAGGAGCATTCTGACTCTCACTGCCTTTAGCTAGGCCCCTC

CCTCATCACAGCTCAGCATAGTCCTGAGCTCTTATCTATATCCACAC

ACAGTTTCTGACGCTGCCCAGCTATCACCATCCCAAGTCTAAAGAAA

AAAATAATGGGTTTGCCCATCTCTGTTGATTAGAAAACAAAACAAAA

TAAA
```

The nucleotide sequence set forth in SEQ ID NO:23 corresponds to nucleotides position 21481 to position 21766 of SEQ ID NO: 19 (GenBank Access No.: NG_000007.3). In SEQ ID NO:23, one GATA-1 binding site having the nucleotide sequence of TTATCT is located at position 173 to position 178, one GATA-1 binding site having the nucleotide sequence of CTATCA located at position 210 to position 215, and one binding site for EKLF having the nucleotide sequence of CCACACACA is located at position 183 to position 191.

In certain embodiments, the β-globin LCR does not comprise a HS1 region that comprises a core sequence of HS1. A HS1 region that comprises a core sequence of HS1 can vary in length and sequence. In non-limiting examples, a HS1 region that comprises a core sequence of HS1 is from about 300 bp to about 1200 bp, e.g., from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, or from about 1100 bp to about 1200 bp, in length. In certain non-limiting embodiments, the β-globin LCR does not comprise an about 1.0 kb bp HS1 region. In certain non-limiting embodiments, the β-globin LCR does not comprise an about 1.1 kb HS1 region.

In certain embodiments, the β-globin LCR does not comprise a HS1 region that sustains the activity of HS1, e.g., enhancer activity, or functioning as a facilitator or regulatory element to tether the enhancer activity of other HS regions, e.g., HS2-4. In certain embodiments, the β-globin LCR does not comprise a HS1 region that is capable of enhancing the transcription of a globin gene (e.g., human β-globin gene). In non-limiting examples, the β-globin LCR does not comprise a HS1 region whose ability to enhance the transcription of a globin gene (e.g., human β-globin gene) is no less than about 60%, no less than about 70%, no less than about 80%, no less than about 90%, or no less than about 95% in comparison to a native HS1 region. In non-limiting examples, the β-globin LCR does not comprise a HS1 region whose ability to tether the enhancer activity of one or more of HS2-HS4 is no less than about 60%, no less than about 70%, no less-than about 80%, no less than about 90%, or no less than about 95% in comparison to a native HS1 region.

In certain embodiments, the β-globin LCR does not comprise a HS1 region that comprises one, two, or three of the following binding sites: two GATA-1 binding sites (e.g., TTATCT, and CTATCA), and one binding site for EKLF (e.g., CCACACACA). In certain embodiments, the β-globin LCR does not comprise a HS1 region that comprises two of the above-described binding sites. For example, in certain embodiments, the β-globin LCR does not comprise a HS1 region that comprises two GATA-1 binding sites and does not comprise one binding site for EKLF. In certain embodiments, the β-globin LCR does not comprise a HS1 region that comprises one not two AP1/NF-E2 binding site and one binding site for EKLF.

In certain embodiments, the β-globin LCR comprises a HS3 region and a HS4 region, and the β-globin LCR does not comprise a HS1 region or a HS2 region. In certain embodiments, the HS3 region and HS4 region within the β-globin LCR are contiguous. In certain non-limiting embodiments, the β-globin LCR consisting essentially of a HS3 region and a HS4 region. In another embodiment, the β-globin LCR comprises two introduced GATA-1 binding sites at the junction between the HS3 region and the HS4 region. The HS3 region can lie between the globin gene or functional portion thereof and the HS4 region.

In certain embodiments, the β-globin LCR comprises a HS3 region having the nucleotide sequence set forth in SEQ ID NO:5 and a HS4 region having the nucleotide sequence set forth in SEQ ID NO: 6, SEQ ID NO:7 or SEQ ID NO:8, and the β-globin LCR does not comprise a HS1 region or a HS2 region.

Figure 4:
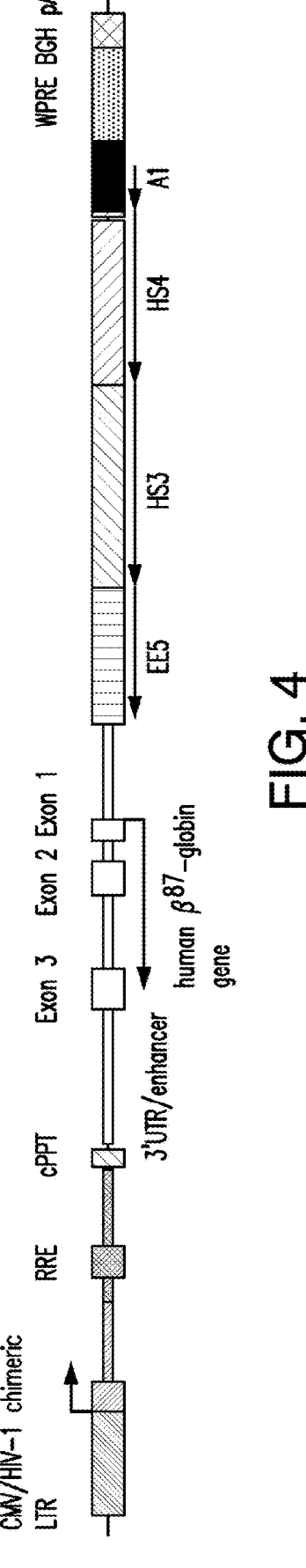
FIG. 4 depicts a recombinant vector an expression cas-
sette in accordance with one non-limiting embodiment of the
presently disclosed subject matter.

In certain non-limiting embodiments, the β-globin LCR comprises a HS3 region having the nucleotide sequence set forth in SEQ ID NO:5 and a HS4 region having the nucleotide sequence set forth in SEQ ID NO:6, and the β-globin LCR does not comprise a HS1 region or a HS2 region, as shown in FIG. 4.

In certain embodiments, the β-globin LCR does not comprise a HS1 region, a HS2 region, or a HS4 region. In certain embodiments, the β-globin LCR does not comprise the full length of a core sequence of HS4. In certain embodiments, the core sequence of a HS4 region is a core sequence of human HS4. In certain embodiments, the β-globin LCR does not comprise the full length of a 280 bp core sequence of human HS4 (e.g., the 280 bp core sequence of human HS4 disclosed in Pruzina et al., *Nucleic Acdis Research* (1991); 19:7:1413-1419).

In certain embodiments, the β-globin LCR does not comprise a HS4 region that comprises a core sequence of HS4. A HS4 region that comprises a core sequence of HS4 can vary in length and sequence. In non-limiting examples, a HS4 region that comprises a core sequence of HS4 is from about 300 bp to about 1200 bp, e.g., from about 300 bp to about 400 bp, from about 400 bp to about 500 bp, from about 500 bp to about 600 bp, from about 600 bp to about 700 bp, from about 700 bp to about 760 bp, from about 700 bp to about 800 bp, from about 800 bp to about 900 bp, from about 900 bp to about 1000 bp, from about 1000 bp to about 1100 bp, or from about 1100 bp to about 1200 bp, in length. In certain non-limiting embodiments, the β-globin LCR does not comprise an about 1.0 kb HS4 region. In certain non-limiting embodiments, the β-globin LCR does not comprise an about 1.1 kb HS4 region. In certain non-limiting embodiments, the β-globin LCR does not comprise an about 760 bp HS4 region. In certain non-limiting embodiments, the β-globin LCR does not comprise an about 754 bp HS4 region.

In certain embodiments, the β-globin LCR does not comprise a HS4 region that sustains the activity of HS4, e.g., enhancer activity. In certain embodiments, the β-globin LCR does not comprise a HS4 region that is capable of enhancing the transcription of a globin gene (e.g., human β-globin gene), conferring position independent expression, and/or increasing β-globin transgene expression. In certain embodiments, the expression cassette comprises at least one erythroid-specific enhancer, which can compensate the activities of HS1, HS2, and/or HS4 regions.

In certain embodiments, the β-globin LCR comprises a HS3 region, and the β-globin LCR does not comprise a HS1 region, a HS2 region or a HS4 region. In certain embodiments, the β-globin LCR consisting essentially of a HS3 region. In certain embodiments, the β-globin LCR comprises a HS3 region having the nucleotide sequence set forth in SEQ ID NO: 5 and a HS4 region having the nucleotide sequence set forth in SEQ ID NO:6, SEQ ID NO:7 or SEQ ID NO:8, and the β-globin LCR does not comprise a HS1 region or a HS2 region. In certain embodiments, the expression cassette comprises at least one erythroid-specific enhancer.

In certain non-limiting embodiments, the β-globin LCR comprises a HS3 region having the nucleotide sequence set forth in SEQ ID NO:5, and the β-globin LCR does not comprise a HS1 region, a HS2 region or a HS4 region. In certain embodiments, the expression cassette comprises at least one erythroid-specific enhancer.

In certain non-limiting embodiments, the β-globin LCR comprises a HS3 region having the nucleotide sequence set forth in SEQ ID NO: 34, and the β-globin LCR does not comprise a HS1 region, a HS2 region or a HS4 region, e.g., the β-globin LCR of SNS27.2.B87.A1 shown in FIG. 13. In certain embodiments, the expression cassette comprises at least one erythroid-specific enhancer, e.g., SNS27.2.B87.A1 shown in FIG. 13.

3.2. Globin Gene

In accordance with the presently disclosed subject matter, the expression cassette comprises a globin gene or a functional portion thereof. The globin gene can be a β-globin gene, a γ-globin gene, or a δ-globin gene. In certain embodiments, the expression cassette comprises a human β-globin gene. In accordance with the presently disclosed subject matter, the human β-globin gene can be a wild-type human β-globin gene, a deleted human β-globin gene comprising one or more deletions of intron sequences, or a mutated human β-globin gene encoding at least one anti-sickling amino acid residue. In certain non-limiting embodiments, a presently disclosed expression cassette comprises a wild-type human β-globin gene. A wild-type human β-globin gene comprises three exons (exon 1, exon 2, and exon 3). In certain embodiments, a presently disclosed expression cassette comprises a non-wild-type (mutated or modified) human $\beta^A$-globin gene. In certain embodiments, a presently disclosed expression cassette comprises a human β-globin gene with a deletion in intron 2 (IVS2). In certain embodiments, the deletion in IVS2 is about 370 bp. The deletion in IVS2 can eliminate AT-rich (ATR) sequences that comprise a cryptic polyadenylation site responsible of premature termination of the transcription. In certain embodiments, a presently disclosed expression cassette comprises a human $\beta^A$-globin gene encoding a threonine to glutamine mutation at codon 87 ($\beta^{A-T87Q}$). The glutamine residue at position 87 in the gamma-globin chain augments the anti-sickling activity of the gamma chain relative to the beta chain, while preserving adult oxygen-binding characteristics of the beta chain (Nagel et al., *Proc. Natl. Acad. Sci. U.S.A.* (1979); 76:670-672). In certain embodiments, a functional portion of a globin gene has at least about 80%, at least about 90%, at least about 95%, at least about 99% or at least about 100% identity to a corresponding wild-type reference polynucleotide sequence.

In certain embodiments, the human $\beta^A$-globin gene is a human $\beta^A$-globin gene encoding a threonine to glutamine mutation at codon 87 ($\beta^{A-T87Q}$). In certain embodiments, the human $\beta^A$\_globin gene encoding a threonine to glutamine mutation at codon 87 ($\beta^{A-T87Q}$) further comprises a deletion in intron 2 (e.g., an about 370 bp deletion). In certain embodiments, the human $\beta^A$-globin gene encoding a threonine to glutamine mutation at codon 87 ($\beta^{A-T87Q}$) comprises the nucleotide sequence set forth in SEQ ID NO: 36, which is provided below.

```
                                    [SEQ ID NO: 36]
gc aatgaaaata aatgtttttt attaggcaga atccagatgc tcaaggccct tcataatatc ccccagttta gtagttggac ttagggaaca aaggaacctt taatagaaat tggacagcaa gaaagcgagc ttagtgatac ttgtgggcca gggcattagc cacaccagcc accactttct gataggcagc ctgcactggt ggggtgAATT CTTTGCCAAA GTGATGGGCC AGCACACAGA

CCAGCACGTT GCCCAGGAGC TGTGGGAGGA AGATAAGAGG

TATGAACATG ATTAGCAAAA GGGCCTAGCT TGGACTCAGA

ATAATCCAGC CTTATCCCAA CCATAAAATA AAAGCAGAAT

GGTAGCTGGA TTGTAGCTGC TATTAGCAAT ATGAAACCTC

TTACATCAGT TACAATTTAT ATGCAGAAAT ATTTATATGC

AGAAATATTG CTATTGCCTT AACCCAGAAA TTATCACTGT

TATTCTTTAG AATGGTGCAA AGAGGCATGA TACATTGTAT

CATTATTGCC CTGAAAGAAA GAGATTAGGG AAAGTATTAG

AAATAAGATA AACAAAAAAG TATATTAAAA GAAGAAAGCA

TTTTTTAAAA TTACAAATGC AAAATTACCC TGATTTGGTC

AATATGTGTA CCCTGTTACT TCTCCCCTTC CTATGACATG

AACTTAACCA TAGAAAAGAA GGGGAAAGAA AACATCAAGG

GTCCCATAGA CTCACCCTGA AGTTCTCAGG ATCCACGTGC

AGCTTGTCAC AGTGCAGCTC ACTCAGctgG GCAAAGGTGC

CCTTGAGGTT GTCCAGGTGA GCCAGGCCAT CACTAAAGGC

ACCGAGCACT TTCTTGCCAT GAGCCTTCAC CTTAGGGTTG
```

```
-continued
CCCATAACAG CATCAGGAGT GGACAGATCC CCAAAGGACT

CAAAGAACCT CTGGGTCCAA GGGTAGACCA CCAGCAGCCT

AAGGGTGGGA AAATAGACCA ATAGGCAGAG AGAGTCAGTG

CCTATCAGAA ACCCAAGAGT CTTCTCTGTC TCCACATGCC

CAGTTTCTAT TGGTCTCCTT AAACCTGTCT TGTAACCTTG

ATACCAACCT GCCCAGGGCC TCACCACCAA CTTCATCCAC

GTTCACCTTG CCCCACAGGG CAGTAACGGC AGACTTCTCC

TCAGGAGTCA GGTGCACCAT GGTGTCTGTT TGAGGTTGCT

AGTGAACACA GTTGTGTCAG AAGCAAATGT
```

In certain embodiments, the human $\beta^A$-globin gene encoding a threonine to glutamine mutation at codon 87 ($\beta^{A-T87Q}$) comprises the nucleotide sequence set forth in SEQ ID NO: 53, which is provided below.

```
                                    [SEQ ID NO: 53]
gc aatgaaaata aatgtttttt attaggcaga atccagatgc tcaaggccct tcataatatc ccccagttta gtagttggac ttagggaaca aaggaacctt taatagaaat tggacagcaa gaaagcgagc ttagtgatac ttgtgggcca gggcattagc cacaccagcc accactttct gataggcagc ctgcactggt ggggtgAATT CTTTGCCAAA GTGATGGGCC AGCACACAGA

CCAGCACGTT GCCCAGGAGC TGTGGGAGGA AGATAAGAGG

TATGAACATG ATTAGCAAAA GGGCCTAGCT TGGACTCAGA

ATAATCCAGC CTTATCCCAA CCATAAAATA AAAGCAGAAT

GGTAGCTGGA TTGTAGCTGC TATTAGCAAT ATGAAACCTC

TTACATCAGT TACAATTTAT ATGCAGAAAT ATTTATATGC

AGAAATATTG CTATTGCCTT AACCCAGAAA TTATCACTGT

TATTCTTTAG AATGGTGCAA AGAGGCATGA TACATTGTAT

CATTATTGCC CTGAAAGAAA GAGATTAGGG AAAGTATTAG

AAATAAGATA AACAAAAAAG TATATTAAAA GAAGAAAGCA

TTTTTTAAAA TTACAAATGC AAAATTACCC TGATTTGGTC

AATATGTGTA CCCTGTTACT TCTCCCCTTC CTATGACATG

AACTTAACCA TAGAAAAGAA GGGGAAAGAA AACATCAAGG

GTCCCATAGA CTCACCCTGA AGTTCTCAGG ATCCACGTGC

AGCTTGTCAC AGTGCAGCTC ACTCAGTTGG GCAAAGGTGC

CCTTGAGGTT GTCCAGGTGA GCCAGGCCAT CACTAAAGGC

ACCGAGCACT TTCTTGCCAT GAGCCTTCAC CTTAGGGTTG

CCCATAACAG CATCAGGAGT GGACAGATCC CCAAAGGACT

CAAAGAACCT CTGGGTCCAA GGGTAGACCA CCAGCAGCCT

AAGGGTGGGA AAATAGACCA ATAGGCAGAG AGAGTCAGTG

CCTATCAGAA ACCCAAGAGT CTTCTCTGTC TCCACATGCC

CAGTTTCTAT TGGTCTCCTT AAACCTGTCT TGTAACCTTG

ATACCAACCT GCCCAGGGCC TCACCACCAA CTTCATCCAC
```

-continued

```
GTTCACCTTG CCCCACAGGG CAGTAACGGC AGACTTCTCC

TCAGGAGTCA GGTGCACCAT GGTGTCTGTT TGAGGTTGCT

AGTGAACACA GTTGTGTCAG AAGCAAATGT
```

In certain non-limiting embodiments, the human β-globin gene is a human $\beta^A$-globin gene encoding a glutamic acid to alanine mutation at codon 22 ($\beta^{A-E22A}$). In certain embodiments, the human $\beta^A$-globin gene encoding a glutamic acid to alanine mutation at codon 22 ($\beta^{A-E22A}$) further: comprises a deletion in intron 2 (e.g., an about 370 bp deletion). In certain embodiments, the human $\beta^A$-globin gene encoding a glutamic acid to alanine mutation at codon 22 ($\beta^{A-E22A}$) comprises the nucleotide sequence set forth in SEQ ID NO: 54, which is provided below:

```
                                        [SEQ ID NO: 54]
gcaatgaaaataaatgttttttattaggcagaatccagatgctcaag gcccttcataatatcccccagtttagtagttggacttagggaacaaa ggaacctttaatagaaattggacagcaagaaagcgagcttagtgata cttgtgggccagggcattagccacaccagccaccactttctgatagg cagcctgcactggtggggtgAATTCTTTGCCAAAGTGATGGGCCAGC

ACACAGACCAGCACGTTGCCCAGGAGCTGTGGGAGGAAGATAAGAGG

TATGAACATGATTAGCAAAAGGGCCTAGCTTGGACTCAGAATAATCC

AGCCTTATCCCAACCATAAAATAAAAGCAGAATGGTAGCTGGATTGT

AGCTGCTATTAGCAATATGAAACCTCTTACATCAGTTACAATTTATA

TGCAGAAATATTTATATGCAGAAATATTGCTATTGCCTTAACCCAGA

AATTATCACTGTTATTCTTTAGAATGGTGCAAAGAGGCATGATACAT

TGTATCATTATTGCCCTGAAAGAAAGAGATTAGGGAAAGTATTAGAA

ATAAGATAAACAAAAAAGTATATTAAAAGAAGAAAGCATTTTTTAAA

ATTACAAATGCAAAATTACCCTGATTTGGTCAATATGTGTACCCTGT

TACTTCTCCCCTTCCTATGACATGAACTTAACCATAGAAAGAAGGG

GAAAGAAAACATCAAGGGTCCCATAGACTCACCCTGAAGTTCTCAGG

ATCCACGTGCAGCTTGTCACAGTGCAGCTCACTCAGtgtGGCAAAGG

TGCCCTTGAGgttGTCCAGGTGAGCCAGGCCATCACTAAAGGCACCG

AGCACTTTCTTGCCATGAGCCTTCACCTTAGGGTTGCCCATAACAGC

ATCAGGAGTGGACAGATCCCCAAAGGACTCAAAGAACCTCTGGGTCC

AAGGGTAGACCACCAGCAGCCTAAGGGTGGGAAAATAGACCAATAGG

CAGAGAGAGTCAGTGCCTATCAGAAACCCAAGAGTCTTCTCTGTCTC

CACATGCCCAGTTTCTATTGGTCTCCTTAAACCTGTCTTGTAACCTT

GATACCAACCTGCCCAGGGCCTCACCACCAACGgcATCCACGTTCAC

CTTGCCCCACAGGGCAGTAACGGCAGACTTCTCCTCAGGAGTCAGGT

GCACCATGGTGTCTGTTTGAGGTTGCTAGTGAACACAGTTGTGTCAG

AAGCAAATGT
```

In certain embodiments, the human $\beta^A$-globin gene encoding a glutamic acid to alanine mutation at codon 22 ($\beta^{A-E22A}$) comprises the nucleotide sequence set forth in SEQ ID NO: 55, which is provided below:

```
                                        [SEQ ID NO: 55]
gcaatgaaaataaatgttttttattaggcagaatccagatgctcaag gcccttcataatatcccccagtttagtagttggacttagggaacaaa ggaacctttaatagaaattggacagcaagaaagcgagcttagtgata cttgtgggccagggcattagccacaccagccaccactttctgatagg cagcctgcactggtggggtgAATTCTTTGCCAAAGTGATGGGCCAGC

ACACAGACCAGCACGTTGCCCAGGAGCTGTGGGAGGAAGATAAGAGG

TATGAACATGATTAGCAAAAGGGCCTAGCTTGGACTCAGAATAATCC

AGCCTTATCCCAACCATAAAATAAAAGCAGAATGGTAGCTGGATTGT

AGCTGCTATTAGCAATATGAAACCTCTTACATCAGTTACAATTTATA

TGCAGAAATATTTATATGCAGAAATATTGCTATTGCCTTAACCCAGA

AATTATCACTGTTATTCTTTAGAATGGTGCAAAGAGGCATGATACAT

TGTATCATTATTGCCCTGAAAGAAAGAGATTAGGGAAAGTATTAGAA

ATAAGATAAACAAAAAAGTATATTAAAAGAAGAAAGCATTTTTTAAA

ATTACAAATGCAAAATTACCCTGATTTGGTCAATATGTGTACCCTGT

TACTTCTCCCCTTCCTATGACATGAACTTAACCATAGAAAGAAGGG

GAAAGAAAACATCAAGGGTCCCATAGACTCACCCTGAAGTTCTCAGG

ATCCACGTGCAGCTTGTCACAGTGCAGCTCACTCAGtgtGGCAAAGG

TGCCCTTGAGgttGTCCAGGTGAGCCAGGCCATCACTAAAGGCACCG

AGCACTTTCTTGCCATGAGCCTTCACCTTAGGGTTGCCCATAACAGC

ATCAGGAGTGGACAGATCCCCAAAGGACTCAAAGAACCTCTGGGTCC

AAGGGTAGACCACCAGCAGCCTAAGGGTGGGAAAATAGACCAATAGG

CAGAGAGAGTCAGTGCCTATCAGAAACCCAAGAGTCTTCTCTGTCTC

CACATGCCCAGTTTCTATTGGTCTCCTTAAACCTGTCTTGTAACCTT

GATACCAACCTGCCCAGGGCCTCACCACCAACTGCATCCACGTTCAC

CTTGCCCCACAGGGCAGTAACGGCAGACTTCTCCTCAGGAGTCAGGT

GCACCATGGTGTCTGTTTGAGGTTGCTAGTGAACACAGTTGTGTCAG

AAGCAAATGT
```

In certain embodiments, the human $\beta^A$-globin gene encoding a glutamic acid to alanine mutation at codon 22 ($\beta^{A-E22A}$) comprises the nucleotide sequence set forth in SEQ ID NO: 56, which . . . is provided below:

```
                                        [SEQ ID NO: 56]
gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg AgtggggtgAATTCTTTGCCAAAGTGATGGGCCAGCACACGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT
```

-continued

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAG

AAGGGGAAAGAAAACATCAAGGGTCCCATAGACTCACCCTGAAGTTCTCA

GGATCCACGTGCAGCTTGTCACAGTGCAGCTCACTCAGtgtGGCAAAGGT

GCCCTTGAGgttGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACAGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain embodiments, the human β$^A$-globin gene encoding a glutamic acid to alanine mutation at codon 22 (β$^{A-822}$A) comprises the nucleotide sequence set forth in SEQ ID NO: 57, which is provided below:

[SEQ ID NO: 57]
gcaatgaaaataaatgttttttattaggcagaatccagatgctcaaggccc ttcataatatcccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAGAAGGGGAAAGAAAA

CATCAAGGGTCCCATAGACTCACCCTGAAGTTCTCAGGATCCACGTGCAGC

TTGTCACAGTGCAGCTCACTCAGtgtGGCAAAGGTGCCCTTGAGcttGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

-continued

TTGTAACCTTGATACCAACCTGCCCAGGGCCTCACCACCAACCGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT

In certain non-limiting embodiments, the human β-globin gene is a human β$^A$-globin gene encoding an asparagine to lysine mutation at codon 80 (B$^{-N80K}$). In certain embodiments, the human β$^A$-globin gene encoding an asparagine to lysine mutation at codon 80 (B$^{-N80K}$) further comprises a deletion in intron 2 (e.g., an about 370 bp deletion). In certain embodiments, the human β$^A$-globin gene encoding an asparagine to lysine mutation at codon 80 (B$^{-N80K}$) comprises the nucleotide sequence set forth in SEQ ID NO: 58, which is provided below:

[SEQ ID NO: 58]
gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAG

AAGGGGAAAGAAAACATCAAGGGTCCCATAGACTCACCCTGAAGTTCTCA

GGATCCACGTGCAGCTTGTCACAGTGCAGCTCACTCAGtgtGGCAAAGGT

GCCCTTGAGcttGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACttcATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain embodiments, the human β$^A$-globin gene encoding an asparagine to lysine mutation at codon 80 (B$^{-N80K}$) comprises the nucleotide sequence set forth in SEQ ID NO: 59, which is provided below:

-continued

```
                                    [SEQ ID NO: 59]
gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGtgtGGCAAAGGT

GCCCTTGAGTTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACttcATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT
```

In certain non-limiting embodiments, the human β-globin gene is human β<sup>A</sup>-globin gene encoding a glutamic acid to alanine mutation at codon 22 and an asparagine to lysine mutation at codon 80. In certain embodiments, the human β<sup>A</sup>-globin gene encoding a glutamic acid to alanine mutation at codon 22 and an asparagine to lysine mutation at codon 80 further comprises a deletion in intron 2 (e.g., an about 370 bp deletion). In certain embodiments, the human β<sup>A</sup>-globin gene encoding a glutamic acid to alanine mutation at codon 22 and an asparagine to lysine mutation at codon 80 comprises the nucleotide sequence set forth in SEQ ID NO: 60, which is provided below:

```
                                    [SEQ ID NO: 60]
gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattaGCCACACCAGCCACCACTTTCTGATAGGCAGCCTGCACTG

GTGGGGTGAATTCTTTGCCAAAGTGATGGGCCAGCACACAGACCAGCACG

TTGCCCAGGAGCTGTGGGAGGAAGATAAGAGGTATGAACATGATTAGCAA
```

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGTGTGGCAAAGGT

GCCCTTGAGCTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACGGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain embodiments, the human β<sup>A</sup>-globin gene encoding a glutamic acid to alanine mutation at codon 22 and an asparagine to lysine mutation at codon 80 comprises the nucleotide sequence set forth in SEQ ID NO: 61, which is provided below:

```
                                    [SEQ ID NO: 61]
gcaatgaaaataaatgttttttattaggcagaatccagatgctcaaggccc ttcataatatcccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGtgtGGCAAAGGTGCCCTTGAGTttGTCC

AGGTGAGCCAGGCCATCACTAAAGGCACCGAGCACTTTCTTGCCATGAGCC
```

-continued

```
TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACggcATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT
```

In certain embodiments, the human β<sup>A</sup>-globin gene encoding a glutamic acid to alanine mutation at codon 22 and an asparagine to lysine mutation at codon 80 comprises the nucleotide sequence set forth in SEQ ID NO: 62, which is provided below:

[SEQ ID NO: 62]
```
GCAATGAAAATAAATGTTTTTTATTAGGCAGAATCCAGATGCTCAAGGCC

CTTCATAATATCCCCCAGTTTAGTAGTTGGACTTAGGGAACAAAGGAACC

TTTAATAGAAATTGGACAGCAAGAAAGCGAGCTTAGTGATACTTGTGGGC

CAGGGCATTAGCCACACCAGCCACCACTTTCTGATAGGCAGCCTGCACTG

GTGGGGTGAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGTGTGGCAAAGGT

GCCCTTGAGCTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACTGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT
```

In certain embodiments, the human β<sup>A</sup>-globin gene encoding a glutamic acid to alanine mutation at codon 22 and an asparagine to lysine mutation at codon 80 comprises the nucleotide sequence set forth in SEQ ID NO: 63, which is provided below:

[SEQ ID NO: 63]
```
gcaatgaaaataaatgttttttattaggcagaatccagatgctcaaggccc ttcataatatcccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTGTGGCAAAGGTGCCCTTGAGCTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACAGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT
```

In certain embodiments, the human β<sup>A</sup>-globin gene encoding a glutamic acid to alanine mutation at codon 22 and an asparagine to lysine mutation at codon 80 comprises the nucleotide sequence set forth in SEQ ID NO: 64, which is provided below:

[SEQ ID NO: 64]
```
gcaatgaaaataaatgttttttattaggcagaatccagatgctcaaggccc ttcataatatcccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT
```

-continued

```
GATACATTGTATCATTATTGCCCTGAAAGAAAGAGATTAGGGAAAGTATTA

GAAATAAGATAAACAAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTGTGGCAAAGGTGCCCTTGAGCTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACCGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT
```

In certain embodiments, the human β^A-globin gene encoding a glutamic acid to alanine mutation at codon 22 and an asparagine to lysine mutation at codon 80 comprises the nucleotide sequence set forth in SEQ ID NO: 65, which is provided below:

[SEQ ID NO: 65]
```
gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

GCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGTGTGGCAAAGGT

GCCCTTGAGTTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT
```

-continued

```
ATTGGTCTCCTTAAACCTGTCTTGTAACCTTGATACCAACCTGCCCAGGG

CCTCACCACCAACTGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT
```

In certain embodiments, the human β^A-globin gene encoding a glutamic acid to alanine mutation at codon 22 and an asparagine to lysine mutation at codon 80 comprises the nucleotide sequence set forth in SEQ ID NO: 66, which is provided below:

[SEQ ID NO: 66]
```
gcaatgaaaataaatgttttttattaggcagaatccagatgctcaaggccc ttcataatatcccccagtttagtagttggACTTAGGGAACAAAGGAACCTT

TAATAGAAATTGGACAGCAAGAAAGCGAGCTTAGTGATACTTGTGGGCCAG

GGCATTAGCCACACCAGCCACCACTTTCTGATAGGCAGCCTGCACTGGTGG

GGTGAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTGTGGCAAAGGTGCCCTTGAGTTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACAGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT
```

In certain embodiments, the human β^A-globin gene encoding a glutamic acid to alanine mutation at codon 22 and an asparagine to lysine mutation at codon 80 comprises the nucleotide sequence set forth in SEQ ID NO: 67, which is provided below:

[SEQ ID NO: 67]
```
gcaatgaaaataaatgttttttattaggcagaatccagatgctcaaggcc cttcataatatcccccagtttagtagttggacttagggaacaaaggaacc
```

-continued

```
tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAG

AAGGGGAAAGAAAACATCAAGGGTCCCATAGACTCACCCTGAAGTTCTCA

GGATCCACGTGCAGCTTGTCACAGTGCAGCTCACTCAGTGTGGCAAAGGT

GCCCTTGAGTTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACCGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT
```

In certain non-limiting embodiments, the human β-globin gene is a human β$^{A}$-globin gene encoding a glutamic acid to alanine mutation at codon 22 and a threonine to glutamine mutation at codon 87. In certain embodiments, the human β$^{A}$-globin gene encoding a glutamic acid to alanine mutation at codon 22 and a threonine to glutamine mutation at codon 87 further comprises a deletion in intron 2 (e.g., an about 370 bp deletion). In certain embodiments, the human β$^{A}$-globin gene encoding a glutamic acid to alanine mutation at codon 22 and a threonine to glutamine mutation at codon 87 comprises the nucleotide sequence set forth in SEQ ID NO: 68, which is provided below:

```
                                        [SEQ ID NO: 68]
gcaatgaaaataaatgtttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC
```

-continued

```
TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAG

AAGGGGAAAGAAAACATCAAGGGTCCCATAGACTCACCCTGAAGTTCTCA

GGATCCACGTGCAGCTTGTCACAGTGCAGCTCACTCAGCTGGGCAAAGGT

GCCCTTGAGGTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACGGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT
```

In certain embodiments, the human β$^{A}$-globin gene encoding a glutamic acid to alanine mutation at codon 22 and a threonine to glutamine mutation at codon 87 comprises the nucleotide sequence set forth in SEQ ID NO: 69. which is provided below:

```
                                        [SEQ ID NO: 69]
gcaatgaaaataaatgtttttttattaggcagaatccagatgctcaaggccc ttcataatatcccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTTGGGCAAAGGTGCCCTTGAGGTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG
```

-continued

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACGGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT

In certain embodiments, the human β⁴-globin gene encoding a glutamic acid to alanine mutation at codon 22 and a threonine to glutamine mutation at codon 87 comprises the nucleotide sequence set forth in SEQ ID NO: 70, which is provided below:

[SEQ ID NO: 70]
gcaatgaaaataaatgtttttttattaggcagaatccagatgctcaaggccc ttcataatatcccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAGAAGGGGAAAGAAAA

CATCAAGGGTCCCATAGACTCACCCTGAAGTTCTCAGGATCCACGTGCAGC

TTGTCACAGTGCAGCTCACTCAGCTGGGCAAAGGTGCCCTTGAGGTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACTGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT

In certain embodiments, the human β⁴-globin gene encoding a glutamic acid to alanine mutation at codon 22 and a threonine to glutamine mutation at codon 87 comprises the nucleotide sequence set forth in SEQ ID NO: 71, which is provided below:

[SEQ ID NO: 71]
gcaatgaaaataaatgtttttttattaggcagaatccagatgctcaagg cccttcataatatcccccagtttagtagttggacttagggaacaaagg aacctttaatagaaattggacagcaagaaagcgagcttagtgatactt gtgggccagggcattagccacaccagccaccactttctgataggcagc ctgcactggtgggggtgAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGCTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACAGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT

In certain embodiments, the human β⁴-globin gene encoding a glutamic acid to alanine mutation at codon 22 and a threonine to glutamine mutation at codon 87 comprises the nucleotide sequence set forth in SEQ ID NO: 72, which is provided below:

[SEQ ID NO: 72]
gcaatgaaaataaatgtttttttattaggcagaatccagatgctcaagg cccttcataatatcccccagtttagtagttggacttagggaacaaagg aacctttaatagaaattggacagcaagaaagcgagcttagtgatactt gtgggccagggcattagccacaccagccaccactttctgataggcagc ctgcactggtgggggtgAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

-continued

```
ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGCTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACCGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT
```

In certain embodiments, the human β<sup>A</sup>-globin gene encoding a glutamic acid to alanine mutation at codon 22 and a threonine to glutamine mutation at codon 87 comprises the nucleotide sequence set forth in SEQ ID NO: 73, which is provided below:

[SEQ ID NO: 73]
```
gcaatgaaaataaatgttttttattaggcagaatccagatgctcaagg cccttcataatatcccccagtttagtagttggacttagggaacaaagg aacctttaatagaaattggacagcaagaaagcgagcttagtgatactt gtgggccagggcattaGCCACACCAGCCACCACTTTCTGATAGGCAGC

CTGCACTGGTGGGGTGAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGTTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC
```

-continued

```
CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACTGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT
```

In certain embodiments, the human β<sup>A</sup>-globin gene encoding a glutamic acid to alanine mutation at codon 22 and a threonine to glutamine mutation at codon 87 comprises the nucleotide sequence set forth in SEQ ID NO: 74, which is provided below:

[SEQ ID NO: 74]
```
gcaatgaaaataaatgttttttattaggcagaatccagatgctcaagg cccttcataatatcccccagtttagtagttggACTTAGGGAACAAAGG

AACCTTTAATAGAAATTGGACAGCAAGAAAGCGAGCTTAGTGATACTT

GTGGGCCAGGGCATTAGCCACACCAGCCACCACTTTCTGATAGGCAGC

CTGCACTGGTGGGGTGAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGTTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACAGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT
```

In certain embodiments, the human β<sup>A</sup>-globin gene encoding a glutamic acid to alanine mutation at codon 22 and a threonine to glutamine mutation at codon 87 comprises the nucleotide sequence set forth in SEQ ID NO: 75, which is provided below:

[SEQ ID NO: 75]

gcaatgaaaataaatgttttttattaggcagaatccagatgctcaagg cccttcataatatcccccagtttagtagttggACTTAGGGAACAAAGG

AACCTTTAATAGAAATTGGACAGCAAGAAAGCGAGCTTAGTGATACTT

GTGGGCCAGGGCATTAGCCACACCAGCCACCACTTTCTGATAGGCAGC

CTGCACTGGTGGGGTGAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGTTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACCGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT

In certain embodiments, the site of the human β-globin gene IVS2 deletion is located at nucleotides 650-652 of SEQ ID NO: 36. In certain embodiments, nucleotides 1 to 261 of SEQ ID NO: 36 is the nucleotide sequence of exon 3 of the human β-globin gene. In certain embodiments, nucleotides 738 to 960 of SEQ ID NO: 36 is the nucleotide sequence of exon 2 of the human β-globin gene. certain embodiments, nucleotides 1091 to 1232 of SEQ ID NO: 36 is the nucleotide sequence of exon 1 of the human β-globin gene.

3.3. Promoters

In accordance with the presently disclosed subject matter, the expression cassette can further comprise a β-globin promoter. In certain embodiments, the β-globin promoter is positioned between the globin gene or functional portion thereof and the β-globin LCR. The length and the sequence of the β-globin promoter can vary. In certain embodiments, the β-globin promoter is from about 100 bp to about 1600 bp in length, e.g., from about 200 bp to about 700 bp, from about 100 bp to about 200 bp, from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, from about 1100 bp to about 1200 bp, from about 1200 bp to about 1300 bp, from about 1300 bp to about 1400 bp, from about 1400 bp to about 1500 bp, or from about 1500 bp to about 1600 bp in length. In certain embodiments, the β-globin promoter a human β-globin promoter that is about 130 bp, about 613 bp, about 265 bp, or about 1555 bp, in length. In certain embodiments, the β-globin promoter is a human β-globin promoter that is about 613 bp in length. In certain non-limiting embodiments, the human β-globin promoter has the nucleotide sequence set forth in SEQ ID NO:10, which is provided below:

[SEQ ID NO: 10]

AAGCAATAGATGGCTCTGCCCTGACTTTTATGCCCAGCCCTGGCTCCT

GCCCTCCCTGCTCCTGGGAGTAGATTGGCCAACCCTAGGGTGTGGCTC

CACAGGGTGAGGTCTAAGTGATGACAGCCGTACCTGTCCTTGGCTCTT

CTGGCACTGGCTTAGGAGTTGGACTTCAAACCCTCAGCCCTCCCTCTA

AGATATATCTCTTGGCCCCATACCATCAGTACAAATTGCTACTAAAAA

CATCCTCCTTTGCAAGTGTATTTACGTAATATTTGGAATCACAGCTTG

GTAAGCATATTGAAGATCGTTTTCCCAATTTTCTTATTACACAAATAA

GAAATTGATGCACTAAAAGTGGAAGAGTTTTGTCTACCATAATTCAGC

TTTGGGATATGTAGATGGATCTCTTCCTGCGTCTCCAGAATATGCAAA

ATACTTACAGGACAGAATGGATGAAAACTCTACCTCAGTTCTAAGCAT

ATCTTCTCCTTATTTGGATTAAAACCTTCTGGTAAGAAAAGAAAAAAA

ATATATATATATATGTGTATATATACACACATACATATACATATATAT

GCATTCATTTGTTGTTGTTTTTCTTAATTTGCTCATG

In certain embodiments, the β-globin promoter is a human β-globin promoter that is about 265 bp in length. In certain non-limiting embodiments, the human β-globin promoter has the nucleotide sequence set forth in SEQ ID NO:11.

[SEQ ID NO: 11]

AAGCAATAGATGGCTCTGCCCTGACTTTTATGCCCAGCCCTGGCTCCT

GCCCTCCCTGCTCCTGGGAGTAGATTGGCCAACCCTAGGGTGTGGCTC

CACAGGGTGAGGTCTAAGTGATGACAGCCGTACCTGTCCTTGGCTCTT

CTGGCACTGGCTTAGGAGTTGGACTTCAAACCCTCAGCCCTCCCTCTA

AGATATATCTCTTGGCCCCATACCATCAGTACAAATTGCTACTAAAAA

CATCCTCCTTTGCAAGTGTATTTAC 3.4. Human β-Globin 3' Enhancers

Additionally or alternatively, a presently disclosed expression cassette can further comprise a human β-globin 3' enhancer. In certain embodiments, the human β-globin 3' enhancer is positioned in the upstream of the globin gene or functional portion thereof. In certain embodiments, the β-globin 3' enhancer is from about 500 bp to about 1000 bp in length, e.g., from about 500 bp to about 600 bp, from about 600 bp to about 700 bp, from about 700 bp to about 800 bp, or from about 800 bp to about 900 bp in length. In certain embodiments, the human β-globin 3' enhancer is about 879 bp in length. In certain embodiments, the human β-globin 3' enhancer has the nucleotide sequence set forth in SEQ ID NO: 12, which is provided below.

[SEQ ID NO: 12]
TAGGTATTGAATAAGAAAAATGAAGTTAAGGTGGTTGATGGTAACACT

ATGCTAATAACTGCAGAGCCAGAAGCACCATAAGGGACATGATAAGGG

AGCCAGCAGACCTCTGATCTCTTCCTGAATGCTAATCTTAAACATCCT

GAGGAAGAATGGGACTTCCATTTGGGGTGGGCCTATGATAGGGTAATA

AGACAGTAGTGAATATCAAGCTACAAAAAGCCCCCTTTCAAATTCTTC

TCAGTCCTAACTTTTCATACTAAGCCCAGTCCTTCCAAAGCAGACTGT

GAAAGAGTGATAGTTCCGGGAGACTAGCACTGCAGATTCCGGGTCACT

GTGAGTGGGGGAGGCAGGGAAGAAGGGCTCACAGGACAGTCAAACCAT

GCCCCCTGTTTTTCCTTCTTCAAGTAGACCTCTATAAGACAACAGAGA

CAACTAAGGCTGAGTGGCCAGGCGAGGAGAAACCATCTCGCCGTAAAA

CATGGAAGGAACACTTCAGGGGAAAGGTGGTATCTCTAAGCAAGAGAA

CTGAGTGGAGTCAAGGCTGAGAGATGCAGGATAAGCAAATGGGTAGTG

AAAAGACATTCATGAGGACAGCTAAAACAATAAGTAATGTAAAATACA

GCATAGCAAAACTTTAACCTCCAAATCAAGCCTCTACTTGAATCCTTT

TCTGAGGGATGAATAAGGCATAGGCATCAGGGGCTGTTGCCAATGTGC

ATTAGCTGTTTGCAGCCTCACCTTCTTTCATGGAGTTTAAGATATAGT

GTATTTTCCCAAGGTTTGAACTAGCTCTTCATTTCTTTATGTTTTAAA

TGCACTGACCTCCCACATTCCCTTTTTAGTAAAATATTCAGAAATAAT

TTAAATACATCATTG

In certain embodiments, the human β-globin 3' enhancer has the nucleotide sequence set forth in SEQ ID NO: 78, which is provided below.

[SEQ ID NO: 78]
CTAGGTATTGA ATAAGAAAAA TGAAGTTAAG GTGGTTGATG

GTAACACTAT GCTAATAACT GCAGAGCCAG AAGCACCATA

AGGGACATGA TAAGGGAGCC AGCAGACCTC TGATCTCTTC

CTGAATGCTA ATCTTAAACA TCCTGAGGAA GAATGGGACT

TCCATTTGGG GTGGGCCTAT GATAGGGTAA TAAGACAGTA

GTGAATATCA AGCTACAAAA AGCCCCCTTT CAAATTCTTC

TCAGTCCTAA CTTTTCATAC TAAGCCCAGT CCTTCCAAAG

CAGACTGTGA AAGAGTGATA GTTCCGGGAG ACTAGCACTG

CAGATTCCGG GTCACTGTGA GTGGGGGAGG CAGGGAAGAA

GGGCTCACAG GACAGTCAAA CCATGCCCCC TGTTTTTCCT

TCTTCAAGTA GACCTCTATA AGACAACAGA GACAACTAAG

GCTGAGTGGC AGGCGAGGA GAAACCATCT CGCCGTAAAA

CATGGAAGGA ACACTTCAGG GGAAAGGTGG TATCTCTAAG

CAAGAGAACT GAGTGGAGTC AAGGCTGAGA GATGCAGGAT

AAGCAAATGG GTAGTGAAAA GACATTCATG AGGACAGCTA

AAACAATAAG TAATGTAAAA TACAGCATAG CAAAACTTTA

ACCTCCAAAT CAAGCCTCTA CTTGAATCCT TTTCTGAGGG

ATGAATAAGG CATAGGCATC AGGGGCTGTT GCCAATGTGC

-continued
ATTAGCTGTT TGCAGCCTCA CCTTCTTTCA TGGAGTTTAA

GATATAGTGT ATTTTCCCAA GGTTTGAACT AGCTCTTCAT

TTCTTTATGT TTTAAATGCA CTGACCTCCC ACATTCCCTT

TTTAGTAAAA TATTCAGAAA TAATTTAAAT ACATCATT

3.5. Erythroid-Specific Enhancers

Furthermore, a presently disclosed expression cassette can further comprise at least one erythroid-specific enhancer. The presently disclosed expression cassette allows for expression of a globin gene (e.g., human β-globin gene) in erythroid-specific fashion. The erythroid-specific enhancer can enhance the expression of the globin gene in erythroid-specific fashion. For example, the erythroid-specific enhancer lack enhancer activity in non-erythroid tissues. In particularly, for the β-globin LCR that lacks a HS2 region, which primarily functions as an expression enhancer, the addition of one or more erythroid-specific enhancers can compensate the enhancing activity of a HS2 region. Additionally, for an expression cassette that lacks a β-globin LCR (e.g., SNS26.B87.A1) or the β-globin LCR consists essentially of a HS3 region and does not comprise a HS1 region, a HS2 region, or a HS4 region (e.g., SN27.2B87.A1), the addition of one or more erythroid-specific enhancers are capable of driving the expression of the β-globin gene. See e.g., Table 1 and FIG. 16. Furthermore, the presently disclosed erythroid-specific enhancers do not decrease or reduce the titer of a vector comprising the expression cassette. The length of the erythroid-specific enhancer can vary, e.g., from about 100 bp to about 200 bp, from about 100 bp to about 120 bp, from about 120 bp to about 140 bp, from about 140 bp to about 200 (e.g., from about 140 bp to about 150 bp, from about 150 bp to about 160 bp, from about 160 bp to about 170 bp, from about 170 bp to about 180 bp, from about 180 bp to about 190 bp, or from about 190 bp to about 200 bp). In certain embodiments, the erythroid-specific enhancer has a length of from about 140 bp to about 200 bp. In certain non-limiting embodiments, the erythroid-specific enhancer has a length of 152 bp, which has the nucleotide sequence set forth in SEQ ID NO: 13, which is provided below:

[SEQ ID NO: 13]
TCTCCCACGCCCTGGTCTCAGCTTGGGGAGTGGTCAGACCCCAATGGC

GATAAACTCTGGCAACTTTATCTGTGcaCTGCAGGCTCAGCCCCAAca

GCTTTAGCTTTCACAAGCAGGCAGGGGAAGGGAAACACATATCTCCAG

ATATGAGG

In certain non-limiting embodiments, the erythroid-specific enhancer has a length of 157 bp, which has the nucleotide sequence set forth in SEQ ID NO:14, which is provided below:

[SEQ ID NO: 14]
CTAAACCCCTCCCCCACCCTAGCCCCAAGCTTCATCTTAGCTCCACTC

CTGACCCTATCCAGCTAAAGGTCCCCACCCAGCTCCTGCCTATCTAGT

CATTGCATATGGCAAGACTTGAAAGTCCTATCTCAAAGCAGCAGAATT

ATCAGCTACGACT

In certain non-limiting embodiments, the erythroid-specific enhancer has a length of 141 bp, which has the nucleotide sequence set forth in SEQ ID NO:15, which is provided below:

[SEQ ID NO: 15]

CCATCCCCCAGCACTCCCTGCCCCCACAGCCCAGACTTGACCAACTCC

CAGCTcCGCCTGGGACTTCCAGATATGGGGCCCCACCCTTGCAGGCCT

TGGGGACGCTGAAGATATTGACTATCTGCGTGCCggAAAAGGGTG

In certain non-limiting embodiments, the erythroid-specific enhancer has a length of 171 bp, which has the nucleotide sequence set forth in SEQ ID NO:16, which is provided below:

[SEQ ID NO: 16]

AAAGGCTGGGGGTGGGAGTAGCGGATTTGAAGCACTTGTTGGCCTACA

GAGGTGTGGCAAGCAGAGCACCTCAGAACTCAGGCGTACTGCCCGCCG

CCCGAGCCCTGCGAGGGCCGATAGCGAGGGTGTGGCCCTTATCTGCAC

CCAGCAGAGCGCCGGCGGGGTACGGTC

In certain non-limiting embodiments, the erythroid-specific enhancer has a length of 195 bp, which has the nucleotide sequence set forth in SEQ ID NO:17, which is provided below:

[SEQ ID NO: 17]

CAGTTGCCTCAGCTGAGTATGTCTTCTAAAGATAATGTCGATTGTGTA

TGGCTGATGGGATTCTAGGACCAAGCAAGAGGTTTTTTTTTTCCCCC

ACATACTTAACGTTTCTATATTTCTATTTGAATTCGACTGGACAGTTC

CATTTGAATTATTTCTCTCTCTCTCTCTCTCTGACACATTTTATCTTG

CCA

The erythroid-specific enhancer can be located within the β-globin LCR, e.g., between any two of the HS1, HS2, HS3, and HS4 regions. In certain embodiments, the erythroid-specific enhancer is located between the HS1 and HS3 regions within the β-globin LCR.

Alternatively, the erythroid-specific enhancer can be located upstream or downstream of the insulator, e.g., where the expression cassette does not comprise a β-globin LCR. In certain embodiments, the erythroid-specific enhancer is located upstream of the erythroid-specific enhancer.

Furthermore, the erythroid-specific enhancer can be located upstream or downstream of any of the HS1, HS2, HS3, and HS4 regions. In certain embodiments, the erythroid-specific enhancer is located upstream of the HS3 region.

In certain embodiments, the β-globin LCR comprises or consists essentially of a HS1 region having the nucleotide sequence set forth in SEQ ID NO: 3; a HS3 region having the nucleotide sequence set forth in SEQ ID NO: 5; a HS4 region having nucleotides 115 to 868 of SEQ ID NO: 6; and an erythroid-specific enhancer having the nucleotide sequence set forth in SEQ ID NO: 15, wherein the erythroid-specific enhancer is positioned between the HS1 region and the HS3 region, e.g., the β-globin LCR of SNS24.B87.A1 shown in FIG. 15.

In certain non-limiting embodiments, the β-globin LCR comprises or consists essentially of a HS1 region having the nucleotide sequence set forth in SEQ ID NO: 3; a HS3 region having the nucleotide sequence set forth in SEQ ID NO: 34; and a HS4 region having the nucleotide sequence set forth in SEQ ID NO: 35; and an erythroid-specific enhancer having the nucleotide sequence set forth in SEQ ID NO: 15, wherein the erythroid-specific enhancer is positioned between the HS1 region and the HS3 region, e.g., as the β-globin LCR of SNS22.2.B87.A1 shown in FIG. 13.

Erythroid-specific enhancers can be identified and determined by any suitable methods known in the art. The erythroid-specific enhancers can be positioned at the 3' UTR (downstream) or 5' UTR (downstream) of the β-globin LCR. In certain embodiments, the at least one erythroid-specific enhancer is positioned in 5' UTR of the β-globin LCR, e.g., the upstream of the HS3 region. The expression cassette can comprise one, two, three, four, or five erythroid-specific enhancers. In certain embodiments, the expression cassette comprises one erythroid-specific enhancer. In certain embodiments, the expression cassette comprises two erythroid-specific enhancers. In certain embodiments, the expression cassette comprises three erythroid-specific enhancers. In certain embodiments, the expression cassette comprises four erythroid-specific enhancers. In certain non-limiting embodiments, the expression cassette comprises five erythroid-specific enhancers.

3.6. Insulators

In accordance with the presently disclosed subject matter, the expression cassette comprises at least one of the above-described insulators. In certain embodiments, a presently disclosed expression cassette comprises at least one insulator comprising the CTCF binding site sequence set forth in SEQ ID NO: 18, for example, but not limited to, an insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32 or a fragment thereof. In certain embodiments, a presently disclosed expression cassette comprises at least one insulator comprising or having the nucleotide sequence set forth in SEQ ID NO: 1. In various non-limiting embodiments, the insulator can be incorporated or inserted into one or both LTRs or elsewhere in the region of a presently disclosed expression cassette that integrates into the cellular genome. In certain embodiments, the insulator is positioned at the 3' end of the expression cassette. In certain embodiments, the insulator is positioned at the 5' end of the expression cassette. In certain embodiments, the expression cassette comprises two of the insulator disclosed herein, e.g., an insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32 or a fragment thereof, where one insulator is positioned at the 3' end and the other insulator is positioned at the 5' end of the expression cassette.

The presently disclosed insulators possess powerful enhancer blocking activity. In certain embodiments, the insulators possess barrier activity in addition to enhancer blocking activity. The presently disclosed insulators substantially decrease the risks of insertional mutagenesis and genotoxicity associated with viral vectors. Furthermore, when a presently disclosed insulator is incorporated into a vector, the insulator does not adversely effect vector titers of the vector. In certain embodiments, the insulators increase the in vivo expression of the globin gene or functional portion thereof.

3.7. Exemplary Expression Cassettes

For the purpose of illustration and not limitation, FIGS. 1-4, 13, 14, and 15 show recombinant vectors comprising exemplary expression cassettes in accordance with certain embodiments of the presently disclosed subject matter.

FIG. 1 shows a recombinant vector comprising a presently disclosed expression cassette that comprises a human $\beta^{A-T87Q}$ globin gene, which is operably linked to a $\beta$-globin LCR that comprises a 860 bp HS2 region (e.g., one having the nucleotide sequence set forth in SEQ ID NO:9), a 1301 bp HS3 region (e.g., one having the nucleotide sequence set forth in SEQ ID NO:5), and a 1065 bp HS4 region (e.g., one having the nucleotide sequence set forth in SEQ ID NO:7).

FIG. 2 shows one exemplary recombinant vector comprising an expression cassette in accordance with one embodiment of the presently disclosed subject matter. FIG. 2 shows a recombinant vector comprising a presently disclosed expression cassette that comprises a human $\beta^A$-T87Q globin gene, which is operably linked to a $\beta$-globin LCR that comprises a 1.1 kb HS1 region (e.g., one having the nucleotide sequence set forth in SEQ ID NO:2), a 1301 bp HS3 region (e.g., one having the nucleotide sequence set forth in SEQ ID NO:5), and a 1065 bp HS4 region (e.g., one having the nucleotide sequence set forth in SEQ ID NO:6).

FIG. 3 shows one exemplary recombinant vector comprising an expression cassette in accordance with one embodiment of the presently disclosed subject matter. FIG. 3 shows a recombinant vector comprising a presently disclosed expression cassette that comprises a human $\beta^A$-T87Q globin gene, which is operably linked to a $\beta$-globin LCR that comprises a 602 bp HS1 region (e.g., one having the nucleotide sequence set forth in SEQ ID NO:3), a 1301 bp HS3 region (e.g., one having the nucleotide sequence set forth in SEQ ID NO:5), and a 446 bp HS4 region (e.g., one having the nucleotide sequence set forth in SEQ ID NO:8).

FIG. 4 shows one exemplary recombinant vector comprising an expression cassette in accordance with one embodiment of the presently disclosed subject matter. FIG. 4 shows a recombinant vector comprising a presently disclosed expression cassette that comprises a human $\beta^A$-T87Q globin gene, which is operably linked to a $\beta$-globin LCR that comprises a 1301 bp HS3 region (e.g., one having the nucleotide sequence set forth in SEQ ID NO:5), and a 1065 bp HS4 region (e.g., one having the nucleotide sequence set forth in SEQ ID NO:6). The expression cassette shown in FIG. 4 also comprises the following five erythroid-specific enhancers (shown as "EE5" in FIG. 4): one erythroid-specific enhancer having the nucleotide sequence set forth in SEQ ID NO:13, one erythroid-specific enhancer having the nucleotide sequence set forth in SEQ ID NO:14, one erythroid-specific enhancer having the nucleotide sequence set forth in SEQ ID NO:15, one erythroid-specific enhancer having the nucleotide sequence set forth in SEQ ID NO:16, and one erythroid-specific enhancer having the nucleotide sequence set forth in SEQ ID NO:17.

FIG. 13 shows the following five exemplary recombinant vectors: SNS22.2.B87A1, which comprises an expression cassette that comprises a human $\beta^{A-T87Q}$ globin gene, which is operably linked to a $\beta$-globin LCR that comprises a 602 bp HS1 region (e.g., one having the nucleotide sequence set forth in SEQ ID NO:3), a 816 bp HS2 region (e.g., one having the nucleotide sequence set forth in SEQ ID NO: 33), a 1301 bp HS3 region (e.g., one having the nucleotide sequence set forth in SEQ ID NO: 34), and a 754 bp HS4 region (e.g., one having the nucleotide sequence set forth in SEQ ID NO: 35);

SNS23.2.B87A1, which comprises an expression cassette that comprises a human $\beta^{A-T87Q}$ globin gene, which is operably linked to a $\beta$-globin LCR that comprises a 816 bp HS2 region (e.g., one having the nucleotide sequence set forth in SEQ ID NO:33), a 1301 bp HS3 region (e.g., one having the nucleotide sequence set forth in SEQ ID NO:34), and a 754 bp HS4 region (e.g., one having the nucleotide sequence set forth in SEQ ID NO:35), wherein the $\beta$-globin LCR does not comprise a HS1 region;

SNS24.2.B87A1, which comprises an expression cassette that comprises a human $\beta^{A-T87Q}$ globin gene, which is operably linked to a $\beta$-globin LCR that comprises a 602 bp HS1 region (e.g., one having the nucleotide sequence set forth in SEQ ID NO:3), a 1301 bp HS3 region (e.g., one having the nucleotide sequence set forth in SEQ ID NO:34), a 754 bp HS4 region (e.g., one having the nucleotide sequence set forth in SEQ ID NO:35); and an erythroid-specific enhancer having the nucleotide sequence set forth in SEQ ID NO:15, wherein the $\beta$-globin LCR does not comprise a HS2 region;

SNS26.B87A1, which comprises an expression cassette that comprises a human $\beta^{A-T87Q}$ globin gene, and an erythroid-specific enhancer having the nucleotide sequence set forth in SEQ ID NO:15, wherein the expression cassette does not comprise a $\beta$-globin LCR; and SNS27.2.B87.A1, which comprises an expression cassette that comprises an insulator comprising the nucleotide sequence set forth in SEQ ID NO: 1, and a human $\beta^{A-T87Q}$ globin gene that is operably linked to a $\beta$-globin LCR comprising a 1301 bp HS3 region (e.g., one having the nucleotide sequence set forth in SEQ ID NO:34), and an erythroid-specific enhancer having the nucleotide sequence set forth in SEQ ID NO:15, wherein the $\beta$-globin LCR does not comprise a HS1 region, a HS2 region, or a HS4 region.

FIG. 15 shows five exemplary recombinant vectors including SNS22.B87A1, which comprises an expression cassette that comprises a human $\beta^{A-T87Q}$ globin gene, which is operably linked to a $\beta$-globin LCR that comprises a 602 bp HS1 region (e.g., one having the nucleotide sequence set forth in SEQ ID NO:3), a 816 bp HS2 region (e.g., one having nucleotides 45 to 860 of SEQ ID NO: 9), a 1301 bp HS3 region (e.g., one having the nucleotide sequence set forth in SEQ ID NO:5), and a 754 bp HS4 region (e.g., one having nucleotides 115 to 868 of SEQ ID NO: 6);

SNS23.B87A1, which comprises an expression cassette that comprises a human $\beta^{A-T87Q}$ globin gene, which is operably linked to a $\beta$-globin LCR that comprises a 816 bp HS2 region (e.g., one having nucleotides 45 to 860 of SEQ ID NO: 9), a 1301 bp HS3 region (e.g., one having the nucleotide sequence set forth in SEQ ID NO:5), and a 754 bp HS4 region (e.g., one having nucleotides 115 to 868 of SEQ ID NO: 6); SNS24.B87A1, which comprises an expression cassette that comprises a human $\beta^{A-T87Q}$ globin gene, which is operably linked to a $\beta$-globin LCR that comprises a 602 bp HS1 region (e.g., one having the nucleotide sequence set forth in SEQ ID NO:3), a 1301 bp HS3 region (e.g., one having the nucleotide sequence set forth in SEQ ID NO:5), a 754 bp HS4 region (e.g., one having nucleotides 115 to 868 of SEQ ID NO: 6); and an erythroid-specific enhancer having the nucleotide sequence set forth in SEQ ID NO:15; and SNS26.B87.A1, which is also disclosed in FIG. 13 as described above.

As shown in FIGS. 1-4, 13, and 15, each of the expression cassettes comprises an insulator, wherein the insulator has the nucleotide sequence set forth in SEQ ID NO:1 (i.e., insulator A1). In addition, as shown in FIGS. 1-4, 13, 15, each of the expression cassettes comprises a human $\beta$-globin 3' enhancer that is positioned upstream of the human $\beta$-globin gene, wherein the human $\beta$-globin 3' enhancer has a length of 879 bp and has the nucleotide sequence set forth in SEQ ID NO: 12. Additionally, as shown in FIGS. 13 and 15, each of SNS22.B87.A1, SNS23.B87.A1, SNS24.B87.A1, SNS22.2.B87.A1, SNS23.2.B87.A1, SNS24.2.B87.A1, SNS26.B87.A1, and SNS27.2B87.A1 comprises a 265 bp human β-globin promoter, wherein the human β-globin promoter has the nucleotide sequence set forth in SEQ ID NO: 11. TNS9.B87.A1 shown in FIG. 15 comprises a 613 bp human β-globin promoter, wherein the human β-globin promoter has the nucleotide sequence set forth in SEQ ID NO: 10.

III. Vectors, Nucleases and CRISPR-Cas Systems

The presently disclosed subject matter provides vectors and delivery systems (e.g., a non-naturally occurring or engineered nucleases or a CRISPR-Cas system) comprising the above-described expression cassettes. The vectors and delivery systems are suitable delivery vehicles for the stable introduction of globin gene (e.g., human β-globin) into the genome of a broad range of target cells to increase expression of the globin protein (human β-globin protein) in the cell.

In certain embodiments, the vector is a retroviral vector (e.g., gamma retroviral vector or a lentiviral vector) that is employed for the introduction or transduction of the above-described expression cassette into the genome of a host cell (e.g., a hematopoietic stem cell, an embryonic stem cell, an induced pluripotent stem cell, or a hemogenic endothelium cell). In certain embodiments, the retroviral vector comprises an expression cassette that comprises one of the above-described insulators, e.g., insulator A1. The insulator can be positioned at the 3' or 5' end of the expression cassette. In certain embodiments, the insulator is positioned at the 3' end of the expression cassette. During reverse transcription and vector integration, the insulator positioned at the 3' end is copied into the 5' end of the expression cassette. The resulting topology places copies of the insulator between the genomic regions located at 5' LTR and 3' LTR of the integrated virus and enhancer activity from 5' LTR and internal package promoter, but does not contain the enhancer in 3' LTR. This topology can decrease genotoxicity, thereby resulting in decreased tumor formation and increased survival of the animals.

In certain embodiments, the vector is an Adeno-associated virus (AAV) vector. Non-limiting examples of AAV vectors include AAV1, AAV2, AAV3, AAV4, AAV5, AAV6, AAV7, AAV8, AAV9, AAV10, and AAV11. In certain embodiments, the vector is an AAV6 vector.

In certain embodiments, the recombinant vector is a retroviral vector. In certain embodiments, the retroviral vector is a lentiviral vector. In certain embodiments, the recombinant vector is a self-inactivating (SIN) lentiviral vector in which the enhancer and promoter region of 3' long terminal repeat ("LTR") is modified (e.g., a 133 bp deletion in the U3 region). SIN vectors can infect and integrate into the genome of non-dividing cells in vivo with an efficacy similar to that of wild-type vectors. SIN lentivirus vectors are disclosed in Miyoshi et al., *J. Virol.* (October 1998); 72:8150-8157, which is incorporated by reference in its entirety. SIN vectors can reduce the risk of creating undesired replication-competent virus because there is no complete U3 region in 3' LTR, thereby eliminating the ability of the virus to be passed (see Miyoshi 1998).

In certain embodiments, the retroviral vector is a gamma-retroviral vector. In certain embodiments, the retroviral vector is a SIN gamma-retroviral vector.

In certain embodiments, the recombinant vector further comprises one or more of a rev-responsive element ("RRE"), a central polypurine tract ("cPPT"), a 5' LTR (in which the U3 region of 5' LTR comprises a heterologous promoter (e.g., replaced with a cytomegalovirus (CMV) HIV heterologous promoter) resulting in Tat-independent transcription with no decreases in virus titer), and a 3' SIN LTR (e.g., a 3' SIN LTR comprising a 389 bp deletion in the U3 region).

In certain embodiments, the recombinant vector further comprises a Woodchuck hepatitis post-regulatory element (WPRE) in 3' long terminal repeat (LTR) of the vector (e.g., 3' to the R region in 3' LTR of the vector). In certain embodiments, the recombinant vector further comprises a bovine growth hormone polyadenylation signal in addition to the WPRE in 3' long terminal repeat (LTR) of the vector (e.g., 3' to the R region in 3' LTR of the vector). The WPRE can increase the titer of the recombinant vector (e.g., can increase the vector titer by at least about 5 folds). Addition of a bovine growth hormone ("BGH") polyadenylation ("polyA") signal ("BGH/polyA") to the WPRE can further increase the titer of the recombinant vector. In certain embodiments, the WPRE and BGH/polyA are eliminated after the vector is transfused to target cells, and thus, are not present in the proviruses. In certain embodiments, the WPRE and the BGH/polyA are not comprised within the expression cassette, and thus, not transferred to the cells transduced with the recombinant vector.

As shown in FIGS. 1-4, 13, and 15, the recombinant vector can further comprises a rev-responsive element ("RRE"), a central polypurine tract ("cPPT"), a 5' LTR (in which the U3 region of 5' LTR comprises a heterologous promoter (e.g., replaced with a cytomegalovirus (CMV) HIV heterologous promoter) resulting in Tat-independent transcription with no decreases in virus titer), a 3' SIN LTR comprising a 389 bp deletion in the U3 region, a WPRE, and a BGH/polyA in 3' long terminal repeat (LTR) of the vector (e.g., 3' to the R region in 3' LTR). The heterologous promoter (e.g., a CMV/HIVheterologous promoter) can increase the RNA transcription and the production of the vector. The heterologous promoter (e.g., a CMV/HIVheterologous promoter) is eliminated after reverse transcription, and thus, is not present in the proviruses.

In certain non-limiting embodiments, a presently disclosed expression cassette can be cloned into a retroviral vector and expression can be driven from its endogenous promoter, from the retroviral long terminal repeat, or from an alternative internal promoter. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Suitable methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a globin gene (e.g., a human β-globin gene) in a host cell (e.g., hematopoietic stem cells, an embryonic stem cell, or an induced pluripotent stem cell). In certain embodiments, the chosen vector exhibits high efficiency of infection and stable integration and expression (see, e.g., Cayouette et al., Human Gene Therapy (1997); 8:423-430; Kido et al., Current Eye Research (1996); 15:833-844; Bloomer et al., Journal of Virology (1997); 71:6641-6649; Naldini et al., Science (1996); 272:263 267; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, *Human Gene Therapy* (1990); 15-14; Friedman, *Science* (1989); 244:1275-1281; Eglitis et al., *BioTechniques* 6:608-614, 1988; Tolstoshev et al., *Current Opinion in Biotechnology* (1990); 1:55-61; Sharp, *The Lancet* (1991); 337:1277-1278; Cornetta et al., *Nucleic Acid Research and Molecular Biology* (1987) 36:311-322; Anderson, *Science* (1984); 226:401-409; Moen, *Blood Cells* (1991); 17:407-416; Miller et al., *Biotechnology* (1989); 7:980-990; Le Gal La Salle et al., *Science* (1993); 259:988-990; and Johnson, *Chest* (1995); 107:77S-83S). Retroviral vectors are particularly well developed and have been used in clinical settings (Rosenberg et al., *N. Engl. J. Med* (1990); 323:370; Anderson et al., U.S. Pat. No. 5,399,346).

The requirement for efficient delivery and integration make retroviral vectors suitable for transducing a presently disclosed expression cassette. Retroviral vectors can be derived from three genera of the retroviridae: the γ-retroviruses (also known as C-type murine retroviruses or oncoretroviruses), the lentiviruses, and the spumaviruses (also known as foamy viruses). Several reviews detailing molecular approaches for the generation of replication-defective retroviral particles are available (Cornetta et al. (2005); Cockrell & Kafri (2007)). The vector itself, which encodes the therapeutic transgene or cDNA, retains the minimal viral sequences needed to enable packaging in viral particles in a packaging cell line, reverse transcription, and integration. The packaging cell expresses the necessary structural proteins and enzymes that are required to assemble an infectious recombinant particle that contains the vector sequence and the machinery needed for its reverse transcription and integration in the transduced cell.

While the manufacturing aspects of all retroviral vector types follow the same general principles, γ-retroviral, lentiviral and spumaviral vectors differ in some of their intrinsic biological properties. Gamma-retroviruses, including the prototypic murine leukaemia viruses (MLV), effectively infect many cell types but are unable to integrate in cells that do not proceed to S phase soon after infection. In contrast, lentiviruses and their vector derivatives can transduce non-dividing cells (Follenzi & Naldini, 2002; Salmon & Trono, 2002) owing to their ability to translocate to the nucleus and integrate in the absence of cell division (Lewis & Emerman, 1994; Goff, 2001). Another fundamental attribute of lentiviral vectors is their relative genomic stability, as established for globin lentiviral vectors (May et al., 2000), which contrasts with the genomic instability of MLV-based globin vectors (Leboulch et al., 1994; Sadelain et al., 1995). Lentiviral and foamy vectors further provide a greater packaging capacity (Kumar et al., 2001; Rethwilm, 2007). All three vector types have been used successfully for the transduction of cytokineactivated HSCs (Miyoshi et al., 1999; Josephson et al., 2002; Leurs et al., 2003).

These three vector systems differ in their integration patterns. The integration pattern of retroviruses is semi-random and biased towards genes and their vicinity in approximately two-thirds of all integration events (Schroder et al., 2002; Wu et al., 2003; Mitchell et al., 2004; De Palma et al., 2005; Trobridge et al., 2006). There are however subtle and possibly significant differences in their exact distribution. Gamma-retroviruses have a propensity to integrate upstream of transcribed genes, whereas lentiviruses and lentiviral vectors target the entire transcribed gene sequence. Foamy vectors appear to be less prone to intragenic integration (Trobridge et al., 2006). In certain embodiments, the vector comprising the expression cassette is a lentivirus vector. The vectors can be derived from human immunodeficiency-1 (HIV-1), human immunodeficiency-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), caprine arthritis encephalitis virus (CAEV) and the like. In one non-limiting embodiment, the lentiviral vector is an HIV vector. HIV-based constructs are the most efficient at transduction of human cells.

The semi-random pattern of vector integration exposes patients to the risk of insertional oncogenesis when the vector trans-activates a neighboring oncogene. This may result in clonal expansion (Ott et al, 2006; Cavazzana-Calvo et al, 2010), myelodysplasia (Stein et al, 2010) or leukaemia (Hacein-Bey-Abina et al, 2003, 2008; Howe et al, 2008). Targeted gene delivery strategies, utilizing a non-naturally occurring or engineered nuclease (including, but not limited to, Zinc-finger nuclease (ZNFs), meganuclease, transcription activator-like effector nuclease (TALEN)), or a CRISPR-Cas system, can reduce or even eliminate the concern of insertional oncogenesis that is inherent to the use of retroviral vectors.

Eukaryotic cells utilize two distinct DNA repair mechanisms in response to DNA double strand breaks (DSBs): Homologous recombination (HR) and non-homologous end-joining (NHEJ). The activation of the HR repair machinery depends on the cell cycle status, and it is restricted to the S and G2 phases; in contrast, the NHEJ pathway is active throughout the cell cycle. Mechanistically, HR is an error-free DNA repair mechanism, because it requires a homologous template to repair the damaged DNA strand. On the other hand, NHEJ is a template-independent repair mechanism that is imprecise, due to DNA end processing during repair that leads to insertions or deletions at the DNA break site (Moynahan & Jasin, 2010). Because of its homology-based mechanism, HR has been used as a tool to site-specifically engineer the genome of different species. From a therapeutic perspective, HR has been successfully used to repair mutated genes, thus offering a promising approach to cell-mediated treatment of monogenic diseases (Porteus et al, 2006).

Gene targeting by HR requires the use of two homology arms that flank the transgene/target site of interest. Generally, standard plasmid DNAs have been used to deliver 5-10 kb homology arms along with transgenes for positive and negative selection. This method is commonly used to knock-out/knockin genes in mouse embryonic stem (mES) cells (Capecchi, 2005; FIG. 2B). In human cells, the use of this approach has allowed gene targeting with efficiencies in the order of 10-6, which are lower than in mES cells and are not therapeutically practical. HR efficiency can be increased by the introduction of DNA-doubled stranded breaks (DSBs) at the target site using specific rare-cutting endonucleases, resulting in over 1,000-fold increase in correct gene targeting (Jasin, 1996). The discovery of this phenomenon prompted the development of methods to create site-specific DSBs in the genome of different species. Various chimeric enzymes have been designed for this purpose over the last decade, namely zinc-finger nucleases (ZFNs), meganucleases, and transcription activator-like effector nucleases (TALENs).

ZFNs are modular chimeric proteins that contain a ZF-based DNA binding domain (DBD) and a FokI nuclease domain (Porteus & Carroll, 2005). DBD is usually composed of three ZF domains, each with 3-base pair specificity; the FokI nuclease domain provides a DNA nicking activity, which is targeted by two flanking ZFNs. Owing to the modular nature of the DBD, any site in a genome could be targeted in principle. However, as a single ZFN can bind and nick DNA, there is potential for a high number of off-target effects, resulting in the activation of the NHEJ pathway that may either introduce insertions/deletions or integrate the targeting vector in a non-specific manner. Obligate FokI domains that can nick their respective DNA strand only when they form a heterodimer were recently reported (Doyon et al, 2011). The use of such obligate ZFNs can reduce the genotoxic effects of this approach.

Meganucleases (MNs)/homing endonucleases (HEs) are dsDNA nucleases that recognize and cleave large DNA sites (14-40 bp) with low cleavage frequencies in eukaryotic genomes (Paques & Duchateau, 2007). Although this limits the potential target sites, MN-DNA structures have been used as a guide to specifically modify DNA-interacting residues in order to change the MN specificity (Marcaida et al, 2010). I-CreI has been successfully engineered to generate chimeric meganucleases that target the human XPC and RAGI genes, and they have been shown to stimulate HR activity in mammalian cells with no evident genotoxicity (Redondo et al, 2008; Grizot et al, 2009). The genotoxicity of this approach will need to be compared to that of ZFNs and TALE nucleases.

TALENs are similar ZFN except that the DBD is derived from transcription activator-like effcetors (TALEs), which are virulent factors used by phytopathogenic bacteria (Herbers, 1992). The TALE DBD is modular, and it is composed of 34-residue repeats, and its DNA specificity is determined by the number and order of repeats (Herbers, 1992). Each repeat binds a single nucleotide in the target sequence through only two residues (Boch, 2011). The advantage over ZFN technology is the rapid construction of DBDs.

A number of studies have used these chimeric enzymes to stimulate HR for either gene addition or gene repair at their target site (Paques & Duchateau, 2007; Urnov et al, 2010). Porteus designed a ZFN to a half site sequence from the human HBB that surrounds the sickle cell mutation nucleotide (Porteus, 2006). This ZFN targets the sequence and stimulates HR at a chimeric DNA target when combined with a ZFN targeting the Zif268 binding site. There have been recent advances in targeting genes in cord blood CD34$^+$ cells. Use of non-integrating lentiviruses to deliver ZFNs and the donor DNA in these cells to target the CCR5 gene was reported in Lombardo et al, 2007. Lombardo et al, 2007 showed gene addition at this locus with correct targeting in 80% of the positively selected cells.

The presently disclosed subject matter provides a non-naturally occurring or engineered nuclease comprising a presently disclosed expression cassette, as described above. Suitable nucleases include, but are not limited to, ZFNs, meganucleases, and TALENs. A presently disclosed nuclease comprises a DNA binding domain and a nuclease cleavage domain. The DNA binding domain of the nuclease can be engineered to bind to a sequence of choice, e.g., a predetermined site. An engineered DNA binding domain can have a distinct binding specificity, compared to a naturally occurring nuclease. Engineering methods include, but are not limited to, rational design and various types of selection. Any suitable cleavage domain can be operatively linked to a DNA-binding domain to form a nuclease. For example, Zinc-finger protein (ZFP) DNA-binding domains can be fused to nuclease cleavage domains to create ZFNs-a functional entity that is able to recognize its intended nucleic acid target through its engineered ZFP DNA binding domain and cause the DNA to be cut near the ZFP binding site via the nuclease activity. See, e.g., Kim et al. *Proc Nat'l Acad Sci USA* (1996); 93(3):1156-1160. Likewise, TALE DNA-binding domains can be fused to nuclease cleavage domains to create TALENs. See, e.g., U.S. Publication No. 20110301073.

The cleavage domain can be heterologous to the DNA-binding domain, e.g., a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalog, New England Biolabs, Beverly, Mass.; and Belfort et al. (1997) *Nucleic Acids Res.*25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional regions thereof) can be used as a source of cleavage domains and cleavage half-domains.

Similarly, a cleavage half-domain can be derived from the above-described nuclease that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional portions thereof), or each cleavage half-domain can be derived from a different endonuclease (or functional portions thereof).

In certain embodiments, the nuclease comprises an expression cassette that comprises two of the insulators disclosed herein, e.g., two of the insulator having the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, or SEQ ID NO: 31. One of the two insulators is positioned at the 3' end of the expression cassette, and the other insulator is positioned at the 5' end of the expression cassette.

The presently disclosed subject matter also provides a non-naturally occurring or engineer CRISPR-Cas system comprising the above-described expression cassette. The CRISPR (Clustered Regularly Interspaced Short Palindromic Repeats)-Cas (CRISPR Associated) system is an engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide a CRISPR-Cas nuclease to a region homologous to the crRNA in the target DNA called a "proto spacer". The CRISPR-Cas nuclease cleaves the DNA to generate blunt ends at the DSB at sites specified by a 20-nucleotide guide sequence contained within the crRNA transcript. The CRISPR-Cas nuclease requires both the crRNA and the tracrRNA for site specific DNA recognition and cleavage. This system has been engineered such that the crRNA and tracrRNA can be combined into one molecule (the "single guide RNA"); and the crRNA equivalent portion of the single guide RNA can be engineered to guide the CRISPR-Cas nuclease to target any desired sequence (see Jinek et al., *Science* (2012); 337:816-821). Thus, the CRISPR-Cas system can be engineered to create a DSB at a desired target in a genome. In certain embodiments, the CRISPR-Cas system comprises a CRISPR-Cas nuclease and a single-guide RNA. Suitable examples of CRISPR-Cas nucleases include, but are not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These CRISPR-Cas nucleases are known; for example, the amino acid sequence of *S. pyogenes* Cas9 protein may be found in the SwissProt database under accession number Q99ZW2. In some embodiments, the CRISPR-Cas nuclease has DNA cleavage activity, e.g., Cas9. In certain embodiments, the CRISPR-Cas nuclease is Cas9. The CRISPR-Cas nuclease can direct cleavage of one or both strands at the location of a target sequence (e.g., a genomic safe harbor site). Additionally, the CRISPR-Cas nuclease can direct cleavage of one or both strands within about 1, 2, 3, 4, 5, 6, 7, 8, 9, 10, 15, 20, 25, 50, 100, 200, 500, or more base pairs from the first or last nucleotide of a target sequence.

The presently disclosed nucleases and CRISPR-Cas system allow for targeted delivery of the expression cassette. In certain embodiments, a presently disclosed CRISPR-Cas system or the DNA binding domain of a presently disclosed nuclease binds to a genomic safe harbor site. A nuclease or the CRISPR-Cas system generates a double strand break at the genomic safe harbor site. Genomic safe harbor sites are intragenic or extragenic regions of the human genome that are able to accommodate the predictable expression of newly integrated DNA without adverse effects on the host cell or organism. A useful safe harbor must permit sufficient transgene expression to yield desired levels of the vector-encoded protein or non-coding RNA. A genomic safe harbor site also must not predispose cells to malignant transformation nor alter cellular functions. Methods for identifying genomic safe harbor sites are described in Sadelain et al., "Safe Harbours for the integration of new DNA in the human genome," Nature Reviews (2012); 12:51-58; Papapetrou et al., "Genomic safe harbors permit high β-globin transgene expression in thalassemia induced pluripotent stem cells" *Nat Biotechnol.* (2011) January; 29(1):73-8, which are incorporated by reference in their entireties. A presently disclosed genomic safe harbor site meets one or more (one, two, three, four, or five) of the following five criteria: (1) distance of at least 50 kb from the 5' end of any gene (e.g., from the 5' end of the gene), (2) distance of at least 300 kb from any cancer-related gene, (3) within an open/accessible chromatin structure (measured by DNA cleavage with natural or engineered nucleases), (4) location outside a gene transcription unit and (5) location outside ultraconserved regions (UCRs), microRNA or long non-coding RNA of the human genome. As the most common insertional oncogenesis event is transactivation of neighboring tumor-promoting genes, the first two criteria exclude the portion of the human genome located near promoters of genes, in particular, cancer-related genes, which are genes functionally implicated in human cancers or the human homologs of genes implicated in cancer in model organisms. Proximity to miRNA genes is one exclusion criterion because miRNAs are implicated in the regulation of many cellular processes, including cell proliferation and differentiation. As vector integration within a transcription unit can disrupt gene function through the loss of function of a tumor suppressor gene or the generation of an aberrantly spliced gene product, the fourth (iv) criterion excludes all sites located inside transcribed genes. UCRs, which are regions that are highly conserved over multiple vertebrates and known to be enriched for enhancers and exons, and long non-coding RNAs, are also excluded. In certain embodiments, the genomic safe harbor site is an extragenic genomic safe harbor site. In certain embodiments, the genomic safe harbor site is located on chromosome 1.

The presently disclosed subject matter also provides polynucleotides encoding the above-described nucleases, vectors comprising the polynucleotides encoding the above-described nucleases, polynucleotides encoding the above-described CRISPR-Cas system, and vectors comprising the polynucleotides encoding the above-described CRISPR-Cas system.

The nucleases and polynucleotides encoding these nucleases, and the CRISPR-Cas system and polynucleotides encoding the CRISPR-Cas system can be delivered in vivo or ex vivo by any suitable means. For example, nucleases and CRISPR-Cas system as described herein can be delivered to a cell (e.g., a hematopoietic stem cell, an embryonic stem cell, an induced pluripotent stem cell, or an hemogenic endothelium cell) by a vector comprising polynucleotides encoding the nuclease or the CRISPR-Cas system. Any vectors can be used including, but not limited to, plasmid vectors, retroviral vectors (e.g., γ-retroviral vectors, lentiviral vectors and foamy viral vectors), adenovirus vectors, poxvirus vectors; herpes virus vectors and adena-associated virus vectors, etc. In certain embodiments, the vector comprising a polynucleotide encoding an above-described nuclease or an above-described CRISPR-Cas system is a lentiviral vector. In one particular embodiment, the lentiviral vector is a non-integrating lentiviral vector. Examples of non-integrating lentiviral vector are described in Ory et al. (1996) *Proc. Natl. A cad. Sci. USA* 93:11382-11388; Dull et al., (1998) *J. Viral.* 72:8463-8471; Zuffery et al. (1998) *J. Viral.* 72:9873-9880; Follenzi et al., (2000) *Nature Genetics* 25:217-222; U.S. Patent Publication No 2009/054985.

Additionally, non-viral approaches (e.g., single-stranded DNA) can also be employed for the expression of a globin gene in cells. For example, a nucleic acid molecule can be introduced into a cell by administering the nucleic acid in the presence of lipofection (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., Journal of Biological Chemistry 263:14621, 1988; Wu et al., *Journal of Biological Chemistry* 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases. Transient expression may be obtained by RNA electroporation.

IV. Cells

Genetic modification of cells (e.g., hematopoietic stem cells, embryonic stem cells, induced pluripotent stem cells, and hemogenic endothelium cells) can be accomplished by transducing a substantially homogeneous cell composition with a recombinant DNA or RNA construct (e.g., a vector or a delivery system comprising the above-described expression cassette). The presently disclosed subject matter provides cells transduced with the above-described expression cassettes, cells transduced with the above-described vectors, and cells transduced with the above-described nucleases or with vectors comprising polynucleotides encoding the nucleases, and cell transduced with the above-described CRISPR Cas system or with vectors comprising polynucleotides encoding the CRISPR Cas system, which are collectively referred to as "transduced cells". As described above, the vectors, nucleases and CRISPR-Cas system are employed for transduction of the expression cassette to the cells to express a globin gene (e.g., a human β-globin gene). In certain embodiments, the transduced cells are administered to a subject to treat and/or prevent a hematopoietic disease, disorder, or condition. The presently disclosed insulators can enhance the efficiency of the transduction of the expression cassette to cells.

Suitable transduced cells include, but are not limited to, stem cells, progenitor cells, and differentiated cells. As used herein, the term "progenitor" or "progenitor cells" refers to cells that have the capacity to self-renew and to differentiate into more mature cells. Progenitor cells have a reduced potency compared to pluripotent and multipotent stem cells. Many progenitor cells differentiate along a single lineage, but may also have quite extensive proliferative capacity.

In certain embodiments, the transduced cells are stem cells. Stem cells have the ability to differentiate into the appropriate cell types when administered to a particular biological niche, in vivo. A stem cell is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are sub-classified according to their developmental potential as totipotent, pluripotent, multipotent and oligo/unipotent. As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

In certain embodiments, the transduced cells are embryonic stem cells, bone marrow stem cells, umbilical cord stem cells, placental stem cells, mesenchymal stem cells, neural stem cells, liver stem cells, pancreatic stem cells, cardiac stem cells, kidney stem cells, and/or hematopoietic stem cells. In certain embodiments, the transduced cells are hematopoietic stem cells (HSCs). HSCs give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to all blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells). When transplanted into lethally irradiated animals or humans, hematopoietic stem and progenitor cells can repopulate the erythroid, neutrophil-macrophage, megakaryocyte and lymphoid hematopoietic cell pool.

HSCs can be isolated or collected from bone marrow, umbilical cord blood, or peripheral blood. HSCs can be identified according to certain phenotypic or genotypic markers. For example, HSCs can be identified by their small size, lack of lineage (lin) markers, low staining (side population) with vital dyes such as rhodamine 123 (rhodamineDULL, also called rholo) or Hoechst 33342, and presence of various antigenic markers on their surface, many of which belong to the cluster of differentiation series (e.g., CD34, CD38, CD90, CD133, CD105, CD45, Terl 19, and c-kit, the receptor for stem cell factor). In certain embodiments, the transduced cell is a CD34$^+$ HSC.

In certain embodiments, the transduced cell is an embryonic stem cell. In certain embodiments, the transduced cell is an induced pluripotent stem cell. In certain embodiments, the transduced cell is a hemogenic endothelium cell.

While HSCs are the natural vehicle for restoring long-term hematopoiesis, their use has some important limitations. The first is their relative scarcity, which can eventually preclude autologous HSC therapy when the harvested cellular product is too small. The second is the difficulty to perform biosafety testing such as integration site analysis and consequently to select cells with chosen integration sites, because adult HSCs cannot be replicated in vitro. The third limitation is that homologous recombination using current technologies is practically impossible thus compromising the advent of gene correction. All of these limitations are ultimately due to the fact that adult HSCs cannot be expanded in vitro without losing their stem cell potency. These limitations explain the importance of viral vectors such as gamma-retroviral and lentiviral vectors, which are remarkably quick and efficient in achieving stable gene transfer.

Use of ESs and induced pluripotent stem (iPS) cells for globin gene therapy is disclosed in Moi et al., *Haematol* Mar. 1, 2008; 93(3):325-330. Embryonic stem (ES) cells are amenable to gene targeting and correction, which requires unlimited in vitro cell division without losing multipotency. Chang et al., *Proc Natl Acad Sci USA* 2006; 103:1036-40 provided proof of principle of the feasibility of the homologous recombination approach in mice with sickle cell anemia. Takahashi et al. *Cell* 2006; 126:663-76 reported the successful reprogramming of fibroblasts to an embryonic stem-like state. Cells obtained by this reverse-differentiation process, called induced pluripotent stem (iPS) cells, were produced by exposing embryonic or young adult bulk fibroblast cultures to gamma-retroviral vectors encoding 4 transcription factors, which are physiologically active in the embryonic stem cells, but generally turned off when differentiation progresses. The cultured cells formed colonies similar to ES cell colonies. These findings have been confirmed and extended by others to both mouse and human fibroblasts (Meissner et al., Nat Biotechnol 2007; 25:1177-81; Nakagawa et al., Nat Biotechnol 2007; 26:101-6; Okita et al., Nature 2007; 448:313-7; Park et al., Nature 2007; 451:141-6; Takahashi et al., Nat Protoc 2007; 2:3081-9; Takahashi K et al., Cell 2007; 131:861-72; Wernig et al., Nature 2007; 448:318-24; Yu J et al., Science 2007; 318:1917-20). Rudolf Jaenisch and co-workers achieved a successful gene therapy in a mouse model of sickle cell disease, using homologous recombination in ES-like iPS cells (Hanna et al., Science 2007; 318:1920-3). The process has so far been mostly applied to fibroblast harvested from a skin biopsy, which are then induced to become iPS by transduction with retroviral vectors that encode four stem cell transcription factors. iPS are amenable to the correction of the SC mutation by standard homologous recombination techniques and can then be differentiated in vitro into unlimited amounts of hematopoietic stem cells. The whole process ends with the autologous transplantation of the corrected HSC into the original mouse donor, which will now be cured of its SC disease. This technique is not only useful for homologous recombination, but can also enhance lentiviral-mediated globin gene transfer for the treatment of β-thalassemia by providing a means to perform detailed integration site analysis and adequate in vitro cell expansion before infusing cells into the recipient.

The cell of the presently disclosed subject matter can be autologous ("self") or non-autologous ("non-self," e.g., allogeneic, syngeneic or xenogeneic). As used herein, "autologous" refers to cells from the same subject. As used herein, "allogeneic" refers to cells of the same species that differ genetically to the cell in comparison. As used herein, "syngeneic" refers to cells of a different subject that are genetically identical to the cell in comparison. As used herein, "xenogeneic" refers to cells of a different species to the cell in comparison. In certain embodiments, the cell is autologous, e.g., a cell transduced with the presently disclosed expression cassette is administered to a subject from whom the cell is collected, e.g., the cell is collected from bone marrow, umbilical cord blood, peripheral blood, and/or adipose tissue of the subject. In certain embodiments, the cell is obtained or collected from bone marrow of a subject.

In certain embodiments, prior to transduction with the expression cassette, the cell is pre-stimulated, e.g., in the presence of one or more cytokines (e.g., IL-3, IL-la, IL-6, Kit ligand (also known as "Stem Cell Factor (SCF)"), and Flt-3 ligand), and/or one or more glycoproteins (e.g., thrombopoietin and fibronectin). In certain embodiments, the cell is pre-stimulated in the presence of Flt-3 ligand, SCF, thrombopoietin, interleukin-3, and fibronectin. The cell can be pre-stimulated for about 24 hours or longer, e.g., about 48 hours, or about 36 hours. Subsequently, the cell is transduced with a presently disclosed expression cassette, or a vector or another delivery system comprising such expression cassette. Transduction can be performed on a fresh cell, or on a frozen cell. Genomic DNA of the cell is isolated to determine the vector copy number and analyze the integration site or integrated vector structure, e.g., by South blot analysis and/or by Quantitative PCR. For quantification of globin mRNA (e.g., human β-globin transgene analysis), total RNA is extracted from the cell. Quantitative primer extension assay can be used for quantification of globin mRNA.

V. Compositions and Formulations

The presently disclosed subject matter provides pharmaceutical compositions comprising a presently disclosed transduced cell as described above and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible, including pharmaceutically acceptable cell culture media. The pharmaceutically acceptable carrier can be suitable for parenteral (e.g., intravenous, intramuscular, subcutaneous, or intraperitoneal), spinal or epidermal administration (e.g., by injection, infusion or implantation). Depending on the route of administration, the active compound, e.g., the transduced cell, may be coated in a material to protect the compound from the action of acids and other natural conditions that may inactivate the compound.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the transduced cells, use thereof in the pharmaceutical compositions of the invention is contemplated.

The pharmaceutical compositions of the presently disclosed subject matter can further comprise one or more polypeptides, polynucleotides, vectors comprising the same, transduced cells, etc., as described herein, formulated in pharmaceutically-acceptable or physiologically-acceptable solutions for administration to a cell or an animal, either alone, or in combination with one or more other modalities of therapy. If desired, the pharmaceutical compositions of the presently disclosed subject matter can be administered in combination with other agents, including, but not limited to, cytokines, growth factors, hormones, small molecules or various pharmaceutically-active agents. Any additional agents that do not adversely affect the ability of the composition to deliver the intended gene therapy can be included in the compositions.

In the pharmaceutical compositions of the presently disclosed subject matter, formulation of pharmaceutically-acceptable excipients and carrier solutions is well known to those of ordinary skill in the art, as is the development of suitable dosing and treatment regimens for using the particular compositions described herein in a variety of treatment regimens, including, e.g., oral, parenteral, intravenous, intranasal, and intramuscular administration and formulation.

The pharmaceutical compositions of the presently disclosed subject matter can be delivered parenterally (e.g., intravenously, intramuscularly, or intraperitoneally) as described, for example, in U.S. Pat. Nos. 5,543,158; 5,641,515 and 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

The pharmaceutical compositions of the presently disclosed subject matter can be conveniently provided as sterile liquid preparations, e.g., isotonic aqueous solutions, suspensions, emulsions, dispersions, or viscous compositions, which can be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin.

The compositions can be isotonic, i.e., they can have the same osmotic pressure as blood and lacrimal fluid. The desired isotonicity of the compositions of the presently disclosed subject matter can be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

For parenteral administration in an aqueous solution, for example, the solution should be suitably buffered if necessary and the liquid diluent first rendered isotonic with sufficient saline or glucose. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

In certain embodiments, the compositions can be delivered by intranasal sprays, inhalation, and/or other aerosol delivery vehicles. Methods for delivering genes, polynucleotides, and peptide compositions directly to the lungs via nasal aerosol sprays are described, e.g., in U.S. Pat. Nos. 5,756,353 and 5,804,212. Methods of delivering drugs using lysophosphatidyl-glycerol compounds are described, e.g., in U.S. Pat. No. 5,725,871. Transmucosal drug delivery in the form of a polytetrafluoroetheylene support matrix is described, e.g., in U.S. Pat. No. 5,780,045. The compositions of the presently disclosed subject matter can be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the presently disclosed subject matter can comprise one or more repressors and/or activators comprising a combination of any number of polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy.

In certain aspects, the presently disclosed subject matter provides formulations or compositions suitable for the delivery of viral vector systems (i.e., viral-mediated transduction) including, but not limited to, retroviral (e.g., lentiviral) vectors. Exemplary formulations for ex vivo delivery can also include the use of various transfection agents known in the art, such as calcium phosphate, electoporation, heat shock and various liposome formulations (i.e., lipid-mediated transfection). Liposomes are lipid bilayers entrapping a fraction of aqueous fluid. DNA spontaneously associates to the external surface of cationic liposomes (by virtue of its charge) and these liposomes will interact with the cell membrane.

The skilled artisan can readily determine the amount of cells and optional additives, vehicles, and/or carrier in compositions and to be administered in methods of the presently disclosed subject matter. Typically, any additives (in addition to the transduced cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, 129                                    130 from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

VI. Uses and Methods

Vectors and other delivery systems (nucleases and CRISPR-Cas systems) comprising the presently disclosed expression cassette provide improved methods of gene therapy. As used herein, the term "gene therapy" refers to the introduction of a polynucleotide into a cell's genome that restores, corrects, or modifies the gene and/or expression of the gene. In various non-limiting embodiments, a presently disclosed vector or other delivery system (e.g., a nuclease or a CRISPR-Cas system) comprises an expression cassette comprising a globin gene or a functional portion thereof that encodes a globin protein (e.g., human β globin protein), which provides curative, preventative, or ameliorative benefits to a subject diagnosed with or that is suspected of having a disease, disorder, or condition of the hematopoietic system. The vector or other delivery systems (e.g., a nuclease and the CRISPR-Cas system) can infect and transduce the cell in vivo, ex vivo, or in vitro. In ex vivo and in vitro embodiments, the transduced cells can then be administered to a subject in need of therapy. The presently disclosed subject matter contemplates that the vectors and other delivery systems (e.g., nucleases or CRISPR-Cas systems), viral particles, and transduced cells of the presently disclosed subject matter are be used to treat, prevent, and/or ameliorate a disease, disorder, or condition of the hematopoietic system in a subject, e.g., a hemoglobinopathy.

As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

As used herein, "thalassemia" refers to a hereditary disorder characterized by defective production of hemoglobin. Examples of thalassemias include α- and β-thalassemia. β-thalassemias are caused by a mutation in the beta globin chain, and can occur in a major or minor form. In the major form of β-thalassemia, children are normal at birth, but develop anemia during the first year of life. The mild form of β-thalassemia produces small red blood cells and the thalassemias are caused by deletion of a gene or genes from the globin chain. α-thalassemia typically results from deletions involving the HBA1 and HBA2 genes. Both of these genes encode α-globin, which is a component (subunit) of hemoglobin. There are two copies of the HBA1 gene and two copies of the HBA2 gene in each cellular genome. As a result, there are four alleles that produce α-globin. The different types of a thalassemia result from the loss of some or all of these alleles. Hb Bart syndrome, the most severe form of a thalassemia, results from the loss of all four α-globin alleles. HbH disease is caused by a loss of three of the four [alpha]-globin alleles. In these two conditions, a shortage of [alpha]-globin prevents cells from making normal hemoglobin. Instead, cells produce abnormal forms of hemoglobin called hemoglobin Bart (Hb Bart) or hemoglobin H (HbH). These abnormal hemoglobin molecules cannot effectively carry oxygen to the body's tissues. The substitution of Hb Bart or HbH for normal hemoglobin causes anemia and the other serious health problems associated with a thalassemia.

As used herein, the term "sickle cell disease" refers to a group of autosomal recessive genetic blood disorders, which results from mutations in a globin gene and which is characterized by red blood cells that assume an abnormal, rigid, sickle shape. They are defined by the presence of $\beta^S$-gene coding for a β-globin chain variant in which glutamic acid is substituted by valine at amino acid position 6 of the peptide, and second B-gene that has a mutation that allows for the crystallization of HbS leading to a clinical phenotype. As used herein, the term "sickle cell anemia" refers to a specific form of sickle cell disease in patients who are homozygous for the mutation that causes HbS. Other common forms of sickle cell disease include HbS/β-thalassemia, HbS/HbC and HbS/HbD.

In certain embodiments, gene therapy methods of the presently disclosed subject mater are used to treat, prevent, or ameliorate a hemoglobinopathy that is selected from the group consisting of: hemoglobin C disease, hemoglobin sickle cell disease (SCD), sickle cell anemia, hereditary anemia, thalassemia, β-thalassemia, thalassemia major, thalassemia intermedia, a-thalassemia, and hemoglobin H disease. In certain embodiments, the hemoglobinopathy is β-thalassemia. In certain embodiments, the hemoglobinopathy is sickle cell anemia In various non-limiting embodiments, vectors or other delivery systems (e.g., nucleases or CRISPR-Cas systems) comprising a presently disclosed expression cassette are administered by direct injection to a cell, tissue, or organ of a subject in need of gene therapy, in vivo. In certain embodiments, cells are transduced in vitro or ex vivo with vectors or other delivery systems (e.g., nucleases or CRISPR-Cas systems) of the presently disclosed subject matter, and optionally expanded ex vivo. The transduced cells are then administered to a subject in need of gene therapy, e.g., within a pharmaceutical formulation disclosed herein.

The presently disclosed subject matter provides a method of providing a transduced cell to a subject. In various non-limiting embodiments, the method comprises administering (e.g., parenterally) one or more cells (a population of cells) transduced with a presently disclosed expression cassette or a vector or another delivery system (e.g., a nuclease or CRISPR-Cas system) comprising such expression cassette to the subject.

The presently disclosed subject matter provides a method of treating a hemoglobinopathy in a subject. In various non-limiting embodiments, the method comprises administering an effective amount of a presently disclosed transduced cell or a population of the presently disclosed transduced cells (e.g., HSCs, embryonic stem cells, or iPSCs) to the subject.

For treatment, the amount administered is an amount effective in producing the desired effect. An effective amount can be provided in one or a series of administrations.

An effective amount can be provided in a bolus or by continuous perfusion. An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

In certain embodiments, following administration of one or more of the presently disclosed transduced cells, peripheral blood of the subject is collected and hemoglobin levels is measured. A therapeutically relevant level of hemoglobin is produced following administration of one or more of the presently disclosed transduced cells. Therapeutically relevant level of hemoglobin is a level of hemoglobin that is sufficient (1) to improve or correct anemia, (2) to restore the ability of the subject to produce red blood cells containing normal hemoglobin, (3) to correct ineffective erythropoiesis in the subject, (4) to correct extra-medullary hematopoiesis (e.g., splenic and hepatic extra-medullary hematopoiesis), and/or (5) to reduce iron accumulation, e.g., in peripheral tissues and organs. Therapeutically relevant level of hemoglobin can be at least about 7 g/dL Hb, at least about 7.5 g/dl Hb, at least about 8 g/dL Hb, at least about 8.5 g/dL Hb, at least about 9 g/dL Hb, at least about 9.5 g/dL Hb, at least about 10 g/dL Hb, at least about 10.5 g/dL Hb, at least about 11 g/dL Hb, at least about 11.5 g/dL Hb, at least about 12 g/dL Hb, at least about 12.5 g/dL Hb, at least about 13 g/dL Hb, at least about 13.5 g/dL Hb, at least about 14 g/dL Hb, at least about 14.5 g/dL Hb, or at least about 15 g/dL Hb. Additionally or alternatively, therapeutically relevant level of hemoglobin can be from about 7 g/dL Hb to about 7.5 g/dL Hb, from about 7.5 g/dL Hb to about 8 g/dL Hb, from about 8 g/dL Hb to about 8.5 g/dL Hb, from about 8.5 g/dL Hb to about 9 g/dL Hb, from about 9 g/dL Hb to about 9.5 g/dL Hb, from about 9.5 g/dL Hb to about 10 g/dL Hb, from about 10 g/dL Hb to about 10.5 g/dL Hb, from about 10.5 g/dL Hb to about 11 g/dL Hb, from about 11 g/dL Hb to about 11.5 g/dL Hb, from about 11.5 g/dL Hb to about 12 g/dL Hb, from about 12 g/dL Hb to about 12.5 g/dL Hb, from about 12.5 g/dL Hb to about 13 g/dL Hb, from about 13 g/dL Hb to about 13.5 g/dL Hb, from about 13.5 g/dL Hb to about 14 g/dL Hb, from about 14 g/dL Hb to about 14.5 g/dL Hb, from about 14.5 g/dL Hb to about 15 g/dL Hb, from about 7 g/dL Hb to about 8 g/dL Hb, from about 8 g/dL Hb to about 9 g/dL Hb, from about 9 g/dL Hb to about 10 g/dL Hb, from about 10 g/dL Hb to about 11 g/dL Hb, from about 11 g/dL Hb to about 12 g/dL Hb, from about 12 g/dL Hb to about 13 g/dL Hb, from about 13 g/dL Hb to about 14 g/dL Hb, from about 14 g/dL Hb to about 15 g/dL Hb, from about 7 g/dL Hb to about 9 g/dL Hb, from about 9 g/dL Hb to about 11 g/dL Hb, from about 11 g/dL Hb to about 13 g/dL Hb, or from about 13 g/dL Hb to about 15 g/dL Hb. In certain embodiments, the therapeutically relevant level of hemoglobin is maintained in the subject for at least about 6 months, for at least about 12 months (or 1 year), for at least about 24 months (or 2 years). In certain embodiments, the therapeutically relevant level of hemoglobin is maintained in the subject for up to about 6 months, for up to about 12 months (or 1 year), for up to about 24 months (or 2 years). In certain embodiments, the therapeutically relevant level of hemoglobin is maintained in the subject for about 6 months, for about 12 months (or 1 year), for about 24 months (or 2 years). In certain embodiments, the therapeutically relevant level of hemoglobin is maintained in the subject for from about 6 months to about 12 months (e.g., from about 6 months to about 8 months, from about 8 months to about 10 months, from about 10 months to about 12 months), from about 12 months to about 18 months (e.g., from about 12 months to about 14 months, from about 14 months to about 16 months, or from about 16 months to about 18 months), or from about 18 months to about 24 months (e.g., from about 18 months to about 20 months, from about 20 months to about 22 months, or from about 22 months to about 24 months).

In certain embodiments, the method comprises administering one or more cells transduced with a recombinant vector comprising a presently disclosed expression cassette as described above. The vector copy number of the recombinant vector in the cells that provide for the therapeutically relevant level of hemoglobin (e.g., 9-10 g/dL) in the subject is from about 0.5 to about 2, from about 0.5 to about 1, or from about 1 to about 2 vector copy number per cell. In certain embodiments, the vector copy number of the presently disclosed vector is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 vector copy number per cell.

In certain embodiments, the subject lacks a human leukocyte antigen (HLA)-matched donor. In certain embodiments, the transduced cell is from the same subject. In certain embodiments, the transduced cell is from bone marrow of the same subject. Thus, administration of the transduced cells do not incur the risk of graft-versus host disease in the subject. The method does not require immune suppression to prevent graft rejection, e.g., the method does not comprise administering an immunosuppressive agent to the subject.

The present disclosed subject matter also provides a method of increasing the proportion of red blood cells or erythrocytes compared to white blood cells or leukocytes in a subject. In various non-limiting embodiments, the method comprises administering an effective amount of a presently disclosed transduced cell or a population of the presently disclosed transduced cells (e.g., HSCs, embryonic stem cells, or iPSCs) to the subject, wherein the proportion of red blood cell progeny cells of the hematopoietic stem cells are increased compared to white blood cell progeny cells of the hematopoietic stem cells in the subject.

Aan important advantage provided by the expression cassette, vectors and other delivery systems (e.g., nucleases and CRISPR-Cas systems), compositions, and methods of the presently disclosed subject is the high efficacy of globin gene therapy that can be achieved by administering populations of cells comprising lower percentages of transduced cells compared to existing methods. This provides important safety advantages associated with reduced chances of deleterious mutation, transformation, or oncogene activation of cellular genes in transduced cells. The transduced cells can be administered as part of a bone marrow or cord blood transplant in an individual that has or has not undergone bone marrow ablative therapy.

One consideration concerning the therapeutic use of the presently disclosed cells transduced with the expression cassette described herein ("transduced cells") is the quantity of cells necessary to achieve an optimal effect. The quantity of transduced cells to be administered will vary for the subject being treated. In certain embodiments, from about $1\times10^4$ to about $1\times10^5$ cells/kg, from about $1\times10^5$ to about $1\times10^6$ cells/kg, from about $1\times10^6$ to about $1\times10^7$ cells/kg, from about $1\times10^7$ to about $1\times10^8$ cells/kg, from about $1\times10^8$ to about $1\times10^9$ cells/kg, or from about $1\times10^9$ to about $1\times10^{10}$ cells/kg of the presently disclosed transduced cells are administered to a subject. More effective cells may be administered in even smaller numbers. In certain embodiments, at least about $1\times10^8$ cells/kg, at least about $2\times10^8$ cells/kg, at least about $3\times10^8$ cells/kg, at least about $4\times10^8$ cells/kg, or at least about $5\times10^8$ cells/kg of the presently disclosed transduced cells are administered to a subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

In certain embodiments, the expression cassettes, vectors and other delivery systems (nucleases and CRISPR-Cas systems), compositions, and methods of the presently disclosed subject matter offer improved methods of gene therapy using ex vivo gene therapy and autologous transplantation. Transplantation of cells transduced with the expression cassette or into subjects having a hemoglobinopathy results in long-term correction of the disease.

One or more presently disclosed transduced cells can be administered by any methods known in the art, including, but not limited to, parenteral administration (e.g., intramuscular administration, intravenous administration, subcutaneous administration, or intraperitoneal administration), spinal administration, and epidermal administration. In certain embodiments, one or more transduced cells are delivered to a subject intravenously. One or more presently disclosed transduced cells can be administered by injection, infusion, or implantation. In certain embodiments, one or more transduced cells are administered by injection. In certain embodiments, one or more transduced cells are administered by intravenous injection.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

VII. Kits

The presently disclosed subject matter provides kits for the treatment or prevention of a hemoglobinopathy. In certain embodiments, the kit comprises a therapeutic or prophylactic composition containing an effective amount of a cell transduced with the presently disclosed expression cassette in unit dosage form. In certain embodiments, the kit comprises one or more expression cassettes disclosed herein. In certain embodiments, the kit comprises one or more vectors comprising an expression cassette disclosed herein. In certain embodiments, the kit comprises a sterile container, which can be a box, an ampule, a bottle, a vial, a tube, a bag, a pouch, a blister-pack, or other suitable container forms known in the art. Such containers can be made of plastic, glass, laminated paper, metal foil, or other materials suitable for holding medicaments.

If desired, the transduced cell is provided together with instructions for administering the cell to a subject having or at risk of developing a hemoglobinopathy. The instructions will generally include information about the use of the composition for the treatment or prevention of a hemoglobinopathy. In certain embodiments, the instructions include at least one of the following: description of the therapeutic agent; dosage schedule and administration for treatment or prevention of a hemoglobinopathy or symptoms thereof; precautions; warnings; indications; counter-indications; overdosage information; adverse reactions; animal pharmacology; clinical studies; and/or references. Alternatively or additionally, the kit can include instructions for transducing a cell with the one or more expression cassettes and/or vectors comprising such expression cassettes. The instructions may be printed directly on the container (when present), or as a label applied to the container, or as a separate sheet, pamphlet, card, or folder supplied in or with the container.

EXAMPLES

The practice of the presently disclosed subject matter employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the presently disclosed subject matter, and, as such, may be considered in making and practicing the presently disclosed subject matter. Particularly useful techniques for particular embodiments will be discussed in the sections that follow.

The following examples are put forth so as to provide those of ordinary skill in the art with a complete disclosure and description of how to make and use the expression cassettes, vectors, delivery systems, and therapeutic methods of the presently disclosed subject matter, and are not intended to limit the scope of what the inventors regard as their invention.

Example 1: Discovery of Novel Insulators

The problems created by insertional mutagenesis of viral vectors are widely known (Nienhuis (2013), Baum et al. (2006), Nienhuis et al. (2006)) as is the evidence that the risks of genotoxicity can be reduced by the use of chromatin insulators (Arumugam et al. (2007), Emery (2011), Evans-Galea et al. (2007), Rivella et al. (2000), Emery et al. (2000), Emery et al. (2002), Yannaki et al. (2002), Hino et al. (2004), Ramezani et al. (2003), Ramezani et al. (2008)). Approaches allowing the efficient identification of enhancer blocking insulators in the human genome have been developed. These new insulators are short, on the average 150 bp, and they do not affect adversely the titers of viral vectors and they are several times more powerful than the insulator cHS4. Genomic approaches were used to discover the most powerful enhancer blocker and barrier insulators of the human genome. For gene therapy of the hemoglobinopathies, powerful enhancers are required to achieve therapeutic levels of globin gene expression. Powerful insulators may thus provide one means to protect the genomic environment from the powerful enhancers of the integrating vectors.

Several studies have demonstrated the ability of the cHS4 insulator to reduce position-effect silencing of gammaretroviral vectors (Evans-Galea et al. (2007), Rivella et al. (2000), Emery et al. (2000), Emery et al. (2002), Yannaki et al. (2002), Hino et al. (2004), Ramezani et al. (2006), Yao et al. (2003), Nishino et al. (2006), Aker et al. (2007), Li and Emery (2008)), and lentiviral vectors (Evans-Galea et al. (2007), Ramezani et al. (2003), Puthenveetil et al. (2004), Arumugam et al. (2007), Bank et al. (2005), Aker et al. (2007), Ma et al. (2003), Chang et al. (2005), Pluta et al. (2005)). Those studies that were appropriately designed demonstrated that inclusion of the 1.2 kb version of the cHS4 insulator increased the likelihood and/or consistency of vector transgene expression in at least some settings (Arumugam et al. (2007), Evans-Galea et al. (2007), Emery et al. (2002), Yannaki et al. (2002), Hino et al. (2004), Ramezani et al. (2006), Aker et al. (2007), *Li and Emery* (2008), Pluta et al. (2005), Jakobsson et al. (2004)). Nevertheless, the degree of protection afforded by the cHS4 insulator is far from complete. In addition, the inclusion of the 1.2 Kb cHS4 can adversely affect vector titers while the smallest cHS4 core has been proven ineffective (Aker et al. (2007), Jakobsson et al. (2004)).

Effects on genotoxicity were tested using an in vivo assay based on quantitation of tumor formation in mice. Vectors insulated by insulator A1 decreased tumor formation induced by random vector integration in hematopoietic chimeras compared to mice that received uninsulated or cHS4-insulated controls.

To assess effects on vector titers, insulator A1 was introduced into the double-copy region of a third-generation lentiviral vector expressing GFP from a constitutive package promoter, and the viral titers and GFP expression were measured. Insulator A1 did not affect adversely vector GFP expression.

In the in vivo genotoxicity assay, a cell line transduced with gammaretroviral vectors produced tumors after transplantation in mice and allowed quantitation of genotoxic effects by measuring rates of tumor free survival. Effects of an insulator on genotoxicity were quantitated by the number of tumors formed in the mice and the rates of tumor free survival. Insulator A1 was inserted in the proximal portion of 3' LTR, from which it is copied into 5' LTR during reverse transcription and vector integration. The resulting topology places copies of the insulator between the genomic regions located 5' and 3' of the integrated provirus and enhancer activity from the 5' viral LTR and internal Pgk promoter, but does not contain the enhancer in 3' LTR. This can decrease genotoxicity thus resulting in decreased tumor formation and increased survival of the animals. Gamma-retroviral reporter vectors flanked with insulator A1 or control regions were used to transduce the growth factor-dependent cell line 32D, and 10 independent sub-pools for each vector were transplanted into syngeneic C3H/HeJ mice. All 10 mice transplanted with mock-transduced cells remained free of 32D cell-derived tumors, while nearly all mice transplanted with 32D cells transduced with vectors containing no inserts or a 790 bp neutral spacer developed tumors within a median of 16 weeks (FIG. 5B). Flanking this vector with the cHS4 insulator delayed the onset of tumor formation by several weeks, and reduced the frequency of animals that developed tumors to 6 of 10. In contrast, only two of 10 animals developed tumors following transplantation with 32D cells transduced with the vector flanked with insulator A1 (FIG. 5B). The frequency of animals with tumors and the number of vector transduction events in the original sub-pools suggested that flanking the vector with insulator A1 reduced the overall rate of tumor formation 12-fold, from 46.9 tumors per $10^5$ provirus to 3.9 tumors per $10^5$ provirus (FIG. 5C). In comparison, the cHS4 insulator reduced the overall rate of tumor formation 2.8-fold (to 16.9 tumors per $10^5$ provirus), while the neutral spacer had no statistically discernable effect on the rate of tumor formation. These results indicate that the discovered enhancer blocking insulators can decrease substantially the risks of insertional mutagenesis and genotoxicity.

Example 2: Characterization of Globin Vectors Comprising at Least One Insulator

A presently disclosed expression cassette (designated as "Expression Cassette 1"; as shown in FIG. 1), which comprises insulator A1, and a human $\beta^A$-globin gene encoding a threonine to glutamine mutation at codon 87 ($\beta^{A-T87Q}$) operably linked to a $\beta$-globin LCR comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO: 7, was generated. The rationale for using the variant $\beta$ chain ($\beta^A$) is to facilitate the detection of the vector-encoded $\beta$-globin gene, distinguishing it from endogenous or transfused beta chains. The glutamine (GLN) residue at position 87 in the $\gamma$-globin chain augments the anti-sickling activity of the gamma chain relative to the $\beta$ chain, while preserving adult oxygen-binding characteristics of the $\beta$ chain (Nagel et al. (1979)). In Vector 1, a point mutation altering codon 87 ($\beta^{A-T87Q}$, or $\beta$87) replaces the normal threonine with glutamine and augments anti-sickling activity of the vector-encoded $\beta$ chain. This $\beta$87 chain has been safely used in a patient with HbE-thalassemia (Cavazzana-Calvo et al. (2010)).

Figure 6:
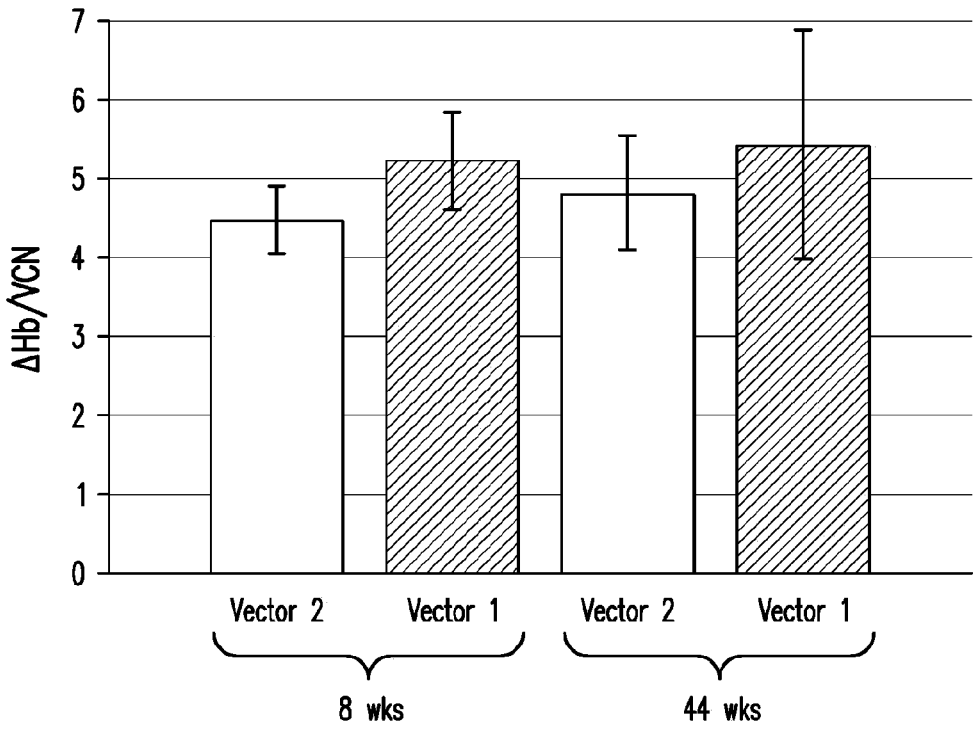
FIG. 6 represents normalized β chain expression in thal-
assemic Hbb$^{th3/+}$ mice 8 and 44 weeks post-treatment.

Expression cassette 1 was incorporated or introduced to a lentivirus vector (designated as "Vector 1"). Vector 1 was introduced in bone marrow cells of C57BL/6-Hbb th3/+ mice and transplanted to syngeneic lethally irradiated recipients as previously described (May et al. (2000), May et al. (2002), Lisowski et al. (2007)). The vector titer of V1 was comparable to that of a lentivirus vector comprising an expression cassette lacking insulator A1. The $\beta$-globin expression of Vector 1 was compared to that of a lentivirus vector (designated as "Vector 2") comprising an expression cassette that lacks an insulator and comprises a wild human $\beta$-globin gene operably linked to a $\beta$-globin LCR comprising a HS2 region having the nucleotide sequence set forth in SEQ ID NO:9, a: HS3 region having the nucleotide sequence set forth in SEQ ID NO:5, and a HS4 region having the nucleotide sequence set forth in SEQ ID NO:6. In comparison to Vector 2, $\beta$-globin expression of Vector 1 normalized to vector copy was equivalent or slightly increased, suggesting an added benefit for in vivo expression provided by the flanking barrier elements, as shown in FIG. 6.

Example 3: Evaluation of Enhancer Activity in Non-Erythroid K562 Cells

Figure 7:
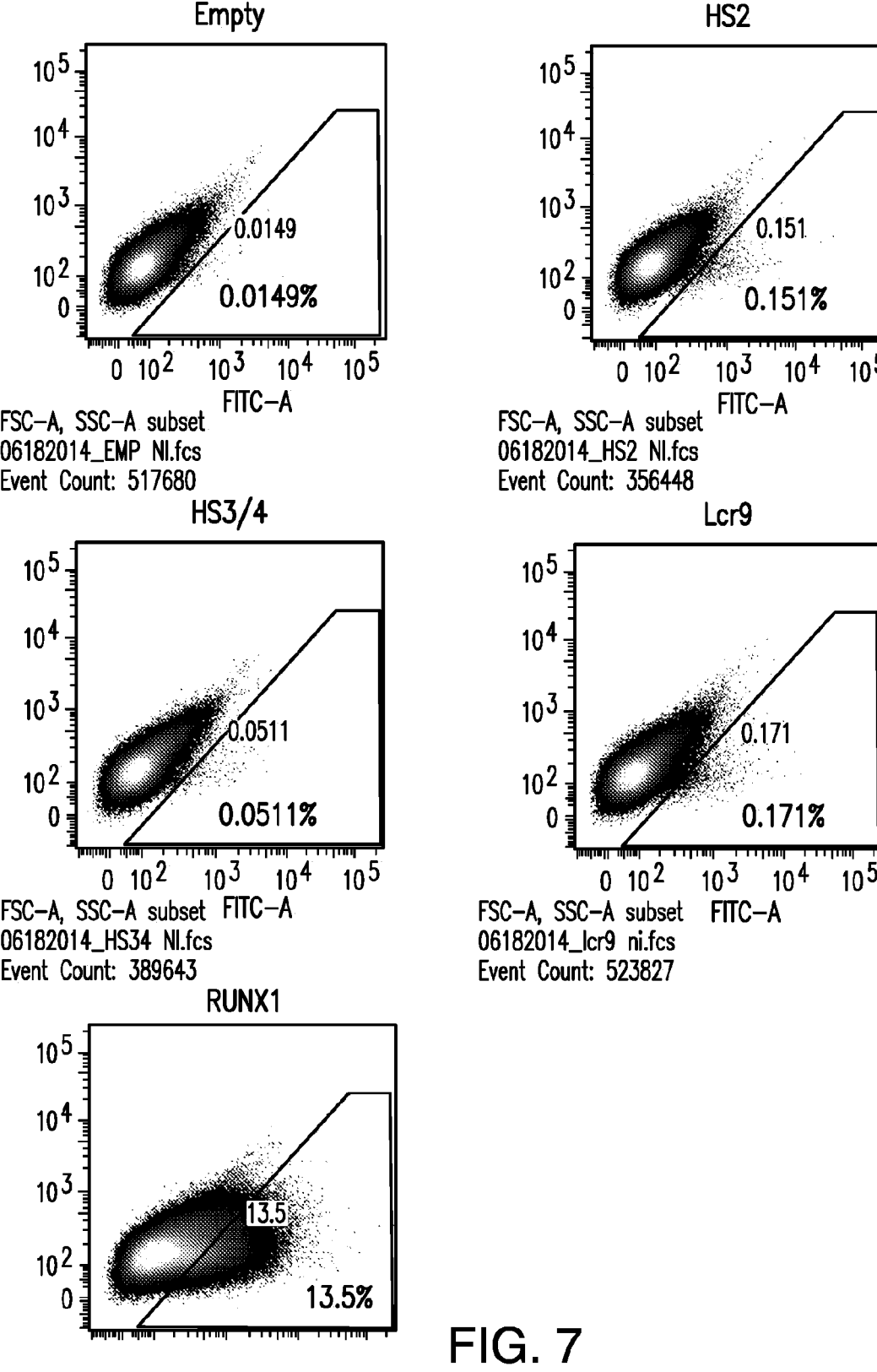
FIG. 7 represents the evaluation of enhancer activity in
non-erythroid K562 cells.

The enhancer activity of HS2 was evaluated in Non-erythroid K562 Cells. As shown in FIG. 7, GFP expression in K562 cells transduced with vectors driven by a minimal promoter linked to no enhancer ("Empty", HS2, HS3-4, HS2-3-4 or the runx 1 enhancer used as positive control ("RUNX1"). Background expression was on the order or 0.01% ("empty"), but increased over 10-fold with HS2-3-4 ("Lcr9", 0.17%). This enhancement was mostly due to HS2 (0,15%) but not HS3-4 (0.05%). All cell lines were comparably transduced (mean vector copy number 2.5). The results support that HS2 30 but not HS3-HS4 may pose an oncogenic risk in non-erythroid hematopoietic stem and progenitor cells.

Example 4: Novel Erythroid-Specific Enhancers

As shown in FIGS. 8 and 9, five erythroid-specific enhancers were substituted for HS2: ALAS Intron 1, ALAS Intron 8, BLVRB, PPOX, and Spectrin-alpha. The inventors have shown that all these five enhancers are powerful enhancers, and lack enhancer activity in non-erythroid tissues, and do not reduce the vector titer.

Example 5: Increasing Globin Lentiviral Vector Production Through 3' LTR Modifications An essential feature of therapeutic globin vectors is to achieve a high titer, sufficient for effective transduction of patient cells. By virtue of their large cargo, comprising a gene, promoter, enhancers and/or LCR elements, globin lentiviral vectors inherently have low titer, complicating their manufacture and limiting their clinical use. This problem is further compounded by the incorporation of additional genomic elements such as an insulator, which further increase the size of the vector.

Figure 10A:
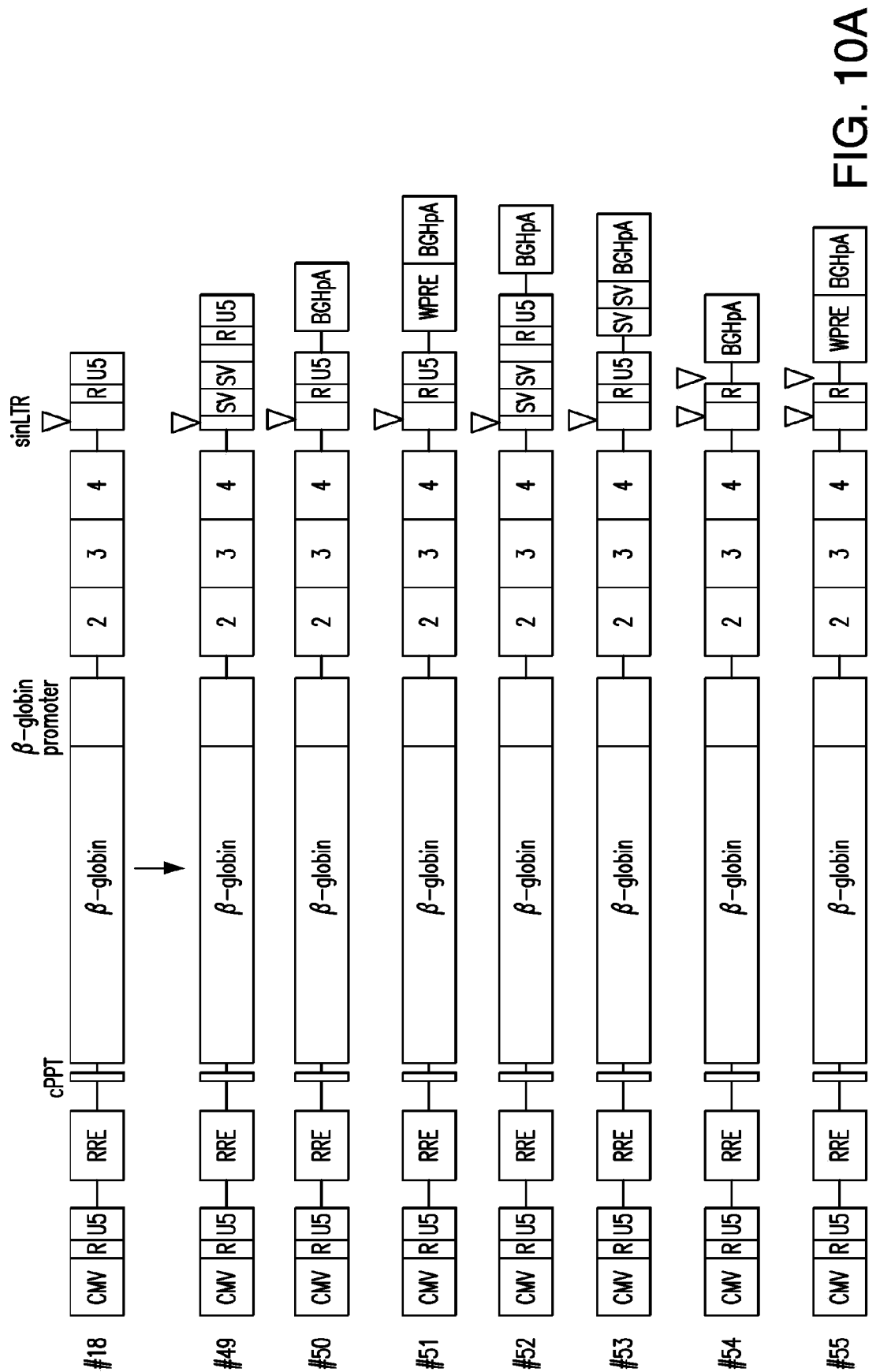
FIGS. 10A-10B depict various recombinant vectors com-
prising the presently disclosed expression cassettes.
Figure 10B:
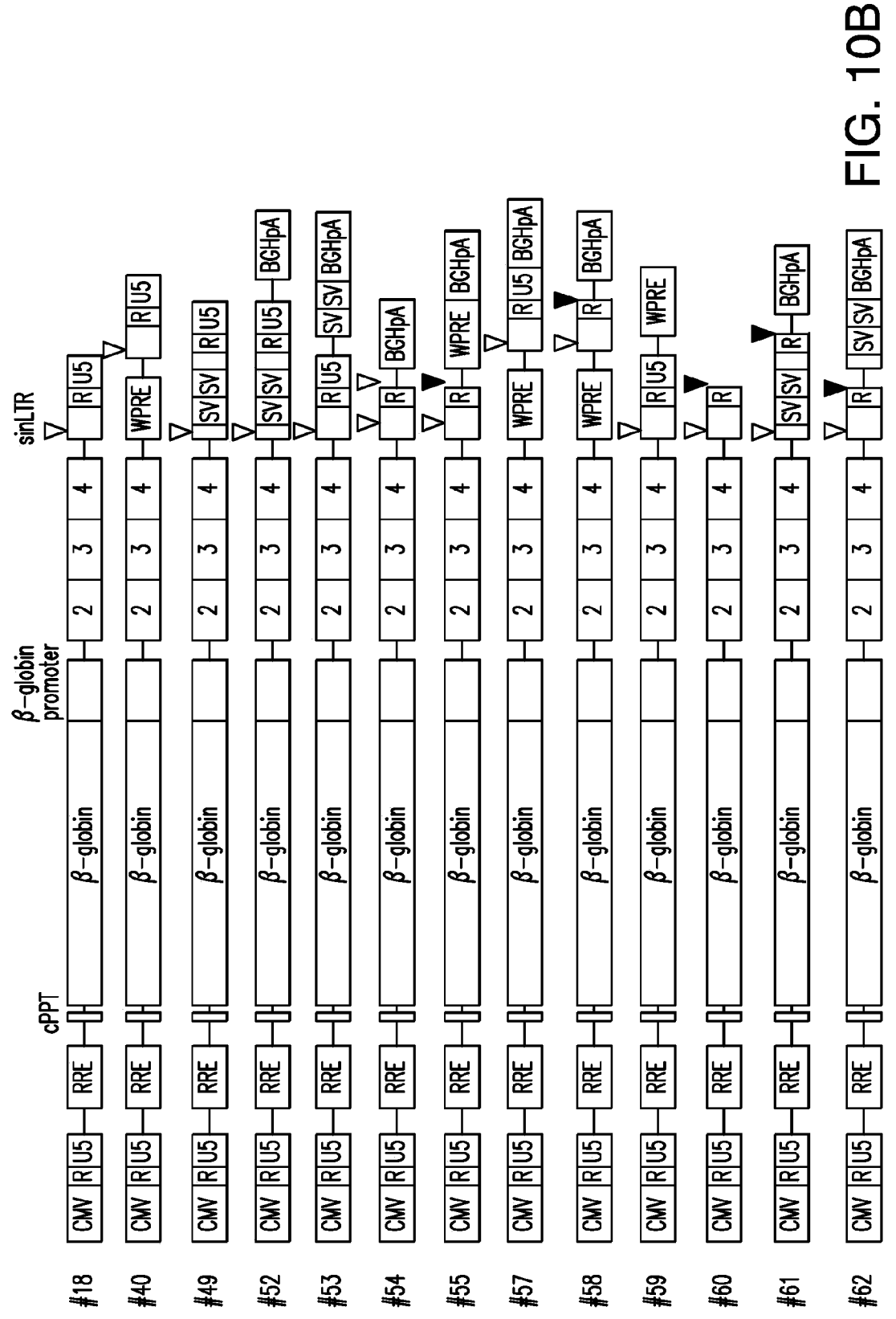

The inventors explored different modifications of 3' long terminal repeat (LTR) of globin vectors to increase the titer of globin vectors. Over 62 variations were evaluated, numbered 1 through 62, modeled on a lentivirus vector comprising a human β-globin gene operably linked to a β-globin LCR comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7. In other words, all of Vectors #1 through Vector 62 comprise a β-globin LCR comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7. Vector #18 served as a baseline, comprising a standard U3 deletion in 3'LTR. Vector #1 (not depicted) comprised a full, i.e., wild-type LTR, which cannot be used clinically. Modifications to 3'LTR are depicted in FIGS. 10A and 10B, and their titers shown in FIGS. 11 and 12 (the Y axis shows the vector copy number of vector stocks manufactured and tested under strictly identical conditions). Titrations were measured in triple replicas, performed in parallel by two operators, and repeated in multiple experiments.

Figure 11:
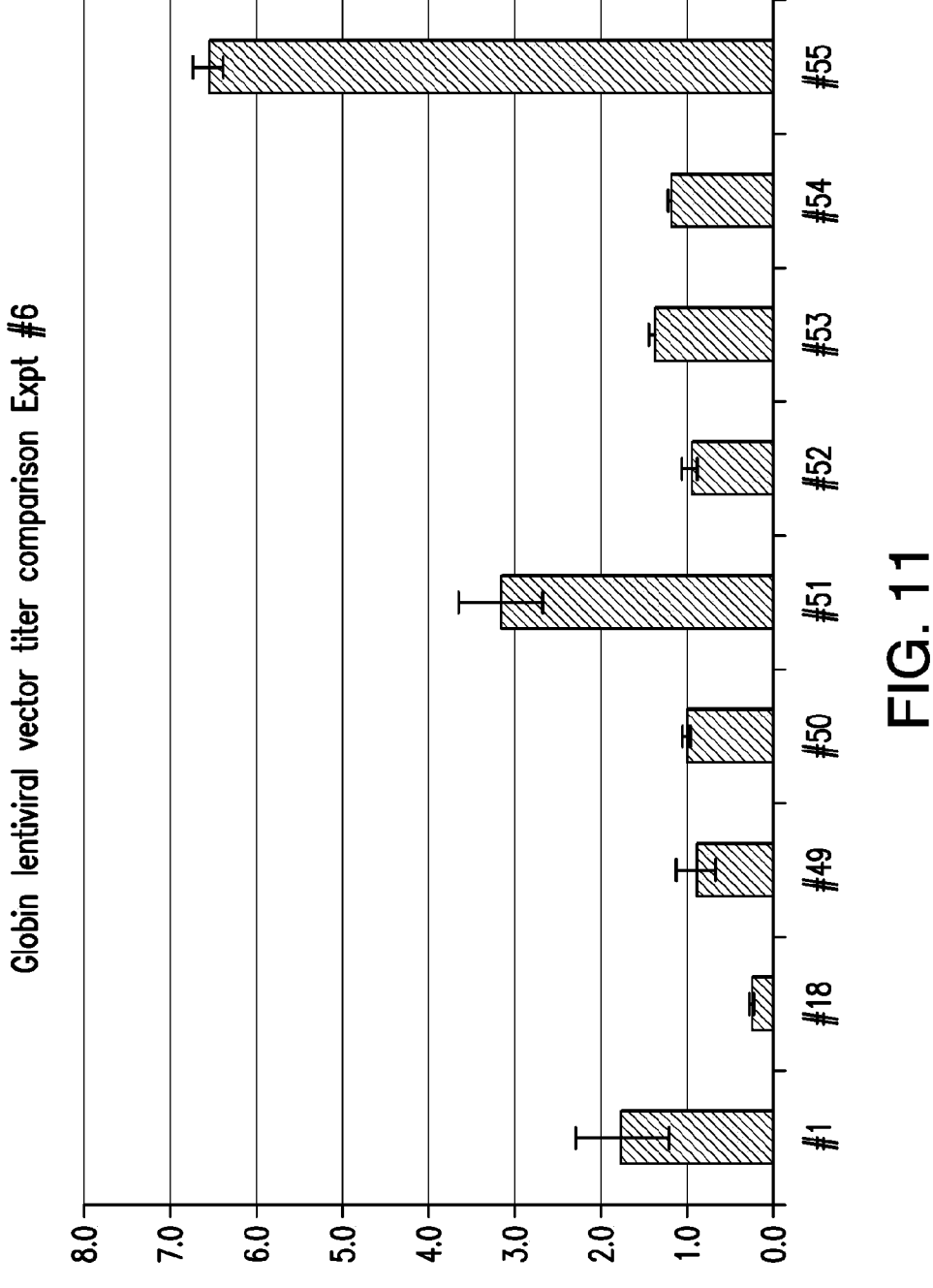
FIG. 11 represents the titer of the recombinant vectors
comprising the presently disclosed expression cassettes.
Figure 12:
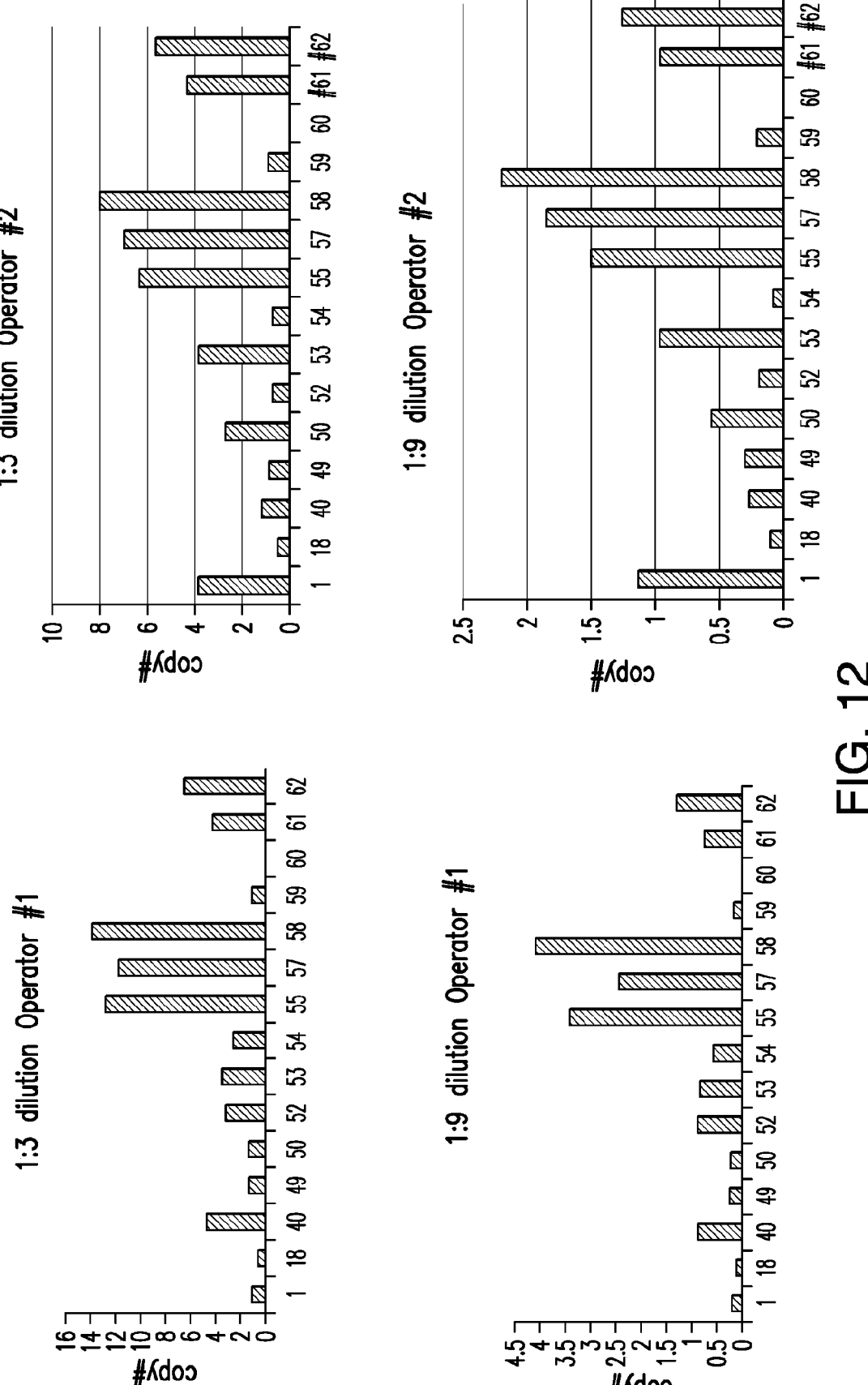
FIG. 12 represents the titer of the recombinant vectors
comprising the presently disclosed expression cassettes.

As shown in FIGS. 11 and 12, Vector #55 repeatedly showed a higher titer. This vector comprises a Woodchuck hepatitis post-regulatory element (WPRE) and a bovine growth hormone polyadenylation signal 3' to the R region in 3' LTR. The WPRE element is therefore not transferred to the transduced cells.

Example 6: Generation of Globin Vectors

Methods and Materials
Vector Production

Various lentiviral vectors were produced, including TNS9.B87.A1, SNS22.2.B87.A1, SNS23.2.B87.A1, and SNS24.2.B87.A1. The nucleotide sequences of TNS9.B87.A1, SNS22.2.B87.A1, SNS23.2.B87.A1, SNS24.2.B87.A1, SNS26.B87.A1 and SNS27.2.B87.A1 are set forth in SEQ ID NO: 37, SEQ ID NO: 38, SEQ ID NO: 39, SEQ ID NO: 40, SEQ ID NO: 76, and SEQ ID NO: 77, respectively.

[SEQ ID NO: 37]

```
attggccattgcatacgttgtatccatatcataatatgtacatttatattggctcatgtccaacattaccgccatgttga
cattgattattgactagttattaatagtaatcaattacggggtcattagttcatagcccatatatggagttccgcgttac
ataacttacggtaaatggcccgcctggctgaccgcccaacgaccccgcccattgacgtcaataatgacgtatgttccca
tagtaacgccaatagggactttccattgacgtcaatgggtggagtatttacggtaaactgcccacttggcagtacatcaa
gtgtatcatatgccaagtacgccccctattgacgtcaatgacggtaaatggcccgcctggcattatgcccagtacatgac
cttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttgg
caccaaaatcaacgggactttccaaaatgtcgtaacaactccgccccattgacgcaaatgggcggtaggcgtgtacggtg
ggaggtctatataagcagagctcgtttagtgaaccggggtctctctggttagaccagatctgagcctgggagctctctgg
ctaactagggaacccactgcttaagcctcaataaagcttgccttgagtgcttcaagtagtgtgtgcccgtctgttgtgtg
actctggtaactagagatccctcagacccttttagtcagtgtggaaaatctctagcagtggcgcccgaacagggacttga
aagcgaaagggaaaccagaggagctctctcgacgcaggactcggcttgctgaagcgcgcacggcaagaggcgaggggcgg
cgactggtgagtacgccaaaaattttgactagcggaggctagaaggagagagacgggtgcgagagcgtcagtattaagcg
ggggtgaataagatcgcgatgggaaaaaattcggttaaggccaggggggaaagaaaaaatataaattaaaacatatagtat
gggcaagcaggggagctagaacgattcgcagttaatcctggcctgttagaaacatcagaaggctgtagacaaatactggga
cagctacaaccatcccttcagacaggatcagaagaacttagatcattatataatacagtagcaaccctctattgtgtgca
tcaaaggatagagataaaagacaccaaggaagctttagacaagatagaggaagagcaaaacaaaagtaagaccaccgcac
agcaagcggccgctgatcttcagacctggaggaggagatatgagggacaattggagaagtgaattatataaatataaagt
agtaaaaattgaaccattaggagtagcacccaccaaggcaagaagaggtggtgcagagagaaaaaagacagtgggaa
taggagctttgttccttgggttcttgggagcagcaggaagcactatgggcgcagcgtcaatgacgctgacggtacaggcc
agacaattattgtctggtatagtgcagcagcagaacaatttgctgagggctattgaggcgcaacagcatctgttgcaact
cacagtctgggccatcaagcagctccaggcaagaatcctggctgtggaaagatacctaaaggatcaacagctcctgggga
tttggggttgctctggaaaactcatttgcaccactgctgtgccttggaatgctagttggagtaataaatctctggaacag
atttggaatcacacgacctggatggagtgggacagagaaattaacaattacacaagcttaatacactccttaattgaaga
atcgcaaaaccagcaagaaaagaatgaacaagaattattggaattagataaatgggcaagtttgtggaattggtttaaca
taacaaattggctgtggtatataaaattattcataatgatagtaggaggcttggtaggtttaagaatagtttttgctgta
ctttctatagtgaatagagttaggcagggatattcaccattatcgtttcagacccacctcccaacccgagggggacccga
caggcccgaaggaatagaagaagaaggtggagagagagacagagacagatccattcgattagtgaacggatctcgacggt
atcgttttaaaagaaaaggggggattggggggtacagtgcaggggaaagaatagtagacataataagcaacagacatacaa
actaaagaattacaaaaacaaattacaaaaattcaaaattttatcggcgtgttgggggtggaccatcctctaggtattga
ataagaaaaatgaagttaaggtggttgatggtaacactatgctaataactgcagagccagaagcaccataagggacatga
taagggagccagcagacctctgatctcttcctgaatgctaatcttaaacatcctgaggaagaatgggacttccatttggg
gtgggcctatgatagggtaataagacagtagtgaatatcaagctacaaaaagccccctttcaaattcttctcagtcctaa
```

-continued

```
cttttcatactaagcccagtccttccaaagcagactgtgaaagagtgatagttccgggagactagcactgcagattccgg
gtcactgtgagtgggggaggcagggaagaagggctcacaggacagtcaaaccatgcccctgttttttccttcttcaagta
gacctctataagacaacagagacaactaaggctgagtggccaggcgaggagaaaccatctcgccgtaaaacatggaagga
acacttcaggggaaaggtggtatctctaagcaagagaactgagtggagtcaaggctgagagatgcaggataagcaaatgg
gtagtgaaaagacattcatgaggacagctaaaacaataagtaatgtaaaatacagcatagcaaaactttaacctccaaat
caagcctctacttgaatccttttctgagggatgaataaggcataggcatcaggggctgttgccaatgtgcattagctgtt
tgcagcctcaccttctttcatggagtttaagatatagtgtattttcccaaggtttgaactagctcttcatttctttatgt
tttaaatgcactgacctcccacattccctttttagtaaaatattcagaaataatttaaatacatcattgcaatgaaaata
aatgtttttttattaggcagaatccagatgctcaaggcccttcataatatcccccagtttagtagttggacttagggaaca
aaggaacctttaatagaaattggacagcaagaaagcgagcttagtgatacttgtggggccagggcattagccacaccagcc
accactttctgataggcagcctgcactggtggggtgAATTCTTTGCCAAAGTGATGGGCCAGCACACAGACCAGCACGTT
GCCCAGGAGCTGTGGGAGGAAGATAAGAGGGTATGAACATGATTAGCAAAAGGGCCTAGCTTGGACTCAGAATAATCCAGC
CTTATCCCAACCATAAAATAAAAGCAGAATGGTAGCTGGATTGTAGCTGCTATTAGCAATATGAAACCTCTTACATCAGT
TACAATTTATATGCAGAAATATTTATATGCAGAAATATTGCTATTGCCTTAACCCAGAAATTATCACTGTTATTCTTTAG
AATGGTGCAAAGAGGCATGATACATTGTATCATTATTGCCCTGAAAGAAAGAGATTAGGGAAAGTATTAGAAATAAGATA
AACAAAAAGTATATTAAAAGAAGAAAGCATTTTTTAAAATTACAAATGCAAAATTACCCTGATTTGGTCAATATGTGTA
CCCTGTTACTTCTCCCCTTCCTATGACATGAACTTAACCATAGAAAAGAAGGGGAAAGAAAACATCAAGGGTCCCATAGA
CTCACCCTGAAGTTCTCAGGATCCACGTGCAGCTTGTCACAGTGCAGCTCACTCAGctgGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCctagggtgtggctccacagggtgaggtctaagtgatgacagccgtacctgtccttggc
tcttctggcactggcttaggagttggacttcaaaccctcagccctccctctaagtatatctcttggccccataccatca
gtacaaattgctactaaaaacatcctcctttgcaagtgtatttacgtaatatttggaatcacagcttggtaagcatattg
aagatcgttttcccaattttcttattacacaaataagaaattgatgcactaaaagtggaagagtttgtctaccataatt
cagctttgggatatgtagatggatctcttcctgcgtctccagaatatgcaaaatacttacaggacagaatggatgaaaac
tctacctcagttctaagcatatcttctccttatttggattaaaaccttctggtaagaaaagaaaaaaaatatatatatat
atgtgtatatatacacacatacatatacatatatgcattcatttgttgttttttcttaatttgctcatggtatatg
tgtatatatatatatatattcaggaaataatatattctagaatatgtcacattctgtctcaggcatccattttcttta
tgatgccgtttgaggtggagtttttagtcaggtggtcagcttctcccttttttttgccatctgccctgtaagcatcctgctg
gggacccagataggagtcatcactctaggctgagaacatctgggcacacacacctaagcctcagcatgactcatcatgact
cagcattgctgtgcttgagccagaaggtttgcttagaaggttacacagaacccgaaggcggggtggggcactgacccccg
acaggggcctggccagaactgctcatgcttggactatgggaggtcactaatggagacacacagaaatgtaacaggaacta
aggaaaaactgaagcttatttaatcagagatgagatgctggaagggatagagggagctgagcttgtaaaaagtatagtaa
tcattcagcaaatggttttgaagcacctgctggatgctaaacactattttcagtgcttgaatcataaataagaataaaac
atgtatcttattccccacaagagtccaagtaaaaaataacagttaattataatgtgctctgtcccccaggctggagtgca
gtggcacgatctcagctcactgcaacctccgcctcccgggttcaagcaattctcctgcctcagccaccctaatagctggg
attacaggtgcacaccaccatgccaggctaattttttgtacttttttgtagaggcagggtatcaccatgttgtccaagatgg
tcttgaactcctgagctccaagcagtccacccacctcagcctcccaaagtgctatctgcggccgcctatctgtaccacta
gtctcgagaagctttcattaaaaaagtctaaccagctgcattcgaccttgactgcagcagctggttaggaaggtttctact
ggaggagggtcccagcccattgctaaattaacatcaggctctgagactggcagtatatctctaacagtggttgatgctat
cttctggaacttgcctgctacattgagaccactgacccatacataggaagcccatagctctgtcctgaactgttaggcca
ctggtccagagagtgtgcatctcctttgatcctcataataaccctatgagatagacacaattattactcttacttttatag
atgatgatcctgaaaacataggagtcaaggcacttgcccctagctggggggtaataagtgctctgtccccccaggctggagtgca
atgaaaaatgctgctatgctgtgcctcccccacctttccatgtctgccctctactcatggtctatctctcctggctcct
gggagtcatggactccaccccagcaccaccaacctgacctaaccacctatctgagcctgccagcctataacccatctgggc
cctgatagctggtggccagccctgaccccacccacccctccctggaacctctgatagacacatctggcacaccagctcgc
aaagtcaccgtgagggtcttgtgtttgctgagtcaaaattccttgaaatccaagtcctagagactcctgctcccaaatt
tacagtcatagacttcttcatggctgtgtctcctttatccacagaatgattcctttgcttcattgccccatccatctgatcc
tcctcatcagtgcagcacagggcccatgagcagtagctgcagagtctcacataggtctggcactgcctctgacatgtccg
accttaggcaaatgcttgactcttctgagctcagtcttgtcatggcaaaataaagataataatagtgtttttttatggag
ttagcgtgaggatggaaaacaatagcaaaattgattagactataaaaggtctcaacaaatagtagtagattttatcatcc
attaatccttccctctcctctcttactcatcccatcacgtatgcctcttaattttccttacctataataagagttattc
ctcttattatattcttcttatagtgattctggatattaaagtgggaatgaggggcaggccactaacgaagaagatgtttc
tcaaagaagccattctccccacatagatcatctcagcagggttcaggaagataaaggaggatcaaggtcgaaggtaggaa
ctaaggaagaacactgggcaagtggatcctgagcccctttcctctaactgaaagaaggaaaaaaaatggaacccaaa
atattctacatagtttccatgtcacagccagggctgggcagtctcctgttattttctttaaaataaatatatcattaaa
tgcataaaataagcaaacccctgctcgggaatgggagggagagtctctggagtccaccccttctcggccctggctctgcaga
tagtgctatcaaagccctgacagagccctgcccattgctgggccttggagtgagtcagcctagtagagaggcagggcaag
ccatctcatagctgctgagtgggagagagaaaagggctcattgtctataaactcaggtcatggctattcttattctcaca
ctaagaaaaagaatgagatgtctacatataccctgcgtccccctcttgtgtactgggggccccaagagctctctaaaagtg
atggcaaagtcattgcgctagatgccatcccatctattataaacctgcatttgtctccacacaccagtcatggacaataa
ccctcctcccaggtccacgtgcttgtctttgtataatactcaagtaatttcggaaaatgtattctttcaatcttgttctg
ttattcctgtttcaatggcttagtagaaaaagtacatacttgttttcccataaattgacaatagacaatttcacatcaat
gtctatatgggtcgttgtgtttgctgtgtttgcaaaaactcacaataacttttatattgttactactctaagaaagttaca
acatggtgaatacaagagaaagctattacaagtccagaaaataaaagttatcatcttgaggcctcagctttctaggaata
atatcaatattacaaaatttaatctaacaattatgaacagcaatgagataatatgtacaaagtacccagacctatgtggt
agagcatcaaggaagcgcattgcggagcagttttttgtttgtttgtttttgtattctgtttcgtgaggcaaggtttcact
ctgctgtccaggctggagtgcagtggcaagatcatgtctcactgcagccttgacacgcgtcgacggtaccgttaacgatc
ttagccacttttttaaaagaaaaagggggggactggaagggctaattcactcccaacgaagacaagatatcctgCTAGTCCTT
CCTTTCTAAATGACGAGAGAGACAGAAGAATTCTTCAAGGTTAGTGTGTCCAGCATGCAACCTTTCCTTCCTGGATGAGC
ATCCCTGGAGTAGGAGAGCCAGCCTGCCTCCTGCGCTGGCACAGAGCCCGGTTCCCTAGACAACTGCCTCTCCAAATCTG
ATGTCCAGCGCCACCTGGTGTCCACATCAAGCAGCACAATTAATAGTCaacACCTGTTCAGGAAAACTGTTGAGGGGGAAAA
AAAAGAAAGAGGATTTATGAAGGGAAAAGAAAGTTTAGAGGATATGCCACGATTGGctagcagctgcttttttgcctgtac
tgggtctctctggttagaccagatctgagcctgggagctctctggctaactagggaacccactgcttaagcctcaataaa
gcttgccttgagtgcttcatccggAATCAACCTCTGGATTACAAAATTTGTGAAAGATTGACTGGTATTCTTAACTATGT
TGCTCCTTTTACGCTATGTGGATACGCTGCTTTAATGCCTTTGTATCATGCTATTGCTTCCCGTATGGCTTTCATTTTCT
CCTCCTTGTATAAATCCTGGTTGCTGTGTCTCTTTATGAGGAGTTGTGGCCCGTTGTCAGGCAACGTGGCGTGGTGTGCACT
```

-continued

GTGTTTGCTGACGCAACCCCCACTGGTTGGGGCATTGCCACCACCTGTCAGCTCCTTTCCGGGACTTTCGCTTTCCCCCT
CCCTATTGCCACGGCGGAACTCATCGCCGCCTGCCTTGCCCGCTGCTGGACAGGGGCTCGGCTGTTGGGCACTGACAATT
CCGTGGTGTTGTCGGGGAAGCTGACGTCCTTTCCATGGCTGCTCGCCTGTGTTGCCACCTGGATTCTGCGCGGGACGTCC
TTCTGCTACGTCCCTTCGGCCCTCAATCCAGCGGACCTTCCTTCCCGCGGCCTGCTGCCGGCTCTGCGGCCTCTTCCGCG
TCTTCGCCTTCGCCCTCAGACGAGTCGGATCTCCCTTTGGGCCGCCTCCCCGCCTGtccggtAGCTTGCCAGCCTCGACT
GTGCCTTCTAGTTGCCAGCCGTCTGTTGTTTGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGcaagcttggcgtaatcatggtcatagctgtttcctgtgtga
aattgttatccgctcacaattccacacaacatacgagccggaagcataaagtgtaaagcctggggtgcctaatgagtgag
ctaactcacattaattgcgttgcgctcactgcccgctttccagtcgggaaacctgtcgtgccagctgcattaatgaatcg
gccaacgcgcggggagaggcggtttgcgtattgggcgctcttccgcttcctcgctcactgactcgctgcgctcggtcgtt
cggctgcggcgagcggtatcagctcactcaaaggcggtaatacggttatccacagaatcaggggataacgcaggaaagaa
catgtgagcaaaaggccagcaaaaggccaggaaccgtaaaaaggccgcgttgctggcgtttttccataggctccgcccccc
ctgacgagcatcacaaaaatcgacgctcaagtcagaggtggcgaaacccgacaggactataaagataccaggcgtttccc
cctggaagctccctcgtgcgctctcctgttccgaccctgccgcttaccggatacctgtccgcctttctcccttcgggaag
cgtggcgctttctcatagctcacgctgtaggtatctcagttcggtgtaggtcgttcgctccaagctgggctgtgtgcacg
aaccccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcc
taactacggctacactagaagaacagtatttggtatctgcgctctgctgaagccagttaccttcggaaaaagagttggta
gctcttgatccggcaaacaaaccaccgctggtagcggtggtttttttgtttgcaagcagcagattacgcgcagaaaaaaa
ggatctcaagaagatcctttgatcttttctacggggtctgacgctcagtggaacgaaaactcacgttaagggattttggt
catgagattatcaaaaaggatcttcacctagatcctttttaaattaaaaatgaagttttaaatcaatctaaagtatatatg
agtaaacttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaatgataccgcg
agacccacgctcaccggctccagatttatcagcaataaaccagccagccggaagggccgagcgcagaagtggtcctgcaa
ctttatccgcctccatccagtctattaattgttgccgggaagctagagtaagtagttcgccagttaatagtttgcgcaac
gttgttgccattgctacaggcatcgtggtgtcacgctcgtcgtttggtatggcttcattcagctccggttcccaacgatc
aaggcgagttacatgatcccccatgttgtgcaaaaaagcggttagctccttcggtcctccgatcgttgtcagaagtaagt
tggccgcagtgttatcactcatggttatggcagcactgcataattctcttactgtcatgccatccgtaagatgcttttct
gtgactggtgagtactcaaccaagtcattctgagaatagtgtatgcggcgaccgagttgctcttgcccggcgtcaatacg
ggataataccgcgccacatagcagaactttaaaagtgctcatcattggaaaacgttcttcggggcgaaaactctcaaggat
cttaccgctgttgagatccagttcgatgtaacccactcgtgcacccaactgatcttcagcatcttttactttcaccagcg
tttctgggtgagcaaaaacaggaaggcaaaatgccgcaaaaaagggaataagggcgacacggaaatgttgaatactcata
ctcttcctttttcaatattattgaagcatttatcagggttattgtctcatgagcggatacatatttgaatgtatttagaa
aaataaacaaataggggttccgcgcacatttccccgaaaagtgccacctgacgtctaagaaaccattattatcatgacat
taacctataaaaataggcgtatcacgaggccctttcgtctcgcgcgtttcggtgatgacggtgaaaacctctgacacatg
cagctcccggagacggtcacagcttgtctgtaagcggatgccgggagcagacaagcccgtcagggcgcgtcagcgggtgt
tggcgggtgtcggggctggcttaactatgcggcatcagagcagattgtactgagagtgcacc

[SEQ ID NO: 38]
ATTGGCCATTGCATACGTTGTATCCATATCATAATATGTACATTTATATTGGCTCATGTCCAACATTACCGCCATGTTGA
CATTGATTATTGACTAGTTATTAATAGTAATCAATTACGGGGTCATTAGTTCATAGCCCATATATGGAGTTCCGCGTTAC
ATAACTTACGGTAAATGGCCCGCCTGGCTGACCGCCCAACGACCCCCGCCCATTGACGTCAATAATGACGTATGTTCCCA
TAGTAACGCCAATAGGGACTTTCCATTGACGTCAATGGGTGGAGTATTTACGGTAAACTGCCCACTTGGCAGTACATCAA
GTGTATCATATGCCAAGTACGCCCCCTATTGACGTCAATGACGGTAAATGGCCCGCCTGGCATTATGCCCAGTACATGAC
CTTATGGGACTTTCCTACTTGGCAGTACATCTACGTATTAGTCATCGCTATTACCATGGTGATGCGGTTTTGGCAGTACA
TCAATGGGCGTGGATAGCGGTTTGACTCACGGGGATTTCCAAGTCTCCACCCCATTGACGTCAATGGGAGTTTGTTTTGG
CACCAAAATCAACGGGACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGGGGTCTCTCTGGTTAGACCAGATCTGAGCCTGGGAGCTCTCTGG
CTAACTAGGGAACCCACTGCTTAAGCCTCAATAAAGCTTGCCTTGAGTGCTTCAAGTAGTGTGTGCCCGTCTGTTGTGTG
ACTCTGGTAACTAGAGATCCCTCAGACCCCTTTTAGTCAGTGTGGAAAATCTCTAGCAGTGGCGCCCGAACAGGGACTTGA
AAGCGAAAGGGAAACCAGAGGAGCTCTCTCGACGCAGGACTCGGCTTGCTGAAGCGCGCACGGCAAGAGGCGAGGGGCGG
CGACTGGTGAGTACGCCAAAAATTTTGACTAGCGGAGGCTAGAAGGAGAGAGATGGGTGCGAGAGCGTCAGTATTAAGCG
GGGGTGAATAAGATCGCGATGGGAAAAAATTCGGTTAAGGCCAGGGGGAAAGAAAAAATATAAATTAAAACATATAGTAT
GGGCAAGCAGGGAGCTAGAACGATTCGCAGTTAATCCTGGCCTGTTAGAAACATCAGAAGGCTGTAGACAAATACTGGGA
CAGCTACAACCATCCCTTCAGACAGGATCAGAAGAACTTAGATCATTATATAATACAGTAGCAACCCTCTATTGTGTGCA
TCAAAGGATAGAGATAAAAGACACCAAGGAAGCTTTAGACAAGATAGAGGAAGAGCAAAACAAAGTAAGACCACCGCAC
AGCAAGCGGCCGCTGATCTTCAGACCTGGAGGAGGAGATATGAGGGACAATTGGAGAAGTGAATTATATAAATATAAAGT
AGTAAAAATTGAACCATTAGGAGTAGCACCCACCAAGGCAAAGAGAAGAGTGGTGCAGAGAGAAAAAAGAGCAGTGGGAA
TAGGAGCTTTGTTCCTTGGGTTCTTGGGAGCAGCAGGAAGCACTATGGGCGCAGCGTCAATGACGCTGACGGTACAGGCC
AGACAATTATTGTCTGGTATAGTGCAGCAGCAGAACAATTTGCTGAGGGCTATTGAGGCGCAACAGCATCTGTTGCAACT
CACAGTCTGGGGCATCAAGCAGCTCCAGGCAAGAATCCTGGCTGTGGAAAGATACCTAAAGGATCAACAGCTCCTGGGGA
TTTGGGGTTGCTCTGGAAAACTCATTTGCACCCACTGCTGTGCCTTGGAATGCTAGTTGGAGTAATAAATCTCTGGAACAG
ATTTGGAATCACACGACCTGGATGGAGTGGGACAGAGAAATTAACAATTACACAAGCTTAATACACTCCTTAATTGAAGA
ATCGCAAAACCAGCAAGAAAAGAATGAACAAGAATTATTGGAATTAGATAAATGGGCAAGTTTGTGGAATTGGTTTAACA
TAACAAATTGGCTGTGGTATATAAAATTATTCATAATGATAGTAGGAGGCTTGGTAGGTTTAAGAATAGTTTTTGCTGTA
CTTTCTATAGTGAATAGAGTTAGGCAGGGATATTCACCATTATCGTTTCAGACCCACCTCCCAACCCCGAGGGGACCCGA
CAGGCCCGAAGGAATAGAAGAAGAAGGTGGAGAGAGAGACAGAGACAGATCCATTCGATTAGTGAACGGATCTCGACGGT
ATCGTTTTAAAAGAAAAGGGGGGATTGGGGGGTACAGTGCAGGGGAAAGAATAGTAGACATAATAGCAACAGACATACAA
ACTAAAGAATTACAAAAACAAATTACAAAAATTCAAAATTTTATCGGCGTGTTGGGGGTGGACCATCCTCTAGGTATTGA
ATAAGAAAAATGAAGTTAAGGTGGTTGATGGTAACACTATGCTAATAACTGCAGAGCCAGAAGCACCATAAGGGACATGA
TAAGGGAGCCAGCAGACCTCTGATCTCTTCCTGAATGCTAATCTTAAACATCCTGAGGAAGAATGGGACTTCCATTTGGG
GTGGGCCTATGATAGGGTAATAAGACAGTAGTGAATATCAAGCTACAAAAAGCCCCCTTTCAAATTCTTCTCAGTCCTAA
CTTTTCATACTAAGCCCAGTCCTTCCAAAGCAGACTGTGAAAGAGTGATAGTTCCGGGGAGACTAGCACTGCAGATTCCGG
GTCACTGTGAGTGGGGGAGGCAGGGAAGAAGGGCTCACAGGACAGTCAAACCATGCCCCCTGTTTTTCCTTCTTCAAGTA
GACCTCTATAAGCAACAGAGACAACTAAGGCTGAGTGGCCAAGAAACCATCTCGCCGTAAAACATGGAAGGA
ACACTTCAGGGGAAAGGTGGTATCTCTAAGCAAGAGAACTGAGTGGAGTCAAGGCTGAGAGATGCAGGATAAGCAAATGG
GTAGTGAAAAGACATTCATGAGGACAGCTAAAACAATAAGTAATGTAAAATACAGCATAGCAAAACTTTAACCTCCAAAT
CAAGCCTCTACTTGAATCCTTTTCTGAGGGGATGAATAAGGCATAGGCATCAGGGGCTGTTGCCAATGTGCATTAGCTGTT
TGCAGCCTCACCTTCTTTCATGGAGTTTAAGATATAGTGTATTTTCCCAAGGTTTGAACTAGCTCTTCATTTCTTTATGT
TTTAAATGCACTGACCTCCCACATTCCCTTTTTAGTAAAATATTCAGAAATAATTTAAATACATCATTGCAATGAAAATA

-continued

```
AATGTTTTTTATTAGGCAGAATCCAGATGCTCAAGGCCCTTCATAATATCCCCCAGTTTAGTAGTTGGACTTAGGGAACA
AAGGAACCTTTAATAGAAATTGGACAGCAAGAAAGCGAGCTTAGTGATACTTGTGGGCCAGGGCATTAGCCACACCAGCC
ACCACTTTCTGATAGGCAGCCTGCACTGGTGGGGTGAATTCTTTGCCAAAGTGATGGGCCAGCACACAGACCAGCACGTT
GCCCAGGAGCTGTGGGAGGAAGATAAGAGGTATGAACATGATTAGCAAAAGGGCCTAGCTTGGACTCAGAATAATCCAGC
CTTATCCCAACCATAAAATAAAAGCAGAATGGTAGCTGGATTGTAGCTGCTATTGAACAATATGAAACCTCTTACATCAGT
TACAATTTATATGCAGAAATATTTATATGCAGAAATATTGCTATTGCCTTAACCCAGAAATTATCACTGTTATTCTTTAG
AATGGTGCAAAGAGGCATGATACATTGTATCATTATTGCCCTGAAAGAAAGAGATTAGGGAAAGTATTAGAAATAAGATA
AACAAAAAAGTATATTAAAAGAAGAAAGCATTTTTTAAAATTACAAATGCAAAATTACCCTGATTTGGTCAATATGTGTA
CCCTGTTACTTCTCCCCTTCCTATGACATGAACTTAACCATAGAAAAGAAGGGGAAAGAAAACATCAAGGGTCCCATAGA
CTCACCCTGAAGTTCTCAGGATCCACGTGCAGCTTGTCACAGTGCAGCTCACTCAGCTGGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGGAGTAGATTGGCCAACCCTAGGGTGTGGCTCCACAGGGTGAGGTCTAAGTGATGACAGCCGTACCTGTCCTTGGC
TCTTCTGGCACTGGCTTAGGAGTTGGACTTCAAACCCTCAGCCCTCCCTCTAAGATATATCTCTTGGCCCCATACCATCA
GTACAAATTGCTACTAAAAACATCCTCCTTTGCAAGTGTATTTACGGCATCTGTGAAGGAAAGAAACATCTCCTCTAAAC
CACTATGCTGCTAGAGCCTCTTTTCTGTACTCAAGCCTCATTCAGACACTAGTGTCACCAGTCTCCTCATATACCTATTG
TATTTTCTTCTTCTTGCTGGTTTAGTCATGTTTTCTGGGAGCTTAGGGGCTTATTTTATTTTGTTTTGTTTTCTAATCAA
CAGAGATGGGCAAACCCATTATTTTTTTCTTTAGACTTGGGATGGTGATAGCTGGGCAGCGTCAGAAACTGTGTGTGGAT
ATAGATAAGAGCTCGGACTATGCTGAGCTGTGATGAGGGAGGGACCTAGCCAAAGGCAGTGAGAGTCAGAATGCTCCTGC
TATTGCCTTCTCAGTCCCCACGCTTGGTTTCTACACAAGTAGATACATAGAAAAGGCTATAGGTTAGTGTTTGAGAGTCC
TGCATGAGTTAGTTGCTCAGAAATGCCCGATAAATATGTTATGTGTGTTTATGTATATATATGTTTTATATATATATATG
TGTGTGTGTGTGTGTGTGTTTGTGTTTACAAATATGTGATTATCATCAAAACGTGAGGGCTAAAGTGACCAGATAAC
TTGCAGGTCTAGAATATGTCACATTCTGTCTCAGGCATCCATTTTCTTTATGATGCCGTTTGAGGTGGAGTTTTAGTCAG
GTGGTCAGCTTCTCCTTTTTTTTGCCATCTGCCCTGTAAGCATCCTGCTGGGGACCCAGATAGGAGTCATCACTCTAGGC
TGAGAACATCTGGGCACACACCCTAAGCCTCAGCATGACTCATCATGACTCAGCATTGCTGTGCTTGAGCCAGAAGGTTT
GCTTAGAAGGTTACACAGAACCAGAAGGCGGGGGTGGGGCACTGACCCCGACAGGGGCCTGGCCAGACTGCTCATGCTT
GGACTATGGGAGGTCACTAATGGAGACACACAGAAATGTAACAGGAACTAAGGAAAAACTGAAGCTTATTTAATCAGAGA
TGAGATGCTGGAAGGGATAGAGGGAGCTGAGCTTGTAAAAAGTATAGTAATCATTCAGCAAATGGTTTTGAAGCACCTGC
TGGATGCTAAACACTATTTTCAGTGCTTGAATCATAAATAAGAACAAAACATGTATCTTATTCCCCACAAGAGTCCAAGT
AAAAAATAACAGTTAATTATAATGTGCTCTGTCCCCCAGGCTGGAGTGCAGTGGCACGATCTCAGCTCACTGCAACCTCC
GCCTCCCGGGTTCAAGCAATTCTCCTGCCTCAGCCACCCTAATAGCTGGGATTACAGGTGCACACCACCATGCCAGGCTA
ATTTTTGTACTTTTTGTAGAGGCAGGGTATCACCATGTTGTCCAAGATGGTCTTGAACTCCTGAGCTCCAAGCAGTCCAC
CCACCTCAGCCTCCCAAAGTGCTATCTGCGGCCGCCTATCTGTACCACTAGTCTCGAGAAGCTTTCATCAAAAAAAGTCT
AACCAGCTGCATTCGACTTTGACTGCAGCAGCTGGTTAGAAGGTTCTACTGGAGGAGGGTCCCAGCCCATTGCTAAATTA
ACATCAGGCTCTGAGACTGGCAGTATATCTCTAACAGTGGTTGATGCTATCTTCTGGAACTTGCCTGCTACATTGAGACC
ACTGACCCATACATAGGAAGCCCATAGCTCTGTCCTGAACTGTTAGGCCACTGGTCCAGAGAGTGTGCATCTCCTTTGAT
CCTCATAATAACCCTATGAGATAGACACAATTATTACTCTTACTTTATAGATGATGATCCTGAAAACATAGGAGTCAAGG
CACTTGCCCCTAGCTGGGGGTATAGGGGAGCAGTCCCATGTAGTAGTAGAATGAAAAATGCTGCTATGCTGTGCCTCCCC
CACCTTTCCCATGTCTGCCCTCTACTCATGGTCTATCTCTCCTGGCTCCTGGGAGTCATGGACTCCACCCAGCACCACCA
ACCTGACCTAACCACCTATCTGAGCCTGCCAGCCTATAACCCATCTGGGCCCTGATAGCTGGTGGCCAGCCCTGACCCCA
CCCCACCCTCCCTGGAACCTCTGATAGACACATCTGGCACACCAGCTCGCAAAGTCACCGTGAGGGTCTTGTGTTTGCTG
AGTCAAAATTCCTTGAAATCCAAGTCCTTAGAGACTCCTGCTCCCAAATTTACAGTCATAGACTTCTTCATGGCTGTCTC
CTTTATCCACAGAATGATTCCTTTGCTTCATTGCCCCATCCATCTGATCCTCCTCATCAGTGCAGCACAGGGCCCATGAG
CAGTAGCTGCAGAGTCTCACATAGGTCTGGCACTGCCTCTGACATGTCCGACCTTAGGCAAATGCTTGACTCTTCTGAGC
TCAGTCTTGTCATGGCAAAACAAAGATAATAATAGTGTTTTTTTTATGGAGTTAGCGTGAGGATGGAAAACAATAGCAAAA
TTGATTAGACTATAAAAGGTCTCAACAAATAGTAGTAGATTTTATCATCCATTAATCCTTCCCTCTCCTCTCTTACTCAT
CCCATCACGTATGCCTCTTAATTTTCCCTTACCTATAATAAGAGTTATTCCTCTTATTATATTCTTCTTATATAGTGATTCT
GGATATCAAAGTGGGAATGAGGGGCAGGCCACTAACGAAGAAGATGTTTCTCAAAGAAGCCATTCTCCCCACATAGATCA
TCTCAGCAGGGTTCAGGAAGATAAAGGAGGATCAAGGTCGAAGGTAGGAACTAAGGAAGAACACTGGGCAAGTGGATCCT
AAATATATCATTTAAATGCATAAATAAGCAAACCCTGCTCGGGAATGGGAGGGAGAGTCTCTGGAGTCCACCCCTTCTCG
GCCCTGGCTCTGCAGATAGTGCTATCAAAGCCCTGACAGAGCCCTGCCCATTGCTGGGCCTTGGAGTGAGTCAGCCTAGT
AGAGAGGCAGGGCAAGCCATCTCATAGCTGCTGAGTGGGAGAGAGAAAAGGGCTCATTGTCTATAAACTCAGGTCATGGC
TATTCTTATTCTCACACTAAGAAAAAGAATGAGATGTCTACATATACCCTGCGTCCCCTCTTGTGTACTGGGGCCCCCAA
GAGCTCTCTAAAAGTGATGGCAAAGTCATTGCGCTAGATGCCATCCCATCTATTATAAACCTGCATTTGTCTCCACACAC
CAGTCATGGACAATAACCCTCCTCCCAGGTCCACGTGCTTGTCTTTGTATAATACTCAAGTAATTTCGGAAAATGTATTC
TTTCAATCTTGTTCTGTTATTCCTGTTTCAATGGCTTAGTAGAAAAAGTACATACTTGTTTTCCCATAAATTGACAATAG
ACAATTTCACATCAATGTCTATATGGGTCGTTGTGTGTTTGCTGTGTGTTTGCAAAAACTCACAATAACTTTATATTGTTACTA
CTCTAAGAAAGTTACAACATGGTGAATACAAGAGAAAGCTATTACAAGTCCAGAAAACAAAAGTTATCATCTTGAGGCCT
CAGCTTTTCTAGGAATAATATCAATATTACAAAACGCGTCGACGGTACCGTTAACGATCTTAGCCACTTTTTAAAAGAAAA
GGGGGGACTGGAAGGGCTAATTCACTCCCAACGAAGACAAGATATCCTGACGGTACCGTTAACGATCTTAGCCACTTTTTAAAAGAAA
CAGAAGAATTCTTCAAGGTTAGTGTGTCCAGCATGCAACCTTTCCTTCCTGGATGAGCATCCCTGGAGTAGGAGAGCCAG
CCTGCCTCCTGCGCTGGCACAGAGCCCGGTTCCCTAGACAACTGCCTCTCCAAATCTGATGTCCAGCGCCACCTGGTGTC
CACATCAAGCAGACACAATTAATAGTCAACCTGTTCAGGAAAACTGTGAGGGGGAAAAAAAAGAAAGAGGATTTATGAAG
GGAAAAGAAAGTTTAGAGGATATGCCACGATTGGCTAGCAGCTGCTTTTTGCCTGTACTGGGTCTCTCTGGTTAGACCAG
ATCTGAGCCTGGGAGCTCTCTGGCTAACTAGGGAACCCACTGCTTAAGCCTCAATAAAGCTTGCCTTGAGTGCTTCATCC
GGAATCAACCTCTGGATTACAAAATTTGTGAAAGATTGACTGGTATTCTTAACTATGTTGCTCCTTTTACGCTATGTGGA
TACGCTGCTTTAATGCCTTTGTATCATGCTATTGCTTCCCGTATGGCTTTCATTTTCTCCTCCTTGTATAAATCCTGGTT
GCTGTCTCTTTATGAGGAGTTGTGGCCCGTTGTCAGGCAACGTGGCGTGGTGTGCACTGTGTTTGCTGACGCAACCCCCA
CTGGTTGGGGCATTGCCACCACCTGTCAGCTCCTTTCCGGGACTTTCGCTTTCCCCCTCCCTATTGCCACGGCGGAACTC
ATCGCCGCCTGCCTTGCCCGCTGCTGGACAGGGGCTCGGCTGTTGGGCACTGACAATTCCGTGGTGTTGTCGGGGAAGCT
GACGTCCTTTCCATGGCTGCTCGCCTGTGTTGCCACCTGGATTCTGCGCGGGACGTCCTTCTGCTACGTCCCTTCGGCCC
TCAATCCAGCGGACCTTCCTTCCCGCGGCCTGCTGCCGGCTCGTGCCGCCTCTTCCGCGTCTTCGCCTTCGCCCTCAGACG
AGTCGGATCTCCCTTTGGGCCGCCTCCCCGCCTGTCCGGTAGCTTGCCAGCCTCAGCTGTGCCTTCTAGTTGCCAGCCGT
CTGTTGTTTGCCCCTCCCCCGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGACAGCAAGGGGGAGGATTGGGA
AGACAATAGCAGGCATGCAAGCTTGGCGTAATCATGGTCATAGCTGTTTCCTGTGTGAAATTGTTATCCGCTCACAATTC
CACACAACATACGAGCCGGAAGCATAAAGTGTAAAGCCTGGGGTGCCTAATGAGTGAGCTAACTCACATTAATTGCGTTG
```

```
CGCTCACTGCCCGCTTTCCAGTCGGGAAACCTGTCGTGCCAGCTGCATTAATGAATCGGCCAACGCGCGGGGAGAGGCGG
TTTGCGTATTGGGCGCTCTTCCGCTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCCCCTGACGAGCATCACAAAAATCG
ACGCTCAAGTCAGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGGCCTAACTACGGCTACACTAGAAGA
ACAGTATTTGGTATCTGCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATAGTTGCCTGACTCCCCGTCGTGT
AGATAACTACGATACGGGAGGGCTTACCATCTGGCCCCAGTGCTGCAATGATACCGCGAGACCCACGCTCACCGGCTCCA
GATTTATCAGCAATAAACCAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTTGGCCGCAGTGTTATCACTCAT
GGTTATGGCAGCACTGCATAATTCTCTTACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGTCAATACGGGATAATACCGCGCCACATAGC
AGAACTTTAAAAGTGCTCATCATTGGAAAACGTTCTTCGGGGCGAAAACTCTCAAGGATCTTACCGCTGTTGAGATCCAGT
TCGATGTAACCCACTCGTGCACCCAACTGATCTTCAGCATCTTTTACTTTCACCAGCGTTTCTGGGTGAGCAAAAACAGG
AAGGCAAAATGCCGCAAAAAAGGGAATAAGGGCGACACGGAAATGTTGAATACTCATACTCTTCCTTTTTCAATATTATT
GAAGCATTTATCAGGGTTATTGTCTCATGAGCGGATACATATTTGAATGTATTTAGAAAAATAAACAAATAGGGGTTCCG
CGCACATTTCCCCGAAAAGTGCCACCTGACGTCTAAGAAACCATTATTATCATGACAGTTAACCTATAAAAATAGGCGTAT
CACGAGGCCCTTTCGTCTCGCGCGTTTCGGTGATGACGGTGAAAACCTCTGACACATGCAGCTCCCGGAGACGGTCACAG
CTTGTCTGTAAGCGGATGCCGGGAGCAGACAAGCCCGTCAGGGCGCGTCAGCGGGTGTTGGCGGGTGTCGGGGCTGGCTT
AACTATGCGGCATCAGAGCAGATTGTACTGAGAGTGCACC
```

[SEQ ID NO: 39]

```
ATTGGCCATTGCATACGTTGTATCCATATCATAATATGTACATTTATATTGGCTCATGTCCAACATTACCGCCATGTTGA
...
```

-continued

```
CTCACCCTGAAGTTCTCAGGATCCACGTGCAGCTTGTCACAGTGCAGCTCACTCAGCTGGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCCTAGGGTGTGGCTCCACAGGGTGAGGTCTAAGTGATGACAGCCGTACCTGTCCTTGGC
TCTTCTGGCACTGGCTTAGGAGTTGGACTTCAAACCCTCAGCCCTCCCTCTAAGATATATCTTTGGCCCCATACCATCA
GTACAAATTGCTACTAAAAACATCCTCCTTTGCAAGTGTATTTACTCTAGAATATGTCACATTCTGTCTCAGGCATCCAT
TTTCTTTATGATGCCGTTTGAGGTGGAGTTTTAGTCAGGTGGTCAGCTTCTCCTTTTTTTTGCCATCTGCCCTGTAAGCA
TCCTGCTGGGGACCCAGATAGGAGTCATCACTCTAGGCTGAGAACATCTGGGCACACACCCTAAGCCTCAGCATGACTCA
TCATGACTCAGCATTGCTGTGCTTGAGCCAGAAGGTTTGCTTAGAAGGTTACACAGAACCAGAAGGCGGGGGTGGGGCAC
TGACCCCGACAGGGGCCTGGCCAGAACTGCTCATGCTTGGACTATGGGAGGTCACTAATGGAGACACACAGAAATGTAAC
AGGAACTAAGGAAAAACTGAAGCTTATTTAATCAGAGATGAGATGCTGGAAGGGATAGAGGGGAGCTGAGCTTGTAAAAAG
TATAGTAATCATTCAGCAAATGGTTTTGAAGCACCTGCTGGATGCTAAACACTATTTTCAGTGCTTGAATCATAAATAAG
AACAAAACATGTATCTTATTCCCCACAAGAGTCCAAGTAAAAAATAACAGTTAATTATAATGTGCTCTGTCCCCCAGGCT
GGAGTGCAGTGGCACGATCTCAGCTCACTGCAACCTCCGCCTCCCGGGTTCAAGCAATTCTCCTGCCTCAGCCACCCTAA
TAGCTGGGATTACAGGTGCACACCACCATGCCAGGCTAATTTTTGTACTTTTTGTAGAGACGGGGTATCACCATGTTGTC
CAAGATGGTCTTGAACTCCTGAGCTCCAAGCAGTCCACCCACCTCAGCCTCCCAAAGTGCTATCTGCGGCCGCCTATCTG
TACCACTAGTCTCGAGAAGCTTTCATCAAAAAAAGTCTAACCAGCTGCATTCGACTTTGACTGCAGCAGCTGGTTAGAAG
GTTCTACTGGAGGAGGGTCCCAGCCCATTGCTAAATTAACATCAGGCTCTGAGACTGGCAGTATATCTCTAACAGTGGTT
GATGCTATCTTCTGGAACTTGCCTGCTACATTGAGACCACTGACCCATACATAGGAAGCCCATAGCTCTGTCCTGAACTG
TTAGGCCACTGGTCCAGAGAGTGTGCATCTCCTTTGATCCTCATAATAACCCTATGAGATAGACACAATTATTACTCTTA
CTTTATAGATGATGATCCTGAAAACATAGGAGTCAAGGCACTTGCCCCTAGCTGGGGGTATAGGGGAGCAGTCCCATGTA
GTAGTAGAATGAAAAATGCTGCTATGCTGTGCCTCCCCCACCTTTCCCATGTCTGCCCTCTACTCATGGTCTATCTCTCC
TGGCTCCTGGGAGTCATGGACTCCACCCAGCACCACCAACCTGACCTAACCACCTATCTGAGCCTGCCAGCCTATAACCC
ATCTGGGCCCTGATAGCTGGTGGCCAGCCCTGACCCCACCCCACCCTCCCTGGAACCTCTGATAGACACATCTGGCACAC
CAGCTCGCAAAGTCACCGTGAGGGTCTTGTGTTTGCTGAGTCAAAATTCCTTGAAATCCAAGTCCTTAGAGACTCCTGCT
CCCAAATTTACAGTCATAGACTTCTTCATGGCTGTCTCCTTTATCCACAGAATGATTCCTTTGCTTCATTGCCCCATCCA
TCTGATCCTCCTCATCAGTGCAGCACAGGGCCCATGAGCAGTAGCTGCAGAGTCTCACATAGGTCTGGCACTGCCTCTGA
CATGTCCGACCTTAGGCAAATGCTTGACTCTTCTGAGCTCAGTCTTGTCATGGCAAAACAAAGATAATAATAGTGTTTTT
TTATGGAGTTAGCGTGAGGATGGAAAACAATAGCAAAATTGATTAGACTATAAAAGGTCTCAACAAATAGTAGTAGATTT
TATCATCCATTAATCCTTCCCTCTCCTCTCTTACTCATCCCATCACGTATGCCTCTTAATTTTCCCTTACCTATAATAAG
AGTTATTCCTCTTATTATATTCTTCTTATAGTGATTCTGGATATCAAAGTGGGAATGAGGGGCAGGCCACTAACGAAGAA
GATGTTTCTCAAAGAAGCCATTCTCCCCACATAGATCATCTCAGCAGGGTTCAGGAAGATAAAGGAGGATCAAGGTCGAA
GGTAGGAACTAAGGAAGAACACTGGGCAAGTGGATCCTAAATATATCATTTAAATGCATAAATAAGCAAACCCTGCTCGG
GAATGGGAGGGAGAGTCTCTGGAGTCCACCCCTTCTCGGCCCTGGCTCTGCAGATAGTGCTATCAAAGCCCTGACAGAGC
CCTGCCCATTGCTGGGCCTTGGAGTGAGTCAGCCTAGTAGAGAGGCAGGGCAAGCCATCTCATAGCTGCTGAGTGGGAGA
GAGAAAAGGGCTCATTGTCTATAAACTCAGGTCATGGCTATTCTTATTCTCACACTAAGAAAAAGAATGAGATGTCTACA
TATACCCTGCGTCCCCTCTTGTGTACTGGGGCCCCCAAGAGCTCTCTAAAAGTGATGGCAAAGTCATTGCGCTAGATGCC
ATCCCATCTATTATAAACCTGCATTTGTCTCCACACACCAGTCATGGACAATAACCCTCCTCCCAGGTCCACGTGCTTGT
CTTTGTATAATACTCAAGTAATTTCGGAAAATGTATTCTTTCAATCTTGTTCTGTTATTCCTGTTTCAATGGCTTAGTAG
AAAAAGTACATACTTGTTTTCCCATAAATTGACAATAGACAATTTCACATCAATGTCTATATGGGTCGTTGTGTTTGCTG
TGTTTGCAAAAACTCACAATAACTTTATATTGTTACTACTCTAAGAAAGTTACAACATGGTGAATACAAGAGAAAGCTAT
TACAAGTCCAGAAAACAAAAGTTATCATCTTGAGGCCTCAGCTTTCTAGGAATAATATCAATATTACAAAACGCGTCGAC
GGTACCGTTAACGATCTTAGCCACTTTTTAAAAGAAAAGGGGACGTTGGAAGGGCTAATTCACTCCCAACGAAGACAAGA
TATCCTGCTAGTCCTTCCTTTCTAAATGACGAGAGAGACAGAAGAATTCTTCAAGGTTAGTGTGTCCAGCATGCAACCTT
TCCTTCCTGGATGAGCATCCCTGGAGTAGGAGAGCCAGCCTGCCTCCTGCGCTGGCACAGAGCCCGGTTCCCTAGACAAC
TGCCTCTCCAAATCTGATGTCCAGCGCCACCTGGTGTCCACATCAAGCAGACACAATTAATAGTCAACCTGTTCAGGAAA
ACTGTGAGGGGGAAAAAAAGAAAGAGGATTTATGAAGGGAAAAGAAAGTTTAGAGGGATATGCCACGATTGGCTAGCAGC
TGCTTTTTGCCTGTACTGGGTCTCTCTGGTTAGACCAGATCTGAGCCTGGGAGCTCTCTGGCTAACTAGGGAACCCACTG
CTTAAGCCTCAATAAAGCTTGCCTTGAGTGCTTCATCCGGAATCAACCTCTGGATTACAAAATTTGTGAAAGATTGACTG
GTATTCTTAACTATGTTGCTCCTTTTACGCTATGTGGATACGCTGCTTTAATGCCTTTGTATCATGCTATTGCTTCCCGT
ATGGCTTTCATTTTCTCCTCCTTGTATAAATCCTGGTTGCTGTCTCTTTATGAGGAGTTGTGGCCCGTTGTCAGGCAACG
TGGCGTGGTGTGCACTGTGTTTGCTGACGCAACCCCCACTGGTTGGGGCATTGCCACCACCTGTCAGCTCCTTTCCGGGA
CTTTCGCTTTCCCCCTCCCTATTGCCACGGCGGAACTCATCGCCGCCTGCCTTGCCCGCTGCTGGACAGGGGCTCGGCTG
TTGGGCACTGACAATTCCGTGGTGTTGTCGGGGAAGCTGACGTCCTTTCCATGGCTGCTCGCCTGTGTTGCCACCTGGAT
TCTGCGCGGGACGTCCTTCTGCTACGTCCCTTCGGCCCTCAATCCAGCGGACCTTCCTTCCCGCGGCCTGCTGCCGGCTC
TGCGGCCTCTTCCGCGTCTTCGCCTTCGCCCTCAGACGAGTCGGATCTCCCTTTGGGCGCCTCCCCGCCTGTCCGGTAG
CTTGCCAGCCTCGACTGTGCCTTCTAGTTGCCAGCCGTCTGTTGTTTGCCCCTCCCCCGTGCCTTCTTGACCCTGGAAG
GTGCCACTCCCACTGTCCTTTCCTAATAAAATGAGGAAATTGCATCGCATTGTCTGAGTAGGTGTCATTCTATTCTGGGG
GGTGGGGTGGGGCAGGACAGCAAGGGGGAGGATTGGGAAGACAATAGCAGGCATGCAAGCTTGGCGTAATCATGGTCATA
GCTGTTTCCTGTGTGAAATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGGAAACCTGTCGTGCCAG
CTGCATTAATGAATCGGCCAACGCGCGGGGAGAGGCGGTTTGCGTATTGGGCGCTCTTCCGCTTCCTCGCTCACTGACTC
GCTGCGCTCGGTCGTTCGGCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGAACAGTATTTGGTATCTGCGCTCTGCTGAAGCCAGTTACCTTC
GGAAAAAGAGTTGGTAGCTCTTGATCCGGCAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGGCTTACCATCTGGCCCCAGTG
CTGCAATGATACCGCGAGACCCACGCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAGCTAGAGTAAGTAGTTCGCCAGT
```

-continued

TAATAGTTTGCGCAACGTTGTTGCCATTGCTACAGGCATCGTGGTGTCACGCTCGTCGTTTGGTATGGCTTCATTCAGCT
CCGGTTCCCAACGATCAAGGCGAGTTACATGATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTATGCGGCGACCGAGTTGCTCTT
GCCCGGCGTCAATACGGGATAATACCGCGCCACATAGCAGAACTTTAAAAGTGCTCATCATTGGAAAACGTTCTTCGGGG
CAAAACTCTCAAGGATCTTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAATGCCGCAAAAAAGGGAATAAGGGCGACACGGAA
ATGTTGAATACTCATACTCTTCCTTTTTCAATATTATTGAAGCATTTATCAGGGTTATTGTCTCATGAGCGGATACATAT
TTGAATGTATTTAGAAAAATAAACAAATAGGGGTTCCGCGCACATTTCCCCGAAAAGTGCCACCTGACGTCTAAGAAACC
ATTATTATCATGACATTAACCTATAAAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGATGCCGGGAGCAGACAAGCCCGTCAGG
GCGCGTCAGCGGGTGTTGGCGGGTGTCGGGGCTGGCTTAACTATGCGGCATCAGAGCAGATTGTACTGAGAGTGCACC

[SEQ ID NO: 40]
ATTGGCCATTGCATACGTTGTATCCATATCATAATATGTACATTTATATTGGCTCATGTCCAACATTACCGCCATGTTGA
CATTGATTATTGACTAGTTATTAATAGTAATCAATTACGGGGTCATTAGTTCATAGCCCATATATGGAGTTCCGCGTTAC
ATAACTTACGGTAAATGGCCCGCCTGGCTGACCGCCCAACGACCCCCGCCCATTGACGTCAATAATGACGTATGTTCCCA
TAGTAACGCCAATAGGGACTTTCCATTGACGTCAATGGGTGGAGTATTTACGGTAAACTGCCCACTTGGCAGTACATCAA
GTGTATCATATGCCAAGTACGCCCCCTATTGACGTCAATGACGGTAAATGGCCCGCCTGGCATTATGCCCAGTACATGAC
CTTATGGGACTTTCCTACTTGGCAGTACATCTACGTATTAGTCATCGCTATTACCATGGTGATGCGGTTTTGGCAGTACA
TCAATGGGCGTGGATAGCGGTTTGACTCACGGGGATTTCCAAGTCTCCACCCCATTGACGTCAATGGGAGTTTGTTTTGG
CACCAAAATCAACGGGACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGGGGTCTCTCTGGTTAGACCAGATCTGAGCCTGGGAGCTCTCTGG
CTAACTAGGGAACCCACTGCTTAAGCCTCAATAAAGCTTGCCTTGAGTGCTTCAAGTAGTGTGTGCCCGTCTGTTGTGTG
ACTCTGGTAACTAGAGATCCCTCAGACCCTTTTAGTCAGTGTGGAAAATCTCTAGCAGTGGCGCCCGAACAGGGACTTGA
AAGCGAAAGGGAAACCAGAGGAGCTCTCTCGACGCAGGACTCGGCTTGCTGAAGCGCGCACGGCAAGAGGCGAGGGGCGG
CGACTGGTGAGTACGCCAAAAATTTTGACTAGCGGAGGCTAGAAGGAGAGAGAGCGGGTGCGAGAGCGTCAGTATTAAGCG
GGGGTGAATAAGATCGCGATGGGAAAAAATTCGGTTAAGGCCAGGGGGAAAGAAAAAATATAAATTAAAACATATAGTAT
GGGCAAGCAGGGAGCTAGAACGATTCGCAGTTAATCCTGGCCTGTTAGAAACATCAGAAGGCTGTAGACAAATACTGGGA
CAGCTACAACCATCCCTTCAGACAGGATCAGAAGAACTTAGATCATTATATAATACAGTAGCAACCCTCTATTGTGTGCA
TCAAAGGATAGAGATAAAAGACACCAAGGAAGCTTTAGACAAGATAGAGGAAGAGCAAAACAAAAGTAAGACCACCGCAC
AGCAAGCGGCCGCTGATCTTCAGACCTGGAGGAGGAGATATGAGGGACAATTGGAGAAGTGAATTATATAAATATAAAGT
AGTAAAAATTGAACCATTAGGAGTAGCACCCACCAAGGCAAAGAGAAGAGTGGTGCAGAGAGAAAAAAGAGCAGTGGGAA
TAGGAGCTTTGTTCCTTGGGTTCTTGGGAGCAGCAGGAAGCACTATGGGCGCAGCGTCAATGACGCTGACGGTACAGGCC
AGACAATTATTGTCTGGTATAGTGCAGCAGCAGAACAATTTGCTGAGGGCTATTGAGGCGCAACAGCATCTGTTGCAACT
CACAGTCTGGGGCATCAAGCAGCTCCAGGCAAGAATCCTGGCTGTGGAAAGATACCTAAAGGATCAACAGCTCCTGGGGA
TTTGGGGTTGCTCTGGAAAACTCATTTGCACCACTGCTGTGCCTTGGAATGCTAGTTGGAGTAATAAATCTCTGGAACAG
ATTTGGAATCACACGACCTGGATGGAGTGGGACAGAGAAATTAACAATTACACAAGCTTAATACACTCCTTAATTGAAGA
ATCGCAAAACCAGCAAGAAAAGAATGAACAAGAATTATTGGAATTAGATAAATGGGCAAGTTTGTGGAATTGGTTTAACA
TAACAAATTGGCTGTGGTATATAAAATTATTCATAATGATAGTAGGAGGCTTGGTAGGTTTAAGAATAGTTTTTGCTGTA
CTTTCTATAGTGAATAGAGTTAGGCAGGGATATTCACCATTATCGTTTCAGACCCACCTCCCAACCCCGAGGGGACCCGA
CAGGCCCGAAGGAATAGAAGAAGAAGGTGGAGAGAGAGACAGAGACAGATCCATTCGATTAGTGAACGGATCTCGACGGT
ATCGTTTTAAAAGAAAAGGGGGGATTGGGGGGTACAGTGCAGGGGAAAGAATAGTAGACATAATAGCAACAGACATACAA
ACTAAAGAATTACAAAAACAAATTACAAAAATTCAAAATTTTATCGGCGTGTTGGGGGTGGACCATCCTCTAGGATTGA
ATAAGAAAATGAAGTTAAGGTGGTTGATGGTAACACTATGCTAATAACTGCAGAGCCAGAAGCACCATAAGGGACATGA
TAAGGGAGCCAGCAGACCTCTGATCTCTTCCTGAATGCTAATCTTAAACATCCTGAGGAAGAATGGGACTTCCATTTGGG
GTGGGCCTATGATAGGGTAATAAGACAGTAGTGAATATCAAGCTACAAAAAGCCCCCTTTCAAATTCTTCTCAGTCCTAA
CTTTTCATACTAAGCCCAGTCCTTCCAAAGCAGACTGTGAAAGAGTGATAGTTCCGGGAGACTAGCACTGCAGATTCCGG
GTCACTGTGAGTGGGGGAGGCAGGGAAGAAGGGCTCACAGGACAGTCAAACCATGCCCCCTGTTTTTCCTTCTTCAAGTA
GACCTCTATAAGACAACAGAGACAACTAAGGCTGAGTGGCCAGGCGAGGAGAAACCATCTCGCCGTAAAACATGGAAGGA
ACACTTCAGGGGAAAGGTGGTATCTCTAAGCAAGAGAACTGAGTGGAGTCAAGGCTGAGAGATGCAGGATAAGCAAATGG
GTAGTGAAAAGACATTCATGAGGACAGCTAAAACAATAAGTAATGTAAAATACAGCATAGCAAAACTTTAACCTCCAAAT
CAAGCCTCTACTTGAATCCTTTTCTGAGGGATGAATAAGGCATAGGCATCAGGGGCTGTTGCCAATGTGCATTAGCTGTT
TGCAGCCTCACCTTCTTTCATGGAGTTTAAGATATAGTGTATTTTCCCAAGGTTTGAACTAGCTCTTCATTTCTTTATGT
TTTAAATGCACTGACCTCCCACATTCCCTTTTTAGTAAAATATTCAGAAATAATTTAAATACATCATTGCAATGAAAATA
AATGTTTTTTATTAGGCAGAATCCAGATGCTCAAGGCCCTTCATAATATCCCCCAGTTTAGTAGTTGGACTTAGGGAACA
AAGGAACCTTTAATAGAAATTGGACAGCAAGAAAGCGAGCTTAGTGATACTTGTGGGCAGGGCATTAGCCACACCAGCC
ACCACTTTCTGATAGGCAGCCTGCACTGGTGGGGTGAATTCTTTGCCAAAGTGATGGGCCAGCACACAGACCAGCACGTT
GCCCAGGAGCTGTGGGAGGAAGATAAGAGGTATGAACATGATTAGCAAAAGGGCCTAGCTTGGACTCAGAATAATCCAGC
CTTATCCCAACCATAAAATAAAAGCAGAATGGTAGCTGGATTGTAGCTGCTATTAGCAATATGAAACCTCTTACATCAGT
TACAATTTATATGCAGAAATATTTATATGCAGAAATATTGCTATTGCCTTAACCCAGAAATTATCACTGTTATTCTTTAG
AATGGTGCAAAGAGGCATGATACATTGTATCATTATTGCCCTGAAAGAAAGAGATTAGGGAAAGTATTAGAAATAAGATA
AACAAAAAGTATATTAAAAGAAGAAAGCATTTTTTAAAATTACAAATGCAAAATTACCCTGATTTGGTCAATATGTGTA
CCCTGTTACTTCTCCCCTTCCTATGACATGAACTTAACCATAGAAAAAGAAGGGAAAGAAAACATCAAGGGTCCCATAGA
CTCACCCTGAAGTTCTCAGGATCCACGTGCAGCTTGTCACAGTGCAGCTCACTCAGCTGGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAGAAGGTCAGCCAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCCTAGGGTGTGGCTCCACAGGGTGAGGTCTAAGTGATGACAGCCGTACCTGTCCTTGGC
TCTTCTGGCACTGGCTTAGGAGTTGGACTTCAAACCCTCAGCCCTCCCTCTAAGATATATCTCTTGGCCCCATACCATCA
GTACAAATTGCTACTAAAAACATCCTCCTTTGCAAGTGTATTTACGGCATCTGTGAAGGAAAGAAACATCTCCTCTAAAC
CACTATGCTGCTAGAGCCTCTTTTCTGTACTCAAGCCTCATTCAGACACTAGTGTCACCAGTCTCCTCATATACCTATTG
TATTTTCTTCTTCTTGCTGGTTTAGTCATGTTTTCTGGGAGCTTAGGGCCTTATTTTATTTGTTTTGTTTTCTTAATCAA
CAGAGATGGGCAAACCCATTATTTTTTTCTTTAGACTTGGGATGGTGATAGCTGGGCAGCGTCAGAAACTGTGTGTGGAT
ATAGATAAGAGCTCGGACTATGCTGAGCTGTGATGAGGGAGGGACCTAGCCAAAGGCAGTGAGAGTCAGAATGCTCCTGC
TATTGCCTTCTCAGTCCCCACGCTTGGTTTCTACACAAGTAGATACATAGAAAAGGCTATAGGTTAGTGTTTGAGAGTCC
TGCATGAGTTAGTTGCTCAGAAATGCCCGATAAATATGTTATGTGTGTTTATGTATATATATGTTTTATATATATATG
TGTGTGTGTGTGTGTGTGTGTGTTGTGTTTACAAATATGTGATTATCATCAAAACGTGAGGGCTAAAGTGACCAGATAAC

-continued

```
TTGCAGGTCTAGACACCCTTTTCCGGCACGCAGATAGTCAATATCTTCAGCGTCCCCAAGGCCTGCAAGGGTGGGGCCCC
ATATCTGGAAGTCCCAGGCGGAGCTGGGAGTTGGTCAAGTCTGGGCTGTGGGGGCAGGGAGTGCTGGGGGATGGCTCGAG
AAGCTTTCATCAAAAAAAGTCTAACCAGCTGCATTCGACTTTGACTGCAGCAGCTGGTTAGAAGGTTCTACTGGAGGAGG
GTCCCAGCCCATTGCTAAATTAACATCAGGCTCTGAGACTGGCAGTATATCTCTAACAGTGGTTGATGCTATCTTCTGGA
ACTTGCCTGCTACATTGAGACCACTGACCCATACATAGGAAGCCCATAGCTCTGTCCTGAACTGTTAGGCCACTGGTCCA
GAGAGTGTGCATCTCCTTTGATCCTCATAATAACCCTATGAGATAGACACAATTATTACTCTTACTTTATAGATGATGAT
CCTGAAAACATAGGAGTCAAGGCACTTGCCCCTAGCTGGGGGTATAGGGGAGCAGTCCCATGTAGTAGTAGAATGAAAAA
TGCTGCTATGCTGTGCCTCCCCCACCTTTCCCATGTCTGCCCTCTACTCATGGTCTATCTCTCCTGGCTCCTGGGAGTCA
TGGACTCCACCCAGCACCACCAACCTGACCTAACCACCTATCTGAGCCTGCCAGCCTATAACCCATCTGGGCCCTGATAG
CTGGTGGCCAGCCCTGACCCCACCCCACCCTCCCTGGAACCTCTGATAGACACATCTGGCACACCAGCTCGCAAAGTCAC
CGTGAGGGTCTTGTGTTTGCTGAGTCAAAATTCCTTGAAATCCAAGTCCTTAGAGACTCCTGCTCCCAAATTTACAGTCA
TAGACTTCTTCATGGCTGTCTCCTTTATCCACAGAATGATTCCTTTGCTTCATTGCCCCATCCATCTGATCCTCCTCATC
AGTGCAGCACAGGGCCCATGAGCAGTAGCTGCAGAGTCTCACATAGGTCTGGCACTGCCTCTGACATGTCCGACCTTAGG
CAAATGCTTGACTCTTCTGAGCTCAGTCTTGTCATGGCAAAACAAAGATAATAATAGTGTTTTTTTATGGAGTTAGCGTG
AGGATGGAAAACAATAGCAAAATTGATTAGACTATAAAAGGTCTCAACAAATAGTAGTAGATTTTATCATCCATTAATCC
TTCCCTCTCCTCTCTTACTCATCCCATCACGTATGCCTCTTAATTTTCCCTTACCTATAATAAGAGTTATTCCTCTTATT
ATATTCTTCTTATAGTGATTCTGGATATCAAAGTGGGAATGAGGGGCAGGCCACTAACGAAGAAGATGTTTCTCAAAGAA
GCCATTCTCCCCACATAGATCATCTCAGCAGGGTTCAGGAAGATAAAGGAGGATCAAGGTCGAAGGTAGGAACTAAGGAA
GAACACTGGGCAAGTGGATCCTAAATATATCATTTAAATGCATAAATAAGCAAACCCTGCTCGGGAATGGGAGGGAGAGT
CTCTGGAGTCCACCCCTTCTCGGCCCTGGCTCTGCAGATAGTGCTATCAAAGCCCTGACAGAGCCCTGCCCATTGCTGGG
CCTTGGAGTGAGTCAGCCTAGTAGAGAGGCAGGGCAAGCCATCTCATAGCTGCTGAGTGGGAGAGAGAAAAGGGCTCATT
GTCTATAAACTCAGGTCATGGCTATTCTTATTCTCACACTAAGAAAAAGAATGAGATGTCTACATATACCCTGCGTCCCC
TCTTGTGTACTGGGGCCCCCAAGAGCTCTCTAAAAGTGATGGCAAAGTCATTGCGCTAGATGCCATCCCATCTATTATAA
ACCTGCATTTGTCTCCACACACCAGTCATGGACAATAACCCTCCTCCCAGGTCCACGTGCTTGTCTTTGTATAATACTCA
AGTAATTTCGGAAAATGTATTCTTTCAATCTTGTTCTGTTATTCCTGTTTCAATGGCTTAGTAGAAAAAGTACATACTTG
TTTTCCCATAAATTGACAATAGACAATTTCACATCAATGTCTATATGGGTCGTTGTGTTTGCTGTGTTTGCAAAAACTCA
CAATAACTTTATATTGTTACTACTCTAAGAAAGTTACAACATGGTGAATACAAGAGAAAGCTATTACAAGTCCAGAAAAC
AAAAGTTATCATCTTGAGGCCTCAGCTTTCTAGGAATAATATCAATATTACAAAACGCGTCGACGGTACCGTTAACGATC
TTAGCCACTTTTTAAAAGAAAAGGGGGGACTGGAAGGGCTAATTCACTCCCAACGAAGACAAGATATCCTGCTAGTCCTT
CCTTTCTAAATGACGAGAGAGACAGAAGAATTCTTCAAGGTTAGTGTGTCCACGGTCAACCTTTCCTTCCTGGATGAGC
ATCCCTGGAGTAGGAGAGCCAGCCTGCCTCCTGCGCTGGCACAGAGCCCGGTTCCCTAGACAACTGCCTCTCCAAATCTG
ATGTCCAGCGCCACCTGGTGTCCACATCAAGCAGACACAATTAATAGTCAACCTGTTCAGGAAAACTGTGAGGGGGAAAA
AAAAGAAAGAGGATTTATGAAGGGAAAAGAAAGTTTAGAGGATATGCCACGATTGGCTAGCAGCTGCTTTTTGCCTGTAC
TGGGTCTCTCTGGTTAGACCAGATCTGAGCCTGGGAGCTCTCTGGCTAACTAGGGAACCCACTGCTTAAGCCTCAATAAA
GCTTGCCTTGAGTGCTTCATCCGGAATCAACCTCTGGATTACAAAATTTGTGAAAGATTGACTGGTATTCTTAACTATGT
TGCTCCTTTTACGCTATGTGGATACGCTGCTTTAATGCCTTTGTATCATGCTATTGCTTCCCGTATGGCTTTCATTTTCT
CCTCCTTGTATAAATCCTGGTTGCTGTCTCTTTATGAGGAGTTGTGGCCCGTTGTCAGGCAACGTGGCGTGGTGTGCACT
GTGTTTGCTGACGCAACCCCCACTGGTTGGGGCATTGCCACCACCTGTCAGCTCCTTTCCGGGACTTTCGCTTTCCCCCT
CCCTATTGCCACGGCGGAACTCATCGCCGCCGCCTGCCTTGCCCGCTGCTGGACAGGGGCTCGGCTGTTGGGCACTGACAATT
CCGTGGTGTTGTCGGGGAAGCTGACGTCCTTTCCATGGCTGCTCGCCTGTGTTGCCACCTGGATTCTGCGCGGGACGTCC
TTCTGCTACGTCCCTTCGGCCCTCAATCCAGCGGACCTTCCTTCCCGCGGCCTGCTGCCGGCTCTGCGGCCTCTTCCGCG
TCTTCGCCTTCGCCCTCAGACGAGTCGGATCTCCCTTTGGGCCGCCTCCCCGCCTGTCCGGTAGCTTGCCAGCCTCGACT
GTGCCTTCTAGTTGCCAGCCGTCTGTTGTTTGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGCAAGCTTGGCGTAATCATGGTCATAGCTGTTTCCTGTGTGA
AATTGTTATCCGCTCACAATTCCACACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTCGTGCCAGCTGCATTAATGAATCG
GCCAACGCGCGGGGAGAGGCGGTTTGCGTATTGGGCGCTCTTCCGCTTCCTCGCTCACTGACTCGCTGCGCTCGGTCGTT
CGGCTGCGGCGAGCGGTATCAGCTCACTCAAAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTCCAAGCTGGGCTGTGTGCACG
AACCCCCCGTTCAGCCCGACCGCTGCGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAGATTACGCGCAGAAAAAA
GGATCTCAAGAAGATCCTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCAATCTAAAGTATATATG
AGTAAACTTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCAGTTAATAGTTTGCGCAAC
GTTGTTGCCATTGCTACAGGCATCGTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCGTAAGATGCTTTTCT
GTGACTGGTGAGTACTCAACCAAGTCATTCTGAGAATAGTGTATGCGGCGACCGAGTTGCTCTTGCCCGGCGTCAATACG
GGATAATACCGCGCCACATAGCAGAACTTTAAAAGTGCTCATCATTGGAAAACGTTCTTCGGGGCGAAAACTCTCAAGGAT
CTTACCGCTGTTGAGATCCAGTTCGATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGGCGACACGGAAATGTTGAATACTCATA
CTCTTCCTTTTTCAATATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAGAAACCATTATTATCATGACAT
TAACCTATAAAAATAGGCGTATCACGAGGCCCTTTCGTCTCGCGCGTTTCGGTGATGACGGTGAAAACCTCTGACACATG
CAGCTCCCGGAGACGGTCACAGCTTGTCTGTAAGCGGATGCCGGGAGCAGACAAGCCCGTCAGGGCGCGTCAGCGGGTGT
TGGCGGGTGTCGGGGCTGGCTTAACTATGCGGCATCAGAGCAGATTGTACTGAGAGTGCACC
```

[SEQ ID NO: 76]

```
attggccattgcatacgttgtatccatatcataatatgtacatttatattggctcatgtccaacattaccgccatgttga
cattgattattgactagttattaatagtaatcaattacggggtcattagttcatagcccatatatggagttccgcgttac
ataacttacggtaaatggcccgcctggctgaccgcccaacgacccccgcccattgacgtcaataatgacgtatgttccca
tagtaacgccaatagggactttccattgacgtcaatgggtggagtatttacggtaaactgcccacttggcagtacatcaa
```

-continued

```
gtgtatcatatgccaagtacgccccctattgacgtcaatgacggtaaatggcccgcctggcattatgcccagtacatgac
cttatgggactttcctacttggcagtacatctacgtattagtcatcgctattaccatggtgatgcggttttggcagtaca
tcaatgggcgtggatagcggtttgactcacggggatttccaagtctccacccccattgacgtcaatgggagtttgtttggg
caccaaaatcaacgggactttccaaaatgtcgtaacaactccgccccattgacgcaaatgggcggtaggcgtgtacggtg
ggaggtctatataagcagagctcgtttagtgaaccggggtctctctggttagaccagatctgagcctgggagctctctgg
ctaactagggaacccactgcttaagcctcaataaaagcttgccttgagtgcttcaagtagtgtgtgcccgtctgttgtgtg
actctggtaactagagatccctcagacccttttagtcagtgtggaaaatctctagcagtggcgcccgaacagggacttga
aagcgaaagggaaaccagaggagctctctcgacgcaggactcggcttgctgaagcgcgcacggcaagaggcgaggggcgg
cgactggtgagtacgccaaaaattttgactagcggaggctagaaggagagagacgggtgcgagagcgtcagtattaagcg
ggggtgaataagatcgcgatggggaaaaattcggttaaggccaggggaagaaaaaatataaattaaaacatatagtat
gggcaagcagggagctagaacgattcgcagttaatcctggcctgttagaaacatcagaaggctgtagacaaatactggga
cagctacaaccatccctcagacaggatcagaagaacttagatcattatataatacagtagcaaccctctattgtgtgca
tcaaaggatagagataaaagacaccaaggaagctttagacaagatagaggaagagcaaaacaaaagtaagaccaccgcac
agcaagcggccgctgatcttcagacctggaggaggagatatgagggacaattggagaagtgaattatataaatatataaagt
agtaaaaattgaaccattaggagtagcacccaccaaggcaaagagaagagtggtgcagagagaaaaaagagcagtgggaa
taggagctttgttccttgggttcttgggagcagcaggaagcactatgggcgcagcgtcaatgacgctgacggtacaggcc
agacaattattgtctggtatagtgcagcagcagaacaattgctgagggctattgaggcgcaacagcatctgttgcaact
cacagtctggggcatcaagcagctccaggcaagaatcctgggctggtgggaaagatcctaaaggatcaacagctcctggga
tttggggttgctctggaaaactcatttgcaccactgctgtgccttggaatgctagttggagtaataaatctctggaacag
atttggaatcacacgacctggatggagtgggacagagaaattaacaattacacaagcttaatacactccttaattgaaga
atcgcaaaaccagcaagaaaagaatgaacaagaattattggaattagataaatgggcaagtttgtggaattggtttaaca
taacaaattggctgtggtatataaaattattcataatgatagtaggaggcttggtaggtttaagaatagtttttgctgta
ctttctatagtgaatagagttaggcagggatattcaccattatcgtttcagacccacctcccaaccccgaggggacccga
caggcccgaaggaatagaagaagaaggtggagagagagacagagacagatccattcgattagtgaacggatctcgacggt
atcgtttttaaaagaaaaggggggattggggggtacagtgcaggggaaagaatagtagacataatagcaacagacatacaa
actaaagaattacaaaaacaaattcaaaattttatcggcgtgttgggggtggaccatcctctaggattga
ataagaaaatgaagttaaggtggttgatggtaacactatgctaataactgcagagccagaagcaccataaggacatga
taagggagccagcagacctctgatctcttcctgaatgctaatcttaaacatcctgaggaagaatgggacttccatttggg
gtgggcctatgatagggtaataagacagtagtgaatatcaagctacaaaaagccccctttcaaattcttctcagtcctaa
cttttcatactaagcccagtccttccaaagcagactgtgaaagagtgatagttccgggagactagcactgcagattccgg
gtcactgtgagtgggggaggcaggggaagaagggctcacaggacagtcaaaccatgcccccctgttttccttcttcaagta
gacctctataagacaacagagacaactaaggctgagtggccaggcgaggagaaaccatctcgccgtaaaacatggaagga
acacttcaggggaaaggtggtatctctaagcaagagaactgagtggagtcaaggctgagagatgcaggataagcaaatgg
gtagtgaaaagacattcatgaggacagctaaaacaataagtaatgtaaaatacagcatagcaaaactttaacctccaaat
caagcctctacttgaatcctttctgagggatgaataaggcataggcatcaggccttgtgccaatgtgcattagctgtt
tgcagcctcaccttctttcatggagtttaagatatagtgtattttcccaaggtttgaactagctcttcatttctttatgt
tttaaatgcactgacctcccacattcccttttttagtaaaatattcagaaataatttaaatacatcattgcaatgaaaata
aatgttttttattaggcagaatccagatgctcaaggcccttcataatatcccccagtttagtagttggacttagggaaca
aaggaacctttaatagaaattggacagcaagaaagcgagcttagtgatacttgtgggcattagccacaccagcc
accactttctgataggcagcctgcactggtggggtgAATTCTTTGCCAAAGTGATGGGCCAGCACACAGACCAGCACGTT
GCCCAGGAGCTGTGGGAGGAAGATAAGAGGTATGAACATGATTAGCAAAAGGGCCTAGCTTGGACTCAGAATAATCCAGC
CTTATCCCAACCATAAAATAAAAGCAGAATGGTAGCTGGATTGTAGCTGCTATTAGCAATATGAAACCTCTTACATCAGT
TACAATTTATATGCAGAAATATTTATATGCAGAAATATTGCTATTGCCTATTGCTATTTCAACCCAGAAATATTCACTGTTATTCTTTAG
AATGGTGCAAAGAGGCATGATACATTGTATCATTATTGCCCTGAAAGAAAGAGATTAGGGAAAGTATTAGAAATAAGATA
AACAAAAAAGTATATTAAAAGAAGAAAGCATTTTTTAAAATTACAAATGCAAAATTACCCTGATTTGGTCAATATGTGTA
CCCTGTTACTTCTCCCCTTCCTATGACATGAACTTAACCATAGAAAAGAAGGGGAAAGAAAACATCAAGGGTCCCATAGA
CTCACCCTGAAGTTCTCAGGATCCACGTGCAGCTTGTCACAGTGCAGCTCACTCAGctgGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCctagggtgtggctccacagggtgaggtctaagtgatgacagccgtacctgtccttggc
tcttctggcactggcttaggagttggacttcaaaccctcagccctccctctaagatatatctcttggcccccataccatca
gtacaaattgctactaaaaacatcctcctttgcaagtgtatttacCACCCTTTTCCGGCACGCAGATAGTCAATATCTTC
AGCGTCCCCAAGGCCTGCAAGGGTGGGGCCCCATATCTGGAAGTCCCAGGCGGAGCTGGGAGTTGGTCAAGTCTGGGCTG
TGGGGGCAGGGAGTGCTGGGGGATGGacgcgtcgacggtaccgttaacgatcttagccacttttttaaaagaaaaggggg
actggaagggctaattcactcccaacgaagacaagatatcctgCTAGTCCTTCCTTTCTAAATGACGAGAGGAGACAGAAG
AATTCTTCAAGGTTAGTGTGTCCAGCATGCAACCTTTCCTTCCTGGATGAGCATCCCTGGAGTAGGAGAGCCAGCCTGCC
TCCTGCGCTGGCACAGAGCCCGGTTCCCTAGACAACTGCCTCTCCAAATCTGATGTCCAGCGCCACCTGGTGTCCACATC
AAGCAGACACAATTAATAGTCAACCTGTTCAGGAAAACTGTGAGGGGGAAAAAAAAGAAAGAGGATTTATGAAGGGAAAA
GAAAGTTTAGAGGATATGCCACGATTGGctagcagctgcttttttgcctgtactgggtctctctggttagaccagatctga
gcctgggagctctctggctaactagggaacccactgcttaagcctcaataaaagcttgccttgagtgcttcatccggAATC
AACCTCTGGATTACAAAATTTGTGAAAGATTGACTGGTATTCTTAACTATGTTGCTCCTTTTACGCTATGTGGATACGCT
GCTTTAATGCCTTTGTATCATGCTATTGCTTCCCGTATGGCTTTCATTTTCTCCTCCTTGTATAAATCCTGGTTGCTGTC
TCTTTATGAGGAGTTGTGGCCCGTTGTCAGGCAACGTGGCGTGGTGTGCACTGTGTTTGCTGACGCAACCCCCACTGGTT
GGGGCATTGCCACCACCTGTCAGCTCCTTTCCGGGACTTTCGCTTTCCCCCTCCCTATTGCCACGGCGGAACTCATCGCC
GCCTGCCTTGCCCGCTGCTGGACAGGGGCTCGGCTGTTGGGCACTGACAATTCCGTGGTGTTGTCGGGGAAGCTGACGTC
CTTTCCATGGCTGCTCGCCTGTGTTGCCACCTGGATTCTGCGCGGGACGTCCTTCTGCTACGTCCCTTCGGCCCTCAATC
CAGCGGACCTTCCTTCCCGCGGCCTGCTGCCGGCTCTGCGGCCTCTTCCGCGTCTTCGCCTTCGCCCTCAGACGAGTCGG
ATCTCCCTTTGGGCCGCCTCCCCGCCTGtccggtAGCTTGCCAGCCTCGACTGTGCCTTCTAGTTGCCAGCCGTCTGTTG
TTTGCCCCTCCCCCGTGCCTTCCTTGACCCTGGAAGGTGCCACTCCCACTGTCCTTTCCTAATAAAATGAGGAAATTGCA
TCGCATTGTCTGAGTAGGTGTCATTCTATTCTGGGGGGTGGGGTGGGGCAGGACAGCAAGGGGGAGGATTGGGAAGACAA
TAGCAGGCATGCaagcttggcgtaatcatggtcatagctgtttcctgtgtgaaattgttatccgctcacaattccacaca
acatacgagccggaagcataaagtgtaaagcctggggtgcctaatgagtgagctaactcacattaattgcgttgcgctca
ctgcccgctttccagtcgggaaacctgtcgtgccagctgcattaatgaatcggccaacgcgcggggagaggcggtttgcg
tattgggcgctcttccgcttcctcgctcactgactcgctgcgctcggtcgttcggctgcggcgagcggtatcagctcact
caaaggcggtaatacggttatccacagaatcaggggataacgcaggaaagaacatgtgagcaaaaggccagcaaaaggcc
aggaaccgtaaaaaggccgcgttgctggcgtttttccataggctccgcccccctgacgagcatcacaaaaatcgacgctc
aagtcagaggtggcgaaacccgacaggactataaagataccaggcgtttccccctggaagctccctcgtgcgctctcctg
```

-continued

```
ttccgaccctgccgcttaccggatacctgtccgcctttctcccttcgggaagcgtggcgctttctcatagctcacgctgt
aggtatctcagttcggtgtaggtcgttcgctccaagctgggctgtgtgcacgaaccccccgttcagcccgaccgctgcgc
cttatccggtaactatcgtcttgagtccaacccggtaagacacgacttatcgccactggcagcagccactggtaacagga
ttagcagagcgaggtatgtaggcggtgctacagagttcttgaagtggtggcctaactacggctacactagaagaacagta
tttggtatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgatcttttt
ctacggggtctgacgctcagtggaacgaaaactcacgttaagggattttggtcatgagattatcaaaaaggatcttcacc
tagatccttttaaattaaaaatgaagttttaaatcaatctaaagtatatatgagtaaacttggtctgacagttaccaatg
cttaatcagtgaggcacctatctcagcgatctgtctatttcgttcatccatagttgcctgactccccgtcgtgtagataa
ctacgatacgggagggcttaccatctggccccagtgctgcaatgataccgcgagacccacgctcaccggctccagattta
tcagcaataaaccagccagccggaagggccgagcgcagaagtggtcctgcaactttatccgcctccatccagtctattaa
ttgttgccgggaagctagagtaagtagttcgccagttaatagtttgcgcaacgttgttgccattgctacaggcatcgtgg
tgtcacgctcgtcgtttggtatggcttcattcagctccggttcccaacgatcaaggcgagttacatgatcccccatgttg
tgcaaaaaagcggttagctccttcggtcctccgatcgttgtcagaagtaagttggccgcagtgttatcactcatggttat
ggcagcactgcataattctcttactgtcatgccatccgtaagatgcttttctgtgactggtgagtactcaaccaagtcat
tctgagaatagtgtatgcggcgaccgagttgctcttgcccggcgtcaatacgggataataccgcgccacatagcagaact
ttaaaagtgctcatcattggaaaacgttcttcggggcaaaactctcaaggatcttaccgctgttgagatccagttcgatg
taacccactcgtgcacccaactgatcttcagcatcttttactttcaccagcgtttctgggtgagcaaaaacaggaaggca
aaatgccgcaaaaaagggaataagggcgacacggaaatgttgaatactcatactcttcctttttcaatattattgaagca
tttatcaggggttattgtctcatgagcggatacatatttgaatgtatttagaaaaataaacaaatagggggttccgcgcaca
tttccccgaaaagtgccacctgacgtctaagaaaccattattatcatgacattaacctataaaaataggcgtatcacgag
gccctttcgtctcgcgcgtttcggtgatgacggtgaaaacctctgacacatgcagctcccggagacggtcacagcttgtc
tgtaagcggatgccgggagcagacaagcccgtcagggcgcgtcagcgggtgttggcgggtgtcggggctggcttaactat
gcggcatcagagcagattgtactgagagtgcacc
```

[SEQ ID NO: 77]

```
attggccattgcatacgttgtatccatatcataatatgtacatttatattggctcatgtccaacattaccgccatgttga
cattgattattgactagttattaatagtaatcaattacggggtcattagttcatagcccatatatggagttccgcgttac
ataacttacggtaaatggcccgcctggctgaccgcccaacgacccccgcccattgacgtcaataatgacgtatgttccca
tagtaacgccaatagggactttccattgacgtcaatgggtggagtatttacggtaaactgcccacttggcagtacatcaa
gtgtatcatatgccaagtacgccccctattgacgtcaatgacggtaaatggcccgcctggcattatgcccagtacatgac
cttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttgg
caccaaaatcaacgggactttccaaaatgtcgtaacaactccgccccattgacgcaaatgggcggtaggcgtgtacggtg
ggaggtctatataagcagagctcgtttagtgaaccgggggtctctctggttagaccagatctgagcctgggagctctctg
gctaactagggaacccactgcttaagcctcaataaaagcttgccttgagtgcttcaagtagtgtgtgcccgtctgttgtg
actctggtaactagagatccctcagacccttttagtcagtgtggaaaatctctagcagtggcgcccgaacagggacttga
aagcgaaagggaaaccagaggagctctctcgacgcaggactcggcttgctgaagcgcgcacggcaagaggcgaggggcgg
cgactggtgagtacgccaaaaattttgactagcggaggctagaaggagagagatgggtgcgagagcgtcagtattaagcg
gggtgaataagatcgcgatgggaaaaaattcggttaaggccaggggaagaaaaaaatatataatttaaaacatatagtat
gggcaagcagggagctagaacgattcgcagttaatcctggcctgttagaaacatcagaaggctgtagacaaatactggga
cagctacaaccatcccttcagacaggatcagaagaacttagatcattatataatacagtagcaaccctctattgtgtgca
tcaaaggatagagataaaagacaccaaggaagctttagacaagatagaggaagagcaaaacaaaagtaagaccaccgcac
agcaagcggccgctgatcttcagaccggaggaggagatatgagggacaattggagaagtgaattatataaatataaagt
agtaaaaattgaaccattaggagtagcacccaccaaggcaaagagaagagtggtgcagagagaaaaaagagcagtgggaa
taggagctttgttccttgggttcttgggagcagcaggaagcactatgggcgcagcgtcaatgacgctgacggtacaggcc
agacaattattgtctggtatagtgcagcagcagaacaatttgctgagggctattgaggcgcaacagcatctgttgcaact
cacagtctggggcatcaagcagctccaggcaagaatcctggctgtggaaagatacctaaaggatcaacagctcctggggga
tttggggttgctctggaaaactcatttgcaccactgctgtgccttggaatgctagttggagtaataaatctctggaacag
atttggaatcacacgacctggatggagtgggacagagaaattaacaattacacaagcttaatacactccttaattgaaga
atcgcaaaaccagcaagaaaagaatgaacaagaattattggaattagataaatgggcaagtttgtggaattggtttaaca
taacaaattggctgtggtatataaaattattcataatgatagtaggaggcttggtaggtttaagaatagtttttgctgta
ctttctatagtgaatagagttaggcagggatattcaccattatcgtttcagacccacctcccaacccccgaggggacccga
caggcccgaaggaatagaagaagaaggtggagagagagacagagacagatccattcgattagtgaacggatctcgacggt
atcgttttaaagaaaggggggattggggggtacagtgcaggggaaagaatagtagacataataagcaacagacatacaa
actaaagaattacaaaaacaaattcaaaattttatcggggtgttggggggtaccatcctctaggtattga
ataagaaaaatgaagttaaggtggttgatggtaacactatgctaataactgcagatgccagaagcaccataagggacatga
taagggagccagcagacctctgatctcttcctgaatgctaatcttaaacatcctgaggaagaatgggacttccatttggg
gtgggcctatgataggtaataagacagtagtgaatatcaagtacaaaaagcccccttttcaaattcttctcagtcctaa
cttttcatactaagcccagtccttccaaagcagactgtgaaagagtgatagttccgggagactagcactcgagattccgg
gtcactgtgagtggggggaggcagggaagaagggctcacaggacagtcaaaccatgcccctgttttttcccttcttcaagta
gacctctataagacaacagagacaactaaggctgagtggccaggcgaggagaaaccatctcgccgtaaaacatggaagga
acacttcaggggaaaggtggtatctctaagcaagagaactgagtggagtcaaggctgagagatgcaggataagcaaatgg
gtagtgaaaagacattcatgaggacaggatcaaaacaataagtaatacagcatagcaaaactttaacctccaaat
caagcctctacttgaatccttttctgagggatgaataaaggcataggcatcaggggctgttgccaatgtgcattagctgtt
tgcagcctcaccttctttcatggagtttaagatatagtgtattttcccaaggtttgaactagctcttcatttctttatgt
tttaaatgcactgacctcccacattcccttttttagtaaaatattcagaaataattaaatacatcattgcaatgaaaata
aatgtttttattaggcagaatccagatgctcaaggccctccataatatcccccagtttagtagttggacttagggaaca
aaggaacctttaatagaaattggacagcaagaaagcgagcttagtgatacttgtgggccagggcattagccacaccagcc
accacttctgataggcagcctgcactggtggggtgAATTCTTTGCCAAAGTGATGGGCCAGCACACAGACCAGCACGTT
GCCCAGGAGCTGTGGGAGGAAGATAAGAGGGTATGAACATGATTAGCAAAAGGGCCTAGCTTGGACTCAGAATAATCCAGC
CTTATCCCAACCATAAAATAAAAGCAGAATGGTAGCTGGATTGTAGCTGCTATTAGCAATATGAAACCTCTTACATCAGT
TACAATTTATATGCAGAAATATTTATATGCAGAAATATTGCTATTGCCTTAACCCAGAAATTATCACTGTTATTCTTTAG
AATGGTGCAAAGAGGCATGATACATTGTATCATTATTGCCCTGAAAGAAAGAGATTAGGGAAAGTATTAGAAATAAGATA
AACAAAAAAGTATATTAAAAGAAGAAAGCATTTTTTAAAATTACAAATGCAAATTACCCTGATTTGGTCAATATGTGTA
CCCTGTTACTTCTCCCCTTCCTATGACATGAACTTAACCATAGAAAAAGAGGGGGAAGAAGGGAAACATCAAGGGTCCCATAGA
CTCACCCTGAAGTTCTCAGGATCCACGTGCAGCTTGTCACAGTGCAGCTCACTCAGctgGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
```

-continued

```
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCctagggtgtggctccacagggtgaggtctaagtgatgacagccgtacctgtccttggc
tcttctggcactggcttaggagttggacttcaaaccctcagccctccctctaagatatatctcttggccccataccatca
gtacaaattgctactaaaaacatcctcctttgcaagtgtatttacCACCCTTTTCCGGCACGCAGATAGTCAATATCTTC
AGCGTCCCCAAGGCCTGCAAGGGTGGGGCCCCATATCTGGAAGTCCCAGGCGGAGCTGGGAGTTGGTCAAGTCTGGGCTG
TGGGGGCAGGGAGTGCTGGGGGATGGacgcgtatctgcggccgcctatctgtaccactagtctcgagaagctttcatcaa
aaaaagtctaaccagctgcattcgactttgactgcagcagctggttagaaggttctactggaggagggtcccagcccatt
gctaaattaacatcaggctctgagactggcagtatatctctaacagtggttgatgctatcttctggaacttgcctgctac
attgagaccactgacccatacataggaagcccatagctctgtcctgaactgttaggccactggtccagagagtgtgcatc
tcctttgatcctcataataaccctatgagatagacacaattattactcttactttatagatgatgatcctgaaaacatag
gagtcaaggcacttgcccctagctgggggtataggggagcagtcccatgtagtagtagaatgaaaaatgctgctatgctg
tgcctcccccacctttcccatgtctgccctctactcatggtctatctctcctggctcctgggagtcatggactccaccca
gcaccaccaacctgacctaaccacctatctgagcctgccagcctataacccatctgggccctgatagctggtggccagcc
ctgaccccaccccacctccctggaacctctgatagacacatctggcacaccagctcgcaaagtcaccgtgagggtcttg
tgtttgctgagtcaaaattccttgaaatccaagtccttagagactcctgctcccaaatttacagtcatagacttcttcat
ggctgtctcctttatccacagaatgattcctttgcttcattgccccatccatctgatcctcctcatcagtgcagcacagg
gcccatgagcagtagctgcagagtctcacataggtctggcactgcctctgacatgtccgaccttaggcaaatgcttgact
cttctgagctcagtcttgtcatggcaaaacaaagataataatagtgtttttttatggagttagcgtgaggatggaaaaca
atagcaaaattgattagactataaaaggtctcaacaaatagtagtagatttatcatccattaatccttccctctcctct
cttactcatcccatcacgtatgcctcttaattttcccttacctataataagagttattcctcttattatattcttcttat
agtgattctggatatcaaagtgggaatgaggggcaggccactaacgaagaagatgtttctcaaagaagccattctcccca
catagatcatctcagcagggttcaggaagataaaggaggatcaagtcgaaggtaggaactaaggaagaacactgggcaa
gtgacgcgtcgacggtaccgttaacgatcttagccacttttttaaaagaaaagggggggactggaagggctaattcactccc
aacgaagacaagatatcctgCTAGTCCTTCCTTTCTAAATGACGAGAGAGACAGAAGAATTCTTCAAGGTTAGTGTGTCC
AGCATGCAACCTTTCCTTCCTGGATGAGCATCCCTGGAGTAGGAGAGCCAGCCTGCCTCCTGCGCTGGCACAGAGCCCGG
TTCCCTAGACAACTGCCTCTCCAAATCTGATGTCCAGCGCCACCTGGTGTCCACATCAAGCAGACACAATTAATAGTCAA
CCTGTTCAGGAAAACTGTGAGGGGGAAAAAAAAGAAAGAGGATTTATGAAGGGAAAGAAAGTTTAGAGGATATGCCACG
ATTGGctagcagctgcttttttgcctgtactgggtctctctggttagaccagatctgagcctgggagctctctggctaact
agggaacccactgcttaagcctcaataaagcttgccttgagtgcttcatccggAATCAACCTCTGGATTACAAAATTTGT
GAAAGATTGACTGGTATTCTTAACTATGTTGCTCCTTTTACGCTATGTGGATACGCTGCTTTAATGCCTTTGTATCATGC
TATTGCTTCCCGTATGGCTTTCATTTTCTCCTCCTTGTATAAATCCTGGTTGCTGTCTCTTTATGAGGAGTTGTGGCCCG
TTGTCAGGCAACGTGGCGTGGTGTGCACTGTGTTTGCTGACGCAACCCCCACTGGTTGGGGCATTGCCACCACCTGTCAG
CTCCTTTCCGGGACTTTCGCTTTCCCCCTCCCTATTGCCACGGCGGAACTCATCGCCGCCTGCCTTGCCCGCTGCTGGAC
AGGGGCTCGGCTGTTGGGCACTGACAATTCCGTGGTGTTGTCGGGGAAGCTGACGTCCTTTCCATGGCTGCTCGCCTGTG
TTGCCACCTGGATTCTGCGCGGGACGTCCTTCTGCTACGTCCCTTCGGCCCTCAATCCAGCGGACCTTCCTTCCCGCGGC
CTGCTGCCGGCTCTGCGGCCTCTTCCGCGTCTTCGCCTTCGCCCTCAGACGAGTCGGATCTCCCTTTGGGCGCTCTCCCC
GCCTGtccggtAGCTTGCCAGCCTCGACTGTGCCTTCTAGTTGCCAGCCGTCTGTTGTTTGCCCCTCCCCCGTGCCTTCC
TTGACCCTGGAAGGTGCCACTCCCACTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGACAATAGCAGGCATGcaagcttggcgt
aatcatggtcatagctgtttcctgtgtgaaattgttatccgctcacaattccacacaacatacgagccggaagcataaag
tgtaaagcctggggtgcctaatgagtgagctaactcacattaattgcgttgcgctcactgcccgctttccagtcgggaaa
cctgtcgtgccagctgcattaatgaatcggccaacgcgcggggagaggcggtttgcgtattgggcgctcttccgcttcct
cgctcactgactcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaaccgtaaaaaggccgcgtt
gctggcgtttttccataggctccgcccccctgacgagcatcacaaaaatcgacgctcaagtcagaggtggcgaaacccga
caggactataaagataccaggcgtttccccctggaagctccctcgtgcgctctcctgttccgaccctgccgcttaccgga
tacctgtccgcctttctcccttcgggaagcgtggcgctttctcatagctcacgctgtaggtatctcagttcggtgtaggt
cgttcgctccaagctgggctgtgtgcacgaaccccccgttcagcccgaccgctgcgccttatccggtaactatcgtcttg
agtccaacccggtaagacacgacttatcgccactggcagcagccactggtaacaggattagcagagcgaggtatgtaggc
ggtgctacagagttcttgaagtggtggcctaactacggctacactagaagaacagtatttggtatctgcgctctgctgaa
gccagttaccttcggaaaaagagttggtagctcttgatccggcaaacaaaccaccgctggtagcggtggtttttttgttt
gcaagcagcagattacgcgcagaaaaaaaggatctcaagaagatcctttgatcttttctacggggtctgacgctcagtgg
aacgaaaactcacgttaagggattttggtcatgagattatcaaaaaggatcttcacctagatccttttaaattaaaaatg
aagttttaaatcaatctaaagtatatatgagtaaacttggtctgacagttaccaatgcttaatcagtgaggcacctatct
cagcgatctgtctatttcgttcatccatagttgcctgactccccgtcgtgtagataactacgatacgggagggcttacca
tctggccccagtgctgcaatgataccgcgagacccacgctcaccggctccagatttatcagcaataaaccagccagccgg
aagggccgagcgcagaagtggtcctgcaactttatccgcctccatccagtctattaattgttgccgggaagctagagtaa
gtagttcgccagttaatagtttgcgcaacgttgttgccattgctacaggcatcgtggtgtcacgctcgtcgtttggtatg
gcttcattcagctccggttcccaacgatcaaggcgagttacatgatcccccatgttgtgcaaaaaagcggttagctcctt
cggtcctccgatcgttgtcagaagtaagttggccgcagtgttatcactcatggttatggcagcactgcataattctctta
ctgtcatgccatccgtaagatgcttttctgtgactggtgagtactcaaccaagtcattctgagaatagtgtatgcggcga
ccgagttgctcttgcccggcgtcaatacgggataataccgcgccacatagcagaactttaaaagtgctcatcattggaaa
acgttcttcggggcaaaactctcaaggatcttaccgctgttgagatccagttcgatgtaacccactcgtgcacccaactg
atcttcagcatcttttactttcaccagcgtttctgggtgagcaaaaacaggaaggcaaaatgccgcaaaaaagggaataa
gggcgacacggaaatgttgaatactcatactcttcctttttcaatattattgaagcatttatcagggttattgtctcatg
agcggatacatatttgaatgtatttagaaaaataaacaaataggggttccgcgcacatttccccgaaaagtgccacctga
cgtctaagaaaccattattatcatgacattaacctataaaaataggcgtatcacgaggccctttcgtctcgcgcgtttcg
gtgatgacggtgaaaacctctgacacatgcagctcccggagacggtcacagcttgtctgtaagcggatgccgggagcaga
caagcccgtcagggcgcgtcagcgggtgttggcgggtgtcggggctggcttaactatgcggcatcagagcagattgtact
gagagtgcacc
```

These vectors were produced by transient triple transfection of the recombinant vector, pCMVΔR8.9 and pMD.G into 293T cells. A total of $5\times10^6$ 293T cells were seeded in 10-cm-diameter dishes 24 h prior to transfection in DMEM with 10% fetal bovine serum, penicillin (100 IU/ml), and streptomycin (100 µg/ml) in a 5% $CO_2$ incubator. A total of 20 µg of plasmid DNA was used for the transfection of one 10 cm dish: 3.5 ug of the envelope plasmid pMD.G, 6.5 ug of packaging plasmid, and 10 µg of transfer vector plasmid. The medium (10 ml) was replaced after 14 to 16 h; the conditioned medium was collected after another 24 h, cleared by low-speed centrifugation, and filtered through 0.45-µm-pore-size cellulose acetate filters. The pseudotyped virions were than concentrated by ultracentrifugation and resuspended for frozen down in aliquots for subsequent titration and stem cell transduction.

Titration Assay

These vectors were produced by transient triple transfection of the recombinant vector, pCMVΔR8.9 and pMD.G into 293T cells. A total of $5\times10^6$ 293T cells were seeded in 10-cm-diameter dishes 24 h prior to transfection in DMEM with 10% fetal bovine serum, penicillin (100 IU/ml), and streptomycin (100 µg/ml) in a 5% $CO_2$ incubator. A total of 20 µg of plasmid DNA was used for the transfection of one 10 cm dish: 3.5 µg of the envelope plasmid pMD.G, 6.5 µg of packaging plasmid, and 10 µg of transfer vector plasmid. The medium (10 ml) was replaced after 14 to 16 h; the conditioned medium was collected after another 24 h, cleared by low-speed centrifugation, and filtered through 0.45-µm-pore-size cellulose acetate filters. The pseudotyped virions were than used directly for titration assays in Hela cells. Serial dilutions of un-concentrated virus were used to infect 205 cells in a six-well plate in the presence of Polybrene (8 µg/ml). each dilution was tested in triplicate. The cells were kept in culture for no less than 15 days, harvested and genomic DNA were extracted, quantified and used to Vector Copy Number (VCN) quantification. Transducing activity was expressed in transducing units (TU). VCN analysis was performed by TaqMan PCR analysis using:

```
Gag-specific probe
                           (SEQ ID NO: 41)
5'-acagccttctgatgtttctaacaggccagg-3'

Gag-primer-Forward:
                           (SEQ ID NO: 42)
5'-ggagctagaacgattcgcagtt-3'

Gag-primer-Reverse:
                           (SEQ ID NO: 43)
5'-gttgtagctgtcccagtatttgtc-3'

Human Albumin Probe
                           (SEQ ID NO: 44)
5'-tgctgaaacattcaccttccatgcagt-3'

Human Albumin Forward
                           (SEQ ID NO: 45)
5'tgaaacatacgttcccaaagagttt-3'

Human Albumin Reverse
                           (SEQ ID NO: 46)
5'ctctccttctcagaaagtgtgcatat -3'
```

Hematopoietic Stem Cell Transduction and Transplantation

Donor bone marrow was flushed from the femurs of 8- to 16-week-old male Hbb$^{th3/+}$ thalassemic mice that had been injected intravenously (i.v.) 6 days earlier with 5-flurouracil (5-FU, Pharmacia; 150 mg kg$^{-1}$ body weight). Bone marrow cells were resuspended in serum-free medium, and supplemented with rmSCF (100 ng ml$^{-1}$), rmTPO (100 ng ml$^{-1}$), β-mercaptoethanol (55 µM; Sigma), L-glutamine (2 mM), pen/strep (10 IU ml$^{-1}$), and cultured for 18 h. Bone marrow cells were pelleted and resuspended in serum-free medium containing concentrated lentiviral supernatant at a multiplicity of infection (MOI) of 25 and supplemented with polybrene (8 µg ml$^{-1}$), L-glutamine (2 mM), pen/strep (100 IU ml$^{-1}$) and incubated for 8 h. Transduced bone marrow cells ($5\times10^5$)) were then i.v. injected into each of the irradiated female recipients to establish bone marrow chimaeras. Recipient mice (11-to 14-week-old C57/Hbb$^{th3/+}$ mice) were irradiated with 10.5 Gy (split dose 2×5.25 Gy) on the day of transplantation.

Post-Transplant Vector Studies

Peripheral Blood was collected periodically starting 5-6 weeks after hematopoietic stem cell transplantation. Blood samples were obtained by retro-orbital puncture under ether anesthesia, according to MSKCC animal protocol. Total hemoglobin levels, red cell counts, hematocrit levels, neutrophil counts, platelet counts, and reticulocyte counts were measured on a blood cell count analyzer.

VCN analysis: To evaluate the integrated vector copy number in peripheral blood, mouse genomic DNA was isolated, quantified and analyzed with multiplex real-time TaqMan PCR using following probes and primer:

```
Gag-specific probe
                           (SEQ ID NO: 41)
5'-acagccttctgatgtttctaacaggccagg-3'

Gag-primer-Forward
                           (SEQ ID NO: 42)
5'-ggagctagaacgattcgcagtt-3'

Gag-primer-Reverse
                           (SEQ ID NO: 43)
5'-gttgtagctgtcccagtatttgtc-3'

Mouse β-actin Probe
                           (SEQ ID NO: 47)
5'-tacgagggctatgctctccctcacgc-3'

Mouse β-actin-primer-Forward
                           (SEQ ID NO: 48)
5'-tcacccacactgtgcccat-3'

Mouse β-actin-primer-reverse
                           (SEQ ID NO: 49)
5'-agccaggtccagacgcag-3'
```

Hemoglobin assays: automated hemoglobin (Hb) quantification; based line anemia in Hbb$^{th3/+}$ mice is 7.5-8.5 g/dL. Vector performance, i.e., protein output per vector copy, was determined as the ratio of gain in hemoglobin expression (i.e., correction of anemia), ΔHb g/dL, per vector copy number (VCN) measured in circulating blood cells.

Results and Discussion

Figure 16:
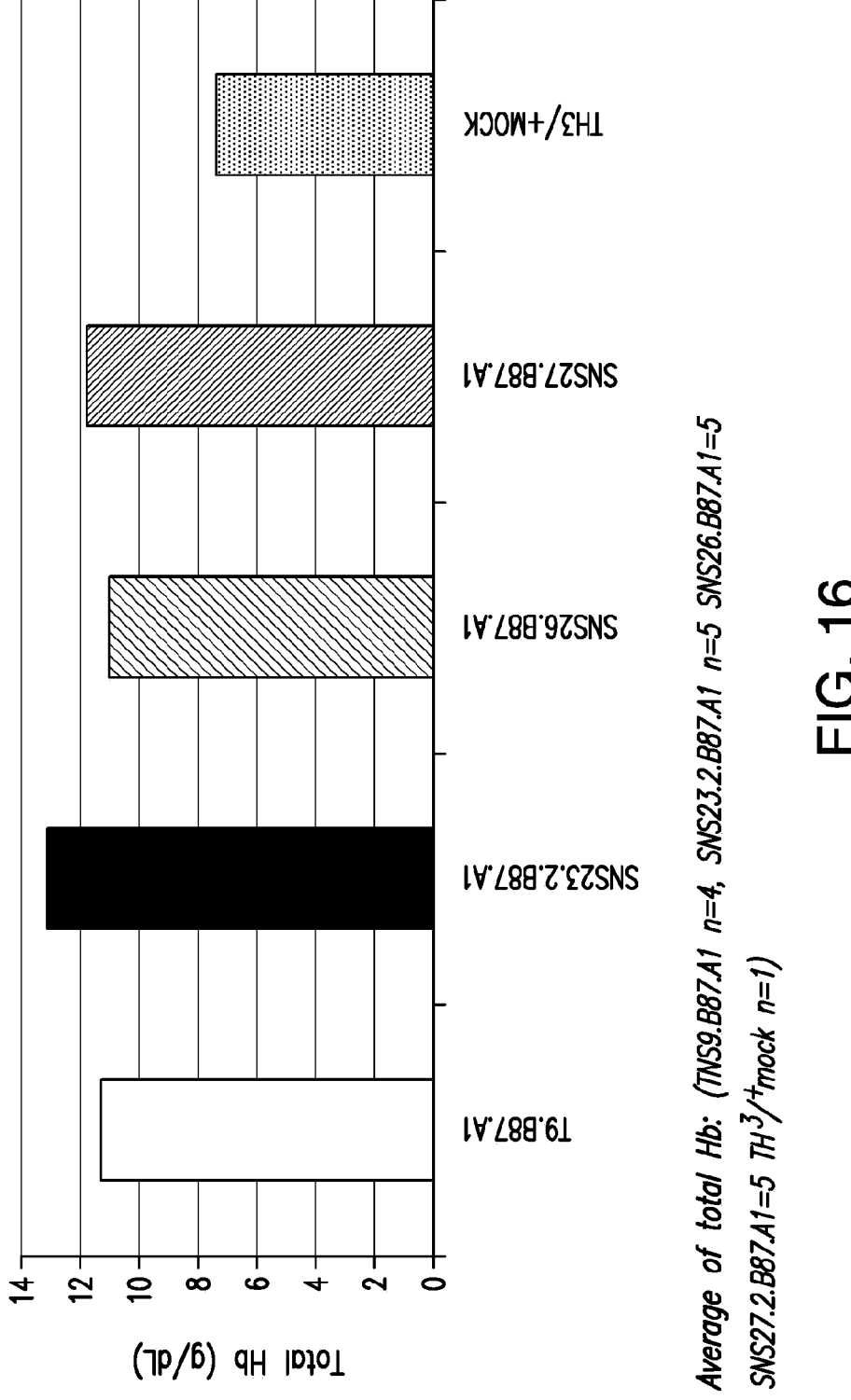
FIG. 16 depicts the average Hb production for vectors
(TNS9.B87.A1 SNS23.2.B87.A1, SNS26.B87.A1, and
SNS27.2B.87.A1).
Figure 17:
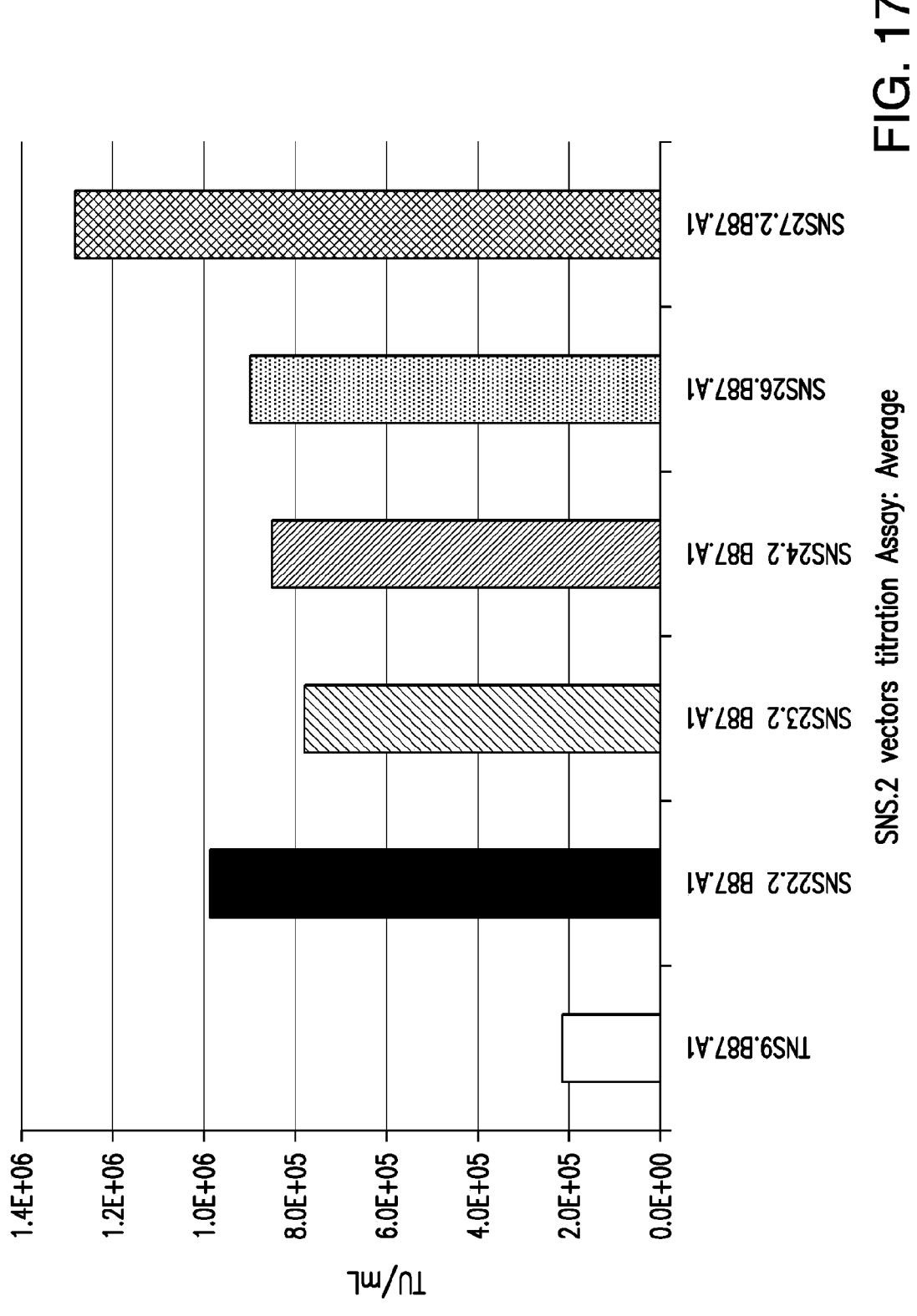
FIG. 17 depicts the titration assay relative to various
vectors.
Figure 18:
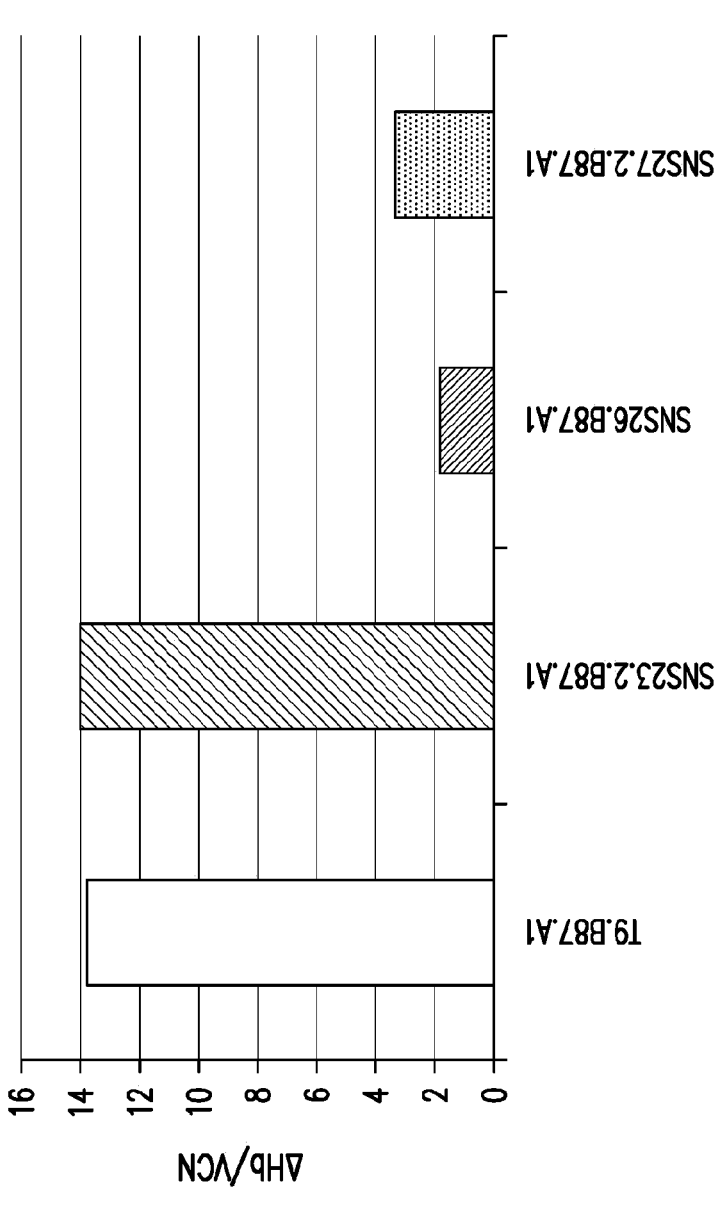
FIG. 18 depicts the average of ΔHb normalized per VCN
for various vectors.

As shown in FIG. 17, the SNS22.2.B87.A1, SNS23.2.B87.A1, SNS24.2.B87.A1, SNS26.B87.A1 and SNS27.2.B87.A1 vectors achieved higher titer than the TNS9.B87.A1 vector. Moreover, as shown in FIG. 16 and Table 1, the multiple mutations and/or deletions introduced into the promoter, HS2, HS3, and HS4 regions of the β-globin LCR of SNS23.2.B87.A1 did not affect (e.g., did not reduce) globin expression in mice. Furthermore, vectors lacking HS2 or all LCR elements but including an BLV enhancer and flanked by the A1 insulator, e.g., SNS26.B87.A1 and SNS27.2.B87.A1, can effectively treat anemia in thalassemic mice. While the globin protein output per copy of the SNS26.B87.A1 vector or the SNS27.2.B87.A1 vector was less than that of the SNS23.2.B87.A1 vector (see FIG. 18 and Table 1), SNS26.B87.A1 and SNS27.2.B87.A1 vectors were able to correct the disease with a higher vector copy number (see FIG. 16). The higher titer of the SNS26.B87.A1 and SNS27.2.B87.A1 vectors facilitated higher gene transfer, resulting in a higher vector copy number (VCN) and therapeutic activity.

As shown in FIG. 16, the expression of an incomplete or lacking LCR required 0.8 or higher copies of vector per cell, while in the case of SNS23.2.B87.A1, a VCN of 0.3 copies was sufficient to achieve correction of anemia

TABLE 1

Vector copy number (VCN) and Hb levels in long-term hematopoietic chimeras. Total Hb level [g/dL] in peripheral blood (PB) of chimeric mice. Representative data for week 6 after transplant is shown. ΔHb level was obtained by subtracting Th3/+ hemoglobin (value = 9 g/dL) from total Hb level for each animal tested. ΔHb/copy = Correlation between delta(Δ)Hb and vector copy number.

| mouse ID | VCN | HGB (g/dL) | Δ(HGB-9) | ΔHGB/ copy |
|---|---|---|---|---|
| TNS9.B87.A1 #1 | 0.2 | 11.3 | 2.3 | 11.5 |
| TNS9.B87.A1 #2 | 0.2 | 12.0 | 3.0 | 16.7 |
| TNS9.B87.A1 #3 | 0.2 | 8.5 | −0.5 | −2.5 |
| TNS9.B87.A1 #4 | 0.2 | 13.5 | 4.5 | 30.0 |
| SNS23.2.B87.A1 #1 | 0.3 | 13.1 | 4.1 | 15.8 |
| SNS23.2.B87.A1 #2 | 0.3 | 13.3 | 4.3 | 13.0 |
| SNS23.2.B87.A1 #3 | 0.3 | 13.2 | 4.2 | 14.5 |
| SNS23.2.B87.A1 #4 | 0.3 | 13.0 | 4.0 | 13.8 |
| SNS23.2.B87.A1 #5 | 0.3 | 13.2 | 4.2 | 13.5 |
| SNS26.B87.A1 #1 | 1.2 | 11.4 | 2.4 | 2.0 |
| SNS26.B87.A1 #2 | 1.2 | 11.9 | 2.9 | 2.3 |
| SNS26.B87.A1 #3 | 1.3 | 9.7 | 0.7 | 0.6 |
| SNS26.B87.A1 #4 | 1.7 | 11.9 | 2.9 | 1.8 |
| SNS26.B87.A1 #5 | 1.3 | 11.3 | 2.3 | 1.8 |
| SNS27.2.B87.A1 #1 | 0.8 | 11.7 | 2.7 | 3.3 |
| SNS27.2.B87.A1 #2 | 0.8 | 13.0 | 4.0 | 5.3 |
| SNS27.2.B87.A1 #3 | 0.9 | 11.5 | 2.5 | 2.7 |
| SNS27.2.B87.A1 #4 | 0.9 | 11.5 | 2.5 | 2.7 |
| SNS27.2.B87.A1 #5 | 0.7 | 11.3 | 2.3 | 3.2 |
| TH3/+ MOCK #1 | — | 7.5 | −1.5 | |

Example 7: Evaluation of Globin Production at Different Time Points

Figure 19:
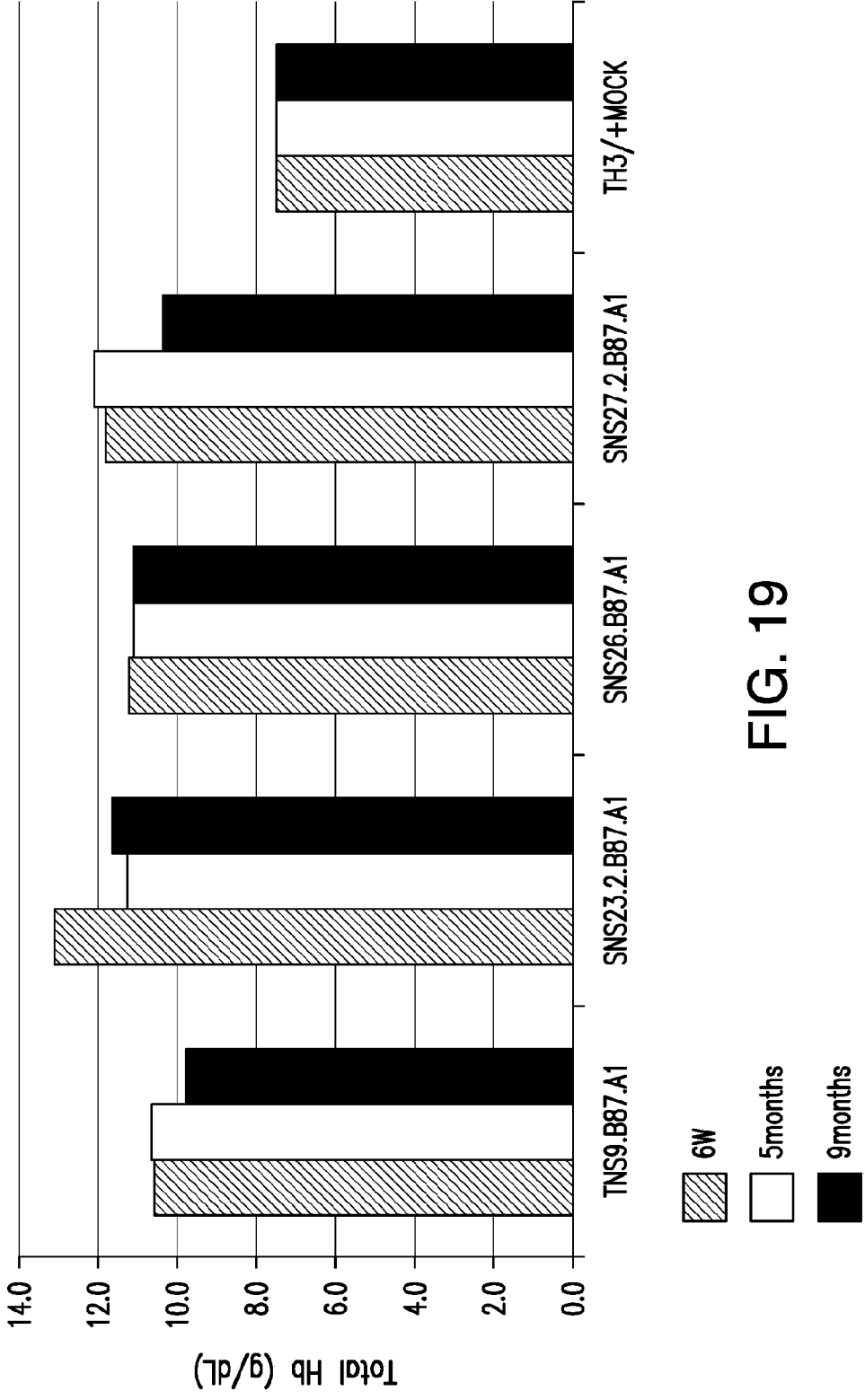
FIG. 19 depicts the average of total Hemoglobin (Hb) in
thalassemic mouse peripheral blood at time points of
6-week, 5-month, and 9-month.
Figure 20:
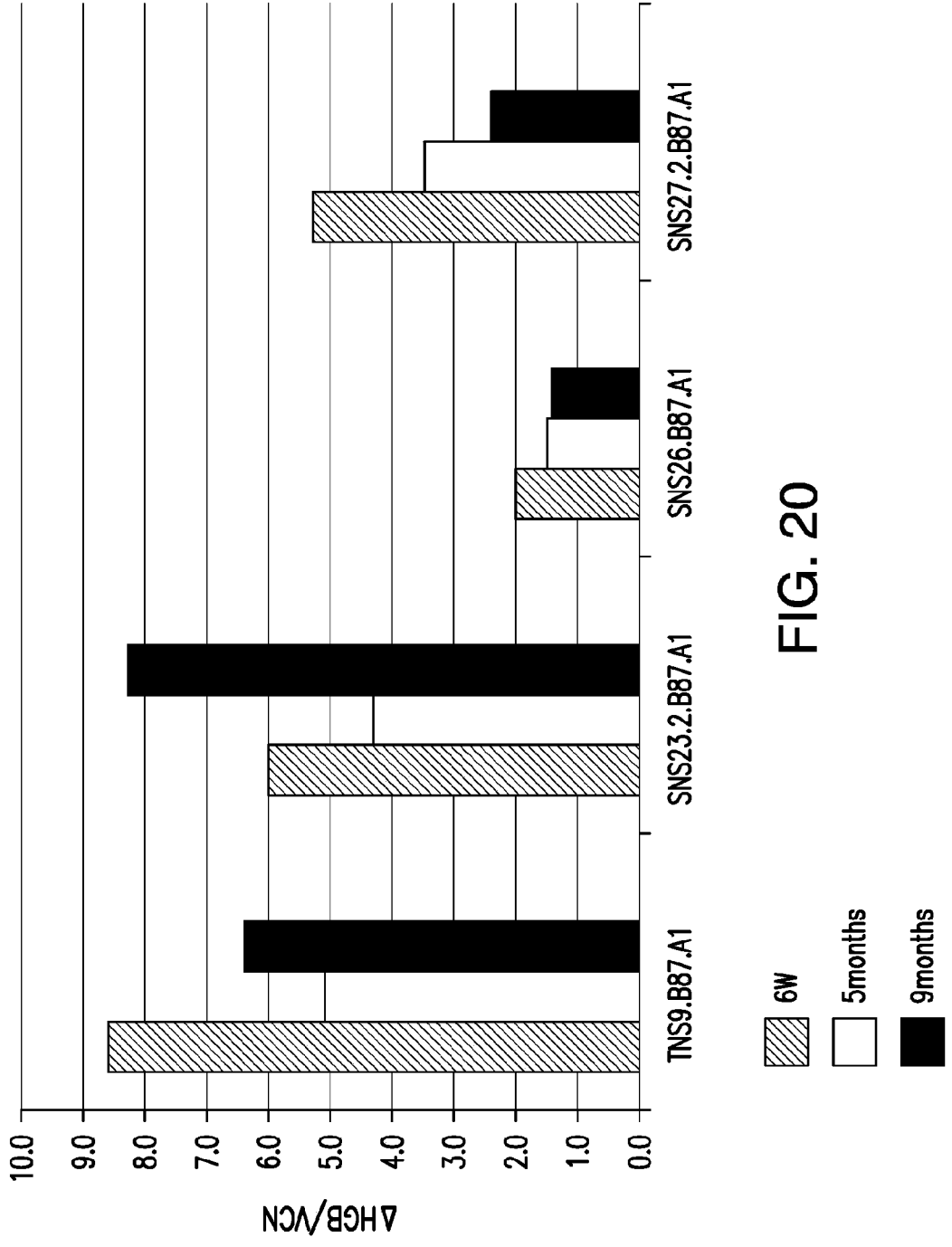
FIG. 20 depicts the average gain in Hb level (ΔHb)
normalized to vector copy (VCN) at time points of 6-week,
5-month, and 9-month. ΔHb=Hb level −7.5 (baseline level
in thalassemic mice).

Additional experiments were conducted to measure the globin production at different time points in thalassemic mice transfected with vectors disclosed herein. The methods used in Example 6 were applied in this Example. Average total Hb levels and average gains in Hb levels (ΔHb) in peripheral blood were measured in thalassemic mice transfected with vectors for 6-week, 5-month, or 9-month. ΔHb was normalized to vector copy (VCN), and ΔHb=Hb level-7.5 (baseline level in thalassemic mice, as all the time points consistently show an HGB value of 7.5 g/dL in the Thalassemic mice used as controls, this value was used). As shown in FIG. 19 and Table 2, globin productions from all vectors, including SNS23.2.B87A1, were stable over time. As shown in FIG. 20, SNS23.2.B87.A1 exhibited equal or better output of β-globin relative to TNS9.B87.A1, especially at late time points.

TABLE 2

Representative data for three different time points after transplant

| Vectors | VCN | HGB (g/dL) | Δ(HGB-7.5) | ΔHGB/ copy |
|---|---|---|---|---|
| TNS9.B87.A1 (6 weeks) | 0.5 | 10.6 | 3.8 | 8.6 |
| TNS9.B87.A1 (5 months) | 0.5 | 10.7 | 3.2 | 5.1 |
| TNS9.B87.A1 (9 months) | 0.4 | 9.8 | 2.3 | 6.4 |
| SNS23.2.B87.A1 (6 weeks) | 1.1 | 13.2 | 5.7 | 6.0 |
| SNS23.2.B87.A1 (5 months) | 1.1 | 11.3 | 3.8 | 4.3 |
| SNS23.2.B87.A1 (9 months) | 0.5 | 11.6 | 4.1 | 8.3 |
| SNS26.B87.A1 (6 weeks) | 2.0 | 11.2 | 3.7 | 2.0 |
| SNS26.B87.A1 (5 months) | 3.0 | 11.1 | 3.6 | 1.5 |
| SNS26.B87.A1 (9 months) | 3.1 | 11.1 | 3.6 | 1.4 |
| SNS27.2.B87.A1 (6 weeks) | 0.8 | 11.8 | 4.3 | 5.3 |
| SNS27.2.B87.A1 (5 months) | 1.5 | 12.1 | 4.6 | 3.5 |
| SNS27.2.B87.A1 (9 months) | 1.1 | 10.4 | 2.7 | 2.4 |
| TH3/+ MOCK (6 weeks) | 0 | 7.5 | 0 | 0 |
| TH3/+ MOCK (5 months) | 0 | 7.5 | 0 | 0 |
| TH3/+ MOCK (9 months) | 0 | 7.5 | 0 | 0 |

Average of Vector copy number (VCN) in long-term hematopoietic chimeras. Average Hb level [g/dL] in peripheral blood (PB) of chimeric mice. ΔHGB level was obtained by subtracting Th3/+ hemoglobin (value = 7.5 g/dL) from the total Hb level for each animal tested. ΔHGB/copy = Correlation between delta(Δ)Hb and vector copy number.

All the ΔHGb calculations are made using TH3/+MOCK (7.5 g/dL) as basal HGB, value that is consistent in all the time points.

Example 8: Human Primary CD34[+] Cells Transduced with Vectors Disclosed Herein Human primary CD34[+] cells were isolated by centrifugation on a gradient of Ficoll-Hypaque Plus density. CD34[+] cells were purified by positive selection using separation columns and beads. After one day of cytokine stimulation the CD34[+] cells were transduced with SNS.23.2.B87.A1 or TNS9.B87.A1 vectors disclosed herein using 4 different MOI. 10 and 15 days after transduction, the cells were harvested and the Vector copy number (VCN) was measured using the methods disclosed in Example 6. As shown in Table 3, at MOIs from 20×1 to 100×1, a linearly increased VCN response was observed in cells transduced with SNS.23.2.B87.A1 vector, with maximum VCN>2. By contrast, cells transduced with TNS9.B87.A1 vector did not exhibit proportional increases in VCN at MOIs from 20×1 to 100×1. Unlike TNS9.B87.A1 vector, the SNS23.2.B87.A1 vector resulted in an increased globin gene transduction in CD34[+] cells up to >2 VCN per cell (2.33 at MOI 100, day 15, Table 3).

TABLE 3

Transduction of human primary CD34+ cells

| Groups | MOI | VCN day10 | VCN day15 |
|---|---|---|---|
| SNS23.2.B87.A1 | 10 × 1 | 1 | 0.21 |
| Concentrate virus | 20 × 1 | 1.78 | 0.56 |
| | 40 × 1 | 3.35 | 0.86 |
| | 100 × 1 | 7.33 | 2.33 |
| TNS9.B87.A1 | 10 × 1 | 0.47 | 0.38 |
| Concentrate virus | 20 × 1 | 0.52 | 0.44 |
| | 40 × 1 | 0.48 | 0.40 |
| | 100 × 1 | 0.60 | 0.44 |
| UT | NA | 0.00 | 0.00 |

REFERENCES

1. Weatherall, D. J. & Clegg, J. B. The Thalassemia Syndrome. Blackwell *Scientific* Oxford (1981).

2 Stamatoyannopoulos, G., Nienhuis, A. W., Majerus, P. & Varmus, H. The Molecular Basis of Blood Diseases. WB Saunders, Philadelphia (1994).

3. Weatherall, D. J. Phenotype-genotype relationships in monogenic disease: lessons from the thalassaemias. *Nat Rev Genet* 2, 245-255. (2001).

4. Steinberg, M. H., Forget, B. G., Higgs, D. R. & Nagel, R. L. *Molecular Mechanism of β Thalassemia*; Bernard G. Forget, (Cambridge University Press, Cambridge, UK, 2001).

5. Cooley, T. B. & Lee, P. A series of cases of splenomegaly in children with anemia and peculiar bone changes. *Trans. Am. Pediatr. Soc.* 37, 29 (1925).

6. Giardina, P. J. & Grady, R. W. Chelation therapy in beta-thalassemia: an optimistic update. *Semin Hematol* 38, 360-366. (2001).

7. Giardini, C. & Lucarelli, G. Bone marrow transplantation in the treatment of thalassemia. *Current opinion in hematology* 1, 170-176. (1994).

8. Boulad, F., Giardina, P., Gillio, A., Kernan, N., Small, T., Brochstein, J., Van Syckle, K., George, D., Szabolcs, P. & O'Reilly, R. J. Bone marrow transplantation for homozygous beta-thalassemia. The Memorial Sloan-Kettering Cancer Center experience. *Ann N Y Acad Sci* 850, 498-502. (1998).

9. Lucarelli, G., Clift, R. A., Galimberti, M., Angelucci, E., Giardini, C., Baronciani, D., Polchi, P., Andreani, M., Gaziev, D., Erer, B., Ciaroni, A., D'Adamo, F., Albertini, F. & Muretto, P. Bone marrow transplantation in adult thalassemic patients. Blood 93, 1164-1167. (1999).

10. Tisdale, J. & Sadelain, M. Toward gene therapy for disorders of globin synthesis. *Semin Hematol* 38, 382-392 (2001).

11. Pauling, L., Itano, H. A., Singer, S. J. & Wells, I. C. Sickle cell anemia, a molecular disease. *Science* 110, 543-546 (1949).

12. Swank, R. A. & Stamatoyannopoulos, G. Fetal gene reactivation. *Curr Opin Genet Dev* 8, 366-370 (1998).

13. Platt, O. S., Orkin, S. H., Dover, G., Beardsley, G. P., Miller, B. & Nathan, D. G. Hydroxyurea enhances fetal hemoglobin production in sickle cell anemia. *J Clin Invest* 74, 652-656. (1984).

14. Charache, S., Dover, G. J., Moore, R. D., Eckert, S., Ballas, S. K., Koshy, M., Milner, P. F., Orringer, E. P., Phillips, G., Jr., Platt, O. S. & et al. Hydroxyurea: effects on hemoglobin F production in patients with sickle cell anemia. *Blood* 79, 2555-2565. (1992).

15. Atweh, G. F. & Loukopoulos, D. Pharmacological induction of fetal hemoglobin in sickle cell disease and beta-thalassemia. *Semin Hematol* 38, 367-373. (2001).

16. Perrine, S. P., Castaneda, S. A., Boosalis, M. S., White, G. L., Jones, B. M. & Bohacek, R. Induction of fetal globin in beta-thalassemia: Cellular obstacles and molecular progress. *Ann N Y Acad Sci* 1054, 257-265 (2005).

17. Stamatoyannopoulos, G. Prospects for developing a molecular cure for thalassemia. *Hematology* 10 Suppl 1, 255-257 (2005).

18. Vermylen, C., Cornu, G., Ferster, A., Brichard, B., Ninane, J., Ferrant, A., Zenebergh, A., Maes, P., Dhooge, C., Benoit, Y., Beguin, Y., Dresse, M. F. & Sariban, E. Haematopoietic stem cell transplantation for sickle cell anaemia: the first 50 patients transplanted in Belgium. *Bone Marrow Transplant* 22, 1-6 (1998).

19. Luzzatto, L. & Goodfellow, P. Sickle cell anaemia. A simple disease with no cure. *Nature* 337, 17-18 (1989).

20. Sadelain, M. Genetic treatment of the haemoglobinopathies: recombinations and new combinations. *Br J Haematol* 98, 247-253 (1997).

21. Sadelain, M., Boulad, F., Galanello, R., Giardina, P., Locatelli, F., Maggio, A., Rivella, S., Riviere, I. & Tisdale, J. Therapeutic options for patients with severe beta-thalassemia: the need for globin gene therapy. *Hum Gene Ther* 18, 1-9 (2007).

22. Borgna-Pignatti, C., Rugolotto, S., De Stefano, P., Zhao, H., Cappellini, M. D., Del Vecchio, G. C., Romeo, M. A., Forni, G. L., Gamberini, M. R., Ghilardi, R., Piga, A. & Cnaan, A. Survival and complications in patients with thalassemia major treated with transfusion and deferoxamine. *Haematologica* 89, 1187-1193 (2004).

23. Telfer, P. T., Warburton, F., Christou, S., Hadjigavriel, M., Sitarou, M., Kolnagou, A. & Angastiniotis, M. Improved survival in thalassemia major patients on switching from desferrioxamine to combined chelation therapy with desferrioxamine and deferiprone. *Haematologica* 94, 1777-1778 (2009).

24. Ladis, V., Chouliaras, G., Berdoukas, V., Chatziliami, A., Fragodimitri, C., Karabatsos, F., Youssef, J., Kattamis, A. & Karagiorga-Lagana, M. Survival in a large cohort of Greek patients with transfusion-dependent beta thalassaemia and mortality ratios compared to the general population. *European journal of haematology* 86, 332-338 (2011).

25. Mancuso, A., Sciarrino, E., Renda, M. C. & Maggio, A. A prospective study of hepatocellular carcinoma incidence in thalassemia. *Hemoglobin* 30, 119-124 (2006).

26. Persons, D. A. & Tisdale, J. F. Gene therapy for the hemoglobin disorders. *Semin Hematol* 41, 279-286 (2004).

27. Sadelain, M. Recent advances in globin gene transfer for the treatment of beta-thalassemia and sickle cell anemia. *Current opinion in hematology* 13, 142-148 (2006).

28. May, C., Rivella, S., Callegari, J., Heller, G., Gaensler, K. M., Luzzatto, L. & Sadelain, M. Therapeutic haemoglobin synthesis in beta-thalassaemic mice expressing lentivirus-encoded human beta-globin. *Nature* 406, 82-86 (2000).

29. May, C., Rivella, S., Chadburn, A. & Sadelain, M. Successful treatment of murine beta-thalassemia intermedia by transfer of the human beta-globin gene. *Blood* 99, 1902-1908 (2002).

30. Rivella, S., May, C., Chadburn, A., Riviere, I. & Sadelain, M. A novel murine model of Cooley anemia and its rescue by lentiviral-mediated human beta-globin gene transfer. *Blood* 101, 2932-2939 (2003).

31. Sadelain, M., Boulad, F., Lisowki, L., Moi, P. & Riviere, I. Stem cell engineering for the treatment of severe hemoglobinopathies. *Curr Mol Med* 8, 690-697 (2008).

32. Bank, A., Dorazio, R. & Leboulch, P. A phase I/II clinical trial of beta-globin gene therapy for beta-thalassemia. *Ann N Y Acad Sci* 1054, 308-316 (2005).

33. Cavazzana-Calvo, M., Payen, E., Negre, O., Wang, G., Hehir, K., Fusil, F., Down, J., Denaro, M., Brady, T., Westerman, K., Cavallesco, R., Gillet-Legrand, B., Caccavelli, L., Sgarra, R., Maouche-Chretien, L., Bernaudin, F., Girot, R., Dorazio, R., Mulder, G. J., Polack, A., Bank, A., Soulier, J., Larghero, J., Kabbara, N., Dalle, B., Gourmel, B., Socie, G., Chretien, S., Cartier, N., Aubourg, P., Fischer, A., Cornetta, K., Galacteros, F., Beuzard, Y., Gluckman, E., Bushman, F., Hacein-Bey-Abina, S. & Leboulch, P. Transfusion independence and HMGA2 activation after gene therapy of human beta-thalassaemia. *Nature* 467, 318-322 (2010).

US 12,606,848 B2

165

166

34. Braun, C. J., Boztug, K., Paruzynski, A., Witzel, M., Schwarzer, A., Rothe, M., Modlich, U., Beier, R., Gohring, G., Steinemann, D., Fronza, R., Ball, C. R., Haemmerle, R., Naundorf, S., Kuhlcke, K., Rose, M., Fraser, C., Mathias, L., Ferrari, R., Abboud, M. R., Al-Herz, W., Kondratenko, I., Marodi, L., Glimm, H., Schlegelberger, B., Schambach, A., Albert, M. H., Schmidt, M., von Kalle, C. & Klein, C. Gene therapy for Wiskott-Aldrich syndrome—long-term efficacy and genotoxicity. *Sci Transl Med* 6, 227ra233 (2014).

35. Chang, A. H. & Sadelain, M. The genetic engineering of hematopoietic stem cells: the rise of lentiviral vectors, the conundrum of the ltr, and the promise of lineage-restricted vectors. *Mol Ther* 15, 445-456 (2007).

36. Pawliuk, R., Westerman, K. A., Fabry, M. E., Payen, E., Tighe, R., Bouhassira, E. E., Acharya, S. A., Ellis, J., London, I. M., Eaves, C. J., Humphries, R. K., Beuzard, Y., Nagel, R. L. & Leboulch, P. Correction of sickle cell disease in transgenic mouse models by gene therapy. *Science* 294, 2368-2371 (2001).

37. Emery, D. W., Chen, H., Li, Q. & Stamatoyannopoulos, G. Development of a condensed locus control region cassette and testing in retrovirus vectors for A gamma-globin. *Blood Cells Mol Dis* 24, 322-339 (1998).

38. Miccio, A., Cesari, R., Lotti, F., Rossi, C., Sanvito, F., Ponzoni, M., Routledge, S. J., Chow, C. M., Antoniou, M. N. & Ferrari, G. In vivo selection of genetically modified erythroblastic progenitors leads to long-term correction of beta-thalassemia. *Proc Natl Acad Sci USA* 105, 10547-10552 (2008).

39. Sadelain, M., Wang, C. H., Antoniou, M., Grosveld, F. & Mulligan, R. C. Generation of a high-titer retroviral vector capable of expressing high levels of the human beta-globin gene. *Proc Natl Acad Sci USA* 92, 6728-6732 (1995).

40. Samakoglu, S., Lisowski, L., Budak-Alpdogan, T., Usachenko, Y., Acuto, S., Di Marzo, R., Maggio, A., Zhu, P., Tisdale, J. F., Riviere, I. & Sadelain, M. A genetic strategy to treat sickle cell anemia by coregulating globin transgene expression and RNA interference. *Nat Biotechnol* 24, 89-94 (2006).

41. Pestina, T. I., Hargrove, P. W., Jay, D., Gray, J. T., Boyd, K. M. & Persons, D. A. Correction of murine sickle cell disease using gamma-globin lentiviral vectors to mediate high-level expression of fetal hemoglobin. *Mol Ther* 17, 245-252 (2009).

42. Hanawa, H., Yamamoto, M., Zhao, H., Shimada, T. & Persons, D. A. Optimized lentiviral vector design improves titer and transgene expression of vectors containing the chicken beta-globin locus HS4 insulator element. *Mol Ther* 17, 667-674 (2009).

43. Arumugam, P. I., Scholes, J., Perelman, N., Xia, P., Yee, J. K. & Malik, P. Improved human beta-globin expression from self-inactivating lentiviral vectors carrying the chicken hypersensitive site-4 (cHS4) insulator element. *Mol Ther* 15, 1863-1871 (2007).

44. Fraser, P., Pruzina, S., Antoniou, M. & Grosveld, F. Each hypersensitive site of the human beta-globin locus control region confers a different developmental pattern of expression on the globin genes. *Genes & development* 7, 106-113 (1993).

45. Navas, P. A., Peterson, K. R., Li, Q., Skarpidi, E., Rohde, A., Shaw, S. E., Clegg, C. H., Asano, H. & Stamatoyannopoulos, G. Developmental specificity of the interaction between the locus control region and embryonic or fetal globin genes in transgenic mice with an HS3 core deletion. *Molecular and cellular biology* 18, 4188-4196 (1998).

46. Li, Q. & Stamatoyannopoulos, G. Hypersensitive site 5 of the human beta locus control region functions as a chromatin insulator. *Blood* 84, 1399-1401 (1994).

47. Li, Q., Zhang, M., Han, H., Rohde, A. & Stamatoyannopoulos, G. Evidence that DNase I hypersensitive site 5 of the human beta-globin locus control region functions as a chromosomal insulator in transgenic mice. *Nucleic Acids Res* 30, 2484-2491 (2002).

48. Puthenveetil, G., Scholes, J., Carbonell, D., Qureshi, N., Xia, P., Zeng, L., Li, S., Yu, Y., Hiti, A. L., Yee, J. K. & Malik, P. Successful correction of the human beta-thalassemia major phenotype using a lentiviral vector. *Blood* 104, 3445-3453 (2004).

49. Wilber, A., Nienhuis, A. W. & Persons, D. A. Transcriptional regulation of fetal to adult hemoglobin switching: new therapeutic opportunities. *Blood* 117, 3945-3953 (2011).

50. Arumugam, P. I., Higashimoto, T., Urbinati, F., Modlich, U., Nestheide, S., Xia, P., Fox, C., Corsinotti, A., Baum, C. & Malik, P. Genotoxic potential of lineage-specific lentivirus vectors carrying the beta-globin locus control region. *Mol Ther* 17, 1929-1937 (2009).

51. Chang, K. H., Fang, X., Wang, H., Huang, A., Cao, H., Yang, Y., Bonig, H., Stamatoyannopoulos, J. A. & Papayannopoulou, T. Epigenetic modifications and chromosome conformations of the beta globin locus throughout development. *Stem cell reviews* 9, 397-407 (2013).

52. Papayannopoulou, T., Priestley, G. V., Rohde, A., Peterson, K. R. & Nakamoto, B. Hemopoietic lineage commitment decisions: in vivo evidence from a transgenic mouse model harboring micro LCR-betapro-LacZ as a transgene. *Blood* 95, 1274-1282 (2000).

53. Nienhuis, A. W. Development of gene therapy for blood disorders: an update. *Blood* 122, 1556-1564 (2013).

54. Baum, C., Kustikova, O., Modlich, U., Li, Z. & Fehse, B. Mutagenesis and oncogenesis by chromosomal insertion of gene transfer vectors. *Hum Gene Ther* 17, 253-263 (2006).

55. Nienhuis, A. W., Dunbar, C. E. & Sorrentino, B. P. Genotoxicity of retroviral integration in hematopoietic cells. *Mol Ther* 13, 1031-1049 (2006).

56. Emery, D. W. The use of chromatin insulators to improve the expression and safety of integrating gene transfer vectors. *Hum Gene Ther* 22, 761-774 (2011).

57. Evans-Galea, M. V., Wielgosz, M. M., Hanawa, H., Srivastava, D. K. & Nienhuis, A. W. Suppression of clonal dominance in cultured human lymphoid cells by addition of the cHS4 insulator to a lentiviral vector. *Mol Ther* 15, 801-809 (2007).

58. Rivella, S., Callegari, J. A., May, C., Tan, C. W. & Sadelain, M. The cHS4 insulator increases the probability of retroviral expression at random chromosomal integration sites. *J Virol* 74, 4679-4687 (2000).

59. Emery, D. W., Yannaki, E., Tubb, J. & Stamatoyannopoulos, G. A chromatin insulator protects retrovirus vectors from chromosomal position effects. *Proc Natl Acad Sci USA* 97, 9150-9155 (2000).

60. Emery, D. W., Yannaki, E., Tubb, J., Nishino, T., Li, Q. & Stamatoyannopoulos, G. Development of virus vectors for gene therapy of beta chain hemoglobinopathies: flanking with a chromatin insulator reduces gamma-globin gene silencing in vivo. *Blood* 100, 2012-2019 (2002).

61. Yannaki, E., Tubb, J., Aker, M., Stamatoyannopoulos, G. & Emery, D. W. Topological constraints governing the use of the chicken HS4 chromatin insulator in oncoretrovirus vectors. *Mol Ther* 5, 589-598 (2002).

62. Hino, S., Fan, J., Taguwa, S., Akasaka, K. & Matsuoka, M. Sea urchin insulator protects lentiviral vector from silencing by maintaining active chromatin structure. *Gene Ther* 11, 819-828 (2004).

63. Ramezani, A., Hawley, T. S. & Hawley, R. G. Performance- and safety-enhanced lentiviral vectors containing the human interferon-beta scaffold attachment region and the chicken beta-globin insulator. *Blood* 101, 4717-4724 (2003).

64. Ramezani, A., Hawley, T. S. & Hawley, R. G. Combinatorial incorporation of enhancer-blocking components of the chicken beta-globin 5'HS4 and human T-cell receptor alpha/delta BEAD-1 insulators in self-inactivating retroviral vectors reduces their genotoxic potential. *Stem Cells* 26, 3257-3266 (2008).

65. Yannaki, E., Emery, D. W. & Stamatoyannopoulos, G. Gene therapy for beta-thalassaemia: the continuing challenge. *Expert reviews in molecular medicine* 12, e31 (2010).

66. Persons, D. A. The challenge of obtaining therapeutic levels of genetically modified hematopoietic stem cells in beta-thalassemia patients. *Ann N Y Acad Sci* 1202, 69-74 (2010).

67. Perumbeti, A. & Malik, P. Therapy for beta-globinopathies: a brief review and determinants for successful and safe correction. *Ann N Y Acad Sci* 1202, 36-44 (2010).

68. Johnson, K. D., Grass, J. A., Park, C., Im, H., Choi, K. & Bresnick, E. H. Highly restricted localization of RNA polymerase II within a locus control region of a tissue-specific chromatin domain. *Molecular and cellular biology* 23, 6484-6493 (2003).

69. Vieira, K. F., Levings, P. P., Hill, M. A., Crusselle, V. J., Kang, S. H., Engel, J. D. & Bungert, J. Recruitment of transcription complexes to the beta-globin gene locus in vivo and in vitro. *J Biol Chem* 279, 50350-50357 (2004).

70. Levings, P. P., Zhou, Z., Vieira, K. F., Crusselle-Davis, V. J. & Bungert, J. Recruitment of transcription complexes to the beta-globin locus control region and transcription of hypersensitive site 3 prior to erythroid differentiation of murine embryonic stem cells. *The FEBS journal* 273, 746-755 (2006).

71. Felsenfeld, G. & Groudine, M. Controlling the double helix. *Nature* 421, 448-453 (2003).

72. Felsenfeld, G. Chromatin as an essential part of the transcriptional mechanism. *Nature* 355, 219-224 (1992).

73. Brownell, J. E. & Allis, C. D. Special HATs for special occasions: linking histone acetylation to chromatin assembly and gene activation. *Curr Opin Genet Dev* 6, 176-184 (1996).

74. Kingston, R. E. & Narlikar, G. J. ATP-dependent remodeling and acetylation as regulators of chromatin fluidity. *Genes & development* 13, 2339-2352 (1999).

75. Tsukiyama, T. & Wu, C. Chromatin remodeling and transcription. *Curr Opin Genet Dev* 7, 182-191 (1997).

76 Wolffe, A. P., Wong, J. & Pruss, D. Activators and repressors: making use of chromatin to regulate transcription. *Genes to cells: devoted to molecular & cellular mechanisms* 2, 291-302 (1997).

77. Kadonaga, J. T. Eukaryotic transcription: an interlaced network of transcription factors and chromatin-modifying machines. *Cell* 92, 307-313 (1998).

78. Struhl, K. Histone acetylation and transcriptional regulatory mechanisms. *Genes & development* 12, 599-606 (1998).

79. Gross, D. S. & Garrard, W. T. Nuclease hypersensitive sites in chromatin. *Annual review of biochemistry* 57, 159-197 (1988).

80. Elgin, S. C. Anatomy of hypersensitive sites. *Nature* 309, 213-214 (1984).

81. Wu, C. The 5' ends of *Drosophila* heat shock genes in chromatin are hypersensitive to DNase I. *Nature* 286, 854-860 (1980).

82. Felsenfeld, G., Boyes, J., Chung, J., Clark, D. & Studitsky, V. Chromatin structure and gene expression. *Proc Natl Acad Sci USA* 93, 9384-9388 (1996).

83. Burgess-Beusse, B., Farrell, C., Gaszner, M., Litt, M., Mutskov, V., Recillas-Targa, F., Simpson, M., West, A. & Felsenfeld, G. The insulation of genes from external enhancers and silencing chromatin. *Proc Natl Acad Sci USA* 99 Suppl 4, 16433-16437 (2002).

84. Elgin, S. C. DNAase I-hypersensitive sites of chromatin. *Cell* 27, 413-415 (1981).

85. McGhee, J. D., Wood, W. I., Dolan, M., Engel, J. D. & Felsenfeld, G. A 200 base pair region at the 5' end of the chicken adult beta-globin gene is accessible to nuclease digestion. *Cell* 27, 45-55 (1981).

86. Lowrey, C. H., Bodine, D. M. & Nienhuis, A. W. Mechanism of DNase I hypersensitive site formation within the human globin locus control region. *Proc Natl Acad Sci USA* 89, 1143-1147 (1992).

87. Adams, C. C. & Workman, J. L. Binding of disparate transcriptional activators to nucleosomal DNA is inherently cooperative. *Molecular and cellular biology* 15, 1405-1421 (1995).

88. McArthur, M., Gerum, S. & Stamatoyannopoulos, G. Quantification of DNaseI-sensitivity by real-time PCR: quantitative analysis of DNaseI-hypersensitivity of the mouse beta-globin LCR. *J Mol Biol* 313, 27-34 (2001).

89. Dorschner, M. O., Hawrylycz, M., Humbert, R., Wallace, J. C., Shafer, A., Kawamoto, J., Mack, J., Hall, R., Goldy, J., Sabo, P. J., *Kohli*, A., Li, Q., McArthur, M. & Stamatoyannopoulos, J. A. High-throughput localization of functional elements by quantitative chromatin profiling. *Nat Methods* 1, 219-225 (2004).

90. Sabo, P. J., Kuehn, M. S., Thurman, R., Johnson, B. E., Johnson, E. M., Cao, H., Yu, M., Rosenzweig, E., Goldy, J., Haydock, A., Weaver, M., Shafer, A., Lee, K., Neri, F., Humbert, R., Singer, M. A., Richmond, T. A., Dorschner, M. O., McArthur, M., Hawrylycz, M., Green, R. D., Navas, P. A., Noble, W. S. & Stamatoyannopoulos, J. A. Genome-scale mapping of DNase I sensitivity in vivo using tiling DNA microarrays. *Nat Methods* 3, 511-518 (2006).

91. Sabo, P. J., Hawrylycz, M., Wallace, J. C., Humbert, R., Yu, M., Shafer, A., Kawamoto, J., Hall, R., Mack, J., Dorschner, M. O., McArthur, M. & Stamatoyannopoulos, J. A. Discovery of functional noncoding elements by digital analysis of chromatin structure. *Proc Natl Acad Sci USA* 101, 16837-16842 (2004).

92. Sabo, P. J., Humbert, R., Hawrylycz, M., Wallace, J. C., Dorschner, M. O., McArthur, M. & Stamatoyannopoulos, J. A. Genome-wide identification of DNaseI hypersensitive sites using active chromatin sequence libraries. *Proc Natl Acad Sci USA* 101, 4537-4542 (2004).

93. Thurman, R. E., Rynes, E., Humbert, R., Vierstra, J., Maurano, M. T., Haugen, E., Sheffield, N. C., Stergachis, A. B., Wang, H., Vernot, B., Garg, K., John, S., Sandstrom, R., Bates, D., Boatman, L., Canfield, T. K., Diegel, M., Dunn, D., Ebersol, A. K., Frum, T., Giste, E., Johnson, A. K., Johnson, E. M., Kutyavin, T., Lajoie, B., Lee, B. K., Lee, K., London, D., Lotakis, D., Neph, S., Neri, F., Nguyen, E. D., Qu, H., Reynolds, A. P., Roach, V., Safi, A., Sanchez, M. E., Sanyal, A., Shafer, A., Simon, J. M., Song, L., Vong, S., Weaver, M., Yan, Y., Zhang, Z., Zhang, Z., Lenhard, B., Tewari, M., Dorschner, M. O., Hansen, R. S., Navas, P. A., Stamatoyannopoulos, G., Iyer, V. R., Lieb, J. D., Sunyaev, S. R., Akey, J. M., Sabo, P. J., Kaul, R., Furey, T. S., Dekker, J., Crawford, G. E. & Stamatoyannopoulos, J. A. The accessible chromatin landscape of the human genome. Nature 489, 75-82 (2012).

94. Stergachis, A. B., Neph, S., Reynolds, A., Humbert, R., Miller, B., Paige, S. L., Vernot, B., Cheng, J. B., Thurman, R. E., Sandstrom, R., Haugen, E., Heimfeld, S., Murry, C. E., Akey, J. M. & Stamatoyannopoulos, J. A. Developmental fate and cellular maturity encoded in human regulatory DNA landscapes. Cell 154, 888-903 (2013).

95. Neph, S., Stergachis, A. B., Reynolds, A., Sandstrom, R., Borenstein, E. & Stamatoyannopoulos, J. A. Circuitry and dynamics of human transcription factor regulatory networks. Cell 150, 1274-1286 (2012).

96. Maurano, M. T., Humbert, R., Rynes, E., Thurman, R. E., Haugen, E., Wang, H., Reynolds, A. P., Sandstrom, R., Qu, H., Brody, J., Shafer, A., Neri, F., Lee, K., Kutyavin, T., Stehling-Sun, S., Johnson, A. K., Canfield, T. K., Giste, E., Diegel, M., Bates, D., Hansen, R. S., Neph, S., Sabo, P. J., Heimfeld, S., Raubitschek, A., Ziegler, S., Cotsapas, C., Sotoodehnia, N., Glass, I., Sunyaev, S. R., Kaul, R. & Stamatoyannopoulos, J. A. Systematic localization of common disease-associated variation in regulatory DNA. Science 337, 1190-1195 (2012).

97. Stergachis, A. B., Haugen, E., Shafer, A., Fu, W., Vernot, B., Reynolds, A., Raubitschek, A., Ziegler, S., LeProust, E. M., Akey, J. M. & Stamatoyannopoulos, J. A. Exonic transcription factor binding directs codon choice and affects protein evolution. Science 342, 1367-1372 (2013).

98. Neph, S., Vierstra, J., Stergachis, A. B., Reynolds, A. P., Haugen, E., Vernot, B., Thurman, R. E., John, S., Sandstrom, R., Johnson, A. K., Maurano, M. T., Humbert, R., Rynes, E., Wang, H., Vong, S., Lee, K., Bates, D., Diegel, M., Roach, V., Dunn, D., Neri, J., Schafer, A., Hansen, R. S., Kutyavin, T., Giste, E., Weaver, M., Canfield, T., Sabo, P., Zhang, M., Balasundaram, G., Byron, R., MacCoss, M. J., Akey, J. M., Bender, M. A., Groudine, M., Kaul, R. & Stamatoyannopoulos, J. A. An expansive human regulatory lexicon encoded in transcription factor footprints. Nature 489, 83-90 (2012).

99. Ramezani, A., Hawley, T. S. & Hawley, R. G. Stable gammaretroviral vector expression during embryonic stem cell-derived in vitro hematopoietic development. Mol Ther 14, 245-254 (2006).

100. Recillas-Targa, F., Pikaart, M. J., Burgess-Beusse, B., Bell, A. C., Litt, M. D., West, A. G., Gaszner, M. & Felsenfeld, G. Position-effect protection and enhancer blocking by the chicken beta-globin insulator are separable activities. Proc Natl Acad Sci USA 99, 6883-6888 (2002).

101. Gaszner, M. & Felsenfeld, G. Insulators: exploiting transcriptional and epigenetic mechanisms. Nat Rev Genet 7, 703-713 (2006).

102. Wallace, J. A. & Felsenfeld, G. We gather together: insulators and genome organization. Curr Opin Genet Dev 17, 400-407 (2007).

103. Chung, J. H., Bell, A. C. & Felsenfeld, G. Characterization of the chicken beta-globin insulator. Proc Natl Acad Sci USA 94, 575-580 (1997).

104. Bell, A. C., West, A. G. & Felsenfeld, G. The protein CTCF is required for the enhancer blocking activity of vertebrate insulators. Cell 98, 387-396 (1999).

105. Ryu, B. Y., Persons, D. A., Evans-Galea, M. V., Gray, J. T. & Nienhuis, A. W. A chromatin insulator blocks interactions between globin regulatory elements and cellular promoters in erythroid cells. Blood Cells Mol Dis 39, 221-228 (2007).

106. Ryu, B. Y., Evans-Galea, M. V., Gray, J. T., Bodine, D. M., Persons, D. A. & Nienhuis, A. W. An experimental system for the evaluation of retroviral vector design to diminish the risk for proto-oncogene activation. Blood 111, 1866-1875 (2008).

107. Yao, S., Osborne, C. S., Bharadwaj, R. R., Pasceri, P., Sukonnik, T., Pannell, D., Recillas-Targa, F., West, A. G. & Ellis, J. Retrovirus silencer blocking by the cHS4 insulator is CTCF independent. Nucleic Acids Res 31, 5317-5323 (2003).

108. Nishino, T., Tubb, J. & Emery, D. W. Partial correction of murine beta-thalassemia with a gammaretrovirus vector for human gamma-globin. Blood Cells Mol Dis 37, 1-7 (2006).

109. Aker, M., Tubb, J., Groth, A. C., Bukovsky, A. A., Bell, A. C., Felsenfeld, G., Kiem, H. P., Stamatoyannopoulos, G. & Emery, D. W. Extended core sequences from the cHS4 insulator are necessary for protecting retroviral vectors from silencing position effects. Hum Gene Ther 18, 333-343 (2007).

110. Li, C. L. & Emery, D. W. The cHS4 chromatin insulator reduces gammaretroviral vector silencing by epigenetic modifications of integrated provirus. Gene Ther 15, 49-53 (2008).

111. Ma, Y., Ramezani, A., Lewis, R., Hawley, R. G. & Thomson, J. A. High-level sustained transgene expression in human embryonic stem cells using lentiviral vectors. Stem Cells 21, 111-117 (2003).

112. Chang, L. J., Liu, X. & He, J. Lentiviral siRNAs targeting multiple highly conserved RNA sequences of human immunodeficiency virus type 1. Gene Ther 12, 1133-1144 (2005).

113. Pluta, K., Luce, M. J., Bao, L., Agha-Mohammadi, S. & Reiser, J. Tight control of transgene expression by lentivirus vectors containing second-generation tetracycline-responsive promoters. J Gene Med 7, 803-817 (2005).

114. Jakobsson, J., Rosenqvist, N., Thompson, L., Barraud, P. & Lundberg, C. Dynamics of transgene expression in a neural stem cell line transduced with lentiviral vectors incorporating the cHS4 insulator. Experimental cell research 298, 611-623 (2004).

115. Leboulch, P., Huang, G. M., Humphries, R. K., Oh, Y. H., Eaves, C. J., Tuan, D. Y. & London, I. M. Mutagenesis of retroviral vectors transducing human beta-globin gene and beta-globin locus control region derivatives results in stable transmission of an active transcriptional structure. EMBO J 13, 3065-3076 (1994).

116. Kim, T. H., Abdullaev, Z. K., Smith, A. D., Ching, K. A., Loukinov, D. I., Green, R. D., Zhang, M. Q., Lobanenkov, V. V. & Ren, B. Analysis of the vertebrate insulator protein CTCF-binding sites in the human genome. Cell 128, 1231-1245 (2007).

117. Yusufzai, T. M. & Felsenfeld, G. The 5'-HS4 chicken beta-globin insulator is a CTCF-dependent nuclear matrix-associated element. Proc Natl Acad Sci USA 101, 8620-8624 (2004).

118. Phillips, J. E. & Corces, V. G. CTCF: master weaver of the genome. Cell 137, 1194-1211 (2009).

119. Giles, K. E., Gowher, H., Ghirlando, R., Jin, C. & Felsenfeld, G. Chromatin boundaries, insulators, and long-range interactions in the nucleus. *Cold Spring Harbor symposia on quantitative biology* 75, 79-85 (2010).
120. Barski, A., Cuddapah, S., Cui, K., Roh, T. Y., Schones, D. E., Wang, Z., Wei, G., Chepelev, I. & Zhao, K. High-resolution profiling of histone methylations in the human genome. *Cell* 129, 823-837 (2007).
121. Wang, H., Maurano, M. T., Qu, H., Varley, K. E., Gertz, J., Pauli, F., Lee, K., Canfield, T., Weaver, M., Sandstrom, R., Thurman, R. E., Kaul, R., Myers, R. M. & Stamatoyannopoulos, J. A. Widespread plasticity in CTCF occupancy linked to DNA methylation. *Genome research* 22, 1680-1688 (2012).
122. Schmidt, D., Schwalie, P. C., Wilson, M. D., Ballester, B., Goncalves, A., Kutter, C., Brown, G. D., Marshall, A., Flicek, P. & Odom, D. T. Waves of retrotransposon expansion remodel genome organization and CTCF binding in multiple mammalian lineages. *Cell* 148, 335-348 (2012).
123. Renda, M., Baglivo, I., Burgess-Beusse, B., Esposito, S., Fattorusso, R., Felsenfeld, G. & Pedone, P. V. Critical DNA binding interactions of the insulator protein CTCF: a small number of zinc fingers mediate strong binding, and a single finger-DNA interaction controls binding at imprinted loci. *J Biol Chem* 282, 33336-33345 (2007).
124. Dickson, J., Gowher, H., Strogantsev, R., Gaszner, M., Hair, A., Felsenfeld, G. & West, A. G. VEZF1 elements mediate protection from DNA methylation. *PLOS Genet* 6, e1000804 (2010).
125. Li, C. L., Xiong, D., Stamatoyannopoulos, G. & Emery, D. W. Genomic and functional assays demonstrate reduced gammaretroviral vector genotoxicity associated with use of the cHS4 chromatin insulator. *Mol Ther* 17, 716-724 (2009).
126. Lisowski, L. & Sadelain, M. Locus control region elements HS1 and HS4 enhance the therapeutic efficacy of globin gene transfer in beta-thalassemic mice. *Blood* 110, 4175-4178 (2007).
127. Nagel, R. L., Bookchin, R. M., Johnson, J., Labie, D., Wajcman, H., Isaac-Sodeye, W. A., Honig, G. R., Schiliro, G., Crookston, J. H. & Matsutomo, K. Structural bases of the inhibitory effects of hemoglobin F and hemoglobin A2 on the polymerization of hemoglobin S. *Proc Natl Acad Sci USA* 76, 670-672 (1979).

128. Sadelain et al., *Proc. Nat'l Acad. Sci.* (USA) (1995); 92:6728-6732.
129. Armstrong, J. A., Emerson, B. M., 1996. NFE2 disrupts chromatin structure at human fl-globin locus control region hypersensitive site 2 in vitro. *Mol. Cell. Biol.* 16, 5634-5644.
130. Caterina, J. J., Ciavatta, D. J., Donze, D., Behringer, R. R., Townes, T. M., 1994. Multiple elements in human fl-globin locus control region 5' HS2 are involved in enhancer activity and position-independent transgene expression. *Nucleic Acids Res.* 22, 1006 1011.
131. Moi, P., Kan, Y. W., 1990. Synergistic enhancement of globin gene expression by activator protein-1-like proteins. *Proc. Natl. Acad, Sci. USA* 87, 9000-9004.
132. Ney, P., Sorrentino, B., McDonagh, K., Nienhuis, A., 1990. Tandem AP-I-binding sites within the human/j-globin dominant control region function as an inducible enhancer in erythroid cells. *Genes Dev.* 4, 993 1006.
133. Shivdasani, R. A., Rosenblatt, M. F., Zucker-Franklin, D., Jackson, C. W., Hunt, P., Saris, C. J. M., Orkin, S. H., 1995. Transcription factor NF-E2 is required for platelet formation independent of the actions of thrombopoietin/MGDF in megakaryocyte development. *Cell* 81,695-704.
134. Talbot, D., Grosveld, F., 1991. The 5'HS2 of the globin locus control region enhances transcription through the interaction of a multimeric complex binding at two functionally distinct NF-E2 binding sites. *EMBO J.* 10, 1391-1398.
135. Hardison et al., *Gene* (1997); 205:73-94.
136. Elnitski et al., *The Journal of Biological Chemistry* (1997); 272 (1):369-378; Horak et al., *PNAS* (2002); 99 (5):2924-2929.
137. Shimotsuma et al., *Journal of Biological Chemistry* (2010); 285 (19):14495-14503.

From the foregoing description, it will be apparent that variations and modifications may be made to the presently disclosed subject matter described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

---

What is claimed is:

1. A method of treating a hemoglobinopathy in a subject, comprising administering an effective amount of an autologous cell transduced with an expression cassette to the subject, wherein the expression cassette comprises:

a) a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of between 600 bp and 900 bp and does not comprise the nucleotide sequence set forth in SEQ ID NO: 50; or b) a globin gene or a functional portion thereof operably linked to a β-globin locus control region (LCR) that comprises a HS1 region, a HS3 region, and a HS4 region and does not comprise a core sequence of HS2 region, wherein the HS4 region has a length of between 600 bp and 900 bp does not comprise the nucleotide sequence set forth in SEQ ID NO:50.

2. The method of claim 1, wherein the β-globin LCR comprises:

a) a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6;

b) a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35;

c) a HS1 region consisting of the nucleotide sequence set forth in SEQ ID NO: 3, a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6;

d) a HS1 region consisting of the nucleotide sequence set forth in SEQ ID NO: 3, a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35;

e) a HS1 region consisting of the nucleotide sequence set forth in SEQ ID NO: 3, a HS3 region consisting of the nucleotide sequence set forth in SEQ ID NO: 5, and a HS4 region consisting of nucleotides 115-868 of SEQ ID NO: 6; or f) a HS1 region consisting of the nucleotide sequence set forth in SEQ ID NO: 3, a HS3 region consisting of the nucleotide sequence set forth in SEQ ID NO: 34, and a HS4 region consisting of the nucleotide sequence set forth in SEQ ID NO: 35.

3. The method of claim 1, wherein the expression cassette, further comprising at least one erythroid-specific enhancer.

4. The method of claim 3, wherein the at least one erythroid-specific enhancer is positioned within the β-globin LCR.

5. The method of claim 3, wherein the at least one erythroid-specific enhancer is positioned between the HS1 region and the HS3 region of the β-globin LCR.

6. The method of claim 3, wherein the at least one erythroid-specific enhancer consists of the nucleotide sequence set forth in SEQ ID NO: 13, SEQ ID NO: 14, SEQ ID NO: 15, SEQ ID NO: 16, or SEQ ID NO: 17.

7. The method of claim 1, wherein the expression cassette further comprising at least one insulator that comprises the CTCF binding site sequence set forth in SEQ ID NO:18.

8. The method of claim 7, wherein the at least one insulator consists of the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32, or a fragment thereof.

9. The method of claim 1, wherein the β-globin gene is a wild-type human β-globin gene or a non-wild-type human β-globin gene.

10. The method of claim 9, wherein non-wild-type human β-globin gene is selected from a human β-globin gene comprising one or more deletions of intron sequences, a human β-globin gene encoding at least one anti-sickling amino acid residue, and a human β-globin gene comprising one or more deletions of intron sequences and encoding at least one anti-sickling amino acid residue.

11. The method of claim 10, wherein the non-wild-type human β-globin gene encoding at least one anti-sickling amino acid residue is selected from the group consisting of a human $\beta^A$-globin gene encoding a threonine to glutamine mutation at codon 87 ($\beta^{A-T87Q}$), a human $\beta^A$-globin gene encoding a glutamic acid to alanine mutation at codon 22 ($\beta^{A-E22A}$), a human $\beta^A$-globin gene encoding an asparagine to lysine mutation at codon 80 ($\beta^{-N80K}$), a human $\beta^A$-globin gene encoding a glutamic acid to alanine mutation at codon 22 and an asparagine to lysine mutation at codon 80, and a human $\beta^A$-globin gene encoding a glutamic acid to alanine mutation at codon 22 and a threonine to glutamine mutation at codon 87.

12. The method of claim 10, wherein the one or more deletions of intron sequences comprise a deletion in intron 2.

13. The method of claim 1, wherein the expression cassette further comprises a β-globin promoter.

14. The method of claim 13, wherein said β-globin promoter is positioned between the globin gene or functional portion thereof and the β-globin LCR.

15. The method of claim 14, wherein said β-globin promoter is a human β-globin promoter that is about 265 bp in length, and/or consists of the nucleotide sequence set forth in SEQ ID NO:11.

16. The method of claim 1, wherein the expression cassette further comprises a human β-globin 3' enhancer.

17. The method of claim 16, wherein said human β-globin 3' enhancer is positioned in the upstream of the globin gene or functional portion thereof.

18. The method of claim 16, wherein said human β-globin 3' enhancer is about 880 bp in length and/or consists of the nucleotide sequence set forth in SEQ ID NO:12.

19. The method of claim 1, wherein the cell is selected from the group consisting of a hematopoietic stem cell, an embryonic stem cell, and an induced pluripotent stem cell, optionally wherein the hematopoietic stem cell is a CD34+ hematopoietic stem cell.

\* \* \* \* \*